(12) United States Patent
Awrey et al.

(10) Patent No.: US 7,799,547 B2
(45) Date of Patent: Sep. 21, 2010

(54) PURIFIED POLYPEPTIDES FROM STAPHYLOCOCCUS AUREUS

(75) Inventors: Donald E. Awrey, Mississauga (CA); Teresa Clarke McGrath, Toronto (CA); Vladimir Romanov, Toronto (CA)

(73) Assignee: Affinium Pharmaceuticals, Inc., Toronto, Ontario (CA)

( * ) Notice: Subject to any disclaimer, the term of this patent is extended or adjusted under 35 U.S.C. 154(b) by 502 days.

(21) Appl. No.: 11/329,987

(22) Filed: Jan. 11, 2006

(65) Prior Publication Data

US 2006/0258845 A1 Nov. 16, 2006

Related U.S. Application Data

(63) Continuation-in-part of application No. PCT/CA2004/001004, filed on Jul. 9, 2004.

(60) Provisional application No. 60/490,383, filed on Jul. 25, 2003, provisional application No. 60/486,540, filed on Jul. 11, 2003.

(51) Int. Cl.
*C12N 9/00* (2006.01)
*G01N 31/00* (2006.01)

(52) U.S. Cl. .......................... 435/183; 436/4

(58) Field of Classification Search .................. None
See application file for complete search history.

(56) References Cited

U.S. PATENT DOCUMENTS

| | | | |
|---|---|---|---|
| 5,302,527 | A | 4/1994 | Birkett et al. |
| 5,539,132 | A | 7/1996 | Royer et al. |
| 5,614,551 | A | 3/1997 | Dick et al. |
| 5,759,837 | A | 6/1998 | Kuhajda et al. |
| 5,965,402 | A | 10/1999 | Black et al. |
| 6,228,619 | B1 | 5/2001 | Foster et al. |
| 6,274,376 | B1 | 8/2001 | Black et al. |
| 6,380,370 | B1 | 4/2002 | Doucette-Stamm et al. |
| 6,403,337 | B1 | 6/2002 | Bailey et al. |
| 6,432,670 | B1 | 8/2002 | Payne et al. |
| 6,593,114 | B1 | 7/2003 | Kunsch et al. |
| 6,613,553 | B1 | 9/2003 | Rock et al. |
| 6,753,172 | B1 | 6/2004 | Black et al. |
| 6,821,746 | B2 | 11/2004 | DeWolf, Jr. et al. |
| 6,951,729 | B1 | 10/2005 | Dewolf et al. |
| 6,995,254 | B1 | 2/2006 | Payne et al. |
| 7,033,795 | B2 | 4/2006 | DeWolf, Jr. et al. |
| 7,048,926 | B2 | 5/2006 | Brandt et al. |
| 7,176,299 | B2 | 2/2007 | Black et al. |
| 2002/0076766 | A1 | 6/2002 | Black et al. |
| 2003/0032161 | A1 | 2/2003 | Borneman et al. |
| 2004/0053814 | A1 | 3/2004 | Brandt et al. |
| 2005/0032161 | A1 | 2/2005 | Black et al. |
| 2005/0112713 | A1 | 5/2005 | DeWolf et al. |
| 2006/0083752 | A1 | 4/2006 | Black et al. |
| 2006/0258845 | A1 | 11/2006 | Awrey |
| 2007/0009546 | A1 | 1/2007 | Black et al. |

FOREIGN PATENT DOCUMENTS

| | | |
|---|---|---|
| DE | 26 20 777 | 12/1977 |
| EP | 0 78 6519 A2 | 7/1997 |
| EP | 0 826 774 A2 | 4/1998 |
| JP | 10-174590 | 6/1998 |
| WO | WO 97/30070 | 8/1997 |
| WO | WO 97/30149 | 8/1997 |
| WO | WO 00/70017 | 11/2000 |
| WO | WO 01/30988 | 5/2001 |
| WO | WO 01/48248 | 7/2001 |
| WO | WO 02/31128 | 4/2002 |
| WO | WO 03/027139 | 4/2003 |
| WO | WO 03/102190 | 12/2003 |
| WO | WO 2005/005469 | 1/2005 |
| WO | WO 2006/008660 | 1/2006 |
| WO | WO 2006/028561 | 3/2006 |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Bergler et al., "Protein EnvM is the NADH-dependent Enoyl-ACP Reductase (FabI) of *Escherichia coli*\*", The Journal of Biological Chemistry, vol. 269, No. 8, pp. 5493-5496 (1994).
Bergler et al., "Sequences of the *envM* gene and of two mutated alleles in *Escherichia coli*", Journal of General Microbiology (1992), 138, pp. 2093-2100.
Broadwater et al., "Spinach Holo-Acyl Carrier Protein: Overproduction and Phosphopantetheinylation in *Escherichia coli* BL21(DE3), in Vitro Acylation, and Enzymatic Desaturation of Histidine-Tagged Isoform I¹'", Protein Expression and Purification 15, 314-326 (1999).
Courchesne, P. L., et al., "Identification of Proteins by Matrix-Assisted Laser Desorption/Ionization Mass Spectroscopy Using Peptide and Fragment Ion Masses," Methods in Molecular Biology, vol. 112: 2D Proteome Analysis Protocols, 1999.
Database Embl [Online] Aug. 10, 2000, "*Streptococcus pneumoniae* Fab Gene Cluster, Complete Sequence," Heath, R.J., et al., "A Triclosan-Resistant Bacterial Enzyme."
Edwards, et al., "Cloning of the fabF gene in an expression vector and in vitro characterization of recombinant *fabF* and *fabB* encoded enzymes from *Escherichia coli*", FEBS Letters, 402:62-66 (1997).

(Continued)

*Primary Examiner*—Suzanne M. Noakes
(74) *Attorney, Agent, or Firm*—Goodwin Procter LLP

(57) ABSTRACT

The present invention relates to novel drug targets for pathogenic bacteria. Accordingly, the invention provides purified protein comprising the amino acid sequence set forth in SEQ ID NO: 4. The invention also provides biochemical and biophysical characteristics of the polypeptides of the invention.

1 Claim, 169 Drawing Sheets

(20 of 169 Drawing Sheet(s) Filed in Color)

OTHER PUBLICATIONS

Grassberger et al., "Preparation and Antibacterial Activates of New 1,2,3-Diazaborine Derivatives and Analogues", Journal of Medicinal Chemistry, 1984. vol. 24, No. 8, pp. 947-953.

Gronowitz et al., "Antibacterial borazaro derivatives", Acta Pharm. Suecica 8, pp. 377-390 (1971).

Heath et al., "Enoyl-Acyl Carrier Protein Reductase (fabs) Plays a Determinant Role in Completing Cycles of Fatty Acid Elongation in *Escherichia coli*\*", The Journal of Biological Chemistry, vol. 270, No. 44, pp. 26538-26542 (1995).

Heath et al., "Regulation of Fatty Acid Elongation and Initiation by Acyl-Acyl Carrier Protein in *Escherichia coli*\*", The Journal of Biological Chemistry, vol. 271, No. 4, pp. 1833-1836 (1996).

Kay, L., E., "Nuclear Magnetic Resonance Methods for High Molecular Weight Proteins: A Study Involving a Complex of Maltose Binding Protein and Beta-Cyclodextrin," Methods in Enzymology, Academic Press, Inc., vol. 339, 2001, pp. 174-203.

Lam et al., "Effect of diazabrine derivative (Sa 84.474) on the virulence of *Escherichia coli*", Journal of Antimicrobial Chemotherapy (1987) 20, pp. 37-45.

Lambalot, et al., "Cloning, Over production, and Characterization of the *Escherichia coli* Holo-acyl Carrier Protein Synthase\*", The Journal of Biological Chemistry, vol. 270, No. 42, pp. 24658-24661 (1995).

Marrakchi, Hedia, et al., "Characterization of *Streptococcus pneumoniae* Enoyl-(acyl-carrier protein) Reductase (FabK)" Biochemical Journal, vol. 370, No. 3, Mar. 15, 2003, pp. 1055-1062.

Ngo et al., "Computational complexity, protein structure prediction, and the Levinthal paradox", Chapter 14 in 'The Protein Folding Problem and Tertiary Structure Prediction', Merz et al. (eds.), Birkhauser: Boston, MA, pp. 433 & 492-495, Aug. 1994.

Qui, Xiayang, et al., "Molecular Basis for Triclosan Activity Involves a Flipping Loop in the Active Site," Protein Science, vol. 8, No. 11, Nov. 1999, p. 2529-2532.

Rock et al., "Preparative Enzymatic Synthesis and Hydrophobic Chromatography of Acyl-Acyl Carrier Protein", *The Journal of Biological Chemistry*, 254(15): 7123-7128 (1979).0.

Rock et al., "Acyl Carrier Protein from *Escherichia coli*", *Methods in Enzymology*, 71:341-351 (1981).

Rodgers, D. W., "Cryocrystallography," Structure, vol. 2, No. 12, Dec. 15, 1994.

Roujeinkova et al., "Inhibitor Binding Studies on Enoyl Reductase Reveal Conformational Changes Related to Substrate Recognition", *The Journal of Biological Chemistry*, 274(43): 30811-30817 (1999).

Sequence Search Alignments Between Accession No. AAZ96201 and Applicants' SEQ ID No. 1.

Sequence Search Alignment Between Accession No. AAY85822 and Applicants' SEQ ID No. 2.

Turnowsky et al., "envM genes of *Salmonella typhimuium* and *Escherichia coli*", Journal of Bacteriology, Dec. 1989 pp. 6555-6565.

Ward et al., "Kinetic and Structural Characteristics of the Inhibition of Enoyl (Acyl Carrier Protein) Reductase by Triclosan", Biochemistry, 38: 12514-12525 (1999).

\* cited by examiner

FIGURE 1

ATGTTAAATCTTGAAAACAAAACATATGTCATCATGGGAATCGCTAATAAGCGT
AGTATTGCTTTTGGTGTCGCTAAAGTTTTAGATCAATTAGGTGCTAAATTAGTATTTACT
TACCGTAAAGAACGTAGCCGTAAAGAGCTTGAAAAATTATTAGAACAATTAAATCAAC
CAGAAGCGCACTTATATCAAATTGATGTTCAAAGCGATGAAGAGGTTATTAATGGTTTT
GAGCAAATTGGTAAAGATGTTGGCAATATTGATGGTGTATATCATTCAATCGCATTTGC
TAATATGGAAGACTTACGCGGACGCTTTTCTGAAACTTCACGTGAAGGCTTCTTGTTAG
CTCAAGACATTAGTTCTTACTCATTAACAATTGTGGCTCATGAAGCTAAAAAATTAATG
CCAGAAGGTGGTAGCATTGTTGCAACAACATATTTAGGTGGCGAATTCGCAGTTCAAA
ACTATAATGTGATGGGTGTTGCTAAAGCGAGCTTAGAAGCAAATGTTAAATATTTAGC
ATTAGACTTAGGTCCAGATAATATTCGCGTTAATGCAATTTCAGCTGGTCCAATCCGTA
CATTAAGTGCAAAAGGTGTGGGTGGTTTCAATACAATTCTTAAAGAAATCGAAGAGCG
TGCACCTTTAAAACGTAATGTTGATCAAGTAGAAGTAGGTAAAACTGCGGCTTACTTAT
TAAGTGATTTATCAAGTGGCGTTACAGGTGAAAATATTCATGTAGATAGCGGATTCCAC
GCAATTAAATAA

FIGURE 2

SEQ ID NO: 2

MLNLENKTYVIMGIANKRSIAFGVAKVLDQLGAKLVFTYRKERSRKELEKLLEQLN
QPEAHLYQIDVQSDEEVINGFEQIGKDVGNIDGVYHSIAFANMEDLRGRFSETSREGFLLAQ
DISSYSLTIVAHEAKKLMPEGGSIVATTYLGGEFAVQNYNVMGVAKASLEANVKYLALDL
GPDNIRVNAISAGPIRTLSAKGVGGFNTILKEIEERAPLKRNVDQVEVGKTAAYLLSDLSSG
VTGENIHVDSGFHAIK

FIGURE 3

SEQ ID NO: 3

ATGTTAAATCTTGAAAACAAAACATATGTCATCATGGGAATCGCTAATA
AGCGTAGTATTGCTTTTGGTGTCGCTAAAGTTTTAGATCAATTAGGTGCTAAAT
TAGTATTTACTTACCGTAAAGAACGTAGCCGTAAAGAGCTTGAAAAATTATTAG
AACAATTAAATCAACCAGAAGCGCACTTATATCAAATTGATGTTCAAAGCGAT
GAAGAGGTTATTAATGGTTTTGAGCAAATTGGTAAAGATGTTGGCAATATTGAT
GGTGTATATCATTCAATCGCATTTGCTAATATGGAAGACTTACGCGGACGCTTT
TCTGAAACTTCACGTGAAGGCTTCTTGTTAGCTCAAGACATTAGTTCTTACTCAT
TAACAATTGTGGCTCATGAAGCTAAAAAATTAATGCCAGAAGGTGGTAGCATT
GTTGCAACAACATATTTAGGTGGCGAATTCGCAGTTCAAAACTATAATGTGATG
GGTGTTGCTAAAGCGAGCTTAGAAGCAAATGTTAAATATTTAGCATTAGACTTA
GGTCCAGATAATATTCGCGTTAATGCAATTTCAGCTGGTCCAATCCGTACATTA
AGTGCAAAAGGTGTGGGTGGTTTCAATACAATTCTTAAAGAAATCGAAGAGCG
TGCACCTTTAAAACGTAATGTTGATCAAGTAGAAGTAGGTAAAACTGCGGCTTA
CTTATTAAGTGATTTATCAAGTGGCGTTACAGGTGAAAATATTCATGTAGATAG
CGGATTCCACGCAATTAAATAA

FIGURE 4

SEQ ID NO: 4

MLNLENKTYVIMGIANKRSIAFGVAKVLDQLGAKLVFTYRKERSRKELEKL
LEQLNQPEAHLYQIDVQSDEEVINGFEQIGKDVGNIDGVYHSIAFANMEDLRGRFSE
TSREGFLLAQDISSYSLTIVAHEAKKLMPEGGSIVATTYLGGEFAVQNYNVMGVAK
ASLEANVKYLALDLGPDNIRVNAISAGPIRTLSAKGVGGFNTILKEIEERAPLKRNV
DQVEVGKTAAYLLSDLSSGVTGENIHVDSGFHAIK

FIGURE 5

SEQ ID NO: 5

> Forward PCR Primer
>
> CGCGGGGTACCATGTTAAATCTTGAAAACAAAACATATG

SEQ ID NO: 6

> Reverse PCR Primer
>
> GCGCGGATCCTTTAATTGCGTGGAATCCGC

FIGURE 6

TABLE 1: Amino Acid and Nucleic Acid Properties

| | |
|---|---|
| Melting temperature (°C) of SEQ ID NO: 5 (forward PCR primer) | 68 |
| Restriction enzyme for SEQ ID NO: 5 (forward PCR primer) | KpnI |
| Melting temperature (°C) of SEQ ID NO: 6 (reverse PCR primer) | 58 |
| Restriction enzyme for SEQ ID NO: 6 (reverse PCR primer) | BamHI |
| Number of nucleic acid residues in SEQ ID NO: 1 | 771 |
| Number of amino acid residues in SEQ ID NO: 2 | 356 |
| Number of different nucleic acid residues between SEQ ID NO: 1 and SEQ ID NO: 3 | 1 |
| Number of different amino acid residues between SEQ ID NO: 2 and SEQ ID NO: 4 | 1 |
| Calculated Molecular weight of SEQ ID NO: 2 polypeptide (kDa) | 27.9 |
| Calculated pI of SEQ ID NO: 2 polypeptide | 6 |
| Solubility of SEQ ID NO: 4 polypeptide, determined as described in EXAMPLE 2 (with the His tag at the N-terminus) | Approaching 100% |
| Amount of purified polypeptide having SEQ ID NO: 4, prepared and purified as described in EXAMPLE 9 (mg/L of culture) | 72 |
| Amount of purified polypeptide having SEQ ID NO: 4 soluble in buffer, as described in EXAMPLE 9 (mg/ml of buffer) | 22.5 |

FIGURE 7

TABLE 2: Bioinformatic Analyses

| Protein annotation and gene designation, if any | enoyl-[acyl-carrier-protein] reductase (NADH), *FabI* |
|---|---|
| COG Category | Lipid metabolism |
| COG ID Number | COG0623 |
| Is SEQ ID NO: 2 classified as an essential gene? | yes |
| Most closely related protein from PDB | Enoyl-[Acyl-Carrier-Protein] Reductase (1_mfp) |
| Source organism for closest PDB protein | *E. coli* |
| e-value for closest PDB Protein | 2E-55 |
| % Identity between SEQ ID NO: 2 and the closest protein from PDB | 43 |
| % Positives between SEQ ID NO: 2 and the closest protein from PDB | 63 |
| Number of Protein Hits in the VGDB | 18 |
| Number of Microorganisms having VGDB Hits | 10 |
| Microorganisms having VGDB Hits[1] | ecoli nmen saur rpro efae ctra hinf bsub hpyl paer |

[1] Organisms are abbreviated as follows: ecoli = *Eschericia coli*; hpyl = *Helicobacter pylori*; paer = *Pseudomonas aeruginosa*; ctra = *Chlaydia trachomatis*; hinf = *Haemophilus influenzae*; nmen = *Neisseria meningitidis*; rpxx = *Rickettsia prowazekii*; bbur = *Borrelia burgdorferi*; bsub = *Bacillus subtilis*; staph = *Staphylococcus aureus*; spne = *Streptococcus pneumoniae*; mgen = *Mycoplasma genitalium*; efae = *Enterococcus faecalis*.

FIGURE 8

TABLE 3: Crystallographic Data

| Wavelength (Å) | 1.00 |
|---|---|
| Resolution (Å) | 50-2.3 |
| Total Data (last shell)* | 198157 (29285) |
| Unique Data (last shell) | 52886 (7715) |
| Multiplicity (last shell) | 3.7 (3.8) |
| Completeness (last shell)* | 99.4 (99.8) |
| $R_{sym}$ (last shell) | 0.086 (0.119) |
| $<I/\sigma(I)>$ | 5.7 (5.5) |
| *last shell includes all reflections between 2.42 and 2.30 . | |

TABLE 4: Refinement & Model Parameters

| Final Model parameters | Number of amino acid chains | 4 |
|---|---|---|
| | Number of protein atoms | 7852 |
| | Number of solvent atoms / SO4 / NADPH / API-1135 | 346 / 29 / 195 / 115 |
| | Resolution range (Å) | 30-2.3 |
| | R-factor[a] | 22.3 |
| | $R_{free}$[b] | 26.0 |
| | Average main chain / side chain B-factor (Å$^2$) | 24.7 |
| | Average solvent / SO4/ NADPH / API-1135 B-factor (Å$^2$) | 26.2 / 48.4 / 21.1 / 20.3 |
| RMS deviation from ideal geometry | Covalent bond lengths (Å) | 0.0083 |
| | Bond angles (°) | 1.356 |
| [a]R-factor – $\Sigma_{hkl}||F_{obs}| - |F_{calc}||/\Sigma_{hkl}|F_{obs}|$ [b]$R_{free}$ is a cross-validation residual calculated using 10% of the native data which were chosen randomly and excluded from the refinement. | | |

FIGURE 9

| ATOM | 1 | CB | LEU | A | 2 | 51.491 | 28.086 | 42.690 | 1.00 | 39.41 | C |
|---|---|---|---|---|---|---|---|---|---|---|---|
| ATOM | 2 | CG | LEU | A | 2 | 50.631 | 29.023 | 43.535 | 1.00 | 38.98 | C |
| ATOM | 3 | CD1 | LEU | A | 2 | 49.362 | 29.357 | 42.805 | 1.00 | 40.94 | C |
| ATOM | 4 | CD2 | LEU | A | 2 | 50.301 | 28.347 | 44.861 | 1.00 | 40.65 | C |
| ATOM | 5 | C | LEU | A | 2 | 50.224 | 26.868 | 40.917 | 1.00 | 39.49 | C |
| ATOM | 6 | O | LEU | A | 2 | 49.874 | 27.969 | 40.479 | 1.00 | 39.87 | O |
| ATOM | 7 | N | LEU | A | 2 | 51.885 | 25.654 | 42.358 | 1.00 | 39.65 | N |
| ATOM | 8 | CA | LEU | A | 2 | 50.859 | 26.745 | 42.305 | 1.00 | 39.54 | C |
| ATOM | 9 | N | ASN | A | 3 | 50.081 | 25.742 | 40.226 | 1.00 | 38.72 | N |
| ATOM | 10 | CA | ASN | A | 3 | 49.462 | 25.715 | 38.898 | 1.00 | 37.54 | C |
| ATOM | 11 | CB | ASN | A | 3 | 50.154 | 24.655 | 38.042 | 1.00 | 39.56 | C |
| ATOM | 12 | CG | ASN | A | 3 | 49.492 | 24.466 | 36.694 | 1.00 | 40.43 | C |
| ATOM | 13 | OD1 | ASN | A | 3 | 48.272 | 24.629 | 36.555 | 1.00 | 40.68 | O |
| ATOM | 14 | ND2 | ASN | A | 3 | 50.292 | 24.100 | 35.690 | 1.00 | 41.47 | N |
| ATOM | 15 | C | ASN | A | 3 | 48.006 | 25.318 | 39.129 | 1.00 | 36.36 | C |
| ATOM | 16 | O | ASN | A | 3 | 47.716 | 24.152 | 39.378 | 1.00 | 36.08 | O |
| ATOM | 17 | N | LEU | A | 4 | 47.077 | 26.264 | 39.028 | 1.00 | 34.94 | N |
| ATOM | 18 | CA | LEU | A | 4 | 45.682 | 25.928 | 39.307 | 1.00 | 32.93 | C |
| ATOM | 19 | CB | LEU | A | 4 | 45.062 | 27.069 | 40.101 | 1.00 | 31.99 | C |
| ATOM | 20 | CG | LEU | A | 4 | 45.977 | 27.554 | 41.236 | 1.00 | 32.71 | C |
| ATOM | 21 | CD1 | LEU | A | 4 | 45.224 | 28.579 | 42.067 | 1.00 | 31.34 | C |
| ATOM | 22 | CD2 | LEU | A | 4 | 46.438 | 26.383 | 42.119 | 1.00 | 29.93 | C |
| ATOM | 23 | C | LEU | A | 4 | 44.777 | 25.534 | 38.136 | 1.00 | 32.47 | C |
| ATOM | 24 | O | LEU | A | 4 | 43.549 | 25.631 | 38.227 | 1.00 | 29.84 | O |
| ATOM | 25 | N | GLU | A | 5 | 45.377 | 25.072 | 37.041 | 1.00 | 33.68 | N |
| ATOM | 26 | CA | GLU | A | 5 | 44.592 | 24.647 | 35.883 | 1.00 | 34.55 | C |
| ATOM | 27 | CB | GLU | A | 5 | 45.499 | 24.457 | 34.662 | 1.00 | 36.51 | C |
| ATOM | 28 | CG | GLU | A | 5 | 46.549 | 23.357 | 34.825 | 1.00 | 40.22 | C |
| ATOM | 29 | CD | GLU | A | 5 | 47.442 | 23.187 | 33.597 | 1.00 | 43.07 | C |
| ATOM | 30 | OE1 | GLU | A | 5 | 46.926 | 22.779 | 32.520 | 1.00 | 43.30 | O |
| ATOM | 31 | OE2 | GLU | A | 5 | 48.668 | 23.459 | 33.715 | 1.00 | 45.00 | O |
| ATOM | 32 | C | GLU | A | 5 | 43.957 | 23.322 | 36.292 | 1.00 | 33.68 | C |
| ATOM | 33 | O | GLU | A | 5 | 44.585 | 22.523 | 36.991 | 1.00 | 34.81 | O |
| ATOM | 34 | N | ASN | A | 6 | 42.715 | 23.089 | 35.885 | 1.00 | 32.25 | N |
| ATOM | 35 | CA | ASN | A | 6 | 42.013 | 21.850 | 36.249 | 1.00 | 31.07 | C |
| ATOM | 36 | CB | ASN | A | 6 | 42.917 | 20.615 | 36.086 | 1.00 | 31.87 | C |
| ATOM | 37 | CG | ASN | A | 6 | 43.351 | 20.395 | 34.654 | 1.00 | 32.24 | C |
| ATOM | 38 | OD1 | ASN | A | 6 | 42.528 | 20.438 | 33.731 | 1.00 | 30.92 | O |
| ATOM | 39 | ND2 | ASN | A | 6 | 44.646 | 20.147 | 34.456 | 1.00 | 31.19 | N |
| ATOM | 40 | C | ASN | A | 6 | 41.520 | 21.883 | 37.688 | 1.00 | 29.48 | C |
| ATOM | 41 | O | ASN | A | 6 | 40.966 | 20.891 | 38.172 | 1.00 | 28.38 | O |
| ATOM | 42 | N | LYS | A | 7 | 41.736 | 23.015 | 38.363 | 1.00 | 27.71 | N |
| ATOM | 43 | CA | LYS | A | 7 | 41.313 | 23.209 | 39.753 | 1.00 | 26.19 | C |
| ATOM | 44 | CB | LYS | A | 7 | 42.417 | 23.913 | 40.546 | 1.00 | 27.29 | C |
| ATOM | 45 | CG | LYS | A | 7 | 43.741 | 23.190 | 40.561 | 1.00 | 28.07 | C |
| ATOM | 46 | CD | LYS | A | 7 | 43.855 | 22.290 | 41.769 | 1.00 | 29.17 | C |
| ATOM | 47 | CE | LYS | A | 7 | 45.005 | 21.317 | 41.620 | 1.00 | 28.09 | C |
| ATOM | 48 | NZ | LYS | A | 7 | 44.562 | 20.131 | 40.842 | 1.00 | 28.49 | N |
| ATOM | 49 | C | LYS | A | 7 | 40.070 | 24.094 | 39.777 | 1.00 | 25.28 | C |
| ATOM | 50 | O | LYS | A | 7 | 39.948 | 25.021 | 38.976 | 1.00 | 25.29 | O |
| ATOM | 51 | N | THR | A | 8 | 39.164 | 23.830 | 40.713 | 1.00 | 23.92 | N |
| ATOM | 52 | CA | THR | A | 8 | 37.942 | 24.617 | 40.829 | 1.00 | 22.31 | C |
| ATOM | 53 | CB | THR | A | 8 | 36.728 | 23.795 | 40.365 | 1.00 | 22.08 | C |
| ATOM | 54 | OG1 | THR | A | 8 | 36.902 | 23.462 | 38.985 | 1.00 | 22.06 | O |
| ATOM | 55 | CG2 | THR | A | 8 | 35.429 | 24.573 | 40.535 | 1.00 | 20.79 | C |
| ATOM | 56 | C | THR | A | 8 | 37.715 | 25.096 | 42.261 | 1.00 | 21.49 | C |
| ATOM | 57 | O | THR | A | 8 | 37.826 | 24.313 | 43.210 | 1.00 | 21.13 | O |
| ATOM | 58 | N | TYR | A | 9 | 37.395 | 26.382 | 42.412 | 1.00 | 21.11 | N |
| ATOM | 59 | CA | TYR | A | 9 | 37.153 | 26.960 | 43.735 | 1.00 | 20.39 | C |
| ATOM | 60 | CB | TYR | A | 9 | 38.334 | 27.841 | 44.151 | 1.00 | 18.51 | C |
| ATOM | 61 | CG | TYR | A | 9 | 39.666 | 27.117 | 44.216 | 1.00 | 18.90 | C |
| ATOM | 62 | CD1 | TYR | A | 9 | 40.571 | 27.176 | 43.152 | 1.00 | 18.85 | C |
| ATOM | 63 | CE1 | TYR | A | 9 | 41.796 | 26.498 | 43.209 | 1.00 | 20.03 | C |

FIGURE 9 (cont.)

| ATOM | 64 | CD2 | TYR | A | 9 | 40.015 | 26.363 | 45.338 | 1.00 | 16.08 | C |
| ATOM | 65 | CE2 | TYR | A | 9 | 41.224 | 25.684 | 45.405 | 1.00 | 16.83 | C |
| ATOM | 66 | CZ | TYR | A | 9 | 42.112 | 25.753 | 44.341 | 1.00 | 18.83 | C |
| ATOM | 67 | OH | TYR | A | 9 | 43.308 | 25.076 | 44.408 | 1.00 | 18.96 | O |
| ATOM | 68 | C | TYR | A | 9 | 35.867 | 27.788 | 43.846 | 1.00 | 20.83 | C |
| ATOM | 69 | O | TYR | A | 9 | 35.485 | 28.495 | 42.913 | 1.00 | 20.82 | O |
| ATOM | 70 | N | VAL | A | 10 | 35.207 | 27.699 | 45.001 | 1.00 | 20.73 | N |
| ATOM | 71 | CA | VAL | A | 10 | 33.991 | 28.472 | 45.265 | 1.00 | 19.54 | C |
| ATOM | 72 | CB | VAL | A | 10 | 32.989 | 27.666 | 46.130 | 1.00 | 19.00 | C |
| ATOM | 73 | CG1 | VAL | A | 10 | 31.766 | 28.503 | 46.430 | 1.00 | 17.01 | C |
| ATOM | 74 | CG2 | VAL | A | 10 | 32.589 | 26.381 | 45.408 | 1.00 | 18.52 | C |
| ATOM | 75 | C | VAL | A | 10 | 34.411 | 29.725 | 46.046 | 1.00 | 19.16 | C |
| ATOM | 76 | O | VAL | A | 10 | 35.086 | 29.619 | 47.068 | 1.00 | 18.18 | O |
| ATOM | 77 | N | ILE | A | 11 | 34.032 | 30.906 | 45.562 | 1.00 | 19.45 | N |
| ATOM | 78 | CA | ILE | A | 11 | 34.384 | 32.148 | 46.249 | 1.00 | 18.82 | C |
| ATOM | 79 | CB | ILE | A | 11 | 35.075 | 33.147 | 45.304 | 1.00 | 19.13 | C |
| ATOM | 80 | CG2 | ILE | A | 11 | 35.692 | 34.278 | 46.123 | 1.00 | 17.35 | C |
| ATOM | 81 | CG1 | ILE | A | 11 | 36.172 | 32.449 | 44.496 | 1.00 | 20.86 | C |
| ATOM | 82 | CD1 | ILE | A | 11 | 37.369 | 31.987 | 45.321 | 1.00 | 21.27 | C |
| ATOM | 83 | C | ILE | A | 11 | 33.128 | 32.812 | 46.818 | 1.00 | 18.64 | C |
| ATOM | 84 | O | ILE | A | 11 | 32.298 | 33.337 | 46.069 | 1.00 | 17.77 | O |
| ATOM | 85 | N | MET | A | 12 | 33.001 | 32.787 | 48.143 | 1.00 | 17.09 | N |
| ATOM | 86 | CA | MET | A | 12 | 31.841 | 33.353 | 48.820 | 1.00 | 16.79 | C |
| ATOM | 87 | CB | MET | A | 12 | 31.390 | 32.412 | 49.941 | 1.00 | 16.39 | C |
| ATOM | 88 | CG | MET | A | 12 | 31.234 | 30.957 | 49.553 | 1.00 | 15.12 | C |
| ATOM | 89 | SD | MET | A | 12 | 30.556 | 29.952 | 50.941 | 1.00 | 19.91 | S |
| ATOM | 90 | CE | MET | A | 12 | 28.751 | 30.260 | 50.746 | 1.00 | 9.94 | C |
| ATOM | 91 | C | MET | A | 12 | 32.109 | 34.733 | 49.429 | 1.00 | 18.20 | C |
| ATOM | 92 | O | MET | A | 12 | 33.061 | 34.906 | 50.191 | 1.00 | 18.59 | O |
| ATOM | 93 | N | GLY | A | 13 | 31.267 | 35.713 | 49.107 | 1.00 | 18.70 | N |
| ATOM | 94 | CA | GLY | A | 13 | 31.450 | 37.037 | 49.678 | 1.00 | 16.92 | C |
| ATOM | 95 | C | GLY | A | 13 | 31.820 | 38.221 | 48.796 | 1.00 | 17.54 | C |
| ATOM | 96 | O | GLY | A | 13 | 32.153 | 39.283 | 49.323 | 1.00 | 18.49 | O |
| ATOM | 97 | N | ILE | A | 14 | 31.795 | 38.087 | 47.476 | 1.00 | 16.95 | N |
| ATOM | 98 | CA | ILE | A | 14 | 32.122 | 39.253 | 46.656 | 1.00 | 18.18 | C |
| ATOM | 99 | CB | ILE | A | 14 | 32.500 | 38.879 | 45.205 | 1.00 | 18.81 | C |
| ATOM | 100 | CG2 | ILE | A | 14 | 32.695 | 40.150 | 44.381 | 1.00 | 19.56 | C |
| ATOM | 101 | CG1 | ILE | A | 14 | 33.801 | 38.085 | 45.175 | 1.00 | 18.49 | C |
| ATOM | 102 | CD1 | ILE | A | 14 | 34.271 | 37.772 | 43.764 | 1.00 | 18.33 | C |
| ATOM | 103 | C | ILE | A | 14 | 30.906 | 40.195 | 46.611 | 1.00 | 17.69 | C |
| ATOM | 104 | O | ILE | A | 14 | 29.785 | 39.769 | 46.296 | 1.00 | 17.02 | O |
| ATOM | 105 | N | ALA | A | 15 | 31.127 | 41.464 | 46.950 | 1.00 | 17.71 | N |
| ATOM | 106 | CA | ALA | A | 15 | 30.048 | 42.459 | 46.940 | 1.00 | 18.32 | C |
| ATOM | 107 | CB | ALA | A | 15 | 29.975 | 43.170 | 48.275 | 1.00 | 16.54 | C |
| ATOM | 108 | C | ALA | A | 15 | 30.264 | 43.476 | 45.822 | 1.00 | 17.54 | C |
| ATOM | 109 | O | ALA | A | 15 | 29.330 | 43.822 | 45.100 | 1.00 | 17.97 | O |
| ATOM | 110 | N | ASN | A | 16 | 31.499 | 43.951 | 45.696 | 1.00 | 17.86 | N |
| ATOM | 111 | CA | ASN | A | 16 | 31.859 | 44.919 | 44.665 | 1.00 | 16.68 | C |
| ATOM | 112 | CB | ASN | A | 16 | 31.510 | 46.337 | 45.122 | 1.00 | 17.22 | C |
| ATOM | 113 | CG | ASN | A | 16 | 32.457 | 46.862 | 46.195 | 1.00 | 18.10 | C |
| ATOM | 114 | OD1 | ASN | A | 16 | 33.392 | 46.178 | 46.606 | 1.00 | 18.90 | O |
| ATOM | 115 | ND2 | ASN | A | 16 | 32.211 | 48.088 | 46.651 | 1.00 | 17.70 | N |
| ATOM | 116 | C | ASN | A | 16 | 33.350 | 44.822 | 44.379 | 1.00 | 16.36 | C |
| ATOM | 117 | O | ASN | A | 16 | 34.053 | 44.020 | 44.985 | 1.00 | 16.96 | O |
| ATOM | 118 | N | LYS | A | 17 | 33.831 | 45.654 | 43.463 | 1.00 | 16.21 | N |
| ATOM | 119 | CA | LYS | A | 17 | 35.237 | 45.671 | 43.086 | 1.00 | 14.78 | C |
| ATOM | 120 | CB | LYS | A | 17 | 35.475 | 46.757 | 42.028 | 1.00 | 16.16 | C |
| ATOM | 121 | CG | LYS | A | 17 | 35.216 | 48.169 | 42.533 | 1.00 | 18.54 | C |
| ATOM | 122 | CD | LYS | A | 17 | 35.241 | 49.184 | 41.404 | 1.00 | 20.78 | C |
| ATOM | 123 | CE | LYS | A | 17 | 34.948 | 50.583 | 41.927 | 1.00 | 21.31 | C |
| ATOM | 124 | NZ | LYS | A | 17 | 35.004 | 51.594 | 40.845 | 1.00 | 21.08 | N |
| ATOM | 125 | C | LYS | A | 17 | 36.226 | 45.874 | 44.236 | 1.00 | 15.93 | C |
| ATOM | 126 | O | LYS | A | 17 | 37.416 | 45.583 | 44.081 | 1.00 | 17.59 | O |
| ATOM | 127 | N | ARG | A | 18 | 35.773 | 46.389 | 45.375 | 1.00 | 14.90 | N |
| ATOM | 128 | CA | ARG | A | 18 | 36.697 | 46.596 | 46.488 | 1.00 | 14.82 | C |

FIGURE 9 (cont.)

```
ATOM    129  CB   ARG A  18      36.346  47.879  47.258  1.00 16.98           C
ATOM    130  CG   ARG A  18      36.593  49.176  46.490  1.00 16.91           C
ATOM    131  CD   ARG A  18      37.987  49.190  45.872  1.00 18.49           C
ATOM    132  NE   ARG A  18      38.232  50.407  45.105  1.00 21.10           N
ATOM    133  CZ   ARG A  18      38.458  51.605  45.639  1.00 21.29           C
ATOM    134  NH1  ARG A  18      38.485  51.755  46.958  1.00 20.51           N
ATOM    135  NH2  ARG A  18      38.627  52.658  44.845  1.00 21.75           N
ATOM    136  C    ARG A  18      36.758  45.416  47.462  1.00 14.18           C
ATOM    137  O    ARG A  18      37.574  45.409  48.377  1.00 14.63           O
ATOM    138  N    SER A  19      35.903  44.417  47.264  1.00 13.74           N
ATOM    139  CA   SER A  19      35.884  43.250  48.145  1.00 14.74           C
ATOM    140  CB   SER A  19      34.773  42.275  47.705  1.00 14.16           C
ATOM    141  OG   SER A  19      33.480  42.761  48.054  1.00 15.11           O
ATOM    142  C    SER A  19      37.226  42.499  48.223  1.00 14.90           C
ATOM    143  O    SER A  19      37.980  42.453  47.253  1.00 14.23           O
ATOM    144  N    ILE A  20      37.522  41.918  49.382  1.00 14.83           N
ATOM    145  CA   ILE A  20      38.759  41.157  49.544  1.00 16.18           C
ATOM    146  CB   ILE A  20      38.986  40.735  51.024  1.00 15.06           C
ATOM    147  CG2  ILE A  20      40.192  39.803  51.119  1.00 15.01           C
ATOM    148  CG1  ILE A  20      39.205  41.975  51.906  1.00 14.31           C
ATOM    149  CD1  ILE A  20      39.452  41.677  53.397  1.00  8.47           C
ATOM    150  C    ILE A  20      38.612  39.907  48.679  1.00 17.09           C
ATOM    151  O    ILE A  20      39.563  39.448  48.047  1.00 18.91           O
ATOM    152  N    ALA A  21      37.396  39.371  48.642  1.00 18.99           N
ATOM    153  CA   ALA A  21      37.103  38.180  47.851  1.00 18.30           C
ATOM    154  CB   ALA A  21      35.638  37.772  48.037  1.00 16.94           C
ATOM    155  C    ALA A  21      37.418  38.426  46.370  1.00 18.72           C
ATOM    156  O    ALA A  21      37.954  37.540  45.688  1.00 19.89           O
ATOM    157  N    PHE A  22      37.110  39.619  45.868  1.00 16.73           N
ATOM    158  CA   PHE A  22      37.414  39.917  44.471  1.00 17.16           C
ATOM    159  CB   PHE A  22      36.859  41.292  44.072  1.00 16.55           C
ATOM    160  CG   PHE A  22      36.941  41.576  42.594  1.00 16.05           C
ATOM    161  CD1  PHE A  22      37.238  42.856  42.130  1.00 17.61           C
ATOM    162  CD2  PHE A  22      36.737  40.564  41.664  1.00 17.34           C
ATOM    163  CE1  PHE A  22      37.334  43.117  40.757  1.00 16.52           C
ATOM    164  CE2  PHE A  22      36.830  40.816  40.288  1.00 15.99           C
ATOM    165  CZ   PHE A  22      37.129  42.093  39.839  1.00 17.94           C
ATOM    166  C    PHE A  22      38.941  39.859  44.261  1.00 16.10           C
ATOM    167  O    PHE A  22      39.424  39.328  43.259  1.00 15.71           O
ATOM    168  N    GLY A  23      39.699  40.399  45.211  1.00 16.09           N
ATOM    169  CA   GLY A  23      41.150  40.339  45.109  1.00 15.94           C
ATOM    170  C    GLY A  23      41.592  38.875  45.034  1.00 16.95           C
ATOM    171  O    GLY A  23      42.513  38.523  44.293  1.00 16.00           O
ATOM    172  N    VAL A  24      40.927  38.010  45.797  1.00 15.72           N
ATOM    173  CA   VAL A  24      41.252  36.585  45.775  1.00 15.46           C
ATOM    174  CB   VAL A  24      40.495  35.831  46.897  1.00 14.01           C
ATOM    175  CG1  VAL A  24      40.777  34.341  46.818  1.00 11.82           C
ATOM    176  CG2  VAL A  24      40.910  36.377  48.251  1.00 11.43           C
ATOM    177  C    VAL A  24      40.864  36.007  44.406  1.00 16.19           C
ATOM    178  O    VAL A  24      41.586  35.184  43.838  1.00 15.36           O
ATOM    179  N    ALA A  25      39.728  36.456  43.872  1.00 17.57           N
ATOM    180  CA   ALA A  25      39.254  35.986  42.571  1.00 18.17           C
ATOM    181  CB   ALA A  25      37.910  36.599  42.248  1.00 17.98           C
ATOM    182  C    ALA A  25      40.242  36.333  41.468  1.00 19.52           C
ATOM    183  O    ALA A  25      40.571  35.495  40.616  1.00 20.39           O
ATOM    184  N    LYS A  26      40.708  37.574  41.483  1.00 18.86           N
ATOM    185  CA   LYS A  26      41.649  38.035  40.473  1.00 19.61           C
ATOM    186  CB   LYS A  26      41.979  39.512  40.703  1.00 19.16           C
ATOM    187  CG   LYS A  26      40.894  40.441  40.177  1.00 20.55           C
ATOM    188  CD   LYS A  26      41.243  41.918  40.377  1.00 20.79           C
ATOM    189  CE   LYS A  26      41.032  42.367  41.823  1.00 20.74           C
ATOM    190  NZ   LYS A  26      41.363  43.815  41.992  1.00 21.94           N
ATOM    191  C    LYS A  26      42.925  37.203  40.435  1.00 19.56           C
ATOM    192  O    LYS A  26      43.453  36.919  39.352  1.00 20.45           O
ATOM    193  N    VAL A  27      43.408  36.815  41.614  1.00 18.14           N
```

FIGURE 9 (cont.)

```
ATOM    194  CA   VAL A   27      44.622  36.018  41.746  1.00 17.60           C
ATOM    195  CB   VAL A   27      45.131  36.016  43.220  1.00 17.26           C
ATOM    196  CG1  VAL A   27      46.275  35.025  43.383  1.00 13.73           C
ATOM    197  CG2  VAL A   27      45.592  37.421  43.614  1.00 14.15           C
ATOM    198  C    VAL A   27      44.426  34.572  41.282  1.00 18.17           C
ATOM    199  O    VAL A   27      45.230  34.058  40.508  1.00 18.67           O
ATOM    200  N    LEU A   28      43.370  33.913  41.755  1.00 18.62           N
ATOM    201  CA   LEU A   28      43.108  32.536  41.360  1.00 18.91           C
ATOM    202  CB   LEU A   28      41.910  31.972  42.123  1.00 18.40           C
ATOM    203  CG   LEU A   28      42.045  31.926  43.647  1.00 18.75           C
ATOM    204  CD1  LEU A   28      40.746  31.426  44.265  1.00 16.55           C
ATOM    205  CD2  LEU A   28      43.215  31.010  44.038  1.00 21.33           C
ATOM    206  C    LEU A   28      42.834  32.490  39.863  1.00 20.62           C
ATOM    207  O    LEU A   28      43.283  31.571  39.165  1.00 19.39           O
ATOM    208  N    ASP A   29      42.113  33.494  39.366  1.00 21.66           N
ATOM    209  CA   ASP A   29      41.786  33.547  37.947  1.00 22.98           C
ATOM    210  CB   ASP A   29      40.891  34.755  37.629  1.00 24.03           C
ATOM    211  CG   ASP A   29      40.635  34.917  36.125  1.00 25.12           C
ATOM    212  OD1  ASP A   29      39.858  34.124  35.543  1.00 24.19           O
ATOM    213  OD2  ASP A   29      41.228  35.835  35.516  1.00 25.27           O
ATOM    214  C    ASP A   29      43.052  33.627  37.109  1.00 23.63           C
ATOM    215  O    ASP A   29      43.136  33.015  36.044  1.00 24.67           O
ATOM    216  N    GLN A   30      44.039  34.373  37.591  1.00 23.14           N
ATOM    217  CA   GLN A   30      45.288  34.523  36.860  1.00 22.56           C
ATOM    218  CB   GLN A   30      46.105  35.678  37.457  1.00 24.50           C
ATOM    219  CG   GLN A   30      47.432  35.944  36.769  1.00 26.94           C
ATOM    220  CD   GLN A   30      47.463  37.274  36.035  1.00 30.86           C
ATOM    221  OE1  GLN A   30      46.699  37.500  35.092  1.00 31.52           O
ATOM    222  NE2  GLN A   30      48.355  38.171  36.469  1.00 32.77           N
ATOM    223  C    GLN A   30      46.120  33.240  36.857  1.00 23.19           C
ATOM    224  O    GLN A   30      46.956  33.046  35.967  1.00 24.05           O
ATOM    225  N    LEU A   31      45.911  32.370  37.845  1.00 21.78           N
ATOM    226  CA   LEU A   31      46.659  31.118  37.905  1.00 20.52           C
ATOM    227  CB   LEU A   31      46.863  30.651  39.350  1.00 20.04           C
ATOM    228  CG   LEU A   31      47.862  31.327  40.306  1.00 20.17           C
ATOM    229  CD1  LEU A   31      48.867  32.177  39.533  1.00 19.27           C
ATOM    230  CD2  LEU A   31      47.102  32.171  41.323  1.00 20.19           C
ATOM    231  C    LEU A   31      45.991  29.995  37.112  1.00 20.44           C
ATOM    232  O    LEU A   31      46.475  28.871  37.111  1.00 21.27           O
ATOM    233  N    GLY A   32      44.880  30.297  36.447  1.00 20.66           N
ATOM    234  CA   GLY A   32      44.200  29.290  35.640  1.00 19.69           C
ATOM    235  C    GLY A   32      43.050  28.510  36.254  1.00 19.63           C
ATOM    236  O    GLY A   32      42.504  27.618  35.613  1.00 19.77           O
ATOM    237  N    ALA A   33      42.661  28.842  37.479  1.00 20.06           N
ATOM    238  CA   ALA A   33      41.585  28.123  38.151  1.00 20.75           C
ATOM    239  CB   ALA A   33      41.616  28.438  39.646  1.00 21.13           C
ATOM    240  C    ALA A   33      40.195  28.412  37.604  1.00 20.79           C
ATOM    241  O    ALA A   33      39.937  29.491  37.076  1.00 20.68           O
ATOM    242  N    LYS A   34      39.302  27.434  37.712  1.00 20.72           N
ATOM    243  CA   LYS A   34      37.931  27.653  37.278  1.00 21.22           C
ATOM    244  CB   LYS A   34      37.247  26.351  36.836  1.00 23.95           C
ATOM    245  CG   LYS A   34      35.767  26.551  36.464  1.00 26.83           C
ATOM    246  CD   LYS A   34      35.183  25.405  35.630  1.00 29.80           C
ATOM    247  CE   LYS A   34      34.898  24.179  36.478  1.00 31.91           C
ATOM    248  NZ   LYS A   34      34.019  23.187  35.771  1.00 35.05           N
ATOM    249  C    LYS A   34      37.308  28.172  38.562  1.00 19.48           C
ATOM    250  O    LYS A   34      37.608  27.661  39.639  1.00 18.60           O
ATOM    251  N    LEU A   35      36.457  29.182  38.450  1.00 18.20           N
ATOM    252  CA   LEU A   35      35.846  29.792  39.623  1.00 17.75           C
ATOM    253  CB   LEU A   35      36.319  31.243  39.753  1.00 18.80           C
ATOM    254  CG   LEU A   35      37.825  31.519  39.886  1.00 18.11           C
ATOM    255  CD1  LEU A   35      38.062  32.998  39.802  1.00 19.70           C
ATOM    256  CD2  LEU A   35      38.355  30.974  41.199  1.00 18.63           C
ATOM    257  C    LEU A   35      34.334  29.779  39.630  1.00 18.52           C
ATOM    258  O    LEU A   35      33.689  29.847  38.579  1.00 18.65           O
```

FIGURE 9 (cont.)

| | | | | | | | | | | |
|---|---|---|---|---|---|---|---|---|---|---|
| ATOM | 259 | N | VAL | A | 36 | 33.785 | 29.689 | 40.838 | 1.00 19.55 | N |
| ATOM | 260 | CA | VAL | A | 36 | 32.344 | 29.698 | 41.077 | 1.00 20.07 | C |
| ATOM | 261 | CB | VAL | A | 36 | 31.863 | 28.362 | 41.657 | 1.00 20.49 | C |
| ATOM | 262 | CG1 | VAL | A | 36 | 30.406 | 28.472 | 42.053 | 1.00 22.28 | C |
| ATOM | 263 | CG2 | VAL | A | 36 | 32.054 | 27.253 | 40.636 | 1.00 21.45 | C |
| ATOM | 264 | C | VAL | A | 36 | 32.100 | 30.793 | 42.115 | 1.00 20.21 | C |
| ATOM | 265 | O | VAL | A | 36 | 32.953 | 31.011 | 42.983 | 1.00 21.00 | O |
| ATOM | 266 | N | PHE | A | 37 | 30.953 | 31.469 | 42.048 | 1.00 19.29 | N |
| ATOM | 267 | CA | PHE | A | 37 | 30.664 | 32.542 | 42.999 | 1.00 18.34 | C |
| ATOM | 268 | CB | PHE | A | 37 | 30.774 | 33.910 | 42.319 | 1.00 19.50 | C |
| ATOM | 269 | CG | PHE | A | 37 | 32.073 | 34.141 | 41.609 | 1.00 21.23 | C |
| ATOM | 270 | CD1 | PHE | A | 37 | 32.284 | 33.626 | 40.327 | 1.00 21.74 | C |
| ATOM | 271 | CD2 | PHE | A | 37 | 33.083 | 34.900 | 42.207 | 1.00 21.55 | C |
| ATOM | 272 | CE1 | PHE | A | 37 | 33.482 | 33.869 | 39.651 | 1.00 21.58 | C |
| ATOM | 273 | CE2 | PHE | A | 37 | 34.282 | 35.148 | 41.539 | 1.00 21.58 | C |
| ATOM | 274 | CZ | PHE | A | 37 | 34.485 | 34.636 | 40.263 | 1.00 21.77 | C |
| ATOM | 275 | C | PHE | A | 37 | 29.303 | 32.486 | 43.686 | 1.00 17.51 | C |
| ATOM | 276 | O | PHE | A | 37 | 28.326 | 32.008 | 43.125 | 1.00 17.46 | O |
| ATOM | 277 | N | THR | A | 38 | 29.249 | 33.004 | 44.907 | 1.00 16.83 | N |
| ATOM | 278 | CA | THR | A | 38 | 27.996 | 33.059 | 45.638 | 1.00 18.34 | C |
| ATOM | 279 | CB | THR | A | 38 | 27.972 | 32.072 | 46.831 | 1.00 17.30 | C |
| ATOM | 280 | OG1 | THR | A | 38 | 28.918 | 32.487 | 47.817 | 1.00 16.85 | O |
| ATOM | 281 | CG2 | THR | A | 38 | 28.327 | 30.660 | 46.373 | 1.00 17.67 | C |
| ATOM | 282 | C | THR | A | 38 | 27.801 | 34.487 | 46.150 | 1.00 18.75 | C |
| ATOM | 283 | O | THR | A | 38 | 28.756 | 35.149 | 46.558 | 1.00 18.95 | O |
| ATOM | 284 | N | TYR | A | 39 | 26.561 | 34.961 | 46.105 | 1.00 20.43 | N |
| ATOM | 285 | CA | TYR | A | 39 | 26.216 | 36.307 | 46.565 | 1.00 22.30 | C |
| ATOM | 286 | CB | TYR | A | 39 | 25.945 | 37.224 | 45.367 | 1.00 21.57 | C |
| ATOM | 287 | CG | TYR | A | 39 | 24.948 | 36.643 | 44.390 | 1.00 22.63 | C |
| ATOM | 288 | CD1 | TYR | A | 39 | 23.581 | 36.901 | 44.517 | 1.00 23.34 | C |
| ATOM | 289 | CE1 | TYR | A | 39 | 22.658 | 36.323 | 43.651 | 1.00 23.84 | C |
| ATOM | 290 | CD2 | TYR | A | 39 | 25.370 | 35.790 | 43.364 | 1.00 22.73 | C |
| ATOM | 291 | CE2 | TYR | A | 39 | 24.466 | 35.211 | 42.498 | 1.00 24.51 | C |
| ATOM | 292 | CZ | TYR | A | 39 | 23.109 | 35.479 | 42.643 | 1.00 25.29 | C |
| ATOM | 293 | OH | TYR | A | 39 | 22.211 | 34.909 | 41.769 | 1.00 26.85 | O |
| ATOM | 294 | C | TYR | A | 39 | 24.981 | 36.204 | 47.458 | 1.00 23.46 | C |
| ATOM | 295 | O | TYR | A | 39 | 24.263 | 35.212 | 47.417 | 1.00 23.89 | O |
| ATOM | 296 | N | ARG | A | 40 | 24.723 | 37.237 | 48.248 | 1.00 26.76 | N |
| ATOM | 297 | CA | ARG | A | 40 | 23.608 | 37.226 | 49.188 | 1.00 29.10 | C |
| ATOM | 298 | CB | ARG | A | 40 | 23.858 | 38.255 | 50.295 | 1.00 29.34 | C |
| ATOM | 299 | CG | ARG | A | 40 | 23.052 | 38.024 | 51.562 | 1.00 31.24 | C |
| ATOM | 300 | CD | ARG | A | 40 | 23.273 | 39.150 | 52.573 | 1.00 34.07 | C |
| ATOM | 301 | NE | ARG | A | 40 | 22.581 | 40.377 | 52.183 | 1.00 38.16 | N |
| ATOM | 302 | CZ | ARG | A | 40 | 22.698 | 41.545 | 52.810 | 1.00 40.33 | C |
| ATOM | 303 | NH1 | ARG | A | 40 | 23.497 | 41.667 | 53.875 | 1.00 41.30 | N |
| ATOM | 304 | NH2 | ARG | A | 40 | 21.998 | 42.592 | 52.380 | 1.00 41.29 | N |
| ATOM | 305 | C | ARG | A | 40 | 22.200 | 37.431 | 48.644 | 1.00 30.55 | C |
| ATOM | 306 | O | ARG | A | 40 | 21.326 | 36.582 | 48.853 | 1.00 30.64 | O |
| ATOM | 307 | N | LYS | A | 41 | 21.954 | 38.549 | 47.967 | 1.00 32.87 | N |
| ATOM | 308 | CA | LYS | A | 41 | 20.601 | 38.806 | 47.468 | 1.00 34.35 | C |
| ATOM | 309 | CB | LYS | A | 41 | 20.069 | 40.121 | 48.043 | 1.00 34.22 | C |
| ATOM | 310 | CG | LYS | A | 41 | 20.497 | 40.400 | 49.478 | 1.00 35.25 | C |
| ATOM | 311 | CD | LYS | A | 41 | 21.885 | 41.078 | 49.545 | 1.00 35.54 | C |
| ATOM | 312 | CE | LYS | A | 41 | 21.849 | 42.544 | 49.081 | 1.00 35.99 | C |
| ATOM | 313 | NZ | LYS | A | 41 | 23.153 | 43.270 | 49.277 | 1.00 35.13 | N |
| ATOM | 314 | C | LYS | A | 41 | 20.441 | 38.833 | 45.953 | 1.00 34.78 | C |
| ATOM | 315 | O | LYS | A | 41 | 21.358 | 39.223 | 45.228 | 1.00 34.06 | O |
| ATOM | 316 | N | GLU | A | 42 | 19.255 | 38.422 | 45.499 | 1.00 36.37 | N |
| ATOM | 317 | CA | GLU | A | 42 | 18.902 | 38.386 | 44.079 | 1.00 38.17 | C |
| ATOM | 318 | CB | GLU | A | 42 | 17.407 | 38.082 | 43.921 | 1.00 40.28 | C |
| ATOM | 319 | CG | GLU | A | 42 | 16.942 | 36.843 | 44.696 | 1.00 44.23 | C |
| ATOM | 320 | CD | GLU | A | 42 | 15.457 | 36.498 | 44.478 | 1.00 45.48 | C |
| ATOM | 321 | OE1 | GLU | A | 42 | 14.586 | 37.295 | 44.911 | 1.00 45.56 | O |
| ATOM | 322 | OE2 | GLU | A | 42 | 15.171 | 35.423 | 43.877 | 1.00 45.41 | O |
| ATOM | 323 | C | GLU | A | 42 | 19.228 | 39.721 | 43.406 | 1.00 38.74 | C |

FIGURE 9 (cont.)

| ATOM | 324 | O | GLU A | 42 | 19.938 | 39.764 | 42.398 | 1.00 | 38.52 | O |
|---|---|---|---|---|---|---|---|---|---|---|
| ATOM | 325 | N | ARG A | 43 | 18.705 | 40.820 | 43.942 | 1.00 | 39.08 | N |
| ATOM | 326 | CA | ARG A | 43 | 19.026 | 42.096 | 43.331 | 1.00 | 40.23 | C |
| ATOM | 327 | CB | ARG A | 43 | 18.061 | 43.209 | 43.764 | 1.00 | 42.84 | C |
| ATOM | 328 | CG | ARG A | 43 | 17.286 | 42.967 | 45.054 | 1.00 | 46.21 | C |
| ATOM | 329 | CD | ARG A | 43 | 16.228 | 44.072 | 45.217 | 1.00 | 49.19 | C |
| ATOM | 330 | NE | ARG A | 43 | 16.830 | 45.382 | 45.488 | 1.00 | 52.00 | N |
| ATOM | 331 | CZ | ARG A | 43 | 16.176 | 46.546 | 45.414 | 1.00 | 53.16 | C |
| ATOM | 332 | NH1 | ARG A | 43 | 14.890 | 46.576 | 45.065 | 1.00 | 52.52 | N |
| ATOM | 333 | NH2 | ARG A | 43 | 16.804 | 47.684 | 45.710 | 1.00 | 52.84 | N |
| ATOM | 334 | C | ARG A | 43 | 20.442 | 42.427 | 43.726 | 1.00 | 39.36 | C |
| ATOM | 335 | O | ARG A | 43 | 20.686 | 43.298 | 44.566 | 1.00 | 40.30 | O |
| ATOM | 336 | N | SER A | 44 | 21.377 | 41.701 | 43.121 | 1.00 | 37.63 | N |
| ATOM | 337 | CA | SER A | 44 | 22.793 | 41.895 | 43.376 | 1.00 | 35.44 | C |
| ATOM | 338 | CB | SER A | 44 | 23.130 | 41.410 | 44.791 | 1.00 | 35.05 | C |
| ATOM | 339 | OG | SER A | 44 | 24.444 | 41.808 | 45.166 | 1.00 | 36.23 | O |
| ATOM | 340 | C | SER A | 44 | 23.567 | 41.103 | 42.320 | 1.00 | 33.88 | C |
| ATOM | 341 | O | SER A | 44 | 24.752 | 41.318 | 42.102 | 1.00 | 33.77 | O |
| ATOM | 342 | N | ARG A | 45 | 22.865 | 40.205 | 41.641 | 1.00 | 33.14 | N |
| ATOM | 343 | CA | ARG A | 45 | 23.454 | 39.356 | 40.606 | 1.00 | 32.11 | C |
| ATOM | 344 | CB | ARG A | 45 | 22.425 | 38.304 | 40.185 | 1.00 | 29.77 | C |
| ATOM | 345 | CG | ARG A | 45 | 22.979 | 37.217 | 39.282 | 1.00 | 31.00 | C |
| ATOM | 346 | CD | ARG A | 45 | 21.886 | 36.275 | 38.792 | 1.00 | 30.27 | C |
| ATOM | 347 | NE | ARG A | 45 | 22.414 | 35.275 | 37.863 | 1.00 | 31.76 | N |
| ATOM | 348 | CZ | ARG A | 45 | 23.069 | 34.178 | 38.229 | 1.00 | 31.12 | C |
| ATOM | 349 | NH1 | ARG A | 45 | 23.277 | 33.922 | 39.517 | 1.00 | 32.74 | N |
| ATOM | 350 | NH2 | ARG A | 45 | 23.528 | 33.341 | 37.310 | 1.00 | 31.48 | N |
| ATOM | 351 | C | ARG A | 45 | 23.946 | 40.108 | 39.364 | 1.00 | 32.59 | C |
| ATOM | 352 | O | ARG A | 45 | 25.015 | 39.815 | 38.819 | 1.00 | 32.63 | O |
| ATOM | 353 | N | LYS A | 46 | 23.160 | 41.071 | 38.902 | 1.00 | 33.66 | N |
| ATOM | 354 | CA | LYS A | 46 | 23.523 | 41.832 | 37.713 | 1.00 | 33.36 | C |
| ATOM | 355 | CB | LYS A | 46 | 22.460 | 42.888 | 37.409 | 1.00 | 34.33 | C |
| ATOM | 356 | CG | LYS A | 46 | 21.802 | 42.716 | 36.047 | 1.00 | 35.43 | C |
| ATOM | 357 | CD | LYS A | 46 | 20.850 | 43.866 | 35.721 | 1.00 | 35.55 | C |
| ATOM | 358 | CE | LYS A | 46 | 21.613 | 45.125 | 35.308 | 1.00 | 36.53 | C |
| ATOM | 359 | NZ | LYS A | 46 | 22.348 | 44.939 | 34.023 | 1.00 | 36.03 | N |
| ATOM | 360 | C | LYS A | 46 | 24.871 | 42.508 | 37.842 | 1.00 | 33.38 | C |
| ATOM | 361 | O | LYS A | 46 | 25.706 | 42.404 | 36.939 | 1.00 | 32.83 | O |
| ATOM | 362 | N | GLU A | 47 | 25.087 | 43.205 | 38.958 | 1.00 | 33.62 | N |
| ATOM | 363 | CA | GLU A | 47 | 26.355 | 43.905 | 39.177 | 1.00 | 33.38 | C |
| ATOM | 364 | CB | GLU A | 47 | 26.274 | 44.804 | 40.418 | 1.00 | 35.36 | C |
| ATOM | 365 | CG | GLU A | 47 | 25.855 | 44.091 | 41.705 | 1.00 | 39.47 | C |
| ATOM | 366 | CD | GLU A | 47 | 26.985 | 43.301 | 42.399 | 1.00 | 40.61 | C |
| ATOM | 367 | OE1 | GLU A | 47 | 26.647 | 42.329 | 43.115 | 1.00 | 40.51 | O |
| ATOM | 368 | OE2 | GLU A | 47 | 28.192 | 43.651 | 42.252 | 1.00 | 41.04 | O |
| ATOM | 369 | C | GLU A | 47 | 27.524 | 42.949 | 39.320 | 1.00 | 31.92 | C |
| ATOM | 370 | O | GLU A | 47 | 28.603 | 43.195 | 38.776 | 1.00 | 30.99 | O |
| ATOM | 371 | N | LEU A | 48 | 27.321 | 41.859 | 40.053 | 1.00 | 31.76 | N |
| ATOM | 372 | CA | LEU A | 48 | 28.394 | 40.881 | 40.242 | 1.00 | 31.36 | C |
| ATOM | 373 | CB | LEU A | 48 | 27.975 | 39.798 | 41.240 | 1.00 | 31.49 | C |
| ATOM | 374 | CG | LEU A | 48 | 29.077 | 38.812 | 41.636 | 1.00 | 30.30 | C |
| ATOM | 375 | CD1 | LEU A | 48 | 30.062 | 39.493 | 42.561 | 1.00 | 30.75 | C |
| ATOM | 376 | CD2 | LEU A | 48 | 28.475 | 37.634 | 42.347 | 1.00 | 31.45 | C |
| ATOM | 377 | C | LEU A | 48 | 28.693 | 40.240 | 38.902 | 1.00 | 31.19 | C |
| ATOM | 378 | O | LEU A | 48 | 29.829 | 39.853 | 38.615 | 1.00 | 31.45 | O |
| ATOM | 379 | N | GLU A | 49 | 27.676 | 40.134 | 38.059 | 1.00 | 31.60 | N |
| ATOM | 380 | CA | GLU A | 49 | 27.899 | 39.513 | 36.764 | 1.00 | 33.91 | C |
| ATOM | 381 | CB | GLU A | 49 | 26.570 | 39.140 | 36.122 | 1.00 | 34.30 | C |
| ATOM | 382 | CG | GLU A | 49 | 26.724 | 38.112 | 35.019 | 1.00 | 36.47 | C |
| ATOM | 383 | CD | GLU A | 49 | 25.409 | 37.797 | 34.335 | 1.00 | 37.72 | C |
| ATOM | 384 | OE1 | GLU A | 49 | 24.423 | 37.477 | 35.048 | 1.00 | 36.67 | O |
| ATOM | 385 | OE2 | GLU A | 49 | 25.369 | 37.868 | 33.081 | 1.00 | 37.80 | O |
| ATOM | 386 | C | GLU A | 49 | 28.712 | 40.421 | 35.835 | 1.00 | 34.42 | C |
| ATOM | 387 | O | GLU A | 49 | 29.510 | 39.940 | 35.041 | 1.00 | 35.31 | O |
| ATOM | 388 | N | LYS A | 50 | 28.521 | 41.731 | 35.935 | 1.00 | 35.25 | N |

FIGURE 9 (cont.)

| ATOM | 389 | CA | LYS | A | 50 | 29.273 | 42.658 | 35.094 | 1.00 | 36.00 | C |
| ATOM | 390 | CB | LYS | A | 50 | 28.651 | 44.057 | 35.137 | 1.00 | 37.43 | C |
| ATOM | 391 | CG | LYS | A | 50 | 27.239 | 44.118 | 34.563 | 1.00 | 39.91 | C |
| ATOM | 392 | CD | LYS | A | 50 | 26.682 | 45.539 | 34.624 | 1.00 | 41.82 | C |
| ATOM | 393 | CE | LYS | A | 50 | 25.202 | 45.569 | 34.231 | 1.00 | 42.77 | C |
| ATOM | 394 | NZ | LYS | A | 50 | 24.968 | 44.904 | 32.902 | 1.00 | 42.33 | N |
| ATOM | 395 | C | LYS | A | 50 | 30.715 | 42.742 | 35.553 | 1.00 | 34.91 | C |
| ATOM | 396 | O | LYS | A | 50 | 31.638 | 42.849 | 34.744 | 1.00 | 34.38 | O |
| ATOM | 397 | N | LEU | A | 51 | 30.896 | 42.693 | 36.866 | 1.00 | 34.91 | N |
| ATOM | 398 | CA | LEU | A | 51 | 32.209 | 42.774 | 37.497 | 1.00 | 34.37 | C |
| ATOM | 399 | CB | LEU | A | 51 | 32.022 | 42.843 | 39.020 | 1.00 | 33.67 | C |
| ATOM | 400 | CG | LEU | A | 51 | 33.278 | 42.850 | 39.902 | 1.00 | 33.09 | C |
| ATOM | 401 | CD1 | LEU | A | 51 | 34.120 | 44.118 | 39.621 | 1.00 | 30.38 | C |
| ATOM | 402 | CD2 | LEU | A | 51 | 32.854 | 42.791 | 41.367 | 1.00 | 31.22 | C |
| ATOM | 403 | C | LEU | A | 51 | 33.124 | 41.602 | 37.161 | 1.00 | 34.97 | C |
| ATOM | 404 | O | LEU | A | 51 | 34.349 | 41.756 | 37.076 | 1.00 | 34.81 | O |
| ATOM | 405 | N | LEU | A | 52 | 32.529 | 40.426 | 36.988 | 1.00 | 35.74 | N |
| ATOM | 406 | CA | LEU | A | 52 | 33.289 | 39.212 | 36.708 | 1.00 | 35.78 | C |
| ATOM | 407 | CB | LEU | A | 52 | 32.455 | 37.983 | 37.118 | 1.00 | 36.27 | C |
| ATOM | 408 | CG | LEU | A | 52 | 32.063 | 38.076 | 38.604 | 1.00 | 36.81 | C |
| ATOM | 409 | CD1 | LEU | A | 52 | 31.384 | 36.793 | 39.065 | 1.00 | 36.34 | C |
| ATOM | 410 | CD2 | LEU | A | 52 | 33.319 | 38.334 | 39.443 | 1.00 | 36.31 | C |
| ATOM | 411 | C | LEU | A | 52 | 33.779 | 39.085 | 35.275 | 1.00 | 35.34 | C |
| ATOM | 412 | O | LEU | A | 52 | 34.767 | 38.402 | 35.015 | 1.00 | 35.04 | O |
| ATOM | 413 | N | GLU | A | 53 | 33.103 | 39.747 | 34.344 | 1.00 | 36.01 | N |
| ATOM | 414 | CA | GLU | A | 53 | 33.524 | 39.716 | 32.941 | 1.00 | 36.11 | C |
| ATOM | 415 | CB | GLU | A | 53 | 32.637 | 40.634 | 32.100 | 1.00 | 37.23 | C |
| ATOM | 416 | CG | GLU | A | 53 | 31.162 | 40.346 | 32.241 | 1.00 | 39.90 | C |
| ATOM | 417 | CD | GLU | A | 53 | 30.315 | 41.523 | 31.803 | 1.00 | 41.93 | C |
| ATOM | 418 | OE1 | GLU | A | 53 | 29.063 | 41.371 | 31.747 | 1.00 | 41.67 | O |
| ATOM | 419 | OE2 | GLU | A | 53 | 30.913 | 42.599 | 31.526 | 1.00 | 42.70 | O |
| ATOM | 420 | C | GLU | A | 53 | 34.950 | 40.242 | 32.897 | 1.00 | 34.94 | C |
| ATOM | 421 | O | GLU | A | 53 | 35.707 | 39.992 | 31.956 | 1.00 | 35.74 | O |
| ATOM | 422 | N | GLN | A | 54 | 35.304 | 40.988 | 33.927 | 1.00 | 33.32 | N |
| ATOM | 423 | CA | GLN | A | 54 | 36.635 | 41.561 | 34.034 | 1.00 | 33.17 | C |
| ATOM | 424 | CB | GLN | A | 54 | 36.663 | 42.498 | 35.236 | 1.00 | 32.88 | C |
| ATOM | 425 | CG | GLN | A | 54 | 37.964 | 43.215 | 35.483 | 1.00 | 33.39 | C |
| ATOM | 426 | CD | GLN | A | 54 | 37.757 | 44.368 | 36.442 | 1.00 | 35.20 | C |
| ATOM | 427 | OE1 | GLN | A | 54 | 38.649 | 44.727 | 37.214 | 1.00 | 35.92 | O |
| ATOM | 428 | NE2 | GLN | A | 54 | 36.562 | 44.961 | 36.396 | 1.00 | 34.78 | N |
| ATOM | 429 | C | GLN | A | 54 | 37.710 | 40.485 | 34.165 | 1.00 | 32.32 | C |
| ATOM | 430 | O | GLN | A | 54 | 38.893 | 40.753 | 33.941 | 1.00 | 31.27 | O |
| ATOM | 431 | N | LEU | A | 55 | 37.289 | 39.269 | 34.518 | 1.00 | 31.89 | N |
| ATOM | 432 | CA | LEU | A | 55 | 38.199 | 38.136 | 34.683 | 1.00 | 31.93 | C |
| ATOM | 433 | CB | LEU | A | 55 | 37.677 | 37.211 | 35.795 | 1.00 | 31.77 | C |
| ATOM | 434 | CG | LEU | A | 55 | 37.579 | 37.757 | 37.232 | 1.00 | 32.25 | C |
| ATOM | 435 | CD1 | LEU | A | 55 | 36.727 | 39.014 | 37.280 | 1.00 | 31.87 | C |
| ATOM | 436 | CD2 | LEU | A | 55 | 36.969 | 36.690 | 38.119 | 1.00 | 31.79 | C |
| ATOM | 437 | C | LEU | A | 55 | 38.364 | 37.332 | 33.379 | 1.00 | 32.32 | C |
| ATOM | 438 | O | LEU | A | 55 | 37.842 | 37.719 | 32.326 | 1.00 | 32.13 | O |
| ATOM | 439 | N | ASN | A | 56 | 39.092 | 36.217 | 33.459 | 1.00 | 33.18 | N |
| ATOM | 440 | CA | ASN | A | 56 | 39.324 | 35.331 | 32.307 | 1.00 | 34.19 | C |
| ATOM | 441 | CB | ASN | A | 56 | 40.809 | 35.002 | 32.173 | 1.00 | 35.99 | C |
| ATOM | 442 | CG | ASN | A | 56 | 41.683 | 36.232 | 32.220 | 1.00 | 38.10 | C |
| ATOM | 443 | OD1 | ASN | A | 56 | 42.908 | 36.132 | 32.331 | 1.00 | 39.12 | O |
| ATOM | 444 | ND2 | ASN | A | 56 | 41.061 | 37.407 | 32.131 | 1.00 | 39.05 | N |
| ATOM | 445 | C | ASN | A | 56 | 38.576 | 34.017 | 32.507 | 1.00 | 34.13 | C |
| ATOM | 446 | O | ASN | A | 56 | 39.171 | 32.936 | 32.407 | 1.00 | 35.08 | O |
| ATOM | 447 | N | GLN | A | 57 | 37.283 | 34.103 | 32.794 | 1.00 | 33.87 | N |
| ATOM | 448 | CA | GLN | A | 57 | 36.481 | 32.911 | 33.021 | 1.00 | 34.99 | C |
| ATOM | 449 | CB | GLN | A | 57 | 35.607 | 33.106 | 34.260 | 1.00 | 32.65 | C |
| ATOM | 450 | CG | GLN | A | 57 | 36.427 | 33.265 | 35.564 | 1.00 | 29.49 | C |
| ATOM | 451 | CD | GLN | A | 57 | 37.088 | 31.967 | 36.010 | 1.00 | 28.36 | C |
| ATOM | 452 | OE1 | GLN | A | 57 | 38.304 | 31.908 | 36.184 | 1.00 | 27.41 | O |
| ATOM | 453 | NE2 | GLN | A | 57 | 36.284 | 30.922 | 36.202 | 1.00 | 24.80 | N |

FIGURE 9 (cont.)

| ATOM | 454 | C | GLN | A | 57 | 35.622 | 32.543 | 31.819 | 1.00 | 37.23 | C |
| --- | --- | --- | --- | --- | --- | --- | --- | --- | --- | --- | --- |
| ATOM | 455 | O | GLN | A | 57 | 34.875 | 33.364 | 31.293 | 1.00 | 37.36 | O |
| ATOM | 456 | N | PRO | A | 58 | 35.735 | 31.289 | 31.359 | 1.00 | 39.41 | N |
| ATOM | 457 | CD | PRO | A | 58 | 36.668 | 30.255 | 31.844 | 1.00 | 39.98 | C |
| ATOM | 458 | CA | PRO | A | 58 | 34.968 | 30.804 | 30.210 | 1.00 | 41.11 | C |
| ATOM | 459 | CB | PRO | A | 58 | 35.414 | 29.346 | 30.085 | 1.00 | 40.78 | C |
| ATOM | 460 | CG | PRO | A | 58 | 36.828 | 29.379 | 30.623 | 1.00 | 41.13 | C |
| ATOM | 461 | C | PRO | A | 58 | 33.473 | 30.907 | 30.478 | 1.00 | 41.82 | C |
| ATOM | 462 | O | PRO | A | 58 | 32.688 | 31.277 | 29.602 | 1.00 | 42.75 | O |
| ATOM | 463 | N | GLU | A | 59 | 33.089 | 30.583 | 31.703 | 1.00 | 42.47 | N |
| ATOM | 464 | CA | GLU | A | 59 | 31.687 | 30.600 | 32.089 | 1.00 | 42.32 | C |
| ATOM | 465 | CB | GLU | A | 59 | 31.181 | 29.167 | 32.263 | 1.00 | 43.95 | C |
| ATOM | 466 | CG | GLU | A | 59 | 29.896 | 28.837 | 31.528 | 1.00 | 45.80 | C |
| ATOM | 467 | CD | GLU | A | 59 | 30.130 | 28.660 | 30.042 | 1.00 | 47.17 | C |
| ATOM | 468 | OE1 | GLU | A | 59 | 31.041 | 27.867 | 29.680 | 1.00 | 48.32 | O |
| ATOM | 469 | OE2 | GLU | A | 59 | 29.407 | 29.304 | 29.236 | 1.00 | 47.59 | O |
| ATOM | 470 | C | GLU | A | 59 | 31.524 | 31.323 | 33.405 | 1.00 | 41.77 | C |
| ATOM | 471 | O | GLU | A | 59 | 32.457 | 31.385 | 34.219 | 1.00 | 42.22 | O |
| ATOM | 472 | N | ALA | A | 60 | 30.323 | 31.850 | 33.619 | 1.00 | 40.69 | N |
| ATOM | 473 | CA | ALA | A | 60 | 29.998 | 32.556 | 34.847 | 1.00 | 38.63 | C |
| ATOM | 474 | CB | ALA | A | 60 | 29.359 | 33.905 | 34.522 | 1.00 | 38.74 | C |
| ATOM | 475 | C | ALA | A | 60 | 29.023 | 31.679 | 35.629 | 1.00 | 36.59 | C |
| ATOM | 476 | O | ALA | A | 60 | 27.874 | 31.522 | 35.224 | 1.00 | 38.11 | O |
| ATOM | 477 | N | HIS | A | 61 | 29.488 | 31.096 | 36.731 | 1.00 | 33.57 | N |
| ATOM | 478 | CA | HIS | A | 61 | 28.656 | 30.243 | 37.574 | 1.00 | 31.20 | C |
| ATOM | 479 | CB | HIS | A | 61 | 29.382 | 28.949 | 37.917 | 1.00 | 33.26 | C |
| ATOM | 480 | CG | HIS | A | 61 | 29.721 | 28.107 | 36.734 | 1.00 | 32.59 | C |
| ATOM | 481 | CD2 | HIS | A | 61 | 30.916 | 27.770 | 36.194 | 1.00 | 33.67 | C |
| ATOM | 482 | ND1 | HIS | A | 61 | 28.760 | 27.476 | 35.973 | 1.00 | 32.99 | N |
| ATOM | 483 | CE1 | HIS | A | 61 | 29.350 | 26.781 | 35.016 | 1.00 | 34.23 | C |
| ATOM | 484 | NE2 | HIS | A | 61 | 30.658 | 26.941 | 35.127 | 1.00 | 34.29 | N |
| ATOM | 485 | C | HIS | A | 61 | 28.393 | 30.977 | 38.871 | 1.00 | 30.34 | C |
| ATOM | 486 | O | HIS | A | 61 | 29.209 | 30.917 | 39.801 | 1.00 | 29.37 | O |
| ATOM | 487 | N | LEU | A | 62 | 27.261 | 31.665 | 38.950 | 1.00 | 27.96 | N |
| ATOM | 488 | CA | LEU | A | 62 | 26.938 | 32.408 | 40.150 | 1.00 | 26.00 | C |
| ATOM | 489 | CB | LEU | A | 62 | 26.599 | 33.852 | 39.803 | 1.00 | 27.46 | C |
| ATOM | 490 | CG | LEU | A | 62 | 27.451 | 34.587 | 38.764 | 1.00 | 28.19 | C |
| ATOM | 491 | CD1 | LEU | A | 62 | 27.102 | 36.073 | 38.836 | 1.00 | 29.33 | C |
| ATOM | 492 | CD2 | LEU | A | 62 | 28.935 | 34.375 | 39.021 | 1.00 | 27.87 | C |
| ATOM | 493 | C | LEU | A | 62 | 25.754 | 31.766 | 40.847 | 1.00 | 25.05 | C |
| ATOM | 494 | O | LEU | A | 62 | 24.824 | 31.270 | 40.202 | 1.00 | 25.59 | O |
| ATOM | 495 | N | TYR | A | 63 | 25.792 | 31.756 | 42.169 | 1.00 | 23.27 | N |
| ATOM | 496 | CA | TYR | A | 63 | 24.706 | 31.173 | 42.935 | 1.00 | 21.98 | C |
| ATOM | 497 | CB | TYR | A | 63 | 25.104 | 29.805 | 43.482 | 1.00 | 21.84 | C |
| ATOM | 498 | CG | TYR | A | 63 | 25.556 | 28.864 | 42.399 | 1.00 | 20.39 | C |
| ATOM | 499 | CD1 | TYR | A | 63 | 26.786 | 29.041 | 41.772 | 1.00 | 19.85 | C |
| ATOM | 500 | CE1 | TYR | A | 63 | 27.171 | 28.240 | 40.718 | 1.00 | 20.18 | C |
| ATOM | 501 | CD2 | TYR | A | 63 | 24.722 | 27.844 | 41.945 | 1.00 | 20.61 | C |
| ATOM | 502 | CE2 | TYR | A | 63 | 25.105 | 27.025 | 40.881 | 1.00 | 19.62 | C |
| ATOM | 503 | CZ | TYR | A | 63 | 26.330 | 27.236 | 40.275 | 1.00 | 20.41 | C |
| ATOM | 504 | OH | TYR | A | 63 | 26.723 | 26.451 | 39.213 | 1.00 | 21.87 | O |
| ATOM | 505 | C | TYR | A | 63 | 24.362 | 32.085 | 44.075 | 1.00 | 22.32 | C |
| ATOM | 506 | O | TYR | A | 63 | 25.245 | 32.591 | 44.772 | 1.00 | 21.71 | O |
| ATOM | 507 | N | GLN | A | 64 | 23.066 | 32.304 | 44.245 | 1.00 | 23.55 | N |
| ATOM | 508 | CA | GLN | A | 64 | 22.556 | 33.142 | 45.308 | 1.00 | 23.75 | C |
| ATOM | 509 | CB | GLN | A | 64 | 21.158 | 33.636 | 44.938 | 1.00 | 25.29 | C |
| ATOM | 510 | CG | GLN | A | 64 | 20.676 | 34.804 | 45.776 | 1.00 | 27.69 | C |
| ATOM | 511 | CD | GLN | A | 64 | 19.707 | 34.384 | 46.844 | 1.00 | 30.25 | C |
| ATOM | 512 | OE1 | GLN | A | 64 | 18.518 | 34.182 | 46.571 | 1.00 | 33.14 | O |
| ATOM | 513 | NE2 | GLN | A | 64 | 20.201 | 34.244 | 48.080 | 1.00 | 32.07 | N |
| ATOM | 514 | C | GLN | A | 64 | 22.502 | 32.281 | 46.570 | 1.00 | 23.24 | C |
| ATOM | 515 | O | GLN | A | 64 | 21.750 | 31.310 | 46.631 | 1.00 | 22.38 | O |
| ATOM | 516 | N | ILE | A | 65 | 23.314 | 32.629 | 47.565 | 1.00 | 22.76 | N |
| ATOM | 517 | CA | ILE | A | 65 | 23.350 | 31.881 | 48.822 | 1.00 | 21.92 | C |
| ATOM | 518 | CB | ILE | A | 65 | 24.556 | 30.905 | 48.904 | 1.00 | 22.07 | C |

FIGURE 9 (cont.)

| | | | | | | | | | | |
|---|---|---|---|---|---|---|---|---|---|---|
| ATOM | 519 | CG2 | ILE | A | 65 | 24.601 | 30.256 | 50.284 | 1.00 21.55 | C |
| ATOM | 520 | CG1 | ILE | A | 65 | 24.451 | 29.831 | 47.823 | 1.00 22.55 | C |
| ATOM | 521 | CD1 | ILE | A | 65 | 25.533 | 28.756 | 47.907 | 1.00 23.51 | C |
| ATOM | 522 | C | ILE | A | 65 | 23.463 | 32.799 | 50.018 | 1.00 21.21 | C |
| ATOM | 523 | O | ILE | A | 65 | 24.473 | 33.493 | 50.184 | 1.00 20.56 | O |
| ATOM | 524 | N | ASP | A | 66 | 22.418 | 32.806 | 50.839 | 1.00 20.21 | N |
| ATOM | 525 | CA | ASP | A | 66 | 22.397 | 33.598 | 52.057 | 1.00 18.57 | C |
| ATOM | 526 | CB | ASP | A | 66 | 21.019 | 34.185 | 52.302 | 1.00 17.50 | C |
| ATOM | 527 | CG | ASP | A | 66 | 20.959 | 35.000 | 53.577 | 1.00 18.95 | C |
| ATOM | 528 | OD1 | ASP | A | 66 | 21.637 | 34.636 | 54.559 | 1.00 17.06 | O |
| ATOM | 529 | OD2 | ASP | A | 66 | 20.218 | 36.006 | 53.602 | 1.00 22.14 | O |
| ATOM | 530 | C | ASP | A | 66 | 22.696 | 32.598 | 53.156 | 1.00 18.39 | C |
| ATOM | 531 | O | ASP | A | 66 | 21.835 | 31.792 | 53.514 | 1.00 18.78 | O |
| ATOM | 532 | N | VAL | A | 67 | 23.906 | 32.653 | 53.695 | 1.00 17.02 | N |
| ATOM | 533 | CA | VAL | A | 67 | 24.309 | 31.723 | 54.739 | 1.00 16.61 | C |
| ATOM | 534 | CB | VAL | A | 67 | 25.774 | 31.996 | 55.150 | 1.00 16.39 | C |
| ATOM | 535 | CG1 | VAL | A | 67 | 26.692 | 31.787 | 53.936 | 1.00 15.45 | C |
| ATOM | 536 | CG2 | VAL | A | 67 | 25.918 | 33.404 | 55.701 | 1.00 15.13 | C |
| ATOM | 537 | C | VAL | A | 67 | 23.416 | 31.625 | 55.996 | 1.00 16.36 | C |
| ATOM | 538 | O | VAL | A | 67 | 23.597 | 30.721 | 56.802 | 1.00 14.93 | O |
| ATOM | 539 | N | GLN | A | 68 | 22.456 | 32.531 | 56.164 | 1.00 16.49 | N |
| ATOM | 540 | CA | GLN | A | 68 | 21.568 | 32.466 | 57.325 | 1.00 19.02 | C |
| ATOM | 541 | CB | GLN | A | 68 | 20.877 | 33.809 | 57.581 | 1.00 20.31 | C |
| ATOM | 542 | CG | GLN | A | 68 | 21.739 | 34.856 | 58.275 | 1.00 23.44 | C |
| ATOM | 543 | CD | GLN | A | 68 | 20.896 | 35.940 | 58.957 | 1.00 25.46 | C |
| ATOM | 544 | OE1 | GLN | A | 68 | 20.406 | 36.872 | 58.308 | 1.00 25.14 | O |
| ATOM | 545 | NE2 | GLN | A | 68 | 20.715 | 35.806 | 60.274 | 1.00 25.31 | N |
| ATOM | 546 | C | GLN | A | 68 | 20.485 | 31.417 | 57.103 | 1.00 20.84 | C |
| ATOM | 547 | O | GLN | A | 68 | 19.678 | 31.134 | 58.000 | 1.00 20.87 | O |
| ATOM | 548 | N | SER | A | 69 | 20.467 | 30.847 | 55.901 | 1.00 20.98 | N |
| ATOM | 549 | CA | SER | A | 69 | 19.468 | 29.847 | 55.541 | 1.00 20.58 | C |
| ATOM | 550 | CB | SER | A | 69 | 18.673 | 30.323 | 54.325 | 1.00 20.66 | C |
| ATOM | 551 | OG | SER | A | 69 | 17.871 | 29.278 | 53.820 | 1.00 22.56 | O |
| ATOM | 552 | C | SER | A | 69 | 20.073 | 28.492 | 55.222 | 1.00 20.40 | C |
| ATOM | 553 | O | SER | A | 69 | 20.835 | 28.357 | 54.265 | 1.00 18.94 | O |
| ATOM | 554 | N | ASP | A | 70 | 19.723 | 27.487 | 56.016 | 1.00 20.14 | N |
| ATOM | 555 | CA | ASP | A | 70 | 20.238 | 26.149 | 55.776 | 1.00 21.43 | C |
| ATOM | 556 | CB | ASP | A | 70 | 19.619 | 25.140 | 56.748 | 1.00 21.08 | C |
| ATOM | 557 | CG | ASP | A | 70 | 20.144 | 25.284 | 58.147 | 1.00 21.67 | C |
| ATOM | 558 | OD1 | ASP | A | 70 | 19.968 | 24.335 | 58.942 | 1.00 23.73 | O |
| ATOM | 559 | OD2 | ASP | A | 70 | 20.727 | 26.342 | 58.464 | 1.00 21.85 | O |
| ATOM | 560 | C | ASP | A | 70 | 19.913 | 25.710 | 54.356 | 1.00 21.86 | C |
| ATOM | 561 | O | ASP | A | 70 | 20.784 | 25.262 | 53.614 | 1.00 23.14 | O |
| ATOM | 562 | N | GLU | A | 71 | 18.651 | 25.852 | 53.978 | 1.00 22.39 | N |
| ATOM | 563 | CA | GLU | A | 71 | 18.222 | 25.436 | 52.657 | 1.00 24.23 | C |
| ATOM | 564 | CB | GLU | A | 71 | 16.723 | 25.717 | 52.482 | 1.00 26.28 | C |
| ATOM | 565 | CG | GLU | A | 71 | 16.261 | 25.595 | 51.044 | 1.00 30.92 | C |
| ATOM | 566 | CD | GLU | A | 71 | 14.800 | 25.191 | 50.907 | 1.00 34.55 | C |
| ATOM | 567 | OE1 | GLU | A | 71 | 14.371 | 24.932 | 49.753 | 1.00 36.30 | O |
| ATOM | 568 | OE2 | GLU | A | 71 | 14.083 | 25.125 | 51.938 | 1.00 35.58 | O |
| ATOM | 569 | C | GLU | A | 71 | 19.015 | 26.040 | 51.501 | 1.00 23.55 | C |
| ATOM | 570 | O | GLU | A | 71 | 19.311 | 25.358 | 50.523 | 1.00 24.35 | O |
| ATOM | 571 | N | GLU | A | 72 | 19.374 | 27.311 | 51.595 | 1.00 23.62 | N |
| ATOM | 572 | CA | GLU | A | 72 | 20.110 | 27.912 | 50.495 | 1.00 22.11 | C |
| ATOM | 573 | CB | GLU | A | 72 | 20.132 | 29.432 | 50.641 | 1.00 22.00 | C |
| ATOM | 574 | CG | GLU | A | 72 | 18.747 | 30.033 | 50.793 | 1.00 23.76 | C |
| ATOM | 575 | CD | GLU | A | 72 | 18.724 | 31.544 | 50.585 | 1.00 27.08 | C |
| ATOM | 576 | OE1 | GLU | A | 72 | 17.726 | 32.185 | 50.996 | 1.00 27.98 | O |
| ATOM | 577 | OE2 | GLU | A | 72 | 19.693 | 32.094 | 49.996 | 1.00 28.25 | O |
| ATOM | 578 | C | GLU | A | 72 | 21.525 | 27.366 | 50.387 | 1.00 21.53 | C |
| ATOM | 579 | O | GLU | A | 72 | 22.046 | 27.205 | 49.289 | 1.00 22.68 | O |
| ATOM | 580 | N | VAL | A | 73 | 22.150 | 27.068 | 51.520 | 1.00 19.40 | N |
| ATOM | 581 | CA | VAL | A | 73 | 23.510 | 26.551 | 51.491 | 1.00 19.36 | C |
| ATOM | 582 | CB | VAL | A | 73 | 24.147 | 26.526 | 52.900 | 1.00 17.21 | C |
| ATOM | 583 | CG1 | VAL | A | 73 | 25.590 | 26.073 | 52.793 | 1.00 14.20 | C |

FIGURE 9 (cont.)

| ATOM | 584 | CG2 | VAL | A | 73 | 24.061 | 27.895 | 53.540 | 1.00 | 15.79 | C |
|------|-----|-----|-----|---|----|--------|--------|--------|------|-------|---|
| ATOM | 585 | C | VAL | A | 73 | 23.542 | 25.134 | 50.937 | 1.00 | 20.80 | C |
| ATOM | 586 | O | VAL | A | 73 | 24.384 | 24.798 | 50.095 | 1.00 | 21.59 | O |
| ATOM | 587 | N | ILE | A | 74 | 22.620 | 24.308 | 51.430 | 1.00 | 21.76 | N |
| ATOM | 588 | CA | ILE | A | 74 | 22.508 | 22.916 | 51.022 | 1.00 | 20.56 | C |
| ATOM | 589 | CB | ILE | A | 74 | 21.431 | 22.188 | 51.863 | 1.00 | 20.66 | C |
| ATOM | 590 | CG2 | ILE | A | 74 | 21.266 | 20.753 | 51.387 | 1.00 | 18.15 | C |
| ATOM | 591 | CG1 | ILE | A | 74 | 21.830 | 22.218 | 53.342 | 1.00 | 19.47 | C |
| ATOM | 592 | CD1 | ILE | A | 74 | 20.716 | 21.806 | 54.284 | 1.00 | 17.78 | C |
| ATOM | 593 | C | ILE | A | 74 | 22.156 | 22.800 | 49.544 | 1.00 | 20.44 | C |
| ATOM | 594 | O | ILE | A | 74 | 22.879 | 22.150 | 48.772 | 1.00 | 20.35 | O |
| ATOM | 595 | N | ASN | A | 75 | 21.054 | 23.424 | 49.144 | 1.00 | 18.82 | N |
| ATOM | 596 | CA | ASN | A | 75 | 20.645 | 23.360 | 47.751 | 1.00 | 19.08 | C |
| ATOM | 597 | CB | ASN | A | 75 | 19.229 | 23.913 | 47.574 | 1.00 | 20.70 | C |
| ATOM | 598 | CG | ASN | A | 75 | 18.202 | 23.130 | 48.355 | 1.00 | 23.21 | C |
| ATOM | 599 | OD1 | ASN | A | 75 | 18.372 | 21.928 | 48.602 | 1.00 | 25.04 | O |
| ATOM | 600 | ND2 | ASN | A | 75 | 17.119 | 23.796 | 48.740 | 1.00 | 22.69 | N |
| ATOM | 601 | C | ASN | A | 75 | 21.611 | 24.135 | 46.864 | 1.00 | 18.33 | C |
| ATOM | 602 | O | ASN | A | 75 | 21.670 | 23.907 | 45.650 | 1.00 | 19.22 | O |
| ATOM | 603 | N | GLY | A | 76 | 22.353 | 25.059 | 47.470 | 1.00 | 17.47 | N |
| ATOM | 604 | CA | GLY | A | 76 | 23.309 | 25.847 | 46.722 | 1.00 | 16.44 | C |
| ATOM | 605 | C | GLY | A | 76 | 24.497 | 24.984 | 46.339 | 1.00 | 16.68 | C |
| ATOM | 606 | O | GLY | A | 76 | 24.845 | 24.841 | 45.168 | 1.00 | 14.01 | O |
| ATOM | 607 | N | PHE | A | 77 | 25.130 | 24.384 | 47.333 | 1.00 | 18.04 | N |
| ATOM | 608 | CA | PHE | A | 77 | 26.272 | 23.544 | 47.037 | 1.00 | 18.63 | C |
| ATOM | 609 | CB | PHE | A | 77 | 27.006 | 23.196 | 48.325 | 1.00 | 18.54 | C |
| ATOM | 610 | CG | PHE | A | 77 | 27.967 | 24.264 | 48.765 | 1.00 | 20.77 | C |
| ATOM | 611 | CD1 | PHE | A | 77 | 27.513 | 25.416 | 49.392 | 1.00 | 21.57 | C |
| ATOM | 612 | CD2 | PHE | A | 77 | 29.329 | 24.131 | 48.517 | 1.00 | 21.81 | C |
| ATOM | 613 | CE1 | PHE | A | 77 | 28.404 | 26.427 | 49.767 | 1.00 | 22.46 | C |
| ATOM | 614 | CE2 | PHE | A | 77 | 30.228 | 25.134 | 48.886 | 1.00 | 21.98 | C |
| ATOM | 615 | CZ | PHE | A | 77 | 29.762 | 26.286 | 49.513 | 1.00 | 22.56 | C |
| ATOM | 616 | C | PHE | A | 77 | 25.888 | 22.289 | 46.247 | 1.00 | 18.65 | C |
| ATOM | 617 | O | PHE | A | 77 | 26.711 | 21.743 | 45.506 | 1.00 | 17.27 | O |
| ATOM | 618 | N | GLU | A | 78 | 24.642 | 21.836 | 46.379 | 1.00 | 17.92 | N |
| ATOM | 619 | CA | GLU | A | 78 | 24.237 | 20.664 | 45.620 | 1.00 | 20.13 | C |
| ATOM | 620 | CB | GLU | A | 78 | 22.890 | 20.126 | 46.095 | 1.00 | 21.00 | C |
| ATOM | 621 | CG | GLU | A | 78 | 22.513 | 18.844 | 45.364 | 1.00 | 26.59 | C |
| ATOM | 622 | CD | GLU | A | 78 | 21.220 | 18.230 | 45.857 | 1.00 | 29.20 | C |
| ATOM | 623 | OE1 | GLU | A | 78 | 20.188 | 18.947 | 45.852 | 1.00 | 29.68 | O |
| ATOM | 624 | OE2 | GLU | A | 78 | 21.237 | 17.032 | 46.244 | 1.00 | 31.01 | O |
| ATOM | 625 | C | GLU | A | 78 | 24.162 | 21.004 | 44.123 | 1.00 | 18.96 | C |
| ATOM | 626 | O | GLU | A | 78 | 24.620 | 20.235 | 43.286 | 1.00 | 18.29 | O |
| ATOM | 627 | N | GLN | A | 79 | 23.591 | 22.156 | 43.789 | 1.00 | 18.16 | N |
| ATOM | 628 | CA | GLN | A | 79 | 23.498 | 22.554 | 42.387 | 1.00 | 19.45 | C |
| ATOM | 629 | CB | GLN | A | 79 | 22.643 | 23.807 | 42.228 | 1.00 | 20.90 | C |
| ATOM | 630 | CG | GLN | A | 79 | 22.438 | 24.209 | 40.770 | 1.00 | 25.25 | C |
| ATOM | 631 | CD | GLN | A | 79 | 21.526 | 23.234 | 40.033 | 1.00 | 27.45 | C |
| ATOM | 632 | OE1 | GLN | A | 79 | 20.345 | 23.133 | 40.354 | 1.00 | 29.62 | O |
| ATOM | 633 | NE2 | GLN | A | 79 | 22.076 | 22.501 | 39.054 | 1.00 | 25.98 | N |
| ATOM | 634 | C | GLN | A | 79 | 24.892 | 22.827 | 41.836 | 1.00 | 19.34 | C |
| ATOM | 635 | O | GLN | A | 79 | 25.148 | 22.646 | 40.648 | 1.00 | 21.10 | O |
| ATOM | 636 | N | ILE | A | 80 | 25.794 | 23.266 | 42.705 | 1.00 | 18.73 | N |
| ATOM | 637 | CA | ILE | A | 80 | 27.168 | 23.554 | 42.314 | 1.00 | 18.32 | C |
| ATOM | 638 | CB | ILE | A | 80 | 27.961 | 24.213 | 43.481 | 1.00 | 16.01 | C |
| ATOM | 639 | CG2 | ILE | A | 80 | 29.448 | 24.136 | 43.203 | 1.00 | 15.40 | C |
| ATOM | 640 | CG1 | ILE | A | 80 | 27.503 | 25.665 | 43.675 | 1.00 | 17.45 | C |
| ATOM | 641 | CD1 | ILE | A | 80 | 28.149 | 26.404 | 44.858 | 1.00 | 13.94 | C |
| ATOM | 642 | C | ILE | A | 80 | 27.863 | 22.254 | 41.908 | 1.00 | 19.54 | C |
| ATOM | 643 | O | ILE | A | 80 | 28.686 | 22.231 | 40.990 | 1.00 | 19.24 | O |
| ATOM | 644 | N | GLY | A | 81 | 27.533 | 21.178 | 42.614 | 1.00 | 20.82 | N |
| ATOM | 645 | CA | GLY | A | 81 | 28.122 | 19.886 | 42.314 | 1.00 | 21.07 | C |
| ATOM | 646 | C | GLY | A | 81 | 27.584 | 19.368 | 40.993 | 1.00 | 21.93 | C |
| ATOM | 647 | O | GLY | A | 81 | 28.310 | 18.756 | 40.211 | 1.00 | 20.45 | O |
| ATOM | 648 | N | LYS | A | 82 | 26.304 | 19.622 | 40.736 | 1.00 | 22.35 | N |

FIGURE 9 (cont.)

| | | | | | | | | | |
|---|---|---|---|---|---|---|---|---|---|
| ATOM | 649 | CA | LYS | A | 82 | 25.700 | 19.170 | 39.493 | 1.00 23.21 | C |
| ATOM | 650 | CB | LYS | A | 82 | 24.181 | 19.330 | 39.522 | 1.00 24.33 | C |
| ATOM | 651 | CG | LYS | A | 82 | 23.446 | 18.452 | 40.507 | 1.00 25.03 | C |
| ATOM | 652 | CD | LYS | A | 82 | 21.943 | 18.534 | 40.234 | 1.00 26.61 | C |
| ATOM | 653 | CE | LYS | A | 82 | 21.117 | 18.294 | 41.486 | 1.00 28.13 | C |
| ATOM | 654 | NZ | LYS | A | 82 | 21.525 | 17.048 | 42.202 | 1.00 30.08 | N |
| ATOM | 655 | C | LYS | A | 82 | 26.233 | 19.953 | 38.313 | 1.00 22.81 | C |
| ATOM | 656 | O | LYS | A | 82 | 26.373 | 19.403 | 37.224 | 1.00 22.85 | O |
| ATOM | 657 | N | ASP | A | 83 | 26.536 | 21.233 | 38.527 | 1.00 22.80 | N |
| ATOM | 658 | CA | ASP | A | 83 | 27.017 | 22.092 | 37.443 | 1.00 21.61 | C |
| ATOM | 659 | CB | ASP | A | 83 | 26.608 | 23.544 | 37.691 | 1.00 22.81 | C |
| ATOM | 660 | CG | ASP | A | 83 | 25.104 | 23.731 | 37.739 | 1.00 23.85 | C |
| ATOM | 661 | OD1 | ASP | A | 83 | 24.372 | 22.893 | 37.177 | 1.00 24.40 | O |
| ATOM | 662 | OD2 | ASP | A | 83 | 24.647 | 24.732 | 38.330 | 1.00 26.49 | O |
| ATOM | 663 | C | ASP | A | 83 | 28.499 | 22.069 | 37.107 | 1.00 20.49 | C |
| ATOM | 664 | O | ASP | A | 83 | 28.863 | 22.274 | 35.948 | 1.00 22.11 | O |
| ATOM | 665 | N | VAL | A | 84 | 29.366 | 21.854 | 38.091 | 1.00 19.89 | N |
| ATOM | 666 | CA | VAL | A | 84 | 30.806 | 21.820 | 37.807 | 1.00 18.35 | C |
| ATOM | 667 | CB | VAL | A | 84 | 31.534 | 23.084 | 38.345 | 1.00 18.45 | C |
| ATOM | 668 | CG1 | VAL | A | 84 | 30.807 | 24.336 | 37.890 | 1.00 19.02 | C |
| ATOM | 669 | CG2 | VAL | A | 84 | 31.626 | 23.040 | 39.869 | 1.00 18.64 | C |
| ATOM | 670 | C | VAL | A | 84 | 31.504 | 20.587 | 38.379 | 1.00 18.38 | C |
| ATOM | 671 | O | VAL | A | 84 | 32.693 | 20.372 | 38.145 | 1.00 16.73 | O |
| ATOM | 672 | N | GLY | A | 85 | 30.765 | 19.782 | 39.138 | 1.00 18.70 | N |
| ATOM | 673 | CA | GLY | A | 85 | 31.351 | 18.585 | 39.722 | 1.00 18.93 | C |
| ATOM | 674 | C | GLY | A | 85 | 32.080 | 18.852 | 41.026 | 1.00 18.74 | C |
| ATOM | 675 | O | GLY | A | 85 | 31.686 | 19.728 | 41.795 | 1.00 19.25 | O |
| ATOM | 676 | N | ASN | A | 86 | 33.148 | 18.104 | 41.284 | 1.00 18.46 | N |
| ATOM | 677 | CA | ASN | A | 86 | 33.897 | 18.289 | 42.523 | 1.00 18.57 | C |
| ATOM | 678 | CB | ASN | A | 86 | 34.798 | 17.083 | 42.789 | 1.00 17.49 | C |
| ATOM | 679 | CG | ASN | A | 86 | 34.002 | 15.828 | 43.116 | 1.00 17.73 | C |
| ATOM | 680 | OD1 | ASN | A | 86 | 32.861 | 15.915 | 43.580 | 1.00 17.43 | O |
| ATOM | 681 | ND2 | ASN | A | 86 | 34.605 | 14.657 | 42.895 | 1.00 13.17 | N |
| ATOM | 682 | C | ASN | A | 86 | 34.724 | 19.562 | 42.508 | 1.00 18.42 | C |
| ATOM | 683 | O | ASN | A | 86 | 35.110 | 20.063 | 41.450 | 1.00 19.81 | O |
| ATOM | 684 | N | ILE | A | 87 | 34.983 | 20.097 | 43.691 | 1.00 18.19 | N |
| ATOM | 685 | CA | ILE | A | 87 | 35.769 | 21.314 | 43.800 | 1.00 19.10 | C |
| ATOM | 686 | CB | ILE | A | 87 | 34.954 | 22.437 | 44.483 | 1.00 18.38 | C |
| ATOM | 687 | CG2 | ILE | A | 87 | 33.663 | 22.662 | 43.715 | 1.00 18.17 | C |
| ATOM | 688 | CG1 | ILE | A | 87 | 34.640 | 22.057 | 45.935 | 1.00 18.53 | C |
| ATOM | 689 | CD1 | ILE | A | 87 | 33.797 | 23.086 | 46.677 | 1.00 16.87 | C |
| ATOM | 690 | C | ILE | A | 87 | 37.030 | 21.030 | 44.601 | 1.00 18.69 | C |
| ATOM | 691 | O | ILE | A | 87 | 37.151 | 19.978 | 45.227 | 1.00 18.03 | O |
| ATOM | 692 | N | ASP | A | 88 | 37.968 | 21.970 | 44.581 | 1.00 19.31 | N |
| ATOM | 693 | CA | ASP | A | 88 | 39.218 | 21.795 | 45.307 | 1.00 18.89 | C |
| ATOM | 694 | CB | ASP | A | 88 | 40.391 | 22.139 | 44.397 | 1.00 20.11 | C |
| ATOM | 695 | CG | ASP | A | 88 | 40.506 | 21.187 | 43.234 | 1.00 20.85 | C |
| ATOM | 696 | OD1 | ASP | A | 88 | 41.031 | 20.073 | 43.434 | 1.00 24.05 | O |
| ATOM | 697 | OD2 | ASP | A | 88 | 40.055 | 21.541 | 42.123 | 1.00 22.98 | O |
| ATOM | 698 | C | ASP | A | 88 | 39.279 | 22.629 | 46.570 | 1.00 17.86 | C |
| ATOM | 699 | O | ASP | A | 88 | 40.185 | 22.462 | 47.390 | 1.00 17.01 | O |
| ATOM | 700 | N | GLY | A | 89 | 38.312 | 23.521 | 46.732 | 1.00 15.30 | N |
| ATOM | 701 | CA | GLY | A | 89 | 38.302 | 24.352 | 47.910 | 1.00 16.58 | C |
| ATOM | 702 | C | GLY | A | 89 | 37.223 | 25.414 | 47.938 | 1.00 16.58 | C |
| ATOM | 703 | O | GLY | A | 89 | 36.440 | 25.558 | 47.000 | 1.00 18.80 | O |
| ATOM | 704 | N | VAL | A | 90 | 37.193 | 26.156 | 49.038 | 1.00 15.35 | N |
| ATOM | 705 | CA | VAL | A | 90 | 36.231 | 27.221 | 49.243 | 1.00 14.48 | C |
| ATOM | 706 | CB | VAL | A | 90 | 35.035 | 26.740 | 50.094 | 1.00 15.24 | C |
| ATOM | 707 | CG1 | VAL | A | 90 | 34.091 | 27.897 | 50.361 | 1.00 16.78 | C |
| ATOM | 708 | CG2 | VAL | A | 90 | 34.300 | 25.610 | 49.391 | 1.00 16.44 | C |
| ATOM | 709 | C | VAL | A | 90 | 36.895 | 28.373 | 49.997 | 1.00 14.49 | C |
| ATOM | 710 | O | VAL | A | 90 | 37.663 | 28.150 | 50.936 | 1.00 13.33 | O |
| ATOM | 711 | N | TYR | A | 91 | 36.600 | 29.601 | 49.578 | 1.00 15.16 | N |
| ATOM | 712 | CA | TYR | A | 91 | 37.123 | 30.780 | 50.256 | 1.00 15.53 | C |
| ATOM | 713 | CB | TYR | A | 91 | 37.810 | 31.743 | 49.276 | 1.00 15.60 | C |

FIGURE 9 (cont.)

| | | | | | | | | | |
|---|---|---|---|---|---|---|---|---|---|
| ATOM | 714 | CG | TYR A | 91 | 38.561 | 32.838 | 50.000 | 1.00 18.20 | C |
| ATOM | 715 | CD1 | TYR A | 91 | 39.894 | 32.664 | 50.393 | 1.00 16.27 | C |
| ATOM | 716 | CE1 | TYR A | 91 | 40.542 | 33.608 | 51.187 | 1.00 15.82 | C |
| ATOM | 717 | CD2 | TYR A | 91 | 37.902 | 33.996 | 50.411 | 1.00 18.11 | C |
| ATOM | 718 | CE2 | TYR A | 91 | 38.536 | 34.942 | 51.201 | 1.00 18.93 | C |
| ATOM | 719 | CZ | TYR A | 91 | 39.853 | 34.742 | 51.593 | 1.00 18.72 | C |
| ATOM | 720 | OH | TYR A | 91 | 40.439 | 35.662 | 52.433 | 1.00 15.57 | O |
| ATOM | 721 | C | TYR A | 91 | 35.936 | 31.478 | 50.922 | 1.00 14.66 | C |
| ATOM | 722 | O | TYR A | 91 | 35.025 | 31.939 | 50.245 | 1.00 15.09 | O |
| ATOM | 723 | N | HIS A | 92 | 35.952 | 31.536 | 52.251 | 1.00 15.10 | N |
| ATOM | 724 | CA | HIS A | 92. | 34.890 | 32.162 | 53.031 | 1.00 15.50 | C |
| ATOM | 725 | CB | HIS A | 92 | 34.691 | 31.381 | 54.329 | 1.00 16.98 | C |
| ATOM | 726 | CG | HIS A | 92 | 33.553 | 31.869 | 55.170 | 1.00 16.37 | C |
| ATOM | 727 | CD2 | HIS A | 92 | 32.349 | 31.312 | 55.449 | 1.00 17.36 | C |
| ATOM | 728 | ND1 | HIS A | 92 | 33.593 | 33.061 | 55.861 | 1.00 18.25 | N |
| ATOM | 729 | CE1 | HIS A | 92 | 32.465 | 33.215 | 56.533 | 1.00 20.01 | C |
| ATOM | 730 | NE2 | HIS A | 92 | 31.692 | 32.167 | 56.300 | 1.00 17.84 | N |
| ATOM | 731 | C | HIS A | 92 | 35.254 | 33.617 | 53.332 | 1.00 16.97 | C |
| ATOM | 732 | O | HIS A | 92 | 36.196 | 33.896 | 54.075 | 1.00 18.13 | O |
| ATOM | 733 | N | SER A | 93 | 34.495 | 34.537 | 52.746 | 1.00 17.46 | N |
| ATOM | 734 | CA | SER A | 93 | 34.733 | 35.969 | 52.896 | 1.00 16.47 | C |
| ATOM | 735 | CB | SER A | 93 | 35.234 | 36.520 | 51.554 | 1.00 16.03 | C |
| ATOM | 736 | OG | SER A | 93 | 35.764 | 37.823 | 51.667 | 1.00 16.14 | O |
| ATOM | 737 | C | SER A | 93 | 33.422 | 36.637 | 53.297 | 1.00 15.92 | C |
| ATOM | 738 | O | SER A | 93 | 32.987 | 37.611 | 52.684 | 1.00 15.79 | O |
| ATOM | 739 | N | ILE A | 94 | 32.787 | 36.100 | 54.332 | 1.00 16.01 | N |
| ATOM | 740 | CA | ILE A | 94 | 31.506 | 36.621 | 54.791 | 1.00 13.77 | C |
| ATOM | 741 | CB | ILE A | 94 | 30.395 | 35.597 | 54.512 | 1.00 13.52 | C |
| ATOM | 742 | CG2 | ILE A | 94 | 29.087 | 36.039 | 55.157 | 1.00 11.53 | C |
| ATOM | 743 | CG1 | ILE A | 94 | 30.244 | 35.407 | 53.007 | 1.00 11.85 | C |
| ATOM | 744 | CD1 | ILE A | 94 | 29.234 | 34.336 | 52.635 | 1.00 14.61 | C |
| ATOM | 745 | C | ILE A | 94 | 31.468 | 36.987 | 56.277 | 1.00 14.03 | C |
| ATOM | 746 | O | ILE A | 94 | 32.060 | 36.305 | 57.111 | 1.00 12.40 | O |
| ATOM | 747 | N | ALA A | 95 | 30.753 | 38.065 | 56.591 | 1.00 14.08 | N |
| ATOM | 748 | CA | ALA A | 95 | 30.598 | 38.526 | 57.963 | 1.00 14.08 | C |
| ATOM | 749 | CB | ALA A | 95 | 31.951 | 38.983 | 58.525 | 1.00 13.85 | C |
| ATOM | 750 | C | ALA A | 95 | 29.586 | 39.672 | 58.022 | 1.00 14.62 | C |
| ATOM | 751 | O | ALA A | 95 | 29.430 | 40.431 | 57.063 | 1.00 14.70 | O |
| ATOM | 752 | N | PHE A | 96 | 28.889 | 39.791 | 59.144 | 1.00 14.06 | N |
| ATOM | 753 | CA | PHE A | 96 | 27.918 | 40.868 | 59.305 | 1.00 16.27 | C |
| ATOM | 754 | CB | PHE A | 96 | 26.640 | 40.579 | 58.498 | 1.00 15.53 | C |
| ATOM | 755 | CG | PHE A | 96 | 25.589 | 41.665 | 58.601 | 1.00 15.20 | C |
| ATOM | 756 | CD1 | PHE A | 96 | 25.686 | 42.826 | 57.840 | 1.00 17.36 | C |
| ATOM | 757 | CD2 | PHE A | 96 | 24.520 | 41.542 | 59.489 | 1.00 15.35 | C |
| ATOM | 758 | CE1 | PHE A | 96 | 24.732 | 43.857 | 57.964 | 1.00 16.47 | C |
| ATOM | 759 | CE2 | PHE A | 96 | 23.562 | 42.566 | 59.620 | 1.00 15.41 | C |
| ATOM | 760 | CZ | PHE A | 96 | 23.672 | 43.724 | 58.855 | 1.00 14.21 | C |
| ATOM | 761 | C | PHE A | 96 | 27.553 | 41.057 | 60.771 | 1.00 17.70 | C |
| ATOM | 762 | O | PHE A | 96 | 27.569 | 40.109 | 61.558 | 1.00 19.08 | O |
| ATOM | 763 | N | ALA A | 97 | 27.227 | 42.294 | 61.126 | 1.00 19.54 | N |
| ATOM | 764 | CA | ALA A | 97 | 26.817 | 42.640 | 62.477 | 1.00 18.93 | C |
| ATOM | 765 | CB | ALA A | 97 | 28.043 | 42.855 | 63.361 | 1.00 20.31 | C |
| ATOM | 766 | C | ALA A | 97 | 26.022 | 43.932 | 62.347 | 1.00 18.57 | C |
| ATOM | 767 | O | ALA A | 97 | 26.308 | 44.727 | 61.468 | 1.00 18.08 | O |
| ATOM | 768 | N | ASN A | 98 | 25.012 | 44.132 | 63.189 | 1.00 19.26 | N |
| ATOM | 769 | CA | ASN A | 98 | 24.225 | 45.373 | 63.136 | 1.00 19.99 | C |
| ATOM | 770 | CB | ASN A | 98 | 23.112 | 45.346 | 64.182 | 1.00 18.67 | C |
| ATOM | 771 | CG | ASN A | 98 | 21.945 | 44.453 | 63.785 | 1.00 20.10 | C |
| ATOM | 772 | OD1 | ASN A | 98 | 21.275 | 43.892 | 64.650 | 1.00 24.12 | O |
| ATOM | 773 | ND2 | ASN A | 98 | 21.681 | 44.334 | 62.487 | 1.00 17.99 | N |
| ATOM | 774 | C | ASN A | 98 | 25.189 | 46.524 | 63.426 | 1.00 21.17 | C |
| ATOM | 775 | O | ASN A | 98 | 25.970 | 46.455 | 64.372 | 1.00 21.73 | O |
| ATOM | 776 | N | MET A | 99 | 25.135 | 47.574 | 62.612 | 1.00 21.78 | N |
| ATOM | 777 | CA | MET A | 99 | 26.030 | 48.714 | 62.760 | 1.00 22.87 | C |
| ATOM | 778 | CB | MET A | 99 | 25.663 | 49.801 | 61.742 | 1.00 23.73 | C |

FIGURE 9 (cont.)

| | | | | | | | | | |
|---|---|---|---|---|---|---|---|---|---|
| ATOM | 779 | CG | MET | A | 99 | 26.648 | 50.966 | 61.688 | 1.00 25.72 | C |
| ATOM | 780 | SD | MET | A | 99 | 28.201 | 50.616 | 60.795 | 1.00 26.77 | S |
| ATOM | 781 | CE | MET | A | 99 | 27.731 | 51.059 | 59.111 | 1.00 27.02 | C |
| ATOM | 782 | C | MET | A | 99 | 26.052 | 49.316 | 64.160 | 1.00 23.78 | C |
| ATOM | 783 | O | MET | A | 99 | 27.113 | 49.702 | 64.663 | 1.00 22.18 | O |
| ATOM | 784 | N | GLU | A | 100 | 24.885 | 49.391 | 64.793 | 1.00 24.12 | N |
| ATOM | 785 | CA | GLU | A | 100 | 24.801 | 49.966 | 66.128 | 1.00 24.84 | C |
| ATOM | 786 | CB | GLU | A | 100 | 23.363 | 49.949 | 66.626 | 1.00 24.92 | C |
| ATOM | 787 | CG | GLU | A | 100 | 22.821 | 48.550 | 66.776 | 1.00 28.72 | C |
| ATOM | 788 | CD | GLU | A | 100 | 21.471 | 48.514 | 67.436 | 1.00 28.89 | C |
| ATOM | 789 | OE1 | GLU | A | 100 | 20.882 | 47.420 | 67.494 | 1.00 28.52 | O |
| ATOM | 790 | OE2 | GLU | A | 100 | 20.999 | 49.581 | 67.901 | 1.00 32.64 | O |
| ATOM | 791 | C | GLU | A | 100 | 25.682 | 49.224 | 67.122 | 1.00 24.48 | C |
| ATOM | 792 | O | GLU | A | 100 | 26.082 | 49.784 | 68.132 | 1.00 25.15 | O |
| ATOM | 793 | N | ASP | A | 101 | 25.969 | 47.958 | 66.854 | 1.00 25.42 | N |
| ATOM | 794 | CA | ASP | A | 101 | 26.819 | 47.187 | 67.760 | 1.00 25.51 | C |
| ATOM | 795 | CB | ASP | A | 101 | 26.479 | 45.688 | 67.694 | 1.00 26.55 | C |
| ATOM | 796 | CG | ASP | A | 101 | 25.084 | 45.379 | 68.195 | 1.00 26.64 | C |
| ATOM | 797 | OD1 | ASP | A | 101 | 24.699 | 45.912 | 69.254 | 1.00 27.35 | O |
| ATOM | 798 | OD2 | ASP | A | 101 | 24.375 | 44.593 | 67.538 | 1.00 27.04 | O |
| ATOM | 799 | C | ASP | A | 101 | 28.302 | 47.376 | 67.428 | 1.00 24.43 | C |
| ATOM | 800 | O | ASP | A | 101 | 29.163 | 46.737 | 68.042 | 1.00 25.46 | O |
| ATOM | 801 | N | LEU | A | 102 | 28.604 | 48.240 | 66.460 | 1.00 23.18 | N |
| ATOM | 802 | CA | LEU | A | 102 | 29.996 | 48.473 | 66.072 | 1.00 21.80 | C |
| ATOM | 803 | CB | LEU | A | 102 | 30.196 | 48.170 | 64.584 | 1.00 20.89 | C |
| ATOM | 804 | CG | LEU | A | 102 | 29.920 | 46.720 | 64.159 | 1.00 20.95 | C |
| ATOM | 805 | CD1 | LEU | A | 102 | 30.196 | 46.552 | 62.674 | 1.00 20.36 | C |
| ATOM | 806 | CD2 | LEU | A | 102 | 30.805 | 45.770 | 64.955 | 1.00 22.45 | C |
| ATOM | 807 | C | LEU | A | 102 | 30.439 | 49.898 | 66.390 | 1.00 22.16 | C |
| ATOM | 808 | O | LEU | A | 102 | 31.299 | 50.474 | 65.721 | 1.00 21.07 | O |
| ATOM | 809 | N | ARG | A | 103 | 29.831 | 50.443 | 67.436 | 1.00 22.21 | N |
| ATOM | 810 | CA | ARG | A | 103 | 30.120 | 51.774 | 67.938 | 1.00 23.10 | C |
| ATOM | 811 | CB | ARG | A | 103 | 29.338 | 52.844 | 67.165 | 1.00 24.96 | C |
| ATOM | 812 | CG | ARG | A | 103 | 27.830 | 52.871 | 67.443 | 1.00 28.12 | C |
| ATOM | 813 | CD | ARG | A | 103 | 27.166 | 54.140 | 66.870 | 1.00 30.36 | C |
| ATOM | 814 | NE | ARG | A | 103 | 26.866 | 54.005 | 65.445 | 1.00 33.78 | N |
| ATOM | 815 | CZ | ARG | A | 103 | 25.644 | 53.802 | 64.952 | 1.00 35.37 | C |
| ATOM | 816 | NH1 | ARG | A | 103 | 24.593 | 53.712 | 65.767 | 1.00 35.79 | N |
| ATOM | 817 | NH2 | ARG | A | 103 | 25.472 | 53.684 | 63.640 | 1.00 35.33 | N |
| ATOM | 818 | C | ARG | A | 103 | 29.632 | 51.703 | 69.379 | 1.00 23.04 | C |
| ATOM | 819 | O | ARG | A | 103 | 28.933 | 50.755 | 69.751 | 1.00 21.33 | O |
| ATOM | 820 | N | GLY | A | 104 | 30.006 | 52.686 | 70.191 | 1.00 23.25 | N |
| ATOM | 821 | CA | GLY | A | 104 | 29.585 | 52.681 | 71.581 | 1.00 22.31 | C |
| ATOM | 822 | C | GLY | A | 104 | 30.251 | 51.599 | 72.424 | 1.00 22.79 | C |
| ATOM | 823 | O | GLY | A | 104 | 31.337 | 51.098 | 72.092 | 1.00 23.41 | O |
| ATOM | 824 | N | ARG | A | 105 | 29.580 | 51.227 | 73.512 | 1.00 21.21 | N |
| ATOM | 825 | CA | ARG | A | 105 | 30.085 | 50.231 | 74.450 | 1.00 20.00 | C |
| ATOM | 826 | CB | ARG | A | 105 | 29.731 | 50.673 | 75.861 | 1.00 21.91 | C |
| ATOM | 827 | CG | ARG | A | 105 | 30.064 | 52.131 | 76.101 | 1.00 23.41 | C |
| ATOM | 828 | CD | ARG | A | 105 | 29.859 | 52.493 | 77.547 | 1.00 25.86 | C |
| ATOM | 829 | NE | ARG | A | 105 | 30.820 | 51.806 | 78.397 | 1.00 27.26 | N |
| ATOM | 830 | CZ | ARG | A | 105 | 30.935 | 52.026 | 79.698 | 1.00 27.02 | C |
| ATOM | 831 | NH1 | ARG | A | 105 | 30.147 | 52.912 | 80.286 | 1.00 27.55 | N |
| ATOM | 832 | NH2 | ARG | A | 105 | 31.833 | 51.360 | 80.407 | 1.00 28.71 | N |
| ATOM | 833 | C | ARG | A | 105 | 29.607 | 48.804 | 74.219 | 1.00 17.89 | C |
| ATOM | 834 | O | ARG | A | 105 | 28.400 | 48.530 | 74.126 | 1.00 17.14 | O |
| ATOM | 835 | N | PHE | A | 106 | 30.571 | 47.893 | 74.144 | 1.00 16.31 | N |
| ATOM | 836 | CA | PHE | A | 106 | 30.280 | 46.487 | 73.906 | 1.00 16.09 | C |
| ATOM | 837 | CB | PHE | A | 106 | 31.583 | 45.685 | 73.780 | 1.00 15.21 | C |
| ATOM | 838 | CG | PHE | A | 106 | 31.370 | 44.192 | 73.740 | 1.00 13.73 | C |
| ATOM | 839 | CD1 | PHE | A | 106 | 30.857 | 43.577 | 72.597 | 1.00 10.56 | C |
| ATOM | 840 | CD2 | PHE | A | 106 | 31.634 | 43.411 | 74.865 | 1.00 13.88 | C |
| ATOM | 841 | CE1 | PHE | A | 106 | 30.604 | 42.208 | 72.572 | 1.00 13.00 | C |
| ATOM | 842 | CE2 | PHE | A | 106 | 31.383 | 42.028 | 74.855 | 1.00 13.83 | C |
| ATOM | 843 | CZ | PHE | A | 106 | 30.865 | 41.426 | 73.702 | 1.00 13.71 | C |

FIGURE 9 (cont.)

| | | | | | | | | | |
|---|---|---|---|---|---|---|---|---|---|
| ATOM | 844 | C | PHE | A | 106 | 29.409 | 45.855 | 74.989 | 1.00 15.52 | C |
| ATOM | 845 | O | PHE | A | 106 | 28.646 | 44.931 | 74.713 | 1.00 15.02 | O |
| ATOM | 846 | N | SER | A | 107 | 29.533 | 46.344 | 76.217 | 1.00 16.15 | N |
| ATOM | 847 | CA | SER | A | 107 | 28.766 | 45.796 | 77.328 | 1.00 17.64 | C |
| ATOM | 848 | CB | SER | A | 107 | 29.239 | 46.404 | 78.647 | 1.00 18.10 | C |
| ATOM | 849 | OG | SER | A | 107 | 29.080 | 47.813 | 78.646 | 1.00 18.90 | O |
| ATOM | 850 | C | SER | A | 107 | 27.264 | 46.013 | 77.176 | 1.00 17.66 | C |
| ATOM | 851 | O | SER | A | 107 | 26.468 | 45.428 | 77.901 | 1.00 17.11 | O |
| ATOM | 852 | N | GLU | A | 108 | 26.874 | 46.848 | 76.229 | 1.00 18.85 | N |
| ATOM | 853 | CA | GLU | A | 108 | 25.459 | 47.109 | 76.012 | 1.00 21.53 | C |
| ATOM | 854 | CB | GLU | A | 108 | 25.251 | 48.605 | 75.735 | 1.00 22.78 | C |
| ATOM | 855 | CG | GLU | A | 108 | 25.368 | 49.472 | 76.973 | 1.00 24.81 | C |
| ATOM | 856 | CD | GLU | A | 108 | 25.435 | 50.957 | 76.654 | 1.00 27.73 | C |
| ATOM | 857 | OE1 | GLU | A | 108 | 25.481 | 51.770 | 77.605 | 1.00 28.36 | O |
| ATOM | 858 | OE2 | GLU | A | 108 | 25.451 | 51.317 | 75.456 | 1.00 29.84 | O |
| ATOM | 859 | C | GLU | A | 108 | 24.855 | 46.273 | 74.876 | 1.00 20.60 | C |
| ATOM | 860 | O | GLU | A | 108 | 23.656 | 46.335 | 74.630 | 1.00 22.70 | O |
| ATOM | 861 | N | THR | A | 109 | 25.675 | 45.482 | 74.197 | 1.00 18.87 | N |
| ATOM | 862 | CA | THR | A | 109 | 25.195 | 44.658 | 73.089 | 1.00 18.67 | C |
| ATOM | 863 | CB | THR | A | 109 | 26.315 | 43.737 | 72.580 | 1.00 17.91 | C |
| ATOM | 864 | OG1 | THR | A | 109 | 27.474 | 44.527 | 72.282 | 1.00 16.79 | O |
| ATOM | 865 | CG2 | THR | A | 109 | 25.869 | 42.996 | 71.329 | 1.00 14.17 | C |
| ATOM | 866 | C | THR | A | 109 | 23.965 | 43.798 | 73.423 | 1.00 19.07 | C |
| ATOM | 867 | O | THR | A | 109 | 23.872 | 43.214 | 74.506 | 1.00 17.18 | O |
| ATOM | 868 | N | SER | A | 110 | 23.034 | 43.717 | 72.471 | 1.00 18.45 | N |
| ATOM | 869 | CA | SER | A | 110 | 21.808 | 42.941 | 72.640 | 1.00 18.07 | C |
| ATOM | 870 | CB | SER | A | 110 | 20.721 | 43.457 | 71.691 | 1.00 18.92 | C |
| ATOM | 871 | OG | SER | A | 110 | 20.995 | 43.094 | 70.338 | 1.00 18.20 | O |
| ATOM | 872 | C | SER | A | 110 | 22.027 | 41.449 | 72.369 | 1.00 18.11 | C |
| ATOM | 873 | O | SER | A | 110 | 22.941 | 41.057 | 71.639 | 1.00 17.23 | O |
| ATOM | 874 | N | ARG | A | 111 | 21.176 | 40.622 | 72.960 | 1.00 17.48 | N |
| ATOM | 875 | CA | ARG | A | 111 | 21.277 | 39.188 | 72.771 | 1.00 19.58 | C |
| ATOM | 876 | CB | ARG | A | 111 | 20.197 | 38.474 | 73.590 | 1.00 18.61 | C |
| ATOM | 877 | CG | ARG | A | 111 | 20.318 | 36.960 | 73.600 | 1.00 18.32 | C |
| ATOM | 878 | CD | ARG | A | 111 | 19.171 | 36.329 | 74.382 | 1.00 18.70 | C |
| ATOM | 879 | NE | ARG | A | 111 | 19.175 | 36.728 | 75.789 | 1.00 18.01 | N |
| ATOM | 880 | CZ | ARG | A | 111 | 19.923 | 36.167 | 76.734 | 1.00 16.98 | C |
| ATOM | 881 | NH1 | ARG | A | 111 | 20.744 | 35.166 | 76.436 | 1.00 16.37 | N |
| ATOM | 882 | NH2 | ARG | A | 111 | 19.835 | 36.599 | 77.987 | 1.00 18.47 | N |
| ATOM | 883 | C | ARG | A | 111 | 21.096 | 38.894 | 71.284 | 1.00 19.76 | C |
| ATOM | 884 | O | ARG | A | 111 | 21.820 | 38.084 | 70.705 | 1.00 20.40 | O |
| ATOM | 885 | N | GLU | A | 112 | 20.134 | 39.569 | 70.663 | 1.00 19.77 | N |
| ATOM | 886 | CA | GLU | A | 112 | 19.874 | 39.371 | 69.245 | 1.00 20.35 | C |
| ATOM | 887 | CB | GLU | A | 112 | 18.655 | 40.173 | 68.813 | 1.00 23.90 | C |
| ATOM | 888 | CG | GLU | A | 112 | 18.384 | 40.106 | 67.317 | 1.00 29.42 | C |
| ATOM | 889 | CD | GLU | A | 112 | 18.094 | 41.476 | 66.733 | 1.00 33.50 | C |
| ATOM | 890 | OE1 | GLU | A | 112 | 17.388 | 42.238 | 67.432 | 1.00 34.04 | O |
| ATOM | 891 | OE2 | GLU | A | 112 | 18.556 | 41.787 | 65.591 | 1.00 33.43 | O |
| ATOM | 892 | C | GLU | A | 112 | 21.055 | 39.770 | 68.363 | 1.00 18.52 | C |
| ATOM | 893 | O | GLU | A | 112 | 21.442 | 39.020 | 67.472 | 1.00 17.75 | O |
| ATOM | 894 | N | GLY | A | 113 | 21.602 | 40.963 | 68.609 | 1.00 17.23 | N |
| ATOM | 895 | CA | GLY | A | 113 | 22.723 | 41.454 | 67.833 | 1.00 16.22 | C |
| ATOM | 896 | C | GLY | A | 113 | 23.917 | 40.523 | 67.922 | 1.00 16.93 | C |
| ATOM | 897 | O | GLY | A | 113 | 24.601 | 40.277 | 66.930 | 1.00 16.72 | O |
| ATOM | 898 | N | PHE | A | 114 | 24.148 | 39.997 | 69.120 | 1.00 16.55 | N |
| ATOM | 899 | CA | PHE | A | 114 | 25.257 | 39.088 | 69.383 | 1.00 17.06 | C |
| ATOM | 900 | CB | PHE | A | 114 | 25.342 | 38.820 | 70.895 | 1.00 16.80 | C |
| ATOM | 901 | CG | PHE | A | 114 | 26.464 | 37.902 | 71.292 | 1.00 17.87 | C |
| ATOM | 902 | CD1 | PHE | A | 114 | 26.350 | 36.526 | 71.124 | 1.00 17.64 | C |
| ATOM | 903 | CD2 | PHE | A | 114 | 27.632 | 38.417 | 71.846 | 1.00 17.60 | C |
| ATOM | 904 | CE1 | PHE | A | 114 | 27.377 | 35.665 | 71.501 | 1.00 17.08 | C |
| ATOM | 905 | CE2 | PHE | A | 114 | 28.669 | 37.570 | 72.229 | 1.00 19.14 | C |
| ATOM | 906 | CZ | PHE | A | 114 | 28.544 | 36.189 | 72.057 | 1.00 18.29 | C |
| ATOM | 907 | C | PHE | A | 114 | 25.105 | 37.776 | 68.610 | 1.00 16.15 | C |
| ATOM | 908 | O | PHE | A | 114 | 26.036 | 37.320 | 67.952 | 1.00 16.17 | O |

FIGURE 9 (cont.)

| | | | | | | | | | |
|---|---|---|---|---|---|---|---|---|---|
| ATOM | 909 | N | LEU A 115 | 23.924 | 37.176 | 68.687 | 1.00 | 15.62 | N |
| ATOM | 910 | CA | LEU A 115 | 23.675 | 35.925 | 67.990 | 1.00 | 14.58 | C |
| ATOM | 911 | CB | LEU A 115 | 22.356 | 35.318 | 68.461 | 1.00 | 14.43 | C |
| ATOM | 912 | CG | LEU A 115 | 22.374 | 34.817 | 69.909 | 1.00 | 15.60 | C |
| ATOM | 913 | CD1 | LEU A 115 | 21.052 | 34.142 | 70.222 | 1.00 | 15.94 | C |
| ATOM | 914 | CD2 | LEU A 115 | 23.518 | 33.837 | 70.111 | 1.00 | 15.40 | C |
| ATOM | 915 | C | LEU A 115 | 23.654 | 36.112 | 66.480 | 1.00 | 14.63 | C |
| ATOM | 916 | O | LEU A 115 | 23.980 | 35.196 | 65.732 | 1.00 | 14.40 | O |
| ATOM | 917 | N | LEU A 116 | 23.265 | 37.303 | 66.034 | 1.00 | 14.34 | N |
| ATOM | 918 | CA | LEU A 116 | 23.216 | 37.591 | 64.605 | 1.00 | 13.78 | C |
| ATOM | 919 | CB | LEU A 116 | 22.565 | 38.961 | 64.354 | 1.00 | 14.13 | C |
| ATOM | 920 | CG | LEU A 116 | 21.981 | 39.297 | 62.971 | 1.00 | 16.39 | C |
| ATOM | 921 | CD1 | LEU A 116 | 22.678 | 40.516 | 62.393 | 1.00 | 17.65 | C |
| ATOM | 922 | CD2 | LEU A 116 | 22.095 | 38.107 | 62.031 | 1.00 | 15.48 | C |
| ATOM | 923 | C | LEU A 116 | 24.644 | 37.572 | 64.062 | 1.00 | 12.30 | C |
| ATOM | 924 | O | LEU A 116 | 24.893 | 37.014 | 63.000 | 1.00 | 12.35 | O |
| ATOM | 925 | N | ALA A 117 | 25.585 | 38.161 | 64.798 | 1.00 | 11.38 | N |
| ATOM | 926 | CA | ALA A 117 | 26.979 | 38.182 | 64.357 | 1.00 | 10.61 | C |
| ATOM | 927 | CB | ALA A 117 | 27.785 | 39.113 | 65.230 | 1.00 | 11.32 | C |
| ATOM | 928 | C | ALA A 117 | 27.606 | 36.781 | 64.360 | 1.00 | 11.77 | C |
| ATOM | 929 | O | ALA A 117 | 28.394 | 36.450 | 63.475 | 1.00 | 12.72 | O |
| ATOM | 930 | N | GLN A 118 | 27.247 | 35.960 | 65.346 | 1.00 | 12.36 | N |
| ATOM | 931 | CA | GLN A 118 | 27.772 | 34.601 | 65.453 | 1.00 | 13.35 | C |
| ATOM | 932 | CB | GLN A 118 | 27.382 | 33.991 | 66.805 | 1.00 | 11.56 | C |
| ATOM | 933 | CG | GLN A 118 | 28.098 | 34.596 | 67.995 | 1.00 | 13.58 | C |
| ATOM | 934 | CD | GLN A 118 | 29.523 | 34.084 | 68.137 | 1.00 | 13.93 | C |
| ATOM | 935 | OE1 | GLN A 118 | 30.399 | 34.788 | 68.638 | 1.00 | 16.06 | O |
| ATOM | 936 | NE2 | GLN A 118 | 29.758 | 32.847 | 67.709 | 1.00 | 13.90 | N |
| ATOM | 937 | C | GLN A 118 | 27.231 | 33.711 | 64.334 | 1.00 | 15.03 | C |
| ATOM | 938 | O | GLN A 118 | 27.943 | 32.863 | 63.782 | 1.00 | 16.70 | O |
| ATOM | 939 | N | ASP A 119 | 25.961 | 33.912 | 64.012 | 1.00 | 14.72 | N |
| ATOM | 940 | CA | ASP A 119 | 25.293 | 33.130 | 62.995 | 1.00 | 14.85 | C |
| ATOM | 941 | CB | ASP A 119 | 23.809 | 33.502 | 62.946 | 1.00 | 15.06 | C |
| ATOM | 942 | CG | ASP A 119 | 22.998 | 32.509 | 62.145 | 1.00 | 16.93 | C |
| ATOM | 943 | OD1 | ASP A 119 | 21.840 | 32.818 | 61.796 | 1.00 | 17.06 | O |
| ATOM | 944 | OD2 | ASP A 119 | 23.527 | 31.407 | 61.875 | 1.00 | 16.58 | O |
| ATOM | 945 | C | ASP A 119 | 25.904 | 33.312 | 61.614 | 1.00 | 14.78 | C |
| ATOM | 946 | O | ASP A 119 | 26.235 | 32.340 | 60.934 | 1.00 | 14.80 | O |
| ATOM | 947 | N | ILE A 120 | 26.047 | 34.567 | 61.205 | 1.00 | 14.46 | N |
| ATOM | 948 | CA | ILE A 120 | 26.591 | 34.897 | 59.901 | 1.00 | 13.52 | C |
| ATOM | 949 | CB | ILE A 120 | 26.148 | 36.311 | 59.482 | 1.00 | 14.26 | C |
| ATOM | 950 | CG2 | ILE A 120 | 26.821 | 36.704 | 58.179 | 1.00 | 12.73 | C |
| ATOM | 951 | CG1 | ILE A 120 | 24.622 | 36.365 | 59.371 | 1.00 | 13.28 | C |
| ATOM | 952 | CD1 | ILE A 120 | 24.057 | 37.780 | 59.191 | 1.00 | 13.40 | C |
| ATOM | 953 | C | ILE A 120 | 28.109 | 34.833 | 59.807 | 1.00 | 13.69 | C |
| ATOM | 954 | O | ILE A 120 | 28.648 | 34.278 | 58.858 | 1.00 | 13.41 | O |
| ATOM | 955 | N | SER A 121 | 28.799 | 35.389 | 60.797 | 1.00 | 15.32 | N |
| ATOM | 956 | CA | SER A 121 | 30.262 | 35.435 | 60.776 | 1.00 | 16.02 | C |
| ATOM | 957 | CB | SER A 121 | 30.753 | 36.633 | 61.591 | 1.00 | 15.57 | C |
| ATOM | 958 | OG | SER A 121 | 29.984 | 37.791 | 61.326 | 1.00 | 16.40 | O |
| ATOM | 959 | C | SER A 121 | 31.009 | 34.189 | 61.258 | 1.00 | 16.28 | C |
| ATOM | 960 | O | SER A 121 | 32.213 | 34.068 | 61.037 | 1.00 | 15.21 | O |
| ATOM | 961 | N | SER A 122 | 30.316 | 33.266 | 61.914 | 1.00 | 17.93 | N |
| ATOM | 962 | CA | SER A 122 | 30.989 | 32.070 | 62.424 | 1.00 | 17.78 | C |
| ATOM | 963 | CB | SER A 122 | 31.157 | 32.182 | 63.941 | 1.00 | 18.85 | C |
| ATOM | 964 | OG | SER A 122 | 31.842 | 31.061 | 64.471 | 1.00 | 17.47 | O |
| ATOM | 965 | C | SER A 122 | 30.328 | 30.734 | 62.077 | 1.00 | 17.06 | C |
| ATOM | 966 | O | SER A 122 | 30.988 | 29.830 | 61.562 | 1.00 | 17.87 | O |
| ATOM | 967 | N | TYR A 123 | 29.037 | 30.591 | 62.349 | 1.00 | 16.11 | N |
| ATOM | 968 | CA | TYR A 123 | 28.390 | 29.323 | 62.033 | 1.00 | 15.05 | C |
| ATOM | 969 | CB | TYR A 123 | 26.954 | 29.290 | 62.544 | 1.00 | 16.10 | C |
| ATOM | 970 | CG | TYR A 123 | 26.266 | 27.985 | 62.203 | 1.00 | 15.76 | C |
| ATOM | 971 | CD1 | TYR A 123 | 26.603 | 26.801 | 62.860 | 1.00 | 15.13 | C |
| ATOM | 972 | CE1 | TYR A 123 | 26.024 | 25.586 | 62.497 | 1.00 | 16.79 | C |
| ATOM | 973 | CD2 | TYR A 123 | 25.331 | 27.922 | 61.176 | 1.00 | 16.02 | C |

FIGURE 9 (cont.)

```
ATOM    974  CE2 TYR A 123      24.750  26.718  60.806  1.00 16.76           C
ATOM    975  CZ  TYR A 123      25.099  25.556  61.468  1.00 17.24           C
ATOM    976  OH  TYR A 123      24.510  24.375  61.096  1.00 19.61           O
ATOM    977  C   TYR A 123      28.375  29.014  60.539  1.00 14.26           C
ATOM    978  O   TYR A 123      28.373  27.860  60.141  1.00 15.36           O
ATOM    979  N   SER A 124      28.361  30.047  59.713  1.00 14.46           N
ATOM    980  CA  SER A 124      28.314  29.851  58.279  1.00 13.96           C
ATOM    981  CB  SER A 124      28.254  31.208  57.570  1.00 12.67           C
ATOM    982  OG  SER A 124      29.361  32.015  57.901  1.00 14.72           O
ATOM    983  C   SER A 124      29.456  28.999  57.726  1.00 14.28           C
ATOM    984  O   SER A 124      29.263  28.260  56.757  1.00 13.40           O
ATOM    985  N   LEU A 125      30.635  29.091  58.339  1.00 15.02           N
ATOM    986  CA  LEU A 125      31.785  28.306  57.886  1.00 15.26           C
ATOM    987  CB  LEU A 125      33.073  28.718  58.622  1.00 14.78           C
ATOM    988  CG  LEU A 125      34.360  27.950  58.252  1.00 13.82           C
ATOM    989  CD1 LEU A 125      34.786  28.304  56.837  1.00 10.43           C
ATOM    990  CD2 LEU A 125      35.484  28.288  59.237  1.00 13.45           C
ATOM    991  C   LEU A 125      31.516  26.830  58.145  1.00 15.06           C
ATOM    992  O   LEU A 125      31.947  25.971  57.379  1.00 15.00           O
ATOM    993  N   THR A 126      30.798  26.553  59.232  1.00 15.22           N
ATOM    994  CA  THR A 126      30.453  25.187  59.625  1.00 15.29           C
ATOM    995  CB  THR A 126      29.744  25.156  60.973  1.00 14.64           C
ATOM    996  OG1 THR A 126      30.649  25.570  61.996  1.00 14.38           O
ATOM    997  CG2 THR A 126      29.242  23.754  61.275  1.00 16.75           C
ATOM    998  C   THR A 126      29.529  24.527  58.629  1.00 14.41           C
ATOM    999  O   THR A 126      29.852  23.487  58.073  1.00 15.26           O
ATOM   1000  N   ILE A 127      28.362  25.127  58.434  1.00 14.24           N
ATOM   1001  CA  ILE A 127      27.376  24.615  57.500  1.00 12.41           C
ATOM   1002  CB  ILE A 127      26.123  25.503  57.501  1.00 13.05           C
ATOM   1003  CG2 ILE A 127      26.507  26.936  57.226  1.00 14.07           C
ATOM   1004  CG1 ILE A 127      25.110  25.002  56.473  1.00 14.39           C
ATOM   1005  CD1 ILE A 127      24.320  23.798  56.928  1.00 16.80           C
ATOM   1006  C   ILE A 127      27.972  24.561  56.090  1.00 12.07           C
ATOM   1007  O   ILE A 127      27.757  23.594  55.364  1.00 10.80           O
ATOM   1008  N   VAL A 128      28.725  25.592  55.706  1.00 12.58           N
ATOM   1009  CA  VAL A 128      29.337  25.618  54.378  1.00 13.20           C
ATOM   1010  CB  VAL A 128      30.080  26.957  54.110  1.00 12.64           C
ATOM   1011  CG1 VAL A 128      30.989  26.820  52.912  1.00 11.57           C
ATOM   1012  CG2 VAL A 128      29.077  28.060  53.830  1.00 11.91           C
ATOM   1013  C   VAL A 128      30.314  24.458  54.190  1.00 15.32           C
ATOM   1014  O   VAL A 128      30.325  23.815  53.140  1.00 16.47           O
ATOM   1015  N   ALA A 129      31.131  24.193  55.209  1.00 16.22           N
ATOM   1016  CA  ALA A 129      32.104  23.101  55.155  1.00 16.86           C
ATOM   1017  CB  ALA A 129      33.005  23.137  56.394  1.00 14.97           C
ATOM   1018  C   ALA A 129      31.418  21.734  55.058  1.00 17.77           C
ATOM   1019  O   ALA A 129      31.905  20.826  54.366  1.00 17.42           O
ATOM   1020  N   HIS A 130      30.302  21.588  55.766  1.00 17.96           N
ATOM   1021  CA  HIS A 130      29.554  20.332  55.771  1.00 20.40           C
ATOM   1022  CB  HIS A 130      28.372  20.435  56.742  1.00 22.57           C
ATOM   1023  CG  HIS A 130      27.620  19.151  56.930  1.00 25.71           C
ATOM   1024  CD2 HIS A 130      28.029  17.926  57.340  1.00 26.42           C
ATOM   1025  ND1 HIS A 130      26.262  19.046  56.711  1.00 27.23           N
ATOM   1026  CE1 HIS A 130      25.868  17.813  56.977  1.00 27.19           C
ATOM   1027  NE2 HIS A 130      26.921  17.113  57.361  1.00 27.20           N
ATOM   1028  C   HIS A 130      29.051  20.006  54.360  1.00 20.67           C
ATOM   1029  O   HIS A 130      29.188  18.870  53.878  1.00 19.29           O
ATOM   1030  N   GLU A 131      28.487  21.010  53.692  1.00 19.57           N
ATOM   1031  CA  GLU A 131      27.977  20.808  52.342  1.00 19.55           C
ATOM   1032  CB  GLU A 131      27.032  21.949  51.951  1.00 19.31           C
ATOM   1033  CG  GLU A 131      25.795  22.075  52.844  1.00 20.91           C
ATOM   1034  CD  GLU A 131      25.075  20.750  53.039  1.00 22.60           C
ATOM   1035  OE1 GLU A 131      24.777  20.065  52.032  1.00 24.62           O
ATOM   1036  OE2 GLU A 131      24.802  20.389  54.203  1.00 23.98           O
ATOM   1037  C   GLU A 131      29.089  20.694  51.303  1.00 18.41           C
ATOM   1038  O   GLU A 131      29.000  19.878  50.393  1.00 19.20           O
```

FIGURE 9 (cont.)

| | | | | | | | | | | |
|---|---|---|---|---|---|---|---|---|---|---|
| ATOM | 1039 | N | ALA | A | 132 | 30.137 | 21.499 | 51.444 | 1.00 16.44 | N |
| ATOM | 1040 | CA | ALA | A | 132 | 31.239 | 21.492 | 50.484 | 1.00 15.81 | C |
| ATOM | 1041 | CB | ALA | A | 132 | 32.140 | 22.716 | 50.708 | 1.00 15.25 | C |
| ATOM | 1042 | C | ALA | A | 132 | 32.066 | 20.212 | 50.543 | 1.00 14.27 | C |
| ATOM | 1043 | O | ALA | A | 132 | 32.682 | 19.805 | 49.554 | 1.00 12.68 | O |
| ATOM | 1044 | N | LYS | A | 133 | 32.092 | 19.591 | 51.712 | 1.00 15.40 | N |
| ATOM | 1045 | CA | LYS | A | 133 | 32.826 | 18.348 | 51.885 | 1.00 15.90 | C |
| ATOM | 1046 | CB | LYS | A | 133 | 32.687 | 17.858 | 53.330 | 1.00 18.02 | C |
| ATOM | 1047 | CG | LYS | A | 133 | 33.299 | 16.495 | 53.595 | 1.00 22.05 | C |
| ATOM | 1048 | CD | LYS | A | 133 | 33.105 | 16.086 | 55.049 | 1.00 23.68 | C |
| ATOM | 1049 | CE | LYS | A | 133 | 33.178 | 14.575 | 55.199 | 1.00 23.13 | C |
| ATOM | 1050 | NZ | LYS | A | 133 | 32.698 | 14.168 | 56.552 | 1.00 25.63 | N |
| ATOM | 1051 | C | LYS | A | 133 | 32.273 | 17.308 | 50.910 | 1.00 15.94 | C |
| ATOM | 1052 | O | LYS | A | 133 | 33.009 | 16.450 | 50.447 | 1.00 15.49 | O |
| ATOM | 1053 | N | LYS | A | 134 | 30.980 | 17.400 | 50.589 | 1.00 16.55 | N |
| ATOM | 1054 | CA | LYS | A | 134 | 30.344 | 16.465 | 49.651 | 1.00 18.38 | C |
| ATOM | 1055 | CB | LYS | A | 134 | 28.840 | 16.690 | 49.582 | 1.00 19.48 | C |
| ATOM | 1056 | CG | LYS | A | 134 | 28.071 | 16.386 | 50.846 | 1.00 20.78 | C |
| ATOM | 1057 | CD | LYS | A | 134 | 26.654 | 16.932 | 50.698 | 1.00 22.34 | C |
| ATOM | 1058 | CE | LYS | A | 134 | 25.768 | 16.532 | 51.867 | 1.00 24.40 | C |
| ATOM | 1059 | NZ | LYS | A | 134 | 26.317 | 16.992 | 53.176 | 1.00 26.47 | N |
| ATOM | 1060 | C | LYS | A | 134 | 30.895 | 16.599 | 48.234 | 1.00 18.35 | C |
| ATOM | 1061 | O | LYS | A | 134 | 30.730 | 15.699 | 47.413 | 1.00 20.60 | O |
| ATOM | 1062 | N | LEU | A | 135 | 31.526 | 17.727 | 47.939 | 1.00 17.79 | N |
| ATOM | 1063 | CA | LEU | A | 135 | 32.105 | 17.940 | 46.615 | 1.00 16.76 | C |
| ATOM | 1064 | CB | LEU | A | 135 | 31.732 | 19.323 | 46.062 | 1.00 16.93 | C |
| ATOM | 1065 | CG | LEU | A | 135 | 30.246 | 19.680 | 46.052 | 1.00 16.27 | C |
| ATOM | 1066 | CD1 | LEU | A | 135 | 30.027 | 20.951 | 45.242 | 1.00 16.14 | C |
| ATOM | 1067 | CD2 | LEU | A | 135 | 29.459 | 18.530 | 45.445 | 1.00 16.21 | C |
| ATOM | 1068 | C | LEU | A | 135 | 33.620 | 17.824 | 46.707 | 1.00 16.09 | C |
| ATOM | 1069 | O | LEU | A | 135 | 34.333 | 18.265 | 45.808 | 1.00 13.96 | O |
| ATOM | 1070 | N | MET | A | 136 | 34.104 | 17.241 | 47.805 | 1.00 15.50 | N |
| ATOM | 1071 | CA | MET | A | 136 | 35.538 | 17.054 | 47.993 | 1.00 17.12 | C |
| ATOM | 1072 | CB | MET | A | 136 | 36.095 | 18.123 | 48.941 | 1.00 17.57 | C |
| ATOM | 1073 | CG | MET | A | 136 | 35.966 | 19.541 | 48.412 | 1.00 19.51 | C |
| ATOM | 1074 | SD | MET | A | 136 | 36.738 | 20.782 | 49.462 | 1.00 20.52 | S |
| ATOM | 1075 | CE | MET | A | 136 | 35.707 | 20.690 | 50.889 | 1.00 19.00 | C |
| ATOM | 1076 | C | MET | A | 136 | 35.849 | 15.657 | 48.537 | 1.00 17.49 | C |
| ATOM | 1077 | O | MET | A | 136 | 36.452 | 15.509 | 49.603 | 1.00 16.74 | O |
| ATOM | 1078 | N | PRO | A | 137 | 35.432 | 14.610 | 47.806 | 1.00 18.08 | N |
| ATOM | 1079 | CD | PRO | A | 137 | 34.765 | 14.632 | 46.488 | 1.00 18.52 | C |
| ATOM | 1080 | CA | PRO | A | 137 | 35.680 | 13.231 | 48.240 | 1.00 18.26 | C |
| ATOM | 1081 | CB | PRO | A | 137 | 34.961 | 12.399 | 47.180 | 1.00 19.23 | C |
| ATOM | 1082 | CG | PRO | A | 137 | 35.090 | 13.257 | 45.938 | 1.00 18.66 | C |
| ATOM | 1083 | C | PRO | A | 137 | 37.160 | 12.892 | 48.317 | 1.00 19.05 | C |
| ATOM | 1084 | O | PRO | A | 137 | 37.550 | 12.001 | 49.061 | 1.00 19.43 | O |
| ATOM | 1085 | N | GLU | A | 138 | 37.976 | 13.609 | 47.552 | 1.00 18.84 | N |
| ATOM | 1086 | CA | GLU | A | 138 | 39.410 | 13.367 | 47.529 | 1.00 21.56 | C |
| ATOM | 1087 | CB | GLU | A | 138 | 39.933 | 13.481 | 46.104 | 1.00 24.27 | C |
| ATOM | 1088 | CG | GLU | A | 138 | 40.043 | 12.179 | 45.365 | 1.00 29.66 | C |
| ATOM | 1089 | CD | GLU | A | 138 | 40.645 | 12.381 | 43.987 | 1.00 33.95 | C |
| ATOM | 1090 | OE1 | GLU | A | 138 | 39.901 | 12.794 | 43.058 | 1.00 35.25 | O |
| ATOM | 1091 | OE2 | GLU | A | 138 | 41.872 | 12.149 | 43.843 | 1.00 35.00 | O |
| ATOM | 1092 | C | GLU | A | 138 | 40.246 | 14.282 | 48.413 | 1.00 21.01 | C |
| ATOM | 1093 | O | GLU | A | 138 | 41.457 | 14.079 | 48.544 | 1.00 20.72 | O |
| ATOM | 1094 | N | GLY | A | 139 | 39.611 | 15.288 | 49.009 | 1.00 21.58 | N |
| ATOM | 1095 | CA | GLY | A | 139 | 40.336 | 16.220 | 49.859 | 1.00 20.16 | C |
| ATOM | 1096 | C | GLY | A | 139 | 40.223 | 17.627 | 49.307 | 1.00 19.54 | C |
| ATOM | 1097 | O | GLY | A | 139 | 39.645 | 17.830 | 48.240 | 1.00 19.66 | O |
| ATOM | 1098 | N | GLY | A | 140 | 40.768 | 18.604 | 50.021 | 1.00 18.86 | N |
| ATOM | 1099 | CA | GLY | A | 140 | 40.683 | 19.970 | 49.547 | 1.00 18.97 | C |
| ATOM | 1100 | C | GLY | A | 140 | 41.087 | 20.981 | 50.598 | 1.00 18.71 | C |
| ATOM | 1101 | O | GLY | A | 140 | 41.706 | 20.612 | 51.593 | 1.00 19.94 | O |
| ATOM | 1102 | N | SER | A | 141 | 40.719 | 22.244 | 50.388 | 1.00 17.36 | N |
| ATOM | 1103 | CA | SER | A | 141 | 41.076 | 23.317 | 51.311 | 1.00 17.90 | C |

FIGURE 9 (cont.)

| ATOM | 1104 | CB  | SER A 141 | 42.374 | 23.965 | 50.855 | 1.00 | 18.24 | C |
| ATOM | 1105 | OG  | SER A 141 | 42.537 | 25.217 | 51.486 | 1.00 | 23.12 | O |
| ATOM | 1106 | C   | SER A 141 | 40.033 | 24.413 | 51.512 | 1.00 | 17.68 | C |
| ATOM | 1107 | O   | SER A 141 | 39.494 | 24.970 | 50.550 | 1.00 | 17.46 | O |
| ATOM | 1108 | N   | ILE A 142 | 39.771 | 24.727 | 52.778 | 1.00 | 16.97 | N |
| ATOM | 1109 | CA  | ILE A 142 | 38.804 | 25.752 | 53.160 | 1.00 | 15.78 | C |
| ATOM | 1110 | CB  | ILE A 142 | 37.811 | 25.228 | 54.193 | 1.00 | 16.07 | C |
| ATOM | 1111 | CG2 | ILE A 142 | 36.648 | 26.203 | 54.322 | 1.00 | 15.58 | C |
| ATOM | 1112 | CG1 | ILE A 142 | 37.329 | 23.832 | 53.813 | 1.00 | 16.19 | C |
| ATOM | 1113 | CD1 | ILE A 142 | 36.342 | 23.805 | 52.683 | 1.00 | 19.56 | C |
| ATOM | 1114 | C   | ILE A 142 | 39.544 | 26.906 | 53.821 | 1.00 | 14.77 | C |
| ATOM | 1115 | O   | ILE A 142 | 40.300 | 26.696 | 54.766 | 1.00 | 14.44 | O |
| ATOM | 1116 | N   | VAL A 143 | 39.335 | 28.122 | 53.331 | 1.00 | 15.75 | N |
| ATOM | 1117 | CA  | VAL A 143 | 39.996 | 29.294 | 53.918 | 1.00 | 15.12 | C |
| ATOM | 1118 | CB  | VAL A 143 | 41.040 | 29.897 | 52.956 | 1.00 | 13.84 | C |
| ATOM | 1119 | CG1 | VAL A 143 | 41.668 | 31.132 | 53.579 | 1.00 | 14.62 | C |
| ATOM | 1120 | CG2 | VAL A 143 | 42.113 | 28.871 | 52.643 | 1.00 | 14.47 | C |
| ATOM | 1121 | C   | VAL A 143 | 38.994 | 30.384 | 54.304 | 1.00 | 15.45 | C |
| ATOM | 1122 | O   | VAL A 143 | 38.112 | 30.736 | 53.525 | 1.00 | 15.37 | O |
| ATOM | 1123 | N   | ALA A 144 | 39.134 | 30.903 | 55.519 | 1.00 | 16.78 | N |
| ATOM | 1124 | CA  | ALA A 144 | 38.257 | 31.957 | 56.025 | 1.00 | 18.15 | C |
| ATOM | 1125 | CB  | ALA A 144 | 37.585 | 31.512 | 57.309 | 1.00 | 18.07 | C |
| ATOM | 1126 | C   | ALA A 144 | 39.052 | 33.227 | 56.283 | 1.00 | 18.88 | C |
| ATOM | 1127 | O   | ALA A 144 | 40.272 | 33.183 | 56.487 | 1.00 | 19.34 | O |
| ATOM | 1128 | N   | THR A 145 | 38.347 | 34.355 | 56.286 | 1.00 | 19.91 | N |
| ATOM | 1129 | CA  | THR A 145 | 38.960 | 35.658 | 56.514 | 1.00 | 18.69 | C |
| ATOM | 1130 | CB  | THR A 145 | 38.472 | 36.670 | 55.470 | 1.00 | 19.74 | C |
| ATOM | 1131 | OG1 | THR A 145 | 38.554 | 36.084 | 54.167 | 1.00 | 21.00 | O |
| ATOM | 1132 | CG2 | THR A 145 | 39.328 | 37.906 | 55.498 | 1.00 | 19.70 | C |
| ATOM | 1133 | C   | THR A 145 | 38.627 | 36.204 | 57.906 | 1.00 | 17.74 | C |
| ATOM | 1134 | O   | THR A 145 | 37.453 | 36.295 | 58.289 | 1.00 | 16.42 | O |
| ATOM | 1135 | N   | THR A 146 | 39.663 | 36.567 | 58.656 | 1.00 | 15.56 | N |
| ATOM | 1136 | CA  | THR A 146 | 39.480 | 37.119 | 59.993 | 1.00 | 13.94 | C |
| ATOM | 1137 | CB  | THR A 146 | 39.816 | 36.073 | 61.076 | 1.00 | 13.38 | C |
| ATOM | 1138 | OG1 | THR A 146 | 39.520 | 36.617 | 62.366 | 1.00 | 12.39 | O |
| ATOM | 1139 | CG2 | THR A 146 | 41.279 | 35.680 | 61.006 | 1.00 | 10.26 | C |
| ATOM | 1140 | C   | THR A 146 | 40.318 | 38.388 | 60.211 | 1.00 | 14.00 | C |
| ATOM | 1141 | O   | THR A 146 | 40.971 | 38.868 | 59.288 | 1.00 | 11.31 | O |
| ATOM | 1142 | N   | TYR A 147 | 40.303 | 38.909 | 61.439 | 1.00 | 13.84 | N |
| ATOM | 1143 | CA  | TYR A 147 | 41.009 | 40.149 | 61.787 | 1.00 | 14.92 | C |
| ATOM | 1144 | CB  | TYR A 147 | 39.999 | 41.312 | 61.709 | 1.00 | 13.13 | C |
| ATOM | 1145 | CG  | TYR A 147 | 40.506 | 42.672 | 62.129 | 1.00 | 13.78 | C |
| ATOM | 1146 | CD1 | TYR A 147 | 41.655 | 43.212 | 61.560 | 1.00 | 15.14 | C |
| ATOM | 1147 | CE1 | TYR A 147 | 42.103 | 44.484 | 61.903 | 1.00 | 16.03 | C |
| ATOM | 1148 | CD2 | TYR A 147 | 39.805 | 43.448 | 63.066 | 1.00 | 15.11 | C |
| ATOM | 1149 | CE2 | TYR A 147 | 40.243 | 44.739 | 63.418 | 1.00 | 12.76 | C |
| ATOM | 1150 | CZ  | TYR A 147 | 41.395 | 45.246 | 62.827 | 1.00 | 15.35 | C |
| ATOM | 1151 | OH  | TYR A 147 | 41.846 | 46.516 | 63.113 | 1.00 | 16.34 | O |
| ATOM | 1152 | C   | TYR A 147 | 41.625 | 40.048 | 63.192 | 1.00 | 14.44 | C |
| ATOM | 1153 | O   | TYR A 147 | 41.158 | 39.251 | 64.001 | 1.00 | 15.81 | O |
| ATOM | 1154 | N   | LEU A 148 | 42.658 | 40.847 | 63.484 | 1.00 | 13.76 | N |
| ATOM | 1155 | CA  | LEU A 148 | 43.314 | 40.803 | 64.799 | 1.00 | 13.97 | C |
| ATOM | 1156 | CB  | LEU A 148 | 44.454 | 41.824 | 64.897 | 1.00 | 16.68 | C |
| ATOM | 1157 | CG  | LEU A 148 | 45.853 | 41.427 | 64.417 | 1.00 | 18.20 | C |
| ATOM | 1158 | CD1 | LEU A 148 | 46.801 | 42.592 | 64.632 | 1.00 | 19.81 | C |
| ATOM | 1159 | CD2 | LEU A 148 | 46.355 | 40.208 | 65.189 | 1.00 | 20.81 | C |
| ATOM | 1160 | C   | LEU A 148 | 42.346 | 41.035 | 65.948 | 1.00 | 13.81 | C |
| ATOM | 1161 | O   | LEU A 148 | 42.632 | 40.682 | 67.089 | 1.00 | 13.88 | O |
| ATOM | 1162 | N   | GLY A 149 | 41.203 | 41.641 | 65.645 | 1.00 | 15.07 | N |
| ATOM | 1163 | CA  | GLY A 149 | 40.199 | 41.875 | 66.670 | 1.00 | 14.39 | C |
| ATOM | 1164 | C   | GLY A 149 | 39.667 | 40.565 | 67.242 | 1.00 | 13.98 | C |
| ATOM | 1165 | O   | GLY A 149 | 38.987 | 40.554 | 68.266 | 1.00 | 14.48 | O |
| ATOM | 1166 | N   | GLY A 150 | 39.966 | 39.456 | 66.576 | 1.00 | 14.20 | N |
| ATOM | 1167 | CA  | GLY A 150 | 39.520 | 38.167 | 67.070 | 1.00 | 13.97 | C |
| ATOM | 1168 | C   | GLY A 150 | 40.416 | 37.650 | 68.186 | 1.00 | 15.21 | C |

FIGURE 9 (cont.)

| | | | | | | | | | | |
|---|---|---|---|---|---|---|---|---|---|---|
| ATOM | 1169 | O | GLY | A | 150 | 40.010 | 36.789 | 68.974 | 1.00 15.47 | O |
| ATOM | 1170 | N | GLU | A | 151 | 41.627 | 38.198 | 68.275 | 1.00 15.27 | N |
| ATOM | 1171 | CA | GLU | A | 151 | 42.599 | 37.779 | 69.282 | 1.00 16.88 | C |
| ATOM | 1172 | CB | GLU | A | 151 | 43.945 | 37.493 | 68.619 | 1.00 18.10 | C |
| ATOM | 1173 | CG | GLU | A | 151 | 43.961 | 36.401 | 67.569 | 1.00 18.66 | C |
| ATOM | 1174 | CD | GLU | A | 151 | 45.353 | 36.247 | 66.968 | 1.00 20.93 | C |
| ATOM | 1175 | OE1 | GLU | A | 151 | 45.561 | 36.620 | 65.781 | 1.00 19.65 | O |
| ATOM | 1176 | OE2 | GLU | A | 151 | 46.246 | 35.770 | 67.707 | 1.00 21.33 | O |
| ATOM | 1177 | C | GLU | A | 151 | 42.831 | 38.802 | 70.396 | 1.00 17.62 | C |
| ATOM | 1178 | O | GLU | A | 151 | 43.204 | 38.436 | 71.513 | 1.00 18.04 | O |
| ATOM | 1179 | N | PHE | A | 152 | 42.624 | 40.077 | 70.084 | 1.00 17.40 | N |
| ATOM | 1180 | CA | PHE | A | 152 | 42.827 | 41.161 | 71.044 | 1.00 17.07 | C |
| ATOM | 1181 | CB | PHE | A | 152 | 44.079 | 41.961 | 70.660 | 1.00 18.02 | C |
| ATOM | 1182 | CG | PHE | A | 152 | 45.323 | 41.118 | 70.498 | 1.00 19.51 | C |
| ATOM | 1183 | CD1 | PHE | A | 152 | 46.101 | 40.764 | 71.605 | 1.00 21.72 | C |
| ATOM | 1184 | CD2 | PHE | A | 152 | 45.693 | 40.636 | 69.247 | 1.00 20.01 | C |
| ATOM | 1185 | CE1 | PHE | A | 152 | 47.225 | 39.936 | 71.463 | 1.00 21.72 | C |
| ATOM | 1186 | CE2 | PHE | A | 152 | 46.820 | 39.804 | 69.097 | 1.00 20.07 | C |
| ATOM | 1187 | CZ | PHE | A | 152 | 47.581 | 39.456 | 70.207 | 1.00 20.00 | C |
| ATOM | 1188 | C | PHE | A | 152 | 41.604 | 42.089 | 71.016 | 1.00 17.10 | C |
| ATOM | 1189 | O | PHE | A | 152 | 40.907 | 42.167 | 70.001 | 1.00 16.67 | O |
| ATOM | 1190 | N | ALA | A | 153 | 41.333 | 42.782 | 72.120 | 1.00 16.12 | N |
| ATOM | 1191 | CA | ALA | A | 153 | 40.198 | 43.700 | 72.156 | 1.00 15.33 | C |
| ATOM | 1192 | CB | ALA | A | 153 | 39.861 | 44.072 | 73.594 | 1.00 13.79 | C |
| ATOM | 1193 | C | ALA | A | 153 | 40.549 | 44.956 | 71.351 | 1.00 16.03 | C |
| ATOM | 1194 | O | ALA | A | 153 | 41.496 | 45.675 | 71.677 | 1.00 14.42 | O |
| ATOM | 1195 | N | VAL | A | 154 | 39.789 | 45.204 | 70.289 | 1.00 17.30 | N |
| ATOM | 1196 | CA | VAL | A | 154 | 40.018 | 46.365 | 69.426 | 1.00 18.05 | C |
| ATOM | 1197 | CB | VAL | A | 154 | 40.175 | 45.943 | 67.947 | 1.00 18.09 | C |
| ATOM | 1198 | CG1 | VAL | A | 154 | 40.244 | 47.175 | 67.059 | 1.00 19.02 | C |
| ATOM | 1199 | CG2 | VAL | A | 154 | 41.438 | 45.093 | 67.781 | 1.00 17.30 | C |
| ATOM | 1200 | C' | VAL | A | 154 | 38.841 | 47.324 | 69.541 | 1.00 18.15 | C |
| ATOM | 1201 | O | VAL | A | 154 | 37.686 | 46.902 | 69.426 | 1.00 19.41 | O |
| ATOM | 1202 | N | GLN | A | 155 | 39.141 | 48.603 | 69.767 | 1.00 18.03 | N |
| ATOM | 1203 | CA | GLN | A | 155 | 38.113 | 49.637 | 69.932 | 1.00 19.79 | C |
| ATOM | 1204 | CB | GLN | A | 155 | 38.737 | 51.049 | 69.874 | 1.00 22.11 | C |
| ATOM | 1205 | CG | GLN | A | 155 | 39.972 | 51.256 | 70.774 | 1.00 26.08 | C |
| ATOM | 1206 | CD | GLN | A | 155 | 39.663 | 51.278 | 72.271 | 1.00 27.99 | C |
| ATOM | 1207 | OE1 | GLN | A | 155 | 40.528 | 50.951 | 73.088 | 1.00 29.74 | O |
| ATOM | 1208 | NE2 | GLN | A | 155 | 38.443 | 51.685 | 72.638 | 1.00 28.95 | N |
| ATOM | 1209 | C | GLN | A | 155 | 37.003 | 49.542 | 68.886 | 1.00 17.65 | C |
| ATOM | 1210 | O | GLN | A | 155 | 37.268 | 49.421 | 67.691 | 1.00 14.36 | O |
| ATOM | 1211 | N | ASN | A | 156 | 35.766 | 49.591 | 69.370 | 1.00 16.81 | N |
| ATOM | 1212 | CA | ASN | A | 156 | 34.566 | 49.537 | 68.541 | 1.00 17.34 | C |
| ATOM | 1213 | CB | ASN | A | 156 | 34.545 | 50.701 | 67.530 | 1.00 17.81 | C |
| ATOM | 1214 | CG | ASN | A | 156 | 34.423 | 52.060 | 68.196 | 1.00 19.67 | C |
| ATOM | 1215 | OD1 | ASN | A | 156 | 33.622 | 52.250 | 69.106 | 1.00 20.31 | O |
| ATOM | 1216 | ND2 | ASN | A | 156 | 35.211 | 53.017 | 67.732 | 1.00 20.82 | N |
| ATOM | 1217 | C | ASN | A | 156 | 34.315 | 48.234 | 67.790 | 1.00 16.48 | C |
| ATOM | 1218 | O | ASN | A | 156 | 33.200 | 48.021 | 67.311 | 1.00 17.93 | O |
| ATOM | 1219 | N | TYR | A | 157 | 35.315 | 47.365 | 67.661 | 1.00 14.88 | N |
| ATOM | 1220 | CA | TYR | A | 157 | 35.078 | 46.118 | 66.931 | 1.00 14.49 | C |
| ATOM | 1221 | CB | TYR | A | 157 | 36.364 | 45.315 | 66.778 | 1.00 12.54 | C |
| ATOM | 1222 | CG | TYR | A | 157 | 36.303 | 44.366 | 65.605 | 1.00 13.22 | C |
| ATOM | 1223 | CD1 | TYR | A | 157 | 35.869 | 44.810 | 64.358 | 1.00 13.73 | C |
| ATOM | 1224 | CE1 | TYR | A | 157 | 35.803 | 43.951 | 63.271 | 1.00 14.29 | C |
| ATOM | 1225 | CD2 | TYR | A | 157 | 36.670 | 43.033 | 65.733 | 1.00 14.41 | C |
| ATOM | 1226 | CE2 | TYR | A | 157 | 36.604 | 42.152 | 64.643 | 1.00 14.53 | C |
| ATOM | 1227 | CZ | TYR | A | 157 | 36.173 | 42.622 | 63.418 | 1.00 14.45 | C |
| ATOM | 1228 | OH | TYR | A | 157 | 36.136 | 41.790 | 62.322 | 1.00 15.49 | O |
| ATOM | 1229 | C | TYR | A | 157 | 34.004 | 45.289 | 67.652 | 1.00 14.86 | C |
| ATOM | 1230 | O | TYR | A | 157 | 33.212 | 44.580 | 67.030 | 1.00 14.71 | O |
| ATOM | 1231 | N | ASN | A | 158 | 33.999 | 45.396 | 68.973 | 1.00 15.36 | N |
| ATOM | 1232 | CA | ASN | A | 158 | 33.018 | 44.747 | 69.826 | 1.00 17.18 | C |
| ATOM | 1233 | CB | ASN | A | 158 | 31.876 | 45.733 | 70.082 | 1.00 17.04 | C |

FIGURE 9 (cont.)

| | | | | | | | | | |
|---|---|---|---|---|---|---|---|---|---|
| ATOM | 1234 | CG | ASN | A | 158 | 32.376 | 47.137 | 70.408 | 1.00 17.59 | C |
| ATOM | 1235 | OD1 | ASN | A | 158 | 33.521 | 47.324 | 70.840 | 1.00 16.99 | O |
| ATOM | 1236 | ND2 | ASN | A | 158 | 31.509 | 48.130 | 70.220 | 1.00 17.15 | N |
| ATOM | 1237 | C | ASN | A | 158 | 32.430 | 43.396 | 69.396 | 1.00 17.17 | C |
| ATOM | 1238 | O | ASN | A | 158 | 33.119 | 42.380 | 69.390 | 1.00 18.43 | O |
| ATOM | 1239 | N | VAL | A | 159 | 31.147 | 43.386 | 69.051 | 1.00 17.60 | N |
| ATOM | 1240 | CA | VAL | A | 159 | 30.470 | 42.144 | 68.677 | 1.00 17.57 | C |
| ATOM | 1241 | CB | VAL | A | 159 | 29.006 | 42.410 | 68.249 | 1.00 16.42 | C |
| ATOM | 1242 | CG1 | VAL | A | 159 | 28.965 | 43.054 | 66.890 | 1.00 16.40 | C |
| ATOM | 1243 | CG2 | VAL | A | 159 | 28.235 | 41.112 | 68.238 | 1.00 20.36 | C |
| ATOM | 1244 | C | VAL | A | 159 | 31.172 | 41.315 | 67.595 | 1.00 16.08 | C |
| ATOM | 1245 | O | VAL | A | 159 | 31.208 | 40.095 | 67.685 | 1.00 16.73 | O |
| ATOM | 1246 | N | MET | A | 160 | 31.732 | 41.964 | 66.582 | 1.00 15.13 | N |
| ATOM | 1247 | CA | MET | A | 160 | 32.430 | 41.237 | 65.521 | 1.00 14.60 | C |
| ATOM | 1248 | CB | MET | A | 160 | 32.711 | 42.158 | 64.330 | 1.00 15.91 | C |
| ATOM | 1249 | CG | MET | A | 160 | 31.547 | 42.344 | 63.388 | 1.00 14.60 | C |
| ATOM | 1250 | SD | MET | A | 160 | 31.002 | 40.792 | 62.660 | 1.00 16.57 | S |
| ATOM | 1251 | CE | MET | A | 160 | 32.563 | 40.080 | 62.063 | 1.00 16.01 | C |
| ATOM | 1252 | C | MET | A | 160 | 33.743 | 40.626 | 66.015 | 1.00 13.95 | C |
| ATOM | 1253 | O | MET | A | 160 | 34.226 | 39.641 | 65.460 | 1.00 13.41 | O |
| ATOM | 1254 | N | GLY | A | 161 | 34.321 | 41.212 | 67.058 | 1.00 14.01 | N |
| ATOM | 1255 | CA | GLY | A | 161 | 35.559 | 40.677 | 67.604 | 1.00 13.15 | C |
| ATOM | 1256 | C | GLY | A | 161 | 35.344 | 39.311 | 68.230 | 1.00 11.92 | C |
| ATOM | 1257 | O | GLY | A | 161 | 36.160 | 38.401 | 68.086 | 1.00 12.30 | O |
| ATOM | 1258 | N | VAL | A | 162 | 34.236 | 39.178 | 68.942 | 1.00 11.58 | N |
| ATOM | 1259 | CA | VAL | A | 162 | 33.884 | 37.930 | 69.589 | 1.00 11.68 | C |
| ATOM | 1260 | CB | VAL | A | 162 | 32.724 | 38.161 | 70.588 | 1.00 12.32 | C |
| ATOM | 1261 | CG1 | VAL | A | 162 | 32.233 | 36.840 | 71.163 | 1.00 11.46 | C |
| ATOM | 1262 | CG2 | VAL | A | 162 | 33.202 | 39.077 | 71.708 | 1.00 10.88 | C |
| ATOM | 1263 | C | VAL | A | 162 | 33.479 | 36.928 | 68.509 | 1.00 11.49 | C |
| ATOM | 1264 | O | VAL | A | 162 | 33.738 | 35.729 | 68.626 | 1.00 11.14 | O |
| ATOM | 1265 | N | ALA | A | 163 | 32.853 | 37.430 | 67.449 | 1.00 10.67 | N |
| ATOM | 1266 | CA | ALA | A | 163 | 32.438 | 36.577 | 66.345 | 1.00 11.39 | C |
| ATOM | 1267 | CB | ALA | A | 163 | 31.527 | 37.344 | 65.399 | 1.00 9.74 | C |
| ATOM | 1268 | C | ALA | A | 163 | 33.667 | 36.059 | 65.593 | 1.00 11.93 | C |
| ATOM | 1269 | O | ALA | A | 163 | 33.640 | 34.969 | 65.021 | 1.00 12.84 | O |
| ATOM | 1270 | N | LYS | A | 164 | 34.742 | 36.841 | 65.595 | 1.00 11.37 | N |
| ATOM | 1271 | CA | LYS | A | 164 | 35.959 | 36.434 | 64.915 | 1.00 10.57 | C |
| ATOM | 1272 | CB | LYS | A | 164 | 36.837 | 37.647 | 64.605 | 1.00 9.76 | C |
| ATOM | 1273 | CG | LYS | A | 164 | 36.328 | 38.506 | 63.445 | 1.00 8.11 | C |
| ATOM | 1274 | CD | LYS | A | 164 | 36.157 | 37.693 | 62.163 | 1.00 6.11 | C |
| ATOM | 1275 | CE | LYS | A | 164 | 35.656 | 38.563 | 61.026 | 1.00 4.15 | C |
| ATOM | 1276 | NZ | LYS | A | 164 | 35.469 | 37.812 | 59.766 | 1.00 4.32 | N |
| ATOM | 1277 | C | LYS | A | 164 | 36.717 | 35.419 | 65.759 | 1.00 10.99 | C |
| ATOM | 1278 | O | LYS | A | 164 | 37.336 | 34.506 | 65.224 | 1.00 13.11 | O |
| ATOM | 1279 | N | ALA | A | 165 | 36.659 | 35.572 | 67.078 | 1.00 11.97 | N |
| ATOM | 1280 | CA | ALA | A | 165 | 37.319 | 34.630 | 67.987 | 1.00 12.72 | C |
| ATOM | 1281 | CB | ALA | A | 165 | 37.229 | 35.128 | 69.421 | 1.00 9.45 | C |
| ATOM | 1282 | C | ALA | A | 165 | 36.605 | 33.279 | 67.842 | 1.00 12.92 | C |
| ATOM | 1283 | O | ALA | A | 165 | 37.220 | 32.212 | 67.943 | 1.00 12.65 | O |
| ATOM | 1284 | N | SER | A | 166 | 35.302 | 33.354 | 67.595 | 1.00 11.87 | N |
| ATOM | 1285 | CA | SER | A | 166 | 34.456 | 32.185 | 67.395 | 1.00 12.77 | C |
| ATOM | 1286 | CB | SER | A | 166 | 32.983 | 32.623 | 67.383 | 1.00 14.56 | C |
| ATOM | 1287 | OG | SER | A | 166 | 32.099 | 31.579 | 67.019 | 1.00 15.87 | O |
| ATOM | 1288 | C | SER | A | 166 | 34.826 | 31.541 | 66.052 | 1.00 13.40 | C |
| ATOM | 1289 | O | SER | A | 166 | 34.939 | 30.318 | 65.942 | 1.00 11.89 | O |
| ATOM | 1290 | N | LEU | A | 167 | 35.043 | 32.384 | 65.044 | 1.00 13.00 | N |
| ATOM | 1291 | CA | LEU | A | 167 | 35.386 | 31.921 | 63.711 | 1.00 12.27 | C |
| ATOM | 1292 | CB | LEU | A | 167 | 35.436 | 33.089 | 62.726 | 1.00 11.68 | C |
| ATOM | 1293 | CG | LEU | A | 167 | 35.892 | 32.701 | 61.311 | 1.00 11.31 | C |
| ATOM | 1294 | CD1 | LEU | A | 167 | 34.832 | 31.813 | 60.647 | 1.00 8.75 | C |
| ATOM | 1295 | CD2 | LEU | A | 167 | 36.135 | 33.965 | 60.487 | 1.00 9.98 | C |
| ATOM | 1296 | C | LEU | A | 167 | 36.713 | 31.193 | 63.672 | 1.00 13.37 | C |
| ATOM | 1297 | O | LEU | A | 167 | 36.845 | 30.188 | 62.966 | 1.00 14.36 | O |
| ATOM | 1298 | N | GLU | A | 168 | 37.695 | 31.705 | 64.415 | 1.00 12.34 | N |

FIGURE 9 (cont.)

| | | | | | | | | | | |
|---|---|---|---|---|---|---|---|---|---|---|
| ATOM | 1299 | CA | GLU | A | 168 | 39.018 | 31.103 | 64.446 | 1.00 13.13 | C |
| ATOM | 1300 | CB | GLU | A | 168 | 40.019 | 32.079 | 65.063 | 1.00 14.52 | C |
| ATOM | 1301 | CG | GLU | A | 168 | 40.047 | 33.400 | 64.310 | 1.00 19.28 | C |
| ATOM | 1302 | CD | GLU | A | 168 | 41.092 | 34.382 | 64.826 | 1.00 23.21 | C |
| ATOM | 1303 | OE1 | GLU | A | 168 | 41.044 | 35.568 | 64.399 | 1.00 21.97 | O |
| ATOM | 1304 | OE2 | GLU | A | 168 | 41.960 | 33.970 | 65.641 | 1.00 24.15 | O |
| ATOM | 1305 | C | GLU | A | 168 | 39.018 | 29.769 | 65.184 | 1.00 13.64 | C |
| ATOM | 1306 | O | GLU | A | 168 | 39.803 | 28.874 | 64.865 | 1.00 14.65 | O |
| ATOM | 1307 | N | ALA | A | 169 | 38.134 | 29.633 | 66.167 | 1.00 12.04 | N |
| ATOM | 1308 | CA | ALA | A | 169 | 38.019 | 28.381 | 66.900 | 1.00 12.22 | C |
| ATOM | 1309 | CB | ALA | A | 169 | 37.142 | 28.574 | 68.128 | 1.00 13.37 | C |
| ATOM | 1310 | C | ALA | A | 169 | 37.379 | 27.373 | 65.938 | 1.00 12.47 | C |
| ATOM | 1311 | O | ALA | A | 169 | 37.790 | 26.213 | 65.853 | 1.00 10.90 | O |
| ATOM | 1312 | N | ASN | A | 170 | 36.373 | 27.851 | 65.209 | 1.00 12.13 | N |
| ATOM | 1313 | CA | ASN | A | 170 | 35.649 | 27.058 | 64.230 | 1.00 11.69 | C |
| ATOM | 1314 | CB | ASN | A | 170 | 34.674 | 27.965 | 63.473 | 1.00 11.14 | C |
| ATOM | 1315 | CG | ASN | A | 170 | 33.433 | 27.235 | 63.002 | 1.00 11.52 | C |
| ATOM | 1316 | OD1 | ASN | A | 170 | 33.510 | 26.116 | 62.488 | 1.00 11.45 | O |
| ATOM | 1317 | ND2 | ASN | A | 170 | 32.274 | 27.876 | 63.161 | 1.00 8.92 | N |
| ATOM | 1318 | C | ASN | A | 170 | 36.663 | 26.442 | 63.251 | 1.00 12.77 | C |
| ATOM | 1319 | O | ASN | A | 170 | 36.545 | 25.281 | 62.874 | 1.00 10.98 | O |
| ATOM | 1320 | N | VAL | A | 171 | 37.654 | 27.240 | 62.844 | 1.00 12.64 | N |
| ATOM | 1321 | CA | VAL | A | 171 | 38.691 | 26.783 | 61.917 | 1.00 12.51 | C |
| ATOM | 1322 | CB | VAL | A | 171 | 39.672 | 27.929 | 61.557 | 1.00 11.91 | C |
| ATOM | 1323 | CG1 | VAL | A | 171 | 40.904 | 27.359 | 60.882 | 1.00 12.23 | C |
| ATOM | 1324 | CG2 | VAL | A | 171 | 38.997 | 28.930 | 60.646 | 1.00 11.08 | C |
| ATOM | 1325 | C | VAL | A | 171 | 39.509 | 25.614 | 62.485 | 1.00 11.59 | C |
| ATOM | 1326 | O | VAL | A | 171 | 39.729 | 24.620 | 61.805 | 1.00 10.42 | O |
| ATOM | 1327 | N | LYS | A | 172 | 39.968 | 25.743 | 63.726 | 1.00 11.72 | N |
| ATOM | 1328 | CA | LYS | A | 172 | 40.746 | 24.676 | 64.345 | 1.00 13.09 | C |
| ATOM | 1329 | CB | LYS | A | 172 | 41.247 | 25.126 | 65.720 | 1.00 12.68 | C |
| ATOM | 1330 | CG | LYS | A | 172 | 42.053 | 26.419 | 65.664 | 1.00 15.11 | C |
| ATOM | 1331 | CD | LYS | A | 172 | 42.453 | 26.921 | 67.032 | 1.00 15.79 | C |
| ATOM | 1332 | CE | LYS | A | 172 | 43.122 | 28.280 | 66.917 | 1.00 18.32 | C |
| ATOM | 1333 | NZ | LYS | A | 172 | 43.493 | 28.854 | 68.247 | 1.00 20.90 | N |
| ATOM | 1334 | C | LYS | A | 172 | 39.895 | 23.404 | 64.467 | 1.00 12.69 | C |
| ATOM | 1335 | O | LYS | A | 172 | 40.339 | 22.312 | 64.130 | 1.00 14.14 | O |
| ATOM | 1336 | N | TYR | A | 173 | 38.658 | 23.556 | 64.919 | 1.00 13.48 | N |
| ATOM | 1337 | CA | TYR | A | 173 | 37.763 | 22.419 | 65.080 | 1.00 13.29 | C |
| ATOM | 1338 | CB | TYR | A | 173 | 36.524 | 22.847 | 65.857 | 1.00 11.44 | C |
| ATOM | 1339 | CG | TYR | A | 173 | 36.758 | 22.751 | 67.340 | 1.00 13.36 | C |
| ATOM | 1340 | CD1 | TYR | A | 173 | 36.595 | 21.535 | 68.007 | 1.00 11.02 | C |
| ATOM | 1341 | CE1 | TYR | A | 173 | 36.890 | 21.409 | 69.364 | 1.00 13.10 | C |
| ATOM | 1342 | CD2 | TYR | A | 173 | 37.222 | 23.853 | 68.068 | 1.00 10.52 | C |
| ATOM | 1343 | CE2 | TYR | A | 173 | 37.520 | 23.741 | 69.419 | 1.00 12.66 | C |
| ATOM | 1344 | CZ | TYR | A | 173 | 37.354 | 22.514 | 70.064 | 1.00 13.07 | C |
| ATOM | 1345 | OH | TYR | A | 173 | 37.664 | 22.388 | 71.398 | 1.00 14.29 | O |
| ATOM | 1346 | C | TYR | A | 173 | 37.367 | 21.704 | 63.800 | 1.00 12.98 | C |
| ATOM | 1347 | O | TYR | A | 173 | 37.148 | 20.498 | 63.814 | 1.00 14.24 | O |
| ATOM | 1348 | N | LEU | A | 174 | 37.275 | 22.439 | 62.696 | 1.00 14.15 | N |
| ATOM | 1349 | CA | LEU | A | 174 | 36.934 | 21.838 | 61.414 | 1.00 13.14 | C |
| ATOM | 1350 | CB | LEU | A | 174 | 36.413 | 22.907 | 60.457 | 1.00 12.66 | C |
| ATOM | 1351 | CG | LEU | A | 174 | 34.997 | 23.435 | 60.751 | 1.00 11.93 | C |
| ATOM | 1352 | CD1 | LEU | A | 174 | 34.744 | 24.719 | 59.975 | 1.00 11.18 | C |
| ATOM | 1353 | CD2 | LEU | A | 174 | 33.961 | 22.370 | 60.380 | 1.00 11.72 | C |
| ATOM | 1354 | C | LEU | A | 174 | 38.181 | 21.164 | 60.838 | 1.00 13.65 | C |
| ATOM | 1355 | O | LEU | A | 174 | 38.088 | 20.260 | 60.017 | 1.00 14.76 | O |
| ATOM | 1356 | N | ALA | A | 175 | 39.349 | 21.617 | 61.282 | 1.00 14.16 | N |
| ATOM | 1357 | CA | ALA | A | 175 | 40.616 | 21.066 | 60.832 | 1.00 13.18 | C |
| ATOM | 1358 | CB | ALA | A | 175 | 41.750 | 21.993 | 61.227 | 1.00 10.88 | C |
| ATOM | 1359 | C | ALA | A | 175 | 40.822 | 19.684 | 61.451 | 1.00 13.86 | C |
| ATOM | 1360 | O | ALA | A | 175 | 41.283 | 18.753 | 60.786 | 1.00 13.30 | O |
| ATOM | 1361 | N | LEU | A | 176 | 40.481 | 19.556 | 62.730 | 1.00 13.64 | N |
| ATOM | 1362 | CA | LEU | A | 176 | 40.620 | 18.286 | 63.422 | 1.00 14.24 | C |
| ATOM | 1363 | CB | LEU | A | 176 | 40.355 | 18.453 | 64.929 | 1.00 14.06 | C |

FIGURE 9 (cont.)

```
ATOM   1364  CG   LEU A 176      40.412  17.177  65.789  1.00 14.95           C
ATOM   1365  CD1  LEU A 176      41.756  16.499  65.586  1.00 14.69           C
ATOM   1366  CD2  LEU A 176      40.202  17.509  67.278  1.00 13.24           C
ATOM   1367  C    LEU A 176      39.621  17.300  62.836  1.00 14.86           C
ATOM   1368  O    LEU A 176      39.982  16.190  62.472  1.00 16.44           O
ATOM   1369  N    ASP A 177      38.364  17.726  62.741  1.00 14.82           N
ATOM   1370  CA   ASP A 177      37.279  16.898  62.225  1.00 15.90           C
ATOM   1371  CB   ASP A 177      35.943  17.628  62.425  1.00 18.94           C
ATOM   1372  CG   ASP A 177      34.751  16.800  61.990  1.00 19.96           C
ATOM   1373  OD1  ASP A 177      33.670  17.378  61.731  1.00 20.44           O
ATOM   1374  OD2  ASP A 177      34.896  15.564  61.916  1.00 23.90           O
ATOM   1375  C    ASP A 177      37.416  16.494  60.749  1.00 16.98           C
ATOM   1376  O    ASP A 177      37.064  15.378  60.380  1.00 16.70           O
ATOM   1377  N    LEU A 178      37.931  17.391  59.910  1.00 15.31           N
ATOM   1378  CA   LEU A 178      38.064  17.102  58.485  1.00 14.58           C
ATOM   1379  CB   LEU A 178      37.635  18.327  57.665  1.00 14.27           C
ATOM   1380  CG   LEU A 178      36.219  18.856  57.950  1.00 15.47           C
ATOM   1381  CD1  LEU A 178      35.933  20.077  57.067  1.00 15.82           C
ATOM   1382  CD2  LEU A 178      35.191  17.758  57.701  1.00 14.99           C
ATOM   1383  C    LEU A 178      39.456  16.651  58.056  1.00 14.68           C
ATOM   1384  O    LEU A 178      39.628  16.116  56.959  1.00 14.52           O
ATOM   1385  N    GLY A 179      40.445  16.855  58.918  1.00 13.49           N
ATOM   1386  CA   GLY A 179      41.796  16.447  58.591  1.00 14.28           C
ATOM   1387  C    GLY A 179      41.866  15.026  58.058  1.00 16.03           C
ATOM   1388  O    GLY A 179      42.530  14.774  57.049  1.00 16.87           O
ATOM   1389  N    PRO A 180      41.205  14.065  58.724  1.00 16.13           N
ATOM   1390  CD   PRO A 180      40.761  14.141  60.125  1.00 15.29           C
ATOM   1391  CA   PRO A 180      41.224  12.672  58.265  1.00 17.14           C
ATOM   1392  CB   PRO A 180      40.492  11.935  59.383  1.00 16.14           C
ATOM   1393  CG   PRO A 180      40.929  12.704  60.592  1.00 15.80           C
ATOM   1394  C    PRO A 180      40.576  12.477  56.890  1.00 17.72           C
ATOM   1395  O    PRO A 180      40.802  11.460  56.235  1.00 17.55           O
ATOM   1396  N    ASP A 181      39.781  13.452  56.453  1.00 17.63           N
ATOM   1397  CA   ASP A 181      39.142  13.385  55.137  1.00 16.55           C
ATOM   1398  CB   ASP A 181      37.762  14.037  55.169  1.00 18.32           C
ATOM   1399  CG   ASP A 181      36.712  13.178  55.841  1.00 19.95           C
ATOM   1400  OD1  ASP A 181      35.607  13.699  56.049  1.00 25.17           O
ATOM   1401  OD2  ASP A 181      36.951  11.993  56.157  1.00 22.51           O
ATOM   1402  C    ASP A 181      40.018  14.118  54.112  1.00 16.39           C
ATOM   1403  O    ASP A 181      39.576  14.408  52.999  1.00 15.32           O
ATOM   1404  N    ASN A 182      41.258  14.417  54.512  1.00 16.52           N
ATOM   1405  CA   ASN A 182      42.243  15.118  53.675  1.00 15.64           C
ATOM   1406  CB   ASN A 182      42.556  14.313  52.401  1.00 16.80           C
ATOM   1407  CG   ASN A 182      43.811  14.817  51.675  1.00 17.38           C
ATOM   1408  OD1  ASN A 182      43.834  14.931  50.445  1.00 16.29           O
ATOM   1409  ND2  ASN A 182      44.856  15.112  52.436  1.00 17.09           N
ATOM   1410  C    ASN A 182      41.807  16.535  53.284  1.00 15.50           C
ATOM   1411  O    ASN A 182      42.208  17.054  52.243  1.00 15.26           O
ATOM   1412  N    ILE A 183      40.981  17.156  54.118  1.00 14.94           N
ATOM   1413  CA   ILE A 183      40.523  18.514  53.856  1.00 14.46           C
ATOM   1414  CB   ILE A 183      38.985  18.620  53.974  1.00 14.53           C
ATOM   1415  CG2  ILE A 183      38.551  20.067  53.813  1.00 14.92           C
ATOM   1416  CG1  ILE A 183      38.319  17.748  52.898  1.00 15.56           C
ATOM   1417  CD1  ILE A 183      36.788  17.694  52.979  1.00 15.98           C
ATOM   1418  C    ILE A 183      41.184  19.443  54.875  1.00 13.83           C
ATOM   1419  O    ILE A 183      41.075  19.232  56.081  1.00 12.78           O
ATOM   1420  N    ARG A 184      41.877  20.464  54.380  1.00 13.01           N
ATOM   1421  CA   ARG A 184      42.566  21.419  55.243  1.00 13.85           C
ATOM   1422  CB   ARG A 184      43.948  21.752  54.651  1.00 12.80           C
ATOM   1423  CG   ARG A 184      44.889  20.542  54.542  1.00 13.56           C
ATOM   1424  CD   ARG A 184      46.246  20.888  53.921  1.00 12.51           C
ATOM   1425  NE   ARG A 184      46.093  21.455  52.583  1.00 13.43           N
ATOM   1426  CZ   ARG A 184      46.246  22.744  52.288  1.00 11.46           C
ATOM   1427  NH1  ARG A 184      46.568  23.615  53.234  1.00  8.76           N
ATOM   1428  NH2  ARG A 184      46.057  23.161  51.046  1.00 11.18           N
```

FIGURE 9 (cont.)

| | | | | | | | | | | |
|---|---|---|---|---|---|---|---|---|---|---|
| ATOM | 1429 | C | ARG | A | 184 | 41.748 | 22.702 | 55.430 | 1.00 14.19 | C |
| ATOM | 1430 | O | ARG | A | 184 | 41.135 | 23.197 | 54.481 | 1.00 15.89 | O |
| ATOM | 1431 | N | VAL | A | 185 | 41.733 | 23.227 | 56.655 | 1.00 14.14 | N |
| ATOM | 1432 | CA | VAL | A | 185 | 41.004 | 24.458 | 56.971 | 1.00 13.30 | C |
| ATOM | 1433 | CB | VAL | A | 185 | 39.816 | 24.182 | 57.890 | 1.00 11.89 | C |
| ATOM | 1434 | CG1 | VAL | A | 185 | 38.769 | 25.267 | 57.705 | 1.00 11.65 | C |
| ATOM | 1435 | CG2 | VAL | A | 185 | 39.241 | 22.820 | 57.590 | 1.00 9.60 | C |
| ATOM | 1436 | C | VAL | A | 185 | 41.932 | 25.470 | 57.656 | 1.00 14.47 | C |
| ATOM | 1437 | O | VAL | A | 185 | 42.550 | 25.175 | 58.682 | 1.00 14.03 | O |
| ATOM | 1438 | N | ASN | A | 186 | 42.016 | 26.669 | 57.085 | 1.00 14.85 | N |
| ATOM | 1439 | CA | ASN | A | 186 | 42.893 | 27.708 | 57.607 | 1.00 14.03 | C |
| ATOM | 1440 | CB | ASN | A | 186 | 44.194 | 27.725 | 56.804 | 1.00 10.60 | C |
| ATOM | 1441 | CG | ASN | A | 186 | 45.028 | 26.479 | 57.014 | 1.00 11.20 | C |
| ATOM | 1442 | OD1 | ASN | A | 186 | 45.578 | 26.276 | 58.086 | 1.00 10.81 | O |
| ATOM | 1443 | ND2 | ASN | A | 186 | 45.121 | 25.633 | 55.984 | 1.00 11.42 | N |
| ATOM | 1444 | C | ASN | A | 186 | 42.264 | 29.095 | 57.570 | 1.00 14.23 | C |
| ATOM | 1445 | O | ASN | A | 186 | 41.166 | 29.277 | 57.061 | 1.00 14.34 | O |
| ATOM | 1446 | N | ALA | A | 187 | 42.976 | 30.076 | 58.107 | 1.00 14.69 | N |
| ATOM | 1447 | CA | ALA | A | 187 | 42.482 | 31.439 | 58.115 | 1.00 16.92 | C |
| ATOM | 1448 | CB | ALA | A | 187 | 41.896 | 31.781 | 59.482 | 1.00 17.27 | C |
| ATOM | 1449 | C | ALA | A | 187 | 43.548 | 32.464 | 57.739 | 1.00 18.20 | C |
| ATOM | 1450 | O | ALA | A | 187 | 44.760 | 32.242 | 57.898 | 1.00 15.67 | O |
| ATOM | 1451 | N | ILE | A | 188 | 43.071 | 33.587 | 57.215 | 1.00 17.48 | N |
| ATOM | 1452 | CA | ILE | A | 188 | 43.936 | 34.681 | 56.841 | 1.00 16.95 | C |
| ATOM | 1453 | CB | ILE | A | 188 | 43.811 | 35.022 | 55.346 | 1.00 19.05 | C |
| ATOM | 1454 | CG2 | ILE | A | 188 | 44.625 | 36.286 | 55.028 | 1.00 18.27 | C |
| ATOM | 1455 | CG1 | ILE | A | 188 | 44.301 | 33.832 | 54.514 | 1.00 19.47 | C |
| ATOM | 1456 | CD1 | ILE | A | 188 | 44.222 | 34.048 | 53.016 | 1.00 22.47 | C |
| ATOM | 1457 | C | ILE | A | 188 | 43.447 | 35.841 | 57.681 | 1.00 16.93 | C |
| ATOM | 1458 | O | ILE | A | 188 | 42.255 | 36.161 | 57.679 | 1.00 14.67 | O |
| ATOM | 1459 | N | SER | A | 189 | 44.362 | 36.437 | 58.439 | 1.00 16.14 | N |
| ATOM | 1460 | CA | SER | A | 189 | 44.008 | 37.563 | 59.286 | 1.00 16.52 | C |
| ATOM | 1461 | CB | SER | A | 189 | 44.613 | 37.387 | 60.672 | 1.00 15.46 | C |
| ATOM | 1462 | OG | SER | A | 189 | 44.112 | 38.364 | 61.554 | 1.00 19.00 | O |
| ATOM | 1463 | C | SER | A | 189 | 44.565 | 38.798 | 58.594 | 1.00 16.35 | C |
| ATOM | 1464 | O | SER | A | 189 | 45.747 | 39.110 | 58.688 | 1.00 15.85 | O |
| ATOM | 1465 | N | ALA | A | 190 | 43.691 | 39.490 | 57.880 | 1.00 17.27 | N |
| ATOM | 1466 | CA | ALA | A | 190 | 44.087 | 40.663 | 57.121 | 1.00 17.95 | C |
| ATOM | 1467 | CB | ALA | A | 190 | 43.159 | 40.839 | 55.921 | 1.00 15.53 | C |
| ATOM | 1468 | C | ALA | A | 190 | 44.147 | 41.958 | 57.908 | 1.00 18.98 | C |
| ATOM | 1469 | O | ALA | A | 190 | 43.459 | 42.135 | 58.913 | 1.00 19.50 | O |
| ATOM | 1470 | N | SER | A | 191 | 45.006 | 42.846 | 57.413 | 1.00 19.64 | N |
| ATOM | 1471 | CA | SER | A | 191 | 45.222 | 44.181 | 57.940 | 1.00 20.06 | C |
| ATOM | 1472 | CB | SER | A | 191 | 46.543 | 44.713 | 57.383 | 1.00 21.39 | C |
| ATOM | 1473 | OG | SER | A | 191 | 46.882 | 45.955 | 57.956 | 1.00 26.42 | O |
| ATOM | 1474 | C | SER | A | 191 | 44.037 | 44.979 | 57.373 | 1.00 20.05 | C |
| ATOM | 1475 | O | SER | A | 191 | 43.517 | 44.646 | 56.310 | 1.00 19.09 | O |
| ATOM | 1476 | N | PRO | A | 192 | 43.601 | 46.042 | 58.064 | 1.00 20.04 | N |
| ATOM | 1477 | CD | PRO | A | 192 | 44.113 | 46.622 | 59.315 | 1.00 20.94 | C |
| ATOM | 1478 | CA | PRO | A | 192 | 42.466 | 46.811 | 57.548 | 1.00 20.59 | C |
| ATOM | 1479 | CB | PRO | A | 192 | 42.317 | 47.950 | 58.566 | 1.00 21.18 | C |
| ATOM | 1480 | CG | PRO | A | 192 | 43.658 | 48.039 | 59.213 | 1.00 21.47 | C |
| ATOM | 1481 | C | PRO | A | 192 | 42.570 | 47.303 | 56.108 | 1.00 19.81 | C |
| ATOM | 1482 | O | PRO | A | 192 | 43.614 | 47.786 | 55.673 | 1.00 21.57 | O |
| ATOM | 1483 | N | ILE | A | 193 | 41.472 | 47.156 | 55.374 | 1.00 18.05 | N |
| ATOM | 1484 | CA | ILE | A | 193 | 41.388 | 47.583 | 53.982 | 1.00 17.10 | C |
| ATOM | 1485 | CB | ILE | A | 193 | 41.450 | 46.362 | 53.039 | 1.00 17.20 | C |
| ATOM | 1486 | CG2 | ILE | A | 193 | 41.431 | 46.818 | 51.592 | 1.00 16.75 | C |
| ATOM | 1487 | CG1 | ILE | A | 193 | 42.722 | 45.554 | 53.328 | 1.00 16.40 | C |
| ATOM | 1488 | CD1 | ILE | A | 193 | 42.809 | 44.213 | 52.594 | 1.00 13.46 | C |
| ATOM | 1489 | C | ILE | A | 193 | 40.055 | 48.323 | 53.802 | 1.00 17.12 | C |
| ATOM | 1490 | O | ILE | A | 193 | 39.035 | 47.913 | 54.358 | 1.00 16.77 | O |
| ATOM | 1491 | N | ARG | A | 194 | 40.054 | 49.414 | 53.040 | 1.00 18.17 | N |
| ATOM | 1492 | CA | ARG | A | 194 | 38.821 | 50.184 | 52.841 | 1.00 17.87 | C |
| ATOM | 1493 | CB | ARG | A | 194 | 39.140 | 51.614 | 52.389 | 1.00 20.41 | C |

FIGURE 9 (cont.)

| | | | | | | | | | |
|---|---|---|---|---|---|---|---|---|---|
| ATOM | 1494 | CG | ARG | A | 194 | 37.913 | 52.535 | 52.417 | 1.00 23.04 | C |
| ATOM | 1495 | CD | ARG | A | 194 | 38.240 | 53.965 | 52.039 | 1.00 23.75 | C |
| ATOM | 1496 | NE | ARG | A | 194 | 39.129 | 54.647 | 52.983 | 1.00 26.65 | N |
| ATOM | 1497 | CZ | ARG | A | 194 | 38.761 | 55.083 | 54.187 | 1.00 28.38 | C |
| ATOM | 1498 | NH1 | ARG | A | 194 | 37.512 | 54.897 | 54.613 | 1.00 30.06 | N |
| ATOM | 1499 | NH2 | ARG | A | 194 | 39.629 | 55.745 | 54.948 | 1.00 27.37 | N |
| ATOM | 1500 | C | ARG | A | 194 | 37.875 | 49.527 | 51.840 | 1.00 16.28 | C |
| ATOM | 1501 | O | ARG | A | 194 | 38.087 | 49.589 | 50.638 | 1.00 14.74 | O |
| ATOM | 1502 | N | THR | A | 195 | 36.824 | 48.904 | 52.359 | 1.00 17.33 | N |
| ATOM | 1503 | CA | THR | A | 195 | 35.829 | 48.209 | 51.541 | 1.00 17.37 | C |
| ATOM | 1504 | CB | THR | A | 195 | 35.982 | 46.682 | 51.671 | 1.00 16.61 | C |
| ATOM | 1505 | OG1 | THR | A | 195 | 35.586 | 46.290 | 52.992 | 1.00 15.65 | O |
| ATOM | 1506 | CG2 | THR | A | 195 | 37.426 | 46.253 | 51.438 | 1.00 14.88 | C |
| ATOM | 1507 | C | THR | A | 195 | 34.440 | 48.579 | 52.076 | 1.00 17.48 | C |
| ATOM | 1508 | O | THR | A | 195 | 34.328 | 49.419 | 52.970 | 1.00 18.62 | O |
| ATOM | 1509 | N | LEU | A | 196 | 33.397 | 47.950 | 51.534 | 1.00 16.09 | N |
| ATOM | 1510 | CA | LEU | A | 196 | 32.024 | 48.184 | 51.980 | 1.00 16.46 | C |
| ATOM | 1511 | CB | LEU | A | 196 | 31.050 | 47.294 | 51.200 | 1.00 16.17 | C |
| ATOM | 1512 | CG | LEU | A | 196 | 30.703 | 47.620 | 49.745 | 1.00 17.92 | C |
| ATOM | 1513 | CD1 | LEU | A | 196 | 29.981 | 46.435 | 49.115 | 1.00 17.50 | C |
| ATOM | 1514 | CD2 | LEU | A | 196 | 29.824 | 48.847 | 49.689 | 1.00 18.46 | C |
| ATOM | 1515 | C | LEU | A | 196 | 31.874 | 47.874 | 53.471 | 1.00 16.68 | C |
| ATOM | 1516 | O | LEU | A | 196 | 30.944 | 48.347 | 54.124 | 1.00 16.74 | O |
| ATOM | 1517 | N | SER | A | 197 | 32.771 | 47.051 | 54.005 | 1.00 16.71 | N |
| ATOM | 1518 | CA | SER | A | 197 | 32.708 | 46.715 | 55.414 | 1.00 18.59 | C |
| ATOM | 1519 | CB | SER | A | 197 | 33.232 | 45.301 | 55.646 | 1.00 19.89 | C |
| ATOM | 1520 | OG | SER | A | 197 | 32.299 | 44.370 | 55.123 | 1.00 22.83 | O |
| ATOM | 1521 | C | SER | A | 197 | 33.468 | 47.726 | 56.264 | 1.00 19.04 | C |
| ATOM | 1522 | O | SER | A | 197 | 33.644 | 47.541 | 57.467 | 1.00 19.33 | O |
| ATOM | 1523 | N | ALA | A | 198 | 33.910 | 48.801 | 55.623 | 1.00 19.34 | N |
| ATOM | 1524 | CA | ALA | A | 198 | 34.608 | 49.874 | 56.319 | 1.00 20.81 | C |
| ATOM | 1525 | CB | ALA | A | 198 | 35.950 | 50.158 | 55.650 | 1.00 19.85 | C |
| ATOM | 1526 | C | ALA | A | 198 | 33.711 | 51.118 | 56.255 | 1.00 21.46 | C |
| ATOM | 1527 | O | ALA | A | 198 | 33.930 | 52.098 | 56.961 | 1.00 21.12 | O |
| ATOM | 1528 | N | LYS | A | 199 | 32.689 | 51.057 | 55.410 | 1.00 22.79 | N |
| ATOM | 1529 | CA | LYS | A | 199 | 31.776 | 52.178 | 55.248 | 1.00 25.68 | C |
| ATOM | 1530 | CB | LYS | A | 199 | 30.765 | 51.880 | 54.130 | 1.00 27.12 | C |
| ATOM | 1531 | CG | LYS | A | 199 | 29.817 | 53.030 | 53.794 | 1.00 28.32 | C |
| ATOM | 1532 | CD | LYS | A | 199 | 29.195 | 52.795 | 52.419 | 1.00 30.54 | C |
| ATOM | 1533 | CE | LYS | A | 199 | 27.788 | 53.376 | 52.302 | 1.00 31.73 | C |
| ATOM | 1534 | NZ | LYS | A | 199 | 27.759 | 54.860 | 52.487 | 1.00 32.49 | N |
| ATOM | 1535 | C | LYS | A | 199 | 31.045 | 52.493 | 56.536 | 1.00 26.11 | C |
| ATOM | 1536 | O | LYS | A | 199 | 30.383 | 51.630 | 57.114 | 1.00 26.46 | O |
| ATOM | 1537 | N | GLY | A | 200 | 31.180 | 53.732 | 56.996 | 1.00 26.14 | N |
| ATOM | 1538 | CA | GLY | A | 200 | 30.499 | 54.131 | 58.212 | 1.00 26.81 | C |
| ATOM | 1539 | C | GLY | A | 200 | 31.227 | 53.769 | 59.490 | 1.00 27.18 | C |
| ATOM | 1540 | O | GLY | A | 200 | 30.800 | 54.143 | 60.578 | 1.00 28.72 | O |
| ATOM | 1541 | N | VAL | A | 201 | 32.312 | 53.022 | 59.391 | 1.00 26.58 | N |
| ATOM | 1542 | CA | VAL | A | 201 | 33.041 | 52.695 | 60.607 | 1.00 25.16 | C |
| ATOM | 1543 | CB | VAL | A | 201 | 34.087 | 51.601 | 60.356 | 1.00 23.69 | C |
| ATOM | 1544 | CG1 | VAL | A | 201 | 34.868 | 51.345 | 61.625 | 1.00 21.37 | C |
| ATOM | 1545 | CG2 | VAL | A | 201 | 33.398 | 50.326 | 59.887 | 1.00 22.70 | C |
| ATOM | 1546 | C | VAL | A | 201 | 33.733 | 53.993 | 61.010 | 1.00 26.09 | C |
| ATOM | 1547 | O | VAL | A | 201 | 34.158 | 54.769 | 60.142 | 1.00 26.67 | O |
| ATOM | 1548 | N | GLY | A | 202 | 33.837 | 54.239 | 62.313 | 1.00 26.06 | N |
| ATOM | 1549 | CA | GLY | A | 202 | 34.461 | 55.464 | 62.776 | 1.00 26.04 | C |
| ATOM | 1550 | C | GLY | A | 202 | 35.970 | 55.383 | 62.854 | 1.00 26.35 | C |
| ATOM | 1551 | O | GLY | A | 202 | 36.525 | 54.313 | 63.098 | 1.00 27.87 | O |
| ATOM | 1552 | N | GLY | A | 203 | 36.629 | 56.520 | 62.642 | 1.00 26.18 | N |
| ATOM | 1553 | CA | GLY | A | 203 | 38.078 | 56.590 | 62.706 | 1.00 25.02 | C |
| ATOM | 1554 | C | GLY | A | 203 | 38.820 | 55.609 | 61.821 | 1.00 24.20 | C |
| ATOM | 1555 | O | GLY | A | 203 | 39.968 | 55.250 | 62.106 | 1.00 24.88 | O |
| ATOM | 1556 | N | PHE | A | 204 | 38.183 | 55.185 | 60.736 | 1.00 22.79 | N |
| ATOM | 1557 | CA | PHE | A | 204 | 38.802 | 54.229 | 59.836 | 1.00 20.90 | C |
| ATOM | 1558 | CB | PHE | A | 204 | 37.768 | 53.721 | 58.827 | 1.00 19.63 | C |

FIGURE 9 (cont.)

```
ATOM   1559  CG   PHE A 204      38.088  52.364  58.279  1.00 18.63           C
ATOM   1560  CD1  PHE A 204      38.971  52.217  57.210  1.00 17.32           C
ATOM   1561  CD2  PHE A 204      37.555  51.220  58.878  1.00 18.98           C
ATOM   1562  CE1  PHE A 204      39.328  50.947  56.740  1.00 17.44           C
ATOM   1563  CE2  PHE A 204      37.903  49.940  58.421  1.00 18.78           C
ATOM   1564  CZ   PHE A 204      38.794  49.806  57.346  1.00 19.19           C
ATOM   1565  C    PHE A 204      40.011  54.841  59.129  1.00 21.91           C
ATOM   1566  O    PHE A 204      40.931  54.134  58.716  1.00 20.21           O
ATOM   1567  N    ASN A 205      40.021  56.165  59.020  1.00 22.61           N
ATOM   1568  CA   ASN A 205      41.126  56.856  58.380  1.00 23.55           C
ATOM   1569  CB   ASN A 205      40.728  58.307  58.072  1.00 25.49           C
ATOM   1570  CG   ASN A 205      39.471  58.399  57.203  1.00 27.33           C
ATOM   1571  OD1  ASN A 205      38.363  58.659  57.699  1.00 29.80           O
ATOM   1572  ND2  ASN A 205      39.636  58.169  55.908  1.00 25.19           N
ATOM   1573  C    ASN A 205      42.367  56.825  59.276  1.00 23.31           C
ATOM   1574  O    ASN A 205      43.492  56.703  58.791  1.00 22.61           O
ATOM   1575  N    THR A 206      42.162  56.925  60.585  1.00 23.25           N
ATOM   1576  CA   THR A 206      43.279  56.919  61.520  1.00 24.44           C
ATOM   1577  CB   THR A 206      42.901  57.632  62.846  1.00 26.81           C
ATOM   1578  OG1  THR A 206      42.335  56.695  63.767  1.00 30.00           O
ATOM   1579  CG2  THR A 206      41.872  58.737  62.575  1.00 26.22           C
ATOM.  1580  C    THR A 206      43.715  55.477  61.771  1.00 23.62           C
ATOM   1581  O    THR A 206      44.879  55.205  62.052  1.00 23.65           O
ATOM   1582  N    ILE A 207      42.769  54.554  61.650  1.00 24.02           N
ATOM   1583  CA   ILE A 207      43.040  53.127  61.801  1.00 22.81           C
ATOM   1584  CB   ILE A 207      41.736  52.308  61.642  1.00 23.80           C
ATOM   1585  CG2  ILE A 207      42.052  50.855  61.339  1.00 23.48           C
ATOM   1586  CG1  ILE A 207      40.876  52.450  62.900  1.00 24.29           C
ATOM   1587  CD1  ILE A 207      39.498  51.833  62.759  1.00 23.34           C
ATOM   1588  C    ILE A 207      43.984  52.756  60.663  1.00 22.40           C
ATOM   1589  O    ILE A 207      44.881  51.923  60.801  1.00 21.66           O
ATOM   1590  N    LEU A 208      43.760  53.390  59.523  1.00 23.39           N
ATOM   1591  CA   LEU A 208      44.565  53.149  58.340  1.00 22.42           C
ATOM   1592  CB   LEU A 208      43.867  53.740  57.115  1.00 21.15           C
ATOM   1593  CG   LEU A 208      43.415  52.753  56.035  1.00 20.69           C
ATOM   1594  CD1  LEU A 208      42.931  51.460  56.675  1.00 20.74           C
ATOM   1595  CD2  LEU A 208      42.319  53.385  55.199  1.00 18.09           C
ATOM   1596  C    LEU A 208      45.950  53.750  58.493  1.00 23.53           C
ATOM   1597  O    LEU A 208      46.951  53.091  58.187  1.00 23.07           O
ATOM   1598  N    LYS A 209      46.013  54.990  58.980  1.00 23.29           N
ATOM   1599  CA   LYS A 209      47.303  55.653  59.157  1.00 23.62           C
ATOM   1600  CB   LYS A 209      47.105  57.133  59.498  1.00 23.77           C
ATOM   1601  CG   LYS A 209      46.417  57.911  58.390  1.00 23.47           C
ATOM   1602  CD   LYS A 209      46.336  59.384  58.706  1.00 21.42           C
ATOM   1603  CE   LYS A 209      45.796  60.142  57.504  1.00 21.42           C
ATOM   1604  NZ   LYS A 209      46.211  61.560  57.559  1.00 20.33           N
ATOM   1605  C    LYS A 209      48.175  55.001  60.221  1.00 23.28           C
ATOM   1606  O    LYS A 209      49.403  55.095  60.161  1.00 23.35           O
ATOM   1607  N    GLU A 210      47.546  54.339  61.188  1.00 23.70           N
ATOM   1608  CA   GLU A 210      48.279  53.687  62.280  1.00 23.97           C
ATOM   1609  CB   GLU A 210      47.295  53.180  63.332  1.00 25.88           C
ATOM   1610  CG   GLU A 210      47.940  52.553  64.562  1.00 30.29           C
ATOM   1611  CD   GLU A 210      46.941  51.746  65.386  1.00 32.64           C
ATOM   1612  OE1  GLU A 210      45.770  52.188  65.521  1.00 34.27           O
ATOM   1613  OE2  GLU A 210      47.328  50.672  65.902  1.00 33.78           O
ATOM   1614  C    GLU A 210      49.142  52.528  61.780  1.00 23.89           C
ATOM   1615  O    GLU A 210      50.240  52.297  62.290  1.00 24.50           O
ATOM   1616  N    ILE A 211      48.641  51.796  60.786  1.00 22.88           N
ATOM   1617  CA   ILE A 211      49.376  50.679  60.214  1.00 22.46           C
ATOM   1618  CB   ILE A 211      48.463  49.771  59.336  1.00 23.34           C
ATOM   1619  CG2  ILE A 211      49.302  49.092  58.254  1.00 21.21           C
ATOM   1620  CG1  ILE A 211      47.804  48.676  60.197  1.00 24.32           C
ATOM   1621  CD1  ILE A 211      47.005  49.191  61.388  1.00 24.13           C
ATOM   1622  C    ILE A 211      50.560  51.153  59.369  1.00 22.26           C
ATOM   1623  O    ILE A 211      51.685  50.690  59.561  1.00 22.83           O
```

FIGURE 9 (cont.)

| ATOM | 1624 | N | GLU | A | 212 | 50.315 | 52.060 | 58.429 | 1.00 | 23.05 | N |
| ATOM | 1625 | CA | GLU | A | 212 | 51.398 | 52.553 | 57.585 | 1.00 | 24.83 | C |
| ATOM | 1626 | CB | GLU | A | 212 | 50.905 | 53.610 | 56.587 | 1.00 | 26.41 | C |
| ATOM | 1627 | CG | GLU | A | 212 | 52.066 | 54.231 | 55.802 | 1.00 | 31.97 | C |
| ATOM | 1628 | CD | GLU | A | 212 | 51.634 | 55.299 | 54.811 | 1.00 | 35.45 | C |
| ATOM | 1629 | OE1 | GLU | A | 212 | 50.404 | 55.531 | 54.699 | 1.00 | 37.97 | O |
| ATOM | 1630 | OE2 | GLU | A | 212 | 52.526 | 55.902 | 54.144 | 1.00 | 36.12 | O |
| ATOM | 1631 | C | GLU | A | 212 | 52.486 | 53.171 | 58.447 | 1.00 | 24.35 | C |
| ATOM | 1632 | O | GLU | A | 212 | 53.668 | 53.146 | 58.092 | 1.00 | 22.66 | O |
| ATOM | 1633 | N | GLU | A | 213 | 52.069 | 53.721 | 59.582 | 1.00 | 24.65 | N |
| ATOM | 1634 | CA | GLU | A | 213 | 52.970 | 54.366 | 60.524 | 1.00 | 26.62 | C |
| ATOM | 1635 | CB | GLU | A | 213 | 52.186 | 55.403 | 61.335 | 1.00 | 30.34 | C |
| ATOM | 1636 | CG | GLU | A | 213 | 52.899 | 55.911 | 62.575 | 1.00 | 35.56 | C |
| ATOM | 1637 | CD | GLU | A | 213 | 52.036 | 56.867 | 63.388 | 1.00 | 40.67 | C |
| ATOM | 1638 | OE1 | GLU | A | 213 | 50.920 | 56.455 | 63.821 | 1.00 | 42.26 | O |
| ATOM | 1639 | OE2 | GLU | A | 213 | 52.475 | 58.034 | 63.601 | 1.00 | 42.93 | O |
| ATOM | 1640 | C | GLU | A | 213 | 53.700 | 53.433 | 61.497 | 1.00 | 26.21 | C |
| ATOM | 1641 | O | GLU | A | 213 | 54.885 | 53.639 | 61.769 | 1.00 | 26.78 | O |
| ATOM | 1642 | N | ARG | A | 214 | 53.001 | 52.420 | 62.018 | 1.00 | 24.41 | N |
| ATOM | 1643 | CA | ARG | A | 214 | 53.582 | 51.500 | 63.005 | 1.00 | 22.41 | C |
| ATOM | 1644 | CB | ARG | A | 214 | 52.622 | 51.340 | 64.194 | 1.00 | 22.85 | C |
| ATOM | 1645 | CG | ARG | A | 214 | 52.291 | 52.643 | 64.929 | 1.00 | 22.83 | C |
| ATOM | 1646 | CD | ARG | A | 214 | 51.362 | 52.391 | 66.118 | 1.00 | 23.05 | C |
| ATOM | 1647 | NE | ARG | A | 214 | 51.931 | 51.402 | 67.025 | 1.00 | 23.09 | N |
| ATOM | 1648 | CZ | ARG | A | 214 | 51.213 | 50.521 | 67.713 | 1.00 | 24.11 | C |
| ATOM | 1649 | NH1 | ARG | A | 214 | 49.885 | 50.512 | 67.596 | 1.00 | 24.01 | N |
| ATOM | 1650 | NH2 | ARG | A | 214 | 51.820 | 49.642 | 68.511 | 1.00 | 22.56 | N |
| ATOM | 1651 | C | ARG | A | 214 | 53.998 | 50.110 | 62.535 | 1.00 | 21.73 | C |
| ATOM | 1652 | O | ARG | A | 214 | 54.933 | 49.530 | 63.088 | 1.00 | 21.61 | O |
| ATOM | 1653 | N | ALA | A | 215 | 53.308 | 49.562 | 61.541 | 1.00 | 19.72 | N |
| ATOM | 1654 | CA | ALA | A | 215 | 53.646 | 48.232 | 61.044 | 1.00 | 19.56 | C |
| ATOM | 1655 | CB | ALA | A | 215 | 52.694 | 47.837 | 59.912 | 1.00 | 17.94 | C |
| ATOM | 1656 | C | ALA | A | 215 | 55.098 | 48.155 | 60.556 | 1.00 | 20.38 | C |
| ATOM | 1657 | O | ALA | A | 215 | 55.640 | 49.131 | 60.027 | 1.00 | 20.58 | O |
| ATOM | 1658 | N | PRO | A | 216 | 55.746 | 46.991 | 60.724 | 1.00 | 19.80 | N |
| ATOM | 1659 | CD | PRO | A | 216 | 55.231 | 45.787 | 61.400 | 1.00 | 20.38 | C |
| ATOM | 1660 | CA | PRO | A | 216 | 57.133 | 46.790 | 60.300 | 1.00 | 20.40 | C |
| ATOM | 1661 | CB | PRO | A | 216 | 57.329 | 45.285 | 60.476 | 1.00 | 21.18 | C |
| ATOM | 1662 | CG | PRO | A | 216 | 56.502 | 44.991 | 61.674 | 1.00 | 20.42 | C |
| ATOM | 1663 | C | PRO | A | 216 | 57.421 | 47.239 | 58.862 | 1.00 | 22.07 | C |
| ATOM | 1664 | O | PRO | A | 216 | 58.425 | 47.907 | 58.613 | 1.00 | 22.64 | O |
| ATOM | 1665 | N | LEU | A | 217 | 56.549 | 46.870 | 57.921 | 1.00 | 21.58 | N |
| ATOM | 1666 | CA | LEU | A | 217 | 56.741 | 47.231 | 56.513 | 1.00 | 22.67 | C |
| ATOM | 1667 | CB | LEU | A | 217 | 56.046 | 46.205 | 55.602 | 1.00 | 22.13 | C |
| ATOM | 1668 | CG | LEU | A | 217 | 56.618 | 44.777 | 55.603 | 1.00 | 21.69 | C |
| ATOM | 1669 | CD1 | LEU | A | 217 | 55.726 | 43.860 | 54.772 | 1.00 | 21.19 | C |
| ATOM | 1670 | CD2 | LEU | A | 217 | 58.038 | 44.789 | 55.043 | 1.00 | 21.05 | C |
| ATOM | 1671 | C | LEU | A | 217 | 56.262 | 48.645 | 56.153 | 1.00 | 22.87 | C |
| ATOM | 1672 | O | LEU | A | 217 | 56.331 | 49.044 | 54.987 | 1.00 | 23.81 | O |
| ATOM | 1673 | N | LYS | A | 218 | 55.773 | 49.378 | 57.151 | 1.00 | 21.53 | N |
| ATOM | 1674 | CA | LYS | A | 218 | 55.301 | 50.751 | 56.989 | 1.00 | 20.75 | C |
| ATOM | 1675 | CB | LYS | A | 218 | 56.494 | 51.703 | 56.869 | 1.00 | 21.77 | C |
| ATOM | 1676 | CG | LYS | A | 218 | 57.453 | 51.669 | 58.051 | 1.00 | 22.08 | C |
| ATOM | 1677 | CD | LYS | A | 218 | 56.769 | 52.087 | 59.326 | 1.00 | 24.81 | C |
| ATOM | 1678 | CE | LYS | A | 218 | 57.768 | 52.259 | 60.482 | 1.00 | 26.62 | C |
| ATOM | 1679 | NZ | LYS | A | 218 | 58.543 | 51.019 | 60.809 | 1.00 | 25.22 | N |
| ATOM | 1680 | C | LYS | A | 218 | 54.375 | 50.979 | 55.810 | 1.00 | 20.10 | C |
| ATOM | 1681 | O | LYS | A | 218 | 54.586 | 51.888 | 55.011 | 1.00 | 19.69 | O |
| ATOM | 1682 | N | ARG | A | 219 | 53.342 | 50.158 | 55.705 | 1.00 | 20.82 | N |
| ATOM | 1683 | CA | ARG | A | 219 | 52.391 | 50.283 | 54.617 | 1.00 | 20.67 | C |
| ATOM | 1684 | CB | ARG | A | 219 | 53.031 | 49.870 | 53.293 | 1.00 | 22.50 | C |
| ATOM | 1685 | CG | ARG | A | 219 | 53.275 | 48.372 | 53.191 | 1.00 | 23.73 | C |
| ATOM | 1686 | CD | ARG | A | 219 | 54.006 | 48.011 | 51.912 | 1.00 | 25.54 | C |
| ATOM | 1687 | NE | ARG | A | 219 | 54.193 | 46.568 | 51.794 | 1.00 | 26.15 | N |
| ATOM | 1688 | CZ | ARG | A | 219 | 53.199 | 45.702 | 51.609 | 1.00 | 27.21 | C |

FIGURE 9 (cont.)

```
ATOM   1689  NH1 ARG A 219      51.946  46.133  51.520  1.00 25.28           N
ATOM   1690  NH2 ARG A 219      53.460  44.407  51.502  1.00 26.34           N
ATOM   1691  C   ARG A 219      51.237  49.360  54.904  1.00 20.15           C
ATOM   1692  O   ARG A 219      51.369  48.435  55.697  1.00 21.22           O
ATOM   1693  N   ASN A 220      50.112  49.629  54.251  1.00 20.63           N
ATOM   1694  CA  ASN A 220      48.901  48.831  54.383  1.00 19.69           C
ATOM   1695  CB  ASN A 220      47.667  49.698  54.137  1.00 19.39           C
ATOM   1696  CG  ASN A 220      47.289  50.521  55.340  1.00 20.08           C
ATOM   1697  OD1 ASN A 220      46.997  49.970  56.406  1.00 18.57           O
ATOM   1698  ND2 ASN A 220      47.287  51.850  55.186  1.00 19.11           N
ATOM   1699  C   ASN A 220      48.955  47.748  53.317  1.00 20.45           C
ATOM   1700  O   ASN A 220      49.822  47.776  52.446  1.00 20.24           O
ATOM   1701  N   VAL A 221      48.031  46.795  53.382  1.00 20.26           N
ATOM   1702  CA  VAL A 221      47.991  45.734  52.387  1.00 20.60           C
ATOM   1703  CB  VAL A 221      47.913  44.323  53.061  1.00 21.01           C
ATOM   1704  CG1 VAL A 221      49.048  44.164  54.064  1.00 17.79           C
ATOM   1705  CG2 VAL A 221      46.560  44.125  53.741  1.00 19.36           C
ATOM   1706  C   VAL A 221      46.757  45.968  51.518  1.00 19.71           C
ATOM   1707  O   VAL A 221      45.918  46.799  51.845  1.00 20.08           O
ATOM   1708  N   ASP A 222      46.651  45.270  50.396  1.00 21.39           N
ATOM   1709  CA  ASP A 222      45.469  45.437  49.558  1.00 22.71           C
ATOM   1710  CB  ASP A 222      45.809  46.114  48.219  1.00 26.22           C
ATOM   1711  CG  ASP A 222      46.958  45.441  47.488  1.00 30.37           C
ATOM   1712  OD1 ASP A 222      47.119  44.206  47.621  1.00 32.55           O
ATOM   1713  OD2 ASP A 222      47.697  46.155  46.765  1.00 31.58           O
ATOM   1714  C   ASP A 222      44.783  44.097  49.331  1.00 21.17           C
ATOM   1715  O   ASP A 222      45.267  43.051  49.785  1.00 22.59           O
ATOM   1716  N   GLN A 223      43.650  44.132  48.644  1.00 20.16           N
ATOM   1717  CA  GLN A 223      42.873  42.933  48.382  1.00 19.02           C
ATOM   1718  CB  GLN A 223      41.611  43.291  47.587  1.00 18.73           C
ATOM   1719  CG  GLN A 223      40.625  44.203  48.344  1.00 16.42           C
ATOM   1720  CD  GLN A 223      40.934  45.686  48.173  1.00 18.15           C
ATOM   1721  OE1 GLN A 223      42.087  46.069  47.974  1.00 16.99           O
ATOM   1722  NE2 GLN A 223      39.906  46.530  48.268  1.00 15.80           N
ATOM   1723  C   GLN A 223      43.668  41.830  47.675  1.00 19.59           C
ATOM   1724  O   GLN A 223      43.559  40.659  48.043  1.00 18.73           O
ATOM   1725  N   VAL A 224      44.470  42.199  46.681  1.00 18.72           N
ATOM   1726  CA  VAL A 224      45.277  41.219  45.944  1.00 19.85           C
ATOM   1727  CB  VAL A 224      46.007  41.875  44.740  1.00 20.03           C
ATOM   1728  CG1 VAL A 224      47.167  40.999  44.292  1.00 20.02           C
ATOM   1729  CG2 VAL A 224      45.038  42.076  43.586  1.00 19.55           C
ATOM   1730  C   VAL A 224      46.328  40.519  46.826  1.00 20.18           C
ATOM   1731  O   VAL A 224      46.575  39.321  46.680  1.00 19.47           O
ATOM   1732  N   GLU A 225      46.948  41.272  47.728  1.00 19.40           N
ATOM   1733  CA  GLU A 225      47.957  40.718  48.624  1.00 19.24           C
ATOM   1734  CB  GLU A 225      48.467  41.839  49.535  1.00 21.73           C
ATOM   1735  CG  GLU A 225      49.746  41.550  50.288  1.00 24.14           C
ATOM   1736  CD  GLU A 225      50.710  42.742  50.253  1.00 26.33           C
ATOM   1737  OE1 GLU A 225      50.230  43.895  50.201  1.00 27.80           O
ATOM   1738  OE2 GLU A 225      51.941  42.529  50.290  1.00 24.66           O
ATOM   1739  C   GLU A 225      47.321  39.573  49.434  1.00 19.37           C
ATOM   1740  O   GLU A 225      47.945  38.540  49.673  1.00 19.16           O
ATOM   1741  N   VAL A 226      46.070  39.757  49.840  1.00 18.90           N
ATOM   1742  CA  VAL A 226      45.349  38.731  50.578  1.00 18.73           C
ATOM   1743  CB  VAL A 226      43.995  39.255  51.078  1.00 18.89           C
ATOM   1744  CG1 VAL A 226      43.171  38.100  51.672  1.00 18.22           C
ATOM   1745  CG2 VAL A 226      44.216  40.351  52.099  1.00 17.00           C
ATOM   1746  C   VAL A 226      45.098  37.563  49.625  1.00 19.09           C
ATOM   1747  O   VAL A 226      45.187  36.392  50.008  1.00 19.46           O
ATOM   1748  N   GLY A 227      44.790  37.896  48.374  1.00 18.55           N
ATOM   1749  CA  GLY A 227      44.536  36.878  47.367  1.00 17.90           C
ATOM   1750  C   GLY A 227      45.745  35.989  47.128  1.00 17.51           C
ATOM   1751  O   GLY A 227      45.592  34.791  46.885  1.00 17.60           O
ATOM   1752  N   LYS A 228      46.947  36.563  47.210  1.00 16.27           N
ATOM   1753  CA  LYS A 228      48.164  35.788  46.997  1.00 16.64           C
```

FIGURE 9 (cont.)

```
ATOM   1754  CB  LYS A 228      49.387  36.709  46.892  1.00 17.38           C
ATOM   1755  CG  LYS A 228      49.395  37.560  45.621  1.00 15.95           C
ATOM   1756  CD  LYS A 228      50.763  38.156  45.327  1.00 15.27           C
ATOM   1757  CE  LYS A 228      51.211  39.079  46.444  1.00 16.70           C
ATOM   1758  NZ  LYS A 228      52.515  39.741  46.145  1.00 17.87           N
ATOM   1759  C   LYS A 228      48.371  34.749  48.093  1.00 15.67           C
ATOM   1760  O   LYS A 228      48.777  33.620  47.809  1.00 17.19           O
ATOM   1761  N   THR A 229      48.086  35.115  49.341  1.00 15.00           N
ATOM   1762  CA  THR A 229      48.230  34.167  50.445  1.00 15.10           C
ATOM   1763  CB  THR A 229      48.228  34.895  51.819  1.00 14.52           C
ATOM   1764  OG1 THR A 229      49.462  35.605  51.977  1.00 14.15           O
ATOM   1765  CG2 THR A 229      48.090  33.909  52.964  1.00 14.66           C
ATOM   1766  C   THR A 229      47.089  33.143  50.360  1.00 16.25           C
ATOM   1767  O   THR A 229      47.233  31.995  50.781  1.00 15.88           O
ATOM   1768  N   ALA A 230      45.959  33.561  49.795  1.00 17.94           N
ATOM   1769  CA  ALA A 230      44.821  32.662  49.631  1.00 19.21           C
ATOM   1770  CB  ALA A 230      43.607  33.433  49.077  1.00 18.35           C
ATOM   1771  C   ALA A 230      45.242  31.559  48.654  1.00 19.20           C
ATOM   1772  O   ALA A 230      44.954  30.385  48.868  1.00 20.49           O
ATOM   1773  N   ALA A 231      45.938  31.950  47.587  1.00 19.75           N
ATOM   1774  CA  ALA A 231      46.402  31.003  46.568  1.00 19.23           C
ATOM   1775  CB  ALA A 231      47.142  31.750  45.456  1.00 17.63           C
ATOM   1776  C   ALA A 231      47.307  29.941  47.189  1.00 18.01           C
ATOM   1777  O   ALA A 231      47.246  28.766  46.828  1.00 18.83           O
ATOM   1778  N   TYR A 232      48.147  30.368  48.122  1.00 17.33           N
ATOM   1779  CA  TYR A 232      49.055  29.463  48.825  1.00 16.96           C
ATOM   1780  CB  TYR A 232      49.929  30.264  49.809  1.00 14.91           C
ATOM   1781  CG  TYR A 232      50.602  29.462  50.914  1.00 15.14           C
ATOM   1782  CD1 TYR A 232      51.594  28.520  50.625  1.00 15.77           C
ATOM   1783  CE1 TYR A 232      52.232  27.798  51.646  1.00 13.44           C
ATOM   1784  CD2 TYR A 232      50.261  29.664  52.256  1.00 14.98           C
ATOM   1785  CE2 TYR A 232      50.893  28.949  53.287  1.00 15.88           C
ATOM   1786  CZ  TYR A 232      51.878  28.020  52.969  1.00 15.88           C
ATOM   1787  OH  TYR A 232      52.514  27.324  53.972  1.00 16.54           O
ATOM   1788  C   TYR A 232      48.243  28.417  49.580  1.00 15.52           C
ATOM   1789  O   TYR A 232      48.467  27.223  49.425  1.00 16.41           O
ATOM   1790  N   LEU A 233      47.282  28.884  50.374  1.00 14.48           N
ATOM   1791  CA  LEU A 233      46.444  28.014  51.200  1.00 14.94           C
ATOM   1792  CB  LEU A 233      45.718  28.864  52.254  1.00 12.03           C
ATOM   1793  CG  LEU A 233      46.565  29.512  53.354  1.00  9.74           C
ATOM   1794  CD1 LEU A 233      45.737  30.532  54.114  1.00  7.01           C
ATOM   1795  CD2 LEU A 233      47.085  28.437  54.293  1.00  9.16           C
ATOM   1796  C   LEU A 233      45.429  27.104  50.484  1.00 15.61           C
ATOM   1797  O   LEU A 233      45.047  26.058  51.017  1.00 14.83           O
ATOM   1798  N   LEU A 234      44.991  27.493  49.290  1.00 15.64           N
ATOM   1799  CA  LEU A 234      44.013  26.691  48.562  1.00 16.70           C
ATOM   1800  CB  LEU A 234      43.155  27.593  47.671  1.00 16.53           C
ATOM   1801  CG  LEU A 234      42.278  28.599  48.416  1.00 17.97           C
ATOM   1802  CD1 LEU A 234      41.657  29.592  47.444  1.00 17.66           C
ATOM   1803  CD2 LEU A 234      41.201  27.837  49.177  1.00 18.44           C
ATOM   1804  C   LEU A 234      44.663  25.605  47.710  1.00 17.90           C
ATOM   1805  O   LEU A 234      44.065  24.550  47.476  1.00 18.79           O
ATOM   1806  N   SER A 235      45.887  25.872  47.262  1.00 18.60           N
ATOM   1807  CA  SER A 235      46.642  24.958  46.418  1.00 19.58           C
ATOM   1808  CB  SER A 235      47.586  25.752  45.510  1.00 21.01           C
ATOM   1809  OG  SER A 235      48.579  26.421  46.277  1.00 23.86           O
ATOM   1810  C   SER A 235      47.447  23.930  47.201  1.00 20.11           C
ATOM   1811  O   SER A 235      47.317  23.811  48.418  1.00 19.99           O
ATOM   1812  N   ASP A 236      48.294  23.200  46.479  1.00 22.45           N
ATOM   1813  CA  ASP A 236      49.126  22.139  47.045  1.00 23.46           C
ATOM   1814  CB  ASP A 236      49.471  21.109  45.945  1.00 27.06           C
ATOM   1815  CG  ASP A 236      50.545  20.096  46.375  1.00 30.59           C
ATOM   1816  OD1 ASP A 236      50.273  19.264  47.271  1.00 31.61           O
ATOM   1817  OD2 ASP A 236      51.671  20.131  45.804  1.00 33.56           O
ATOM   1818  C   ASP A 236      50.395  22.669  47.684  1.00 22.70           C
```

FIGURE 9 (cont.)

```
ATOM  1819  O    ASP A 236    51.142  21.904  48.290  1.00 23.66           O
ATOM  1820  N    LEU A 237    50.649  23.969  47.555  1.00 21.64           N
ATOM  1821  CA   LEU A 237    51.850  24.548  48.152  1.00 20.34           C
ATOM  1822  CB   LEU A 237    51.988  26.031  47.796  1.00 20.52           C
ATOM  1823  CG   LEU A 237    52.838  26.431  46.585  1.00 21.52           C
ATOM  1824  CD1  LEU A 237    53.085  27.942  46.647  1.00 20.39           C
ATOM  1825  CD2  LEU A 237    54.173  25.681  46.588  1.00 17.52           C
ATOM  1826  C    LEU A 237    51.869  24.426  49.663  1.00 20.59           C
ATOM  1827  O    LEU A 237    52.932  24.344  50.266  1.00 20.22           O
ATOM  1828  N    SER A 238    50.691  24.416  50.278  1.00 21.28           N
ATOM  1829  CA   SER A 238    50.596  24.338  51.732  1.00 21.07           C
ATOM  1830  CB   SER A 238    49.697  25.472  52.241  1.00 20.60           C
ATOM  1831  OG   SER A 238    48.410  25.406  51.656  1.00 19.00           O
ATOM  1832  C    SER A 238    50.068  23.005  52.239  1.00 22.21           C
ATOM  1833  O    SER A 238    49.470  22.933  53.316  1.00 23.18           O
ATOM  1834  N    SER A 239    50.307  21.948  51.473  1.00 23.52           N
ATOM  1835  CA   SER A 239    49.832  20.613  51.821  1.00 23.37           C
ATOM  1836  CB   SER A 239    50.490  19.573  50.893  1.00 24.07           C
ATOM  1837  OG   SER A 239    51.904  19.537  51.054  1.00 27.58           O
ATOM  1838  C    SER A 239    49.990  20.191  53.298  1.00 22.75           C
ATOM  1839  O    SER A 239    49.165  19.448  53.825  1.00 23.55           O
ATOM  1840  N    GLY A 240    51.025  20.657  53.985  1.00 21.97           N
ATOM  1841  CA   GLY A 240    51.174  20.253  55.378  1.00 18.97           C
ATOM  1842  C    GLY A 240    50.631  21.248  56.391  1.00 18.83           C
ATOM  1843  O    GLY A 240    50.837  21.084  57.601  1.00 17.25           O
ATOM  1844  N    VAL A 241    49.927  22.269  55.903  1.00 16.50           N
ATOM  1845  CA   VAL A 241    49.376  23.304  56.770  1.00 16.00           C
ATOM  1846  CB   VAL A 241    49.728  24.715  56.252  1.00 15.29           C
ATOM  1847  CG1  VAL A 241    49.112  25.766  57.161  1.00 12.31           C
ATOM  1848  CG2  VAL A 241    51.244  24.888  56.172  1.00 16.57           C
ATOM  1849  C    VAL A 241    47.867  23.264  56.944  1.00 14.40           C
ATOM  1850  O    VAL A 241    47.120  23.275  55.977  1.00 15.71           O
ATOM  1851  N    THR A 242    47.421  23.247  58.190  1.00 14.85           N
ATOM  1852  CA   THR A 242    45.998  23.243  58.487  1.00 14.86           C
ATOM  1853  CB   THR A 242    45.403  21.828  58.294  1.00 13.52           C
ATOM  1854  OG1  THR A 242    44.005  21.844  58.605  1.00 14.49           O
ATOM  1855  CG2  THR A 242    46.110  20.829  59.156  1.00 14.04           C
ATOM  1856  C    THR A 242    45.754  23.765  59.908  1.00 15.04           C
ATOM  1857  O    THR A 242    46.622  23.645  60.771  1.00 15.75           O
ATOM  1858  N    GLY A 243    44.585  24.372  60.127  1.00 16.29           N
ATOM  1859  CA   GLY A 243    44.234  24.915  61.433  1.00 16.72           C
ATOM  1860  C    GLY A 243    45.150  26.057  61.845  1.00 16.79           C
ATOM  1861  O    GLY A 243    45.356  26.314  63.031  1.00 17.40           O
ATOM  1862  N    GLU A 244    45.704  26.740  60.851  1.00 17.44           N
ATOM  1863  CA   GLU A 244    46.629  27.842  61.076  1.00 17.16           C
ATOM  1864  CB   GLU A 244    47.872  27.632  60.204  1.00 18.19           C
ATOM  1865  CG   GLU A 244    48.957  28.705  60.305  1.00 21.43           C
ATOM  1866  CD   GLU A 244    49.629  28.763  61.672  1.00 22.59           C
ATOM  1867  OE1  GLU A 244    48.946  29.125  62.661  1.00 24.72           O
ATOM  1868  OE2  GLU A 244    50.838  28.452  61.755  1.00 21.67           O
ATOM  1869  C    GLU A 244    45.971  29.182  60.755  1.00 18.33           C
ATOM  1870  O    GLU A 244    44.917  29.247  60.106  1.00 17.29           O
ATOM  1871  N    ASN A 245    46.600  30.254  61.223  1.00 17.83           N
ATOM  1872  CA   ASN A 245    46.100  31.600  60.999  1.00 16.84           C
ATOM  1873  CB   ASN A 245    45.480  32.140  62.293  1.00 15.86           C
ATOM  1874  CG   ASN A 245    44.847  33.491  62.112  1.00 18.36           C
ATOM  1875  OD1  ASN A 245    44.500  33.882  60.996  1.00 19.91           O
ATOM  1876  ND2  ASN A 245    44.672  34.216  63.211  1.00 20.71           N
ATOM  1877  C    ASN A 245    47.276  32.466  60.543  1.00 16.35           C
ATOM  1878  O    ASN A 245    48.089  32.919  61.352  1.00 15.85           O
ATOM  1879  N    ILE A 246    47.354  32.674  59.233  1.00 16.71           N
ATOM  1880  CA   ILE A 246    48.413  33.465  58.617  1.00 16.87           C
ATOM  1881  CB   ILE A 246    48.699  32.945  57.202  1.00 17.49           C
ATOM  1882  CG2  ILE A 246    49.822  33.779  56.553  1.00 17.29           C
ATOM  1883  CG1  ILE A 246    49.041  31.453  57.276  1.00 16.02           C
```

FIGURE 9 (cont.)

| ATOM | 1884 | CD1 | ILE | A | 246 | 49.253 | 30.793 | 55.943 | 1.00 | 17.34 | C |
| ATOM | 1885 | C | ILE | A | 246 | 48.046 | 34.949 | 58.534 | 1.00 | 18.44 | C |
| ATOM | 1886 | O | ILE | A | 246 | 47.039 | 35.310 | 57.911 | 1.00 | 18.48 | O |
| ATOM | 1887 | N | HIS | A | 247 | 48.875 | 35.793 | 59.155 | 1.00 | 18.29 | N |
| ATOM | 1888 | CA | HIS | A | 247 | 48.672 | 37.240 | 59.193 | 1.00 | 17.13 | C |
| ATOM | 1889 | CB | HIS | A | 247 | 49.274 | 37.841 | 60.477 | 1.00 | 16.02 | C |
| ATOM | 1890 | CG | HIS | A | 247 | 48.624 | 37.364 | 61.743 | 1.00 | 15.43 | C |
| ATOM | 1891 | CD2 | HIS | A | 247 | 47.694 | 37.946 | 62.539 | 1.00 | 12.64 | C |
| ATOM | 1892 | ND1 | HIS | A | 247 | 48.887 | 36.130 | 62.301 | 1.00 | 13.56 | N |
| ATOM | 1893 | CE1 | HIS | A | 247 | 48.145 | 35.972 | 63.384 | 1.00 | 13.63 | C |
| ATOM | 1894 | NE2 | HIS | A | 247 | 47.411 | 37.058 | 63.549 | 1.00 | 11.92 | N |
| ATOM | 1895 | C | HIS | A | 247 | 49.264 | 37.990 | 58.000 | 1.00 | 18.54 | C |
| ATOM | 1896 | O | HIS | A | 247 | 50.483 | 37.965 | 57.774 | 1.00 | 19.81 | O |
| ATOM | 1897 | N | VAL | A | 248 | 48.394 | 38.653 | 57.242 | 1.00 | 16.96 | N |
| ATOM | 1898 | CA | VAL | A | 248 | 48.794 | 39.464 | 56.089 | 1.00 | 16.99 | C |
| ATOM | 1899 | CB | VAL | A | 248 | 47.933 | 39.140 | 54.848 | 1.00 | 16.84 | C |
| ATOM | 1900 | CG1 | VAL | A | 248 | 48.321 | 40.046 | 53.699 | 1.00 | 15.76 | C |
| ATOM | 1901 | CG2 | VAL | A | 248 | 48.120 | 37.667 | 54.455 | 1.00 | 17.46 | C |
| ATOM | 1902 | C | VAL | A | 248 | 48.515 | 40.885 | 56.560 | 1.00 | 16.13 | C |
| ATOM | 1903 | O | VAL | A | 248 | 47.503 | 41.490 | 56.210 | 1.00 | 15.68 | O |
| ATOM | 1904 | N | ASP | A | 249 | 49.440 | 41.415 | 57.350 | 1.00 | 18.05 | N |
| ATOM | 1905 | CA | ASP | A | 249 | 49.256 | 42.722 | 57.965 | 1.00 | 19.30 | C |
| ATOM | 1906 | CB | ASP | A | 249 | 48.719 | 42.490 | 59.365 | 1.00 | 18.81 | C |
| ATOM | 1907 | CG | ASP | A | 249 | 49.653 | 41.610 | 60.189 | 1.00 | 20.01 | C |
| ATOM | 1908 | OD1 | ASP | A | 249 | 50.664 | 41.127 | 59.627 | 1.00 | 18.00 | O |
| ATOM | 1909 | OD2 | ASP | A | 249 | 49.387 | 41.398 | 61.391 | 1.00 | 22.54 | O |
| ATOM | 1910 | C | ASP | A | 249 | 50.517 | 43.570 | 58.068 | 1.00 | 20.32 | C |
| ATOM | 1911 | O | ASP | A | 249 | 50.579 | 44.488 | 58.892 | 1.00 | 20.90 | O |
| ATOM | 1912 | N | SER | A | 250 | 51.528 | 43.263 | 57.263 | 1.00 | 21.05 | N |
| ATOM | 1913 | CA | SER | A | 250 | 52.763 | 44.033 | 57.299 | 1.00 | 19.51 | C |
| ATOM | 1914 | CB | SER | A | 250 | 52.458 | 45.520 | 57.102 | 1.00 | 20.02 | C |
| ATOM | 1915 | OG | SER | A | 250 | 51.896 | 45.762 | 55.829 | 1.00 | 19.23 | O |
| ATOM | 1916 | C | SER | A | 250 | 53.532 | 43.842 | 58.602 | 1.00 | 18.89 | C |
| ATOM | 1917 | O | SER | A | 250 | 54.375 | 44.672 | 58.959 | 1.00 | 18.02 | O |
| ATOM | 1918 | N | GLY | A | 251 | 53.238 | 42.748 | 59.304 | 1.00 | 18.88 | N |
| ATOM | 1919 | CA | GLY | A | 251 | 53.913 | 42.445 | 60.557 | 1.00 | 17.82 | C |
| ATOM | 1920 | C | GLY | A | 251 | 53.315 | 43.094 | 61.795 | 1.00 | 18.43 | C |
| ATOM | 1921 | O | GLY | A | 251 | 53.825 | 42.899 | 62.899 | 1.00 | 19.62 | O |
| ATOM | 1922 | N | PHE | A | 252 | 52.232 | 43.849 | 61.626 | 1.00 | 17.66 | N |
| ATOM | 1923 | CA | PHE | A | 252 | 51.582 | 44.539 | 62.745 | 1.00 | 17.90 | C |
| ATOM | 1924 | CB | PHE | A | 252 | 50.260 | 45.159 | 62.270 | 1.00 | 18.14 | C |
| ATOM | 1925 | CG | PHE | A | 252 | 49.651 | 46.136 | 63.242 | 1.00 | 18.16 | C |
| ATOM | 1926 | CD1 | PHE | A | 252 | 50.305 | 47.327 | 63.563 | 1.00 | 17.68 | C |
| ATOM | 1927 | CD2 | PHE | A | 252 | 48.408 | 45.878 | 63.823 | 1.00 | 18.64 | C |
| ATOM | 1928 | CE1 | PHE | A | 252 | 49.731 | 48.246 | 64.443 | 1.00 | 17.38 | C |
| ATOM | 1929 | CE2 | PHE | A | 252 | 47.821 | 46.798 | 64.710 | 1.00 | 18.68 | C |
| ATOM | 1930 | CZ | PHE | A | 252 | 48.488 | 47.983 | 65.018 | 1.00 | 19.22 | C |
| ATOM | 1931 | C | PHE | A | 252 | 51.323 | 43.632 | 63.959 | 1.00 | 17.27 | C |
| ATOM | 1932 | O | PHE | A | 252 | 51.474 | 44.055 | 65.109 | 1.00 | 16.63 | O |
| ATOM | 1933 | N | HIS | A | 253 | 50.941 | 42.386 | 63.693 | 1.00 | 16.73 | N |
| ATOM | 1934 | CA | HIS | A | 253 | 50.648 | 41.412 | 64.745 | 1.00 | 17.04 | C |
| ATOM | 1935 | CB | HIS | A | 253 | 50.156 | 40.099 | 64.117 | 1.00 | 15.70 | C |
| ATOM | 1936 | CG | HIS | A | 253 | 51.213 | 39.382 | 63.331 | 1.00 | 14.71 | C |
| ATOM | 1937 | CD2 | HIS | A | 253 | 51.925 | 38.264 | 63.608 | 1.00 | 12.63 | C |
| ATOM | 1938 | ND1 | HIS | A | 253 | 51.703 | 39.859 | 62.131 | 1.00 | 13.97 | N |
| ATOM | 1939 | CE1 | HIS | A | 253 | 52.673 | 39.067 | 61.707 | 1.00 | 13.82 | C |
| ATOM | 1940 | NE2 | HIS | A | 253 | 52.829 | 38.092 | 62.586 | 1.00 | 12.83 | N |
| ATOM | 1941 | C | HIS | A | 253 | 51.864 | 41.084 | 65.620 | 1.00 | 16.62 | C |
| ATOM | 1942 | O | HIS | A | 253 | 51.725 | 40.550 | 66.718 | 1.00 | 15.88 | O |
| ATOM | 1943 | N | ALA | A | 254 | 53.054 | 41.400 | 65.127 | 1.00 | 17.94 | N |
| ATOM | 1944 | CA | ALA | A | 254 | 54.277 | 41.081 | 65.852 | 1.00 | 18.40 | C |
| ATOM | 1945 | CB | ALA | A | 254 | 55.324 | 40.588 | 64.859 | 1.00 | 18.49 | C |
| ATOM | 1946 | C | ALA | A | 254 | 54.868 | 42.186 | 66.726 | 1.00 | 19.52 | C |
| ATOM | 1947 | O | ALA | A | 254 | 55.877 | 41.969 | 67.404 | 1.00 | 21.00 | O |
| ATOM | 1948 | N | ILE | A | 255 | 54.258 | 43.366 | 66.727 | 1.00 | 20.39 | N |

FIGURE 9 (cont.)

| | | | | | | | | | |
|---|---|---|---|---|---|---|---|---|---|
| ATOM | 1949 | CA | ILE | A | 255 | 54.792 | 44.459 | 67.532 | 1.00 21.23 | C |
| ATOM | 1950 | CB | ILE | A | 255 | 54.989 | 45.748 | 66.694 | 1.00 21.96 | C |
| ATOM | 1951 | CG2 | ILE | A | 255 | 55.932 | 45.480 | 65.530 | 1.00 20.64 | C |
| ATOM | 1952 | CG1 | ILE | A | 255 | 53.630 | 46.253 | 66.191 | 1.00 22.67 | C |
| ATOM | 1953 | CD1 | ILE | A | 255 | 53.700 | 47.552 | 65.384 | 1.00 23.14 | C |
| ATOM | 1954 | C | ILE | A | 255 | 53.873 | 44.787 | 68.696 | 1.00 21.90 | C |
| ATOM | 1955 | O | ILE | A | 255 | 52.790 | 44.217 | 68.829 | 1.00 21.11 | O |
| ATOM | 1956 | N | LYS | A | 256 | 54.318 | 45.723 | 69.530 | 1.00 22.64 | N |
| ATOM | 1957 | CA | LYS | A | 256 | 53.555 | 46.143 | 70.699 | 1.00 22.76 | C |
| ATOM | 1958 | CB | LYS | A | 256 | 53.715 | 45.094 | 71.806 | 1.00 21.46 | C |
| ATOM | 1959 | CG | LYS | A | 256 | 52.680 | 45.191 | 72.908 | 1.00 20.48 | C |
| ATOM | 1960 | CD | LYS | A | 256 | 51.284 | 44.842 | 72.407 | 1.00 18.97 | C |
| ATOM | 1961 | CE | LYS | A | 256 | 50.263 | 45.112 | 73.497 | 1.00 19.48 | C |
| ATOM | 1962 | NZ | LYS | A | 256 | 48.901 | 44.832 | 73.037 | 1.00 20.88 | N |
| ATOM | 1963 | C | LYS | A | 256 | 54.033 | 47.519 | 71.199 | 1.00 22.68 | C |
| ATOM | 1964 | O | LYS | A | 256 | 53.193 | 48.436 | 71.384 | 1.00 23.24 | O |
| ATOM | 1965 | OXT | LYS | A | 256 | 55.254 | 47.663 | 71.411 | 1.00 21.15 | O |
| TER | 1966 | | LYS | A | 256 | | | | | |
| ATOM | 1967 | CB | LEU | B | 2 | 43.795 | 38.303 | 100.846 | 1.00 30.04 | C |
| ATOM | 1968 | CG | LEU | B | 2 | 43.458 | 36.800 | 100.737 | 1.00 28.00 | C |
| ATOM | 1969 | CD1 | LEU | B | 2 | 42.246 | 36.486 | 101.586 | 1.00 28.64 | C |
| ATOM | 1970 | CD2 | LEU | B | 2 | 43.206 | 36.410 | 99.293 | 1.00 24.92 | C |
| ATOM | 1971 | C | LEU | B | 2 | 41.571 | 39.279 | 101.408 | 1.00 33.24 | C |
| ATOM | 1972 | O | LEU | B | 2 | 40.455 | 38.920 | 101.021 | 1.00 35.73 | O |
| ATOM | 1973 | N | LEU | B | 2 | 43.340 | 40.682 | 100.266 | 1.00 30.87 | N |
| ATOM | 1974 | CA | LEU | B | 2 | 42.736 | 39.322 | 100.419 | 1.00 31.40 | C |
| ATOM | 1975 | N | ASN | B | 3 | 41.802 | 39.634 | 102.673 | 1.00 33.31 | N |
| ATOM | 1976 | CA | ASN | B | 3 | 40.711 | 39.587 | 103.659 | 1.00 33.21 | C |
| ATOM | 1977 | CB | ASN | B | 3 | 41.078 | 40.347 | 104.934 | 1.00 34.88 | C |
| ATOM | 1978 | CG | ASN | B | 3 | 39.922 | 40.392 | 105.921 | 1.00 36.87 | C |
| ATOM | 1979 | OD1 | ASN | B | 3 | 38.964 | 41.154 | 105.738 | 1.00 37.12 | O |
| ATOM | 1980 | ND2 | ASN | B | 3 | 39.987 | 39.550 | 106.955 | 1.00 35.92 | N |
| ATOM | 1981 | C | ASN | B | 3 | 39.408 | 40.157 | 103.106 | 1.00 31.41 | C |
| ATOM | 1982 | O | ASN | B | 3 | 39.289 | 41.360 | 102.907 | 1.00 30.85 | O |
| ATOM | 1983 | N | LEU | B | 4 | 38.417 | 39.296 | 102.895 | 1.00 30.38 | N |
| ATOM | 1984 | CA | LEU | B | 4 | 37.158 | 39.741 | 102.311 | 1.00 29.88 | C |
| ATOM | 1985 | CB | LEU | B | 4 | 36.677 | 38.690 | 101.312 | 1.00 27.78 | C |
| ATOM | 1986 | CG | LEU | B | 4 | 37.775 | 38.180 | 100.368 | 1.00 27.57 | C |
| ATOM | 1987 | CD1 | LEU | B | 4 | 37.228 | 37.025 | 99.531 | 1.00 25.59 | C |
| ATOM | 1988 | CD2 | LEU | B | 4 | 38.276 | 39.320 | 99.468 | 1.00 26.43 | C |
| ATOM | 1989 | C | LEU | B | 4 | 36.020 | 40.106 | 103.262 | 1.00 30.61 | C |
| ATOM | 1990 | O | LEU | B | 4 | 34.853 | 39.919 | 102.914 | 1.00 28.45 | O |
| ATOM | 1991 | N | GLU | B | 5 | 36.336 | 40.627 | 104.453 | 1.00 33.04 | N |
| ATOM | 1992 | CA | GLU | B | 5 | 35.264 | 41.021 | 105.386 | 1.00 33.91 | C |
| ATOM | 1993 | CB | GLU | B | 5 | 35.795 | 41.379 | 106.783 | 1.00 36.50 | C |
| ATOM | 1994 | CG | GLU | B | 5 | 36.850 | 40.457 | 107.396 | 1.00 40.61 | C |
| ATOM | 1995 | CD | GLU | B | 5 | 37.200 | 40.864 | 108.839 | 1.00 43.16 | C |
| ATOM | 1996 | OE1 | GLU | B | 5 | 37.144 | 42.088 | 109.150 | 1.00 43.89 | O |
| ATOM | 1997 | OE2 | GLU | B | 5 | 37.539 | 39.965 | 109.662 | 1.00 44.30 | O |
| ATOM | 1998 | C | GLU | B | 5 | 34.682 | 42.293 | 104.776 | 1.00 33.05 | C |
| ATOM | 1999 | O | GLU | B | 5 | 35.429 | 43.141 | 104.283 | 1.00 32.92 | O |
| ATOM | 2000 | N | ASN | B | 6 | 33.365 | 42.446 | 104.814 | 1.00 31.60 | N |
| ATOM | 2001 | CA | ASN | B | 6 | 32.739 | 43.644 | 104.246 | 1.00 30.64 | C |
| ATOM | 2002 | CB | ASN | B | 6 | 33.524 | 44.920 | 104.619 | 1.00 32.12 | C |
| ATOM | 2003 | CG | ASN | B | 6 | 33.740 | 45.067 | 106.120 | 1.00 32.86 | C |
| ATOM | 2004 | OD1 | ASN | B | 6 | 32.785 | 45.055 | 106.897 | 1.00 33.13 | O |
| ATOM | 2005 | ND2 | ASN | B | 6 | 35.003 | 45.213 | 106.533 | 1.00 31.96 | N |
| ATOM | 2006 | C | ASN | B | 6 | 32.655 | 43.569 | 102.724 | 1.00 28.58 | C |
| ATOM | 2007 | O | ASN | B | 6 | 32.244 | 44.543 | 102.088 | 1.00 27.40 | O |
| ATOM | 2008 | N | LYS | B | 7 | 33.068 | 42.437 | 102.140 | 1.00 27.15 | N |
| ATOM | 2009 | CA | LYS | B | 7 | 33.008 | 42.250 | 100.680 | 1.00 25.45 | C |
| ATOM | 2010 | CB | LYS | B | 7 | 34.310 | 41.617 | 100.154 | 1.00 27.64 | C |
| ATOM | 2011 | CG | LYS | B | 7 | 35.573 | 42.484 | 100.236 | 1.00 28.10 | C |
| ATOM | 2012 | CD | LYS | B | 7 | 35.441 | 43.772 | 99.424 | 1.00 30.83 | C |
| ATOM | 2013 | CE | LYS | B | 7 | 36.768 | 44.540 | 99.368 | 1.00 31.90 | C |

FIGURE 9 (cont.)

| ATOM | 2014 | NZ | LYS | B | 7 | 37.274 | 44.923 | 100.719 | 1.00 | 32.33 | N |
|------|------|----|----|---|---|--------|--------|---------|------|-------|---|
| ATOM | 2015 | C | LYS | B | 7 | 31.829 | 41.334 | 100.310 | 1.00 | 23.46 | C |
| ATOM | 2016 | O | LYS | B | 7 | 31.574 | 40.351 | 101.004 | 1.00 | 22.03 | O |
| ATOM | 2017 | N | THR | B | 8 | 31.129 | 41.651 | 99.217 | 1.00 | 21.51 | N |
| ATOM | 2018 | CA | THR | B | 8 | 29.984 | 40.852 | 98.754 | 1.00 | 20.87 | C |
| ATOM | 2019 | CB | THR | B | 8 | 28.657 | 41.657 | 98.823 | 1.00 | 20.03 | C |
| ATOM | 2020 | OG1 | THR | B | 8 | 28.377 | 42.013 | 100.184 | 1.00 | 22.50 | O |
| ATOM | 2021 | CG2 | THR | B | 8 | 27.499 | 40.829 | 98.283 | 1.00 | 21.26 | C |
| ATOM | 2022 | C | THR | B | 8 | 30.160 | 40.364 | 97.311 | 1.00 | 20.20 | C |
| ATOM | 2023 | O | THR | B | 8 | 30.441 | 41.162 | 96.414 | 1.00 | 21.19 | O |
| ATOM | 2024 | N | TYR | B | 9 | 29.981 | 39.061 | 97.090 | 1.00 | 19.20 | N |
| ATOM | 2025 | CA | TYR | B | 9 | 30.120 | 38.477 | 95.753 | 1.00 | 17.92 | C |
| ATOM | 2026 | CB | TYR | B | 9 | 31.374 | 37.596 | 95.663 | 1.00 | 17.49 | C |
| ATOM | 2027 | CG | TYR | B | 9 | 32.672 | 38.318 | 95.929 | 1.00 | 19.38 | C |
| ATOM | 2028 | CD1 | TYR | B | 9 | 33.351 | 38.152 | 97.135 | 1.00 | 18.09 | C |
| ATOM | 2029 | CE1 | TYR | B | 9 | 34.520 | 38.863 | 97.403 | 1.00 | 20.48 | C |
| ATOM | 2030 | CD2 | TYR | B | 9 | 33.194 | 39.209 | 94.994 | 1.00 | 18.42 | C |
| ATOM | 2031 | CE2 | TYR | B | 9 | 34.356 | 39.923 | 95.253 | 1.00 | 20.12 | C |
| ATOM | 2032 | CZ | TYR | B | 9 | 35.016 | 39.748 | 96.457 | 1.00 | 18.98 | C |
| ATOM | 2033 | OH | TYR | B | 9 | 36.170 | 40.452 | 96.703 | 1.00 | 19.27 | O |
| ATOM | 2034 | C | TYR | B | 9 | 28.930 | 37.624 | 95.318 | 1.00 | 18.56 | C |
| ATOM | 2035 | O | TYR | B | 9 | 28.360 | 36.863 | 96.116 | 1.00 | 18.21 | O |
| ATOM | 2036 | N | VAL | B | 10 | 28.577 | 37.748 | 94.038 | 1.00 | 17.30 | N |
| ATOM | 2037 | CA | VAL | B | 10 | 27.500 | 36.964 | 93.443 | 1.00 | 16.42 | C |
| ATOM | 2038 | CB | VAL | B | 10 | 26.735 | 37.764 | 92.363 | 1.00 | 14.72 | C |
| ATOM | 2039 | CG1 | VAL | B | 10 | 25.808 | 36.842 | 91.605 | 1.00 | 13.95 | C |
| ATOM | 2040 | CG2 | VAL | B | 10 | 25.929 | 38.883 | 93.013 | 1.00 | 14.84 | C |
| ATOM | 2041 | C | VAL | B | 10 | 28.135 | 35.738 | 92.772 | 1.00 | 16.40 | C |
| ATOM | 2042 | O | VAL | B | 10 | 29.066 | 35.875 | 91.975 | 1.00 | 15.69 | O |
| ATOM | 2043 | N | ILE | B | 11 | 27.631 | 34.548 | 93.104 | 1.00 | 16.63 | N |
| ATOM | 2044 | CA | ILE | B | 11 | 28.150 | 33.299 | 92.541 | 1.00 | 16.24 | C |
| ATOM | 2045 | CB | ILE | B | 11 | 28.617 | 32.361 | 93.662 | 1.00 | 15.33 | C |
| ATOM | 2046 | CG2 | ILE | B | 11 | 29.067 | 31.021 | 93.074 | 1.00 | 15.12 | C |
| ATOM | 2047 | CG1 | ILE | B | 11 | 29.743 | 33.044 | 94.439 | 1.00 | 15.97 | C |
| ATOM | 2048 | CD1 | ILE | B | 11 | 30.366 | 32.201 | 95.527 | 1.00 | 17.43 | C |
| ATOM | 2049 | C | ILE | B | 11 | 27.113 | 32.580 | 91.672 | 1.00 | 16.07 | C |
| ATOM | 2050 | O | ILE | B | 11 | 26.115 | 32.058 | 92.174 | 1.00 | 15.40 | O |
| ATOM | 2051 | N | MET | B | 12 | 27.365 | 32.546 | 90.366 | 1.00 | 16.10 | N |
| ATOM | 2052 | CA | MET | B | 12 | 26.426 | 31.934 | 89.424 | 1.00 | 16.86 | C |
| ATOM | 2053 | CB | MET | B | 12 | 26.239 | 32.857 | 88.221 | 1.00 | 17.50 | C |
| ATOM | 2054 | CG | MET | B | 12 | 26.070 | 34.332 | 88.580 | 1.00 | 15.23 | C |
| ATOM | 2055 | SD | MET | B | 12 | 25.649 | 35.371 | 87.140 | 1.00 | 17.70 | S |
| ATOM | 2056 | CE | MET | B | 12 | 23.866 | 34.947 | 86.963 | 1.00 | 12.17 | C |
| ATOM | 2057 | C | MET | B | 12 | 26.851 | 30.555 | 88.925 | 1.00 | 18.24 | C |
| ATOM | 2058 | O | MET | B | 12 | 27.974 | 30.383 | 88.440 | 1.00 | 17.93 | O |
| ATOM | 2059 | N | GLY | B | 13 | 25.952 | 29.575 | 89.049 | 1.00 | 18.66 | N |
| ATOM | 2060 | CA | GLY | B | 13 | 26.251 | 28.232 | 88.577 | 1.00 | 18.23 | C |
| ATOM | 2061 | C | GLY | B | 13 | 26.422 | 27.056 | 89.535 | 1.00 | 18.68 | C |
| ATOM | 2062 | O | GLY | B | 13 | 26.881 | 26.000 | 89.110 | 1.00 | 19.59 | O |
| ATOM | 2063 | N | ILE | B | 14 | 26.090 | 27.197 | 90.813 | 1.00 | 18.30 | N |
| ATOM | 2064 | CA | ILE | B | 14 | 26.228 | 26.047 | 91.696 | 1.00 | 17.08 | C |
| ATOM | 2065 | CB | ILE | B | 14 | 26.159 | 26.420 | 93.190 | 1.00 | 16.14 | C |
| ATOM | 2066 | CG2 | ILE | B | 14 | 26.108 | 25.151 | 94.030 | 1.00 | 15.56 | C |
| ATOM | 2067 | CG1 | ILE | B | 14 | 27.380 | 27.239 | 93.595 | 1.00 | 16.11 | C |
| ATOM | 2068 | CD1 | ILE | B | 14 | 27.382 | 27.623 | 95.060 | 1.00 | 15.96 | C |
| ATOM | 2069 | C | ILE | B | 14 | 25.066 | 25.107 | 91.398 | 1.00 | 17.74 | C |
| ATOM | 2070 | O | ILE | B | 14 | 23.907 | 25.532 | 91.384 | 1.00 | 17.49 | O |
| ATOM | 2071 | N | ALA | B | 15 | 25.376 | 23.843 | 91.127 | 1.00 | 18.44 | N |
| ATOM | 2072 | CA | ALA | B | 15 | 24.337 | 22.855 | 90.849 | 1.00 | 19.68 | C |
| ATOM | 2073 | CB | ALA | B | 15 | 24.582 | 22.184 | 89.512 | 1.00 | 20.61 | C |
| ATOM | 2074 | C | ALA | B | 15 | 24.282 | 21.808 | 91.961 | 1.00 | 19.63 | C |
| ATOM | 2075 | O | ALA | B | 15 | 23.204 | 21.357 | 92.326 | 1.00 | 19.56 | O |
| ATOM | 2076 | N | ASN | B | 16 | 25.443 | 21.420 | 92.491 | 1.00 | 20.14 | N |
| ATOM | 2077 | CA | ASN | B | 16 | 25.499 | 20.442 | 93.577 | 1.00 | 19.65 | C |
| ATOM | 2078 | CB | ASN | B | 16 | 25.286 | 19.033 | 93.032 | 1.00 | 19.88 | C |

FIGURE 9 (cont.)

| | | | | | | | | | | |
|---|---|---|---|---|---|---|---|---|---|---|
| ATOM | 2079 | CG | ASN | B | 16 | 26.488 | 18.520 | 92.272 | 1.00 20.54 | C |
| ATOM | 2080 | OD1 | ASN | B | 16 | 27.436 | 19.264 | 92.010 | 1.00 20.64 | O |
| ATOM | 2081 | ND2 | ASN | B | 16 | 26.457 | 17.243 | 91.910 | 1.00 21.04 | N |
| ATOM | 2082 | C | ASN | B | 16 | 26.835 | 20.509 | 94.315 | 1.00 19.56 | C |
| ATOM | 2083 | O | ASN | B | 16 | 27.646 | 21.391 | 94.070 | 1.00 19.74 | O |
| ATOM | 2084 | N | LYS | B | 17 | 27.060 | 19.570 | 95.223 | 1.00 19.42 | N |
| ATOM | 2085 | CA | LYS | B | 17 | 28.298 | 19.541 | 95.986 | 1.00 18.88 | C |
| ATOM | 2086 | CB | LYS | B | 17 | 28.325 | 18.296 | 96.892 | 1.00 19.73 | C |
| ATOM | 2087 | CG | LYS | B | 17 | 28.226 | 16.990 | 96.106 | 1.00 21.82 | C |
| ATOM | 2088 | CD | LYS | B | 17 | 28.587 | 15.751 | 96.935 | 1.00 25.01 | C |
| ATOM | 2089 | CE | LYS | B | 17 | 27.486 | 15.326 | 97.872 | 1.00 24.76 | C |
| ATOM | 2090 | NZ | LYS | B | 17 | 27.893 | 14.077 | 98.579 | 1.00 26.32 | N |
| ATOM | 2091 | C | LYS | B | 17 | 29.552 | 19.542 | 95.096 | 1.00 18.05 | C |
| ATOM | 2092 | O | LYS | B | 17 | 30.579 | 20.113 | 95.466 | 1.00 17.57 | O |
| ATOM | 2093 | N | ARG | B | 18 | 29.473 | 18.913 | 93.926 | 1.00 16.65 | N |
| ATOM | 2094 | CA | ARG | B | 18 | 30.638 | 18.826 | 93.049 | 1.00 15.88 | C |
| ATOM | 2095 | CB | ARG | B | 18 | 30.585 | 17.531 | 92.215 | 1.00 17.85 | C |
| ATOM | 2096 | CG | ARG | B | 18 | 30.690 | 16.220 | 93.010 | 1.00 16.90 | C |
| ATOM | 2097 | CD | ARG | B | 18 | 31.852 | 16.265 | 93.983 | 1.00 16.40 | C |
| ATOM | 2098 | NE | ARG | B | 18 | 32.019 | 15.025 | 94.731 | 1.00 18.45 | N |
| ATOM | 2099 | CZ | ARG | B | 18 | 32.469 | 13.883 | 94.216 | 1.00 17.88 | C |
| ATOM | 2100 | NH1 | ARG | B | 18 | 32.800 | 13.812 | 92.932 | 1.00 19.32 | N |
| ATOM | 2101 | NH2 | ARG | B | 18 | 32.606 | 12.814 | 94.995 | 1.00 17.66 | N |
| ATOM | 2102 | C | ARG | B | 18 | 30.898 | 20.005 | 92.116 | 1.00 14.82 | C |
| ATOM | 2103 | O | ARG | B | 18 | 31.907 | 20.029 | 91.423 | 1.00 15.28 | O |
| ATOM | 2104 | N | SER | B | 19 | 29.997 | 20.977 | 92.088 | 1.00 15.05 | N |
| ATOM | 2105 | CA | SER | B | 19 | 30.171 | 22.139 | 91.223 | 1.00 15.54 | C |
| ATOM | 2106 | CB | SER | B | 19 | 28.995 | 23.104 | 91.395 | 1.00 14.62 | C |
| ATOM | 2107 | OG | SER | B | 19 | 27.902 | 22.734 | 90.580 | 1.00 16.64 | O |
| ATOM | 2108 | C | SER | B | 19 | 31.475 | 22.899 | 91.475 | 1.00 15.56 | C |
| ATOM | 2109 | O | SER | B | 19 | 31.949 | 22.980 | 92.607 | 1.00 15.28 | O |
| ATOM | 2110 | N | ILE | B | 20 | 32.053 | 23.455 | 90.415 | 1.00 15.73 | N |
| ATOM | 2111 | CA | ILE | B | 20 | 33.281 | 24.235 | 90.558 | 1.00 16.01 | C |
| ATOM | 2112 | CB | ILE | B | 20 | 33.884 | 24.607 | 89.172 | 1.00 15.61 | C |
| ATOM | 2113 | CG2 | ILE | B | 20 | 35.014 | 25.606 | 89.344 | 1.00 15.50 | C |
| ATOM | 2114 | CG1 | ILE | B | 20 | 34.369 | 23.339 | 88.441 | 1.00 14.02 | C |
| ATOM | 2115 | CD1 | ILE | B | 20 | 35.002 | 23.602 | 87.091 | 1.00 10.18 | C |
| ATOM | 2116 | C | ILE | B | 20 | 32.923 | 25.520 | 91.312 | 1.00 17.76 | C |
| ATOM | 2117 | O | ILE | B | 20 | 33.710 | 26.026 | 92.111 | 1.00 19.26 | O |
| ATOM | 2118 | N | ALA | B | 21 | 31.718 | 26.033 | 91.066 | 1.00 18.81 | N |
| ATOM | 2119 | CA | ALA | B | 21 | 31.257 | 27.256 | 91.718 | 1.00 17.69 | C |
| ATOM | 2120 | CB | ALA | B | 21 | 29.926 | 27.700 | 91.126 | 1.00 17.20 | C |
| ATOM | 2121 | C | ALA | B | 21 | 31.124 | 27.068 | 93.224 | 1.00 18.42 | C |
| ATOM | 2122 | O | ALA | B | 21 | 31.259 | 28.032 | 93.988 | 1.00 17.24 | O |
| ATOM | 2123 | N | PHE | B | 22 | 30.847 | 25.836 | 93.657 | 1.00 18.45 | N |
| ATOM | 2124 | CA | PHE | B | 22 | 30.730 | 25.561 | 95.088 | 1.00 19.08 | C |
| ATOM | 2125 | CB | PHE | B | 22 | 30.057 | 24.209 | 95.336 | 1.00 19.17 | C |
| ATOM | 2126 | CG | PHE | B | 22 | 29.820 | 23.913 | 96.792 | 1.00 18.67 | C |
| ATOM | 2127 | CD1 | PHE | B | 22 | 30.292 | 22.739 | 97.365 | 1.00 20.21 | C |
| ATOM | 2128 | CD2 | PHE | B | 22 | 29.133 | 24.816 | 97.595 | 1.00 18.25 | C |
| ATOM | 2129 | CE1 | PHE | B | 22 | 30.082 | 22.472 | 98.722 | 1.00 17.98 | C |
| ATOM | 2130 | CE2 | PHE | B | 22 | 28.920 | 24.558 | 98.949 | 1.00 17.29 | C |
| ATOM | 2131 | CZ | PHE | B | 22 | 29.395 | 23.387 | 99.509 | 1.00 19.59 | C |
| ATOM | 2132 | C | PHE | B | 22 | 32.140 | 25.562 | 95.688 | 1.00 19.72 | C |
| ATOM | 2133 | O | PHE | B | 22 | 32.344 | 25.857 | 96.874 | 1.00 19.72 | O |
| ATOM | 2134 | N | GLY | B | 23 | 33.116 | 25.216 | 94.856 | 1.00 20.01 | N |
| ATOM | 2135 | CA | GLY | B | 23 | 34.487 | 25.232 | 95.312 | 1.00 20.70 | C |
| ATOM | 2136 | C | GLY | B | 23 | 34.865 | 26.682 | 95.594 | 1.00 21.53 | C |
| ATOM | 2137 | O | GLY | B | 23 | 35.565 | 26.964 | 96.569 | 1.00 20.26 | O |
| ATOM | 2138 | N | VAL | B | 24 | 34.399 | 27.615 | 94.759 | 1.00 19.72 | N |
| ATOM | 2139 | CA | VAL | B | 24 | 34.744 | 29.013 | 95.000 | 1.00 19.01 | C |
| ATOM | 2140 | CB | VAL | B | 24 | 34.478 | 29.925 | 93.746 | 1.00 18.58 | C |
| ATOM | 2141 | CG1 | VAL | B | 24 | 34.808 | 29.172 | 92.465 | 1.00 17.22 | C |
| ATOM | 2142 | CG2 | VAL | B | 24 | 33.052 | 30.422 | 93.736 | 1.00 20.93 | C |
| ATOM | 2143 | C | VAL | B | 24 | 33.964 | 29.541 | 96.207 | 1.00 18.13 | C |

FIGURE 9 (cont.)

| | | | | | | | | | |
|---|---|---|---|---|---|---|---|---|---|
| ATOM | 2144 | O | VAL | B | 24 | 34.497 | 30.309 | 97.005 | 1.00 17.12 | O |
| ATOM | 2145 | N | ALA | B | 25 | 32.711 | 29.110 | 96.353 | 1.00 17.98 | N |
| ATOM | 2146 | CA | ALA | B | 25 | 31.873 | 29.551 | 97.473 | 1.00 17.30 | C |
| ATOM | 2147 | CB | ALA | B | 25 | 30.474 | 28.955 | 97.364 | 1.00 16.84 | C |
| ATOM | 2148 | C | ALA | B | 25 | 32.505 | 29.149 | 98.794 | 1.00 17.53 | C |
| ATOM | 2149 | O | ALA | B | 25 | 32.484 | 29.912 | 99.772 | 1.00 16.57 | O |
| ATOM | 2150 | N | LYS | B | 26 | 33.073 | 27.947 | 98.818 | 1.00 17.23 | N |
| ATOM | 2151 | CA | LYS | B | 26 | 33.720 | 27.452 | 100.012 | 1.00 18.10 | C |
| ATOM | 2152 | CB | LYS | B | 26 | 34.103 | 25.980 | 99.823 | 1.00 19.51 | C |
| ATOM | 2153 | CG | LYS | B | 26 | 32.901 | 25.029 | 99.963 | 1.00 21.00 | C |
| ATOM | 2154 | CD | LYS | B | 26 | 33.057 | 23.732 | 99.174 | 1.00 21.20 | C |
| ATOM | 2155 | CE | LYS | B | 26 | 34.175 | 22.857 | 99.695 | 1.00 22.99 | C |
| ATOM | 2156 | NZ | LYS | B | 26 | 34.078 | 21.480 | 99.112 | 1.00 23.65 | N |
| ATOM | 2157 | C | LYS | B | 26 | 34.943 | 28.295 | 100.368 | 1.00 18.58 | C |
| ATOM | 2158 | O | LYS | B | 26 | 35.202 | 28.569 | 101.547 | 1.00 19.52 | O |
| ATOM | 2159 | N | VAL | B | 27 | 35.690 | 28.724 | 99.358 | 1.00 17.87 | N |
| ATOM | 2160 | CA | VAL | B | 27 | 36.879 | 29.518 | 99.617 | 1.00 17.39 | C |
| ATOM | 2161 | CB | VAL | B | 27 | 37.815 | 29.510 | 98.400 | 1.00 17.13 | C |
| ATOM | 2162 | CG1 | VAL | B | 27 | 39.006 | 30.407 | 98.645 | 1.00 16.53 | C |
| ATOM | 2163 | CG2 | VAL | B | 27 | 38.290 | 28.086 | 98.151 | 1.00 16.91 | C |
| ATOM | 2164 | C | VAL | B | 27 | 36.541 | 30.949 | 100.022 | 1.00 17.11 | C |
| ATOM | 2165 | O | VAL | B | 27 | 37.053 | 31.443 | 101.019 | 1.00 17.04 | O |
| ATOM | 2166 | N | LEU | B | 28 | 35.679 | 31.613 | 99.261 | 1.00 18.09 | N |
| ATOM | 2167 | CA | LEU | B | 28 | 35.288 | 32.979 | 99.596 | 1.00 19.70 | C |
| ATOM | 2168 | CB | LEU | B | 28 | 34.314 | 33.532 | 98.547 | 1.00 17.52 | C |
| ATOM | 2169 | CG | LEU | B | 28 | 34.861 | 33.542 | 97.117 | 1.00 17.14 | C |
| ATOM | 2170 | CD1 | LEU | B | 28 | 33.785 | 33.986 | 96.137 | 1.00 14.29 | C |
| ATOM | 2171 | CD2 | LEU | B | 28 | 36.067 | 34.465 | 97.049 | 1.00 18.03 | C |
| ATOM | 2172 | C | LEU | B | 28 | 34.629 | 32.996 | 100.980 | 1.00 20.68 | C |
| ATOM | 2173 | O | LEU | B | 28 | 34.805 | 33.940 | 101.751 | 1.00 20.36 | O |
| ATOM | 2174 | N | ASP | B | 29 | 33.891 | 31.933 | 101.294 | 1.00 22.21 | N |
| ATOM | 2175 | CA | ASP | B | 29 | 33.196 | 31.824 | 102.578 | 1.00 23.06 | C |
| ATOM | 2176 | CB | ASP | B | 29 | 32.314 | 30.573 | 102.617 | 1.00 22.90 | C |
| ATOM | 2177 | CG | ASP | B | 29 | 31.621 | 30.390 | 103.958 | 1.00 22.48 | C |
| ATOM | 2178 | OD1 | ASP | B | 29 | 30.685 | 31.171 | 104.254 | 1.00 21.18 | O |
| ATOM | 2179 | OD2 | ASP | B | 29 | 32.021 | 29.467 | 104.717 | 1.00 21.13 | O |
| ATOM | 2180 | C | ASP | B | 29 | 34.158 | 31.772 | 103.749 | 1.00 24.17 | C |
| ATOM | 2181 | O | ASP | B | 29 | 33.861 | 32.299 | 104.823 | 1.00 24.68 | O |
| ATOM | 2182 | N | GLN | B | 30 | 35.303 | 31.127 | 103.555 | 1.00 24.93 | N |
| ATOM | 2183 | CA | GLN | B | 30 | 36.277 | 31.033 | 104.627 | 1.00 25.55 | C |
| ATOM | 2184 | CB | GLN | B | 30 | 37.204 | 29.836 | 104.426 | 1.00 27.58 | C |
| ATOM | 2185 | CG | GLN | B | 30 | 38.223 | 29.716 | 105.529 | 1.00 31.50 | C |
| ATOM | 2186 | CD | GLN | B | 30 | 38.733 | 28.318 | 105.708 | 1.00 35.24 | C |
| ATOM | 2187 | OE1 | GLN | B | 30 | 39.512 | 27.810 | 104.883 | 1.00 37.01 | O |
| ATOM | 2188 | NE2 | GLN | B | 30 | 38.297 | 27.667 | 106.793 | 1.00 35.74 | N |
| ATOM | 2189 | C | GLN | B | 30 | 37.096 | 32.303 | 104.742 | 1.00 25.57 | C |
| ATOM | 2190 | O | GLN | B | 30 | 37.734 | 32.536 | 105.768 | 1.00 26.77 | O |
| ATOM | 2191 | N | LEU | B | 31 | 37.096 | 33.124 | 103.694 | 1.00 24.61 | N |
| ATOM | 2192 | CA | LEU | B | 31 | 37.829 | 34.383 | 103.742 | 1.00 23.45 | C |
| ATOM | 2193 | CB | LEU | B | 31 | 38.300 | 34.827 | 102.345 | 1.00 21.80 | C |
| ATOM | 2194 | CG | LEU | B | 31 | 39.615 | 34.284 | 101.764 | 1.00 21.00 | C |
| ATOM | 2195 | CD1 | LEU | B | 31 | 40.588 | 33.976 | 102.887 | 1.00 17.32 | C |
| ATOM | 2196 | CD2 | LEU | B | 31 | 39.352 | 33.035 | 100.934 | 1.00 21.57 | C |
| ATOM | 2197 | C | LEU | B | 31 | 36.933 | 35.468 | 104.347 | 1.00 23.05 | C |
| ATOM | 2198 | O | LEU | B | 31 | 37.298 | 36.646 | 104.367 | 1.00 23.71 | O |
| ATOM | 2199 | N | GLY | B | 32 | 35.756 | 35.061 | 104.824 | 1.00 22.56 | N |
| ATOM | 2200 | CA | GLY | B | 32 | 34.834 | 35.996 | 105.450 | 1.00 22.20 | C |
| ATOM | 2201 | C | GLY | B | 32 | 33.947 | 36.824 | 104.540 | 1.00 22.18 | C |
| ATOM | 2202 | O | GLY | B | 32 | 33.291 | 37.766 | 105.001 | 1.00 22.40 | O |
| ATOM | 2203 | N | ALA | B | 33 | 33.902 | 36.475 | 103.258 | 1.00 22.02 | N |
| ATOM | 2204 | CA | ALA | B | 33 | 33.092 | 37.217 | 102.294 | 1.00 20.62 | C |
| ATOM | 2205 | CB | ALA | B | 33 | 33.473 | 36.805 | 100.887 | 1.00 21.91 | C |
| ATOM | 2206 | C | ALA | B | 33 | 31.595 | 37.018 | 102.503 | 1.00 20.16 | C |
| ATOM | 2207 | O | ALA | B | 33 | 31.176 | 36.075 | 103.168 | 1.00 19.13 | O |
| ATOM | 2208 | N | LYS | B | 34 | 30.798 | 37.932 | 101.951 | 1.00 19.68 | N |

FIGURE 9 (cont.)

| ATOM | 2209 | CA | LYS | B | 34 | 29.339 | 37.848 | 102.032 | 1.00 | 18.70 | C |
| ATOM | 2210 | CB | LYS | B | 34 | 28.719 | 39.231 | 102.248 | 1.00 | 20.20 | C |
| ATOM | 2211 | CG | LYS | B | 34 | 27.208 | 39.229 | 102.513 | 1.00 | 23.64 | C |
| ATOM | 2212 | CD | LYS | B | 34 | 26.626 | 40.642 | 102.336 | 1.00 | 26.85 | C |
| ATOM | 2213 | CE | LYS | B | 34 | 25.160 | 40.754 | 102.777 | 1.00 | 29.50 | C |
| ATOM | 2214 | NZ | LYS | B | 34 | 24.970 | 40.761 | 104.274 | 1.00 | 29.02 | N |
| ATOM | 2215 | C | LYS | B | 34 | 28.991 | 37.319 | 100.647 | 1.00 | 17.65 | C |
| ATOM | 2216 | O | LYS | B | 34 | 29.549 | 37.774 | 99.651 | 1.00 | 16.24 | O |
| ATOM | 2217 | N | LEU | B | 35 | 28.068 | 36.372 | 100.575 | 1.00 | 17.19 | N |
| ATOM | 2218 | CA | LEU | B | 35 | 27.747 | 35.761 | 99.300 | 1.00 | 16.79 | C |
| ATOM | 2219 | CB | LEU | B | 35 | 28.352 | 34.357 | 99.261 | 1.00 | 16.86 | C |
| ATOM | 2220 | CG | LEU | B | 35 | 29.844 | 34.156 | 99.551 | 1.00 | 15.10 | C |
| ATOM | 2221 | CD1 | LEU | B | 35 | 30.108 | 32.682 | 99.757 | 1.00 | 14.55 | C |
| ATOM | 2222 | CD2 | LEU | B | 35 | 30.683 | 34.692 | 98.398 | 1.00 | 15.19 | C |
| ATOM | 2223 | C | LEU | B | 35 | 26.274 | 35.644 | 98.969 | 1.00 | 17.55 | C |
| ATOM | 2224 | O | LEU | B | 35 | 25.439 | 35.478 | 99.858 | 1.00 | 15.79 | O |
| ATOM | 2225 | N | VAL | B | 36 | 25.968 | 35.730 | 97.675 | 1.00 | 18.13 | N |
| ATOM | 2226 | CA | VAL | B | 36 | 24.602 | 35.569 | 97.193 | 1.00 | 19.81 | C |
| ATOM | 2227 | CB | VAL | B | 36 | 23.958 | 36.918 | 96.776 | 1.00 | 19.19 | C |
| ATOM | 2228 | CG1 | VAL | B | 36 | 24.400 | 38.005 | 97.730 | 1.00 | 20.58 | C |
| ATOM | 2229 | CG2 | VAL | B | 36 | 24.299 | 37.271 | 95.357 | 1.00 | 21.23 | C |
| ATOM | 2230 | C | VAL | B | 36 | 24.729 | 34.618 | 96.007 | 1.00 | 20.90 | C |
| ATOM | 2231 | O | VAL | B | 36 | 25.740 | 34.648 | 95.286 | 1.00 | 22.72 | O |
| ATOM | 2232 | N | PHE | B | 37 | 23.723 | 33.765 | 95.811 | 1.00 | 21.27 | N |
| ATOM | 2233 | CA | PHE | B | 37 | 23.762 | 32.783 | 94.731 | 1.00 | 20.03 | C |
| ATOM | 2234 | CB | PHE | B | 37 | 23.829 | 31.369 | 95.318 | 1.00 | 19.94 | C |
| ATOM | 2235 | CG | PHE | B | 37 | 24.730 | 31.256 | 96.508 | 1.00 | 20.18 | C |
| ATOM | 2236 | CD1 | PHE | B | 37 | 24.342 | 31.778 | 97.740 | 1.00 | 18.22 | C |
| ATOM | 2237 | CD2 | PHE | B | 37 | 25.984 | 30.665 | 96.392 | 1.00 | 20.09 | C |
| ATOM | 2238 | CE1 | PHE | B | 37 | 25.189 | 31.717 | 98.835 | 1.00 | 18.57 | C |
| ATOM | 2239 | CE2 | PHE | B | 37 | 26.843 | 30.599 | 97.489 | 1.00 | 20.94 | C |
| ATOM | 2240 | CZ | PHE | B | 37 | 26.443 | 31.128 | 98.713 | 1.00 | 19.40 | C |
| ATOM | 2241 | C | PHE | B | 37 | 22.576 | 32.853 | 93.785 | 1.00 | 20.28 | C |
| ATOM | 2242 | O | PHE | B | 37 | 21.513 | 33.373 | 94.130 | 1.00 | 20.34 | O |
| ATOM | 2243 | N | THR | B | 38 | 22.771 | 32.318 | 92.585 | 1.00 | 19.51 | N |
| ATOM | 2244 | CA | THR | B | 38 | 21.714 | 32.279 | 91.598 | 1.00 | 20.05 | C |
| ATOM | 2245 | CB | THR | B | 38 | 21.936 | 33.318 | 90.461 | 1.00 | 19.60 | C |
| ATOM | 2246 | OG1 | THR | B | 38 | 22.938 | 32.847 | 89.559 | 1.00 | 19.53 | O |
| ATOM | 2247 | CG2 | THR | B | 38 | 22.382 | 34.660 | 91.037 | 1.00 | 19.37 | C |
| ATOM | 2248 | C | THR | B | 38 | 21.677 | 30.867 | 91.014 | 1.00 | 20.83 | C |
| ATOM | 2249 | O | THR | B | 38 | 22.710 | 30.196 | 90.890 | 1.00 | 21.22 | O |
| ATOM | 2250 | N | TYR | B | 39 | 20.482 | 30.420 | 90.659 | 1.00 | 21.59 | N |
| ATOM | 2251 | CA | TYR | B | 39 | 20.306 | 29.086 | 90.112 | 1.00 | 22.21 | C |
| ATOM | 2252 | CB | TYR | B | 39 | 19.748 | 28.167 | 91.195 | 1.00 | 22.09 | C |
| ATOM | 2253 | CG | TYR | B | 39 | 18.521 | 28.734 | 91.875 | 1.00 | 23.15 | C |
| ATOM | 2254 | CD1 | TYR | B | 39 | 18.636 | 29.726 | 92.848 | 1.00 | 24.39 | C |
| ATOM | 2255 | CE1 | TYR | B | 39 | 17.512 | 30.256 | 93.469 | 1.00 | 24.70 | C |
| ATOM | 2256 | CD2 | TYR | B | 39 | 17.244 | 28.287 | 91.537 | 1.00 | 24.04 | C |
| ATOM | 2257 | CE2 | TYR | B | 39 | 16.112 | 28.808 | 92.153 | 1.00 | 24.02 | C |
| ATOM | 2258 | CZ | TYR | B | 39 | 16.253 | 29.791 | 93.121 | 1.00 | 24.93 | C |
| ATOM | 2259 | OH | TYR | B | 39 | 15.135 | 30.290 | 93.763 | 1.00 | 26.95 | O |
| ATOM | 2260 | C | TYR | B | 39 | 19.355 | 29.123 | 88.926 | 1.00 | 22.58 | C |
| ATOM | 2261 | O | TYR | B | 39 | 18.517 | 30.013 | 88.820 | 1.00 | 22.26 | O |
| ATOM | 2262 | N | ARG | B | 40 | 19.463 | 28.132 | 88.049 | 1.00 | 25.12 | N |
| ATOM | 2263 | CA | ARG | B | 40 | 18.623 | 28.081 | 86.855 | 1.00 | 27.74 | C |
| ATOM | 2264 | CB | ARG | B | 40 | 19.130 | 26.996 | 85.897 | 1.00 | 27.94 | C |
| ATOM | 2265 | CG | ARG | B | 40 | 18.482 | 27.045 | 84.509 | 1.00 | 29.92 | C |
| ATOM | 2266 | CD | ARG | B | 40 | 19.158 | 26.078 | 83.554 | 1.00 | 32.25 | C |
| ATOM | 2267 | NE | ARG | B | 40 | 18.974 | 24.686 | 83.966 | 1.00 | 35.58 | N |
| ATOM | 2268 | CZ | ARG | B | 40 | 17.897 | 23.966 | 83.668 | 1.00 | 36.27 | C |
| ATOM | 2269 | NH1 | ARG | B | 40 | 16.921 | 24.509 | 82.949 | 1.00 | 36.46 | N |
| ATOM | 2270 | NH2 | ARG | B | 40 | 17.789 | 22.713 | 84.101 | 1.00 | 37.28 | N |
| ATOM | 2271 | C | ARG | B | 40 | 17.127 | 27.875 | 87.086 | 1.00 | 28.46 | C |
| ATOM | 2272 | O | ARG | B | 40 | 16.316 | 28.742 | 86.752 | 1.00 | 29.36 | O |
| ATOM | 2273 | N | LYS | B | 41 | 16.748 | 26.734 | 87.649 | 1.00 | 29.81 | N |

FIGURE 9 (cont.)

```
ATOM   2274  CA   LYS B  41      15.331  26.473  87.853  1.00 31.40           C
ATOM   2275  CB   LYS B  41      14.974  25.120  87.239  1.00 32.68           C
ATOM   2276  CG   LYS B  41      14.883  25.129  85.714  1.00 32.68           C
ATOM   2277  CD   LYS B  41      13.817  26.121  85.244  1.00 32.86           C
ATOM   2278  CE   LYS B  41      13.533  25.972  83.749  1.00 33.59           C
ATOM   2279  NZ   LYS B  41      14.769  26.111  82.914  1.00 32.00           N
ATOM   2280  C    LYS B  41      14.816  26.543  89.288  1.00 32.13           C
ATOM   2281  O    LYS B  41      15.531  26.236  90.241  1.00 32.24           O
ATOM   2282  N    GLU B  42      13.558  26.954  89.423  1.00 33.83           N
ATOM   2283  CA   GLU B  42      12.907  27.079  90.721  1.00 35.95           C
ATOM   2284  CB   GLU B  42      11.512  27.675  90.546  1.00 37.45           C
ATOM   2285  CG   GLU B  42      10.780  27.940  91.858  1.00 40.97           C
ATOM   2286  CD   GLU B  42       9.556  28.821  91.664  1.00 43.48           C
ATOM   2287  OE1  GLU B  42       9.694  29.883  90.993  1.00 45.06           O
ATOM   2288  OE2  GLU B  42       8.463  28.464  92.179  1.00 44.05           O
ATOM   2289  C    GLU B  42      12.778  25.722  91.377  1.00 36.93           C
ATOM   2290  O    GLU B  42      12.589  25.610  92.588  1.00 37.23           O
ATOM   2291  N    ARG B  43      12.867  24.681  90.565  1.00 38.96           N
ATOM   2292  CA   ARG B  43      12.739  23.326  91.068  1.00 40.53           C
ATOM   2293  CB   ARG B  43      12.552  22.365  89.895  1.00 43.46           C
ATOM   2294  CG   ARG B  43      13.534  22.577  88.731  1.00 46.24           C
ATOM   2295  CD   ARG B  43      13.263  21.546  87.637  1.00 48.88           C
ATOM   2296  NE   ARG B  43      14.116  21.700  86.454  1.00 50.88           N
ATOM   2297  CZ   ARG B  43      14.283  20.740  85.545  1.00 51.70           C
ATOM   2298  NH1  ARG B  43      13.657  19.572  85.701  1.00 52.20           N
ATOM   2299  NH2  ARG B  43      15.074  20.933  84.489  1.00 51.50           N
ATOM   2300  C    ARG B  43      13.900  22.873  91.941  1.00 40.31           C
ATOM   2301  O    ARG B  43      13.722  21.998  92.793  1.00 40.90           O
ATOM   2302  N    SER B  44      15.084  23.461  91.756  1.00 39.87           N
ATOM   2303  CA   SER B  44      16.245  23.054  92.560  1.00 39.29           C
ATOM   2304  CB   SER B  44      17.404  22.627  91.640  1.00 39.39           C
ATOM   2305  OG   SER B  44      17.725  23.645  90.703  1.00 37.93           O
ATOM   2306  C    SER B  44      16.733  24.109  93.556  1.00 38.87           C
ATOM   2307  O    SER B  44      17.941  24.323  93.727  1.00 38.90           O
ATOM   2308  N    ARG B  45      15.788  24.747  94.234  1.00 38.53           N
ATOM   2309  CA   ARG B  45      16.094  25.783  95.218  1.00 37.63           C
ATOM   2310  CB   ARG B  45      14.881  26.702  95.357  1.00 37.54           C
ATOM   2311  CG   ARG B  45      15.192  28.031  95.988  1.00 38.81           C
ATOM   2312  CD   ARG B  45      13.926  28.786  96.398  1.00 39.47           C
ATOM   2313  NE   ARG B  45      14.269  30.130  96.865  1.00 40.00           N
ATOM   2314  CZ   ARG B  45      15.096  30.383  97.876  1.00 40.61           C
ATOM   2315  NH1  ARG B  45      15.662  29.376  98.542  1.00 41.44           N
ATOM   2316  NH2  ARG B  45      15.385  31.640  98.205  1.00 39.52           N
ATOM   2317  C    ARG B  45      16.411  25.147  96.575  1.00 37.16           C
ATOM   2318  O    ARG B  45      17.320  25.579  97.296  1.00 35.64           O
ATOM   2319  N    LYS B  46      15.633  24.122  96.918  1.00 37.00           N
ATOM   2320  CA   LYS B  46      15.787  23.399  98.178  1.00 36.26           C
ATOM   2321  CB   LYS B  46      14.766  22.261  98.250  1.00 37.93           C
ATOM   2322  CG   LYS B  46      14.598  21.534  96.904  1.00 39.51           C
ATOM   2323  CD   LYS B  46      13.891  20.171  97.014  1.00 40.59           C
ATOM   2324  CE   LYS B  46      14.852  19.065  97.464  1.00 40.77           C
ATOM   2325  NZ   LYS B  46      15.184  19.158  98.919  1.00 40.67           N
ATOM   2326  C    LYS B  46      17.185  22.822  98.290  1.00 35.85           C
ATOM   2327  O    LYS B  46      17.828  22.937  99.340  1.00 35.20           O
ATOM   2328  N    GLU B  47      17.656  22.199  97.211  1.00 34.98           N
ATOM   2329  CA   GLU B  47      18.988  21.601  97.209  1.00 34.59           C
ATOM   2330  CB   GLU B  47      19.278  20.891  95.881  1.00 37.27           C
ATOM   2331  CG   GLU B  47      20.484  19.931  95.927  1.00 41.01           C
ATOM   2332  CD   GLU B  47      21.862  20.625  95.909  1.00 42.99           C
ATOM   2333  OE1  GLU B  47      22.863  19.931  96.233  1.00 43.44           O
ATOM   2334  OE2  GLU B  47      21.957  21.839  95.565  1.00 43.01           O
ATOM   2335  C    GLU B  47      20.074  22.633  97.448  1.00 32.94           C
ATOM   2336  O    GLU B  47      20.965  22.411  98.268  1.00 33.48           O
ATOM   2337  N    LEU B  48      20.033  23.751  96.727  1.00 31.22           N
ATOM   2338  CA   LEU B  48      21.068  24.760  96.921  1.00 30.19           C
```

FIGURE 9 (cont.)

```
ATOM   2339  CB  LEU B  48      20.852  25.978  96.006  1.00 30.25           C
ATOM   2340  CG  LEU B  48      21.963  26.338  95.005  1.00 29.79           C
ATOM   2341  CD1 LEU B  48      21.711  27.727  94.474  1.00 29.02           C
ATOM   2342  CD2 LEU B  48      23.324  26.287  95.663  1.00 28.14           C
ATOM   2343  C   LEU B  48      20.970  25.200  98.362  1.00 30.13           C
ATOM   2344  O   LEU B  48      21.979  25.330  99.057  1.00 30.06           O
ATOM   2345  N   GLU B  49      19.734  25.391  98.808  1.00 30.06           N
ATOM   2346  CA  GLU B  49      19.455  25.841 100.159  1.00 31.94           C
ATOM   2347  CB  GLU B  49      17.957  26.122 100.297  1.00 33.58           C
ATOM   2348  CG  GLU B  49      17.525  26.645 101.656  1.00 36.82           C
ATOM   2349  CD  GLU B  49      16.085  27.141 101.645  1.00 39.26           C
ATOM   2350  OE1 GLU B  49      15.524  27.407 102.737  1.00 39.69           O
ATOM   2351  OE2 GLU B  49      15.515  27.269 100.533  1.00 40.30           O
ATOM   2352  C   GLU B  49      19.913  24.874 101.238  1.00 32.24           C
ATOM   2353  O   GLU B  49      20.213  25.290 102.356  1.00 33.45           O
ATOM   2354  N   LYS B  50      19.960  23.586 100.917  1.00 32.79           N
ATOM   2355  CA  LYS B  50      20.397  22.579 101.882  1.00 33.78           C
ATOM   2356  CB  LYS B  50      19.741  21.217 101.585  1.00 35.19           C
ATOM   2357  CG  LYS B  50      18.199  21.204 101.649  1.00 37.60           C
ATOM   2358  CD  LYS B  50      17.634  19.770 101.782  1.00 37.43           C
ATOM   2359  CE  LYS B  50      17.568  19.020 100.448  1.00 38.45           C
ATOM   2360  NZ  LYS B  50      18.879  18.888  99.728  1.00 37.85           N
ATOM   2361  C   LYS B  50      21.914  22.433 101.806  1.00 33.41           C
ATOM   2362  O   LYS B  50      22.568  22.061 102.785  1.00 33.70           O
ATOM   2363  N   LEU B  51      22.464  22.731 100.629  1.00 32.47           N
ATOM   2364  CA  LEU B  51      23.901  22.637 100.372  1.00 31.14           C
ATOM   2365  CB  LEU B  51      24.179  22.732  98.864  1.00 29.85           C
ATOM   2366  CG  LEU B  51      25.199  21.806  98.178  1.00 29.09           C
ATOM   2367  CD1 LEU B  51      25.821  22.585  97.034  1.00 26.87           C
ATOM   2368  CD2 LEU B  51      26.277  21.306  99.134  1.00 25.86           C
ATOM   2369  C   LEU B  51      24.623  23.785 101.053  1.00 32.03           C
ATOM   2370  O   LEU B  51      25.665  23.593 101.684  1.00 31.88           O
ATOM   2371  N   LEU B  52      24.070  24.988 100.899  1.00 32.61           N
ATOM   2372  CA  LEU B  52      24.664  26.190 101.479  1.00 32.76           C
ATOM   2373  CB  LEU B  52      23.863  27.428 101.041  1.00 31.53           C
ATOM   2374  CG  LEU B  52      23.614  27.460  99.529  1.00 30.58           C
ATOM   2375  CD1 LEU B  52      23.063  28.812  99.124  1.00 32.52           C
ATOM   2376  CD2 LEU B  52      24.909  27.192  98.770  1.00 30.30           C
ATOM   2377  C   LEU B  52      24.716  26.070 102.996  1.00 33.20           C
ATOM   2378  O   LEU B  52      25.351  26.878 103.681  1.00 33.60           O
ATOM   2379  N   GLU B  53      24.062  25.033 103.505  1.00 34.40           N
ATOM   2380  CA  GLU B  53      24.018  24.729 104.938  1.00 34.53           C
ATOM   2381  CB  GLU B  53      23.309  23.386 105.162  1.00 35.82           C
ATOM   2382  CG  GLU B  53      22.593  23.253 106.495  1.00 37.84           C
ATOM   2383  CD  GLU B  53      21.314  24.066 106.534  1.00 39.88           C
ATOM   2384  OE1 GLU B  53      20.566  23.972 107.542  1.00 41.29           O
ATOM   2385  OE2 GLU B  53      21.055  24.802 105.549  1.00 40.28           O
ATOM   2386  C   GLU B  53      25.442  24.593 105.458  1.00 33.85           C
ATOM   2387  O   GLU B  53      25.738  24.920 106.613  1.00 34.26           O
ATOM   2388  N   GLN B  54      26.314  24.084 104.595  1.00 33.17           N
ATOM   2389  CA  GLN B  54      27.709  23.856 104.940  1.00 33.55           C
ATOM   2390  CB  GLN B  54      28.433  23.172 103.791  1.00 35.18           C
ATOM   2391  CG  GLN B  54      28.065  21.725 103.541  1.00 37.38           C
ATOM   2392  CD  GLN B  54      28.925  21.145 102.445  1.00 39.38           C
ATOM   2393  OE1 GLN B  54      30.166  21.157 102.535  1.00 39.34           O
ATOM   2394  NE2 GLN B  54      28.284  20.654 101.387  1.00 41.45           N
ATOM   2395  C   GLN B  54      28.509  25.089 105.291  1.00 32.58           C
ATOM   2396  O   GLN B  54      29.376  25.036 106.155  1.00 32.80           O
ATOM   2397  N   LEU B  55      28.230  26.189 104.602  1.00 32.24           N
ATOM   2398  CA  LEU B  55      28.962  27.435 104.799  1.00 32.66           C
ATOM   2399  CB  LEU B  55      28.801  28.315 103.559  1.00 31.02           C
ATOM   2400  CG  LEU B  55      28.721  27.558 102.229  1.00 30.47           C
ATOM   2401  CD1 LEU B  55      28.472  28.544 101.092  1.00 29.26           C
ATOM   2402  CD2 LEU B  55      30.021  26.781 102.015  1.00 29.89           C
ATOM   2403  C   LEU B  55      28.524  28.231 106.024  1.00 33.46           C
```

FIGURE 9 (cont.)

```
ATOM   2404  O   LEU B  55      27.523  27.923 106.669  1.00 32.98           O
ATOM   2405  N   ASN B  56      29.283  29.268 106.342  1.00 35.25           N
ATOM   2406  CA  ASN B  56      28.917  30.107 107.465  1.00 37.47           C
ATOM   2407  CB  ASN B  56      30.097  30.354 108.393  1.00 39.74           C
ATOM   2408  CG  ASN B  56      29.826  31.492 109.356  1.00 41.73           C
ATOM   2409  OD1 ASN B  56      28.718  31.611 109.905  1.00 41.76           O
ATOM   2410  ND2 ASN B  56      30.827  32.347 109.559  1.00 43.23           N
ATOM   2411  C   ASN B  56      28.378  31.445 106.997  1.00 37.32           C
ATOM   2412  O   ASN B  56      28.978  32.487 107.263  1.00 38.94           O
ATOM   2413  N   GLN B  57      27.261  31.409 106.281  1.00 36.44           N
ATOM   2414  CA  GLN B  57      26.612  32.610 105.808  1.00 36.57           C
ATOM   2415  CB  GLN B  57      25.990  32.372 104.431  1.00 33.98           C
ATOM   2416  CG  GLN B  57      27.018  32.210 103.315  1.00 30.79           C
ATOM   2417  CD  GLN B  57      27.833  33.472 103.084  1.00 29.34           C
ATOM   2418  OE1 GLN B  57      27.285  34.535 102.761  1.00 27.37           O
ATOM   2419  NE2 GLN B  57      29.147  33.364 103.252  1.00 26.14           N
ATOM   2420  C   GLN B  57      25.518  32.885 106.835  1.00 38.85           C
ATOM   2421  O   GLN B  57      24.887  31.955 107.336  1.00 39.22           O
ATOM   2422  N   PRO B  58      25.283  34.164 107.170  1.00 40.87           N
ATOM   2423  CD  PRO B  58      26.063  35.341 106.735  1.00 41.90           C
ATOM   2424  CA  PRO B  58      24.256  34.544 108.152  1.00 42.02           C
ATOM   2425  CB  PRO B  58      24.689  35.937 108.572  1.00 42.22           C
ATOM   2426  CG  PRO B  58      25.211  36.507 107.246  1.00 43.02           C
ATOM   2427  C   PRO B  58      22.828  34.550 107.610  1.00 43.01           C
ATOM   2428  O   PRO B  58      21.863  34.459 108.382  1.00 43.49           O
ATOM   2429  N   GLU B  59      22.675  34.671 106.295  1.00 43.00           N
ATOM   2430  CA  GLU B  59      21.332  34.696 105.727  1.00 43.32           C
ATOM   2431  CB  GLU B  59      20.646  36.033 106.037  1.00 45.05           C
ATOM   2432  CG  GLU B  59      19.162  36.073 105.626  1.00 48.53           C
ATOM   2433  CD  GLU B  59      18.583  37.497 105.533  1.00 49.79           C
ATOM   2434  OE1 GLU B  59      18.617  38.244 106.547  1.00 50.14           O
ATOM   2435  OE2 GLU B  59      18.086  37.863 104.434  1.00 48.94           O
ATOM   2436  C   GLU B  59      21.378  34.500 104.227  1.00 41.98           C
ATOM   2437  O   GLU B  59      21.458  35.477 103.477  1.00 42.84           O
ATOM   2438  N   ALA B  60      21.318  33.242 103.798  1.00 39.82           N
ATOM   2439  CA  ALA B  60      21.351  32.887 102.381  1.00 37.73           C
ATOM   2440  CB  ALA B  60      20.855  31.445 102.187  1.00 38.61           C
ATOM   2441  C   ALA B  60      20.544  33.832 101.499  1.00 35.22           C
ATOM   2442  O   ALA B  60      19.448  34.251 101.856  1.00 35.21           O
ATOM   2443  N   HIS B  61      21.110  34.158 100.343  1.00 32.85           N
ATOM   2444  CA  HIS B  61      20.487  35.046  99.370  1.00 30.31           C
ATOM   2445  CB  HIS B  61      21.289  36.334  99.257  1.00 32.52           C
ATOM   2446  CG  HIS B  61      21.066  37.288 100.388  1.00 33.30           C
ATOM   2447  CD2 HIS B  61      21.894  37.717 101.371  1.00 32.85           C
ATOM   2448  ND1 HIS B  61      19.862  37.933 100.588  1.00 32.55           N
ATOM   2449  CE1 HIS B  61      19.961  38.720 101.645  1.00 33.32           C
ATOM   2450  NE2 HIS B  61      21.183  38.609 102.137  1.00 32.82           N
ATOM   2451  C   HIS B  61      20.518  34.327  98.044  1.00 29.00           C
ATOM   2452  O   HIS B  61      21.559  34.293  97.377  1.00 28.23           O
ATOM   2453  N   LEU B  62      19.386  33.751  97.657  1.00 26.93           N
ATOM   2454  CA  LEU B  62      19.312  33.002  96.412  1.00 26.03           C
ATOM   2455  CB  LEU B  62      18.866  31.561  96.681  1.00 28.18           C
ATOM   2456  CG  LEU B  62      19.768  30.715  97.589  1.00 29.28           C
ATOM   2457  CD1 LEU B  62      19.006  29.507  98.129  1.00 30.45           C
ATOM   2458  CD2 LEU B  62      20.974  30.267  96.802  1.00 30.57           C
ATOM   2459  C   LEU B  62      18.350  33.637  95.444  1.00 24.67           C
ATOM   2460  O   LEU B  62      17.295  34.143  95.836  1.00 24.41           O
ATOM   2461  N   TYR B  63      18.720  33.613  94.171  1.00 23.37           N
ATOM   2462  CA  TYR B  63      17.877  34.177  93.138  1.00 21.97           C
ATOM   2463  CB  TYR B  63      18.412  35.547  92.724  1.00 22.59           C
ATOM   2464  CG  TYR B  63      18.438  36.511  93.889  1.00 22.74           C
ATOM   2465  CD1 TYR B  63      19.502  36.506  94.806  1.00 23.39           C
ATOM   2466  CE1 TYR B  63      19.489  37.337  95.931  1.00 22.64           C
ATOM   2467  CD2 TYR B  63      17.367  37.375  94.126  1.00 23.01           C
ATOM   2468  CE2 TYR B  63      17.348  38.212  95.250  1.00 22.58           C
```

FIGURE 9 (cont.)

| | | | | | | | | | | |
|---|---|---|---|---|---|---|---|---|---|---|
| ATOM | 2469 | CZ | TYR | B | 63 | 18.408 | 38.182 | 96.142 | 1.00 22.08 | C |
| ATOM | 2470 | OH | TYR | B | 63 | 18.378 | 38.992 | 97.250 | 1.00 22.78 | O |
| ATOM | 2471 | C | TYR | B | 63 | 17.780 | 33.240 | 91.948 | 1.00 21.94 | C |
| ATOM | 2472 | O | TYR | B | 63 | 18.760 | 32.608 | 91.548 | 1.00 20.08 | O |
| ATOM | 2473 | N | GLN | B | 64 | 16.568 | 33.135 | 91.417 | 1.00 22.41 | N |
| ATOM | 2474 | CA | GLN | B | 64 | 16.279 | 32.288 | 90.274 | 1.00 22.81 | C |
| ATOM | 2475 | CB | GLN | B | 64 | 14.779 | 31.966 | 90.265 | 1.00 25.76 | C |
| ATOM | 2476 | CG | GLN | B | 64 | 14.366 | 30.761 | 89.417 | 1.00 29.49 | C |
| ATOM | 2477 | CD | GLN | B | 64 | 14.575 | 30.990 | 87.940 | 1.00 33.20 | C |
| ATOM | 2478 | OE1 | GLN | B | 64 | 15.711 | 31.073 | 87.467 | 1.00 35.40 | O |
| ATOM | 2479 | NE2 | GLN | B | 64 | 13.474 | 31.102 | 87.193 | 1.00 35.16 | N |
| ATOM | 2480 | C | GLN | B | 64 | 16.675 | 33.084 | 89.032 | 1.00 21.30 | C |
| ATOM | 2481 | O | GLN | B | 64 | 16.071 | 34.115 | 88.732 | 1.00 19.93 | O |
| ATOM | 2482 | N | ILE | B | 65 | 17.697 | 32.621 | 88.320 | 1.00 21.18 | N |
| ATOM | 2483 | CA | ILE | B | 65 | 18.149 | 33.327 | 87.130 | 1.00 19.83 | C |
| ATOM | 2484 | CB | ILE | B | 65 | 19.330 | 34.276 | 87.443 | 1.00 20.88 | C |
| ATOM | 2485 | CG2 | ILE | B | 65 | 19.732 | 35.033 | 86.176 | 1.00 19.39 | C |
| ATOM | 2486 | CG1 | ILE | B | 65 | 18.944 | 35.262 | 88.536 | 1.00 18.79 | C |
| ATOM | 2487 | CD1 | ILE | B | 65 | 20.097 | 36.152 | 88.999 | 1.00 22.78 | C |
| ATOM | 2488 | C | ILE | B | 65 | 18.597 | 32.423 | 86.003 | 1.00 20.06 | C |
| ATOM | 2489 | O | ILE | B | 65 | 19.662 | 31.803 | 86.078 | 1.00 20.42 | O |
| ATOM | 2490 | N | ASP | B | 66 | 17.777 | 32.349 | 84.963 | 1.00 19.39 | N |
| ATOM | 2491 | CA | ASP | B | 66 | 18.095 | 31.568 | 83.781 | 1.00 19.64 | C |
| ATOM | 2492 | CB | ASP | B | 66 | 16.821 | 30.919 | 83.203 | 1.00 20.57 | C |
| ATOM | 2493 | CG | ASP | B | 66 | 17.113 | 29.960 | 82.037 | 1.00 23.17 | C |
| ATOM | 2494 | OD1 | ASP | B | 66 | 16.391 | 28.935 | 81.901 | 1.00 24.56 | O |
| ATOM | 2495 | OD2 | ASP | B | 66 | 18.051 | 30.230 | 81.248 | 1.00 21.84 | O |
| ATOM | 2496 | C | ASP | B | 66 | 18.663 | 32.624 | 82.826 | 1.00 19.00 | C |
| ATOM | 2497 | O | ASP | B | 66 | 17.931 | 33.487 | 82.340 | 1.00 17.33 | O |
| ATOM | 2498 | N | VAL | B | 67 | 19.973 | 32.566 | 82.593 | 1.00 18.07 | N |
| ATOM | 2499 | CA | VAL | B | 67 | 20.651 | 33.529 | 81.731 | 1.00 18.28 | C |
| ATOM | 2500 | CB | VAL | B | 67 | 22.177 | 33.263 | 81.693 | 1.00 17.65 | C |
| ATOM | 2501 | CG1 | VAL | B | 67 | 22.760 | 33.435 | 83.084 | 1.00 16.93 | C |
| ATOM | 2502 | CG2 | VAL | B | 67 | 22.461 | 31.867 | 81.165 | 1.00 17.51 | C |
| ATOM | 2503 | C | VAL | B | 67 | 20.119 | 33.615 | 80.298 | 1.00 19.06 | C |
| ATOM | 2504 | O | VAL | B | 67 | 20.592 | 34.442 | 79.512 | 1.00 18.36 | O |
| ATOM | 2505 | N | GLN | B | 68 | 19.130 | 32.782 | 79.965 | 1.00 19.16 | N |
| ATOM | 2506 | CA | GLN | B | 68 | 18.528 | 32.800 | 78.627 | 1.00 21.52 | C |
| ATOM | 2507 | CB | GLN | B | 68 | 17.854 | 31.453 | 78.316 | 1.00 24.01 | C |
| ATOM | 2508 | CG | GLN | B | 68 | 18.819 | 30.350 | 77.873 | 1.00 28.84 | C |
| ATOM | 2509 | CD | GLN | B | 68 | 18.179 | 28.956 | 77.838 | 1.00 31.26 | C |
| ATOM | 2510 | OE1 | GLN | B | 68 | 17.885 | 28.362 | 78.886 | 1.00 32.89 | O |
| ATOM | 2511 | NE2 | GLN | B | 68 | 17.967 | 28.429 | 76.635 | 1.00 31.00 | N |
| ATOM | 2512 | C | GLN | B | 68 | 17.496 | 33.927 | 78.509 | 1.00 21.40 | C |
| ATOM | 2513 | O | GLN | B | 68 | 17.225 | 34.423 | 77.411 | 1.00 21.08 | O |
| ATOM | 2514 | N | SER | B | 69 | 16.930 | 34.331 | 79.645 | 1.00 21.02 | N |
| ATOM | 2515 | CA | SER | B | 69 | 15.932 | 35.396 | 79.682 | 1.00 21.26 | C |
| ATOM | 2516 | CB | SER | B | 69 | 14.797 | 35.033 | 80.638 | 1.00 22.84 | C |
| ATOM | 2517 | OG | SER | B | 69 | 13.969 | 36.160 | 80.885 | 1.00 23.58 | O |
| ATOM | 2518 | C | SER | B | 69 | 16.523 | 36.719 | 80.134 | 1.00 22.32 | C |
| ATOM | 2519 | O | SER | B | 69 | 17.128 | 36.808 | 81.208 | 1.00 21.94 | O |
| ATOM | 2520 | N | ASP | B | 70 | 16.336 | 37.749 | 79.319 | 1.00 21.33 | N |
| ATOM | 2521 | CA | ASP | B | 70 | 16.841 | 39.068 | 79.656 | 1.00 22.81 | C |
| ATOM | 2522 | CB | ASP | B | 70 | 16.588 | 40.041 | 78.498 | 1.00 22.61 | C |
| ATOM | 2523 | CG | ASP | B | 70 | 17.579 | 39.857 | 77.366 | 1.00 24.91 | C |
| ATOM | 2524 | OD1 | ASP | B | 70 | 18.311 | 38.843 | 77.386 | 1.00 24.14 | O |
| ATOM | 2525 | OD2 | ASP | B | 70 | 17.630 | 40.741 | 76.457 | 1.00 26.48 | O |
| ATOM | 2526 | C | ASP | B | 70 | 16.188 | 39.590 | 80.931 | 1.00 22.66 | C |
| ATOM | 2527 | O | ASP | B | 70 | 16.853 | 40.178 | 81.788 | 1.00 22.84 | O |
| ATOM | 2528 | N | GLU | B | 71 | 14.887 | 39.367 | 81.065 | 1.00 23.20 | N |
| ATOM | 2529 | CA | GLU | B | 71 | 14.185 | 39.829 | 82.252 | 1.00 25.00 | C |
| ATOM | 2530 | CB | GLU | B | 71 | 12.699 | 39.532 | 82.153 | 1.00 27.45 | C |
| ATOM | 2531 | CG | GLU | B | 71 | 12.031 | 40.108 | 80.940 | 1.00 31.94 | C |
| ATOM | 2532 | CD | GLU | B | 71 | 10.529 | 40.016 | 81.068 | 1.00 35.99 | C |
| ATOM | 2533 | OE1 | GLU | B | 71 | 9.962 | 40.829 | 81.844 | 1.00 36.98 | O |

FIGURE 9 (cont.)

| | | | | | | | | | |
|---|---|---|---|---|---|---|---|---|---|
| ATOM | 2534 | OE2 | GLU B | 71 | 9.925 | 39.121 | 80.415 | 1.00 36.35 | O |
| ATOM | 2535 | C | GLU B | 71 | 14.712 | 39.178 | 83.514 | 1.00 23.46 | C |
| ATOM | 2536 | O | GLU B | 71 | 14.874 | 39.834 | 84.535 | 1.00 24.44 | O |
| ATOM | 2537 | N | GLU B | 72 | 14.970 | 37.881 | 83.456 | 1.00 23.68 | N |
| ATOM | 2538 | CA | GLU B | 72 | 15.455 | 37.201 | 84.640 | 1.00 22.72 | C |
| ATOM | 2539 | CB | GLU B | 72 | 15.511 | 35.693 | 84.395 | 1.00 23.67 | C |
| ATOM | 2540 | CG | GLU B | 72 | 14.128 | 35.062 | 84.329 | 1.00 24.78 | C |
| ATOM | 2541 | CD | GLU B | 72 | 14.170 | 33.540 | 84.356 | 1.00 26.98 | C |
| ATOM | 2542 | OE1 | GLU B | 72 | 14.810 | 32.975 | 85.270 | 1.00 26.40 | O |
| ATOM | 2543 | OE2 | GLU B | 72 | 13.551 | 32.905 | 83.469 | 1.00 29.84 | O |
| ATOM | 2544 | C | GLU B | 72 | 16.805 | 37.740 | 85.106 | 1.00 22.41 | C |
| ATOM | 2545 | O | GLU B | 72 | 17.064 | 37.818 | 86.310 | 1.00 22.96 | O |
| ATOM | 2546 | N | VAL B | 73 | 17.657 | 38.140 | 84.166 | 1.00 20.46 | N |
| ATOM | 2547 | CA | VAL B | 73 | 18.961 | 38.674 | 84.542 | 1.00 18.57 | C |
| ATOM | 2548 | CB | VAL B | 73 | 19.934 | 38.712 | 83.339 | 1.00 16.40 | C |
| ATOM | 2549 | CG1 | VAL B | 73 | 21.253 | 39.313 | 83.768 | 1.00 13.14 | C |
| ATOM | 2550 | CG2 | VAL B | 73 | 20.141 | 37.303 | 82.782 | 1.00 13.92 | C |
| ATOM | 2551 | C | VAL B | 73 | 18.805 | 40.091 | 85.079 | 1.00 19.69 | C |
| ATOM | 2552 | O | VAL B | 73 | 19.408 | 40.468 | 86.096 | 1.00 19.18 | O |
| ATOM | 2553 | N | ILE B | 74 | 17.992 | 40.879 | 84.384 | 1.00 20.48 | N |
| ATOM | 2554 | CA | ILE B | 74 | 17.766 | 42.265 | 84.776 | 1.00 19.16 | C |
| ATOM | 2555 | CB | ILE B | 74 | 16.883 | 42.978 | 83.724 | 1.00 18.98 | C |
| ATOM | 2556 | CG2 | ILE B | 74 | 16.531 | 44.390 | 84.183 | 1.00 15.32 | C |
| ATOM | 2557 | CG1 | ILE B | 74 | 17.643 | 43.017 | 82.387 | 1.00 18.17 | C |
| ATOM | 2558 | CD1 | ILE B | 74 | 16.828 | 43.494 | 81.187 | 1.00 16.08 | C |
| ATOM | 2559 | C | ILE B | 74 | 17.143 | 42.364 | 86.163 | 1.00 19.62 | C |
| ATOM | 2560 | O | ILE B | 74 | 17.749 | 42.912 | 87.085 | 1.00 20.86 | O |
| ATOM | 2561 | N | ASN B | 75 | 15.942 | 41.821 | 86.319 | 1.00 19.21 | N |
| ATOM | 2562 | CA | ASN B | 75 | 15.258 | 41.867 | 87.604 | 1.00 19.08 | C |
| ATOM | 2563 | CB | ASN B | 75 | 13.822 | 41.356 | 87.462 | 1.00 20.76 | C |
| ATOM | 2564 | CG | ASN B | 75 | 12.962 | 42.282 | 86.641 | 1.00 21.21 | C |
| ATOM | 2565 | OD1 | ASN B | 75 | 13.132 | 43.507 | 86.692 | 1.00 23.01 | O |
| ATOM | 2566 | ND2 | ASN B | 75 | 12.024 | 41.715 | 85.889 | 1.00 20.03 | N |
| ATOM | 2567 | C | ASN B | 75 | 15.972 | 41.075 | 88.693 | 1.00 19.43 | C |
| ATOM | 2568 | O | ASN B | 75 | 15.704 | 41.272 | 89.878 | 1.00 18.79 | O |
| ATOM | 2569 | N | GLY B | 76 | 16.860 | 40.166 | 88.289 | 1.00 19.19 | N |
| ATOM | 2570 | CA | GLY B | 76 | 17.608 | 39.379 | 89.250 | 1.00 17.15 | C |
| ATOM | 2571 | C | GLY B | 76 | 18.621 | 40.256 | 89.968 | 1.00 17.52 | C |
| ATOM | 2572 | O | GLY B | 76 | 18.544 | 40.443 | 91.189 | 1.00 17.51 | O |
| ATOM | 2573 | N | PHE B | 77 | 19.574 | 40.807 | 89.221 | 1.00 17.72 | N |
| ATOM | 2574 | CA | PHE B | 77 | 20.586 | 41.670 | 89.832 | 1.00 18.90 | C |
| ATOM | 2575 | CB | PHE B | 77 | 21.662 | 42.060 | 88.817 | 1.00 17.31 | C |
| ATOM | 2576 | CG | PHE B | 77 | 22.676 | 40.988 | 88.590 | 1.00 16.13 | C |
| ATOM | 2577 | CD1 | PHE B | 77 | 22.424 | 39.950 | 87.697 | 1.00 17.45 | C |
| ATOM | 2578 | CD2 | PHE B | 77 | 23.856 | 40.972 | 89.325 | 1.00 15.48 | C |
| ATOM | 2579 | CE1 | PHE B | 77 | 23.337 | 38.903 | 87.540 | 1.00 16.56 | C |
| ATOM | 2580 | CE2 | PHE B | 77 | 24.771 | 39.940 | 89.183 | 1.00 15.44 | C |
| ATOM | 2581 | CZ | PHE B | 77 | 24.513 | 38.898 | 88.286 | 1.00 17.42 | C |
| ATOM | 2582 | C | PHE B | 77 | 19.978 | 42.924 | 90.440 | 1.00 19.63 | C |
| ATOM | 2583 | O | PHE B | 77 | 20.508 | 43.461 | 91.414 | 1.00 20.35 | O |
| ATOM | 2584 | N | GLU B | 78 | 18.872 | 43.390 | 89.864 | 1.00 20.15 | N |
| ATOM | 2585 | CA | GLU B | 78 | 18.199 | 44.568 | 90.380 | 1.00 21.82 | C |
| ATOM | 2586 | CB | GLU B | 78 | 17.013 | 44.945 | 89.495 | 1.00 24.41 | C |
| ATOM | 2587 | CG | GLU B | 78 | 16.240 | 46.154 | 90.020 | 1.00 29.30 | C |
| ATOM | 2588 | CD | GLU B | 78 | 15.176 | 46.627 | 89.049 | 1.00 31.55 | C |
| ATOM | 2589 | OE1 | GLU B | 78 | 14.312 | 45.800 | 88.681 | 1.00 35.04 | O |
| ATOM | 2590 | OE2 | GLU B | 78 | 15.201 | 47.815 | 88.651 | 1.00 32.73 | O |
| ATOM | 2591 | C | GLU B | 78 | 17.712 | 44.318 | 91.807 | 1.00 22.25 | C |
| ATOM | 2592 | O | GLU B | 78 | 17.911 | 45.152 | 92.695 | 1.00 22.10 | O |
| ATOM | 2593 | N | GLN B | 79 | 17.071 | 43.172 | 92.025 | 1.00 21.40 | N |
| ATOM | 2594 | CA | GLN B | 79 | 16.575 | 42.823 | 93.355 | 1.00 21.41 | C |
| ATOM | 2595 | CB | GLN B | 79 | 15.613 | 41.635 | 93.264 | 1.00 22.85 | C |
| ATOM | 2596 | CG | GLN B | 79 | 15.014 | 41.206 | 94.598 | 1.00 26.61 | C |
| ATOM | 2597 | CD | GLN B | 79 | 14.102 | 42.256 | 95.183 | 1.00 28.97 | C |
| ATOM | 2598 | OE1 | GLN B | 79 | 13.145 | 42.677 | 94.543 | 1.00 30.32 | O |

FIGURE 9 (cont.)

| ATOM | 2599 | NE2 | GLN | B | 79 | 14.398 | 42.694 | 96.407 | 1.00 | 31.76 | N |
| ATOM | 2600 | C | GLN | B | 79 | 17.746 | 42.483 | 94.286 | 1.00 | 20.20 | C |
| ATOM | 2601 | O | GLN | B | 79 | 17.637 | 42.610 | 95.500 | 1.00 | 20.40 | O |
| ATOM | 2602 | N | ILE | B | 80 | 18.859 | 42.034 | 93.712 | 1.00 | 19.41 | N |
| ATOM | 2603 | CA | ILE | B | 80 | 20.040 | 41.708 | 94.501 | 1.00 | 18.58 | C |
| ATOM | 2604 | CB | ILE | B | 80 | 21.156 | 41.065 | 93.615 | 1.00 | 17.00 | C |
| ATOM | 2605 | CG2 | ILE | B | 80 | 22.536 | 41.250 | 94.255 | 1.00 | 16.30 | C |
| ATOM | 2606 | CG1 | ILE | B | 80 | 20.848 | 39.578 | 93.413 | 1.00 | 17.29 | C |
| ATOM | 2607 | CD1 | ILE | B | 80 | 21.675 | 38.892 | 92.332 | 1.00 | 15.98 | C |
| ATOM | 2608 | C | ILE | B | 80 | 20.542 | 43.011 | 95.117 | 1.00 | 19.16 | C |
| ATOM | 2609 | O | ILE | B | 80 | 20.926 | 43.062 | 96.291 | 1.00 | 18.57 | O |
| ATOM | 2610 | N | GLY | B | 81 | 20.512 | 44.069 | 94.317 | 1.00 | 19.89 | N |
| ATOM | 2611 | CA | GLY | B | 81 | 20.961 | 45.364 | 94.791 | 1.00 | 20.96 | C |
| ATOM | 2612 | C | GLY | B | 81 | 20.132 | 45.922 | 95.936 | 1.00 | 21.85 | C |
| ATOM | 2613 | O | GLY | B | 81 | 20.678 | 46.500 | 96.880 | 1.00 | 22.80 | O |
| ATOM | 2614 | N | LYS | B | 82 | 18.818 | 45.753 | 95.876 | 1.00 | 21.54 | N |
| ATOM | 2615 | CA | LYS | B | 82 | 17.974 | 46.283 | 96.940 | 1.00 | 23.17 | C |
| ATOM | 2616 | CB | LYS | B | 82 | 16.512 | 46.300 | 96.497 | 1.00 | 24.49 | C |
| ATOM | 2617 | CG | LYS | B | 82 | 16.289 | 47.049 | 95.207 | 1.00 | 25.31 | C |
| ATOM | 2618 | CD | LYS | B | 82 | 14.834 | 47.043 | 94.804 | 1.00 | 27.81 | C |
| ATOM | 2619 | CE | LYS | B | 82 | 14.652 | 47.830 | 93.496 | 1.00 | 31.12 | C |
| ATOM | 2620 | NZ | LYS | B | 82 | 13.218 | 47.861 | 93.044 | 1.00 | 32.92 | N |
| ATOM | 2621 | C | LYS | B | 82 | 18.113 | 45.459 | 98.206 | 1.00 | 22.74 | C |
| ATOM | 2622 | O | LYS | B | 82 | 17.933 | 45.960 | 99.313 | 1.00 | 23.48 | O |
| ATOM | 2623 | N | ASP | B | 83 | 18.445 | 44.188 | 98.037 | 1.00 | 22.28 | N |
| ATOM | 2624 | CA | ASP | B | 83 | 18.580 | 43.284 | 99.167 | 1.00 | 21.29 | C |
| ATOM | 2625 | CB | ASP | B | 83 | 18.311 | 41.858 | 98.699 | 1.00 | 22.72 | C |
| ATOM | 2626 | CG | ASP | B | 83 | 16.856 | 41.613 | 98.390 | 1.00 | 22.49 | C |
| ATOM | 2627 | OD1 | ASP | B | 83 | 16.562 | 40.620 | 97.693 | 1.00 | 21.94 | O |
| ATOM | 2628 | OD2 | ASP | B | 83 | 16.005 | 42.404 | 98.856 | 1.00 | 23.25 | O |
| ATOM | 2629 | C | ASP | B | 83 | 19.917 | 43.333 | 99.891 | 1.00 | 20.74 | C |
| ATOM | 2630 | O | ASP | B | 83 | 19.957 | 43.281 | 101.117 | 1.00 | 22.20 | O |
| ATOM | 2631 | N | VAL | B | 84 | 21.014 | 43.419 | 99.148 | 1.00 | 19.45 | N |
| ATOM | 2632 | CA | VAL | B | 84 | 22.332 | 43.437 | 99.776 | 1.00 | 17.61 | C |
| ATOM | 2633 | CB | VAL | B | 84 | 23.210 | 42.254 | 99.300 | 1.00 | 17.61 | C |
| ATOM | 2634 | CG1 | VAL | B | 84 | 22.596 | 40.938 | 99.700 | 1.00 | 16.80 | C |
| ATOM | 2635 | CG2 | VAL | B | 84 | 23.387 | 42.323 | 97.801 | 1.00 | 18.09 | C |
| ATOM | 2636 | C | VAL | B | 84 | 23.136 | 44.702 | 99.538 | 1.00 | 17.64 | C |
| ATOM | 2637 | O | VAL | B | 84 | 24.114 | 44.942 | 100.244 | 1.00 | 17.38 | O |
| ATOM | 2638 | N | GLY | B | 85 | 22.747 | 45.493 | 98.539 | 1.00 | 17.29 | N |
| ATOM | 2639 | CA | GLY | B | 85 | 23.479 | 46.711 | 98.231 | 1.00 | 17.62 | C |
| ATOM | 2640 | C | GLY | B | 85 | 24.515 | 46.495 | 97.140 | 1.00 | 18.67 | C |
| ATOM | 2641 | O | GLY | B | 85 | 24.426 | 45.531 | 96.392 | 1.00 | 20.84 | O |
| ATOM | 2642 | N | ASN | B | 86 | 25.508 | 47.374 | 97.039 | 1.00 | 19.11 | N |
| ATOM | 2643 | CA | ASN | B | 86 | 26.527 | 47.216 | 96.003 | 1.00 | 20.12 | C |
| ATOM | 2644 | CB | ASN | B | 86 | 27.428 | 48.454 | 95.958 | 1.00 | 19.46 | C |
| ATOM | 2645 | CG | ASN | B | 86 | 26.667 | 49.720 | 95.567 | 1.00 | 19.83 | C |
| ATOM | 2646 | OD1 | ASN | B | 86 | 25.690 | 49.663 | 94.811 | 1.00 | 16.41 | O |
| ATOM | 2647 | ND2 | ASN | B | 86 | 27.125 | 50.871 | 96.069 | 1.00 | 16.04 | N |
| ATOM | 2648 | C | ASN | B | 86 | 27.376 | 45.954 | 96.210 | 1.00 | 20.58 | C |
| ATOM | 2649 | O | ASN | B | 86 | 27.598 | 45.518 | 97.343 | 1.00 | 21.30 | O |
| ATOM | 2650 | N | ILE | B | 87 | 27.845 | 45.364 | 95.115 | 1.00 | 20.55 | N |
| ATOM | 2651 | CA | ILE | B | 87 | 28.659 | 44.155 | 95.196 | 1.00 | 21.11 | C |
| ATOM | 2652 | CB | ILE | B | 87 | 28.069 | 43.014 | 94.323 | 1.00 | 20.56 | C |
| ATOM | 2653 | CG2 | ILE | B | 87 | 26.676 | 42.656 | 94.814 | 1.00 | 17.68 | C |
| ATOM | 2654 | CG1 | ILE | B | 87 | 28.036 | 43.436 | 92.848 | 1.00 | 19.60 | C |
| ATOM | 2655 | CD1 | ILE | B | 87 | 27.569 | 42.344 | 91.905 | 1.00 | 16.26 | C |
| ATOM | 2656 | C | ILE | B | 87 | 30.096 | 44.417 | 94.750 | 1.00 | 22.15 | C |
| ATOM | 2657 | O | ILE | B | 87 | 30.370 | 45.431 | 94.109 | 1.00 | 22.64 | O |
| ATOM | 2658 | N | ASP | B | 88 | 31.004 | 43.497 | 95.082 | 1.00 | 22.65 | N |
| ATOM | 2659 | CA | ASP | B | 88 | 32.421 | 43.632 | 94.725 | 1.00 | 22.23 | C |
| ATOM | 2660 | CB | ASP | B | 88 | 33.304 | 43.297 | 95.918 | 1.00 | 23.52 | C |
| ATOM | 2661 | CG | ASP | B | 88 | 33.056 | 44.197 | 97.083 | 1.00 | 24.61 | C |
| ATOM | 2662 | OD1 | ASP | B | 88 | 33.678 | 45.283 | 97.148 | 1.00 | 26.09 | O |
| ATOM | 2663 | OD2 | ASP | B | 88 | 32.223 | 43.818 | 97.931 | 1.00 | 26.10 | O |

FIGURE 9 (cont.)

```
ATOM   2664  C   ASP B  88      32.845  42.735  93.573  1.00 21.65           C
ATOM   2665  O   ASP B  88      33.992  42.788  93.137  1.00 21.41           O
ATOM   2666  N   GLY B  89      31.936  41.896  93.095  1.00 19.69           N
ATOM   2667  CA  GLY B  89      32.290  41.020  91.998  1.00 19.15           C
ATOM   2668  C   GLY B  89      31.312  39.899  91.730  1.00 17.47           C
ATOM   2669  O   GLY B  89      30.426  39.630  92.531  1.00 17.69           O
ATOM   2670  N   VAL B  90      31.495  39.242  90.592  1.00 17.43           N
ATOM   2671  CA  VAL B  90      30.646  38.135  90.168  1.00 16.58           C
ATOM   2672  CB  VAL B  90      29.675  38.578  89.056  1.00 15.88           C
ATOM   2673  CG1 VAL B  90      28.881  37.382  88.549  1.00 16.23           C
ATOM   2674  CG2 VAL B  90      28.745  39.659  89.578  1.00 16.48           C
ATOM   2675  C   VAL B  90      31.486  36.982  89.615  1.00 17.36           C
ATOM   2676  O   VAL B  90      32.469  37.207  88.894  1.00 18.16           O
ATOM   2677  N   TYR B  91      31.112  35.753  89.968  1.00 16.61           N
ATOM   2678  CA  TYR B  91      31.814  34.590  89.460  1.00 16.71           C
ATOM   2679  CB  TYR B  91      32.226  33.620  90.573  1.00 17.61           C
ATOM   2680  CG  TYR B  91      33.157  32.548  90.048  1.00 18.82           C
ATOM   2681  CD1 TYR B  91      34.534  32.772  89.967  1.00 18.01           C
ATOM   2682  CE1 TYR B  91      35.374  31.872  89.328  1.00 18.32           C
ATOM   2683  CD2 TYR B  91      32.651  31.383  89.490  1.00 18.55           C
ATOM   2684  CE2 TYR B  91      33.481  30.473  88.848  1.00 18.50           C
ATOM   2685  CZ  TYR B  91      34.843  30.722  88.762  1.00 18.94           C
ATOM   2686  OH  TYR B  91      35.653  29.843  88.070  1.00 16.54           O
ATOM   2687  C   TYR B  91      30.841  33.894  88.520  1.00 16.81           C
ATOM   2688  O   TYR B  91      29.759  33.463  88.934  1.00 17.31           O
ATOM   2689  N   HIS B  92      31.230  33.794  87.258  1.00 15.50           N
ATOM   2690  CA  HIS B  92      30.409  33.170  86.232  1.00 16.21           C
ATOM   2691  CB  HIS B  92      30.548  33.988  84.951  1.00 15.89           C
ATOM   2692  CG  HIS B  92      29.679  33.521  83.834  1.00 16.12           C
ATOM   2693  CD2 HIS B  92      28.564  34.058  83.291  1.00 14.84           C
ATOM   2694  ND1 HIS B  92      29.937  32.368  83.127  1.00 18.33           N
ATOM   2695  CE1 HIS B  92      29.018  32.218  82.191  1.00 18.34           C
ATOM   2696  NE2 HIS B  92      28.173  33.231  82.270  1.00 15.99           N
ATOM   2697  C   HIS B  92      30.839  31.713  86.006  1.00 16.66           C
ATOM   2698  O   HIS B  92      31.912  31.448  85.469  1.00 18.27           O
ATOM   2699  N   SER B  93      30.001  30.770  86.426  1.00 16.07           N
ATOM   2700  CA  SER B  93      30.316  29.343  86.290  1.00 15.18           C
ATOM   2701  CB  SER B  93      30.481  28.733  87.690  1.00 15.59           C
ATOM   2702  OG  SER B  93      31.173  27.502  87.663  1.00 15.05           O
ATOM   2703  C   SER B  93      29.177  28.663  85.543  1.00 14.81           C
ATOM   2704  O   SER B  93      28.639  27.648  85.987  1.00 13.65           O
ATOM   2705  N   ILE B  94      28.818  29.234  84.397  1.00 14.63           N
ATOM   2706  CA  ILE B  94      27.711  28.729  83.595  1.00 13.74           C
ATOM   2707  CB  ILE B  94      26.559  29.759  83.563  1.00 11.86           C
ATOM   2708  CG2 ILE B  94      25.463  29.277  82.640  1.00 11.06           C
ATOM   2709  CG1 ILE B  94      26.019  29.992  84.972  1.00  8.82           C
ATOM   2710  CD1 ILE B  94      25.088  31.177  85.076  1.00 10.31           C
ATOM   2711  C   ILE B  94      28.066  28.383  82.150  1.00 14.97           C
ATOM   2712  O   ILE B  94      28.724  29.160  81.458  1.00 16.10           O
ATOM   2713  N   ALA B  95      27.610  27.217  81.700  1.00 14.51           N
ATOM   2714  CA  ALA B  95      27.836  26.769  80.328  1.00 14.36           C
ATOM   2715  CB  ALA B  95      29.289  26.310  80.143  1.00 12.84           C
ATOM   2716  C   ALA B  95      26.867  25.630  79.994  1.00 15.45           C
ATOM   2717  O   ALA B  95      26.471  24.865  80.879  1.00 14.60           O
ATOM   2718  N   PHE B  96      26.459  25.537  78.730  1.00 15.95           N
ATOM   2719  CA  PHE B  96      25.551  24.467  78.307  1.00 17.04           C
ATOM   2720  CB  PHE B  96      24.113  24.725  78.793  1.00 17.06           C
ATOM   2721  CG  PHE B  96      23.151  23.611  78.442  1.00 15.57           C
ATOM   2722  CD1 PHE B  96      23.148  22.428  79.163  1.00 16.19           C
ATOM   2723  CD2 PHE B  96      22.317  23.715  77.334  1.00 16.77           C
ATOM   2724  CE1 PHE B  96      22.332  21.352  78.783  1.00 16.98           C
ATOM   2725  CE2 PHE B  96      21.496  22.648  76.941  1.00 16.40           C
ATOM   2726  CZ  PHE B  96      21.506  21.463  77.667  1.00 17.22           C
ATOM   2727  C   PHE B  96      25.512  24.260  76.791  1.00 18.31           C
ATOM   2728  O   PHE B  96      25.622  25.208  76.013  1.00 19.75           O
```

FIGURE 9 (cont.)

| ATOM | 2729 | N   | ALA B 97  | 25.340 | 23.004 | 76.391 | 1.00 | 19.06 | N |
|------|------|-----|-----------|--------|--------|--------|------|-------|---|
| ATOM | 2730 | CA  | ALA B 97  | 25.230 | 22.611 | 74.987 | 1.00 | 19.32 | C |
| ATOM | 2731 | CB  | ALA B 97  | 26.619 | 22.395 | 74.383 | 1.00 | 18.74 | C |
| ATOM | 2732 | C   | ALA B 97  | 24.439 | 21.300 | 74.985 | 1.00 | 19.51 | C |
| ATOM | 2733 | O   | ALA B 97  | 24.413 | 20.593 | 75.996 | 1.00 | 19.60 | O |
| ATOM | 2734 | N   | ASN B 98  | 23.778 | 20.977 | 73.877 | 1.00 | 19.67 | N |
| ATOM | 2735 | CA  | ASN B 98  | 23.030 | 19.729 | 73.826 | 1.00 | 20.98 | C |
| ATOM | 2736 | CB  | ASN B 98  | 22.067 | 19.698 | 72.628 | 1.00 | 20.66 | C |
| ATOM | 2737 | CG  | ASN B 98  | 20.928 | 20.712 | 72.755 | 1.00 | 19.42 | C |
| ATOM | 2738 | OD1 | ASN B 98  | 20.310 | 20.849 | 73.817 | 1.00 | 20.13 | O |
| ATOM | 2739 | ND2 | ASN B 98  | 20.640 | 21.412 | 71.667 | 1.00 | 18.64 | N |
| ATOM | 2740 | C   | ASN B 98  | 24.068 | 18.622 | 73.706 | 1.00 | 22.94 | C |
| ATOM | 2741 | O   | ASN B 98  | 25.078 | 18.790 | 73.022 | 1.00 | 24.58 | O |
| ATOM | 2742 | N   | MET B 99  | 23.830 | 17.503 | 74.381 | 1.00 | 23.14 | N |
| ATOM | 2743 | CA  | MET B 99  | 24.763 | 16.393 | 74.357 | 1.00 | 25.24 | C |
| ATOM | 2744 | CB  | MET B 99  | 24.200 | 15.211 | 75.156 | 1.00 | 26.09 | C |
| ATOM | 2745 | CG  | MET B 99  | 24.591 | 15.221 | 76.620 | 1.00 | 29.73 | C |
| ATOM | 2746 | SD  | MET B 99  | 26.288 | 14.649 | 76.963 | 1.00 | 32.70 | S |
| ATOM | 2747 | CE  | MET B 99  | 27.240 | 15.944 | 76.300 | 1.00 | 32.05 | C |
| ATOM | 2748 | C   | MET B 99  | 25.136 | 15.926 | 72.961 | 1.00 | 25.24 | C |
| ATOM | 2749 | O   | MET B 99  | 26.308 | 15.652 | 72.684 | 1.00 | 25.59 | O |
| ATOM | 2750 | N   | GLU B 100 | 24.139 | 15.850 | 72.086 | 1.00 | 25.03 | N |
| ATOM | 2751 | CA  | GLU B 100 | 24.351 | 15.384 | 70.730 | 1.00 | 25.43 | C |
| ATOM | 2752 | CB  | GLU B 100 | 23.034 | 15.449 | 69.958 | 1.00 | 26.60 | C |
| ATOM | 2753 | CG  | GLU B 100 | 22.507 | 16.854 | 69.735 | 1.00 | 29.45 | C |
| ATOM | 2754 | CD  | GLU B 100 | 21.225 | 16.860 | 68.925 | 1.00 | 30.46 | C |
| ATOM | 2755 | OE1 | GLU B 100 | 20.851 | 17.933 | 68.409 | 1.00 | 29.81 | O |
| ATOM | 2756 | OE2 | GLU B 100 | 20.588 | 15.784 | 68.804 | 1.00 | 32.58 | O |
| ATOM | 2757 | C   | GLU B 100 | 25.446 | 16.127 | 69.967 | 1.00 | 24.75 | C |
| ATOM | 2758 | O   | GLU B 100 | 26.021 | 15.589 | 69.018 | 1.00 | 24.05 | O |
| ATOM | 2759 | N   | ASP B 101 | 25.729 | 17.366 | 70.362 | 1.00 | 24.59 | N |
| ATOM | 2760 | CA  | ASP B 101 | 26.780 | 18.133 | 69.691 | 1.00 | 23.67 | C |
| ATOM | 2761 | CB  | ASP B 101 | 26.408 | 19.623 | 69.599 | 1.00 | 24.18 | C |
| ATOM | 2762 | CG  | ASP B 101 | 25.119 | 19.867 | 68.836 | 1.00 | 23.74 | C |
| ATOM | 2763 | OD1 | ASP B 101 | 24.977 | 19.359 | 67.699 | 1.00 | 23.72 | O |
| ATOM | 2764 | OD2 | ASP B 101 | 24.252 | 20.583 | 69.371 | 1.00 | 23.37 | O |
| ATOM | 2765 | C   | ASP B 101 | 28.106 | 17.998 | 70.443 | 1.00 | 23.48 | C |
| ATOM | 2766 | O   | ASP B 101 | 29.096 | 18.625 | 70.067 | 1.00 | 23.89 | O |
| ATOM | 2767 | N   | LEU B 102 | 28.122 | 17.184 | 71.500 | 1.00 | 22.46 | N |
| ATOM | 2768 | CA  | LEU B 102 | 29.325 | 16.983 | 72.315 | 1.00 | 21.42 | C |
| ATOM | 2769 | CB  | LEU B 102 | 28.996 | 17.176 | 73.803 | 1.00 | 20.74 | C |
| ATOM | 2770 | CG  | LEU B 102 | 29.203 | 18.558 | 74.457 | 1.00 | 19.47 | C |
| ATOM | 2771 | CD1 | LEU B 102 | 29.200 | 19.675 | 73.427 | 1.00 | 20.62 | C |
| ATOM | 2772 | CD2 | LEU B 102 | 28.116 | 18.788 | 75.489 | 1.00 | 17.63 | C |
| ATOM | 2773 | C   | LEU B 102 | 29.932 | 15.605 | 72.079 | 1.00 | 22.14 | C |
| ATOM | 2774 | O   | LEU B 102 | 30.650 | 15.043 | 72.924 | 1.00 | 21.67 | O |
| ATOM | 2775 | N   | ARG B 103 | 29.639 | 15.071 | 70.905 | 1.00 | 22.15 | N |
| ATOM | 2776 | CA  | ARG B 103 | 30.149 | 13.777 | 70.495 | 1.00 | 21.89 | C |
| ATOM | 2777 | CB  | ARG B 103 | 29.339 | 12.650 | 71.141 | 1.00 | 23.96 | C |
| ATOM | 2778 | CG  | ARG B 103 | 27.840 | 12.743 | 70.915 | 1.00 | 25.20 | C |
| ATOM | 2779 | CD  | ARG B 103 | 27.152 | 11.444 | 71.335 | 1.00 | 29.76 | C |
| ATOM | 2780 | NE  | ARG B 103 | 25.730 | 11.423 | 70.973 | 1.00 | 32.24 | N |
| ATOM | 2781 | CZ  | ARG B 103 | 24.722 | 11.502 | 71.843 | 1.00 | 32.87 | C |
| ATOM | 2782 | NH1 | ARG B 103 | 24.967 | 11.608 | 73.148 | 1.00 | 32.43 | N |
| ATOM | 2783 | NH2 | ARG B 103 | 23.463 | 11.464 | 71.408 | 1.00 | 33.78 | N |
| ATOM | 2784 | C   | ARG B 103 | 29.985 | 13.758 | 68.991 | 1.00 | 21.55 | C |
| ATOM | 2785 | O   | ARG B 103 | 29.245 | 14.581 | 68.435 | 1.00 | 21.24 | O |
| ATOM | 2786 | N   | GLY B 104 | 30.676 | 12.840 | 68.325 | 1.00 | 20.08 | N |
| ATOM | 2787 | CA  | GLY B 104 | 30.565 | 12.770 | 66.881 | 1.00 | 18.46 | C |
| ATOM | 2788 | C   | GLY B 104 | 31.292 | 13.899 | 66.177 | 1.00 | 18.24 | C |
| ATOM | 2789 | O   | GLY B 104 | 32.192 | 14.521 | 66.751 | 1.00 | 17.74 | O |
| ATOM | 2790 | N   | ARG B 105 | 30.886 | 14.183 | 64.939 | 1.00 | 17.98 | N |
| ATOM | 2791 | CA  | ARG B 105 | 31.530 | 15.218 | 64.138 | 1.00 | 16.93 | C |
| ATOM | 2792 | CB  | ARG B 105 | 31.426 | 14.856 | 62.662 | 1.00 | 17.68 | C |
| ATOM | 2793 | CG  | ARG B 105 | 31.754 | 13.406 | 62.397 | 1.00 | 19.76 | C |

FIGURE 9 (cont.)

```
ATOM   2794  CD   ARG B 105      32.024  13.146  60.933  1.00 20.95           C
ATOM   2795  NE   ARG B 105      33.342  13.613  60.515  1.00 21.23           N
ATOM   2796  CZ   ARG B 105      33.875  13.338  59.329  1.00 21.79           C
ATOM   2797  NH1  ARG B 105      33.196  12.596  58.460  1.00 20.85           N
ATOM   2798  NH2  ARG B 105      35.074  13.809  59.007  1.00 20.80           N
ATOM   2799  C    ARG B 105      31.040  16.648  64.336  1.00 16.27           C
ATOM   2800  O    ARG B 105      29.848  16.944  64.228  1.00 15.44           O
ATOM   2801  N    PHE B 106      31.983  17.538  64.612  1.00 15.18           N
ATOM   2802  CA   PHE B 106      31.659  18.934  64.802  1.00 15.84           C
ATOM   2803  CB   PHE B 106      32.920  19.732  65.160  1.00 15.25           C
ATOM   2804  CG   PHE B 106      32.699  21.213  65.177  1.00 13.67           C
ATOM   2805  CD1  PHE B 106      31.799  21.783  66.085  1.00 11.91           C
ATOM   2806  CD2  PHE B 106      33.320  22.031  64.238  1.00 15.06           C
ATOM   2807  CE1  PHE B 106      31.512  23.146  66.051  1.00 12.33           C
ATOM   2808  CE2  PHE B 106      33.039  23.408  64.193  1.00 13.59           C
ATOM   2809  CZ   PHE B 106      32.128  23.962  65.105  1.00 13.90           C
ATOM   2810  C    PHE B 106      31.025  19.514  63.534  1.00 15.82           C
ATOM   2811  O    PHE B 106      30.143  20.374  63.613  1.00 15.15           O
ATOM   2812  N    SER B 107      31.469  19.038  62.373  1.00 15.84           N
ATOM   2813  CA   SER B 107      30.950  19.533  61.099  1.00 17.10           C
ATOM   2814  CB   SER B 107      31.725  18.910  59.930  1.00 18.29           C
ATOM   2815  OG   SER B 107      31.700  17.492  59.980  1.00 19.14           O
ATOM   2816  C    SER B 107      29.449  19.298  60.906  1.00 17.60           C
ATOM   2817  O    SER B 107      28.824  19.932  60.062  1.00 15.71           O
ATOM   2818  N    GLU B 108      28.872  18.396  61.691  1.00 18.50           N
ATOM   2819  CA   GLU B 108      27.448  18.092  61.586  1.00 20.04           C
ATOM   2820  CB   GLU B 108      27.211  16.599  61.866  1.00 21.24           C
ATOM   2821  CG   GLU B 108      27.853  15.636  60.878  1.00 23.99           C
ATOM   2822  CD   GLU B 108      27.857  14.195  61.379  1.00 26.62           C
ATOM   2823  OE1  GLU B 108      28.200  13.292  60.585  1.00 26.00           O
ATOM   2824  OE2  GLU B 108      27.531  13.961  62.571  1.00 28.28           O
ATOM   2825  C    GLU B 108      26.610  18.912  62.575  1.00 19.90           C
ATOM   2826  O    GLU B 108      25.423  18.632  62.768  1.00 21.12           O
ATOM   2827  N    THR B 109      27.215  19.904  63.215  1.00 18.25           N
ATOM   2828  CA   THR B 109      26.482  20.715  64.191  1.00 17.94           C
ATOM   2829  CB   THR B 109      27.444  21.621  65.004  1.00 18.77           C
ATOM   2830  OG1  THR B 109      28.455  20.814  65.628  1.00 16.31           O
ATOM   2831  CG2  THR B 109      26.669  22.386  66.087  1.00 15.42           C
ATOM   2832  C    THR B 109      25.388  21.583  63.559  1.00 17.24           C
ATOM   2833  O    THR B 109      25.578  22.181  62.509  1.00 16.20           O
ATOM   2834  N    SER B 110      24.236  21.651  64.209  1.00 17.74           N
ATOM   2835  CA   SER B 110      23.127  22.441  63.689  1.00 16.67           C
ATOM   2836  CB   SER B 110      21.809  21.903  64.227  1.00 16.80           C
ATOM   2837  OG   SER B 110      21.731  22.131  65.627  1.00 20.26           O
ATOM   2838  C    SER B 110      23.252  23.906  64.084  1.00 15.98           C
ATOM   2839  O    SER B 110      23.902  24.243  65.074  1.00 15.32           O
ATOM   2840  N    ARG B 111      22.617  24.771  63.300  1.00 16.24           N
ATOM   2841  CA   ARG B 111      22.631  26.201  63.568  1.00 17.17           C
ATOM   2842  CB   ARG B 111      21.794  26.944  62.517  1.00 17.01           C
ATOM   2843  CG   ARG B 111      21.933  28.467  62.559  1.00 16.94           C
ATOM   2844  CD   ARG B 111      21.024  29.140  61.539  1.00 14.94           C
ATOM   2845  NE   ARG B 111      21.275  28.659  60.184  1.00 13.14           N
ATOM   2846  CZ   ARG B 111      22.211  29.132  59.368  1.00 13.34           C
ATOM   2847  NH1  ARG B 111      23.008  30.122  59.752  1.00 14.34           N
ATOM   2848  NH2  ARG B 111      22.360  28.605  58.160  1.00 13.99           N
ATOM   2849  C    ARG B 111      22.055  26.458  64.959  1.00 16.42           C
ATOM   2850  O    ARG B 111      22.630  27.199  65.759  1.00 16.86           O
ATOM   2851  N    GLU B 112      20.924  25.822  65.244  1.00 15.98           N
ATOM   2852  CA   GLU B 112      20.248  25.980  66.525  1.00 16.74           C
ATOM   2853  CB   GLU B 112      18.903  25.245  66.475  1.00 19.32           C
ATOM   2854  CG   GLU B 112      18.467  24.604  67.761  1.00 25.41           C
ATOM   2855  CD   GLU B 112      17.031  24.130  67.704  1.00 30.94           C
ATOM   2856  OE1  GLU B 112      16.617  23.362  68.613  1.00 33.44           O
ATOM   2857  OE2  GLU B 112      16.307  24.538  66.755  1.00 34.16           O
ATOM   2858  C    GLU B 112      21.084  25.528  67.728  1.00 15.55           C
```

FIGURE 9 (cont.)

```
ATOM   2859  O    GLU B 112      21.105  26.196  68.765  1.00 13.73           O
ATOM   2860  N    GLY B 113      21.773  24.400  67.586  1.00 14.55           N
ATOM   2861  CA   GLY B 113      22.600  23.909  68.670  1.00 14.98           C
ATOM   2862  C    GLY B 113      23.799  24.821  68.872  1.00 16.15           C
ATOM   2863  O    GLY B 113      24.241  25.056  70.001  1.00 15.67           O
ATOM   2864  N    PHE B 114      24.327  25.337  67.765  1.00 16.20           N
ATOM   2865  CA   PHE B 114      25.480  26.225  67.801  1.00 15.05           C
ATOM   2866  CB   PHE B 114      25.922  26.538  66.372  1.00 14.31           C
ATOM   2867  CG   PHE B 114      27.132  27.427  66.283  1.00 15.18           C
ATOM   2868  CD1  PHE B 114      27.020  28.802  66.466  1.00 12.91           C
ATOM   2869  CD2  PHE B 114      28.386  26.888  65.986  1.00 15.35           C
ATOM   2870  CE1  PHE B 114      28.135  29.641  66.353  1.00 13.28           C
ATOM   2871  CE2  PHE B 114      29.512  27.716  65.870  1.00 16.58           C
ATOM   2872  CZ   PHE B 114      29.383  29.101  66.054  1.00 15.35           C
ATOM   2873  C    PHE B 114      25.132  27.513  68.542  1.00 14.60           C
ATOM   2874  O    PHE B 114      25.797  27.874  69.507  1.00 15.03           O
ATOM   2875  N    LEU B 115      24.086  28.195  68.086  1.00 14.46           N
ATOM   2876  CA   LEU B 115      23.650  29.446  68.697  1.00 13.39           C
ATOM   2877  CB   LEU B 115      22.467  30.028  67.911  1.00 13.63           C
ATOM   2878  CG   LEU B 115      22.846  30.624  66.540  1.00 14.40           C
ATOM   2879  CD1  LEU B 115      21.614  31.054  65.765  1.00 12.92           C
ATOM   2880  CD2  LEU B 115      23.780  31.806  66.759  1.00 15.69           C
ATOM   2881  C    LEU B 115      23.273  29.283  70.165  1.00 14.52           C
ATOM   2882  O    LEU B 115      23.475  30.195  70.960  1.00 13.56           O
ATOM   2883  N    LEU B 116      22.730  28.120  70.522  1.00 14.62           N
ATOM   2884  CA   LEU B 116      22.330  27.854  71.898  1.00 15.42           C
ATOM   2885  CB   LEU B 116      21.603  26.507  71.995  1.00 16.62           C
ATOM   2886  CG   LEU B 116      21.344  26.014  73.424  1.00 17.53           C
ATOM   2887  CD1  LEU B 116      20.243  26.841  74.066  1.00 17.89           C
ATOM   2888  CD2  LEU B 116      20.948  24.546  73.394  1.00 20.13           C
ATOM   2889  C    LEU B 116      23.546  27.847  72.827  1.00 16.02           C
ATOM   2890  O    LEU B 116      23.500  28.387  73.941  1.00 16.34           O
ATOM   2891  N    ALA B 117      24.637  27.241  72.374  1.00 15.10           N
ATOM   2892  CA   ALA B 117      25.835  27.189  73.198  1.00 14.55           C
ATOM   2893  CB   ALA B 117      26.839  26.214  72.600  1.00 15.58           C
ATOM   2894  C    ALA B 117      26.454  28.576  73.349  1.00 15.11           C
ATOM   2895  O    ALA B 117      27.000  28.896  74.407  1.00 14.51           O
ATOM   2896  N    GLN B 118      26.365  29.391  72.294  1.00 15.00           N
ATOM   2897  CA   GLN B 118      26.898  30.756  72.311  1.00 14.81           C
ATOM   2898  CB   GLN B 118      26.821  31.383  70.910  1.00 13.25           C
ATOM   2899  CG   GLN B 118      27.821  30.875  69.883  1.00 14.92           C
ATOM   2900  CD   GLN B 118      29.245  31.293  70.204  1.00 15.35           C
ATOM   2901  OE1  GLN B 118      29.495  32.448  70.547  1.00 17.09           O
ATOM   2902  NE2  GLN B 118      30.188  30.357  70.089  1.00 13.96           N
ATOM   2903  C    GLN B 118      26.080  31.625  73.272  1.00 15.56           C
ATOM   2904  O    GLN B 118      26.619  32.452  74.023  1.00 16.63           O
ATOM   2905  N    ASP B 119      24.769  31.423  73.226  1.00 15.42           N
ATOM   2906  CA   ASP B 119      23.813  32.168  74.029  1.00 14.78           C
ATOM   2907  CB   ASP B 119      22.387  31.742  73.603  1.00 17.36           C
ATOM   2908  CG   ASP B 119      21.293  32.642  74.164  1.00 18.73           C
ATOM   2909  OD1  ASP B 119      21.468  33.876  74.184  1.00 20.27           O
ATOM   2910  OD2  ASP B 119      20.239  32.117  74.567  1.00 20.15           O
ATOM   2911  C    ASP B 119      24.025  31.977  75.530  1.00 13.83           C
ATOM   2912  O    ASP B 119      24.139  32.942  76.281  1.00 11.92           O
ATOM   2913  N    ILE B 120      24.103  30.728  75.962  1.00 14.37           N
ATOM   2914  CA   ILE B 120      24.265  30.425  77.381  1.00 13.81           C
ATOM   2915  CB   ILE B 120      23.674  29.027  77.700  1.00 13.89           C
ATOM   2916  CG2  ILE B 120      23.809  28.717  79.181  1.00 14.27           C
ATOM   2917  CG1  ILE B 120      22.205  28.979  77.283  1.00 15.03           C
ATOM   2918  CD1  ILE B 120      21.589  27.610  77.407  1.00 16.02           C
ATOM   2919  C    ILE B 120      25.712  30.465  77.882  1.00 14.33           C
ATOM   2920  O    ILE B 120      25.987  30.979  78.976  1.00 13.19           O
ATOM   2921  N    SER B 121      26.629  29.935  77.075  1.00 14.45           N
ATOM   2922  CA   SER B 121      28.037  29.861  77.448  1.00 15.18           C
ATOM   2923  CB   SER B 121      28.688  28.692  76.710  1.00 15.70           C
```

FIGURE 9 (cont.)

| | | | | | | | | | | |
|---|---|---|---|---|---|---|---|---|---|---|
| ATOM | 2924 | OG | SER | B | 121 | 27.877 | 27.536 | 76.795 | 1.00 14.42 | O |
| ATOM | 2925 | C | SER | B | 121 | 28.879 | 31.124 | 77.240 | 1.00 15.22 | C |
| ATOM | 2926 | O | SER | B | 121 | 29.967 | 31.227 | 77.792 | 1.00 16.84 | O |
| ATOM | 2927 | N | SER | B | 122 | 28.394 | 32.087 | 76.464 | 1.00 15.57 | N |
| ATOM | 2928 | CA | SER | B | 122 | 29.178 | 33.303 | 76.236 | 1.00 15.14 | C |
| ATOM | 2929 | CB | SER | B | 122 | 29.846 | 33.228 | 74.866 | 1.00 14.77 | C |
| ATOM | 2930 | OG | SER | B | 122 | 30.458 | 34.455 | 74.535 | 1.00 16.66 | O |
| ATOM | 2931 | C | SER | B | 122 | 28.417 | 34.635 | 76.371 | 1.00 15.60 | C |
| ATOM | 2932 | O | SER | B | 122 | 28.834 | 35.519 | 77.131 | 1.00 15.71 | O |
| ATOM | 2933 | N | TYR | B | 123 | 27.315 | 34.796 | 75.642 | 1.00 15.66 | N |
| ATOM | 2934 | CA | TYR | B | 123 | 26.569 | 36.046 | 75.741 | 1.00 14.90 | C |
| ATOM | 2935 | CB | TYR | B | 123 | 25.323 | 36.050 | 74.846 | 1.00 14.15 | C |
| ATOM | 2936 | CG | TYR | B | 123 | 24.537 | 37.350 | 74.990 | 1.00 15.52 | C |
| ATOM | 2937 | CD1 | TYR | B | 123 | 25.043 | 38.551 | 74.487 | 1.00 15.52 | C |
| ATOM | 2938 | CE1 | TYR | B | 123 | 24.416 | 39.764 | 74.755 | 1.00 16.79 | C |
| ATOM | 2939 | CD2 | TYR | B | 123 | 23.370 | 37.399 | 75.754 | 1.00 13.77 | C |
| ATOM | 2940 | CE2 | TYR | B | 123 | 22.736 | 38.601 | 76.029 | 1.00 15.75 | C |
| ATOM | 2941 | CZ | TYR | B | 123 | 23.260 | 39.781 | 75.533 | 1.00 16.90 | C |
| ATOM | 2942 | OH | TYR | B | 123 | 22.642 | 40.978 | 75.827 | 1.00 17.59 | O |
| ATOM | 2943 | C | TYR | B | 123 | 26.138 | 36.317 | 77.177 | 1.00 15.52 | C |
| ATOM | 2944 | O | TYR | B | 123 | 26.005 | 37.471 | 77.579 | 1.00 16.05 | O |
| ATOM | 2945 | N | SER | B | 124 | 25.922 | 35.255 | 77.951 | 1.00 16.93 | N |
| ATOM | 2946 | CA | SER | B | 124 | 25.487 | 35.408 | 79.335 | 1.00 17.73 | C |
| ATOM | 2947 | CB | SER | B | 124 | 25.322 | 34.031 | 80.004 | 1.00 17.47 | C |
| ATOM | 2948 | OG | SER | B | 124 | 26.536 | 33.299 | 80.016 | 1.00 19.99 | O |
| ATOM | 2949 | C | SER | B | 124 | 26.419 | 36.306 | 80.165 | 1.00 17.91 | C |
| ATOM | 2950 | O | SER | B | 124 | 25.957 | 37.049 | 81.046 | 1.00 17.38 | O |
| ATOM | 2951 | N | LEU | B | 125 | 27.718 | 36.243 | 79.875 | 1.00 17.98 | N |
| ATOM | 2952 | CA | LEU | B | 125 | 28.712 | 37.052 | 80.581 | 1.00 16.73 | C |
| ATOM | 2953 | CB | LEU | B | 125 | 30.141 | 36.638 | 80.184 | 1.00 15.06 | C |
| ATOM | 2954 | CG | LEU | B | 125 | 31.264 | 37.402 | 80.909 | 1.00 15.73 | C |
| ATOM | 2955 | CD1 | LEU | B | 125 | 31.158 | 37.115 | 82.413 | 1.00 12.79 | C |
| ATOM | 2956 | CD2 | LEU | B | 125 | 32.645 | 37.001 | 80.376 | 1.00 10.67 | C |
| ATOM | 2957 | C | LEU | B | 125 | 28.495 | 38.522 | 80.242 | 1.00 16.67 | C |
| ATOM | 2958 | O | LEU | B | 125 | 28.630 | 39.392 | 81.100 | 1.00 16.50 | O |
| ATOM | 2959 | N | THR | B | 126 | 28.152 | 38.788 | 78.985 | 1.00 16.53 | N |
| ATOM | 2960 | CA | THR | B | 126 | 27.894 | 40.152 | 78.519 | 1.00 15.94 | C |
| ATOM | 2961 | CB | THR | B | 126 | 27.564 | 40.171 | 77.000 | 1.00 16.74 | C |
| ATOM | 2962 | OG1 | THR | B | 126 | 28.665 | 39.632 | 76.270 | 1.00 16.67 | O |
| ATOM | 2963 | CG2 | THR | B | 126 | 27.303 | 41.587 | 76.509 | 1.00 17.45 | C |
| ATOM | 2964 | C | THR | B | 126 | 26.722 | 40.765 | 79.284 | 1.00 15.05 | C |
| ATOM | 2965 | O | THR | B | 126 | 26.880 | 41.778 | 79.956 | 1.00 14.61 | O |
| ATOM | 2966 | N | ILE | B | 127 | 25.551 | 40.140 | 79.183 | 1.00 15.62 | N |
| ATOM | 2967 | CA | ILE | B | 127 | 24.352 | 40.636 | 79.861 | 1.00 14.42 | C |
| ATOM | 2968 | CB | ILE | B | 127 | 23.109 | 39.732 | 79.563 | 1.00 15.62 | C |
| ATOM | 2969 | CG2 | ILE | B | 127 | 23.353 | 38.313 | 80.002 | 1.00 16.66 | C |
| ATOM | 2970 | CG1 | ILE | B | 127 | 21.875 | 40.274 | 80.282 | 1.00 17.42 | C |
| ATOM | 2971 | CD1 | ILE | B | 127 | 21.339 | 41.560 | 79.692 | 1.00 20.40 | C |
| ATOM | 2972 | C | ILE | B | 127 | 24.561 | 40.760 | 81.369 | 1.00 13.56 | C |
| ATOM | 2973 | O | ILE | B | 127 | 24.204 | 41.778 | 81.961 | 1.00 14.64 | O |
| ATOM | 2974 | N | VAL | B | 128 | 25.145 | 39.739 | 81.991 | 1.00 13.73 | N |
| ATOM | 2975 | CA | VAL | B | 128 | 25.397 | 39.769 | 83.432 | 1.00 12.95 | C |
| ATOM | 2976 | CB | VAL | B | 128 | 26.014 | 38.422 | 83.933 | 1.00 12.97 | C |
| ATOM | 2977 | CG1 | VAL | B | 128 | 26.556 | 38.576 | 85.352 | 1.00 10.64 | C |
| ATOM | 2978 | CG2 | VAL | B | 128 | 24.950 | 37.334 | 83.933 | 1.00 10.23 | C |
| ATOM | 2979 | C | VAL | B | 128 | 26.309 | 40.940 | 83.811 | 1.00 14.80 | C |
| ATOM | 2980 | O | VAL | B | 128 | 26.029 | 41.663 | 84.771 | 1.00 17.39 | O |
| ATOM | 2981 | N | ALA | B | 129 | 27.382 | 41.149 | 83.053 | 1.00 15.26 | N |
| ATOM | 2982 | CA | ALA | B | 129 | 28.299 | 42.260 | 83.331 | 1.00 16.84 | C |
| ATOM | 2983 | CB | ALA | B | 129 | 29.471 | 42.244 | 82.355 | 1.00 15.72 | C |
| ATOM | 2984 | C | ALA | B | 129 | 27.564 | 43.590 | 83.229 | 1.00 17.05 | C |
| ATOM | 2985 | O | ALA | B | 129 | 27.785 | 44.498 | 84.028 | 1.00 19.64 | O |
| ATOM | 2986 | N | HIS | B | 130 | 26.684 | 43.705 | 82.246 | 1.00 18.16 | N |
| ATOM | 2987 | CA | HIS | B | 130 | 25.933 | 44.938 | 82.056 | 1.00 19.63 | C |
| ATOM | 2988 | CB | HIS | B | 130 | 25.081 | 44.850 | 80.778 | 1.00 20.88 | C |

FIGURE 9 (cont.)

| | | | | | | | | | | |
|---|---|---|---|---|---|---|---|---|---|---|
| ATOM | 2989 | CG | HIS | B | 130 | 24.372 | 46.127 | 80.439 | 1.00 22.89 | C |
| ATOM | 2990 | CD2 | HIS | B | 130 | 24.648 | 47.084 | 79.520 | 1.00 24.20 | C |
| ATOM | 2991 | ND1 | HIS | B | 130 | 23.258 | 46.564 | 81.122 | 1.00 23.31 | N |
| ATOM | 2992 | CE1 | HIS | B | 130 | 22.876 | 47.733 | 80.639 | 1.00 23.03 | C |
| ATOM | 2993 | NE2 | HIS | B | 130 | 23.703 | 48.072 | 79.667 | 1.00 24.79 | N |
| ATOM | 2994 | C | HIS | B | 130 | 25.042 | 45.271 | 83.260 | 1.00 19.81 | C |
| ATOM | 2995 | O | HIS | B | 130 | 25.003 | 46.418 | 83.714 | 1.00 19.43 | O |
| ATOM | 2996 | N | GLU | B | 131 | 24.347 | 44.266 | 83.790 | 1.00 19.46 | N |
| ATOM | 2997 | CA | GLU | B | 131 | 23.459 | 44.495 | 84.926 | 1.00 18.72 | C |
| ATOM | 2998 | CB | GLU | B | 131 | 22.384 | 43.405 | 84.988 | 1.00 18.14 | C |
| ATOM | 2999 | CG | GLU | B | 131 | 21.522 | 43.314 | 83.731 | 1.00 18.05 | C |
| ATOM | 3000 | CD | GLU | B | 131 | 20.986 | 44.666 | 83.293 | 1.00 20.49 | C |
| ATOM | 3001 | OE1 | GLU | B | 131 | 20.403 | 45.384 | 84.141 | 1.00 22.13 | O |
| ATOM | 3002 | OE2 | GLU | B | 131 | 21.141 | 45.018 | 82.101 | 1.00 21.04 | O |
| ATOM | 3003 | C | GLU | B | 131 | 24.191 | 44.578 | 86.257 | 1.00 18.74 | C |
| ATOM | 3004 | O | GLU | B | 131 | 23.730 | 45.254 | 87.180 | 1.00 19.04 | O |
| ATOM | 3005 | N | ALA | B | 132 | 25.333 | 43.903 | 86.350 | 1.00 18.34 | N |
| ATOM | 3006 | CA | ALA | B | 132 | 26.134 | 43.898 | 87.575 | 1.00 17.83 | C |
| ATOM | 3007 | CB | ALA | B | 132 | 27.081 | 42.685 | 87.583 | 1.00 16.83 | C |
| ATOM | 3008 | C | ALA | B | 132 | 26.937 | 45.191 | 87.737 | 1.00 16.33 | C |
| ATOM | 3009 | O | ALA | B | 132 | 27.293 | 45.579 | 88.851 | 1.00 16.32 | O |
| ATOM | 3010 | N | LYS | B | 133 | 27.244 | 45.839 | 86.624 | 1.00 15.57 | N |
| ATOM | 3011 | CA | LYS | B | 133 | 27.973 | 47.094 | 86.667 | 1.00 16.01 | C |
| ATOM | 3012 | CB | LYS | B | 133 | 28.174 | 47.632 | 85.245 | 1.00 17.44 | C |
| ATOM | 3013 | CG | LYS | B | 133 | 28.527 | 49.116 | 85.202 | 1.00 22.31 | C |
| ATOM | 3014 | CD | LYS | B | 133 | 28.822 | 49.648 | 83.789 | 1.00 22.52 | C |
| ATOM | 3015 | CE | LYS | B | 133 | 29.100 | 51.148 | 83.859 | 1.00 23.47 | C |
| ATOM | 3016 | NZ | LYS | B | 133 | 29.448 | 51.758 | 82.534 | 1.00 26.57 | N |
| ATOM | 3017 | C | LYS | B | 133 | 27.173 | 48.109 | 87.505 | 1.00 15.66 | C |
| ATOM | 3018 | O | LYS | B | 133 | 27.743 | 48.858 | 88.301 | 1.00 13.11 | O |
| ATOM | 3019 | N | LYS | B | 134 | 25.849 | 48.105 | 87.334 | 1.00 16.03 | N |
| ATOM | 3020 | CA | LYS | B | 134 | 24.957 | 49.019 | 88.054 | 1.00 17.83 | C |
| ATOM | 3021 | CB | LYS | B | 134 | 23.503 | 48.739 | 87.679 | 1.00 17.47 | C |
| ATOM | 3022 | CG | LYS | B | 134 | 23.225 | 48.754 | 86.181 | 1.00 20.53 | C |
| ATOM | 3023 | CD | LYS | B | 134 | 21.731 | 48.541 | 85.885 | 1.00 21.80 | C |
| ATOM | 3024 | CE | LYS | B | 134 | 21.466 | 48.537 | 84.385 | 1.00 22.05 | C |
| ATOM | 3025 | NZ | LYS | B | 134 | 20.023 | 48.785 | 84.083 | 1.00 25.27 | N |
| ATOM | 3026 | C | LYS | B | 134 | 25.101 | 48.920 | 89.578 | 1.00 18.99 | C |
| ATOM | 3027 | O | LYS | B | 134 | 24.659 | 49.811 | 90.315 | 1.00 20.06 | O |
| ATOM | 3028 | N | LEU | B | 135 | 25.715 | 47.837 | 90.046 | 1.00 18.61 | N |
| ATOM | 3029 | CA | LEU | B | 135 | 25.903 | 47.624 | 91.474 | 1.00 18.73 | C |
| ATOM | 3030 | CB | LEU | B | 135 | 25.380 | 46.241 | 91.882 | 1.00 19.97 | C |
| ATOM | 3031 | CG | LEU | B | 135 | 23.962 | 45.876 | 91.439 | 1.00 20.32 | C |
| ATOM | 3032 | CD1 | LEU | B | 135 | 23.554 | 44.578 | 92.134 | 1.00 20.46 | C |
| ATOM | 3033 | CD2 | LEU | B | 135 | 22.987 | 47.008 | 91.799 | 1.00 20.64 | C |
| ATOM | 3034 | C | LEU | B | 135 | 27.366 | 47.735 | 91.870 | 1.00 18.27 | C |
| ATOM | 3035 | O | LEU | B | 135 | 27.722 | 47.452 | 93.014 | 1.00 16.67 | O |
| ATOM | 3036 | N | MET | B | 136 | 28.211 | 48.132 | 90.923 | 1.00 18.21 | N |
| ATOM | 3037 | CA | MET | B | 136 | 29.635 | 48.284 | 91.190 | 1.00 19.18 | C |
| ATOM | 3038 | CB | MET | B | 136 | 30.436 | 47.216 | 90.425 | 1.00 18.77 | C |
| ATOM | 3039 | CG | MET | B | 136 | 30.006 | 45.768 | 90.717 | 1.00 20.47 | C |
| ATOM | 3040 | SD | MET | B | 136 | 31.150 | 44.476 | 90.057 | 1.00 22.69 | S |
| ATOM | 3041 | CE | MET | B | 136 | 30.723 | 44.496 | 88.333 | 1.00 19.85 | C |
| ATOM | 3042 | C | MET | B | 136 | 30.091 | 49.698 | 90.791 | 1.00 19.47 | C |
| ATOM | 3043 | O | MET | B | 136 | 30.918 | 49.877 | 89.883 | 1.00 19.20 | O |
| ATOM | 3044 | N | PRO | B | 137 | 29.556 | 50.725 | 91.476 | 1.00 19.11 | N |
| ATOM | 3045 | CD | PRO | B | 137 | 28.553 | 50.647 | 92.557 | 1.00 19.71 | C |
| ATOM | 3046 | CA | PRO | B | 137 | 29.904 | 52.120 | 91.191 | 1.00 18.69 | C |
| ATOM | 3047 | CB | PRO | B | 137 | 28.941 | 52.906 | 92.086 | 1.00 19.91 | C |
| ATOM | 3048 | CG | PRO | B | 137 | 28.724 | 51.974 | 93.246 | 1.00 19.35 | C |
| ATOM | 3049 | C | PRO | B | 137 | 31.362 | 52.494 | 91.435 | 1.00 18.15 | C |
| ATOM | 3050 | O | PRO | B | 137 | 31.891 | 53.378 | 90.772 | 1.00 17.02 | O |
| ATOM | 3051 | N | GLU | B | 138 | 32.009 | 51.826 | 92.384 | 1.00 19.54 | N |
| ATOM | 3052 | CA | GLU | B | 138 | 33.410 | 52.111 | 92.694 | 1.00 20.23 | C |
| ATOM | 3053 | CB | GLU | B | 138 | 33.682 | 51.950 | 94.190 | 1.00 23.20 | C |

FIGURE 9 (cont.)

| | | | | | | | | | |
|---|---|---|---|---|---|---|---|---|---|
| ATOM | 3054 | CG  | GLU | B | 138 | 32.724 | 52.698 | 95.126 | 1.00 27.35 | C |
| ATOM | 3055 | CD  | GLU | B | 138 | 33.106 | 52.511 | 96.597 | 1.00 31.40 | C |
| ATOM | 3056 | OE1 | GLU | B | 138 | 34.249 | 52.890 | 96.978 | 1.00 33.64 | O |
| ATOM | 3057 | OE2 | GLU | B | 138 | 32.273 | 51.979 | 97.374 | 1.00 32.91 | O |
| ATOM | 3058 | C   | GLU | B | 138 | 34.320 | 51.159 | 91.944 | 1.00 19.88 | C |
| ATOM | 3059 | O   | GLU | B | 138 | 35.541 | 51.303 | 91.970 | 1.00 19.97 | O |
| ATOM | 3060 | N   | GLY | B | 139 | 33.720 | 50.173 | 91.287 | 1.00 20.91 | N |
| ATOM | 3061 | CA  | GLY | B | 139 | 34.495 | 49.195 | 90.549 | 1.00 19.45 | C |
| ATOM | 3062 | C   | GLY | B | 139 | 34.338 | 47.826 | 91.177 | 1.00 18.03 | C |
| ATOM | 3063 | O   | GLY | B | 139 | 33.683 | 47.685 | 92.202 | 1.00 16.99 | O |
| ATOM | 3064 | N   | GLY | B | 140 | 34.937 | 46.814 | 90.560 | 1.00 18.46 | N |
| ATOM | 3065 | CA  | GLY | B | 140 | 34.843 | 45.473 | 91.096 | 1.00 17.93 | C |
| ATOM | 3066 | C   | GLY | B | 140 | 35.545 | 44.443 | 90.231 | 1.00 16.83 | C |
| ATOM | 3067 | O   | GLY | B | 140 | 36.493 | 44.768 | 89.518 | 1.00 17.23 | O |
| ATOM | 3068 | N   | SER | B | 141 | 35.068 | 43.204 | 90.275 | 1.00 15.56 | N |
| ATOM | 3069 | CA  | SER | B | 141 | 35.689 | 42.138 | 89.503 | 1.00 16.03 | C |
| ATOM | 3070 | CB  | SER | B | 141 | 36.796 | 41.502 | 90.326 | 1.00 14.89 | C |
| ATOM | 3071 | OG  | SER | B | 141 | 37.334 | 40.404 | 89.633 | 1.00 19.22 | O |
| ATOM | 3072 | C   | SER | B | 141 | 34.741 | 41.049 | 89.010 | 1.00 15.71 | C |
| ATOM | 3073 | O   | SER | B | 141 | 33.872 | 40.573 | 89.742 | 1.00 17.17 | O |
| ATOM | 3074 | N   | ILE | B | 142 | 34.917 | 40.652 | 87.757 | 1.00 15.10 | N |
| ATOM | 3075 | CA  | ILE | B | 142 | 34.077 | 39.617 | 87.173 | 1.00 15.72 | C |
| ATOM | 3076 | CB  | ILE | B | 142 | 33.244 | 40.175 | 86.021 | 1.00 14.81 | C |
| ATOM | 3077 | CG2 | ILE | B | 142 | 32.326 | 39.101 | 85.481 | 1.00 16.94 | C |
| ATOM | 3078 | CG1 | ILE | B | 142 | 32.428 | 41.372 | 86.502 | 1.00 15.60 | C |
| ATOM | 3079 | CD1 | ILE | B | 142 | 31.696 | 42.084 | 85.388 | 1.00 14.38 | C |
| ATOM | 3080 | C   | ILE | B | 142 | 34.969 | 38.500 | 86.655 | 1.00 15.41 | C |
| ATOM | 3081 | O   | ILE | B | 142 | 35.889 | 38.749 | 85.889 | 1.00 14.75 | O |
| ATOM | 3082 | N   | VAL | B | 143 | 34.719 | 37.273 | 87.103 | 1.00 17.00 | N |
| ATOM | 3083 | CA  | VAL | B | 143 | 35.522 | 36.138 | 86.661 | 1.00 16.24 | C |
| ATOM | 3084 | CB  | VAL | B | 143 | 36.314 | 35.506 | 87.829 | 1.00 17.65 | C |
| ATOM | 3085 | CG1 | VAL | B | 143 | 37.215 | 34.392 | 87.297 | 1.00 18.75 | C |
| ATOM | 3086 | CG2 | VAL | B | 143 | 37.139 | 36.566 | 88.549 | 1.00 15.61 | C |
| ATOM | 3087 | C   | VAL | B | 143 | 34.638 | 35.064 | 86.049 | 1.00 16.81 | C |
| ATOM | 3088 | O   | VAL | B | 143 | 33.592 | 34.729 | 86.597 | 1.00 16.25 | O |
| ATOM | 3089 | N   | ALA | B | 144 | 35.050 | 34.548 | 84.896 | 1.00 17.76 | N |
| ATOM | 3090 | CA  | ALA | B | 144 | 34.308 | 33.494 | 84.215 | 1.00 18.08 | C |
| ATOM | 3091 | CB  | ALA | B | 144 | 33.857 | 33.963 | 82.849 | 1.00 17.69 | C |
| ATOM | 3092 | C   | ALA | B | 144 | 35.229 | 32.287 | 84.083 | 1.00 18.39 | C |
| ATOM | 3093 | O   | ALA | B | 144 | 36.445 | 32.425 | 84.012 | 1.00 18.86 | O |
| ATOM | 3094 | N   | THR | B | 145 | 34.653 | 31.097 | 84.060 | 1.00 19.02 | N |
| ATOM | 3095 | CA  | THR | B | 145 | 35.468 | 29.909 | 83.949 | 1.00 17.73 | C |
| ATOM | 3096 | CB  | THR | B | 145 | 35.063 | 28.871 | 85.032 | 1.00 19.18 | C |
| ATOM | 3097 | OG1 | THR | B | 145 | 34.879 | 27.599 | 84.421 | 1.00 20.01 | O |
| ATOM | 3098 | CG2 | THR | B | 145 | 33.785 | 29.286 | 85.743 | 1.00 17.28 | C |
| ATOM | 3099 | C   | THR | B | 145 | 35.423 | 29.292 | 82.554 | 1.00 17.67 | C |
| ATOM | 3100 | O   | THR | B | 145 | 34.357 | 29.089 | 81.984 | 1.00 18.93 | O |
| ATOM | 3101 | N   | THR | B | 146 | 36.599 | 29.015 | 82.000 | 1.00 16.43 | N |
| ATOM | 3102 | CA  | THR | B | 146 | 36.710 | 28.423 | 80.673 | 1.00 15.22 | C |
| ATOM | 3103 | CB  | THR | B | 146 | 37.334 | 29.427 | 79.687 | 1.00 14.56 | C |
| ATOM | 3104 | OG1 | THR | B | 146 | 37.358 | 28.853 | 78.375 | 1.00 15.78 | O |
| ATOM | 3105 | CG2 | THR | B | 146 | 38.750 | 29.789 | 80.109 | 1.00 10.15 | C |
| ATOM | 3106 | C   | THR | B | 146 | 37.547 | 27.130 | 80.677 | 1.00 14.60 | C |
| ATOM | 3107 | O   | THR | B | 146 | 37.956 | 26.648 | 81.735 | 1.00 15.77 | O |
| ATOM | 3108 | N   | TYR | B | 147 | 37.808 | 26.589 | 79.489 | 1.00 13.52 | N |
| ATOM | 3109 | CA  | TYR | B | 147 | 38.579 | 25.349 | 79.332 | 1.00 14.06 | C |
| ATOM | 3110 | CB  | TYR | B | 147 | 37.608 | 24.171 | 79.148 | 1.00 12.69 | C |
| ATOM | 3111 | CG  | TYR | B | 147 | 38.231 | 22.835 | 78.814 | 1.00 11.64 | C |
| ATOM | 3112 | CD1 | TYR | B | 147 | 39.081 | 22.188 | 79.718 | 1.00 10.73 | C |
| ATOM | 3113 | CE1 | TYR | B | 147 | 39.620 | 20.938 | 79.428 | 1.00  9.97 | C |
| ATOM | 3114 | CD2 | TYR | B | 147 | 37.939 | 22.191 | 77.610 | 1.00 10.10 | C |
| ATOM | 3115 | CE2 | TYR | B | 147 | 38.476 | 20.933 | 77.316 | 1.00  8.82 | C |
| ATOM | 3116 | CZ  | TYR | B | 147 | 39.311 | 20.321 | 78.227 | 1.00  9.07 | C |
| ATOM | 3117 | OH  | TYR | B | 147 | 39.851 | 19.097 | 77.949 | 1.00 11.17 | O |
| ATOM | 3118 | C   | TYR | B | 147 | 39.530 | 25.453 | 78.134 | 1.00 12.92 | C |

FIGURE 9 (cont.)

| ATOM | 3119 | O   | TYR | B | 147 | 39.219 | 26.115 | 77.145 | 1.00 | 13.37 | O |
|------|------|-----|-----|---|-----|--------|--------|--------|------|-------|---|
| ATOM | 3120 | N   | LEU | B | 148 | 40.682 | 24.793 | 78.234 | 1.00 | 12.28 | N |
| ATOM | 3121 | CA  | LEU | B | 148 | 41.699 | 24.806 | 77.180 | 1.00 | 11.06 | C |
| ATOM | 3122 | CB  | LEU | B | 148 | 42.803 | 23.802 | 77.533 | 1.00 | 12.17 | C |
| ATOM | 3123 | CG  | LEU | B | 148 | 44.275 | 24.082 | 77.210 | 1.00 | 14.16 | C |
| ATOM | 3124 | CD1 | LEU | B | 148 | 44.619 | 25.568 | 77.335 | 1.00 | 12.55 | C |
| ATOM | 3125 | CD2 | LEU | B | 148 | 45.136 | 23.258 | 78.176 | 1.00 | 14.80 | C |
| ATOM | 3126 | C   | LEU | B | 148 | 41.101 | 24.491 | 75.807 | 1.00 | 11.10 | C |
| ATOM | 3127 | O   | LEU | B | 148 | 41.678 | 24.840 | 74.773 | 1.00 | 10.35 | O |
| ATOM | 3128 | N   | GLY | B | 149 | 39.949 | 23.821 | 75.802 | 1.00 | 11.11 | N |
| ATOM | 3129 | CA  | GLY | B | 149 | 39.276 | 23.505 | 74.551 | 1.00 | 11.98 | C |
| ATOM | 3130 | C   | GLY | B | 149 | 38.841 | 24.764 | 73.796 | 1.00 | 12.60 | C |
| ATOM | 3131 | O   | GLY | B | 149 | 38.412 | 24.695 | 72.635 | 1.00 | 12.36 | O |
| ATOM | 3132 | N   | GLY | B | 150 | 38.946 | 25.913 | 74.461 | 1.00 | 12.06 | N |
| ATOM | 3133 | CA  | GLY | B | 150 | 38.592 | 27.181 | 73.838 | 1.00 | 13.28 | C |
| ATOM | 3134 | C   | GLY | B | 150 | 39.786 | 27.817 | 73.129 | 1.00 | 14.28 | C |
| ATOM | 3135 | O   | GLY | B | 150 | 39.649 | 28.820 | 72.420 | 1.00 | 14.44 | O |
| ATOM | 3136 | N   | GLU | B | 151 | 40.960 | 27.217 | 73.309 | 1.00 | 14.85 | N |
| ATOM | 3137 | CA  | GLU | B | 151 | 42.202 | 27.707 | 72.709 | 1.00 | 16.09 | C |
| ATOM | 3138 | CB  | GLU | B | 151 | 43.256 | 27.909 | 73.792 | 1.00 | 17.39 | C |
| ATOM | 3139 | CG  | GLU | B | 151 | 43.018 | 29.066 | 74.732 | 1.00 | 19.30 | C |
| ATOM | 3140 | CD  | GLU | B | 151 | 44.118 | 29.159 | 75.779 | 1.00 | 22.22 | C |
| ATOM | 3141 | OE1 | GLU | B | 151 | 43.842 | 28.906 | 76.976 | 1.00 | 21.56 | O |
| ATOM | 3142 | OE2 | GLU | B | 151 | 45.269 | 29.467 | 75.394 | 1.00 | 23.24 | O |
| ATOM | 3143 | C   | GLU | B | 151 | 42.774 | 26.740 | 71.672 | 1.00 | 16.28 | C |
| ATOM | 3144 | O   | GLU | B | 151 | 43.498 | 27.147 | 70.770 | 1.00 | 17.30 | O |
| ATOM | 3145 | N   | PHE | B | 152 | 42.448 | 25.460 | 71.823 | 1.00 | 16.63 | N |
| ATOM | 3146 | CA  | PHE | B | 152 | 42.921 | 24.392 | 70.941 | 1.00 | 15.38 | C |
| ATOM | 3147 | CB  | PHE | B | 152 | 44.052 | 23.622 | 71.617 | 1.00 | 15.08 | C |
| ATOM | 3148 | CG  | PHE | B | 152 | 45.209 | 24.479 | 72.018 | 1.00 | 14.54 | C |
| ATOM | 3149 | CD1 | PHE | B | 152 | 46.139 | 24.890 | 71.076 | 1.00 | 15.91 | C |
| ATOM | 3150 | CD2 | PHE | B | 152 | 45.338 | 24.920 | 73.327 | 1.00 | 14.42 | C |
| ATOM | 3151 | CE1 | PHE | B | 152 | 47.184 | 25.738 | 71.433 | 1.00 | 18.17 | C |
| ATOM | 3152 | CE2 | PHE | B | 152 | 46.378 | 25.769 | 73.697 | 1.00 | 15.97 | C |
| ATOM | 3153 | CZ  | PHE | B | 152 | 47.300 | 26.178 | 72.748 | 1.00 | 16.42 | C |
| ATOM | 3154 | C   | PHE | B | 152 | 41.778 | 23.422 | 70.685 | 1.00 | 15.46 | C |
| ATOM | 3155 | O   | PHE | B | 152 | 40.900 | 23.247 | 71.538 | 1.00 | 15.16 | O |
| ATOM | 3156 | N   | ALA | B | 153 | 41.796 | 22.781 | 69.521 | 1.00 | 14.57 | N |
| ATOM | 3157 | CA  | ALA | B | 153 | 40.754 | 21.817 | 69.178 | 1.00 | 13.83 | C |
| ATOM | 3158 | CB  | ALA | B | 153 | 40.832 | 21.464 | 67.691 | 1.00 | 12.37 | C |
| ATOM | 3159 | C   | ALA | B | 153 | 40.897 | 20.555 | 70.042 | 1.00 | 13.19 | C |
| ATOM | 3160 | O   | ALA | B | 153 | 41.898 | 19.842 | 69.970 | 1.00 | 11.74 | O |
| ATOM | 3161 | N   | VAL | B | 154 | 39.887 | 20.309 | 70.867 | 1.00 | 12.69 | N |
| ATOM | 3162 | CA  | VAL | B | 154 | 39.855 | 19.154 | 71.761 | 1.00 | 13.84 | C |
| ATOM | 3163 | CB  | VAL | B | 154 | 39.563 | 19.584 | 73.233 | 1.00 | 13.46 | C |
| ATOM | 3164 | CG1 | VAL | B | 154 | 39.325 | 18.355 | 74.099 | 1.00 | 12.08 | C |
| ATOM | 3165 | CG2 | VAL | B | 154 | 40.734 | 20.391 | 73.788 | 1.00 | 12.30 | C |
| ATOM | 3166 | C   | VAL | B | 154 | 38.778 | 18.143 | 71.340 | 1.00 | 14.76 | C |
| ATOM | 3167 | O   | VAL | B | 154 | 37.656 | 18.523 | 70.992 | 1.00 | 12.54 | O |
| ATOM | 3168 | N   | GLN | B | 155 | 39.142 | 16.862 | 71.390 | 1.00 | 15.24 | N |
| ATOM | 3169 | CA  | GLN | B | 155 | 38.254 | 15.763 | 71.040 | 1.00 | 17.44 | C |
| ATOM | 3170 | CB  | GLN | B | 155 | 38.833 | 14.431 | 71.523 | 1.00 | 21.11 | C |
| ATOM | 3171 | CG  | GLN | B | 155 | 40.072 | 14.003 | 70.790 | 1.00 | 27.66 | C |
| ATOM | 3172 | CD  | GLN | B | 155 | 39.814 | 13.882 | 69.312 | 1.00 | 31.02 | C |
| ATOM | 3173 | OE1 | GLN | B | 155 | 38.880 | 13.178 | 68.888 | 1.00 | 34.49 | O |
| ATOM | 3174 | NE2 | GLN | B | 155 | 40.632 | 14.559 | 68.507 | 1.00 | 31.66 | N |
| ATOM | 3175 | C   | GLN | B | 155 | 36.877 | 15.911 | 71.648 | 1.00 | 16.32 | C |
| ATOM | 3176 | O   | GLN | B | 155 | 36.744 | 16.122 | 72.847 | 1.00 | 13.55 | O |
| ATOM | 3177 | N   | ASN | B | 156 | 35.863 | 15.785 | 70.799 | 1.00 | 16.20 | N |
| ATOM | 3178 | CA  | ASN | B | 156 | 34.469 | 15.864 | 71.203 | 1.00 | 17.45 | C |
| ATOM | 3179 | CB  | ASN | B | 156 | 34.141 | 14.699 | 72.149 | 1.00 | 19.39 | C |
| ATOM | 3180 | CG  | ASN | B | 156 | 34.324 | 13.349 | 71.482 | 1.00 | 19.21 | C |
| ATOM | 3181 | OD1 | ASN | B | 156 | 33.911 | 13.154 | 70.343 | 1.00 | 19.99 | O |
| ATOM | 3182 | ND2 | ASN | B | 156 | 34.944 | 12.416 | 72.186 | 1.00 | 20.88 | N |
| ATOM | 3183 | C   | ASN | B | 156 | 33.960 | 17.170 | 71.811 | 1.00 | 17.07 | C |

FIGURE 9 (cont.)

| ATOM | 3184 | O   | ASN | B | 156 | 32.747 | 17.387 | 71.836 | 1.00 | 17.45 | O |
|------|------|-----|-----|---|-----|--------|--------|--------|------|-------|---|
| ATOM | 3185 | N   | TYR | B | 157 | 34.851 | 18.038 | 72.290 | 1.00 | 15.98 | N |
| ATOM | 3186 | CA  | TYR | B | 157 | 34.401 | 19.305 | 72.893 | 1.00 | 16.17 | C |
| ATOM | 3187 | CB  | TYR | B | 157 | 35.584 | 20.166 | 73.347 | 1.00 | 16.19 | C |
| ATOM | 3188 | CG  | TYR | B | 157 | 35.214 | 21.111 | 74.466 | 1.00 | 16.88 | C |
| ATOM | 3189 | CD1 | TYR | B | 157 | 34.456 | 20.662 | 75.550 | 1.00 | 18.47 | C |
| ATOM | 3190 | CE1 | TYR | B | 157 | 34.086 | 21.527 | 76.586 | 1.00 | 18.84 | C |
| ATOM | 3191 | CD2 | TYR | B | 157 | 35.601 | 22.450 | 74.446 | 1.00 | 15.42 | C |
| ATOM | 3192 | CE2 | TYR | B | 157 | 35.233 | 23.325 | 75.482 | 1.00 | 16.99 | C |
| ATOM | 3193 | CZ  | TYR | B | 157 | 34.474 | 22.855 | 76.546 | 1.00 | 17.19 | C |
| ATOM | 3194 | OH  | TYR | B | 157 | 34.094 | 23.694 | 77.577 | 1.00 | 18.86 | O |
| ATOM | 3195 | C   | TYR | B | 157 | 33.549 | 20.078 | 71.895 | 1.00 | 15.46 | C |
| ATOM | 3196 | O   | TYR | B | 157 | 32.619 | 20.790 | 72.271 | 1.00 | 17.59 | O |
| ATOM | 3197 | N   | ASN | B | 158 | 33.899 | 19.933 | 70.624 | 1.00 | 15.51 | N |
| ATOM | 3198 | CA  | ASN | B | 158 | 33.176 | 20.524 | 69.505 | 1.00 | 15.85 | C |
| ATOM | 3199 | CB  | ASN | B | 158 | 32.105 | 19.533 | 69.045 | 1.00 | 15.22 | C |
| ATOM | 3200 | CG  | ASN | B | 158 | 32.687 | 18.166 | 68.688 | 1.00 | 16.67 | C |
| ATOM | 3201 | OD1 | ASN | B | 158 | 33.906 | 17.965 | 68.724 | 1.00 | 17.15 | O |
| ATOM | 3202 | ND2 | ASN | B | 158 | 31.819 | 17.225 | 68.332 | 1.00 | 17.88 | N |
| ATOM | 3203 | C   | ASN | B | 158 | 32.548 | 21.903 | 69.687 | 1.00 | 16.12 | C |
| ATOM | 3204 | O   | ASN | B | 158 | 33.255 | 22.906 | 69.768 | 1.00 | 17.89 | O |
| ATOM | 3205 | N   | VAL | B | 159 | 31.219 | 21.947 | 69.739 | 1.00 | 15.19 | N |
| ATOM | 3206 | CA  | VAL | B | 159 | 30.486 | 23.203 | 69.869 | 1.00 | 14.17 | C |
| ATOM | 3207 | CB  | VAL | B | 159 | 28.950 | 22.953 | 69.828 | 1.00 | 14.12 | C |
| ATOM | 3208 | CG1 | VAL | B | 159 | 28.471 | 22.353 | 71.150 | 1.00 | 10.61 | C |
| ATOM | 3209 | CG2 | VAL | B | 159 | 28.223 | 24.254 | 69.527 | 1.00 | 14.04 | C |
| ATOM | 3210 | C   | VAL | B | 159 | 30.837 | 24.026 | 71.118 | 1.00 | 13.30 | C |
| ATOM | 3211 | O   | VAL | B | 159 | 30.802 | 25.258 | 71.089 | 1.00 | 12.58 | O |
| ATOM | 3212 | N   | MET | B | 160 | 31.166 | 23.354 | 72.213 | 1.00 | 12.99 | N |
| ATOM | 3213 | CA  | MET | B | 160 | 31.535 | 24.063 | 73.428 | 1.00 | 12.44 | C |
| ATOM | 3214 | CB  | MET | B | 160 | 31.549 | 23.109 | 74.622 | 1.00 | 15.11 | C |
| ATOM | 3215 | CG  | MET | B | 160 | 30.210 | 22.961 | 75.299 | 1.00 | 15.96 | C |
| ATOM | 3216 | SD  | MET | B | 160 | 29.582 | 24.561 | 75.841 | 1.00 | 19.31 | S |
| ATOM | 3217 | CE  | MET | B | 160 | 30.937 | 25.135 | 76.867 | 1.00 | 17.37 | C |
| ATOM | 3218 | C   | MET | B | 160 | 32.905 | 24.729 | 73.282 | 1.00 | 11.55 | C |
| ATOM | 3219 | O   | MET | B | 160 | 33.193 | 25.707 | 73.955 | 1.00 | 11.36 | O |
| ATOM | 3220 | N   | GLY | B | 161 | 33.748 | 24.191 | 72.406 | 1.00 | 11.23 | N |
| ATOM | 3221 | CA  | GLY | B | 161 | 35.062 | 24.778 | 72.193 | 1.00 | 12.32 | C |
| ATOM | 3222 | C   | GLY | B | 161 | 34.979 | 26.156 | 71.553 | 1.00 | 12.15 | C |
| ATOM | 3223 | O   | GLY | B | 161 | 35.727 | 27.075 | 71.903 | 1.00 | 11.70 | O |
| ATOM | 3224 | N   | VAL | B | 162 | 34.065 | 26.291 | 70.599 | 1.00 | 12.59 | N |
| ATOM | 3225 | CA  | VAL | B | 162 | 33.851 | 27.554 | 69.908 | 1.00 | 13.17 | C |
| ATOM | 3226 | CB  | VAL | B | 162 | 32.973 | 27.337 | 68.648 | 1.00 | 13.32 | C |
| ATOM | 3227 | CG1 | VAL | B | 162 | 32.628 | 28.673 | 67.995 | 1.00 | 13.01 | C |
| ATOM | 3228 | CG2 | VAL | B | 162 | 33.714 | 26.448 | 67.665 | 1.00 | 11.62 | C |
| ATOM | 3229 | C   | VAL | B | 162 | 33.169 | 28.532 | 70.873 | 1.00 | 13.45 | C |
| ATOM | 3230 | O   | VAL | B | 162 | 33.412 | 29.738 | 70.831 | 1.00 | 14.63 | O |
| ATOM | 3231 | N   | ALA | B | 163 | 32.338 | 27.997 | 71.762 | 1.00 | 12.41 | N |
| ATOM | 3232 | CA  | ALA | B | 163 | 31.628 | 28.812 | 72.736 | 1.00 | 11.72 | C |
| ATOM | 3233 | CB  | ALA | B | 163 | 30.554 | 27.983 | 73.427 | 1.00 | 9.98  | C |
| ATOM | 3234 | C   | ALA | B | 163 | 32.592 | 29.388 | 73.770 | 1.00 | 12.36 | C |
| ATOM | 3235 | O   | ALA | B | 163 | 32.403 | 30.510 | 74.242 | 1.00 | 12.25 | O |
| ATOM | 3236 | N   | LYS | B | 164 | 33.617 | 28.613 | 74.113 | 1.00 | 12.32 | N |
| ATOM | 3237 | CA  | LYS | B | 164 | 34.620 | 29.030 | 75.084 | 1.00 | 12.64 | C |
| ATOM | 3238 | CB  | LYS | B | 164 | 35.376 | 27.816 | 75.628 | 1.00 | 13.06 | C |
| ATOM | 3239 | CG  | LYS | B | 164 | 34.562 | 26.954 | 76.602 | 1.00 | 11.90 | C |
| ATOM | 3240 | CD  | LYS | B | 164 | 34.104 | 27.757 | 77.821 | 1.00 | 10.95 | C |
| ATOM | 3241 | CE  | LYS | B | 164 | 33.400 | 26.866 | 78.832 | 1.00 | 8.25  | C |
| ATOM | 3242 | NZ  | LYS | B | 164 | 32.810 | 27.601 | 79.973 | 1.00 | 3.99  | N |
| ATOM | 3243 | C   | LYS | B | 164 | 35.599 | 30.032 | 74.478 | 1.00 | 12.40 | C |
| ATOM | 3244 | O   | LYS | B | 164 | 36.112 | 30.903 | 75.180 | 1.00 | 12.90 | O |
| ATOM | 3245 | N   | ALA | B | 165 | 35.863 | 29.912 | 73.179 | 1.00 | 11.98 | N |
| ATOM | 3246 | CA  | ALA | B | 165 | 36.757 | 30.860 | 72.504 | 1.00 | 11.71 | C |
| ATOM | 3247 | CB  | ALA | B | 165 | 37.098 | 30.370 | 71.112 | 1.00 | 7.44  | C |
| ATOM | 3248 | C   | ALA | B | 165 | 35.982 | 32.182 | 72.430 | 1.00 | 11.45 | C |

FIGURE 9 (cont.)

| ATOM | 3249 | O   | ALA B 165 | 36.548 | 33.269 | 72.549 | 1.00 | 11.31 | O |
|------|------|-----|-----------|--------|--------|--------|------|-------|---|
| ATOM | 3250 | N   | SER B 166 | 34.673 | 32.058 | 72.249 | 1.00 | 11.24 | N |
| ATOM | 3251 | CA  | SER B 166 | 33.775 | 33.201 | 72.174 | 1.00 | 12.64 | C |
| ATOM | 3252 | CB  | SER B 166 | 32.378 | 32.730 | 71.748 | 1.00 | 13.25 | C |
| ATOM | 3253 | OG  | SER B 166 | 31.414 | 33.757 | 71.857 | 1.00 | 13.56 | O |
| ATOM | 3254 | C   | SER B 166 | 33.722 | 33.859 | 73.553 | 1.00 | 13.03 | C |
| ATOM | 3255 | O   | SER B 166 | 33.747 | 35.081 | 73.670 | 1.00 | 13.07 | O |
| ATOM | 3256 | N   | LEU B 167 | 33.662 | 33.035 | 74.595 | 1.00 | 12.67 | N |
| ATOM | 3257 | CA  | LEU B 167 | 33.629 | 33.536 | 75.960 | 1.00 | 11.28 | C |
| ATOM | 3258 | CB  | LEU B 167 | 33.405 | 32.400 | 76.965 | 1.00 | 9.80  | C |
| ATOM | 3259 | CG  | LEU B 167 | 33.415 | 32.861 | 78.431 | 1.00 | 11.26 | C |
| ATOM | 3260 | CD1 | LEU B 167 | 32.169 | 33.692 | 78.734 | 1.00 | 8.57  | C |
| ATOM | 3261 | CD2 | LEU B 167 | 33.481 | 31.649 | 79.341 | 1.00 | 11.28 | C |
| ATOM | 3262 | C   | LEU B 167 | 34.934 | 34.248 | 76.304 | 1.00 | 11.93 | C |
| ATOM | 3263 | O   | LEU B 167 | 34.911 | 35.258 | 77.006 | 1.00 | 13.06 | O |
| ATOM | 3264 | N   | GLU B 168 | 36.060 | 33.715 | 75.826 | 1.00 | 10.04 | N |
| ATOM | 3265 | CA  | GLU B 168 | 37.370 | 34.307 | 76.093 | 1.00 | 10.96 | C |
| ATOM | 3266 | CB  | GLU B 168 | 38.484 | 33.361 | 75.655 | 1.00 | 12.64 | C |
| ATOM | 3267 | CG  | GLU B 168 | 38.879 | 32.365 | 76.728 | 1.00 | 16.42 | C |
| ATOM | 3268 | CD  | GLU B 168 | 39.614 | 31.163 | 76.163 | 1.00 | 19.78 | C |
| ATOM | 3269 | OE1 | GLU B 168 | 40.588 | 31.374 | 75.393 | 1.00 | 21.40 | O |
| ATOM | 3270 | OE2 | GLU B 168 | 39.217 | 30.015 | 76.492 | 1.00 | 17.44 | O |
| ATOM | 3271 | C   | GLU B 168 | 37.556 | 35.663 | 75.424 | 1.00 | 10.88 | C |
| ATOM | 3272 | O   | GLU B 168 | 38.234 | 36.530 | 75.968 | 1.00 | 12.72 | O |
| ATOM | 3273 | N   | ALA B 169 | 36.963 | 35.847 | 74.249 | 1.00 | 8.16  | N |
| ATOM | 3274 | CA  | ALA B 169 | 37.057 | 37.129 | 73.553 | 1.00 | 8.82  | C |
| ATOM | 3275 | CB  | ALA B 169 | 36.620 | 36.969 | 72.091 | 1.00 | 8.46  | C |
| ATOM | 3276 | C   | ALA B 169 | 36.150 | 38.131 | 74.285 | 1.00 | 9.53  | C |
| ATOM | 3277 | O   | ALA B 169 | 36.481 | 39.310 | 74.438 | 1.00 | 9.99  | O |
| ATOM | 3278 | N   | ASN B 170 | 35.009 | 37.625 | 74.742 | 1.00 | 10.59 | N |
| ATOM | 3279 | CA  | ASN B 170 | 34.010 | 38.386 | 75.489 | 1.00 | 11.39 | C |
| ATOM | 3280 | CB  | ASN B 170 | 32.896 | 37.423 | 75.932 | 1.00 | 11.32 | C |
| ATOM | 3281 | CG  | ASN B 170 | 31.557 | 38.109 | 76.128 | 1.00 | 14.08 | C |
| ATOM | 3282 | OD1 | ASN B 170 | 31.483 | 39.256 | 76.568 | 1.00 | 11.82 | O |
| ATOM | 3283 | ND2 | ASN B 170 | 30.479 | 37.387 | 75.819 | 1.00 | 13.99 | N |
| ATOM | 3284 | C   | ASN B 170 | 34.707 | 38.989 | 76.721 | 1.00 | 12.29 | C |
| ATOM | 3285 | O   | ASN B 170 | 34.455 | 40.129 | 77.115 | 1.00 | 10.61 | O |
| ATOM | 3286 | N   | VAL B 171 | 35.586 | 38.194 | 77.326 | 1.00 | 13.44 | N |
| ATOM | 3287 | CA  | VAL B 171 | 36.336 | 38.624 | 78.498 | 1.00 | 13.13 | C |
| ATOM | 3288 | CB  | VAL B 171 | 37.185 | 37.438 | 79.078 | 1.00 | 14.73 | C |
| ATOM | 3289 | CG1 | VAL B 171 | 38.180 | 37.939 | 80.142 | 1.00 | 11.15 | C |
| ATOM | 3290 | CG2 | VAL B 171 | 36.256 | 36.388 | 79.685 | 1.00 | 11.80 | C |
| ATOM | 3291 | C   | VAL B 171 | 37.250 | 39.807 | 78.159 | 1.00 | 13.06 | C |
| ATOM | 3292 | O   | VAL B 171 | 37.242 | 40.822 | 78.860 | 1.00 | 13.28 | O |
| ATOM | 3293 | N   | LYS B 172 | 38.029 | 39.685 | 77.088 | 1.00 | 13.40 | N |
| ATOM | 3294 | CA  | LYS B 172 | 38.937 | 40.763 | 76.690 | 1.00 | 14.01 | C |
| ATOM | 3295 | CB  | LYS B 172 | 39.785 | 40.338 | 75.483 | 1.00 | 14.55 | C |
| ATOM | 3296 | CG  | LYS B 172 | 40.683 | 39.131 | 75.745 | 1.00 | 15.82 | C |
| ATOM | 3297 | CD  | LYS B 172 | 41.443 | 38.703 | 74.494 | 1.00 | 15.95 | C |
| ATOM | 3298 | CE  | LYS B 172 | 42.218 | 37.407 | 74.762 | 1.00 | 20.03 | C |
| ATOM | 3299 | NZ  | LYS B 172 | 42.710 | 36.723 | 73.527 | 1.00 | 20.52 | N |
| ATOM | 3300 | C   | LYS B 172 | 38.155 | 42.033 | 76.350 | 1.00 | 13.98 | C |
| ATOM | 3301 | O   | LYS B 172 | 38.507 | 43.122 | 76.784 | 1.00 | 14.13 | O |
| ATOM | 3302 | N   | TYR B 173 | 37.086 | 41.890 | 75.579 | 1.00 | 14.69 | N |
| ATOM | 3303 | CA  | TYR B 173 | 36.291 | 43.047 | 75.206 | 1.00 | 14.42 | C |
| ATOM | 3304 | CB  | TYR B 173 | 35.276 | 42.660 | 74.137 | 1.00 | 14.14 | C |
| ATOM | 3305 | CG  | TYR B 173 | 35.894 | 42.708 | 72.759 | 1.00 | 15.44 | C |
| ATOM | 3306 | CD1 | TYR B 173 | 35.997 | 43.914 | 72.066 | 1.00 | 14.42 | C |
| ATOM | 3307 | CE1 | TYR B 173 | 36.631 | 43.978 | 70.825 | 1.00 | 15.53 | C |
| ATOM | 3308 | CD2 | TYR B 173 | 36.441 | 41.562 | 72.177 | 1.00 | 12.41 | C |
| ATOM | 3309 | CE2 | TYR B 173 | 37.074 | 41.616 | 70.950 | 1.00 | 14.06 | C |
| ATOM | 3310 | CZ  | TYR B 173 | 37.167 | 42.826 | 70.276 | 1.00 | 15.05 | C |
| ATOM | 3311 | OH  | TYR B 173 | 37.793 | 42.879 | 69.050 | 1.00 | 16.20 | O |
| ATOM | 3312 | C   | TYR B 173 | 35.613 | 43.739 | 76.372 | 1.00 | 14.48 | C |
| ATOM | 3313 | O   | TYR B 173 | 35.572 | 44.961 | 76.418 | 1.00 | 15.73 | O |

FIGURE 9 (cont.)

```
ATOM   3314  N    LEU B 174      35.085  42.968  77.315  1.00 14.88           N
ATOM   3315  CA   LEU B 174      34.440  43.548  78.488  1.00 13.30           C
ATOM   3316  CB   LEU B 174      33.751  42.460  79.317  1.00 11.78           C
ATOM   3317  CG   LEU B 174      32.456  41.857  78.748  1.00  8.79           C
ATOM   3318  CD1  LEU B 174      32.108  40.608  79.506  1.00  5.77           C
ATOM   3319  CD2  LEU B 174      31.321  42.868  78.820  1.00  6.05           C
ATOM   3320  C    LEU B 174      35.495  44.256  79.327  1.00 13.55           C
ATOM   3321  O    LEU B 174      35.229  45.293  79.916  1.00 15.21           O
ATOM   3322  N    ALA B 175      36.698  43.695  79.372  1.00 14.14           N
ATOM   3323  CA   ALA B 175      37.789  44.295  80.134  1.00 13.44           C
ATOM   3324  CB   ALA B 175      39.019  43.399  80.083  1.00 12.25           C
ATOM   3325  C    ALA B 175      38.133  45.677  79.584  1.00 13.73           C
ATOM   3326  O    ALA B 175      38.421  46.606  80.342  1.00 13.16           O
ATOM   3327  N    LEU B 176      38.113  45.812  78.262  1.00 14.27           N
ATOM   3328  CA   LEU B 176      38.420  47.093  77.647  1.00 16.19           C
ATOM   3329  CB   LEU B 176      38.677  46.924  76.141  1.00 16.20           C
ATOM   3330  CG   LEU B 176      39.293  48.110  75.376  1.00 18.20           C
ATOM   3331  CD1  LEU B 176      39.572  47.710  73.930  1.00 18.40           C
ATOM   3332  CD2  LEU B 176      38.362  49.291  75.399  1.00 18.42           C
ATOM   3333  C    LEU B 176      37.270  48.081  77.874  1.00 17.63           C
ATOM   3334  O    LEU B 176      37.506  49.261  78.120  1.00 18.48           O
ATOM   3335  N    ASP B 177      36.033  47.593  77.809  1.00 17.95           N
ATOM   3336  CA   ASP B 177      34.853  48.441  77.978  1.00 17.78           C
ATOM   3337  CB   ASP B 177      33.597  47.694  77.498  1.00 19.10           C
ATOM   3338  CG   ASP B 177      32.361  48.576  77.482  1.00 19.34           C
ATOM   3339  OD1  ASP B 177      31.235  48.037  77.362  1.00 20.88           O
ATOM   3340  OD2  ASP B 177      32.513  49.813  77.578  1.00 21.86           O
ATOM   3341  C    ASP B 177      34.626  48.918  79.413  1.00 18.99           C
ATOM   3342  O    ASP B 177      34.266  50.080  79.631  1.00 18.70           O
ATOM   3343  N    LEU B 178      34.840  48.022  80.379  1.00 17.88           N
ATOM   3344  CA   LEU B 178      34.627  48.317  81.792  1.00 17.35           C
ATOM   3345  CB   LEU B 178      34.022  47.090  82.480  1.00 17.64           C
ATOM   3346  CG   LEU B 178      32.816  46.443  81.791  1.00 16.35           C
ATOM   3347  CD1  LEU B 178      32.320  45.265  82.621  1.00 17.89           C
ATOM   3348  CD2  LEU B 178      31.718  47.465  81.608  1.00 18.56           C
ATOM   3349  C    LEU B 178      35.868  48.763  82.569  1.00 16.83           C
ATOM   3350  O    LEU B 178      35.757  49.211  83.716  1.00 16.49           O
ATOM   3351  N    GLY B 179      37.040  48.624  81.955  1.00 16.69           N
ATOM   3352  CA   GLY B 179      38.280  49.021  82.599  1.00 16.03           C
ATOM   3353  C    GLY B 179      38.206  50.443  83.131  1.00 17.80           C
ATOM   3354  O    GLY B 179      38.627  50.693  84.261  1.00 16.79           O
ATOM   3355  N    PRO B 180      37.693  51.402  82.334  1.00 17.74           N
ATOM   3356  CD   PRO B 180      37.479  51.294  80.880  1.00 18.85           C
ATOM   3357  CA   PRO B 180      37.572  52.803  82.759  1.00 19.62           C
ATOM   3358  CB   PRO B 180      37.006  53.497  81.512  1.00 19.25           C
ATOM   3359  CG   PRO B 180      37.654  52.737  80.415  1.00 19.54           C
ATOM   3360  C    PRO B 180      36.677  52.987  83.992  1.00 18.70           C
ATOM   3361  O    PRO B 180      36.806  53.982  84.697  1.00 17.55           O
ATOM   3362  N    ASP B 181      35.774  52.035  84.237  1.00 18.23           N
ATOM   3363  CA   ASP B 181      34.878  52.089  85.404  1.00 18.61           C
ATOM   3364  CB   ASP B 181      33.525  51.457  85.075  1.00 19.75           C
ATOM   3365  CG   ASP B 181      32.766  52.212  84.005  1.00 21.92           C
ATOM   3366  OD1  ASP B 181      31.849  51.617  83.402  1.00 25.78           O
ATOM   3367  OD2  ASP B 181      33.070  53.398  83.767  1.00 24.15           O
ATOM   3368  C    ASP B 181      35.494  51.339  86.599  1.00 17.87           C
ATOM   3369  O    ASP B 181      34.808  51.039  87.585  1.00 17.01           O
ATOM   3370  N    ASN B 182      36.782  51.020  86.487  1.00 17.57           N
ATOM   3371  CA   ASN B 182      37.513  50.307  87.536  1.00 17.09           C
ATOM   3372  CB   ASN B 182      37.470  51.092  88.855  1.00 18.69           C
ATOM   3373  CG   ASN B 182      38.527  50.627  89.847  1.00 18.58           C
ATOM   3374  OD1  ASN B 182      38.281  50.572  91.054  1.00 19.22           O
ATOM   3375  ND2  ASN B 182      39.716  50.303  89.343  1.00 18.15           N
ATOM   3376  C    ASN B 182      36.953  48.906  87.771  1.00 17.01           C
ATOM   3377  O    ASN B 182      36.913  48.434  88.909  1.00 16.91           O
ATOM   3378  N    ILE B 183      36.508  48.253  86.700  1.00 16.13           N
```

FIGURE 9 (cont.)

```
ATOM   3379  CA   ILE B 183      35.972  46.900  86.798  1.00 15.53           C
ATOM   3380  CB   ILE B 183      34.526  46.803  86.232  1.00 16.84           C
ATOM   3381  CG2  ILE B 183      34.042  45.367  86.287  1.00 16.09           C
ATOM   3382  CG1  ILE B 183      33.572  47.689  87.049  1.00 17.06           C
ATOM   3383  CD1  ILE B 183      32.147  47.696  86.536  1.00 15.41           C
ATOM   3384  C    ILE B 183      36.881  45.975  85.990  1.00 15.34           C
ATOM   3385  O    ILE B 183      37.083  46.176  84.793  1.00 13.42           O
ATOM   3386  N    ARG B 184      37.447  44.976  86.660  1.00 15.18           N
ATOM   3387  CA   ARG B 184      38.331  44.024  86.002  1.00 14.95           C
ATOM   3388  CB   ARG B 184      39.482  43.666  86.940  1.00 14.21           C
ATOM   3389  CG   ARG B 184      40.374  44.865  87.269  1.00 15.77           C
ATOM   3390  CD   ARG B 184      41.528  44.515  88.208  1.00 13.27           C
ATOM   3391  NE   ARG B 184      41.045  44.023  89.494  1.00 15.72           N
ATOM   3392  CZ   ARG B 184      41.024  42.740  89.858  1.00 14.89           C
ATOM   3393  NH1  ARG B 184      41.467  41.804  89.026  1.00 14.22           N
ATOM   3394  NH2  ARG B 184      40.553  42.390  91.051  1.00 10.96           N
ATOM   3395  C    ARG B 184      37.558  42.769  85.581  1.00 15.02           C
ATOM   3396  O    ARG B 184      36.637  42.335  86.283  1.00 15.78           O
ATOM   3397  N    VAL B 185      37.928  42.205  84.431  1.00 13.80           N
ATOM   3398  CA   VAL B 185      37.280  41.003  83.896  1.00 12.66           C
ATOM   3399  CB   VAL B 185      36.391  41.360  82.678  1.00 12.49           C
ATOM   3400  CG1  VAL B 185      35.527  40.169  82.289  1.00 12.09           C
ATOM   3401  CG2  VAL B 185      35.499  42.553  83.021  1.00 12.00           C
ATOM   3402  C    VAL B 185      38.363  39.992  83.483  1.00 12.84           C
ATOM   3403  O    VAL B 185      39.239  40.297  82.675  1.00 10.81           O
ATOM   3404  N    ASN B 186      38.297  38.789  84.051  1.00 12.30           N
ATOM   3405  CA   ASN B 186      39.299  37.757  83.786  1.00 13.00           C
ATOM   3406  CB   ASN B 186      40.339  37.759  84.910  1.00 10.26           C
ATOM   3407  CG   ASN B 186      41.166  39.025  84.940  1.00  8.81           C
ATOM   3408  OD1  ASN B 186      42.055  39.210  84.120  1.00  8.07           O
ATOM   3409  ND2  ASN B 186      40.865  39.911  85.884  1.00 11.51           N
ATOM   3410  C    ASN B 186      38.720  36.351  83.669  1.00 13.92           C
ATOM   3411  O    ASN B 186      37.550  36.122  83.947  1.00 15.23           O
ATOM   3412  N    ALA B 187      39.552  35.403  83.258  1.00 14.94           N
ATOM   3413  CA   ALA B 187      39.095  34.028  83.154  1.00 16.27           C
ATOM   3414  CB   ALA B 187      38.894  33.640  81.701  1.00 14.60           C
ATOM   3415  C    ALA B 187      40.056  33.052  83.818  1.00 17.51           C
ATOM   3416  O    ALA B 187      41.251  33.338  83.992  1.00 16.68           O
ATOM   3417  N    ILE B 188      39.504  31.904  84.206  1.00 17.00           N
ATOM   3418  CA   ILE B 188      40.281  30.834  84.805  1.00 17.57           C
ATOM   3419  CB   ILE B 188      39.804  30.475  86.226  1.00 17.00           C
ATOM   3420  CG2  ILE B 188      40.615  29.298  86.750  1.00 15.70           C
ATOM   3421  CG1  ILE B 188      39.952  31.679  87.155  1.00 16.69           C
ATOM   3422  CD1  ILE B 188      39.455  31.434  88.560  1.00 17.64           C
ATOM   3423  C    ILE B 188      40.065  29.627  83.896  1.00 17.59           C
ATOM   3424  O    ILE B 188      38.923  29.231  83.633  1.00 17.35           O
ATOM   3425  N    SER B 189      41.156  29.064  83.393  1.00 16.53           N
ATOM   3426  CA   SER B 189      41.065  27.902  82.518  1.00 18.34           C
ATOM   3427  CB   SER B 189      42.008  28.083  81.326  1.00 16.70           C
ATOM   3428  OG   SER B 189      41.887  27.027  80.401  1.00 18.04           O
ATOM   3429  C    SER B 189      41.452  26.676  83.349  1.00 17.35           C
ATOM   3430  O    SER B 189      42.625  26.412  83.570  1.00 18.34           O
ATOM   3431  N    ALA B 190      40.455  25.945  83.829  1.00 16.93           N
ATOM   3432  CA   ALA B 190      40.713  24.778  84.661  1.00 16.91           C
ATOM   3433  CB   ALA B 190      39.585  24.608  85.676  1.00 15.03           C
ATOM   3434  C    ALA B 190      40.838  23.521  83.818  1.00 17.36           C
ATOM   3435  O    ALA B 190      40.330  23.468  82.701  1.00 18.33           O
ATOM   3436  N    SER B 191      41.539  22.518  84.340  1.00 16.51           N
ATOM   3437  CA   SER B 191      41.663  21.258  83.627  1.00 16.91           C
ATOM   3438  CB   SER B 191      42.989  20.566  83.974  1.00 17.00           C
ATOM   3439  OG   SER B 191      43.128  20.415  85.370  1.00 20.43           O
ATOM   3440  C    SER B 191      40.451  20.422  84.077  1.00 16.94           C
ATOM   3441  O    SER B 191      39.720  20.824  84.998  1.00 16.26           O
ATOM   3442  N    PRO B 192      40.222  19.260  83.441  1.00 15.94           N
ATOM   3443  CD   PRO B 192      41.037  18.677  82.360  1.00 16.96           C
```

FIGURE 9 (cont.)

| | | | | | | | | | | |
|---|---|---|---|---|---|---|---|---|---|---|
| ATOM | 3444 | CA | PRO | B | 192 | 39.097 | 18.375 | 83.762 | 1.00 16.78 | C |
| ATOM | 3445 | CB | PRO | B | 192 | 39.423 | 17.113 | 82.976 | 1.00 15.62 | C |
| ATOM | 3446 | CG | PRO | B | 192 | 40.101 | 17.649 | 81.775 | 1.00 15.47 | C |
| ATOM | 3447 | C | PRO | B | 192 | 38.817 | 18.077 | 85.230 | 1.00 17.24 | C |
| ATOM | 3448 | O | PRO | B | 192 | 39.730 | 17.809 | 86.009 | 1.00 17.37 | O |
| ATOM | 3449 | N | ILE | B | 193 | 37.534 | 18.129 | 85.587 | 1.00 17.50 | N |
| ATOM | 3450 | CA | ILE | B | 193 | 37.062 | 17.839 | 86.941 | 1.00 17.03 | C |
| ATOM | 3451 | CB | ILE | B | 193 | 36.845 | 19.132 | 87.762 | 1.00 17.60 | C |
| ATOM | 3452 | CG2 | ILE | B | 193 | 36.328 | 18.785 | 89.146 | 1.00 15.23 | C |
| ATOM | 3453 | CG1 | ILE | B | 193 | 38.155 | 19.916 | 87.864 | 1.00 17.57 | C |
| ATOM | 3454 | CD1 | ILE | B | 193 | 38.050 | 21.209 | 88.673 | 1.00 16.79 | C |
| ATOM | 3455 | C | ILE | B | 193 | 35.725 | 17.102 | 86.797 | 1.00 17.05 | C |
| ATOM | 3456 | O | ILE | B | 193 | 34.864 | 17.501 | 86.008 | 1.00 16.23 | O |
| ATOM | 3457 | N | ARG | B | 194 | 35.552 | 16.032 | 87.566 | 1.00 18.69 | N |
| ATOM | 3458 | CA | ARG | B | 194 | 34.336 | 15.222 | 87.490 | 1.00 18.86 | C |
| ATOM | 3459 | CB | ARG | B | 194 | 34.584 | 13.849 | 88.126 | 1.00 20.26 | C |
| ATOM | 3460 | CG | ARG | B | 194 | 33.621 | 12.765 | 87.639 | 1.00 23.27 | C |
| ATOM | 3461 | CD | ARG | B | 194 | 33.882 | 11.420 | 88.293 | 1.00 23.95 | C |
| ATOM | 3462 | NE | ARG | B | 194 | 35.182 | 10.826 | 87.955 | 1.00 24.89 | N |
| ATOM | 3463 | CZ | ARG | B | 194 | 35.463 | 10.176 | 86.825 | 1.00 24.96 | C |
| ATOM | 3464 | NH1 | ARG | B | 194 | 34.545 | 10.020 | 85.884 | 1.00 24.04 | N |
| ATOM | 3465 | NH2 | ARG | B | 194 | 36.674 | 9.662 | 86.645 | 1.00 25.78 | N |
| ATOM | 3466 | C | ARG | B | 194 | 33.146 | 15.904 | 88.154 | 1.00 18.25 | C |
| ATOM | 3467 | O | ARG | B | 194 | 33.007 | 15.874 | 89.371 | 1.00 17.74 | O |
| ATOM | 3468 | N | THR | B | 195 | 32.297 | 16.530 | 87.341 | 1.00 17.45 | N |
| ATOM | 3469 | CA | THR | B | 195 | 31.113 | 17.223 | 87.834 | 1.00 17.30 | C |
| ATOM | 3470 | CB | THR | B | 195 | 31.266 | 18.767 | 87.724 | 1.00 16.62 | C |
| ATOM | 3471 | OG1 | THR | B | 195 | 31.174 | 19.167 | 86.354 | 1.00 14.77 | O |
| ATOM | 3472 | CG2 | THR | B | 195 | 32.614 | 19.211 | 88.259 | 1.00 15.11 | C |
| ATOM | 3473 | C | THR | B | 195 | 29.921 | 16.797 | 86.977 | 1.00 17.39 | C |
| ATOM | 3474 | O | THR | B | 195 | 30.041 | 15.893 | 86.158 | 1.00 17.50 | O |
| ATOM | 3475 | N | LEU | B | 196 | 28.778 | 17.447 | 87.165 | 1.00 16.38 | N |
| ATOM | 3476 | CA | LEU | B | 196 | 27.592 | 17.132 | 86.371 | 1.00 17.47 | C |
| ATOM | 3477 | CB | LEU | B | 196 | 26.380 | 17.928 | 86.867 | 1.00 17.44 | C |
| ATOM | 3478 | CG | LEU | B | 196 | 25.821 | 17.614 | 88.258 | 1.00 18.47 | C |
| ATOM | 3479 | CD1 | LEU | B | 196 | 25.157 | 18.854 | 88.819 | 1.00 19.63 | C |
| ATOM | 3480 | CD2 | LEU | B | 196 | 24.837 | 16.475 | 88.188 | 1.00 16.91 | C |
| ATOM | 3481 | C | LEU | B | 196 | 27.847 | 17.481 | 84.905 | 1.00 17.88 | C |
| ATOM | 3482 | O | LEU | B | 196 | 27.121 | 17.020 | 84.027 | 1.00 17.82 | O |
| ATOM | 3483 | N | SER | B | 197 | 28.861 | 18.311 | 84.645 | 1.00 18.80 | N |
| ATOM | 3484 | CA | SER | B | 197 | 29.212 | 18.688 | 83.275 | 1.00 20.81 | C |
| ATOM | 3485 | CB | SER | B | 197 | 29.850 | 20.075 | 83.234 | 1.00 21.93 | C |
| ATOM | 3486 | OG | SER | B | 197 | 28.833 | 21.064 | 83.242 | 1.00 25.80 | O |
| ATOM | 3487 | C | SER | B | 197 | 30.153 | 17.675 | 82.629 | 1.00 21.30 | C |
| ATOM | 3488 | O | SER | B | 197 | 30.576 | 17.843 | 81.479 | 1.00 20.17 | O |
| ATOM | 3489 | N | ALA | B | 198 | 30.479 | 16.631 | 83.389 | 1.00 21.83 | N |
| ATOM | 3490 | CA | ALA | B | 198 | 31.336 | 15.546 | 82.923 | 1.00 23.44 | C |
| ATOM | 3491 | CB | ALA | B | 198 | 32.447 | 15.295 | 83.922 | 1.00 22.27 | C |
| ATOM | 3492 | C | ALA | B | 198 | 30.475 | 14.283 | 82.775 | 1.00 24.50 | C |
| ATOM | 3493 | O | ALA | B | 198 | 30.920 | 13.262 | 82.246 | 1.00 24.19 | O |
| ATOM | 3494 | N | LYS | B | 199 | 29.237 | 14.361 | 83.245 | 1.00 25.89 | N |
| ATOM | 3495 | CA | LYS | B | 199 | 28.330 | 13.222 | 83.173 | 1.00 28.43 | C |
| ATOM | 3496 | CB | LYS | B | 199 | 27.043 | 13.533 | 83.947 | 1.00 29.22 | C |
| ATOM | 3497 | CG | LYS | B | 199 | 26.106 | 12.348 | 84.134 | 1.00 31.75 | C |
| ATOM | 3498 | CD | LYS | B | 199 | 24.854 | 12.779 | 84.902 | 1.00 33.11 | C |
| ATOM | 3499 | CE | LYS | B | 199 | 24.052 | 11.579 | 85.403 | 1.00 35.79 | C |
| ATOM | 3500 | NZ | LYS | B | 199 | 22.798 | 12.007 | 86.104 | 1.00 37.03 | N |
| ATOM | 3501 | C | LYS | B | 199 | 27.990 | 12.866 | 81.723 | 1.00 28.45 | C |
| ATOM | 3502 | O | LYS | B | 199 | 27.509 | 13.704 | 80.956 | 1.00 28.67 | O |
| ATOM | 3503 | N | GLY | B | 200 | 28.250 | 11.626 | 81.338 | 1.00 28.37 | N |
| ATOM | 3504 | CA | GLY | B | 200 | 27.918 | 11.228 | 79.983 | 1.00 28.52 | C |
| ATOM | 3505 | C | GLY | B | 200 | 28.910 | 11.634 | 78.919 | 1.00 28.14 | C |
| ATOM | 3506 | O | GLY | B | 200 | 28.838 | 11.142 | 77.795 | 1.00 28.42 | O |
| ATOM | 3507 | N | VAL | B | 201 | 29.819 | 12.548 | 79.236 | 1.00 28.05 | N |
| ATOM | 3508 | CA | VAL | B | 201 | 30.813 | 12.934 | 78.245 | 1.00 27.42 | C |

FIGURE 9 (cont.)

| | | | | | | | | | |
|---|---|---|---|---|---|---|---|---|---|
|ATOM|3509|CB|VAL|B|201|31.651|14.160|78.715|1.00 28.37|C|
|ATOM|3510|CG1|VAL|B|201|30.734|15.344|78.947|1.00 28.00|C|
|ATOM|3511|CG2|VAL|B|201|32.365|13.854|79.988|1.00 29.30|C|
|ATOM|3512|C|VAL|B|201|31.678|11.690|78.120|1.00 26.13|C|
|ATOM|3513|O|VAL|B|201|32.026|11.069|79.130|1.00 25.74|O|
|ATOM|3514|N|GLY|B|202|32.001|11.312|76.887|1.00 25.26|N|
|ATOM|3515|CA|GLY|B|202|32.784|10.109|76.662|1.00 23.79|C|
|ATOM|3516|C|GLY|B|202|34.268|10.207|76.925|1.00 22.79|C|
|ATOM|3517|O|GLY|B|202|34.856|11.262|76.742|1.00 22.11|O|
|ATOM|3518|N|GLY|B|203|34.859|9.091|77.355|1.00 23.19|N|
|ATOM|3519|CA|GLY|B|203|36.288|9.022|77.634|1.00 22.99|C|
|ATOM|3520|C|GLY|B|203|36.833|9.899|78.751|1.00 22.27|C|
|ATOM|3521|O|GLY|B|203|38.036|10.168|78.794|1.00 22.98|O|
|ATOM|3522|N|PHE|B|204|35.970|10.312|79.672|1.00 21.12|N|
|ATOM|3523|CA|PHE|B|204|36.375|11.197|80.752|1.00 20.54|C|
|ATOM|3524|CB|PHE|B|204|35.132|11.747|81.445|1.00 20.04|C|
|ATOM|3525|CG|PHE|B|204|35.366|13.043|82.161|1.00 20.64|C|
|ATOM|3526|CD1|PHE|B|204|35.862|13.059|83.466|1.00 21.92|C|
|ATOM|3527|CD2|PHE|B|204|35.105|14.255|81.527|1.00 19.66|C|
|ATOM|3528|CE1|PHE|B|204|36.089|14.265|84.128|1.00 20.49|C|
|ATOM|3529|CE2|PHE|B|204|35.329|15.464|82.171|1.00 19.75|C|
|ATOM|3530|CZ|PHE|B|204|35.822|15.471|83.478|1.00 20.80|C|
|ATOM|3531|C|PHE|B|204|37.361|10.634|81.775|1.00 20.79|C|
|ATOM|3532|O|PHE|B|204|38.175|11.379|82.321|1.00 19.14|O|
|ATOM|3533|N|ASN|B|205|37.312|9.331|82.036|1.00 20.99|N|
|ATOM|3534|CA|ASN|B|205|38.250|8.729|82.990|1.00 22.48|C|
|ATOM|3535|CB|ASN|B|205|37.847|7.287|83.311|1.00 23.25|C|
|ATOM|3536|CG|ASN|B|205|36.364|7.149|83.607|1.00 25.50|C|
|ATOM|3537|OD1|ASN|B|205|35.649|6.418|82.907|1.00 27.56|O|
|ATOM|3538|ND2|ASN|B|205|35.889|7.849|84.639|1.00 22.68|N|
|ATOM|3539|C|ASN|B|205|39.646|8.740|82.373|1.00 22.43|C|
|ATOM|3540|O|ASN|B|205|40.653|8.916|83.064|1.00 21.52|O|
|ATOM|3541|N|THR|B|206|39.689|8.543|81.061|1.00 22.70|N|
|ATOM|3542|CA|THR|B|206|40.939|8.543|80.308|1.00 23.73|C|
|ATOM|3543|CB|THR|B|206|40.694|7.997|78.890|1.00 25.32|C|
|ATOM|3544|OG1|THR|B|206|40.470|6.581|78.972|1.00 27.95|O|
|ATOM|3545|CG2|THR|B|206|41.875|8.287|77.971|1.00 25.20|C|
|ATOM|3546|C|THR|B|206|41.485|9.972|80.244|1.00 23.22|C|
|ATOM|3547|O|THR|B|206|42.693|10.192|80.293|1.00 21.10|O|
|ATOM|3548|N|ILE|B|207|40.573|10.935|80.151|1.00 23.38|N|
|ATOM|3549|CA|ILE|B|207|40.929|12.345|80.108|1.00 23.68|C|
|ATOM|3550|CB|ILE|B|207|39.661|13.206|79.918|1.00 25.11|C|
|ATOM|3551|CG2|ILE|B|207|39.982|14.677|80.127|1.00 26.05|C|
|ATOM|3552|CG1|ILE|B|207|39.096|12.972|78.512|1.00 26.44|C|
|ATOM|3553|CD1|ILE|B|207|37.797|13.701|78.238|1.00 26.29|C|
|ATOM|3554|C|ILE|B|207|41.609|12.710|81.423|1.00 23.53|C|
|ATOM|3555|O|ILE|B|207|42.585|13.462|81.460|1.00 24.00|O|
|ATOM|3556|N|LEU|B|208|41.084|12.163|82.509|1.00 23.48|N|
|ATOM|3557|CA|LEU|B|208|41.637|12.411|83.824|1.00 22.25|C|
|ATOM|3558|CB|LEU|B|208|40.717|11.806|84.898|1.00 20.45|C|
|ATOM|3559|CG|LEU|B|208|39.767|12.740|85.662|1.00 18.55|C|
|ATOM|3560|CD1|LEU|B|208|39.377|13.932|84.818|1.00 17.22|C|
|ATOM|3561|CD2|LEU|B|208|38.545|11.969|86.100|1.00 16.04|C|
|ATOM|3562|C|LEU|B|208|43.017|11.783|83.891|1.00 22.98|C|
|ATOM|3563|O|LEU|B|208|43.997|12.442|84.251|1.00 24.55|O|
|ATOM|3564|N|LYS|B|209|43.093|10.507|83.530|1.00 21.93|N|
|ATOM|3565|CA|LYS|B|209|44.356|9.792|83.562|1.00 22.06|C|
|ATOM|3566|CB|LYS|B|209|44.185|8.380|82.995|1.00 22.98|C|
|ATOM|3567|CG|LYS|B|209|43.444|7.390|83.897|1.00 23.76|C|
|ATOM|3568|CD|LYS|B|209|43.191|6.087|83.137|1.00 25.11|C|
|ATOM|3569|CE|LYS|B|209|42.398|5.057|83.955|1.00 26.46|C|
|ATOM|3570|NZ|LYS|B|209|43.086|4.662|85.208|1.00 24.12|N|
|ATOM|3571|C|LYS|B|209|45.443|10.534|82.789|1.00 21.51|C|
|ATOM|3572|O|LYS|B|209|46.598|10.570|83.214|1.00 22.61|O|
|ATOM|3573|N|GLU|B|210|45.076|11.129|81.659|1.00 22.13|N|

FIGURE 9 (cont.)

| ATOM | 3574 | CA | GLU | B | 210 | 46.043 | 11.863 | 80.843 | 1.00 | 21.85 | C |
| ATOM | 3575 | CB | GLU | B | 210 | 45.381 | 12.418 | 79.573 | 1.00 | 23.19 | C |
| ATOM | 3576 | CG | GLU | B | 210 | 46.276 | 13.420 | 78.828 | 1.00 | 24.86 | C |
| ATOM | 3577 | CD | GLU | B | 210 | 45.693 | 13.889 | 77.508 | 1.00 | 23.97 | C |
| ATOM | 3578 | OE1 | GLU | B | 210 | 44.453 | 14.032 | 77.428 | 1.00 | 25.76 | O |
| ATOM | 3579 | OE2 | GLU | B | 210 | 46.477 | 14.131 | 76.562 | 1.00 | 22.62 | O |
| ATOM | 3580 | C | GLU | B | 210 | 46.663 | 13.014 | 81.624 | 1.00 | 21.60 | C |
| ATOM | 3581 | O | GLU | B | 210 | 47.871 | 13.223 | 81.574 | 1.00 | 21.87 | O |
| ATOM | 3582 | N | ILE | B | 211 | 45.832 | 13.767 | 82.337 | 1.00 | 20.96 | N |
| ATOM | 3583 | CA | ILE | B | 211 | 46.327 | 14.880 | 83.128 | 1.00 | 20.64 | C |
| ATOM | 3584 | CB | ILE | B | 211 | 45.195 | 15.606 | 83.888 | 1.00 | 19.91 | C |
| ATOM | 3585 | CG2 | ILE | B | 211 | 45.793 | 16.734 | 84.710 | 1.00 | 18.77 | C |
| ATOM | 3586 | CG1 | ILE | B | 211 | 44.152 | 16.164 | 82.922 | 1.00 | 20.53 | C |
| ATOM | 3587 | CD1 | ILE | B | 211 | 44.651 | 17.313 | 82.080 | 1.00 | 20.07 | C |
| ATOM | 3588 | C | ILE | B | 211 | 47.299 | 14.374 | 84.193 | 1.00 | 21.50 | C |
| ATOM | 3589 | O | ILE | B | 211 | 48.435 | 14.824 | 84.288 | 1.00 | 22.48 | O |
| ATOM | 3590 | N | GLU | B | 212 | 46.837 | 13.435 | 85.006 | 1.00 | 22.26 | N |
| ATOM | 3591 | CA | GLU | B | 212 | 47.663 | 12.920 | 86.082 | 1.00 | 24.06 | C |
| ATOM | 3592 | CB | GLU | B | 212 | 46.947 | 11.781 | 86.799 | 1.00 | 24.73 | C |
| ATOM | 3593 | CG | GLU | B | 212 | 47.702 | 11.256 | 87.997 | 1.00 | 30.27 | C |
| ATOM | 3594 | CD | GLU | B | 212 | 46.945 | 10.140 | 88.705 | 1.00 | 33.40 | C |
| ATOM | 3595 | OE1 | GLU | B | 212 | 47.477 | 9.575 | 89.702 | 1.00 | 33.63 | O |
| ATOM | 3596 | OE2 | GLU | B | 212 | 45.812 | 9.834 | 88.251 | 1.00 | 35.15 | O |
| ATOM | 3597 | C | GLU | B | 212 | 49.049 | 12.470 | 85.648 | 1.00 | 23.63 | C |
| ATOM | 3598 | O | GLU | B | 212 | 50.022 | 12.730 | 86.349 | 1.00 | 22.07 | O |
| ATOM | 3599 | N | GLU | B | 213 | 49.155 | 11.820 | 84.491 | 1.00 | 24.38 | N |
| ATOM | 3600 | CA | GLU | B | 213 | 50.464 | 11.356 | 84.046 | 1.00 | 25.60 | C |
| ATOM | 3601 | CB | GLU | B | 213 | 50.341 | 9.972 | 83.416 | 1.00 | 28.16 | C |
| ATOM | 3602 | CG | GLU | B | 213 | 49.824 | 9.974 | 81.993 | 1.00 | 34.84 | C |
| ATOM | 3603 | CD | GLU | B | 213 | 49.901 | 8.598 | 81.356 | 1.00 | 39.70 | C |
| ATOM | 3604 | OE1 | GLU | B | 213 | 49.050 | 7.725 | 81.676 | 1.00 | 41.27 | O |
| ATOM | 3605 | OE2 | GLU | B | 213 | 50.830 | 8.380 | 80.536 | 1.00 | 42.79 | O |
| ATOM | 3606 | C | GLU | B | 213 | 51.240 | 12.279 | 83.097 | 1.00 | 24.07 | C |
| ATOM | 3607 | O | GLU | B | 213 | 52.438 | 12.086 | 82.907 | 1.00 | 24.24 | O |
| ATOM | 3608 | N | ARG | B | 214 | 50.582 | 13.273 | 82.506 | 1.00 | 23.54 | N |
| ATOM | 3609 | CA | ARG | B | 214 | 51.275 | 14.185 | 81.585 | 1.00 | 23.46 | C |
| ATOM | 3610 | CB | ARG | B | 214 | 50.504 | 14.315 | 80.272 | 1.00 | 23.72 | C |
| ATOM | 3611 | CG | ARG | B | 214 | 50.526 | 13.073 | 79.410 | 1.00 | 23.37 | C |
| ATOM | 3612 | CD | ARG | B | 214 | 49.943 | 13.377 | 78.037 | 1.00 | 23.53 | C |
| ATOM | 3613 | NE | ARG | B | 214 | 50.764 | 14.326 | 77.289 | 1.00 | 22.58 | N |
| ATOM | 3614 | CZ | ARG | B | 214 | 50.271 | 15.291 | 76.518 | 1.00 | 22.77 | C |
| ATOM | 3615 | NH1 | ARG | B | 214 | 48.953 | 15.442 | 76.396 | 1.00 | 21.66 | N |
| ATOM | 3616 | NH2 | ARG | B | 214 | 51.093 | 16.099 | 75.858 | 1.00 | 20.47 | N |
| ATOM | 3617 | C | ARG | B | 214 | 51.557 | 15.591 | 82.123 | 1.00 | 23.90 | C |
| ATOM | 3618 | O | ARG | B | 214 | 52.585 | 16.185 | 81.791 | 1.00 | 23.58 | O |
| ATOM | 3619 | N | ALA | B | 215 | 50.647 | 16.128 | 82.935 | 1.00 | 22.62 | N |
| ATOM | 3620 | CA | ALA | B | 215 | 50.823 | 17.470 | 83.493 | 1.00 | 21.92 | C |
| ATOM | 3621 | CB | ALA | B | 215 | 49.576 | 17.881 | 84.266 | 1.00 | 20.13 | C |
| ATOM | 3622 | C | ALA | B | 215 | 52.045 | 17.549 | 84.407 | 1.00 | 21.88 | C |
| ATOM | 3623 | O | ALA | B | 215 | 52.302 | 16.641 | 85.186 | 1.00 | 22.72 | O |
| ATOM | 3624 | N | PRO | B | 216 | 52.816 | 18.643 | 84.311 | 1.00 | 22.07 | N |
| ATOM | 3625 | CD | PRO | B | 216 | 52.637 | 19.741 | 83.336 | 1.00 | 21.66 | C |
| ATOM | 3626 | CA | PRO | B | 216 | 54.016 | 18.860 | 85.124 | 1.00 | 21.90 | C |
| ATOM | 3627 | CB | PRO | B | 216 | 54.296 | 20.349 | 84.915 | 1.00 | 22.32 | C |
| ATOM | 3628 | CG | PRO | B | 216 | 53.940 | 20.537 | 83.469 | 1.00 | 20.71 | C |
| ATOM | 3629 | C | PRO | B | 216 | 53.879 | 18.484 | 86.608 | 1.00 | 22.09 | C |
| ATOM | 3630 | O | PRO | B | 216 | 54.808 | 17.929 | 87.193 | 1.00 | 21.05 | O |
| ATOM | 3631 | N | LEU | B | 217 | 52.739 | 18.788 | 87.222 | 1.00 | 21.65 | N |
| ATOM | 3632 | CA | LEU | B | 217 | 52.540 | 18.447 | 88.632 | 1.00 | 22.84 | C |
| ATOM | 3633 | CB | LEU | B | 217 | 51.606 | 19.457 | 89.316 | 1.00 | 20.97 | C |
| ATOM | 3634 | CG | LEU | B | 217 | 52.077 | 20.906 | 89.409 | 1.00 | 20.49 | C |
| ATOM | 3635 | CD1 | LEU | B | 217 | 51.020 | 21.737 | 90.136 | 1.00 | 21.76 | C |
| ATOM | 3636 | CD2 | LEU | B | 217 | 53.399 | 20.969 | 90.145 | 1.00 | 20.91 | C |
| ATOM | 3637 | C | LEU | B | 217 | 51.973 | 17.030 | 88.800 | 1.00 | 23.47 | C |
| ATOM | 3638 | O | LEU | B | 217 | 51.554 | 16.646 | 89.891 | 1.00 | 24.44 | O |

FIGURE 9 (cont.)

| | | | | | | | | | |
|---|---|---|---|---|---|---|---|---|---|
| ATOM | 3639 | N | LYS | B | 218 | 51.956 | 16.268 | 87.712 | 1.00 23.73 | N |
| ATOM | 3640 | CA | LYS | B | 218 | 51.471 | 14.890 | 87.709 | 1.00 23.29 | C |
| ATOM | 3641 | CB | LYS | B | 218 | 52.585 | 13.942 | 88.165 | 1.00 23.46 | C |
| ATOM | 3642 | CG | LYS | B | 218 | 53.922 | 14.147 | 87.452 | 1.00 25.06 | C |
| ATOM | 3643 | CD | LYS | B | 218 | 53.849 | 13.833 | 85.955 | 1.00 28.08 | C |
| ATOM | 3644 | CE | LYS | B | 218 | 55.239 | 13.933 | 85.281 | 1.00 29.75 | C |
| ATOM | 3645 | NZ | LYS | B | 218 | 55.236 | 13.773 | 83.788 | 1.00 27.38 | N |
| ATOM | 3646 | C | LYS | B | 218 | 50.239 | 14.656 | 88.574 | 1.00 23.28 | C |
| ATOM | 3647 | O | LYS | B | 218 | 50.141 | 13.633 | 89.247 | 1.00 23.98 | O |
| ATOM | 3648 | N | ARG | B | 219 | 49.295 | 15.591 | 88.550 | 1.00 22.73 | N |
| ATOM | 3649 | CA | ARG | B | 219 | 48.072 | 15.452 | 89.333 | 1.00 21.83 | C |
| ATOM | 3650 | CB | ARG | B | 219 | 48.313 | 15.903 | 90.771 | 1.00 24.13 | C |
| ATOM | 3651 | CG | ARG | B | 219 | 48.549 | 17.408 | 90.923 | 1.00 23.99 | C |
| ATOM | 3652 | CD | ARG | B | 219 | 48.702 | 17.747 | 92.385 | 1.00 25.24 | C |
| ATOM | 3653 | NE | ARG | B | 219 | 48.863 | 19.175 | 92.622 | 1.00 26.37 | N |
| ATOM | 3654 | CZ | ARG | B | 219 | 47.896 | 20.070 | 92.462 | 1.00 28.37 | C |
| ATOM | 3655 | NH1 | ARG | B | 219 | 46.691 | 19.677 | 92.056 | 1.00 28.94 | N |
| ATOM | 3656 | NH2 | ARG | B | 219 | 48.124 | 21.352 | 92.730 | 1.00 26.58 | N |
| ATOM | 3657 | C | ARG | B | 219 | 46.961 | 16.299 | 88.736 | 1.00 20.70 | C |
| ATOM | 3658 | O | ARG | B | 219 | 47.240 | 17.268 | 88.027 | 1.00 21.04 | O |
| ATOM | 3659 | N | ASN | B | 220 | 45.712 | 15.932 | 89.028 | 1.00 18.69 | N |
| ATOM | 3660 | CA | ASN | B | 220 | 44.534 | 16.660 | 88.548 | 1.00 17.55 | C |
| ATOM | 3661 | CB | ASN | B | 220 | 43.317 | 15.729 | 88.478 | 1.00 18.39 | C |
| ATOM | 3662 | CG | ASN | B | 220 | 43.202 | 15.013 | 87.148 | 1.00 20.26 | C |
| ATOM | 3663 | OD1 | ASN | B | 220 | 43.130 | 15.654 | 86.096 | 1.00 21.24 | O |
| ATOM | 3664 | ND2 | ASN | B | 220 | 43.176 | 13.679 | 87.184 | 1.00 20.63 | N |
| ATOM | 3665 | C | ASN | B | 220 | 44.246 | 17.782 | 89.532 | 1.00 16.22 | C |
| ATOM | 3666 | O | ASN | B | 220 | 44.751 | 17.743 | 90.641 | 1.00 17.03 | O |
| ATOM | 3667 | N | VAL | B | 221 | 43.455 | 18.784 | 89.148 | 1.00 16.03 | N |
| ATOM | 3668 | CA | VAL | B | 221 | 43.147 | 19.866 | 90.090 | 1.00 16.02 | C |
| ATOM | 3669 | CB | VAL | B | 221 | 43.162 | 21.287 | 89.435 | 1.00 16.38 | C |
| ATOM | 3670 | CG1 | VAL | B | 221 | 44.509 | 21.526 | 88.765 | 1.00 14.40 | C |
| ATOM | 3671 | CG2 | VAL | B | 221 | 41.991 | 21.455 | 88.459 | 1.00 14.00 | C |
| ATOM | 3672 | C | VAL | B | 221 | 41.817 | 19.672 | 90.805 | 1.00 16.33 | C |
| ATOM | 3673 | O | VAL | B | 221 | 41.008 | 18.820 | 90.439 | 1.00 15.57 | O |
| ATOM | 3674 | N | ASP | B | 222 | 41.609 | 20.496 | 91.821 | 1.00 19.19 | N |
| ATOM | 3675 | CA | ASP | B | 222 | 40.430 | 20.454 | 92.673 | 1.00 21.38 | C |
| ATOM | 3676 | CB | ASP | B | 222 | 40.884 | 20.434 | 94.137 | 1.00 24.91 | C |
| ATOM | 3677 | CG | ASP | B | 222 | 40.337 | 19.257 | 94.898 | 1.00 30.34 | C |
| ATOM | 3678 | OD1 | ASP | B | 222 | 39.088 | 19.144 | 95.014 | 1.00 33.93 | O |
| ATOM | 3679 | OD2 | ASP | B | 222 | 41.153 | 18.440 | 95.378 | 1.00 32.33 | O |
| ATOM | 3680 | C | ASP | B | 222 | 39.527 | 21.657 | 92.479 | 1.00 20.29 | C |
| ATOM | 3681 | O | ASP | B | 222 | 39.996 | 22.720 | 92.071 | 1.00 21.27 | O |
| ATOM | 3682 | N | GLN | B | 223 | 38.242 | 21.494 | 92.789 | 1.00 19.18 | N |
| ATOM | 3683 | CA | GLN | B | 223 | 37.292 | 22.602 | 92.696 | 1.00 18.06 | C |
| ATOM | 3684 | CB | GLN | B | 223 | 35.875 | 22.184 | 93.116 | 1.00 17.69 | C |
| ATOM | 3685 | CG | GLN | B | 223 | 35.120 | 21.231 | 92.177 | 1.00 16.10 | C |
| ATOM | 3686 | CD | GLN | B | 223 | 35.240 | 19.778 | 92.610 | 1.00 16.93 | C |
| ATOM | 3687 | OE1 | GLN | B | 223 | 34.348 | 18.956 | 92.354 | 1.00 18.01 | O |
| ATOM | 3688 | NE2 | GLN | B | 223 | 36.344 | 19.453 | 93.271 | 1.00 13.63 | N |
| ATOM | 3689 | C | GLN | B | 223 | 37.750 | 23.732 | 93.631 | 1.00 18.37 | C |
| ATOM | 3690 | O | GLN | B | 223 | 37.503 | 24.907 | 93.346 | 1.00 18.53 | O |
| ATOM | 3691 | N | VAL | B | 224 | 38.405 | 23.382 | 94.741 | 1.00 16.60 | N |
| ATOM | 3692 | CA | VAL | B | 224 | 38.876 | 24.397 | 95.678 | 1.00 17.05 | C |
| ATOM | 3693 | CB | VAL | B | 224 | 39.240 | 23.813 | 97.071 | 1.00 18.88 | C |
| ATOM | 3694 | CG1 | VAL | B | 224 | 38.045 | 23.083 | 97.658 | 1.00 18.39 | C |
| ATOM | 3695 | CG2 | VAL | B | 224 | 40.443 | 22.889 | 96.960 | 1.00 22.48 | C |
| ATOM | 3696 | C | VAL | B | 224 | 40.097 | 25.118 | 95.116 | 1.00 17.17 | C |
| ATOM | 3697 | O | VAL | B | 224 | 40.227 | 26.325 | 95.283 | 1.00 15.93 | O |
| ATOM | 3698 | N | GLU | B | 225 | 40.995 | 24.390 | 94.455 | 1.00 16.99 | N |
| ATOM | 3699 | CA | GLU | B | 225 | 42.150 | 25.038 | 93.867 | 1.00 16.80 | C |
| ATOM | 3700 | CB | GLU | B | 225 | 43.001 | 24.043 | 93.065 | 1.00 19.90 | C |
| ATOM | 3701 | CG | GLU | B | 225 | 43.830 | 23.100 | 93.933 | 1.00 24.41 | C |
| ATOM | 3702 | CD | GLU | B | 225 | 45.056 | 22.560 | 93.208 | 1.00 27.76 | C |
| ATOM | 3703 | OE1 | GLU | B | 225 | 44.887 | 21.858 | 92.185 | 1.00 30.15 | O |

FIGURE 9 (cont.)

| | | | | | | | | | |
|---|---|---|---|---|---|---|---|---|---|
| ATOM | 3704 | OE2 | GLU B 225 | 46.195 | 22.837 | 93.657 | 1.00 | 28.50 | O |
| ATOM | 3705 | C | GLU B 225 | 41.617 | 26.135 | 92.953 | 1.00 | 16.27 | C |
| ATOM | 3706 | O | GLU B 225 | 42.117 | 27.261 | 92.957 | 1.00 | 14.25 | O |
| ATOM | 3707 | N | VAL B 226 | 40.596 | 25.804 | 92.167 | 1.00 | 16.29 | N |
| ATOM | 3708 | CA | VAL B 226 | 39.998 | 26.791 | 91.282 | 1.00 | 16.39 | C |
| ATOM | 3709 | CB | VAL B 226 | 38.810 | 26.192 | 90.478 | 1.00 | 16.37 | C |
| ATOM | 3710 | CG1 | VAL B 226 | 38.018 | 27.296 | 89.801 | 1.00 | 14.47 | C |
| ATOM | 3711 | CG2 | VAL B 226 | 39.331 | 25.226 | 89.425 | 1.00 | 15.17 | C |
| ATOM | 3712 | C | VAL B 226 | 39.514 | 27.944 | 92.173 | 1.00 | 16.93 | C |
| ATOM | 3713 | O | VAL B 226 | 39.843 | 29.099 | 91.935 | 1.00 | 17.11 | O |
| ATOM | 3714 | N | GLY B 227 | 38.760 | 27.608 | 93.215 | 1.00 | 16.29 | N |
| ATOM | 3715 | CA | GLY B 227 | 38.248 | 28.611 | 94.131 | 1.00 | 16.83 | C |
| ATOM | 3716 | C | GLY B 227 | 39.308 | 29.541 | 94.696 | 1.00 | 17.93 | C |
| ATOM | 3717 | O | GLY B 227 | 39.044 | 30.731 | 94.890 | 1.00 | 16.88 | O |
| ATOM | 3718 | N | LYS B 228 | 40.505 | 29.008 | 94.961 | 1.00 | 18.97 | N |
| ATOM | 3719 | CA | LYS B 228 | 41.602 | 29.813 | 95.495 | 1.00 | 18.99 | C |
| ATOM | 3720 | CB | LYS B 228 | 42.766 | 28.929 | 95.956 | 1.00 | 19.56 | C |
| ATOM | 3721 | CG | LYS B 228 | 42.482 | 28.190 | 97.252 | 1.00 | 19.10 | C |
| ATOM | 3722 | CD | LYS B 228 | 43.745 | 27.579 | 97.831 | 1.00 | 19.45 | C |
| ATOM | 3723 | CE | LYS B 228 | 44.388 | 26.619 | 96.853 | 1.00 | 20.68 | C |
| ATOM | 3724 | NZ | LYS B 228 | 45.589 | 25.967 | 97.446 | 1.00 | 21.28 | N |
| ATOM | 3725 | C | LYS B 228 | 42.102 | 30.834 | 94.481 | 1.00 | 18.72 | C |
| ATOM | 3726 | O | LYS B 228 | 42.441 | 31.957 | 94.849 | 1.00 | 21.83 | O |
| ATOM | 3727 | N | THR B 229 | 42.152 | 30.460 | 93.207 | 1.00 | 17.30 | N |
| ATOM | 3728 | CA | THR B 229 | 42.592 | 31.405 | 92.193 | 1.00 | 15.78 | C |
| ATOM | 3729 | CB | THR B 229 | 42.958 | 30.691 | 90.887 | 1.00 | 14.48 | C |
| ATOM | 3730 | OG1 | THR B 229 | 44.198 | 30.002 | 91.070 | 1.00 | 14.24 | O |
| ATOM | 3731 | CG2 | THR B 229 | 43.120 | 31.684 | 89.755 | 1.00 | 14.58 | C |
| ATOM | 3732 | C | THR B 229 | 41.490 | 32.441 | 91.965 | 1.00 | 16.04 | C |
| ATOM | 3733 | O | THR B 229 | 41.775 | 33.605 | 91.693 | 1.00 | 15.44 | O |
| ATOM | 3734 | N | ALA B 230 | 40.234 | 32.020 | 92.103 | 1.00 | 16.41 | N |
| ATOM | 3735 | CA | ALA B 230 | 39.097 | 32.924 | 91.948 | 1.00 | 16.79 | C |
| ATOM | 3736 | CB | ALA B 230 | 37.783 | 32.146 | 92.010 | 1.00 | 16.90 | C |
| ATOM | 3737 | C | ALA B 230 | 39.144 | 33.958 | 93.069 | 1.00 | 17.64 | C |
| ATOM | 3738 | O | ALA B 230 | 38.733 | 35.100 | 92.885 | 1.00 | 17.78 | O |
| ATOM | 3739 | N | ALA B 231 | 39.641 | 33.541 | 94.235 | 1.00 | 18.88 | N |
| ATOM | 3740 | CA | ALA B 231 | 39.769 | 34.425 | 95.393 | 1.00 | 18.04 | C |
| ATOM | 3741 | CB | ALA B 231 | 40.225 | 33.625 | 96.621 | 1.00 | 18.23 | C |
| ATOM | 3742 | C | ALA B 231 | 40.779 | 35.523 | 95.075 | 1.00 | 17.52 | C |
| ATOM | 3743 | O | ALA B 231 | 40.600 | 36.684 | 95.458 | 1.00 | 17.81 | O |
| ATOM | 3744 | N | TYR B 232 | 41.840 | 35.141 | 94.374 | 1.00 | 16.42 | N |
| ATOM | 3745 | CA | TYR B 232 | 42.889 | 36.071 | 93.956 | 1.00 | 16.74 | C |
| ATOM | 3746 | CB | TYR B 232 | 44.061 | 35.280 | 93.361 | 1.00 | 15.14 | C |
| ATOM | 3747 | CG | TYR B 232 | 44.960 | 36.053 | 92.423 | 1.00 | 15.30 | C |
| ATOM | 3748 | CD1 | TYR B 232 | 45.780 | 37.086 | 92.888 | 1.00 | 16.47 | C |
| ATOM | 3749 | CE1 | TYR B 232 | 46.644 | 37.769 | 92.020 | 1.00 | 13.96 | C |
| ATOM | 3750 | CD2 | TYR B 232 | 45.018 | 35.726 | 91.067 | 1.00 | 14.29 | C |
| ATOM | 3751 | CE2 | TYR B 232 | 45.865 | 36.395 | 90.199 | 1.00 | 14.15 | C |
| ATOM | 3752 | CZ | TYR B 232 | 46.681 | 37.415 | 90.678 | 1.00 | 16.05 | C |
| ATOM | 3753 | OH | TYR B 232 | 47.544 | 38.053 | 89.809 | 1.00 | 14.74 | O |
| ATOM | 3754 | C | TYR B 232 | 42.368 | 37.078 | 92.930 | 1.00 | 16.84 | C |
| ATOM | 3755 | O | TYR B 232 | 42.689 | 38.254 | 93.008 | 1.00 | 17.63 | O |
| ATOM | 3756 | N | LEU B 233 | 41.562 | 36.615 | 91.975 | 1.00 | 16.65 | N |
| ATOM | 3757 | CA | LEU B 233 | 41.016 | 37.485 | 90.927 | 1.00 | 17.38 | C |
| ATOM | 3758 | CB | LEU B 233 | 40.624 | 36.640 | 89.705 | 1.00 | 15.14 | C |
| ATOM | 3759 | CG | LEU B 233 | 41.724 | 35.991 | 88.846 | 1.00 | 14.35 | C |
| ATOM | 3760 | CD1 | LEU B 233 | 41.092 | 35.042 | 87.845 | 1.00 | 11.47 | C |
| ATOM | 3761 | CD2 | LEU B 233 | 42.541 | 37.056 | 88.124 | 1.00 | 8.73 | C |
| ATOM | 3762 | C | LEU B 233 | 39.820 | 38.380 | 91.335 | 1.00 | 19.06 | C |
| ATOM | 3763 | O | LEU B 233 | 39.538 | 39.378 | 90.668 | 1.00 | 18.48 | O |
| ATOM | 3764 | N | LEU B 234 | 39.123 | 38.030 | 92.418 | 1.00 | 19.83 | N |
| ATOM | 3765 | CA | LEU B 234 | 37.971 | 38.815 | 92.885 | 1.00 | 19.77 | C |
| ATOM | 3766 | CB | LEU B 234 | 36.931 | 37.908 | 93.541 | 1.00 | 18.54 | C |
| ATOM | 3767 | CG | LEU B 234 | 36.229 | 36.889 | 92.656 | 1.00 | 19.87 | C |
| ATOM | 3768 | CD1 | LEU B 234 | 35.480 | 35.882 | 93.524 | 1.00 | 19.60 | C |

FIGURE 9 (cont.)

```
ATOM   3769  CD2 LEU B 234      35.295  37.617  91.705  1.00 19.05           C
ATOM   3770  C   LEU B 234      38.354  39.890  93.897  1.00 20.63           C
ATOM   3771  O   LEU B 234      37.646  40.893  94.049  1.00 22.51           O
ATOM   3772  N   SER B 235      39.463  39.677  94.595  1.00 20.66           N
ATOM   3773  CA  SER B 235      39.922  40.610  95.618  1.00 21.03           C
ATOM   3774  CB  SER B 235      40.524  39.841  96.789  1.00 20.60           C
ATOM   3775  OG  SER B 235      41.749  39.233  96.406  1.00 22.02           O
ATOM   3776  C   SER B 235      40.949  41.602  95.095  1.00 22.03           C
ATOM   3777  O   SER B 235      41.338  41.556  93.931  1.00 21.70           O
ATOM   3778  N   ASP B 236      41.394  42.492  95.976  1.00 23.74           N
ATOM   3779  CA  ASP B 236      42.375  43.509  95.615  1.00 24.95           C
ATOM   3780  CB  ASP B 236      42.516  44.543  96.742  1.00 28.09           C
ATOM   3781  CG  ASP B 236      43.684  45.505  96.520  1.00 31.98           C
ATOM   3782  OD1 ASP B 236      43.587  46.401  95.642  1.00 32.74           O
ATOM   3783  OD2 ASP B 236      44.713  45.362  97.232  1.00 34.91           O
ATOM   3784  C   ASP B 236      43.738  42.926  95.307  1.00 24.45           C
ATOM   3785  O   ASP B 236      44.573  43.605  94.712  1.00 26.03           O
ATOM   3786  N   LEU B 237      43.976  41.681  95.708  1.00 23.41           N
ATOM   3787  CA  LEU B 237      45.272  41.064  95.455  1.00 22.47           C
ATOM   3788  CB  LEU B 237      45.271  39.589  95.853  1.00 23.43           C
ATOM   3789  CG  LEU B 237      45.907  39.157  97.176  1.00 24.46           C
ATOM   3790  CD1 LEU B 237      46.293  37.683  97.054  1.00 23.13           C
ATOM   3791  CD2 LEU B 237      47.150  39.996  97.491  1.00 24.37           C
ATOM   3792  C   LEU B 237      45.686  41.159  93.998  1.00 21.78           C
ATOM   3793  O   LEU B 237      46.872  41.304  93.687  1.00 20.78           O
ATOM   3794  N   SER B 238      44.709  41.075  93.102  1.00 20.94           N
ATOM   3795  CA  SER B 238      44.998  41.117  91.675  1.00 19.92           C
ATOM   3796  CB  SER B 238      44.229  40.003  90.957  1.00 18.68           C
ATOM   3797  OG  SER B 238      42.835  40.138  91.150  1.00 19.23           O
ATOM   3798  C   SER B 238      44.703  42.453  91.021  1.00 20.57           C
ATOM   3799  O   SER B 238      44.289  42.511  89.856  1.00 21.00           O
ATOM   3800  N   SER B 239      44.896  43.539  91.759  1.00 21.11           N
ATOM   3801  CA  SER B 239      44.664  44.847  91.166  1.00 21.22           C
ATOM   3802  CB  SER B 239      44.924  45.966  92.184  1.00 20.97           C
ATOM   3803  OG  SER B 239      46.304  46.084  92.488  1.00 24.00           O
ATOM   3804  C   SER B 239      45.699  44.880  90.054  1.00 21.40           C
ATOM   3805  O   SER B 239      46.744  44.226  90.163  1.00 22.34           O
ATOM   3806  N   GLY B 240      45.421  45.598  88.975  1.00 20.37           N
ATOM   3807  CA  GLY B 240      46.392  45.638  87.893  1.00 18.77           C
ATOM   3808  C   GLY B 240      46.207  44.540  86.859  1.00 18.55           C
ATOM   3809  O   GLY B 240      46.711  44.649  85.736  1.00 17.28           O
ATOM   3810  N   VAL B 241      45.485  43.485  87.231  1.00 16.68           N
ATOM   3811  CA  VAL B 241      45.238  42.371  86.326  1.00 15.84           C
ATOM   3812  CB  VAL B 241      45.491  41.014  87.023  1.00 17.49           C
ATOM   3813  CG1 VAL B 241      45.048  39.865  86.108  1.00 14.79           C
ATOM   3814  CG2 VAL B 241      46.962  40.878  87.379  1.00 14.98           C
ATOM   3815  C   VAL B 241      43.822  42.341  85.772  1.00 14.87           C
ATOM   3816  O   VAL B 241      42.846  42.329  86.517  1.00 15.05           O
ATOM   3817  N   THR B 242      43.715  42.310  84.451  1.00 16.22           N
ATOM   3818  CA  THR B 242      42.415  42.254  83.794  1.00 15.62           C
ATOM   3819  CB  THR B 242      41.736  43.640  83.830  1.00 12.90           C
ATOM   3820  OG1 THR B 242      40.385  43.527  83.375  1.00 13.46           O
ATOM   3821  CG2 THR B 242      42.478  44.616  82.953  1.00 14.29           C
ATOM   3822  C   THR B 242      42.579  41.758  82.346  1.00 15.37           C
ATOM   3823  O   THR B 242      43.631  41.949  81.742  1.00 16.16           O
ATOM   3824  N   GLY B 243      41.545  41.111  81.808  1.00 16.03           N
ATOM   3825  CA  GLY B 243      41.599  40.595  80.446  1.00 15.76           C
ATOM   3826  C   GLY B 243      42.600  39.462  80.310  1.00 16.01           C
ATOM   3827  O   GLY B 243      43.113  39.178  79.227  1.00 14.84           O
ATOM   3828  N   GLU B 244      42.874  38.814  81.434  1.00 16.82           N
ATOM   3829  CA  GLU B 244      43.821  37.708  81.506  1.00 17.25           C
ATOM   3830  CB  GLU B 244      44.703  37.907  82.745  1.00 17.42           C
ATOM   3831  CG  GLU B 244      45.729  36.827  83.013  1.00 20.99           C
ATOM   3832  CD  GLU B 244      46.782  36.737  81.923  1.00 21.40           C
ATOM   3833  OE1 GLU B 244      46.553  36.031  80.913  1.00 22.39           O
```

FIGURE 9 (cont.)

```
ATOM   3834  OE2 GLU B 244      47.831  37.387  82.076  1.00 20.35           O
ATOM   3835  C   GLU B 244      43.065  36.373  81.612  1.00 17.85           C
ATOM   3836  O   GLU B 244      41.864  36.338  81.883  1.00 17.47           O
ATOM   3837  N   ASN B 245      43.785  35.281  81.390  1.00 17.94           N
ATOM   3838  CA  ASN B 245      43.229  33.943  81.490  1.00 17.49           C
ATOM   3839  CB  ASN B 245      43.027  33.343  80.096  1.00 17.67           C
ATOM   3840  CG  ASN B 245      42.378  31.980  80.146  1.00 18.79           C
ATOM   3841  OD1 ASN B 245      41.847  31.577  81.180  1.00 19.66           O
ATOM   3842  ND2 ASN B 245      42.406  31.263  79.030  1.00 20.88           N
ATOM   3843  C   ASN B 245      44.240  33.110  82.280  1.00 17.33           C
ATOM   3844  O   ASN B 245      45.289  32.751  81.755  1.00 16.90           O
ATOM   3845  N   ILE B 246      43.937  32.819  83.542  1.00 16.89           N
ATOM   3846  CA  ILE B 246      44.853  32.038  84.369  1.00 17.30           C
ATOM   3847  CB  ILE B 246      44.836  32.502  85.854  1.00 16.76           C
ATOM   3848  CG2 ILE B 246      45.807  31.678  86.674  1.00 14.79           C
ATOM   3849  CG1 ILE B 246      45.273  33.960  85.965  1.00 17.59           C
ATOM   3850  CD1 ILE B 246      44.278  34.941  85.421  1.00 22.23           C
ATOM   3851  C   ILE B 246      44.532  30.545  84.325  1.00 17.69           C
ATOM   3852  O   ILE B 246      43.411  30.136  84.627  1.00 17.68           O
ATOM   3853  N   HIS B 247      45.530  29.746  83.948  1.00 16.84           N
ATOM   3854  CA  HIS B 247      45.396  28.297  83.862  1.00 17.06           C
ATOM   3855  CB  HIS B 247      46.351  27.728  82.806  1.00 16.46           C
ATOM   3856  CG  HIS B 247      46.040  28.163  81.410  1.00 17.78           C
ATOM   3857  CD2 HIS B 247      45.375  27.536  80.410  1.00 15.36           C
ATOM   3858  ND1 HIS B 247      46.392  29.403  80.921  1.00 18.52           N
ATOM   3859  CE1 HIS B 247      45.954  29.522  79.679  1.00 17.64           C
ATOM   3860  NE2 HIS B 247      45.333  28.404  79.347  1.00 15.62           N
ATOM   3861  C   HIS B 247      45.674  27.575  85.181  1.00 17.06           C
ATOM   3862  O   HIS B 247      46.787  27.619  85.702  1.00 18.66           O
ATOM   3863  N   VAL B 248      44.662  26.898  85.707  1.00 15.71           N
ATOM   3864  CA  VAL B 248      44.804  26.132  86.938  1.00 14.97           C
ATOM   3865  CB  VAL B 248      43.682  26.483  87.942  1.00 14.09           C
ATOM   3866  CG1 VAL B 248      43.905  25.750  89.253  1.00 13.98           C
ATOM   3867  CG2 VAL B 248      43.644  27.977  88.166  1.00 13.22           C
ATOM   3868  C   VAL B 248      44.662  24.693  86.460  1.00 14.07           C
ATOM   3869  O   VAL B 248      43.619  24.061  86.644  1.00 13.40           O
ATOM   3870  N   ASP B 249      45.732  24.186  85.852  1.00 16.15           N
ATOM   3871  CA  ASP B 249      45.744  22.849  85.249  1.00 17.30           C
ATOM   3872  CB  ASP B 249      45.562  23.004  83.746  1.00 15.82           C
ATOM   3873  CG  ASP B 249      46.639  23.886  83.130  1.00 17.24           C
ATOM   3874  OD1 ASP B 249      47.550  24.315  83.863  1.00 14.92           O
ATOM   3875  OD2 ASP B 249      46.591  24.152  81.912  1.00 22.02           O
ATOM   3876  C   ASP B 249      47.008  22.020  85.488  1.00 18.04           C
ATOM   3877  O   ASP B 249      47.350  21.171  84.665  1.00 18.24           O
ATOM   3878  N   SER B 250      47.699  22.257  86.597  1.00 18.74           N
ATOM   3879  CA  SER B 250      48.921  21.514  86.896  1.00 18.44           C
ATOM   3880  CB  SER B 250      48.616  20.021  87.066  1.00 18.40           C
ATOM   3881  OG  SER B 250      47.859  19.772  88.241  1.00 18.71           O
ATOM   3882  C   SER B 250      49.997  21.694  85.824  1.00 18.01           C
ATOM   3883  O   SER B 250      50.912  20.873  85.713  1.00 18.32           O
ATOM   3884  N   GLY B 251      49.887  22.767  85.041  1.00 17.71           N
ATOM   3885  CA  GLY B 251      50.868  23.041  83.999  1.00 15.83           C
ATOM   3886  C   GLY B 251      50.601  22.417  82.637  1.00 15.76           C
ATOM   3887  O   GLY B 251      51.378  22.610  81.706  1.00 15.82           O
ATOM   3888  N   PHE B 252      49.500  21.688  82.499  1.00 16.43           N
ATOM   3889  CA  PHE B 252      49.179  21.027  81.236  1.00 17.46           C
ATOM   3890  CB  PHE B 252      47.788  20.402  81.327  1.00 18.06           C
ATOM   3891  CG  PHE B 252      47.478  19.442  80.214  1.00 18.96           C
ATOM   3892  CD1 PHE B 252      48.225  18.281  80.054  1.00 18.79           C
ATOM   3893  CD2 PHE B 252      46.442  19.700  79.322  1.00 18.46           C
ATOM   3894  CE1 PHE B 252      47.945  17.385  79.021  1.00 19.14           C
ATOM   3895  CE2 PHE B 252      46.154  18.808  78.282  1.00 19.06           C
ATOM   3896  CZ  PHE B 252      46.909  17.649  78.134  1.00 19.76           C
ATOM   3897  C   PHE B 252      49.250  21.950  80.010  1.00 18.33           C
ATOM   3898  O   PHE B 252      49.727  21.547  78.947  1.00 18.39           O
```

FIGURE 9 (cont.)

| | | | | | | | | | |
|---|---|---|---|---|---|---|---|---|---|
| ATOM | 3899 | N | HIS | B | 253 | 48.789 | 23.188 | 80.171 | 1.00 18.40 | N |
| ATOM | 3900 | CA | HIS | B | 253 | 48.769 | 24.177 | 79.089 | 1.00 18.85 | C |
| ATOM | 3901 | CB | HIS | B | 253 | 48.106 | 25.483 | 79.569 | 1.00 17.20 | C |
| ATOM | 3902 | CG | HIS | B | 253 | 48.970 | 26.280 | 80.501 | 1.00 19.10 | C |
| ATOM | 3903 | CD2 | HIS | B | 253 | 49.820 | 27.309 | 80.264 | 1.00 18.27 | C |
| ATOM | 3904 | ND1 | HIS | B | 253 | 49.111 | 25.969 | 81.839 | 1.00 17.68 | N |
| ATOM | 3905 | CE1 | HIS | B | 253 | 50.015 | 26.765 | 82.383 | 1.00 17.97 | C |
| ATOM | 3906 | NE2 | HIS | B | 253 | 50.463 | 27.587 | 81.448 | 1.00 18.80 | N |
| ATOM | 3907 | C | HIS | B | 253 | 50.141 | 24.540 | 78.518 | 1.00 18.26 | C |
| ATOM | 3908 | O | HIS | B | 253 | 50.234 | 25.025 | 77.392 | 1.00 18.27 | O |
| ATOM | 3909 | N | ALA | B | 254 | 51.200 | 24.311 | 79.287 | 1.00 19.45 | N |
| ATOM | 3910 | CA | ALA | B | 254 | 52.545 | 24.690 | 78.854 | 1.00 21.25 | C |
| ATOM | 3911 | CB | ALA | B | 254 | 53.312 | 25.323 | 80.042 | 1.00 21.35 | C |
| ATOM | 3912 | C | ALA | B | 254 | 53.394 | 23.592 | 78.225 | 1.00 21.35 | C |
| ATOM | 3913 | O | ALA | B | 254 | 54.585 | 23.792 | 77.982 | 1.00 21.20 | O |
| ATOM | 3914 | N | ILE | B | 255 | 52.800 | 22.441 | 77.952 | 1.00 21.83 | N |
| ATOM | 3915 | CA | ILE | B | 255 | 53.570 | 21.356 | 77.361 | 1.00 21.62 | C |
| ATOM | 3916 | CB | ILE | B | 255 | 53.641 | 20.115 | 78.295 | 1.00 22.17 | C |
| ATOM | 3917 | CG2 | ILE | B | 255 | 54.104 | 20.531 | 79.675 | 1.00 21.36 | C |
| ATOM | 3918 | CG1 | ILE | B | 255 | 52.268 | 19.435 | 78.368 | 1.00 22.86 | C |
| ATOM | 3919 | CD1 | ILE | B | 255 | 52.245 | 18.173 | 79.223 | 1.00 24.97 | C |
| ATOM | 3920 | C | ILE | B | 255 | 52.957 | 20.915 | 76.055 | 1.00 20.89 | C |
| ATOM | 3921 | O | ILE | B | 255 | 51.836 | 21.298 | 75.730 | 1.00 21.26 | O |
| ATOM | 3922 | N | LYS | B | 256 | 53.710 | 20.094 | 75.326 | 1.00 21.68 | N |
| ATOM | 3923 | CA | LYS | B | 256 | 53.284 | 19.548 | 74.042 | 1.00 22.06 | C |
| ATOM | 3924 | CB | LYS | B | 256 | 53.703 | 20.502 | 72.924 | 1.00 21.78 | C |
| ATOM | 3925 | CG | LYS | B | 256 | 53.015 | 20.240 | 71.604 | 1.00 21.91 | C |
| ATOM | 3926 | CD | LYS | B | 256 | 51.579 | 20.721 | 71.660 | 1.00 20.73 | C |
| ATOM | 3927 | CE | LYS | B | 256 | 50.812 | 20.280 | 70.432 | 1.00 20.60 | C |
| ATOM | 3928 | NZ | LYS | B | 256 | 49.416 | 20.767 | 70.519 | 1.00 21.86 | N |
| ATOM | 3929 | C | LYS | B | 256 | 53.946 | 18.173 | 73.823 | 1.00 22.14 | C |
| ATOM | 3930 | O | LYS | B | 256 | 55.156 | 18.057 | 74.123 | 1.00 21.72 | O |
| ATOM | 3931 | OXT | LYS | B | 256 | 53.271 | 17.231 | 73.343 | 1.00 23.18 | O |
| TER | 3932 | | LYS | B | 256 | | | | | |
| ATOM | 3933 | CB | LEU | C | 2 | 24.087 | 69.404 | -9.812 | 1.00 42.97 | C |
| ATOM | 3934 | CG | LEU | C | 2 | 23.008 | 68.675 | -10.623 | 1.00 42.20 | C |
| ATOM | 3935 | CD1 | LEU | C | 2 | 22.726 | 69.490 | -11.872 | 1.00 40.36 | C |
| ATOM | 3936 | CD2 | LEU | C | 2 | 23.464 | 67.233 | -10.996 | 1.00 40.73 | C |
| ATOM | 3937 | C | LEU | C | 2 | 22.472 | 71.094 | -8.940 | 1.00 44.23 | C |
| ATOM | 3938 | O | LEU | C | 2 | 21.294 | 70.737 | -9.070 | 1.00 43.47 | O |
| ATOM | 3939 | N | LEU | C | 2 | 23.012 | 69.063 | -7.616 | 1.00 44.72 | N |
| ATOM | 3940 | CA | LEU | C | 2 | 23.558 | 70.094 | -8.552 | 1.00 44.02 | C |
| ATOM | 3941 | N | ASN | C | 3 | 22.857 | 72.354 | -9.115 | 1.00 45.03 | N |
| ATOM | 3942 | CA | ASN | C | 3 | 21.885 | 73.360 | -9.529 | 1.00 45.71 | C |
| ATOM | 3943 | CB | ASN | C | 3 | 22.397 | 74.770 | -9.271 | 1.00 46.37 | C |
| ATOM | 3944 | CG | ASN | C | 3 | 22.524 | 75.063 | -7.804 | 1.00 47.31 | C |
| ATOM | 3945 | OD1 | ASN | C | 3 | 23.526 | 74.691 | -7.165 | 1.00 48.32 | O |
| ATOM | 3946 | ND2 | ASN | C | 3 | 21.501 | 75.713 | -7.239 | 1.00 46.17 | N |
| ATOM | 3947 | C | ASN | C | 3 | 21.589 | 73.177 | -11.010 | 1.00 45.30 | C |
| ATOM | 3948 | O | ASN | C | 3 | 21.777 | 72.081 | -11.543 | 1.00 45.23 | O |
| ATOM | 3949 | N | LEU | C | 4 | 21.157 | 74.246 | -11.679 | 1.00 45.85 | N |
| ATOM | 3950 | CA | LEU | C | 4 | 20.787 | 74.150 | -13.098 | 1.00 45.32 | C |
| ATOM | 3951 | CB | LEU | C | 4 | 21.871 | 73.428 | -13.901 | 1.00 45.73 | C |
| ATOM | 3952 | CG | LEU | C | 4 | 21.698 | 73.212 | -15.409 | 1.00 46.42 | C |
| ATOM | 3953 | CD1 | LEU | C | 4 | 22.957 | 72.507 | -15.929 | 1.00 46.45 | C |
| ATOM | 3954 | CD2 | LEU | C | 4 | 20.442 | 72.378 | -15.721 | 1.00 44.93 | C |
| ATOM | 3955 | C | LEU | C | 4 | 19.532 | 73.291 | -13.039 | 1.00 44.02 | C |
| ATOM | 3956 | O | LEU | C | 4 | 19.615 | 72.067 | -12.976 | 1.00 42.66 | O |
| ATOM | 3957 | N | GLU | C | 5 | 18.375 | 73.946 | -13.040 | 1.00 43.21 | N |
| ATOM | 3958 | CA | GLU | C | 5 | 17.101 | 73.255 | -12.941 | 1.00 42.19 | C |
| ATOM | 3959 | CB | GLU | C | 5 | 16.085 | 74.145 | -12.235 | 1.00 41.33 | C |
| ATOM | 3960 | CG | GLU | C | 5 | 15.749 | 73.716 | -10.837 | 1.00 41.05 | C |
| ATOM | 3961 | CD | GLU | C | 5 | 16.926 | 73.789 | -9.899 | 1.00 40.89 | C |
| ATOM | 3962 | OE1 | GLU | C | 5 | 17.844 | 72.948 | -10.024 | 1.00 39.72 | O |
| ATOM | 3963 | OE2 | GLU | C | 5 | 16.927 | 74.695 | -9.030 | 1.00 40.67 | O |

FIGURE 9 (cont.)

```
ATOM  3964  C    GLU C   5      16.524  72.796 -14.266  1.00 42.55           C
ATOM  3965  O    GLU C   5      17.195  72.814 -15.303  1.00 42.94           O
ATOM  3966  N    ASN C   6      15.259  72.392 -14.205  1.00 42.43           N
ATOM  3967  CA   ASN C   6      14.498  71.882 -15.347  1.00 42.40           C
ATOM  3968  CB   ASN C   6      15.373  71.101 -16.317  1.00 43.56           C
ATOM  3969  CG   ASN C   6      14.613  70.683 -17.551  1.00 45.53           C
ATOM  3970  OD1  ASN C   6      15.010  69.754 -18.287  1.00 44.12           O
ATOM  3971  ND2  ASN C   6      13.507  71.384 -17.805  1.00 46.26           N
ATOM  3972  C    ASN C   6      13.529  70.906 -14.699  1.00 41.29           C
ATOM  3973  O    ASN C   6      13.035  69.964 -15.328  1.00 41.58           O
ATOM  3974  N    LYS C   7      13.313  71.138 -13.410  1.00 39.16           N
ATOM  3975  CA   LYS C   7      12.421  70.349 -12.582  1.00 36.05           C
ATOM  3976  CB   LYS C   7      13.103  70.079 -11.241  1.00 36.36           C
ATOM  3977  CG   LYS C   7      14.562  69.609 -11.356  1.00 36.80           C
ATOM  3978  CD   LYS C   7      14.705  68.083 -11.454  1.00 36.85           C
ATOM  3979  CE   LYS C   7      13.978  67.484 -12.660  1.00 37.83           C
ATOM  3980  NZ   LYS C   7      14.280  66.018 -12.843  1.00 36.73           N
ATOM  3981  C    LYS C   7      11.226  71.277 -12.385  1.00 34.34           C
ATOM  3982  O    LYS C   7      11.092  72.278 -13.086  1.00 33.40           O
ATOM  3983  N    THR C   8      10.360  70.970 -11.433  1.00 32.86           N
ATOM  3984  CA   THR C   8       9.219  71.837 -11.200  1.00 31.06           C
ATOM  3985  CB   THR C   8       7.975  71.273 -11.897  1.00 31.32           C
ATOM  3986  OG1  THR C   8       8.230  71.224 -13.314  1.00 32.03           O
ATOM  3987  CG2  THR C   8       6.746  72.152 -11.612  1.00 29.62           C
ATOM  3988  C    THR C   8       8.983  71.996  -9.708  1.00 29.62           C
ATOM  3989  O    THR C   8       9.203  71.066  -8.941  1.00 29.49           O
ATOM  3990  N    TYR C   9       8.554  73.178  -9.287  1.00 28.24           N
ATOM  3991  CA   TYR C   9       8.330  73.401  -7.866  1.00 27.87           C
ATOM  3992  CB   TYR C   9       9.554  74.082  -7.233  1.00 26.52           C
ATOM  3993  CG   TYR C   9      10.837  73.290  -7.385  1.00 26.46           C
ATOM  3994  CD1  TYR C   9      11.688  73.500  -8.473  1.00 26.81           C
ATOM  3995  CE1  TYR C   9      12.850  72.746  -8.638  1.00 26.44           C
ATOM  3996  CD2  TYR C   9      11.183  72.302  -6.461  1.00 25.13           C
ATOM  3997  CE2  TYR C   9      12.339  71.540  -6.619  1.00 26.00           C
ATOM  3998  CZ   TYR C   9      13.166  71.763  -7.708  1.00 26.43           C
ATOM  3999  OH   TYR C   9      14.292  70.983  -7.885  1.00 27.16           O
ATOM  4000  C    TYR C   9       7.085  74.219  -7.567  1.00 27.78           C
ATOM  4001  O    TYR C   9       6.810  75.230  -8.224  1.00 28.61           O
ATOM  4002  N    VAL C  10       6.332  73.765  -6.571  1.00 27.07           N
ATOM  4003  CA   VAL C  10       5.116  74.446  -6.145  1.00 26.55           C
ATOM  4004  CB   VAL C  10       4.085  73.447  -5.593  1.00 26.61           C
ATOM  4005  CG1  VAL C  10       2.925  74.200  -4.961  1.00 25.60           C
ATOM  4006  CG2  VAL C  10       3.597  72.535  -6.714  1.00 26.86           C
ATOM  4007  C    VAL C  10       5.458  75.429  -5.034  1.00 26.37           C
ATOM  4008  O    VAL C  10       5.939  75.019  -3.969  1.00 26.05           O
ATOM  4009  N    ILE C  11       5.204  76.716  -5.277  1.00 25.80           N
ATOM  4010  CA   ILE C  11       5.482  77.741  -4.280  1.00 25.41           C
ATOM  4011  CB   ILE C  11       6.233  78.936  -4.873  1.00 25.15           C
ATOM  4012  CG2  ILE C  11       6.404  80.008  -3.803  1.00 26.35           C
ATOM  4013  CG1  ILE C  11       7.606  78.493  -5.378  1.00 24.62           C
ATOM  4014  CD1  ILE C  11       8.394  79.596  -6.006  1.00 23.52           C
ATOM  4015  C    ILE C  11       4.217  78.268  -3.635  1.00 25.59           C
ATOM  4016  O    ILE C  11       3.463  79.031  -4.236  1.00 26.16           O
ATOM  4017  N    MET C  12       4.006  77.868  -2.390  1.00 26.12           N
ATOM  4018  CA   MET C  12       2.839  78.280  -1.628  1.00 26.94           C
ATOM  4019  CB   MET C  12       2.336  77.095  -0.797  1.00 26.32           C
ATOM  4020  CG   MET C  12       2.263  75.782  -1.561  1.00 28.16           C
ATOM  4021  SD   MET C  12       1.446  74.479  -0.581  1.00 28.23           S
ATOM  4022  CE   MET C  12       2.456  74.577   0.891  1.00 31.90           C
ATOM  4023  C    MET C  12       3.161  79.450  -0.693  1.00 26.90           C
ATOM  4024  O    MET C  12       4.076  79.353   0.139  1.00 25.57           O
ATOM  4025  N    GLY C  13       2.434  80.559  -0.835  1.00 26.63           N
ATOM  4026  CA   GLY C  13       2.665  81.684   0.062  1.00 27.50           C
ATOM  4027  C    GLY C  13       2.926  83.094  -0.449  1.00 27.48           C
ATOM  4028  O    GLY C  13       3.120  84.006   0.364  1.00 27.84           O
```

FIGURE 9 (cont.)

```
ATOM   4029  N   ILE C  14      2.948  83.310  -1.759  1.00 27.72           N
ATOM   4030  CA  ILE C  14      3.192  84.669  -2.244  1.00 27.73           C
ATOM   4031  CB  ILE C  14      3.573  84.684  -3.741  1.00 28.08           C
ATOM   4032  CG2 ILE C  14      3.609  86.130  -4.262  1.00 27.69           C
ATOM   4033  CG1 ILE C  14      4.939  84.025  -3.934  1.00 27.19           C
ATOM   4034  CD1 ILE C  14      5.367  83.917  -5.390  1.00 28.32           C
ATOM   4035  C   ILE C  14      1.959  85.540  -2.036  1.00 26.91           C
ATOM   4036  O   ILE C  14      0.833  85.088  -2.242  1.00 27.04           O
ATOM   4037  N   ALA C  15      2.177  86.784  -1.616  1.00 26.25           N
ATOM   4038  CA  ALA C  15      1.076  87.716  -1.393  1.00 25.98           C
ATOM   4039  CB  ALA C  15      0.960  88.056   0.080  1.00 26.11           C
ATOM   4040  C   ALA C  15      1.306  88.991  -2.198  1.00 25.96           C
ATOM   4041  O   ALA C  15      0.363  89.559  -2.751  1.00 25.58           O
ATOM   4042  N   ASN C  16      2.559  89.446  -2.232  1.00 25.36           N
ATOM   4043  CA  ASN C  16      2.926  90.640  -2.974  1.00 26.13           C
ATOM   4044  CB  ASN C  16      2.571  91.904  -2.183  1.00 26.85           C
ATOM   4045  CG  ASN C  16      3.451  92.107  -0.950  1.00 28.48           C
ATOM   4046  OD1 ASN C  16      3.244  93.047  -0.183  1.00 29.43           O
ATOM   4047  ND2 ASN C  16      4.435  91.234  -0.758  1.00 27.73           N
ATOM   4048  C   ASN C  16      4.413  90.614  -3.285  1.00 26.66           C
ATOM   4049  O   ASN C  16      5.097  89.635  -2.994  1.00 26.99           O
ATOM   4050  N   LYS C  17      4.906  91.690  -3.885  1.00 26.91           N
ATOM   4051  CA  LYS C  17      6.316  91.812  -4.247  1.00 28.12           C
ATOM   4052  CB  LYS C  17      6.550  93.191  -4.854  1.00 29.17           C
ATOM   4053  CG  LYS C  17      5.910  94.300  -4.016  1.00 31.37           C
ATOM   4054  CD  LYS C  17      5.559  95.523  -4.854  1.00 32.15           C
ATOM   4055  CE  LYS C  17      6.801  96.302  -5.221  1.00 34.29           C
ATOM   4056  NZ  LYS C  17      7.470  96.768  -3.972  1.00 34.94           N
ATOM   4057  C   LYS C  17      7.225  91.629  -3.026  1.00 27.74           C
ATOM   4058  O   LYS C  17      8.371  91.191  -3.142  1.00 26.06           O
ATOM   4059  N   ARG C  18      6.705  91.967  -1.855  1.00 27.58           N
ATOM   4060  CA  ARG C  18      7.486  91.853  -0.629  1.00 28.05           C
ATOM   4061  CB  ARG C  18      6.914  92.793   0.431  1.00 29.18           C
ATOM   4062  CG  ARG C  18      7.809  93.952   0.780  1.00 32.04           C
ATOM   4063  CD  ARG C  18      8.050  94.867  -0.406  1.00 34.77           C
ATOM   4064  NE  ARG C  18      8.650  96.126   0.044  1.00 38.38           N
ATOM   4065  CZ  ARG C  18      9.090  97.090  -0.762  1.00 40.65           C
ATOM   4066  NH1 ARG C  18      9.008  96.954  -2.087  1.00 41.29           N
ATOM   4067  NH2 ARG C  18      9.616  98.196  -0.238  1.00 41.28           N
ATOM   4068  C   ARG C  18      7.578  90.446  -0.037  1.00 26.35           C
ATOM   4069  O   ARG C  18      8.330  90.238   0.912  1.00 26.19           O
ATOM   4070  N   SER C  19      6.836  89.489  -0.596  1.00 25.15           N
ATOM   4071  CA  SER C  19      6.825  88.118  -0.076  1.00 24.36           C
ATOM   4072  CB  SER C  19      5.709  87.303  -0.744  1.00 24.21           C
ATOM   4073  OG  SER C  19      4.438  87.626  -0.203  1.00 23.52           O
ATOM   4074  C   SER C  19      8.134  87.336  -0.182  1.00 24.34           C
ATOM   4075  O   SER C  19      8.838  87.411  -1.194  1.00 22.94           O
ATOM   4076  N   ILE C  20      8.445  86.577   0.871  1.00 23.41           N
ATOM   4077  CA  ILE C  20      9.662  85.776   0.903  1.00 22.68           C
ATOM   4078  CB  ILE C  20      9.842  85.093   2.276  1.00 22.40           C
ATOM   4079  CG2 ILE C  20     10.939  84.026   2.201  1.00 19.84           C
ATOM   4080  CG1 ILE C  20     10.201  86.150   3.328  1.00 22.06           C
ATOM   4081  CD1 ILE C  20     10.276  85.617   4.752  1.00 21.85           C
ATOM   4082  C   ILE C  20      9.576  84.723  -0.194  1.00 23.97           C
ATOM   4083  O   ILE C  20     10.579  84.395  -0.848  1.00 23.13           O
ATOM   4084  N   ALA C  21      8.366  84.206  -0.398  1.00 24.61           N
ATOM   4085  CA  ALA C  21      8.118  83.212  -1.434  1.00 24.05           C
ATOM   4086  CB  ALA C  21      6.656  82.794  -1.422  1.00 25.58           C
ATOM   4087  C   ALA C  21      8.480  83.792  -2.793  1.00 23.91           C
ATOM   4088  O   ALA C  21      8.923  83.062  -3.681  1.00 26.00           O
ATOM   4089  N   PHE C  22      8.297  85.099  -2.973  1.00 22.91           N
ATOM   4090  CA  PHE C  22      8.649  85.692  -4.257  1.00 22.44           C
ATOM   4091  CB  PHE C  22      8.174  87.146  -4.392  1.00 22.68           C
ATOM   4092  CG  PHE C  22      8.368  87.701  -5.784  1.00 21.77           C
ATOM   4093  CD1 PHE C  22      9.057  88.890  -5.993  1.00 22.36           C
```

FIGURE 9 (cont.)

| | | | | | | | | | |
|---|---|---|---|---|---|---|---|---|---|
| ATOM | 4094 | CD2 | PHE | C | 22 | 7.908 | 86.991 | -6.891 | 1.00 20.79 | C |
| ATOM | 4095 | CE1 | PHE | C | 22 | 9.298 | 89.367 | -7.290 | 1.00 21.73 | C |
| ATOM | 4096 | CE2 | PHE | C | 22 | 8.138 | 87.448 | -8.186 | 1.00 21.38 | C |
| ATOM | 4097 | CZ | PHE | C | 22 | 8.838 | 88.641 | -8.389 | 1.00 22.53 | C |
| ATOM | 4098 | C | PHE | C | 22 | 10.158 | 85.646 | -4.433 | 1.00 21.84 | C |
| ATOM | 4099 | O | PHE | C | 22 | 10.644 | 85.518 | -5.556 | 1.00 22.90 | O |
| ATOM | 4100 | N | GLY | C | 23 | 10.893 | 85.760 | -3.325 | 1.00 21.32 | N |
| ATOM | 4101 | CA | GLY | C | 23 | 12.345 | 85.695 | -3.376 | 1.00 18.51 | C |
| ATOM | 4102 | C | GLY | C | 23 | 12.779 | 84.307 | -3.817 | 1.00 18.64 | C |
| ATOM | 4103 | O | GLY | C | 23 | 13.773 | 84.151 | -4.518 | 1.00 19.20 | O |
| ATOM | 4104 | N | VAL | C | 24 | 12.035 | 83.290 | -3.398 | 1.00 18.14 | N |
| ATOM | 4105 | CA | VAL | C | 24 | 12.337 | 81.913 | -3.784 | 1.00 19.57 | C |
| ATOM | 4106 | CB | VAL | C | 24 | 11.487 | 80.888 | -2.968 | 1.00 19.22 | C |
| ATOM | 4107 | CG1 | VAL | C | 24 | 11.801 | 79.471 | -3.414 | 1.00 19.53 | C |
| ATOM | 4108 | CG2 | VAL | C | 24 | 11.774 | 81.034 | -1.478 | 1.00 18.81 | C |
| ATOM | 4109 | C | VAL | C | 24 | 11.996 | 81.767 | -5.264 | 1.00 20.12 | C |
| ATOM | 4110 | O | VAL | C | 24 | 12.724 | 81.135 | -6.028 | 1.00 20.28 | O |
| ATOM | 4111 | N | ALA | C | 25 | 10.878 | 82.366 | -5.663 | 1.00 22.08 | N |
| ATOM | 4112 | CA | ALA | C | 25 | 10.434 | 82.319 | -7.051 | 1.00 22.75 | C |
| ATOM | 4113 | CB | ALA | C | 25 | 9.118 | 83.080 | -7.198 | 1.00 23.25 | C |
| ATOM | 4114 | C | ALA | C | 25 | 11.485 | 82.905 | -7.991 | 1.00 23.05 | C |
| ATOM | 4115 | O | ALA | C | 25 | 11.804 | 82.311 | -9.023 | 1.00 25.11 | O |
| ATOM | 4116 | N | LYS | C | 26 | 12.036 | 84.062 | -7.636 | 1.00 23.24 | N |
| ATOM | 4117 | CA | LYS | C | 26 | 13.038 | 84.704 | -8.483 | 1.00 23.87 | C |
| ATOM | 4118 | CB | LYS | C | 26 | 13.355 | 86.112 | -7.964 | 1.00 23.75 | C |
| ATOM | 4119 | CG | LYS | C | 26 | 12.187 | 87.093 | -8.119 | 1.00 26.82 | C |
| ATOM | 4120 | CD | LYS | C | 26 | 12.613 | 88.558 | -7.972 | 1.00 27.81 | C |
| ATOM | 4121 | CE | LYS | C | 26 | 13.065 | 88.891 | -6.554 | 1.00 27.84 | C |
| ATOM | 4122 | NZ | LYS | C | 26 | 13.479 | 90.327 | -6.447 | 1.00 28.77 | N |
| ATOM | 4123 | C | LYS | C | 26 | 14.342 | 83.935 | -8.701 | 1.00 24.14 | C |
| ATOM | 4124 | O | LYS | C | 26 | 14.947 | 84.032 | -9.776 | 1.00 24.57 | O |
| ATOM | 4125 | N | VAL | C | 27 | 14.794 | 83.184 | -7.701 | 1.00 23.51 | N |
| ATOM | 4126 | CA | VAL | C | 27 | 16.035 | 82.427 | -7.856 | 1.00 24.15 | C |
| ATOM | 4127 | CB | VAL | C | 27 | 16.619 | 81.996 | -6.482 | 1.00 24.52 | C |
| ATOM | 4128 | CG1 | VAL | C | 27 | 17.791 | 81.043 | -6.685 | 1.00 24.39 | C |
| ATOM | 4129 | CG2 | VAL | C | 27 | 17.090 | 83.231 | -5.705 | 1.00 23.97 | C |
| ATOM | 4130 | C | VAL | C | 27 | 15.789 | 81.191 | -8.710 | 1.00 24.11 | C |
| ATOM | 4131 | O | VAL | C | 27 | 16.468 | 80.978 | -9.715 | 1.00 24.18 | O |
| ATOM | 4132 | N | LEU | C | 28 | 14.802 | 80.391 | -8.317 | 1.00 24.45 | N |
| ATOM | 4133 | CA | LEU | C | 28 | 14.457 | 79.174 | -9.049 | 1.00 25.64 | C |
| ATOM | 4134 | CB | LEU | C | 28 | 13.222 | 78.520 | -8.435 | 1.00 25.19 | C |
| ATOM | 4135 | CG | LEU | C | 28 | 13.315 | 78.168 | -6.955 | 1.00 25.12 | C |
| ATOM | 4136 | CD1 | LEU | C | 28 | 11.989 | 77.581 | -6.519 | 1.00 25.03 | C |
| ATOM | 4137 | CD2 | LEU | C | 28 | 14.474 | 77.179 | -6.708 | 1.00 25.81 | C |
| ATOM | 4138 | C | LEU | C | 28 | 14.175 | 79.472 | -10.516 | 1.00 25.85 | C |
| ATOM | 4139 | O | LEU | C | 28 | 14.551 | 78.703 | -11.400 | 1.00 24.67 | O |
| ATOM | 4140 | N | ASP | C | 29 | 13.498 | 80.590 | -10.762 | 1.00 27.01 | N |
| ATOM | 4141 | CA | ASP | C | 29 | 13.161 | 80.999 | -12.119 | 1.00 28.21 | C |
| ATOM | 4142 | CB | ASP | C | 29 | 12.232 | 82.210 | -12.072 | 1.00 28.23 | C |
| ATOM | 4143 | CG | ASP | C | 29 | 11.879 | 82.735 | -13.459 | 1.00 29.05 | C |
| ATOM | 4144 | OD1 | ASP | C | 29 | 11.133 | 82.049 | -14.197 | 1.00 27.28 | O |
| ATOM | 4145 | OD2 | ASP | C | 29 | 12.361 | 83.839 | -13.808 | 1.00 29.32 | O |
| ATOM | 4146 | C | ASP | C | 29 | 14.426 | 81.349 | -12.896 | 1.00 28.97 | C |
| ATOM | 4147 | O | ASP | C | 29 | 14.509 | 81.166 | -14.108 | 1.00 29.75 | O |
| ATOM | 4148 | N | GLN | C | 30 | 15.420 | 81.852 | -12.183 | 1.00 30.91 | N |
| ATOM | 4149 | CA | GLN | C | 30 | 16.681 | 82.244 | -12.802 | 1.00 31.92 | C |
| ATOM | 4150 | CB | GLN | C | 30 | 17.405 | 83.213 | -11.856 | 1.00 34.07 | C |
| ATOM | 4151 | CG | GLN | C | 30 | 18.539 | 84.019 | -12.455 | 1.00 37.70 | C |
| ATOM | 4152 | CD | GLN | C | 30 | 19.315 | 84.769 | -11.385 | 1.00 39.72 | C |
| ATOM | 4153 | OE1 | GLN | C | 30 | 19.887 | 84.153 | -10.478 | 1.00 41.86 | O |
| ATOM | 4154 | NE2 | GLN | C | 30 | 19.340 | 86.099 | -11.478 | 1.00 40.16 | N |
| ATOM | 4155 | C | GLN | C | 30 | 17.515 | 80.973 | -13.054 | 1.00 31.79 | C |
| ATOM | 4156 | O | GLN | C | 30 | 18.324 | 80.921 | -13.985 | 1.00 32.63 | O |
| ATOM | 4157 | N | LEU | C | 31 | 17.293 | 79.942 | -12.238 | 1.00 30.40 | N |
| ATOM | 4158 | CA | LEU | C | 31 | 18.016 | 78.672 | -12.368 | 1.00 29.47 | C |

FIGURE 9 (cont.)

| | | | | | | | | | | |
|---|---|---|---|---|---|---|---|---|---|---|
| ATOM | 4159 | CB | LEU | C | 31 | 18.098 | 77.984 | -10.998 | 1.00 28.05 | C |
| ATOM | 4160 | CG | LEU | C | 31 | 19.384 | 78.145 | -10.167 | 1.00 27.59 | C |
| ATOM | 4161 | CD1 | LEU | C | 31 | 20.035 | 79.500 | -10.420 | 1.00 25.34 | C |
| ATOM | 4162 | CD2 | LEU | C | 31 | 19.067 | 77.940 | -8.678 | 1.00 25.02 | C |
| ATOM | 4163 | C | LEU | C | 31 | 17.420 | 77.702 | -13.399 | 1.00 30.21 | C |
| ATOM | 4164 | O | LEU | C | 31 | 17.955 | 76.604 | -13.605 | 1.00 31.34 | O |
| ATOM | 4165 | N | GLY | C | 32 | 16.318 | 78.096 | -14.042 | 1.00 30.33 | N |
| ATOM | 4166 | CA | GLY | C | 32 | 15.698 | 77.249 | -15.055 | 1.00 28.93 | C |
| ATOM | 4167 | C | GLY | C | 32 | 14.442 | 76.479 | -14.661 | 1.00 29.11 | C |
| ATOM | 4168 | O | GLY | C | 32 | 13.830 | 75.796 | -15.491 | 1.00 29.51 | O |
| ATOM | 4169 | N | ALA | C | 33 | 14.036 | 76.584 | -13.403 | 1.00 28.58 | N |
| ATOM | 4170 | CA | ALA | C | 33 | 12.860 | 75.860 | -12.932 | 1.00 27.70 | C |
| ATOM | 4171 | CB | ALA | C | 33 | 12.816 | 75.884 | -11.409 | 1.00 26.97 | C |
| ATOM | 4172 | C | ALA | C | 33 | 11.534 | 76.381 | -13.479 | 1.00 27.64 | C |
| ATOM | 4173 | O | ALA | C | 33 | 11.405 | 77.554 | -13.840 | 1.00 25.60 | O |
| ATOM | 4174 | N | LYS | C | 34 | 10.557 | 75.477 | -13.538 | 1.00 27.24 | N |
| ATOM | 4175 | CA | LYS | C | 34 | 9.203 | 75.806 | -13.966 | 1.00 27.45 | C |
| ATOM | 4176 | CB | LYS | C | 34 | 8.586 | 74.647 | -14.749 | 1.00 29.08 | C |
| ATOM | 4177 | CG | LYS | C | 34 | 7.102 | 74.830 | -15.054 | 1.00 31.39 | C |
| ATOM | 4178 | CD | LYS | C | 34 | 6.425 | 73.502 | -15.404 | 1.00 33.13 | C |
| ATOM | 4179 | CE | LYS | C | 34 | 7.052 | 72.840 | -16.630 | 1.00 33.54 | C |
| ATOM | 4180 | NZ | LYS | C | 34 | 6.442 | 71.493 | -16.852 | 1.00 35.15 | N |
| ATOM | 4181 | C | LYS | C | 34 | 8.513 | 75.946 | -12.609 | 1.00 26.96 | C |
| ATOM | 4182 | O | LYS | C | 34 | 8.809 | 75.180 | -11.692 | 1.00 27.13 | O |
| ATOM | 4183 | N | LEU | C | 35 | 7.600 | 76.901 | -12.462 | 1.00 26.16 | N |
| ATOM | 4184 | CA | LEU | C | 35 | 6.973 | 77.091 | -11.161 | 1.00 25.64 | C |
| ATOM | 4185 | CB | LEU | C | 35 | 7.497 | 78.390 | -10.531 | 1.00 24.97 | C |
| ATOM | 4186 | CG | LEU | C | 35 | 9.023 | 78.595 | -10.505 | 1.00 24.55 | C |
| ATOM | 4187 | CD1 | LEU | C | 35 | 9.333 | 80.040 | -10.160 | 1.00 25.25 | C |
| ATOM | 4188 | CD2 | LEU | C | 35 | 9.678 | 77.660 | -9.505 | 1.00 24.30 | C |
| ATOM | 4189 | C | LEU | C | 35 | 5.455 | 77.105 | -11.147 | 1.00 25.16 | C |
| ATOM | 4190 | O | LEU | C | 35 | 4.806 | 77.498 | -12.120 | 1.00 25.00 | O |
| ATOM | 4191 | N | VAL | C | 36 | 4.906 | 76.662 | -10.021 | 1.00 24.93 | N |
| ATOM | 4192 | CA | VAL | C | 36 | 3.469 | 76.631 | -9.786 | 1.00 25.31 | C |
| ATOM | 4193 | CB | VAL | C | 36 | 2.970 | 75.196 | -9.554 | 1.00 24.28 | C |
| ATOM | 4194 | CG1 | VAL | C | 36 | 1.522 | 75.216 | -9.092 | 1.00 25.13 | C |
| ATOM | 4195 | CG2 | VAL | C | 36 | 3.088 | 74.403 | -10.824 | 1.00 24.10 | C |
| ATOM | 4196 | C | VAL | C | 36 | 3.221 | 77.455 | -8.525 | 1.00 26.40 | C |
| ATOM | 4197 | O | VAL | C | 36 | 3.813 | 77.184 | -7.475 | 1.00 28.26 | O |
| ATOM | 4198 | N | PHE | C | 37 | 2.359 | 78.463 | -8.614 | 1.00 26.51 | N |
| ATOM | 4199 | CA | PHE | C | 37 | 2.096 | 79.311 | -7.451 | 1.00 26.20 | C |
| ATOM | 4200 | CB | PHE | C | 37 | 2.236 | 80.787 | -7.822 | 1.00 25.17 | C |
| ATOM | 4201 | CG | PHE | C | 37 | 3.475 | 81.096 | -8.606 | 1.00 26.07 | C |
| ATOM | 4202 | CD1 | PHE | C | 37 | 3.540 | 80.805 | -9.961 | 1.00 25.16 | C |
| ATOM | 4203 | CD2 | PHE | C | 37 | 4.585 | 81.664 | -7.985 | 1.00 26.53 | C |
| ATOM | 4204 | CE1 | PHE | C | 37 | 4.687 | 81.072 | -10.693 | 1.00 25.38 | C |
| ATOM | 4205 | CE2 | PHE | C | 37 | 5.742 | 81.935 | -8.711 | 1.00 27.00 | C |
| ATOM | 4206 | CZ | PHE | C | 37 | 5.793 | 81.639 | -10.066 | 1.00 27.00 | C |
| ATOM | 4207 | C | PHE | C | 37 | 0.728 | 79.121 | -6.830 | 1.00 26.38 | C |
| ATOM | 4208 | O | PHE | C | 37 | -0.288 | 79.175 | -7.518 | 1.00 27.08 | O |
| ATOM | 4209 | N | THR | C | 38 | 0.693 | 78.905 | -5.525 | 1.00 25.55 | N |
| ATOM | 4210 | CA | THR | C | 38 | -0.582 | 78.771 | -4.862 | 1.00 26.41 | C |
| ATOM | 4211 | CB | THR | C | 38 | -0.666 | 77.469 | -4.030 | 1.00 26.13 | C |
| ATOM | 4212 | OG1 | THR | C | 38 | 0.188 | 77.564 | -2.883 | 1.00 26.51 | O |
| ATOM | 4213 | CG2 | THR | C | 38 | -0.241 | 76.279 | -4.875 | 1.00 25.23 | C |
| ATOM | 4214 | C | THR | C | 38 | -0.711 | 80.006 | -3.973 | 1.00 27.34 | C |
| ATOM | 4215 | O | THR | C | 38 | 0.258 | 80.432 | -3.328 | 1.00 26.82 | O |
| ATOM | 4216 | N | TYR | C | 39 | -1.898 | 80.605 | -3.971 | 1.00 28.36 | N |
| ATOM | 4217 | CA | TYR | C | 39 | -2.147 | 81.799 | -3.168 | 1.00 29.19 | C |
| ATOM | 4218 | CB | TYR | C | 39 | -2.325 | 83.005 | -4.090 | 1.00 30.18 | C |
| ATOM | 4219 | CG | TYR | C | 39 | -3.406 | 82.790 | -5.123 | 1.00 33.72 | C |
| ATOM | 4220 | CD1 | TYR | C | 39 | -3.105 | 82.371 | -6.422 | 1.00 34.16 | C |
| ATOM | 4221 | CE1 | TYR | C | 39 | -4.139 | 82.120 | -7.361 | 1.00 35.86 | C |
| ATOM | 4222 | CD2 | TYR | C | 39 | -4.748 | 82.956 | -4.778 | 1.00 35.76 | C |
| ATOM | 4223 | CE2 | TYR | C | 39 | -5.774 | 82.708 | -5.688 | 1.00 36.87 | C |

FIGURE 9 (cont.)

| ATOM | 4224 | CZ | TYR C | 39 | -5.472 | 82.293 | -6.972 | 1.00 | 36.60 | C |
| ATOM | 4225 | OH | TYR C | 39 | -6.531 | 82.055 | -7.835 | 1.00 | 39.09 | O |
| ATOM | 4226 | C | TYR C | 39 | -3.390 | 81.567 | -2.302 | 1.00 | 28.24 | C |
| ATOM | 4227 | O | TYR C | 39 | -4.202 | 80.690 | -2.593 | 1.00 | 27.20 | O |
| ATOM | 4228 | N | ARG C | 40 | -3.543 | 82.338 | -1.237 | 1.00 | 29.17 | N |
| ATOM | 4229 | CA | ARG C | 40 | -4.686 | 82.140 | -0.346 | 1.00 | 31.99 | C |
| ATOM | 4230 | CB | ARG C | 40 | -4.434 | 82.835 | 0.996 | 1.00 | 33.68 | C |
| ATOM | 4231 | CG | ARG C | 40 | -5.508 | 82.557 | 2.047 | 1.00 | 35.12 | C |
| ATOM | 4232 | CD | ARG C | 40 | -5.408 | 83.531 | 3.221 | 1.00 | 37.41 | C |
| ATOM | 4233 | NE | ARG C | 40 | -5.987 | 82.948 | 4.432 | 1.00 | 40.27 | N |
| ATOM | 4234 | CZ | ARG C | 40 | -6.126 | 83.595 | 5.590 | 1.00 | 41.66 | C |
| ATOM | 4235 | NH1 | ARG C | 40 | -5.734 | 84.865 | 5.697 | 1.00 | 41.46 | N |
| ATOM | 4236 | NH2 | ARG C | 40 | -6.630 | 82.959 | 6.649 | 1.00 | 41.67 | N |
| ATOM | 4237 | C | ARG C | 40 | -6.027 | 82.634 | -0.891 | 1.00 | 32.55 | C |
| ATOM | 4238 | O | ARG C | 40 | -7.002 | 81.869 | -0.986 | 1.00 | 31.23 | O |
| ATOM | 4239 | N | LYS C | 41 | -6.064 | 83.917 | -1.237 | 1.00 | 33.31 | N |
| ATOM | 4240 | CA | LYS C | 41 | -7.283 | 84.569 | -1.720 | 1.00 | 34.97 | C |
| ATOM | 4241 | CB | LYS C | 41 | -7.451 | 85.903 | -0.973 | 1.00 | 36.35 | C |
| ATOM | 4242 | CG | LYS C | 41 | -6.178 | 86.791 | -1.047 | 1.00 | 38.79 | C |
| ATOM | 4243 | CD | LYS C | 41 | -6.300 | 88.123 | -0.272 | 1.00 | 39.69 | C |
| ATOM | 4244 | CE | LYS C | 41 | -6.222 | 87.929 | 1.247 | 1.00 | 38.97 | C |
| ATOM | 4245 | NZ | LYS C | 41 | -6.247 | 89.259 | 1.950 | 1.00 | 38.80 | N |
| ATOM | 4246 | C | LYS C | 41 | -7.266 | 84.814 | -3.225 | 1.00 | 34.81 | C |
| ATOM | 4247 | O | LYS C | 41 | -6.207 | 85.063 | -3.809 | 1.00 | 34.86 | O |
| ATOM | 4248 | N | GLU C | 42 | -8.441 | 84.755 | -3.854 | 1.00 | 34.85 | N |
| ATOM | 4249 | CA | GLU C | 42 | -8.531 | 84.984 | -5.298 | 1.00 | 34.24 | C |
| ATOM | 4250 | CB | GLU C | 42 | -9.967 | 84.758 | -5.796 | 1.00 | 35.12 | C |
| ATOM | 4251 | CG | GLU C | 42 | -10.184 | 85.043 | -7.294 | 1.00 | 36.52 | C |
| ATOM | 4252 | CD | GLU C | 42 | -9.076 | 84.491 | -8.183 | 1.00 | 38.99 | C |
| ATOM | 4253 | OE1 | GLU C | 42 | -8.768 | 83.268 | -8.089 | 1.00 | 39.57 | O |
| ATOM | 4254 | OE2 | GLU C | 42 | -8.510 | 85.289 | -8.982 | 1.00 | 38.95 | O |
| ATOM | 4255 | C | GLU C | 42 | -8.076 | 86.395 | -5.641 | 1.00 | 33.21 | C |
| ATOM | 4256 | O | GLU C | 42 | -7.522 | 86.628 | -6.719 | 1.00 | 31.97 | O |
| ATOM | 4257 | N | ARG C | 43 | -8.311 | 87.327 | -4.717 | 1.00 | 32.92 | N |
| ATOM | 4258 | CA | ARG C | 43 | -7.923 | 88.729 | -4.897 | 1.00 | 32.83 | C |
| ATOM | 4259 | CB | ARG C | 43 | -8.169 | 89.537 | -3.613 | 1.00 | 33.73 | C |
| ATOM | 4260 | CG | ARG C | 43 | -9.622 | 89.810 | -3.249 | 1.00 | 36.76 | C |
| ATOM | 4261 | CD | ARG C | 43 | -10.247 | 88.709 | -2.365 | 1.00 | 38.33 | C |
| ATOM | 4262 | NE | ARG C | 43 | -10.617 | 87.508 | -3.115 | 1.00 | 37.75 | N |
| ATOM | 4263 | CZ | ARG C | 43 | -11.482 | 86.591 | -2.682 | 1.00 | 36.63 | C |
| ATOM | 4264 | NH1 | ARG C | 43 | -12.076 | 86.728 | -1.500 | 1.00 | 36.36 | N |
| ATOM | 4265 | NH2 | ARG C | 43 | -11.755 | 85.537 | -3.436 | 1.00 | 36.85 | N |
| ATOM | 4266 | C | ARG C | 43 | -6.447 | 88.892 | -5.271 | 1.00 | 32.80 | C |
| ATOM | 4267 | O | ARG C | 43 | -6.086 | 89.813 | -6.003 | 1.00 | 32.38 | O |
| ATOM | 4268 | N | SER C | 44 | -5.578 | 88.027 | -4.759 | 1.00 | 33.41 | N |
| ATOM | 4269 | CA | SER C | 44 | -4.163 | 88.183 | -5.078 | 1.00 | 34.70 | C |
| ATOM | 4270 | CB | SER C | 44 | -3.287 | 87.779 | -3.883 | 1.00 | 35.17 | C |
| ATOM | 4271 | OG | SER C | 44 | -3.683 | 86.548 | -3.303 | 1.00 | 36.02 | O |
| ATOM | 4272 | C | SER C | 44 | -3.722 | 87.463 | -6.348 | 1.00 | 34.66 | C |
| ATOM | 4273 | O | SER C | 44 | -2.550 | 87.479 | -6.710 | 1.00 | 34.59 | O |
| ATOM | 4274 | N | ARG C | 45 | -4.669 | 86.861 | -7.052 | 1.00 | 35.91 | N |
| ATOM | 4275 | CA | ARG C | 45 | -4.341 | 86.166 | -8.291 | 1.00 | 37.06 | C |
| ATOM | 4276 | CB | ARG C | 45 | -5.587 | 85.438 | -8.826 | 1.00 | 39.19 | C |
| ATOM | 4277 | CG | ARG C | 45 | -5.507 | 84.922 | -10.277 | 1.00 | 41.41 | C |
| ATOM | 4278 | CD | ARG C | 45 | -5.785 | 86.061 | -11.272 | 1.00 | 44.39 | C |
| ATOM | 4279 | NE | ARG C | 45 | -7.032 | 86.777 | -10.962 | 1.00 | 46.43 | N |
| ATOM | 4280 | CZ | ARG C | 45 | -7.348 | 87.989 | -11.426 | 1.00 | 46.66 | C |
| ATOM | 4281 | NH1 | ARG C | 45 | -6.510 | 88.639 | -12.227 | 1.00 | 47.50 | N |
| ATOM | 4282 | NH2 | ARG C | 45 | -8.503 | 88.556 | -11.086 | 1.00 | 46.10 | N |
| ATOM | 4283 | C | ARG C | 45 | -3.803 | 87.161 | -9.325 | 1.00 | 37.20 | C |
| ATOM | 4284 | O | ARG C | 45 | -3.113 | 86.757 | -10.269 | 1.00 | 36.69 | O |
| ATOM | 4285 | N | LYS C | 46 | -4.096 | 88.455 | -9.133 | 1.00 | 36.82 | N |
| ATOM | 4286 | CA | LYS C | 46 | -3.647 | 89.493 | -10.065 | 1.00 | 36.20 | C |
| ATOM | 4287 | CB | LYS C | 46 | -4.744 | 90.560 | -10.272 | 1.00 | 36.74 | C |
| ATOM | 4288 | CG | LYS C | 46 | -5.109 | 91.409 | -9.050 | 1.00 | 36.33 | C |

FIGURE 9 (cont.)

| | | | | | | | | | | |
|---|---|---|---|---|---|---|---|---|---|---|
| ATOM | 4289 | CD | LYS | C | 46 | -6.059 | 92.544 | -9.449 | 1.00 36.58 | C |
| ATOM | 4290 | CE | LYS | C | 46 | -6.159 | 93.623 | -8.357 | 1.00 37.48 | C |
| ATOM | 4291 | NZ | LYS | C | 46 | -6.699 | 94.958 | -8.861 | 1.00 36.31 | N |
| ATOM | 4292 | C | LYS | C | 46 | -2.321 | 90.163 | -9.692 | 1.00 36.35 | C |
| ATOM | 4293 | O | LYS | C | 46 | -1.701 | 90.818 | -10.541 | 1.00 36.24 | O |
| ATOM | 4294 | N | GLU | C | 47 | -1.887 | 90.027 | -8.435 | 1.00 35.66 | N |
| ATOM | 4295 | CA | GLU | C | 47 | -0.598 | 90.588 | -8.030 | 1.00 34.87 | C |
| ATOM | 4296 | CB | GLU | C | 47 | -0.483 | 90.683 | -6.503 | 1.00 35.68 | C |
| ATOM | 4297 | CG | GLU | C | 47 | -1.421 | 91.699 | -5.906 | 1.00 38.10 | C |
| ATOM | 4298 | CD | GLU | C | 47 | -0.749 | 92.542 | -4.842 | 1.00 40.30 | C |
| ATOM | 4299 | OE1 | GLU | C | 47 | 0.444 | 92.908 | -5.034 | 1.00 39.61 | O |
| ATOM | 4300 | OE2 | GLU | C | 47 | -1.424 | 92.850 | -3.824 | 1.00 41.54 | O |
| ATOM | 4301 | C | GLU | C | 47 | 0.461 | 89.631 | -8.563 | 1.00 33.16 | C |
| ATOM | 4302 | O | GLU | C | 47 | 1.574 | 90.023 | -8.940 | 1.00 31.75 | O |
| ATOM | 4303 | N | LEU | C | 48 | 0.091 | 88.362 | -8.585 | 1.00 32.22 | N |
| ATOM | 4304 | CA | LEU | C | 48 | 0.965 | 87.327 | -9.083 | 1.00 32.02 | C |
| ATOM | 4305 | CB | LEU | C | 48 | 0.324 | 85.962 | -8.830 | 1.00 31.65 | C |
| ATOM | 4306 | CG | LEU | C | 48 | 0.419 | 85.630 | -7.335 | 1.00 31.69 | C |
| ATOM | 4307 | CD1 | LEU | C | 48 | -0.836 | 84.933 | -6.834 | 1.00 31.87 | C |
| ATOM | 4308 | CD2 | LEU | C | 48 | 1.677 | 84.784 | -7.114 | 1.00 30.96 | C |
| ATOM | 4309 | C | LEU | C | 48 | 1.186 | 87.570 | -10.559 | 1.00 32.96 | C |
| ATOM | 4310 | O | LEU | C | 48 | 2.328 | 87.700 | -10.999 | 1.00 32.97 | O |
| ATOM | 4311 | N | GLU | C | 49 | 0.092 | 87.661 | -11.318 | 1.00 34.31 | N |
| ATOM | 4312 | CA | GLU | C | 49 | 0.177 | 87.896 | -12.759 | 1.00 34.71 | C |
| ATOM | 4313 | CB | GLU | C | 49 | -1.193 | 88.263 | -13.346 | 1.00 36.17 | C |
| ATOM | 4314 | CG | GLU | C | 49 | -2.268 | 87.178 | -13.200 | 1.00 37.91 | C |
| ATOM | 4315 | CD | GLU | C | 49 | -3.494 | 87.460 | -14.070 | 1.00 39.47 | C |
| ATOM | 4316 | OE1 | GLU | C | 49 | -4.046 | 88.589 | -14.007 | 1.00 38.42 | O |
| ATOM | 4317 | OE2 | GLU | C | 49 | -3.908 | 86.544 | -14.820 | 1.00 39.99 | O |
| ATOM | 4318 | C | GLU | C | 49 | 1.157 | 89.018 | -13.044 | 1.00 34.07 | C |
| ATOM | 4319 | O | GLU | C | 49 | 1.911 | 88.953 | -14.017 | 1.00 34.08 | O |
| ATOM | 4320 | N | LYS | C | 50 | 1.151 | 90.055 | -12.212 | 1.00 33.68 | N |
| ATOM | 4321 | CA | LYS | C | 50 | 2.091 | 91.158 | -12.428 | 1.00 34.45 | C |
| ATOM | 4322 | CB | LYS | C | 50 | 1.676 | 92.423 | -11.661 | 1.00 33.19 | C |
| ATOM | 4323 | CG | LYS | C | 50 | 2.628 | 93.587 | -11.912 | 1.00 32.71 | C |
| ATOM | 4324 | CD | LYS | C | 50 | 2.271 | 94.845 | -11.113 | 1.00 34.25 | C |
| ATOM | 4325 | CE | LYS | C | 50 | 3.349 | 95.917 | -11.323 | 1.00 34.07 | C |
| ATOM | 4326 | NZ | LYS | C | 50 | 3.109 | 97.199 | -10.604 | 1.00 33.91 | N |
| ATOM | 4327 | C | LYS | C | 50 | 3.502 | 90.750 | -11.994 | 1.00 34.60 | C |
| ATOM | 4328 | O | LYS | C | 50 | 4.489 | 91.191 | -12.587 | 1.00 34.03 | O |
| ATOM | 4329 | N | LEU | C | 51 | 3.597 | 89.922 | -10.950 | 1.00 35.73 | N |
| ATOM | 4330 | CA | LEU | C | 51 | 4.901 | 89.462 | -10.468 | 1.00 35.74 | C |
| ATOM | 4331 | CB | LEU | C | 51 | 4.735 | 88.601 | -9.207 | 1.00 35.13 | C |
| ATOM | 4332 | CG | LEU | C | 51 | 4.246 | 89.450 | -8.019 | 1.00 34.76 | C |
| ATOM | 4333 | CD1 | LEU | C | 51 | 4.236 | 88.624 | -6.750 | 1.00 34.51 | C |
| ATOM | 4334 | CD2 | LEU | C | 51 | 5.155 | 90.664 | -7.838 | 1.00 34.31 | C |
| ATOM | 4335 | C | LEU | C | 51 | 5.545 | 88.693 | -11.620 | 1.00 35.68 | C |
| ATOM | 4336 | O | LEU | C | 51 | 6.737 | 88.878 | -11.920 | 1.00 33.76 | O |
| ATOM | 4337 | N | LEU | C | 52 | 4.768 | 87.826 | -12.268 | 1.00 36.01 | N |
| ATOM | 4338 | CA | LEU | C | 52 | 5.290 | 87.153 | -13.451 | 1.00 36.22 | C |
| ATOM | 4339 | CB | LEU | C | 52 | 4.255 | 86.197 | -14.042 | 1.00 35.25 | C |
| ATOM | 4340 | CG | LEU | C | 52 | 3.872 | 84.986 | -13.187 | 1.00 35.22 | C |
| ATOM | 4341 | CD1 | LEU | C | 52 | 2.817 | 85.389 | -12.166 | 1.00 34.52 | C |
| ATOM | 4342 | CD2 | LEU | C | 52 | 3.324 | 83.873 | -14.081 | 1.00 34.26 | C |
| ATOM | 4343 | C | LEU | C | 52 | 5.405 | 88.418 | -14.301 | 1.00 36.69 | C |
| ATOM | 4344 | O | LEU | C | 52 | 4.532 | 89.276 | -14.220 | 1.00 37.74 | O |
| ATOM | 4345 | N | GLU | C | 53 | 6.470 | 88.554 | -15.077 | 1.00 37.34 | N |
| ATOM | 4346 | CA | GLU | C | 53 | 6.737 | 89.755 | -15.891 | 1.00 37.99 | C |
| ATOM | 4347 | CB | GLU | C | 53 | 5.937 | 90.995 | -15.438 | 1.00 38.94 | C |
| ATOM | 4348 | CG | GLU | C | 53 | 4.504 | 91.141 | -15.990 | 1.00 40.52 | C |
| ATOM | 4349 | CD | GLU | C | 53 | 4.413 | 91.107 | -17.514 | 1.00 41.15 | C |
| ATOM | 4350 | OE1 | GLU | C | 53 | 5.410 | 91.422 | -18.207 | 1.00 41.10 | O |
| ATOM | 4351 | OE2 | GLU | C | 53 | 3.316 | 90.778 | -18.020 | 1.00 41.91 | O |
| ATOM | 4352 | C | GLU | C | 53 | 8.206 | 90.029 | -15.602 | 1.00 37.64 | C |
| ATOM | 4353 | O | GLU | C | 53 | 8.937 | 90.556 | -16.446 | 1.00 37.03 | O |

FIGURE 9 (cont.)

| | | | | | | | | | | |
|---|---|---|---|---|---|---|---|---|---|---|
| ATOM | 4354 | N | GLN | C | 54 | 8.610 | 89.696 | -14.375 | 1.00 37.46 | N |
| ATOM | 4355 | CA | GLN | C | 54 | 9.999 | 89.833 | -13.945 | 1.00 37.01 | C |
| ATOM | 4356 | CB | GLN | C | 54 | 10.077 | 90.243 | -12.473 | 1.00 37.86 | C |
| ATOM | 4357 | CG | GLN | C | 54 | 9.464 | 91.605 | -12.185 | 1.00 41.01 | C |
| ATOM | 4358 | CD | GLN | C | 54 | 9.421 | 91.932 | -10.701 | 1.00 42.49 | C |
| ATOM | 4359 | OE1 | GLN | C | 54 | 8.781 | 92.908 | -10.289 | 1.00 43.58 | O |
| ATOM | 4360 | NE2 | GLN | C | 54 | 10.103 | 91.121 | -9.887 | 1.00 42.59 | N |
| ATOM | 4361 | C | GLN | C | 54 | 10.564 | 88.426 | -14.105 | 1.00 36.06 | C |
| ATOM | 4362 | O | GLN | C | 54 | 11.781 | 88.232 | -14.230 | 1.00 34.18 | O |
| ATOM | 4363 | N | LEU | C | 55 | 9.646 | 87.457 | -14.114 | 1.00 35.03 | N |
| ATOM | 4364 | CA | LEU | C | 55 | 9.988 | 86.048 | -14.234 | 1.00 34.64 | C |
| ATOM | 4365 | CB | LEU | C | 55 | 8.952 | 85.186 | -13.509 | 1.00 33.45 | C |
| ATOM | 4366 | CG | LEU | C | 55 | 8.708 | 85.565 | -12.046 | 1.00 32.06 | C |
| ATOM | 4367 | CD1 | LEU | C | 55 | 7.838 | 84.507 | -11.392 | 1.00 31.15 | C |
| ATOM | 4368 | CD2 | LEU | C | 55 | 10.049 | 85.699 | -11.318 | 1.00 30.53 | C |
| ATOM | 4369 | C | LEU | C | 55 | 10.067 | 85.636 | -15.685 | 1.00 35.14 | C |
| ATOM | 4370 | O | LEU | C | 55 | 10.004 | 86.472 | -16.585 | 1.00 35.90 | O |
| ATOM | 4371 | N | ASN | C | 56 | 10.176 | 84.342 | -15.930 | 1.00 36.24 | N |
| ATOM | 4372 | CA | ASN | C | 56 | 10.300 | 83.900 | -17.306 | 1.00 37.36 | C |
| ATOM | 4373 | CB | ASN | C | 56 | 11.768 | 83.650 | -17.608 | 1.00 38.72 | C |
| ATOM | 4374 | CG | ASN | C | 56 | 12.061 | 83.736 | -19.059 | 1.00 41.12 | C |
| ATOM | 4375 | OD1 | ASN | C | 56 | 11.477 | 83.004 | -19.867 | 1.00 43.22 | O |
| ATOM | 4376 | ND2 | ASN | C | 56 | 12.961 | 84.646 | -19.426 | 1.00 43.01 | N |
| ATOM | 4377 | C | ASN | C | 56 | 9.506 | 82.645 | -17.584 | 1.00 36.89 | C |
| ATOM | 4378 | O | ASN | C | 56 | 9.889 | 81.824 | -18.418 | 1.00 37.24 | O |
| ATOM | 4379 | N | GLN | C | 57 | 8.391 | 82.505 | -16.884 | 1.00 37.47 | N |
| ATOM | 4380 | CA | GLN | C | 57 | 7.541 | 81.338 | -17.024 | 1.00 38.13 | C |
| ATOM | 4381 | CB | GLN | C | 57 | 6.602 | 81.254 | -15.823 | 1.00 37.12 | C |
| ATOM | 4382 | CG | GLN | C | 57 | 7.327 | 81.166 | -14.494 | 1.00 36.05 | C |
| ATOM | 4383 | CD | GLN | C | 57 | 8.130 | 79.892 | -14.373 | 1.00 35.66 | C |
| ATOM | 4384 | OE1 | GLN | C | 57 | 7.562 | 78.789 | -14.365 | 1.00 34.81 | O |
| ATOM | 4385 | NE2 | GLN | C | 57 | 9.461 | 80.026 | -14.287 | 1.00 33.63 | N |
| ATOM | 4386 | C | GLN | C | 57 | 6.727 | 81.341 | -18.311 | 1.00 39.87 | C |
| ATOM | 4387 | O | GLN | C | 57 | 5.903 | 82.233 | -18.537 | 1.00 41.17 | O |
| ATOM | 4388 | N | PRO | C | 58 | 6.958 | 80.348 | -19.183 | 1.00 41.22 | N |
| ATOM | 4389 | CD | PRO | C | 58 | 8.092 | 79.400 | -19.150 | 1.00 41.83 | C |
| ATOM | 4390 | CA | PRO | C | 58 | 6.221 | 80.249 | -20.452 | 1.00 42.01 | C |
| ATOM | 4391 | CB | PRO | C | 58 | 6.795 | 78.985 | -21.079 | 1.00 41.81 | C |
| ATOM | 4392 | CG | PRO | C | 58 | 8.245 | 79.013 | -20.609 | 1.00 42.03 | C |
| ATOM | 4393 | C | PRO | C | 58 | 4.709 | 80.135 | -20.200 | 1.00 42.74 | C |
| ATOM | 4394 | O | PRO | C | 58 | 3.883 | 80.523 | -21.043 | 1.00 43.34 | O |
| ATOM | 4395 | N | GLU | C | 59 | 4.355 | 79.605 | -19.032 | 1.00 42.74 | N |
| ATOM | 4396 | CA | GLU | C | 59 | 2.956 | 79.431 | -18.661 | 1.00 42.68 | C |
| ATOM | 4397 | CB | GLU | C | 59 | 2.559 | 77.958 | -18.766 | 1.00 44.23 | C |
| ATOM | 4398 | CG | GLU | C | 59 | 2.620 | 77.406 | -20.186 | 1.00 46.31 | C |
| ATOM | 4399 | CD | GLU | C | 59 | 1.606 | 78.084 | -21.099 | 1.00 47.95 | C |
| ATOM | 4400 | OE1 | GLU | C | 59 | 0.502 | 77.520 | -21.267 | 1.00 48.80 | O |
| ATOM | 4401 | OE2 | GLU | C | 59 | 1.906 | 79.185 | -21.635 | 1.00 48.33 | O |
| ATOM | 4402 | C | GLU | C | 59 | 2.731 | 79.899 | -17.236 | 1.00 42.21 | C |
| ATOM | 4403 | O | GLU | C | 59 | 3.592 | 79.711 | -16.360 | 1.00 42.67 | O |
| ATOM | 4404 | N | ALA | C | 60 | 1.578 | 80.514 | -17.001 | 1.00 40.61 | N |
| ATOM | 4405 | CA | ALA | C | 60 | 1.247 | 80.971 | -15.665 | 1.00 39.23 | C |
| ATOM | 4406 | CB | ALA | C | 60 | 0.479 | 82.285 | -15.734 | 1.00 38.83 | C |
| ATOM | 4407 | C | ALA | C | 60 | 0.392 | 79.900 | -14.993 | 1.00 38.63 | C |
| ATOM | 4408 | O | ALA | C | 60 | -0.799 | 79.790 | -15.284 | 1.00 38.38 | O |
| ATOM | 4409 | N | HIS | C | 61 | 1.004 | 79.104 | -14.114 | 1.00 37.68 | N |
| ATOM | 4410 | CA | HIS | C | 61 | 0.285 | 78.058 | -13.374 | 1.00 37.33 | C |
| ATOM | 4411 | CB | HIS | C | 61 | 1.176 | 76.823 | -13.149 | 1.00 38.48 | C |
| ATOM | 4412 | CG | HIS | C | 61 | 1.797 | 76.267 | -14.395 | 1.00 40.69 | C |
| ATOM | 4413 | CD2 | HIS | C | 61 | 3.097 | 76.135 | -14.757 | 1.00 41.63 | C |
| ATOM | 4414 | ND1 | HIS | C | 61 | 1.058 | 75.693 | -15.411 | 1.00 41.58 | N |
| ATOM | 4415 | CE1 | HIS | C | 61 | 1.875 | 75.227 | -16.341 | 1.00 41.71 | C |
| ATOM | 4416 | NE2 | HIS | C | 61 | 3.119 | 75.481 | -15.968 | 1.00 41.94 | N |
| ATOM | 4417 | C | HIS | C | 61 | -0.095 | 78.636 | -11.996 | 1.00 35.99 | C |
| ATOM | 4418 | O | HIS | C | 61 | 0.715 | 78.604 | -11.069 | 1.00 35.40 | O |

FIGURE 9 (cont.)

```
ATOM   4419  N    LEU C   62      -1.313  79.156 -11.854  1.00 34.23           N
ATOM   4420  CA   LEU C   62      -1.745  79.740 -10.579  1.00 32.57           C
ATOM   4421  CB   LEU C   62      -2.160  81.201 -10.794  1.00 31.83           C
ATOM   4422  CG   LEU C   62      -1.169  82.089 -11.558  1.00 31.23           C
ATOM   4423  CD1  LEU C   62      -1.879  83.360 -12.010  1.00 31.15           C
ATOM   4424  CD2  LEU C   62       0.048  82.408 -10.696  1.00 29.88           C
ATOM   4425  C    LEU C   62      -2.907  78.960  -9.960  1.00 31.78           C
ATOM   4426  O    LEU C   62      -3.823  78.556 -10.675  1.00 31.10           O
ATOM   4427  N    TYR C   63      -2.866  78.752  -8.639  1.00 31.57           N
ATOM   4428  CA   TYR C   63      -3.920  78.012  -7.926  1.00 31.86           C
ATOM   4429  CB   TYR C   63      -3.506  76.549  -7.727  1.00 30.41           C
ATOM   4430  CG   TYR C   63      -3.162  75.807  -9.000  1.00 29.78           C
ATOM   4431  CD1  TYR C   63      -1.949  76.030  -9.658  1.00 29.60           C
ATOM   4432  CE1  TYR C   63      -1.646  75.374 -10.853  1.00 28.67           C
ATOM   4433  CD2  TYR C   63      -4.064  74.907  -9.566  1.00 28.17           C
ATOM   4434  CE2  TYR C   63      -3.775  74.248 -10.753  1.00 27.94           C
ATOM   4435  CZ   TYR C   63      -2.569  74.486 -11.394  1.00 28.11           C
ATOM   4436  OH   TYR C   63      -2.301  73.857 -12.583  1.00 26.79           O
ATOM   4437  C    TYR C   63      -4.291  78.582  -6.549  1.00 32.91           C
ATOM   4438  O    TYR C   63      -3.419  78.820  -5.718  1.00 33.07           O
ATOM   4439  N    GLN C   64      -5.591  78.783  -6.311  1.00 34.33           N
ATOM   4440  CA   GLN C   64      -6.099  79.284  -5.021  1.00 34.22           C
ATOM   4441  CB   GLN C   64      -7.495  79.893  -5.198  1.00 34.65           C
ATOM   4442  CG   GLN C   64      -8.130  80.516  -3.935  1.00 37.45           C
ATOM   4443  CD   GLN C   64      -8.714  79.487  -2.958  1.00 38.85           C
ATOM   4444  OE1  GLN C   64      -9.220  78.429  -3.366  1.00 38.89           O
ATOM   4445  NE2  GLN C   64      -8.667  79.809  -1.661  1.00 38.28           N
ATOM   4446  C    GLN C   64      -6.191  78.105  -4.059  1.00 33.78           C
ATOM   4447  O    GLN C   64      -6.797  77.078  -4.381  1.00 34.43           O
ATOM   4448  N    ILE C   65      -5.599  78.246  -2.878  1.00 33.46           N
ATOM   4449  CA   ILE C   65      -5.618  77.165  -1.891  1.00 32.13           C
ATOM   4450  CB   ILE C   65      -4.411  76.201  -2.076  1.00 32.68           C
ATOM   4451  CG2  ILE C   65      -4.521  75.426  -3.385  1.00 32.36           C
ATOM   4452  CG1  ILE C   65      -3.101  76.991  -2.023  1.00 33.56           C
ATOM   4453  CD1  ILE C   65      -2.351  76.872  -0.667  1.00 34.79           C
ATOM   4454  C    ILE C   65      -5.552  77.689  -0.462  1.00 31.20           C
ATOM   4455  O    ILE C   65      -4.576  78.335  -0.081  1.00 31.24           O
ATOM   4456  N    ASP C   66      -6.587  77.430   0.328  1.00 30.92           N
ATOM   4457  CA   ASP C   66      -6.572  77.856   1.725  1.00 30.52           C
ATOM   4458  CB   ASP C   66      -7.922  78.432   2.160  1.00 30.80           C
ATOM   4459  CG   ASP C   66      -7.837  79.169   3.484  1.00 30.42           C
ATOM   4460  OD1  ASP C   66      -8.111  80.393   3.506  1.00 31.11           O
ATOM   4461  OD2  ASP C   66      -7.493  78.525   4.502  1.00 30.37           O
ATOM   4462  C    ASP C   66      -6.282  76.587   2.506  1.00 29.90           C
ATOM   4463  O    ASP C   66      -7.142  75.701   2.617  1.00 30.08           O
ATOM   4464  N    VAL C   67      -5.063  76.508   3.039  1.00 28.63           N
ATOM   4465  CA   VAL C   67      -4.599  75.342   3.792  1.00 26.84           C
ATOM   4466  CB   VAL C   67      -3.133  75.548   4.262  1.00 25.42           C
ATOM   4467  CG1  VAL C   67      -2.239  75.784   3.056  1.00 23.38           C
ATOM   4468  CG2  VAL C   67      -3.031  76.732   5.211  1.00 24.87           C
ATOM   4469  C    VAL C   67      -5.460  74.906   4.974  1.00 26.83           C
ATOM   4470  O    VAL C   67      -5.159  73.906   5.609  1.00 27.30           O
ATOM   4471  N    GLN C   68      -6.524  75.643   5.278  1.00 27.98           N
ATOM   4472  CA   GLN C   68      -7.418  75.252   6.376  1.00 28.90           C
ATOM   4473  CB   GLN C   68      -8.299  76.420   6.844  1.00 29.51           C
ATOM   4474  CG   GLN C   68      -7.566  77.581   7.450  1.00 32.48           C
ATOM   4475  CD   GLN C   68      -8.197  78.035   8.756  1.00 33.68           C
ATOM   4476  OE1  GLN C   68      -8.244  77.278   9.736  1.00 34.96           O
ATOM   4477  NE2  GLN C   68      -8.683  79.275   8.781  1.00 33.43           N
ATOM   4478  C    GLN C   68      -8.357  74.166   5.869  1.00 29.21           C
ATOM   4479  O    GLN C   68      -8.903  73.390   6.651  1.00 28.21           O
ATOM   4480  N    SER C   69      -8.561  74.138   4.553  1.00 30.82           N
ATOM   4481  CA   SER C   69      -9.466  73.167   3.926  1.00 31.43           C
ATOM   4482  CB   SER C   69     -10.236  73.818   2.769  1.00 31.77           C
ATOM   4483  OG   SER C   69     -10.957  72.836   2.030  1.00 32.06           O
```

FIGURE 9 (cont.)

```
ATOM   4484  C    SER C  69   -8.788  71.916   3.394  1.00 31.48           C
ATOM   4485  O    SER C  69   -7.970  71.981   2.464  1.00 31.49           O
ATOM   4486  N    ASP C  70   -9.154  70.777   3.969  1.00 31.39           N
ATOM   4487  CA   ASP C  70   -8.605  69.503   3.546  1.00 32.28           C
ATOM   4488  CB   ASP C  70   -9.064  68.384   4.480  1.00 32.29           C
ATOM   4489  CG   ASP C  70   -8.516  68.533   5.877  1.00 32.89           C
ATOM   4490  OD1  ASP C  70   -7.783  69.517   6.125  1.00 31.21           O
ATOM   4491  OD2  ASP C  70   -8.821  67.660   6.727  1.00 33.96           O
ATOM   4492  C    ASP C  70   -9.098  69.201   2.142  1.00 33.18           C
ATOM   4493  O    ASP C  70   -8.840  68.113   1.613  1.00 33.31           O
ATOM   4494  N    GLU C  71   -9.808  70.157   1.537  1.00 33.13           N
ATOM   4495  CA   GLU C  71  -10.326  69.975   0.181  1.00 33.21           C
ATOM   4496  CB   GLU C  71  -11.823  70.297   0.125  1.00 35.83           C
ATOM   4497  CG   GLU C  71  -12.705  69.069   0.304  1.00 38.20           C
ATOM   4498  CD   GLU C  71  -14.187  69.352   0.059  1.00 41.42           C
ATOM   4499  OE1  GLU C  71  -14.993  68.378   0.118  1.00 41.90           O
ATOM   4500  OE2  GLU C  71  -14.546  70.534  -0.194  1.00 41.29           O
ATOM   4501  C    GLU C  71   -9.569  70.818  -0.836  1.00 31.49           C
ATOM   4502  O    GLU C  71   -9.268  70.365  -1.951  1.00 30.02           O
ATOM   4503  N    GLU C  72   -9.249  72.045  -0.461  1.00 31.19           N
ATOM   4504  CA   GLU C  72   -8.510  72.905  -1.371  1.00 31.01           C
ATOM   4505  CB   GLU C  72   -8.535  74.336  -0.856  1.00 30.13           C
ATOM   4506  CG   GLU C  72   -9.963  74.792  -0.635  1.00 32.24           C
ATOM   4507  CD   GLU C  72  -10.102  76.286  -0.578  1.00 32.06           C
ATOM   4508  OE1  GLU C  72   -9.294  76.967  -1.242  1.00 32.94           O
ATOM   4509  OE2  GLU C  72  -11.035  76.779   0.108  1.00 33.64           O
ATOM   4510  C    GLU C  72   -7.085  72.396  -1.527  1.00 31.10           C
ATOM   4511  O    GLU C  72   -6.428  72.652  -2.546  1.00 32.50           O
ATOM   4512  N    VAL C  73   -6.611  71.653  -0.529  1.00 30.26           N
ATOM   4513  CA   VAL C  73   -5.262  71.102  -0.576  1.00 29.86           C
ATOM   4514  CB   VAL C  73   -4.740  70.764   0.838  1.00 29.19           C
ATOM   4515  CG1  VAL C  73   -3.354  70.147   0.749  1.00 27.48           C
ATOM   4516  CG2  VAL C  73   -4.720  72.027   1.697  1.00 28.60           C
ATOM   4517  C    VAL C  73   -5.283  69.832  -1.395  1.00 30.47           C
ATOM   4518  O    VAL C  73   -4.460  69.622  -2.291  1.00 30.87           O
ATOM   4519  N    ILE C  74   -6.247  68.982  -1.079  1.00 31.30           N
ATOM   4520  CA   ILE C  74   -6.405  67.720  -1.755  1.00 32.08           C
ATOM   4521  CB   ILE C  74   -7.474  66.883  -1.035  1.00 33.40           C
ATOM   4522  CG2  ILE C  74   -8.840  67.510  -1.246  1.00 34.25           C
ATOM   4523  CG1  ILE C  74   -7.437  65.441  -1.532  1.00 34.72           C
ATOM   4524  CD1  ILE C  74   -8.224  64.479  -0.651  1.00 36.38           C
ATOM   4525  C    ILE C  74   -6.761  67.938  -3.228  1.00 31.34           C
ATOM   4526  O    ILE C  74   -6.154  67.326  -4.109  1.00 32.01           O
ATOM   4527  N    ASN C  75   -7.718  68.810  -3.522  1.00 30.92           N
ATOM   4528  CA   ASN C  75   -8.056  69.033  -4.926  1.00 30.85           C
ATOM   4529  CB   ASN C  75   -9.442  69.664  -5.068  1.00 31.40           C
ATOM   4530  CG   ASN C  75  -10.555  68.749  -4.584  1.00 31.89           C
ATOM   4531  OD1  ASN C  75  -10.465  67.522  -4.719  1.00 32.61           O
ATOM   4532  ND2  ASN C  75  -11.620  69.339  -4.029  1.00 31.28           N
ATOM   4533  C    ASN C  75   -7.005  69.929  -5.570  1.00 31.33           C
ATOM   4534  O    ASN C  75   -6.674  69.781  -6.752  1.00 30.67           O
ATOM   4535  N    GLY C  76   -6.459  70.847  -4.779  1.00 32.54           N
ATOM   4536  CA   GLY C  76   -5.445  71.754  -5.293  1.00 32.91           C
ATOM   4537  C    GLY C  76   -4.255  71.029  -5.898  1.00 33.01           C
ATOM   4538  O    GLY C  76   -3.869  71.282  -7.051  1.00 33.48           O
ATOM   4539  N    PHE C  77   -3.663  70.120  -5.132  1.00 32.07           N
ATOM   4540  CA   PHE C  77   -2.517  69.378  -5.627  1.00 31.74           C
ATOM   4541  CB   PHE C  77   -1.793  68.678  -4.472  1.00 30.67           C
ATOM   4542  CG   PHE C  77   -0.799  69.555  -3.780  1.00 29.08           C
ATOM   4543  CD1  PHE C  77   -1.221  70.546  -2.910  1.00 28.05           C
ATOM   4544  CD2  PHE C  77    0.558  69.446  -4.075  1.00 28.03           C
ATOM   4545  CE1  PHE C  77   -0.308  71.433  -2.342  1.00 28.56           C
ATOM   4546  CE2  PHE C  77    1.480  70.321  -3.518  1.00 28.33           C
ATOM   4547  CZ   PHE C  77    1.047  71.322  -2.649  1.00 28.84           C
ATOM   4548  C    PHE C  77   -2.903  68.367  -6.689  1.00 32.19           C
```

FIGURE 9 (cont.)

| | | | | | | | | | | |
|---|---|---|---|---|---|---|---|---|---|---|
| ATOM | 4549 | O | PHE | C | 77 | -2.128 | 68.099 | -7.614 | 1.00 32.10 | O |
| ATOM | 4550 | N | GLU | C | 78 | -4.096 | 67.795 | -6.565 | 1.00 33.17 | N |
| ATOM | 4551 | CA | GLU | C | 78 | -4.536 | 66.813 | -7.554 | 1.00 34.17 | C |
| ATOM | 4552 | CB | GLU | C | 78 | -5.896 | 66.233 | -7.176 | 1.00 35.04 | C |
| ATOM | 4553 | CG | GLU | C | 78 | -6.273 | 65.069 | -8.056 | 1.00 36.69 | C |
| ATOM | 4554 | CD | GLU | C | 78 | -7.752 | 64.761 | -8.015 | 1.00 39.16 | C |
| ATOM | 4555 | OE1 | GLU | C | 78 | -8.153 | 63.762 | -8.664 | 1.00 41.39 | O |
| ATOM | 4556 | OE2 | GLU | C | 78 | -8.515 | 65.509 | -7.347 | 1.00 39.56 | O |
| ATOM | 4557 | C | GLU | C | 78 | -4.641 | 67.491 | -8.917 | 1.00 33.22 | C |
| ATOM | 4558 | O | GLU | C | 78 | -4.296 | 66.915 | -9.945 | 1.00 32.77 | O |
| ATOM | 4559 | N | GLN | C | 79 | -5.125 | 68.725 | -8.905 | 1.00 33.72 | N |
| ATOM | 4560 | CA | GLN | C | 79 | -5.279 | 69.515 | -10.117 | 1.00 34.37 | C |
| ATOM | 4561 | CB | GLN | C | 79 | -6.056 | 70.800 | -9.797 | 1.00 35.51 | C |
| ATOM | 4562 | CG | GLN | C | 79 | -6.690 | 71.463 | -11.008 | 1.00 35.60 | C |
| ATOM | 4563 | CD | GLN | C | 79 | -7.656 | 70.524 | -11.703 | 1.00 35.64 | C |
| ATOM | 4564 | OE1 | GLN | C | 79 | -8.702 | 70.172 | -11.150 | 1.00 34.89 | O |
| ATOM | 4565 | NE2 | GLN | C | 79 | -7.299 | 70.093 | -12.912 | 1.00 35.63 | N |
| ATOM | 4566 | C | GLN | C | 79 | -3.893 | 69.867 | -10.656 | 1.00 35.30 | C |
| ATOM | 4567 | O | GLN | C | 79 | -3.607 | 69.689 | -11.847 | 1.00 35.74 | O |
| ATOM | 4568 | N | ILE | C | 80 | -3.028 | 70.376 | -9.782 | 1.00 35.66 | N |
| ATOM | 4569 | CA | ILE | C | 80 | -1.677 | 70.736 | -10.200 | 1.00 35.78 | C |
| ATOM | 4570 | CB | ILE | C | 80 | -0.775 | 71.071 | -8.993 | 1.00 36.31 | C |
| ATOM | 4571 | CG2 | ILE | C | 80 | 0.668 | 71.277 | -9.475 | 1.00 36.41 | C |
| ATOM | 4572 | CG1 | ILE | C | 80 | -1.305 | 72.316 | -8.264 | 1.00 35.95 | C |
| ATOM | 4573 | CD1 | ILE | C | 80 | -0.571 | 72.622 | -6.954 | 1.00 35.18 | C |
| ATOM | 4574 | C | ILE | C | 80 | -1.045 | 69.554 | -10.921 | 1.00 36.16 | C |
| ATOM | 4575 | O | ILE | C | 80 | -0.455 | 69.700 | -11.998 | 1.00 36.63 | O |
| ATOM | 4576 | N | GLY | C | 81 | -1.168 | 68.380 | -10.314 | 1.00 36.11 | N |
| ATOM | 4577 | CA | GLY | C | 81 | -0.590 | 67.189 | -10.897 | 1.00 37.17 | C |
| ATOM | 4578 | C | GLY | C | 81 | -1.307 | 66.819 | -12.170 | 1.00 39.11 | C |
| ATOM | 4579 | O | GLY | C | 81 | -0.867 | 65.926 | -12.909 | 1.00 38.70 | O |
| ATOM | 4580 | N | LYS | C | 82 | -2.422 | 67.503 | -12.425 | 1.00 40.97 | N |
| ATOM | 4581 | CA | LYS | C | 82 | -3.222 | 67.258 | -13.626 | 1.00 42.43 | C |
| ATOM | 4582 | CB | LYS | C | 82 | -4.689 | 67.618 | -13.366 | 1.00 43.21 | C |
| ATOM | 4583 | CG | LYS | C | 82 | -5.659 | 66.432 | -13.392 | 1.00 43.58 | C |
| ATOM | 4584 | CD | LYS | C | 82 | -5.353 | 65.426 | -12.305 | 1.00 44.32 | C |
| ATOM | 4585 | CE | LYS | C | 82 | -6.448 | 64.366 | -12.266 | 1.00 45.30 | C |
| ATOM | 4586 | NZ | LYS | C | 82 | -7.785 | 65.022 | -12.120 | 1.00 44.14 | N |
| ATOM | 4587 | C | LYS | C | 82 | -2.690 | 68.083 | -14.801 | 1.00 43.31 | C |
| ATOM | 4588 | O | LYS | C | 82 | -2.345 | 67.528 | -15.850 | 1.00 43.90 | O |
| ATOM | 4589 | N | ASP | C | 83 | -2.619 | 69.405 | -14.644 | 1.00 43.88 | N |
| ATOM | 4590 | CA | ASP | C | 83 | -2.112 | 70.236 | -15.741 | 1.00 44.46 | C |
| ATOM | 4591 | CB | ASP | C | 83 | -2.531 | 71.703 | -15.584 | 1.00 46.77 | C |
| ATOM | 4592 | CG | ASP | C | 83 | -1.844 | 72.618 | -16.608 | 1.00 49.05 | C |
| ATOM | 4593 | OD1 | ASP | C | 83 | -0.727 | 73.123 | -16.313 | 1.00 49.61 | O |
| ATOM | 4594 | OD2 | ASP | C | 83 | -2.412 | 72.820 | -17.719 | 1.00 49.49 | O |
| ATOM | 4595 | C | ASP | C | 83 | -0.601 | 70.172 | -15.857 | 1.00 43.35 | C |
| ATOM | 4596 | O | ASP | C | 83 | -0.037 | 70.511 | -16.903 | 1.00 43.16 | O |
| ATOM | 4597 | N | VAL | C | 84 | 0.058 | 69.768 | -14.778 | 1.00 42.31 | N |
| ATOM | 4598 | CA | VAL | C | 84 | 1.514 | 69.654 | -14.780 | 1.00 41.48 | C |
| ATOM | 4599 | CB | VAL | C | 84 | 2.164 | 70.666 | -13.805 | 1.00 41.56 | C |
| ATOM | 4600 | CG1 | VAL | C | 84 | 3.504 | 71.149 | -14.356 | 1.00 41.84 | C |
| ATOM | 4601 | CG2 | VAL | C | 84 | 1.233 | 71.839 | -13.570 | 1.00 42.37 | C |
| ATOM | 4602 | C | VAL | C | 84 | 1.800 | 68.238 | -14.295 | 1.00 40.72 | C |
| ATOM | 4603 | O | VAL | C | 84 | 1.055 | 67.692 | -13.475 | 1.00 41.49 | O |
| ATOM | 4604 | N | GLY | C | 85 | 2.862 | 67.625 | -14.797 | 1.00 39.80 | N |
| ATOM | 4605 | CA | GLY | C | 85 | 3.174 | 66.270 | -14.360 | 1.00 37.71 | C |
| ATOM | 4606 | C | GLY | C | 85 | 3.563 | 66.170 | -12.886 | 1.00 35.62 | C |
| ATOM | 4607 | O | GLY | C | 85 | 3.011 | 66.858 | -12.013 | 1.00 34.03 | O |
| ATOM | 4608 | N | ASN | C | 86 | 4.517 | 65.286 | -12.606 | 1.00 34.27 | N |
| ATOM | 4609 | CA | ASN | C | 86 | 4.999 | 65.096 | -11.245 | 1.00 30.86 | C |
| ATOM | 4610 | CB | ASN | C | 86 | 5.723 | 63.759 | -11.145 | 1.00 30.25 | C |
| ATOM | 4611 | CG | ASN | C | 86 | 4.757 | 62.585 | -11.217 | 1.00 29.96 | C |
| ATOM | 4612 | OD1 | ASN | C | 86 | 3.645 | 62.656 | -10.682 | 1.00 29.46 | O |
| ATOM | 4613 | ND2 | ASN | C | 86 | 5.176 | 61.500 | -11.859 | 1.00 28.43 | N |

FIGURE 9 (cont.)

```
ATOM   4614  C    ASN C  86       5.915  66.258 -10.915  1.00 28.74           C
ATOM   4615  O    ASN C  86       6.349  66.981 -11.814  1.00 28.78           O
ATOM   4616  N    ILE C  87       6.205  66.462  -9.638  1.00 27.32           N
ATOM   4617  CA   ILE C  87       7.054  67.585  -9.262  1.00 26.08           C
ATOM   4618  CB   ILE C  87       6.292  68.548  -8.339  1.00 25.40           C
ATOM   4619  CG2  ILE C  87       5.093  69.136  -9.088  1.00 24.50           C
ATOM   4620  CG1  ILE C  87       5.828  67.802  -7.085  1.00 23.74           C
ATOM   4621  CD1  ILE C  87       5.010  68.652  -6.146  1.00 22.79           C
ATOM   4622  C    ILE C  87       8.332  67.158  -8.577  1.00 25.59           C
ATOM   4623  O    ILE C  87       8.544  65.972  -8.341  1.00 25.90           O
ATOM   4624  N    ASP C  88       9.178  68.132  -8.260  1.00 24.48           N
ATOM   4625  CA   ASP C  88      10.438  67.848  -7.591  1.00 24.75           C
ATOM   4626  CB   ASP C  88      11.611  68.412  -8.396  1.00 26.45           C
ATOM   4627  CG   ASP C  88      11.655  67.869  -9.807  1.00 27.79           C
ATOM   4628  OD1  ASP C  88      10.966  68.434 -10.686  1.00 27.60           O
ATOM   4629  OD2  ASP C  88      12.371  66.868 -10.037  1.00 29.72           O
ATOM   4630  C    ASP C  88      10.470  68.418  -6.179  1.00 23.36           C
ATOM   4631  O    ASP C  88      11.430  68.200  -5.442  1.00 23.02           O
ATOM   4632  N    GLY C  89       9.425  69.154  -5.804  1.00 22.46           N
ATOM   4633  CA   GLY C  89       9.384  69.714  -4.468  1.00 21.14           C
ATOM   4634  C    GLY C  89       8.397  70.841  -4.237  1.00 20.77           C
ATOM   4635  O    GLY C  89       7.739  71.335  -5.162  1.00 20.74           O
ATOM   4636  N    VAL C  90       8.291  71.239  -2.975  1.00 18.71           N
ATOM   4637  CA   VAL C  90       7.403  72.322  -2.585  1.00 19.36           C
ATOM   4638  CB   VAL C  90       6.088  71.811  -1.958  1.00 19.17           C
ATOM   4639  CG1  VAL C  90       5.242  73.000  -1.514  1.00 17.75           C
ATOM   4640  CG2  VAL C  90       5.318  70.968  -2.958  1.00 20.13           C
ATOM   4641  C    VAL C  90       8.056  73.235  -1.557  1.00 19.07           C
ATOM   4642  O    VAL C  90       8.729  72.775  -0.628  1.00 17.48           O
ATOM   4643  N    TYR C  91       7.876  74.533  -1.753  1.00 19.34           N
ATOM   4644  CA   TYR C  91       8.386  75.503  -0.809  1.00 20.80           C
ATOM   4645  CB   TYR C  91       9.055  76.685  -1.507  1.00 21.74           C
ATOM   4646  CG   TYR C  91       9.689  77.623  -0.506  1.00 23.00           C
ATOM   4647  CD1  TYR C  91      10.916  77.312   0.080  1.00 23.56           C
ATOM   4648  CE1  TYR C  91      11.464  78.108   1.074  1.00 23.71           C
ATOM   4649  CD2  TYR C  91       9.023  78.768  -0.073  1.00 24.33           C
ATOM   4650  CE2  TYR C  91       9.561  79.580   0.928  1.00 26.23           C
ATOM   4651  CZ   TYR C  91      10.784  79.240   1.497  1.00 26.01           C
ATOM   4652  OH   TYR C  91      11.329  80.024   2.495  1.00 25.49           O
ATOM   4653  C    TYR C  91       7.161  76.002  -0.048  1.00 20.16           C
ATOM   4654  O    TYR C  91       6.228  76.530  -0.647  1.00 19.26           O
ATOM   4655  N    HIS C  92       7.179  75.821   1.268  1.00 20.00           N
ATOM   4656  CA   HIS C  92       6.094  76.223   2.161  1.00 19.47           C
ATOM   4657  CB   HIS C  92       5.933  75.141   3.243  1.00 17.63           C
ATOM   4658  CG   HIS C  92       4.816  75.382   4.214  1.00 17.18           C
ATOM   4659  CD2  HIS C  92       3.577  74.841   4.297  1.00 16.52           C
ATOM   4660  ND1  HIS C  92       4.941  76.216   5.303  1.00 19.51           N
ATOM   4661  CE1  HIS C  92       3.829  76.177   6.018  1.00 17.35           C
ATOM   4662  NE2  HIS C  92       2.986  75.349   5.429  1.00 17.08           N
ATOM   4663  C    HIS C  92       6.469  77.565   2.776  1.00 19.95           C
ATOM   4664  O    HIS C  92       7.514  77.690   3.400  1.00 20.81           O
ATOM   4665  N    SER C  93       5.627  78.576   2.586  1.00 19.44           N
ATOM   4666  CA   SER C  93       5.904  79.904   3.132  1.00 19.77           C
ATOM   4667  CB   SER C  93       6.496  80.792   2.035  1.00 20.27           C
ATOM   4668  OG   SER C  93       6.879  82.053   2.543  1.00 21.84           O
ATOM   4669  C    SER C  93       4.590  80.488   3.653  1.00 20.55           C
ATOM   4670  O    SER C  93       4.221  81.634   3.350  1.00 19.31           O
ATOM   4671  N    ILE C  94       3.905  79.673   4.452  1.00 20.33           N
ATOM   4672  CA   ILE C  94       2.603  80.008   5.010  1.00 21.41           C
ATOM   4673  CB   ILE C  94       1.544  79.006   4.497  1.00 21.02           C
ATOM   4674  CG2  ILE C  94       0.260  79.164   5.280  1.00 19.60           C
ATOM   4675  CG1  ILE C  94       1.339  79.186   2.992  1.00 19.64           C
ATOM   4676  CD1  ILE C  94       0.522  78.068   2.350  1.00 20.36           C
ATOM   4677  C    ILE C  94       2.539  79.989   6.534  1.00 22.39           C
ATOM   4678  O    ILE C  94       2.988  79.037   7.167  1.00 21.10           O
```

FIGURE 9 (cont.)

| ATOM | 4679 | N   | ALA | C | 95  | 1.935  | 81.029 | 7.107  | 1.00 | 23.60 | N |
|------|------|-----|-----|---|-----|--------|--------|--------|------|-------|---|
| ATOM | 4680 | CA  | ALA | C | 95  | 1.766  | 81.141 | 8.552  | 1.00 | 23.69 | C |
| ATOM | 4681 | CB  | ALA | C | 95  | 3.079  | 81.525 | 9.194  | 1.00 | 23.86 | C |
| ATOM | 4682 | C   | ALA | C | 95  | 0.701  | 82.188 | 8.885  | 1.00 | 25.93 | C |
| ATOM | 4683 | O   | ALA | C | 95  | 0.510  | 83.156 | 8.143  | 1.00 | 25.91 | O |
| ATOM | 4684 | N   | PHE | C | 96  | -0.002 | 82.005 | 9.997  | 1.00 | 27.62 | N |
| ATOM | 4685 | CA  | PHE | C | 96  | -1.013 | 82.988 | 10.379 | 1.00 | 27.86 | C |
| ATOM | 4686 | CB  | PHE | C | 96  | -2.243 | 82.863 | 9.476  | 1.00 | 27.63 | C |
| ATOM | 4687 | CG  | PHE | C | 96  | -3.275 | 83.932 | 9.720  | 1.00 | 27.07 | C |
| ATOM | 4688 | CD1 | PHE | C | 96  | -3.175 | 85.172 | 9.094  | 1.00 | 26.00 | C |
| ATOM | 4689 | CD2 | PHE | C | 96  | -4.309 | 83.723 | 10.624 | 1.00 | 26.75 | C |
| ATOM | 4690 | CE1 | PHE | C | 96  | -4.086 | 86.183 | 9.371  | 1.00 | 26.45 | C |
| ATOM | 4691 | CE2 | PHE | C | 96  | -5.225 | 84.732 | 10.904 | 1.00 | 26.74 | C |
| ATOM | 4692 | CZ  | PHE | C | 96  | -5.109 | 85.964 | 10.276 | 1.00 | 26.03 | C |
| ATOM | 4693 | C   | PHE | C | 96  | -1.450 | 82.894 | 11.843 | 1.00 | 27.93 | C |
| ATOM | 4694 | O   | PHE | C | 96  | -1.497 | 81.807 | 12.423 | 1.00 | 27.12 | O |
| ATOM | 4695 | N   | ALA | C | 97  | -1.768 | 84.050 | 12.424 | 1.00 | 28.11 | N |
| ATOM | 4696 | CA  | ALA | C | 97  | -2.226 | 84.152 | 13.808 | 1.00 | 29.07 | C |
| ATOM | 4697 | CB  | ALA | C | 97  | -1.053 | 84.070 | 14.754 | 1.00 | 28.69 | C |
| ATOM | 4698 | C   | ALA | C | 97  | -2.941 | 85.484 | 13.995 | 1.00 | 30.06 | C |
| ATOM | 4699 | O   | ALA | C | 97  | -2.557 | 86.487 | 13.390 | 1.00 | 30.59 | O |
| ATOM | 4700 | N   | ASN | C | 98  | -3.978 | 85.505 | 14.827 | 1.00 | 30.63 | N |
| ATOM | 4701 | CA  | ASN | C | 98  | -4.713 | 86.746 | 15.062 | 1.00 | 31.26 | C |
| ATOM | 4702 | CB  | ASN | C | 98  | -5.861 | 86.498 | 16.048 | 1.00 | 30.15 | C |
| ATOM | 4703 | CG  | ASN | C | 98  | -6.924 | 85.558 | 15.479 | 1.00 | 29.72 | C |
| ATOM | 4704 | OD1 | ASN | C | 98  | -7.240 | 84.518 | 16.069 | 1.00 | 27.75 | O |
| ATOM | 4705 | ND2 | ASN | C | 98  | -7.477 | 85.923 | 14.322 | 1.00 | 29.15 | N |
| ATOM | 4706 | C   | ASN | C | 98  | -3.767 | 87.833 | 15.589 | 1.00 | 32.26 | C |
| ATOM | 4707 | O   | ASN | C | 98  | -2.953 | 87.593 | 16.483 | 1.00 | 31.96 | O |
| ATOM | 4708 | N   | MET | C | 99  | -3.871 | 89.027 | 15.016 | 1.00 | 33.06 | N |
| ATOM | 4709 | CA  | MET | C | 99  | -3.018 | 90.139 | 15.417 | 1.00 | 34.02 | C |
| ATOM | 4710 | CB  | MET | C | 99  | -3.427 | 91.414 | 14.671 | 1.00 | 35.15 | C |
| ATOM | 4711 | CG  | MET | C | 99  | -2.425 | 91.853 | 13.607 | 1.00 | 38.87 | C |
| ATOM | 4712 | SD  | MET | C | 99  | -0.855 | 92.466 | 14.310 | 1.00 | 40.71 | S |
| ATOM | 4713 | CE  | MET | C | 99  | -1.245 | 94.232 | 14.419 | 1.00 | 43.57 | C |
| ATOM | 4714 | C   | MET | C | 99  | -3.074 | 90.395 | 16.914 | 1.00 | 34.01 | C |
| ATOM | 4715 | O   | MET | C | 99  | -2.114 | 90.898 | 17.503 | 1.00 | 34.61 | O |
| ATOM | 4716 | N   | GLU | C | 100 | -4.199 | 90.059 | 17.530 | 1.00 | 33.59 | N |
| ATOM | 4717 | CA  | GLU | C | 100 | -4.360 | 90.288 | 18.955 | 1.00 | 33.39 | C |
| ATOM | 4718 | CB  | GLU | C | 100 | -5.809 | 90.028 | 19.372 | 1.00 | 33.64 | C |
| ATOM | 4719 | CG  | GLU | C | 100 | -6.280 | 88.607 | 19.108 | 1.00 | 33.76 | C |
| ATOM | 4720 | CD  | GLU | C | 100 | -7.603 | 88.300 | 19.787 | 1.00 | 34.55 | C |
| ATOM | 4721 | OE1 | GLU | C | 100 | -8.063 | 87.134 | 19.704 | 1.00 | 34.16 | O |
| ATOM | 4722 | OE2 | GLU | C | 100 | -8.182 | 89.225 | 20.405 | 1.00 | 34.71 | O |
| ATOM | 4723 | C   | GLU | C | 100 | -3.427 | 89.428 | 19.802 | 1.00 | 33.02 | C |
| ATOM | 4724 | O   | GLU | C | 100 | -2.989 | 89.852 | 20.871 | 1.00 | 33.16 | O |
| ATOM | 4725 | N   | ASP | C | 101 | -3.126 | 88.219 | 19.341 | 1.00 | 32.65 | N |
| ATOM | 4726 | CA  | ASP | C | 101 | -2.255 | 87.332 | 20.109 | 1.00 | 32.46 | C |
| ATOM | 4727 | CB  | ASP | C | 101 | -2.627 | 85.872 | 19.839 | 1.00 | 33.27 | C |
| ATOM | 4728 | CG  | ASP | C | 101 | -4.076 | 85.571 | 20.172 | 1.00 | 32.96 | C |
| ATOM | 4729 | OD1 | ASP | C | 101 | -4.575 | 86.112 | 21.183 | 1.00 | 32.56 | O |
| ATOM | 4730 | OD2 | ASP | C | 101 | -4.710 | 84.779 | 19.434 | 1.00 | 32.67 | O |
| ATOM | 4731 | C   | ASP | C | 101 | -0.775 | 87.548 | 19.809 | 1.00 | 31.30 | C |
| ATOM | 4732 | O   | ASP | C | 101 | 0.074  | 86.763 | 20.231 | 1.00 | 32.20 | O |
| ATOM | 4733 | N   | LEU | C | 102 | -0.476 | 88.619 | 19.088 | 1.00 | 30.40 | N |
| ATOM | 4734 | CA  | LEU | C | 102 | 0.893  | 88.941 | 18.698 | 1.00 | 29.60 | C |
| ATOM | 4735 | CB  | LEU | C | 102 | 0.966  | 89.073 | 17.175 | 1.00 | 30.07 | C |
| ATOM | 4736 | CG  | LEU | C | 102 | 0.672  | 87.811 | 16.353 | 1.00 | 29.61 | C |
| ATOM | 4737 | CD1 | LEU | C | 102 | 0.694  | 88.157 | 14.874 | 1.00 | 28.94 | C |
| ATOM | 4738 | CD2 | LEU | C | 102 | 1.722  | 86.748 | 16.656 | 1.00 | 29.37 | C |
| ATOM | 4739 | C   | LEU | C | 102 | 1.319  | 90.243 | 19.351 | 1.00 | 28.78 | C |
| ATOM | 4740 | O   | LEU | C | 102 | 2.155  | 90.985 | 18.835 | 1.00 | 27.58 | O |
| ATOM | 4741 | N   | ARG | C | 103 | 0.706  | 90.510 | 20.493 | 1.00 | 30.36 | N |
| ATOM | 4742 | CA  | ARG | C | 103 | 0.961  | 91.704 | 21.285 | 1.00 | 31.12 | C |
| ATOM | 4743 | CB  | ARG | C | 103 | 0.075  | 92.862 | 20.806 | 1.00 | 33.81 | C |

FIGURE 9 (cont.)

| ATOM | 4744 | CG | ARG | C | 103 | -1.432 | 92.538 | 20.828 | 1.00 | 35.58 | C |
|------|------|-----|-----|---|-----|--------|--------|--------|------|-------|---|
| ATOM | 4745 | CD | ARG | C | 103 | -2.306 | 93.806 | 20.725 | 1.00 | 38.94 | C |
| ATOM | 4746 | NE | ARG | C | 103 | -3.022 | 93.941 | 19.448 | 1.00 | 42.23 | N |
| ATOM | 4747 | CZ | ARG | C | 103 | -2.558 | 94.575 | 18.362 | 1.00 | 43.19 | C |
| ATOM | 4748 | NH1 | ARG | C | 103 | -1.361 | 95.160 | 18.362 | 1.00 | 43.47 | N |
| ATOM | 4749 | NH2 | ARG | C | 103 | -3.298 | 94.627 | 17.262 | 1.00 | 43.65 | N |
| ATOM | 4750 | C | ARG | C | 103 | 0.539 | 91.297 | 22.683 | 1.00 | 30.50 | C |
| ATOM | 4751 | O | ARG | C | 103 | -0.138 | 90.276 | 22.865 | 1.00 | 30.15 | O |
| ATOM | 4752 | N | GLY | C | 104 | 0.934 | 92.077 | 23.674 | 1.00 | 30.24 | N |
| ATOM | 4753 | CA | GLY | C | 104 | 0.547 | 91.749 | 25.032 | 1.00 | 30.74 | C |
| ATOM | 4754 | C | GLY | C | 104 | 1.167 | 90.504 | 25.644 | 1.00 | 30.81 | C |
| ATOM | 4755 | O | GLY | C | 104 | 2.244 | 90.058 | 25.238 | 1.00 | 31.41 | O |
| ATOM | 4756 | N | ARG | C | 105 | 0.462 | 89.947 | 26.630 | 1.00 | 30.78 | N |
| ATOM | 4757 | CA | ARG | C | 105 | 0.900 | 88.772 | 27.375 | 1.00 | 29.52 | C |
| ATOM | 4758 | CB | ARG | C | 105 | 0.375 | 88.855 | 28.808 | 1.00 | 29.18 | C |
| ATOM | 4759 | CG | ARG | C | 105 | 0.514 | 90.222 | 29.440 | 1.00 | 28.00 | C |
| ATOM | 4760 | CD | ARG | C | 105 | 0.378 | 90.113 | 30.949 | 1.00 | 27.99 | C |
| ATOM | 4761 | NE | ARG | C | 105 | 1.366 | 89.183 | 31.488 | 1.00 | 26.20 | N |
| ATOM | 4762 | CZ | ARG | C | 105 | 1.691 | 89.095 | 32.769 | 1.00 | 25.37 | C |
| ATOM | 4763 | NH1 | ARG | C | 105 | 1.110 | 89.884 | 33.661 | 1.00 | 24.63 | N |
| ATOM | 4764 | NH2 | ARG | C | 105 | 2.602 | 88.218 | 33.156 | 1.00 | 25.54 | N |
| ATOM | 4765 | C | ARG | C | 105 | 0.460 | 87.448 | 26.768 | 1.00 | 29.51 | C |
| ATOM | 4766 | O | ARG | C | 105 | -0.740 | 87.201 | 26.584 | 1.00 | 30.74 | O |
| ATOM | 4767 | N | PHE | C | 106 | 1.435 | 86.589 | 26.488 | 1.00 | 28.10 | N |
| ATOM | 4768 | CA | PHE | C | 106 | 1.168 | 85.292 | 25.898 | 1.00 | 27.09 | C |
| ATOM | 4769 | CB | PHE | C | 106 | 2.491 | 84.546 | 25.655 | 1.00 | 26.39 | C |
| ATOM | 4770 | CG | PHE | C | 106 | 2.314 | 83.083 | 25.314 | 1.00 | 25.27 | C |
| ATOM | 4771 | CD1 | PHE | C | 106 | 1.764 | 82.696 | 24.097 | 1.00 | 24.08 | C |
| ATOM | 4772 | CD2 | PHE | C | 106 | 2.681 | 82.096 | 26.225 | 1.00 | 24.70 | C |
| ATOM | 4773 | CE1 | PHE | C | 106 | 1.579 | 81.341 | 23.788 | 1.00 | 23.49 | C |
| ATOM | 4774 | CE2 | PHE | C | 106 | 2.502 | 80.738 | 25.929 | 1.00 | 24.44 | C |
| ATOM | 4775 | CZ | PHE | C | 106 | 1.949 | 80.362 | 24.709 | 1.00 | 24.42 | C |
| ATOM | 4776 | C | PHE | C | 106 | 0.239 | 84.426 | 26.748 | 1.00 | 27.47 | C |
| ATOM | 4777 | O | PHE | C | 106 | -0.656 | 83.772 | 26.212 | 1.00 | 27.84 | O |
| ATOM | 4778 | N | SER | C | 107 | 0.443 | 84.408 | 28.064 | 1.00 | 28.42 | N |
| ATOM | 4779 | CA | SER | C | 107 | -0.396 | 83.575 | 28.934 | 1.00 | 30.16 | C |
| ATOM | 4780 | CB | SER | C | 107 | 0.025 | 83.719 | 30.405 | 1.00 | 28.94 | C |
| ATOM | 4781 | OG | SER | C | 107 | -0.140 | 85.046 | 30.878 | 1.00 | 28.81 | O |
| ATOM | 4782 | C | SER | C | 107 | -1.888 | 83.886 | 28.794 | 1.00 | 31.23 | C |
| ATOM | 4783 | O | SER | C | 107 | -2.734 | 83.136 | 29.286 | 1.00 | 30.79 | O |
| ATOM | 4784 | N | GLU | C | 108 | -2.208 | 84.985 | 28.117 | 1.00 | 32.81 | N |
| ATOM | 4785 | CA | GLU | C | 108 | -3.600 | 85.377 | 27.922 | 1.00 | 34.53 | C |
| ATOM | 4786 | CB | GLU | C | 108 | -3.710 | 86.909 | 27.872 | 1.00 | 35.08 | C |
| ATOM | 4787 | CG | GLU | C | 108 | -4.058 | 87.535 | 29.216 | 1.00 | 37.48 | C |
| ATOM | 4788 | CD | GLU | C | 108 | -3.491 | 88.927 | 29.385 | 1.00 | 39.71 | C |
| ATOM | 4789 | OE1 | GLU | C | 108 | -3.635 | 89.767 | 28.450 | 1.00 | 41.62 | O |
| ATOM | 4790 | OE2 | GLU | C | 108 | -2.900 | 89.183 | 30.464 | 1.00 | 39.95 | O |
| ATOM | 4791 | C | GLU | C | 108 | -4.220 | 84.782 | 26.667 | 1.00 | 34.46 | C |
| ATOM | 4792 | O | GLU | C | 108 | -5.431 | 84.867 | 26.466 | 1.00 | 35.49 | O |
| ATOM | 4793 | N | THR | C | 109 | -3.394 | 84.179 | 25.820 | 1.00 | 34.55 | N |
| ATOM | 4794 | CA | THR | C | 109 | -3.879 | 83.585 | 24.568 | 1.00 | 34.27 | C |
| ATOM | 4795 | CB | THR | C | 109 | -2.766 | 82.766 | 23.893 | 1.00 | 34.69 | C |
| ATOM | 4796 | OG1 | THR | C | 109 | -2.304 | 81.763 | 24.812 | 1.00 | 37.12 | O |
| ATOM | 4797 | CG2 | THR | C | 109 | -1.598 | 83.674 | 23.500 | 1.00 | 33.17 | C |
| ATOM | 4798 | C | THR | C | 109 | -5.111 | 82.694 | 24.749 | 1.00 | 32.12 | C |
| ATOM | 4799 | O | THR | C | 109 | -5.301 | 82.088 | 25.799 | 1.00 | 31.88 | O |
| ATOM | 4800 | N | SER | C | 110 | -5.941 | 82.609 | 23.713 | 1.00 | 31.88 | N |
| ATOM | 4801 | CA | SER | C | 110 | -7.159 | 81.797 | 23.773 | 1.00 | 30.81 | C |
| ATOM | 4802 | CB | SER | C | 110 | -8.305 | 82.508 | 23.044 | 1.00 | 30.43 | C |
| ATOM | 4803 | OG | SER | C | 110 | -8.004 | 82.693 | 21.660 | 1.00 | 29.69 | O |
| ATOM | 4804 | C | SER | C | 110 | -6.951 | 80.424 | 23.152 | 1.00 | 30.67 | C |
| ATOM | 4805 | O | SER | C | 110 | -6.047 | 80.228 | 22.334 | 1.00 | 30.23 | O |
| ATOM | 4806 | N | ARG | C | 111 | -7.797 | 79.474 | 23.538 | 1.00 | 30.37 | N |
| ATOM | 4807 | CA | ARG | C | 111 | -7.699 | 78.124 | 23.004 | 1.00 | 30.53 | C |
| ATOM | 4808 | CB | ARG | C | 111 | -8.789 | 77.230 | 23.617 | 1.00 | 28.96 | C |

FIGURE 9 (cont.)

| ATOM | 4809 | CG | ARG | C | 111 | -8.592 | 75.737 | 23.374 | 1.00 | 28.66 | C |
|------|------|-----|-----|---|-----|--------|--------|--------|------|-------|---|
| ATOM | 4810 | CD | ARG | C | 111 | -9.701 | 74.908 | 24.026 | 1.00 | 26.53 | C |
| ATOM | 4811 | NE | ARG | C | 111 | -9.713 | 75.041 | 25.484 | 1.00 | 27.03 | N |
| ATOM | 4812 | CZ | ARG | C | 111 | -9.063 | 74.237 | 26.324 | 1.00 | 28.77 | C |
| ATOM | 4813 | NH1 | ARG | C | 111 | -8.337 | 73.217 | 25.870 | 1.00 | 26.60 | N |
| ATOM | 4814 | NH2 | ARG | C | 111 | -9.136 | 74.453 | 27.633 | 1.00 | 29.46 | N |
| ATOM | 4815 | C | ARG | C | 111 | -7.867 | 78.190 | 21.487 | 1.00 | 31.16 | C |
| ATOM | 4816 | O | ARG | C | 111 | -7.143 | 77.528 | 20.736 | 1.00 | 30.80 | O |
| ATOM | 4817 | N | GLU | C | 112 | -8.817 | 79.009 | 21.045 | 1.00 | 31.75 | N |
| ATOM | 4818 | CA | GLU | C | 112 | -9.105 | 79.153 | 19.626 | 1.00 | 32.91 | C |
| ATOM | 4819 | CB | GLU | C | 112 | -10.360 | 80.021 | 19.430 | 1.00 | 34.69 | C |
| ATOM | 4820 | CG | GLU | C | 112 | -11.156 | 79.738 | 18.138 | 1.00 | 37.67 | C |
| ATOM | 4821 | CD | GLU | C | 112 | -12.279 | 80.767 | 17.872 | 1.00 | 39.83 | C |
| ATOM | 4822 | OE1 | GLU | C | 112 | -13.082 | 81.079 | 18.795 | 1.00 | 39.75 | O |
| ATOM | 4823 | OE2 | GLU | C | 112 | -12.370 | 81.257 | 16.723 | 1.00 | 41.05 | O |
| ATOM | 4824 | C | GLU | C | 112 | -7.920 | 79.796 | 18.920 | 1.00 | 33.02 | C |
| ATOM | 4825 | O | GLU | C | 112 | -7.408 | 79.264 | 17.932 | 1.00 | 33.95 | O |
| ATOM | 4826 | N | GLY | C | 113 | -7.491 | 80.949 | 19.417 | 1.00 | 33.11 | N |
| ATOM | 4827 | CA | GLY | C | 113 | -6.374 | 81.640 | 18.799 | 1.00 | 33.12 | C |
| ATOM | 4828 | C | GLY | C | 113 | -5.108 | 80.798 | 18.789 | 1.00 | 33.38 | C |
| ATOM | 4829 | O | GLY | C | 113 | -4.276 | 80.929 | 17.887 | 1.00 | 33.66 | O |
| ATOM | 4830 | N | PHE | C | 114 | -4.964 | 79.928 | 19.786 | 1.00 | 31.47 | N |
| ATOM | 4831 | CA | PHE | C | 114 | -3.784 | 79.080 | 19.889 | 1.00 | 31.08 | C |
| ATOM | 4832 | CB | PHE | C | 114 | -3.677 | 78.513 | 21.310 | 1.00 | 29.26 | C |
| ATOM | 4833 | CG | PHE | C | 114 | -2.554 | 77.522 | 21.491 | 1.00 | 30.18 | C |
| ATOM | 4834 | CD1 | PHE | C | 114 | -2.685 | 76.205 | 21.047 | 1.00 | 28.25 | C |
| ATOM | 4835 | CD2 | PHE | C | 114 | -1.358 | 77.907 | 22.110 | 1.00 | 28.96 | C |
| ATOM | 4836 | CE1 | PHE | C | 114 | -1.649 | 75.281 | 21.215 | 1.00 | 27.39 | C |
| ATOM | 4837 | CE2 | PHE | C | 114 | -0.317 | 76.988 | 22.282 | 1.00 | 28.44 | C |
| ATOM | 4838 | CZ | PHE | C | 114 | -0.467 | 75.673 | 21.834 | 1.00 | 28.49 | C |
| ATOM | 4839 | C | PHE | C | 114 | -3.840 | 77.960 | 18.854 | 1.00 | 31.02 | C |
| ATOM | 4840 | O | PHE | C | 114 | -2.893 | 77.767 | 18.076 | 1.00 | 31.63 | O |
| ATOM | 4841 | N | LEU | C | 115 | -4.947 | 77.223 | 18.840 | 1.00 | 29.14 | N |
| ATOM | 4842 | CA | LEU | C | 115 | -5.107 | 76.147 | 17.876 | 1.00 | 28.47 | C |
| ATOM | 4843 | CB | LEU | C | 115 | -6.384 | 75.349 | 18.174 | 1.00 | 29.87 | C |
| ATOM | 4844 | CG | LEU | C | 115 | -6.334 | 74.528 | 19.469 | 1.00 | 30.49 | C |
| ATOM | 4845 | CD1 | LEU | C | 115 | -7.663 | 73.805 | 19.707 | 1.00 | 30.40 | C |
| ATOM | 4846 | CD2 | LEU | C | 115 | -5.188 | 73.532 | 19.366 | 1.00 | 29.85 | C |
| ATOM | 4847 | C | LEU | C | 115 | -5.153 | 76.715 | 16.461 | 1.00 | 27.45 | C |
| ATOM | 4848 | O | LEU | C | 115 | -4.676 | 76.083 | 15.518 | 1.00 | 26.47 | O |
| ATOM | 4849 | N | LEU | C | 116 | -5.718 | 77.909 | 16.301 | 1.00 | 26.08 | N |
| ATOM | 4850 | CA | LEU | C | 116 | -5.772 | 78.506 | 14.969 | 1.00 | 26.13 | C |
| ATOM | 4851 | CB | LEU | C | 116 | -6.524 | 79.841 | 14.989 | 1.00 | 25.30 | C |
| ATOM | 4852 | CG | LEU | C | 116 | -6.599 | 80.607 | 13.656 | 1.00 | 25.67 | C |
| ATOM | 4853 | CD1 | LEU | C | 116 | -5.351 | 81.444 | 13.438 | 1.00 | 26.07 | C |
| ATOM | 4854 | CD2 | LEU | C | 116 | -6.790 | 79.621 | 12.512 | 1.00 | 25.36 | C |
| ATOM | 4855 | C | LEU | C | 116 | -4.366 | 78.712 | 14.400 | 1.00 | 25.53 | C |
| ATOM | 4856 | O | LEU | C | 116 | -4.104 | 78.332 | 13.259 | 1.00 | 25.95 | O |
| ATOM | 4857 | N | ALA | C | 117 | -3.466 | 79.307 | 15.185 | 1.00 | 24.81 | N |
| ATOM | 4858 | CA | ALA | C | 117 | -2.086 | 79.542 | 14.727 | 1.00 | 25.39 | C |
| ATOM | 4859 | CB | ALA | C | 117 | -1.289 | 80.265 | 15.821 | 1.00 | 23.70 | C |
| ATOM | 4860 | C | ALA | C | 117 | -1.395 | 78.221 | 14.370 | 1.00 | 25.75 | C |
| ATOM | 4861 | O | ALA | C | 117 | -0.620 | 78.121 | 13.415 | 1.00 | 25.80 | O |
| ATOM | 4862 | N | GLN | C | 118 | -1.694 | 77.210 | 15.168 | 1.00 | 26.86 | N |
| ATOM | 4863 | CA | GLN | C | 118 | -1.150 | 75.872 | 15.010 | 1.00 | 27.54 | C |
| ATOM | 4864 | CB | GLN | C | 118 | -1.543 | 75.064 | 16.252 | 1.00 | 28.14 | C |
| ATOM | 4865 | CG | GLN | C | 118 | -0.987 | 73.669 | 16.298 | 1.00 | 30.55 | C |
| ATOM | 4866 | CD | GLN | C | 118 | 0.444 | 73.626 | 16.802 | 1.00 | 30.19 | C |
| ATOM | 4867 | OE1 | GLN | C | 118 | 1.091 | 72.582 | 16.735 | 1.00 | 31.43 | O |
| ATOM | 4868 | NE2 | GLN | C | 118 | 0.940 | 74.756 | 17.322 | 1.00 | 28.47 | N |
| ATOM | 4869 | C | GLN | C | 118 | -1.686 | 75.191 | 13.739 | 1.00 | 28.13 | C |
| ATOM | 4870 | O | GLN | C | 118 | -0.950 | 74.509 | 13.021 | 1.00 | 27.03 | O |
| ATOM | 4871 | N | ASP | C | 119 | -2.978 | 75.383 | 13.469 | 1.00 | 28.74 | N |
| ATOM | 4872 | CA | ASP | C | 119 | -3.642 | 74.779 | 12.309 | 1.00 | 28.14 | C |
| ATOM | 4873 | CB | ASP | C | 119 | -5.146 | 75.108 | 12.354 | 1.00 | 29.63 | C |

FIGURE 9 (cont.)

| | | | | | | | | | | |
|---|---|---|---|---|---|---|---|---|---|---|
| ATOM | 4874 | CG | ASP | C | 119 | -5.924 | 74.521 | 11.173 | 1.00 31.59 | C |
| ATOM | 4875 | OD1 | ASP | C | 119 | -5.572 | 73.410 | 10.716 | 1.00 31.73 | O |
| ATOM | 4876 | OD2 | ASP | C | 119 | -6.903 | 75.163 | 10.712 | 1.00 32.14 | O |
| ATOM | 4877 | C | ASP | C | 119 | -3.048 | 75.232 | 10.979 | 1.00 27.11 | C |
| ATOM | 4878 | O | ASP | C | 119 | -2.710 | 74.409 | 10.125 | 1.00 27.20 | O |
| ATOM | 4879 | N | ILE | C | 120 | -2.925 | 76.545 | 10.816 | 1.00 26.02 | N |
| ATOM | 4880 | CA | ILE | C | 120 | -2.396 | 77.137 | 9.586 | 1.00 25.59 | C |
| ATOM | 4881 | CB | ILE | C | 120 | -2.915 | 78.594 | 9.408 | 1.00 26.77 | C |
| ATOM | 4882 | CG2 | ILE | C | 120 | -2.173 | 79.297 | 8.254 | 1.00 26.23 | C |
| ATOM | 4883 | CG1 | ILE | C | 120 | -4.423 | 78.586 | 9.142 | 1.00 27.20 | C |
| ATOM | 4884 | CD1 | ILE | C | 120 | -4.997 | 79.981 | 8.928 | 1.00 28.92 | C |
| ATOM | 4885 | C | ILE | C | 120 | -0.871 | 77.189 | 9.491 | 1.00 24.29 | C |
| ATOM | 4886 | O | ILE | C | 120 | -0.300 | 76.973 | 8.413 | 1.00 22.98 | O |
| ATOM | 4887 | N | SER | C | 121 | -0.212 | 77.492 | 10.606 | 1.00 22.44 | N |
| ATOM | 4888 | CA | SER | C | 121 | 1.238 | 77.615 | 10.591 | 1.00 21.70 | C |
| ATOM | 4889 | CB | SER | C | 121 | 1.679 | 78.591 | 11.679 | 1.00 20.90 | C |
| ATOM | 4890 | OG | SER | C | 121 | 1.058 | 79.846 | 11.491 | 1.00 16.91 | O |
| ATOM | 4891 | C | SER | C | 121 | 2.027 | 76.320 | 10.710 | 1.00 22.04 | C |
| ATOM | 4892 | O | SER | C | 121 | 3.201 | 76.269 | 10.323 | 1.00 21.22 | O |
| ATOM | 4893 | N | SER | C | 122 | 1.403 | 75.273 | 11.238 | 1.00 21.77 | N |
| ATOM | 4894 | CA | SER | C | 122 | 2.114 | 74.015 | 11.377 | 1.00 21.88 | C |
| ATOM | 4895 | CB | SER | C | 122 | 2.418 | 73.751 | 12.847 | 1.00 21.07 | C |
| ATOM | 4896 | OG | SER | C | 122 | 3.150 | 72.548 | 12.987 | 1.00 22.82 | O |
| ATOM | 4897 | C | SER | C | 122 | 1.424 | 72.794 | 10.766 | 1.00 23.34 | C |
| ATOM | 4898 | O | SER | C | 122 | 2.075 | 71.982 | 10.090 | 1.00 23.12 | O |
| ATOM | 4899 | N | TYR | C | 123 | 0.121 | 72.641 | 10.987 | 1.00 23.55 | N |
| ATOM | 4900 | CA | TYR | C | 123 | -0.534 | 71.472 | 10.428 | 1.00 24.34 | C |
| ATOM | 4901 | CB | TYR | C | 123 | -1.963 | 71.285 | 10.965 | 1.00 26.86 | C |
| ATOM | 4902 | CG | TYR | C | 123 | -2.632 | 70.104 | 10.287 | 1.00 28.66 | C |
| ATOM | 4903 | CD1 | TYR | C | 123 | -2.183 | 68.808 | 10.512 | 1.00 30.73 | C |
| ATOM | 4904 | CE1 | TYR | C | 123 | -2.665 | 67.731 | 9.764 | 1.00 30.73 | C |
| ATOM | 4905 | CD2 | TYR | C | 123 | -3.600 | 70.295 | 9.304 | 1.00 29.85 | C |
| ATOM | 4906 | CE2 | TYR | C | 123 | -4.088 | 69.227 | 8.551 | 1.00 30.60 | C |
| ATOM | 4907 | CZ | TYR | C | 123 | -3.611 | 67.951 | 8.779 | 1.00 30.42 | C |
| ATOM | 4908 | OH | TYR | C | 123 | -4.026 | 66.903 | 7.982 | 1.00 29.42 | O |
| ATOM | 4909 | C | TYR | C | 123 | -0.558 | 71.519 | 8.905 | 1.00 24.16 | C |
| ATOM | 4910 | O | TYR | C | 123 | -0.535 | 70.474 | 8.255 | 1.00 23.40 | O |
| ATOM | 4911 | N | SER | C | 124 | -0.581 | 72.720 | 8.330 | 1.00 24.09 | N |
| ATOM | 4912 | CA | SER | C | 124 | -0.602 | 72.844 | 6.873 | 1.00 24.35 | C |
| ATOM | 4913 | CB | SER | C | 124 | -0.609 | 74.321 | 6.459 | 1.00 25.84 | C |
| ATOM | 4914 | OG | SER | C | 124 | 0.491 | 75.024 | 7.007 | 1.00 27.11 | O |
| ATOM | 4915 | C | SER | C | 124 | 0.550 | 72.111 | 6.179 | 1.00 24.17 | C |
| ATOM | 4916 | O | SER | C | 124 | 0.369 | 71.564 | 5.085 | 1.00 23.82 | O |
| ATOM | 4917 | N | LEU | C | 125 | 1.731 | 72.092 | 6.801 | 1.00 23.97 | N |
| ATOM | 4918 | CA | LEU | C | 125 | 2.884 | 71.392 | 6.211 | 1.00 22.65 | C |
| ATOM | 4919 | CB | LEU | C | 125 | 4.145 | 71.613 | 7.061 | 1.00 21.84 | C |
| ATOM | 4920 | CG | LEU | C | 125 | 5.425 | 70.923 | 6.570 | 1.00 21.20 | C |
| ATOM | 4921 | CD1 | LEU | C | 125 | 5.808 | 71.423 | 5.176 | 1.00 18.25 | C |
| ATOM | 4922 | CD2 | LEU | C | 125 | 6.552 | 71.189 | 7.556 | 1.00 21.57 | C |
| ATOM | 4923 | C | LEU | C | 125 | 2.609 | 69.891 | 6.086 | 1.00 22.31 | C |
| ATOM | 4924 | O | LEU | C | 125 | 2.998 | 69.250 | 5.112 | 1.00 23.00 | O |
| ATOM | 4925 | N | THR | C | 126 | 1.924 | 69.340 | 7.078 | 1.00 22.86 | N |
| ATOM | 4926 | CA | THR | C | 126 | 1.579 | 67.920 | 7.110 | 1.00 23.83 | C |
| ATOM | 4927 | CB | THR | C | 126 | 0.933 | 67.577 | 8.448 | 1.00 23.23 | C |
| ATOM | 4928 | OG1 | THR | C | 126 | 1.817 | 67.966 | 9.501 | 1.00 21.98 | O |
| ATOM | 4929 | CG2 | THR | C | 126 | 0.644 | 66.101 | 8.540 | 1.00 23.89 | C |
| ATOM | 4930 | C | THR | C | 126 | 0.637 | 67.461 | 5.985 | 1.00 23.78 | C |
| ATOM | 4931 | O | THR | C | 126 | 0.842 | 66.401 | 5.391 | 1.00 23.21 | O |
| ATOM | 4932 | N | ILE | C | 127 | -0.403 | 68.240 | 5.703 | 1.00 25.08 | N |
| ATOM | 4933 | CA | ILE | C | 127 | -1.334 | 67.876 | 4.632 | 1.00 26.41 | C |
| ATOM | 4934 | CB | ILE | C | 127 | -2.556 | 68.797 | 4.590 | 1.00 26.78 | C |
| ATOM | 4935 | CG2 | ILE | C | 127 | -3.735 | 68.156 | 5.284 | 1.00 27.59 | C |
| ATOM | 4936 | CG1 | ILE | C | 127 | -2.187 | 70.138 | 5.198 | 1.00 27.82 | C |
| ATOM | 4937 | CD1 | ILE | C | 127 | -3.321 | 71.129 | 5.234 | 1.00 32.77 | C |
| ATOM | 4938 | C | ILE | C | 127 | -0.648 | 68.001 | 3.284 | 1.00 26.54 | C |

FIGURE 9 (cont.)

| | | | | | | | | | | |
|---|---|---|---|---|---|---|---|---|---|---|
| ATOM | 4939 | O | ILE | C | 127 | -0.658 | 67.066 | 2.481 | 1.00 28.01 | O |
| ATOM | 4940 | N | VAL | C | 128 | -0.063 | 69.170 | 3.031 | 1.00 26.95 | N |
| ATOM | 4941 | CA | VAL | C | 128 | 0.612 | 69.414 | 1.766 | 1.00 26.86 | C |
| ATOM | 4942 | CB | VAL | C | 128 | 1.281 | 70.813 | 1.735 | 1.00 27.18 | C |
| ATOM | 4943 | CG1 | VAL | C | 128 | 0.253 | 71.892 | 2.076 | 1.00 26.03 | C |
| ATOM | 4944 | CG2 | VAL | C | 128 | 2.434 | 70.864 | 2.705 | 1.00 29.92 | C |
| ATOM | 4945 | C | VAL | C | 128 | 1.655 | 68.329 | 1.525 | 1.00 26.47 | C |
| ATOM | 4946 | O | VAL | C | 128 | 1.833 | 67.874 | 0.395 | 1.00 27.11 | O |
| ATOM | 4947 | N | ALA | C | 129 | 2.325 | 67.894 | 2.586 | 1.00 25.61 | N |
| ATOM | 4948 | CA | ALA | C | 129 | 3.330 | 66.847 | 2.442 | 1.00 25.61 | C |
| ATOM | 4949 | CB | ALA | C | 129 | 4.023 | 66.588 | 3.779 | 1.00 25.34 | C |
| ATOM | 4950 | C | ALA | C | 129 | 2.652 | 65.575 | 1.950 | 1.00 25.23 | C |
| ATOM | 4951 | O | ALA | C | 129 | 3.048 | 65.003 | 0.929 | 1.00 23.94 | O |
| ATOM | 4952 | N | HIS | C | 130 | 1.632 | 65.135 | 2.685 | 1.00 26.27 | N |
| ATOM | 4953 | CA | HIS | C | 130 | 0.888 | 63.925 | 2.329 | 1.00 27.14 | C |
| ATOM | 4954 | CB | HIS | C | 130 | -0.343 | 63.769 | 3.224 | 1.00 28.27 | C |
| ATOM | 4955 | CG | HIS | C | 130 | -1.140 | 62.533 | 2.938 | 1.00 30.84 | C |
| ATOM | 4956 | CD2 | HIS | C | 130 | -0.790 | 61.224 | 2.954 | 1.00 30.08 | C |
| ATOM | 4957 | ND1 | HIS | C | 130 | -2.470 | 62.570 | 2.565 | 1.00 32.25 | N |
| ATOM | 4958 | CE1 | HIS | C | 130 | -2.902 | 61.336 | 2.362 | 1.00 30.63 | C |
| ATOM | 4959 | NE2 | HIS | C | 130 | -1.902 | 60.502 | 2.590 | 1.00 30.26 | N |
| ATOM | 4960 | C | HIS | C | 130 | 0.438 | 63.973 | 0.875 | 1.00 27.81 | C |
| ATOM | 4961 | O | HIS | C | 130 | 0.589 | 63.000 | 0.134 | 1.00 28.73 | O |
| ATOM | 4962 | N | GLU | C | 131 | -0.114 | 65.115 | 0.478 | 1.00 26.98 | N |
| ATOM | 4963 | CA | GLU | C | 131 | -0.598 | 65.325 | -0.883 | 1.00 28.26 | C |
| ATOM | 4964 | CB | GLU | C | 131 | -1.470 | 66.587 | -0.915 | 1.00 29.21 | C |
| ATOM | 4965 | CG | GLU | C | 131 | -2.973 | 66.317 | -0.892 | 1.00 33.46 | C |
| ATOM | 4966 | CD | GLU | C | 131 | -3.405 | 65.372 | 0.219 | 1.00 34.56 | C |
| ATOM | 4967 | OE1 | GLU | C | 131 | -3.504 | 65.818 | 1.385 | 1.00 36.22 | O |
| ATOM | 4968 | OE2 | GLU | C | 131 | -3.642 | 64.175 | -0.077 | 1.00 35.36 | O |
| ATOM | 4969 | C | GLU | C | 131 | 0.496 | 65.428 | -1.957 | 1.00 27.61 | C |
| ATOM | 4970 | O | GLU | C | 131 | 0.393 | 64.815 | -3.023 | 1.00 27.95 | O |
| ATOM | 4971 | N | ALA | C | 132 | 1.539 | 66.206 | -1.692 | 1.00 26.49 | N |
| ATOM | 4972 | CA | ALA | C | 132 | 2.612 | 66.364 | -2.666 | 1.00 26.12 | C |
| ATOM | 4973 | CB | ALA | C | 132 | 3.573 | 67.462 | -2.209 | 1.00 27.54 | C |
| ATOM | 4974 | C | ALA | C | 132 | 3.373 | 65.059 | -2.898 | 1.00 25.40 | C |
| ATOM | 4975 | O | ALA | C | 132 | 3.899 | 64.816 | -3.984 | 1.00 24.65 | O |
| ATOM | 4976 | N | LYS | C | 133 | 3.428 | 64.217 | -1.877 | 1.00 25.01 | N |
| ATOM | 4977 | CA | LYS | C | 133 | 4.137 | 62.957 | -1.998 | 1.00 26.69 | C |
| ATOM | 4978 | CB | LYS | C | 133 | 4.045 | 62.186 | -0.680 | 1.00 25.95 | C |
| ATOM | 4979 | CG | LYS | C | 133 | 4.470 | 60.734 | -0.772 | 1.00 29.10 | C |
| ATOM | 4980 | CD | LYS | C | 133 | 4.646 | 60.124 | 0.617 | 1.00 30.59 | C |
| ATOM | 4981 | CE | LYS | C | 133 | 3.364 | 60.144 | 1.434 | 1.00 32.51 | C |
| ATOM | 4982 | NZ | LYS | C | 133 | 2.425 | 59.064 | 1.001 | 1.00 34.31 | N |
| ATOM | 4983 | C | LYS | C | 133 | 3.551 | 62.148 | -3.153 | 1.00 28.12 | C |
| ATOM | 4984 | O | LYS | C | 133 | 4.236 | 61.323 | -3.753 | 1.00 28.17 | O |
| ATOM | 4985 | N | LYS | C | 134 | 2.283 | 62.400 | -3.470 | 1.00 29.42 | N |
| ATOM | 4986 | CA | LYS | C | 134 | 1.610 | 61.705 | -4.564 | 1.00 30.07 | C |
| ATOM | 4987 | CB | LYS | C | 134 | 0.112 | 62.042 | -4.562 | 1.00 30.55 | C |
| ATOM | 4988 | CG | LYS | C | 134 | -0.676 | 61.348 | -3.439 | 1.00 31.28 | C |
| ATOM | 4989 | CD | LYS | C | 134 | -2.103 | 61.886 | -3.301 | 1.00 31.38 | C |
| ATOM | 4990 | CE | LYS | C | 134 | -2.822 | 61.233 | -2.111 | 1.00 33.29 | C |
| ATOM | 4991 | NZ | LYS | C | 134 | -4.132 | 61.887 | -1.762 | 1.00 33.65 | N |
| ATOM | 4992 | C | LYS | C | 134 | 2.211 | 62.075 | -5.913 | 1.00 30.19 | C |
| ATOM | 4993 | O | LYS | C | 134 | 2.205 | 61.276 | -6.848 | 1.00 30.18 | O |
| ATOM | 4994 | N | LEU | C | 135 | 2.748 | 63.284 | -6.009 | 1.00 30.98 | N |
| ATOM | 4995 | CA | LEU | C | 135 | 3.336 | 63.746 | -7.258 | 1.00 31.55 | C |
| ATOM | 4996 | CB | LEU | C | 135 | 2.933 | 65.211 | -7.501 | 1.00 31.51 | C |
| ATOM | 4997 | CG | LEU | C | 135 | 1.462 | 65.622 | -7.282 | 1.00 31.39 | C |
| ATOM | 4998 | CD1 | LEU | C | 135 | 1.304 | 67.128 | -7.524 | 1.00 32.85 | C |
| ATOM | 4999 | CD2 | LEU | C | 135 | 0.550 | 64.863 | -8.221 | 1.00 30.30 | C |
| ATOM | 5000 | C | LEU | C | 135 | 4.873 | 63.615 | -7.272 | 1.00 32.42 | C |
| ATOM | 5001 | O | LEU | C | 135 | 5.536 | 64.148 | -8.176 | 1.00 31.81 | O |
| ATOM | 5002 | N | MET | C | 136 | 5.436 | 62.904 | -6.291 | 1.00 31.18 | N |
| ATOM | 5003 | CA | MET | C | 136 | 6.886 | 62.734 | -6.218 | 1.00 31.83 | C |

FIGURE 9 (cont.)

| ATOM | 5004 | CB  | MET | C | 136 | 7.442  | 63.455 | -4.978  | 1.00 | 31.07 | C |
| ATOM | 5005 | CG  | MET | C | 136 | 6.965  | 64.882 | -4.834  | 1.00 | 31.01 | C |
| ATOM | 5006 | SD  | MET | C | 136 | 8.041  | 65.932 | -3.821  | 1.00 | 30.85 | S |
| ATOM | 5007 | CE  | MET | C | 136 | 6.957  | 66.345 | -2.481  | 1.00 | 32.53 | C |
| ATOM | 5008 | C   | MET | C | 136 | 7.312  | 61.263 | -6.186  | 1.00 | 32.13 | C |
| ATOM | 5009 | O   | MET | C | 136 | 8.082  | 60.848 | -5.310  | 1.00 | 31.83 | O |
| ATOM | 5010 | N   | PRO | C | 137 | 6.835  | 60.460 | -7.155  | 1.00 | 31.71 | N |
| ATOM | 5011 | CD  | PRO | C | 137 | 6.161  | 60.880 | -8.397  | 1.00 | 30.52 | C |
| ATOM | 5012 | CA  | PRO | C | 137 | 7.180  | 59.034 | -7.208  | 1.00 | 31.66 | C |
| ATOM | 5013 | CB  | PRO | C | 137 | 6.647  | 58.595 | -8.580  | 1.00 | 30.94 | C |
| ATOM | 5014 | CG  | PRO | C | 137 | 6.698  | 59.883 | -9.392  | 1.00 | 31.04 | C |
| ATOM | 5015 | C   | PRO | C | 137 | 8.658  | 58.682 | -7.042  | 1.00 | 31.96 | C |
| ATOM | 5016 | O   | PRO | C | 137 | 8.983  | 57.589 | -6.584  | 1.00 | 32.02 | O |
| ATOM | 5017 | N   | GLU | C | 138 | 9.558  | 59.588 | -7.412  | 1.00 | 32.72 | N |
| ATOM | 5018 | CA  | GLU | C | 138 | 10.983 | 59.279 | -7.309  | 1.00 | 33.53 | C |
| ATOM | 5019 | CB  | GLU | C | 138 | 11.661 | 59.487 | -8.663  | 1.00 | 35.17 | C |
| ATOM | 5020 | CG  | GLU | C | 138 | 11.951 | 58.192 | -9.392  | 1.00 | 38.33 | C |
| ATOM | 5021 | CD  | GLU | C | 138 | 11.167 | 58.081 | -10.678 | 1.00 | 41.29 | C |
| ATOM | 5022 | OE1 | GLU | C | 138 | 11.330 | 58.983 | -11.548 | 1.00 | 41.40 | O |
| ATOM | 5023 | OE2 | GLU | C | 138 | 10.392 | 57.097 | -10.816 | 1.00 | 42.75 | O |
| ATOM | 5024 | C   | GLU | C | 138 | 11.766 | 60.030 | -6.242  | 1.00 | 32.18 | C |
| ATOM | 5025 | O   | GLU | C | 138 | 12.981 | 59.856 | -6.121  | 1.00 | 31.54 | O |
| ATOM | 5026 | N   | GLY | C | 139 | 11.071 | 60.855 | -5.470  | 1.00 | 31.25 | N |
| ATOM | 5027 | CA  | GLY | C | 139 | 11.726 | 61.610 | -4.423  | 1.00 | 29.92 | C |
| ATOM | 5028 | C   | GLY | C | 139 | 11.547 | 63.091 | -4.672  | 1.00 | 29.56 | C |
| ATOM | 5029 | O   | GLY | C | 139 | 10.930 | 63.491 | -5.665  | 1.00 | 29.77 | O |
| ATOM | 5030 | N   | GLY | C | 140 | 12.090 | 63.912 | -3.780  | 1.00 | 28.07 | N |
| ATOM | 5031 | CA  | GLY | C | 140 | 11.960 | 65.344 | -3.932  | 1.00 | 26.18 | C |
| ATOM | 5032 | C   | GLY | C | 140 | 12.393 | 66.060 | -2.672  | 1.00 | 25.43 | C |
| ATOM | 5033 | O   | GLY | C | 140 | 13.069 | 65.476 | -1.821  | 1.00 | 24.83 | O |
| ATOM | 5034 | N   | SER | C | 141 | 11.993 | 67.321 | -2.544  | 1.00 | 24.05 | N |
| ATOM | 5035 | CA  | SER | C | 141 | 12.373 | 68.112 | -1.386  | 1.00 | 23.68 | C |
| ATOM | 5036 | CB  | SER | C | 141 | 13.628 | 68.923 | -1.711  | 1.00 | 23.45 | C |
| ATOM | 5037 | OG  | SER | C | 141 | 14.121 | 69.586 | -0.559  | 1.00 | 25.44 | O |
| ATOM | 5038 | C   | SER | C | 141 | 11.254 | 69.047 | -0.947  | 1.00 | 22.68 | C |
| ATOM | 5039 | O   | SER | C | 141 | 10.518 | 69.583 | -1.771  | 1.00 | 22.82 | O |
| ATOM | 5040 | N   | ILE | C | 142 | 11.135 | 69.225 | 0.364   | 1.00 | 21.34 | N |
| ATOM | 5041 | CA  | ILE | C | 142 | 10.120 | 70.089 | 0.950   | 1.00 | 21.18 | C |
| ATOM | 5042 | CB  | ILE | C | 142 | 9.050  | 69.269 | 1.719   | 1.00 | 19.77 | C |
| ATOM | 5043 | CG2 | ILE | C | 142 | 8.066  | 70.209 | 2.407   | 1.00 | 17.07 | C |
| ATOM | 5044 | CG1 | ILE | C | 142 | 8.310  | 68.344 | 0.749   | 1.00 | 20.25 | C |
| ATOM | 5045 | CD1 | ILE | C | 142 | 7.329  | 67.385 | 1.427   | 1.00 | 20.43 | C |
| ATOM | 5046 | C   | ILE | C | 142 | 10.790 | 71.056 | 1.927   | 1.00 | 21.12 | C |
| ATOM | 5047 | O   | ILE | C | 142 | 11.461 | 70.636 | 2.873   | 1.00 | 19.93 | O |
| ATOM | 5048 | N   | VAL | C | 143 | 10.615 | 72.351 | 1.683   | 1.00 | 20.20 | N |
| ATOM | 5049 | CA  | VAL | C | 143 | 11.199 | 73.360 | 2.552   | 1.00 | 20.64 | C |
| ATOM | 5050 | CB  | VAL | C | 143 | 12.233 | 74.221 | 1.809   | 1.00 | 19.79 | C |
| ATOM | 5051 | CG1 | VAL | C | 143 | 12.780 | 75.288 | 2.748   | 1.00 | 19.26 | C |
| ATOM | 5052 | CG2 | VAL | C | 143 | 13.354 | 73.342 | 1.281   | 1.00 | 19.81 | C |
| ATOM | 5053 | C   | VAL | C | 143 | 10.137 | 74.281 | 3.126   | 1.00 | 20.70 | C |
| ATOM | 5054 | O   | VAL | C | 143 | 9.228  | 74.714 | 2.423   | 1.00 | 21.51 | O |
| ATOM | 5055 | N   | ALA | C | 144 | 10.250 | 74.566 | 4.414   | 1.00 | 20.79 | N |
| ATOM | 5056 | CA  | ALA | C | 144 | 9.310  | 75.461 | 5.080   | 1.00 | 20.20 | C |
| ATOM | 5057 | CB  | ALA | C | 144 | 8.557  | 74.724 | 6.192   | 1.00 | 19.02 | C |
| ATOM | 5058 | C   | ALA | C | 144 | 10.115 | 76.606 | 5.665   | 1.00 | 20.55 | C |
| ATOM | 5059 | O   | ALA | C | 144 | 11.332 | 76.492 | 5.851   | 1.00 | 20.06 | O |
| ATOM | 5060 | N   | THR | C | 145 | 9.433  | 77.706 | 5.962   | 1.00 | 21.16 | N |
| ATOM | 5061 | CA  | THR | C | 145 | 10.083 | 78.882 | 6.527   | 1.00 | 20.64 | C |
| ATOM | 5062 | CB  | THR | C | 145 | 9.619  | 80.155 | 5.802   | 1.00 | 21.11 | C |
| ATOM | 5063 | OG1 | THR | C | 145 | 9.287  | 79.828 | 4.448   | 1.00 | 21.88 | O |
| ATOM | 5064 | CG2 | THR | C | 145 | 10.733 | 81.209 | 5.795   | 1.00 | 21.50 | C |
| ATOM | 5065 | C   | THR | C | 145 | 9.737  | 79.000 | 8.005   | 1.00 | 20.69 | C |
| ATOM | 5066 | O   | THR | C | 145 | 8.580  | 78.831 | 8.408   | 1.00 | 21.94 | O |
| ATOM | 5067 | N   | THR | C | 146 | 10.739 | 79.290 | 8.818   | 1.00 | 19.89 | N |
| ATOM | 5068 | CA  | THR | C | 146 | 10.517 | 79.426 | 10.248  | 1.00 | 17.76 | C |

FIGURE 9 (cont.)

| | | | | | | | | | |
|---|---|---|---|---|---|---|---|---|---|
| ATOM | 5069 | CB | THR | C | 146 | 10.994 | 78.169 | 11.000 | 1.00 18.55 | C |
| ATOM | 5070 | OG1 | THR | C | 146 | 10.551 | 78.230 | 12.363 | 1.00 19.25 | O |
| ATOM | 5071 | CG2 | THR | C | 146 | 12.507 | 78.056 | 10.950 | 1.00 16.68 | C |
| ATOM | 5072 | C | THR | C | 146 | 11.257 | 80.653 | 10.767 | 1.00 17.33 | C |
| ATOM | 5073 | O | THR | C | 146 | 11.916 | 81.367 | 9.999 | 1.00 15.29 | O |
| ATOM | 5074 | N | TYR | C | 147 | 11.144 | 80.891 | 12.070 | 1.00 16.61 | N |
| ATOM | 5075 | CA | TYR | C | 147 | 11.774 | 82.040 | 12.702 | 1.00 15.70 | C |
| ATOM | 5076 | CB | TYR | C | 147 | 10.724 | 83.129 | 12.911 | 1.00 12.56 | C |
| ATOM | 5077 | CG | TYR | C | 147 | 11.211 | 84.380 | 13.605 | 1.00 12.17 | C |
| ATOM | 5078 | CD1 | TYR | C | 147 | 12.221 | 85.171 | 13.049 | 1.00 11.79 | C |
| ATOM | 5079 | CE1 | TYR | C | 147 | 12.633 | 86.349 | 13.677 | 1.00 13.56 | C |
| ATOM | 5080 | CD2 | TYR | C | 147 | 10.625 | 84.799 | 14.805 | 1.00 13.02 | C |
| ATOM | 5081 | CE2 | TYR | C | 147 | 11.021 | 85.971 | 15.438 | 1.00 11.57 | C |
| ATOM | 5082 | CZ | TYR | C | 147 | 12.022 | 86.744 | 14.879 | 1.00 14.33 | C |
| ATOM | 5083 | OH | TYR | C | 147 | 12.421 | 87.898 | 15.528 | 1.00 13.97 | O |
| ATOM | 5084 | C | TYR | C | 147 | 12.389 | 81.623 | 14.034 | 1.00 16.08 | C |
| ATOM | 5085 | O | TYR | C | 147 | 11.902 | 80.704 | 14.699 | 1.00 17.25 | O |
| ATOM | 5086 | N | LEU | C | 148 | 13.454 | 82.315 | 14.419 | 1.00 16.66 | N |
| ATOM | 5087 | CA | LEU | C | 148 | 14.168 | 82.030 | 15.652 | 1.00 17.67 | C |
| ATOM | 5088 | CB | LEU | C | 148 | 15.272 | 83.074 | 15.836 | 1.00 18.33 | C |
| ATOM | 5089 | CG | LEU | C | 148 | 16.583 | 82.639 | 16.478 | 1.00 19.09 | C |
| ATOM | 5090 | CD1 | LEU | C | 148 | 16.947 | 81.229 | 16.045 | 1.00 19.86 | C |
| ATOM | 5091 | CD2 | LEU | C | 148 | 17.673 | 83.625 | 16.072 | 1.00 20.24 | C |
| ATOM | 5092 | C | LEU | C | 148 | 13.219 | 82.016 | 16.854 | 1.00 18.37 | C |
| ATOM | 5093 | O | LEU | C | 148 | 13.467 | 81.337 | 17.857 | 1.00 18.38 | O |
| ATOM | 5094 | N | GLY | C | 149 | 12.118 | 82.755 | 16.742 | 1.00 19.02 | N |
| ATOM | 5095 | CA | GLY | C | 149 | 11.150 | 82.790 | 17.824 | 1.00 18.58 | C |
| ATOM | 5096 | C | GLY | C | 149 | 10.636 | 81.398 | 18.156 | 1.00 19.33 | C |
| ATOM | 5097 | O | GLY | C | 149 | 10.023 | 81.188 | 19.199 | 1.00 18.03 | O |
| ATOM | 5098 | N | GLY | C | 150 | 10.895 | 80.441 | 17.266 | 1.00 19.51 | N |
| ATOM | 5099 | CA | GLY | C | 150 | 10.448 | 79.078 | 17.493 | 1.00 19.25 | C |
| ATOM | 5100 | C | GLY | C | 150 | 11.375 | 78.249 | 18.367 | 1.00 19.47 | C |
| ATOM | 5101 | O | GLY | C | 150 | 10.994 | 77.168 | 18.830 | 1.00 19.49 | O |
| ATOM | 5102 | N | GLU | C | 151 | 12.595 | 78.732 | 18.593 | 1.00 19.37 | N |
| ATOM | 5103 | CA | GLU | C | 151 | 13.552 | 77.998 | 19.433 | 1.00 18.75 | C |
| ATOM | 5104 | CB | GLU | C | 151 | 14.904 | 77.847 | 18.736 | 1.00 19.05 | C |
| ATOM | 5105 | CG | GLU | C | 151 | 14.902 | 77.133 | 17.404 | 1.00 20.47 | C |
| ATOM | 5106 | CD | GLU | C | 151 | 16.281 | 77.176 | 16.760 | 1.00 22.45 | C |
| ATOM | 5107 | OE1 | GLU | C | 151 | 17.211 | 76.527 | 17.306 | 1.00 23.86 | O |
| ATOM | 5108 | OE2 | GLU | C | 151 | 16.442 | 77.869 | 15.726 | 1.00 20.90 | O |
| ATOM | 5109 | C | GLU | C | 151 | 13.783 | 78.742 | 20.743 | 1.00 18.32 | C |
| ATOM | 5110 | O | GLU | C | 151 | 14.200 | 78.148 | 21.732 | 1.00 18.22 | O |
| ATOM | 5111 | N | PHE | C | 152 | 13.525 | 80.045 | 20.730 | 1.00 18.41 | N |
| ATOM | 5112 | CA | PHE | C | 152 | 13.700 | 80.892 | 21.907 | 1.00 19.36 | C |
| ATOM | 5113 | CB | PHE | C | 152 | 14.967 | 81.740 | 21.761 | 1.00 20.62 | C |
| ATOM | 5114 | CG | PHE | C | 152 | 16.231 | 80.937 | 21.658 | 1.00 23.04 | C |
| ATOM | 5115 | CD1 | PHE | C | 152 | 16.733 | 80.256 | 22.763 | 1.00 24.02 | C |
| ATOM | 5116 | CD2 | PHE | C | 152 | 16.917 | 80.856 | 20.453 | 1.00 22.98 | C |
| ATOM | 5117 | CE1 | PHE | C | 152 | 17.910 | 79.501 | 22.666 | 1.00 25.94 | C |
| ATOM | 5118 | CE2 | PHE | C | 152 | 18.094 | 80.106 | 20.338 | 1.00 24.10 | C |
| ATOM | 5119 | CZ | PHE | C | 152 | 18.592 | 79.429 | 21.446 | 1.00 25.69 | C |
| ATOM | 5120 | C | PHE | C | 152 | 12.492 | 81.820 | 22.049 | 1.00 19.67 | C |
| ATOM | 5121 | O | PHE | C | 152 | 11.804 | 82.111 | 21.060 | 1.00 18.36 | O |
| ATOM | 5122 | N | ALA | C | 153 | 12.243 | 82.292 | 23.270 | 1.00 17.60 | N |
| ATOM | 5123 | CA | ALA | C | 153 | 11.115 | 83.189 | 23.517 | 1.00 17.30 | C |
| ATOM | 5124 | CB | ALA | C | 153 | 10.784 | 83.245 | 25.011 | 1.00 13.54 | C |
| ATOM | 5125 | C | ALA | C | 153 | 11.443 | 84.583 | 23.008 | 1.00 17.71 | C |
| ATOM | 5126 | O | ALA | C | 153 | 12.351 | 85.246 | 23.514 | 1.00 18.78 | O |
| ATOM | 5127 | N | VAL | C | 154 | 10.711 | 85.008 | 21.986 | 1.00 18.67 | N |
| ATOM | 5128 | CA | VAL | C | 154 | 10.888 | 86.330 | 21.396 | 1.00 19.28 | C |
| ATOM | 5129 | CB | VAL | C | 154 | 10.970 | 86.235 | 19.858 | 1.00 18.34 | C |
| ATOM | 5130 | CG1 | VAL | C | 154 | 10.981 | 87.620 | 19.235 | 1.00 17.90 | C |
| ATOM | 5131 | CG2 | VAL | C | 154 | 12.231 | 85.489 | 19.478 | 1.00 18.94 | C |
| ATOM | 5132 | C | VAL | C | 154 | 9.673 | 87.150 | 21.815 | 1.00 19.97 | C |
| ATOM | 5133 | O | VAL | C | 154 | 8.531 | 86.679 | 21.737 | 1.00 18.65 | O |

FIGURE 9 (cont.)

| | | | | | | | | | |
|---|---|---|---|---|---|---|---|---|---|
| ATOM | 5134 | N | GLN | C | 155 | 9.918 | 88.368 | 22.280 | 1.00 21.64 | N |
| ATOM | 5135 | CA | GLN | C | 155 | 8.836 | 89.225 | 22.736 | 1.00 23.31 | C |
| ATOM | 5136 | CB | GLN | C | 155 | 9.396 | 90.560 | 23.223 | 1.00 26.34 | C |
| ATOM | 5137 | CG | GLN | C | 155 | 10.244 | 90.415 | 24.475 | 1.00 29.09 | C |
| ATOM | 5138 | CD | GLN | C | 155 | 9.789 | 91.341 | 25.584 | 1.00 31.69 | C |
| ATOM | 5139 | OE1 | GLN | C | 155 | 9.892 | 92.570 | 25.462 | 1.00 34.08 | O |
| ATOM | 5140 | NE2 | GLN | C | 155 | 9.274 | 90.760 | 26.678 | 1.00 32.83 | N |
| ATOM | 5141 | C | GLN | C | 155 | 7.762 | 89.465 | 21.684 | 1.00 22.72 | C |
| ATOM | 5142 | O | GLN | C | 155 | 8.060 | 89.638 | 20.498 | 1.00 22.63 | O |
| ATOM | 5143 | N | ASN | C | 156 | 6.514 | 89.446 | 22.147 | 1.00 22.00 | N |
| ATOM | 5144 | CA | ASN | C | 156 | 5.331 | 89.664 | 21.326 | 1.00 22.34 | C |
| ATOM | 5145 | CB | ASN | C | 156 | 5.401 | 91.041 | 20.659 | 1.00 22.46 | C |
| ATOM | 5146 | CG | ASN | C | 156 | 5.219 | 92.175 | 21.649 | 1.00 22.34 | C |
| ATOM | 5147 | OD1 | ASN | C | 156 | 4.282 | 92.166 | 22.447 | 1.00 23.58 | O |
| ATOM | 5148 | ND2 | ASN | C | 156 | 6.110 | 93.157 | 21.601 | 1.00 20.94 | N |
| ATOM | 5149 | C | ASN | C | 156 | 5.055 | 88.611 | 20.264 | 1.00 22.88 | C |
| ATOM | 5150 | O | ASN | C | 156 | 3.975 | 88.601 | 19.678 | 1.00 22.51 | O |
| ATOM | 5151 | N | TYR | C | 157 | 6.021 | 87.734 | 20.006 | 1.00 22.68 | N |
| ATOM | 5152 | CA | TYR | C | 157 | 5.845 | 86.700 | 18.986 | 1.00 23.80 | C |
| ATOM | 5153 | CB | TYR | C | 157 | 7.185 | 86.048 | 18.657 | 1.00 23.17 | C |
| ATOM | 5154 | CG | TYR | C | 157 | 7.153 | 85.301 | 17.351 | 1.00 22.37 | C |
| ATOM | 5155 | CD1 | TYR | C | 157 | 6.736 | 85.937 | 16.176 | 1.00 19.86 | C |
| ATOM | 5156 | CE1 | TYR | C | 157 | 6.694 | 85.254 | 14.966 | 1.00 19.81 | C |
| ATOM | 5157 | CD2 | TYR | C | 157 | 7.533 | 83.958 | 17.280 | 1.00 21.23 | C |
| ATOM | 5158 | CE2 | TYR | C | 157 | 7.496 | 83.264 | 16.065 | 1.00 20.71 | C |
| ATOM | 5159 | CZ | TYR | C | 157 | 7.075 | 83.922 | 14.918 | 1.00 19.51 | C |
| ATOM | 5160 | OH | TYR | C | 157 | 7.040 | 83.249 | 13.727 | 1.00 20.89 | O |
| ATOM | 5161 | C | TYR | C | 157 | 4.866 | 85.630 | 19.459 | 1.00 24.47 | C |
| ATOM | 5162 | O | TYR | C | 157 | 4.379 | 84.802 | 18.676 | 1.00 25.37 | O |
| ATOM | 5163 | N | ASN | C | 158 | 4.610 | 85.675 | 20.759 | 1.00 25.06 | N |
| ATOM | 5164 | CA | ASN | C | 158 | 3.713 | 84.786 | 21.474 | 1.00 25.16 | C |
| ATOM | 5165 | CB | ASN | C | 158 | 2.493 | 85.583 | 21.936 | 1.00 25.35 | C |
| ATOM | 5166 | CG | ASN | C | 158 | 2.885 | 86.748 | 22.824 | 1.00 27.27 | C |
| ATOM | 5167 | OD1 | ASN | C | 158 | 4.018 | 86.797 | 23.315 | 1.00 26.24 | O |
| ATOM | 5168 | ND2 | ASN | C | 158 | 1.962 | 87.686 | 23.042 | 1.00 25.89 | N |
| ATOM | 5169 | C | ASN | C | 158 | 3.275 | 83.492 | 20.825 | 1.00 24.97 | C |
| ATOM | 5170 | O | ASN | C | 158 | 4.077 | 82.575 | 20.662 | 1.00 25.44 | O |
| ATOM | 5171 | N | VAL | C | 159 | 1.997 | 83.414 | 20.467 | 1.00 25.00 | N |
| ATOM | 5172 | CA | VAL | C | 159 | 1.438 | 82.193 | 19.888 | 1.00 24.59 | C |
| ATOM | 5173 | CB | VAL | C | 159 | -0.098 | 82.345 | 19.654 | 1.00 24.41 | C |
| ATOM | 5174 | CG1 | VAL | C | 159 | -0.359 | 83.163 | 18.419 | 1.00 23.19 | C |
| ATOM | 5175 | CG2 | VAL | C | 159 | -0.757 | 80.969 | 19.572 | 1.00 24.76 | C |
| ATOM | 5176 | C | VAL | C | 159 | 2.105 | 81.693 | 18.602 | 1.00 23.50 | C |
| ATOM | 5177 | O | VAL | C | 159 | 2.039 | 80.496 | 18.295 | 1.00 22.95 | O |
| ATOM | 5178 | N | MET | C | 160 | 2.736 | 82.590 | 17.846 | 1.00 23.80 | N |
| ATOM | 5179 | CA | MET | C | 160 | 3.409 | 82.176 | 16.617 | 1.00 23.04 | C |
| ATOM | 5180 | CB | MET | C | 160 | 3.774 | 83.383 | 15.748 | 1.00 24.34 | C |
| ATOM | 5181 | CG | MET | C | 160 | 2.759 | 83.702 | 14.643 | 1.00 24.98 | C |
| ATOM | 5182 | SD | MET | C | 160 | 2.554 | 82.369 | 13.423 | 1.00 27.51 | S |
| ATOM | 5183 | CE | MET | C | 160 | 1.021 | 81.690 | 13.953 | 1.00 26.51 | C |
| ATOM | 5184 | C | MET | C | 160 | 4.668 | 81.415 | 17.021 | 1.00 23.14 | C |
| ATOM | 5185 | O | MET | C | 160 | 5.065 | 80.454 | 16.362 | 1.00 23.80 | O |
| ATOM | 5186 | N | GLY | C | 161 | 5.286 | 81.834 | 18.120 | 1.00 21.82 | N |
| ATOM | 5187 | CA | GLY | C | 161 | 6.473 | 81.137 | 18.578 | 1.00 21.25 | C |
| ATOM | 5188 | C | GLY | C | 161 | 6.198 | 79.652 | 18.725 | 1.00 21.33 | C |
| ATOM | 5189 | O | GLY | C | 161 | 6.926 | 78.816 | 18.182 | 1.00 21.49 | O |
| ATOM | 5190 | N | VAL | C | 162 | 5.136 | 79.319 | 19.454 | 1.00 21.15 | N |
| ATOM | 5191 | CA | VAL | C | 162 | 4.769 | 77.929 | 19.676 | 1.00 20.82 | C |
| ATOM | 5192 | CB | VAL | C | 162 | 3.544 | 77.819 | 20.606 | 1.00 21.77 | C |
| ATOM | 5193 | CG1 | VAL | C | 162 | 3.335 | 76.362 | 21.027 | 1.00 18.44 | C |
| ATOM | 5194 | CG2 | VAL | C | 162 | 3.737 | 78.711 | 21.829 | 1.00 22.03 | C |
| ATOM | 5195 | C | VAL | C | 162 | 4.448 | 77.235 | 18.360 | 1.00 21.59 | C |
| ATOM | 5196 | O | VAL | C | 162 | 4.805 | 76.067 | 18.155 | 1.00 22.99 | O |
| ATOM | 5197 | N | ALA | C | 163 | 3.772 | 77.948 | 17.464 | 1.00 21.02 | N |
| ATOM | 5198 | CA | ALA | C | 163 | 3.429 | 77.375 | 16.169 | 1.00 20.61 | C |

FIGURE 9 (cont.)

| ATOM | 5199 | CB | ALA | C | 163 | 2.643 | 78.382 | 15.345 | 1.00 | 19.10 | C |
| --- | --- | --- | --- | --- | --- | --- | --- | --- | --- | --- | --- |
| ATOM | 5200 | C | ALA | C | 163 | 4.721 | 76.970 | 15.439 | 1.00 | 20.78 | C |
| ATOM | 5201 | O | ALA | C | 163 | 4.832 | 75.849 | 14.936 | 1.00 | 20.47 | O |
| ATOM | 5202 | N | LYS | C | 164 | 5.690 | 77.884 | 15.388 | 1.00 | 19.82 | N |
| ATOM | 5203 | CA | LYS | C | 164 | 6.969 | 77.605 | 14.735 | 1.00 | 19.23 | C |
| ATOM | 5204 | CB | LYS | C | 164 | 7.871 | 78.845 | 14.771 | 1.00 | 18.10 | C |
| ATOM | 5205 | CG | LYS | C | 164 | 7.392 | 79.985 | 13.880 | 1.00 | 15.63 | C |
| ATOM | 5206 | CD | LYS | C | 164 | 7.282 | 79.545 | 12.421 | 1.00 | 15.35 | C |
| ATOM | 5207 | CE | LYS | C | 164 | 6.820 | 80.690 | 11.524 | 1.00 | 14.50 | C |
| ATOM | 5208 | NZ | LYS | C | 164 | 6.739 | 80.300 | 10.089 | 1.00 | 11.00 | N |
| ATOM | 5209 | C | LYS | C | 164 | 7.674 | 76.420 | 15.400 | 1.00 | 18.60 | C |
| ATOM | 5210 | O | LYS | C | 164 | 8.224 | 75.550 | 14.721 | 1.00 | 19.73 | O |
| ATOM | 5211 | N | ALA | C | 165 | 7.656 | 76.386 | 16.727 | 1.00 | 18.40 | N |
| ATOM | 5212 | CA | ALA | C | 165 | 8.260 | 75.279 | 17.457 | 1.00 | 17.99 | C |
| ATOM | 5213 | CB | ALA | C | 165 | 8.016 | 75.438 | 18.945 | 1.00 | 13.58 | C |
| ATOM | 5214 | C | ALA | C | 165 | 7.620 | 73.989 | 16.951 | 1.00 | 18.33 | C |
| ATOM | 5215 | O | ALA | C | 165 | 8.299 | 72.983 | 16.760 | 1.00 | 19.30 | O |
| ATOM | 5216 | N | SER | C | 166 | 6.309 | 74.030 | 16.730 | 1.00 | 18.32 | N |
| ATOM | 5217 | CA | SER | C | 166 | 5.574 | 72.866 | 16.235 | 1.00 | 18.58 | C |
| ATOM | 5218 | CB | SER | C | 166 | 4.064 | 73.115 | 16.326 | 1.00 | 19.21 | C |
| ATOM | 5219 | OG | SER | C | 166 | 3.339 | 72.016 | 15.798 | 1.00 | 22.38 | O |
| ATOM | 5220 | C | SER | C | 166 | 5.965 | 72.563 | 14.791 | 1.00 | 17.97 | C |
| ATOM | 5221 | O | SER | C | 166 | 6.143 | 71.395 | 14.412 | 1.00 | 17.14 | O |
| ATOM | 5222 | N | LEU | C | 167 | 6.109 | 73.618 | 13.992 | 1.00 | 16.76 | N |
| ATOM | 5223 | CA | LEU | C | 167 | 6.504 | 73.472 | 12.594 | 1.00 | 17.33 | C |
| ATOM | 5224 | CB | LEU | C | 167 | 6.596 | 74.842 | 11.914 | 1.00 | 13.11 | C |
| ATOM | 5225 | CG | LEU | C | 167 | 6.956 | 74.845 | 10.420 | 1.00 | 15.13 | C |
| ATOM | 5226 | CD1 | LEU | C | 167 | 5.880 | 74.098 | 9.631 | 1.00 | 14.02 | C |
| ATOM | 5227 | CD2 | LEU | C | 167 | 7.090 | 76.285 | 9.906 | 1.00 | 12.39 | C |
| ATOM | 5228 | C | LEU | C | 167 | 7.857 | 72.754 | 12.499 | 1.00 | 17.90 | C |
| ATOM | 5229 | O | LEU | C | 167 | 8.010 | 71.794 | 11.741 | 1.00 | 19.52 | O |
| ATOM | 5230 | N | GLU | C | 168 | 8.832 | 73.212 | 13.276 | 1.00 | 18.69 | N |
| ATOM | 5231 | CA | GLU | C | 168 | 10.156 | 72.598 | 13.266 | 1.00 | 18.92 | C |
| ATOM | 5232 | CB | GLU | C | 168 | 11.094 | 73.382 | 14.197 | 1.00 | 20.03 | C |
| ATOM | 5233 | CG | GLU | C | 168 | 11.463 | 74.778 | 13.637 | 1.00 | 24.03 | C |
| ATOM | 5234 | CD | GLU | C | 168 | 12.150 | 75.704 | 14.656 | 1.00 | 26.31 | C |
| ATOM | 5235 | OE1 | GLU | C | 168 | 13.100 | 75.268 | 15.340 | 1.00 | 28.07 | O |
| ATOM | 5236 | OE2 | GLU | C | 168 | 11.752 | 76.884 | 14.763 | 1.00 | 27.99 | O |
| ATOM | 5237 | C | GLU | C | 168 | 10.091 | 71.109 | 13.643 | 1.00 | 18.94 | C |
| ATOM | 5238 | O | GLU | C | 168 | 10.843 | 70.293 | 13.110 | 1.00 | 17.78 | O |
| ATOM | 5239 | N | ALA | C | 169 | 9.185 | 70.754 | 14.550 | 1.00 | 18.90 | N |
| ATOM | 5240 | CA | ALA | C | 169 | 9.028 | 69.358 | 14.946 | 1.00 | 20.48 | C |
| ATOM | 5241 | CB | ALA | C | 169 | 8.099 | 69.257 | 16.150 | 1.00 | 21.46 | C |
| ATOM | 5242 | C | ALA | C | 169 | 8.433 | 68.597 | 13.768 | 1.00 | 19.97 | C |
| ATOM | 5243 | O | ALA | C | 169 | 8.838 | 67.475 | 13.448 | 1.00 | 19.25 | O |
| ATOM | 5244 | N | ASN | C | 170 | 7.451 | 69.231 | 13.141 | 1.00 | 21.71 | N |
| ATOM | 5245 | CA | ASN | C | 170 | 6.753 | 68.686 | 11.983 | 1.00 | 22.39 | C |
| ATOM | 5246 | CB | ASN | C | 170 | 5.783 | 69.728 | 11.435 | 1.00 | 23.02 | C |
| ATOM | 5247 | CG | ASN | C | 170 | 4.462 | 69.127 | 11.014 | 1.00 | 23.82 | C |
| ATOM | 5248 | OD1 | ASN | C | 170 | 4.420 | 68.077 | 10.366 | 1.00 | 22.39 | O |
| ATOM | 5249 | ND2 | ASN | C | 170 | 3.366 | 69.803 | 11.369 | 1.00 | 24.89 | N |
| ATOM | 5250 | C | ASN | C | 170 | 7.780 | 68.365 | 10.913 | 1.00 | 22.86 | C |
| ATOM | 5251 | O | ASN | C | 170 | 7.677 | 67.363 | 10.198 | 1.00 | 24.46 | O |
| ATOM | 5252 | N | VAL | C | 171 | 8.772 | 69.234 | 10.790 | 1.00 | 21.23 | N |
| ATOM | 5253 | CA | VAL | C | 171 | 9.819 | 69.019 | 9.805 | 1.00 | 19.46 | C |
| ATOM | 5254 | CB | VAL | C | 171 | 10.806 | 70.200 | 9.786 | 1.00 | 18.12 | C |
| ATOM | 5255 | CG1 | VAL | C | 171 | 12.028 | 69.840 | 8.967 | 1.00 | 16.40 | C |
| ATOM | 5256 | CG2 | VAL | C | 171 | 10.108 | 71.436 | 9.180 | 1.00 | 19.18 | C |
| ATOM | 5257 | C | VAL | C | 171 | 10.578 | 67.727 | 10.067 | 1.00 | 17.96 | C |
| ATOM | 5258 | O | VAL | C | 171 | 10.733 | 66.894 | 9.173 | 1.00 | 19.39 | O |
| ATOM | 5259 | N | LYS | C | 172 | 11.031 | 67.552 | 11.298 | 1.00 | 17.25 | N |
| ATOM | 5260 | CA | LYS | C | 172 | 11.796 | 66.369 | 11.668 | 1.00 | 16.58 | C |
| ATOM | 5261 | CB | LYS | C | 172 | 12.302 | 66.530 | 13.097 | 1.00 | 17.52 | C |
| ATOM | 5262 | CG | LYS | C | 172 | 13.122 | 67.788 | 13.284 | 1.00 | 19.24 | C |
| ATOM | 5263 | CD | LYS | C | 172 | 13.407 | 68.036 | 14.744 | 1.00 | 21.36 | C |

FIGURE 9 (cont.)

```
ATOM  5264  CE   LYS C 172    14.360  69.193  14.910  1.00 21.79           C
ATOM  5265  NZ   LYS C 172    14.502  69.514  16.348  1.00 26.04           N
ATOM  5266  C    LYS C 172    10.993  65.086  11.537  1.00 15.69           C
ATOM  5267  O    LYS C 172    11.492  64.081  11.038  1.00 12.39           O
ATOM  5268  N    TYR C 173     9.741  65.128  11.980  1.00 17.19           N
ATOM  5269  CA   TYR C 173     8.886  63.956  11.909  1.00 17.64           C
ATOM  5270  CB   TYR C 173     7.627  64.161  12.764  1.00 17.27           C
ATOM  5271  CG   TYR C 173     7.861  63.752  14.206  1.00 17.36           C
ATOM  5272  CD1  TYR C 173     7.846  62.407  14.575  1.00 15.69           C
ATOM  5273  CE1  TYR C 173     8.192  62.005  15.858  1.00 14.60           C
ATOM  5274  CD2  TYR C 173     8.223  64.696  15.176  1.00 16.29           C
ATOM  5275  CE2  TYR C 173     8.573  64.302  16.464  1.00 14.42           C
ATOM  5276  CZ   TYR C 173     8.558  62.953  16.795  1.00 13.79           C
ATOM  5277  OH   TYR C 173     8.920  62.546  18.051  1.00 13.90           O
ATOM  5278  C    TYR C 173     8.539  63.576  10.480  1.00 17.98           C
ATOM  5279  O    TYR C 173     8.376  62.400  10.183  1.00 19.27           O
ATOM  5280  N    LEU C 174     8.455  64.559   9.589  1.00 19.13           N
ATOM  5281  CA   LEU C 174     8.157  64.269   8.183  1.00 19.05           C
ATOM  5282  CB   LEU C 174     7.643  65.530   7.458  1.00 17.54           C
ATOM  5283  CG   LEU C 174     6.207  65.989   7.768  1.00 16.32           C
ATOM  5284  CD1  LEU C 174     5.903  67.313   7.091  1.00 13.60           C
ATOM  5285  CD2  LEU C 174     5.231  64.925   7.295  1.00 15.96           C
ATOM  5286  C    LEU C 174     9.425  63.748   7.504  1.00 18.93           C
ATOM  5287  O    LEU C 174     9.364  62.922   6.592  1.00 20.21           O
ATOM  5288  N    ALA C 175    10.577  64.228   7.964  1.00 19.05           N
ATOM  5289  CA   ALA C 175    11.865  63.805   7.416  1.00 18.50           C
ATOM  5290  CB   ALA C 175    12.996  64.638   8.015  1.00 18.89           C
ATOM  5291  C    ALA C 175    12.112  62.335   7.698  1.00 17.16           C
ATOM  5292  O    ALA C 175    12.667  61.616   6.864  1.00 17.90           O
ATOM  5293  N    LEU C 176    11.719  61.884   8.884  1.00 16.60           N
ATOM  5294  CA   LEU C 176    11.909  60.491   9.254  1.00 16.90           C
ATOM  5295  CB   LEU C 176    11.640  60.275  10.749  1.00 16.55           C
ATOM  5296  CG   LEU C 176    12.225  59.019  11.420  1.00 17.77           C
ATOM  5297  CD1  LEU C 176    11.432  58.722  12.688  1.00 16.61           C
ATOM  5298  CD2  LEU C 176    12.176  57.826  10.503  1.00 15.75           C
ATOM  5299  C    LEU C 176    10.912  59.679   8.447  1.00 18.04           C
ATOM  5300  O    LEU C 176    11.252  58.648   7.870  1.00 18.02           O
ATOM  5301  N    ASP C 177     9.677  60.164   8.401  1.00 18.52           N
ATOM  5302  CA   ASP C 177     8.614  59.481   7.680  1.00 19.46           C
ATOM  5303  CB   ASP C 177     7.276  60.169   7.968  1.00 19.31           C
ATOM  5304  CG   ASP C 177     6.094  59.437   7.355  1.00 20.57           C
ATOM  5305  OD1  ASP C 177     6.246  58.262   6.944  1.00 20.43           O
ATOM  5306  OD2  ASP C 177     5.002  60.040   7.298  1.00 20.96           O
ATOM  5307  C    ASP C 177     8.839  59.389   6.172  1.00 20.28           C
ATOM  5308  O    ASP C 177     8.820  58.296   5.604  1.00 19.96           O
ATOM  5309  N    LEU C 178     9.071  60.521   5.516  1.00 19.77           N
ATOM  5310  CA   LEU C 178     9.244  60.487   4.072  1.00 19.79           C
ATOM  5311  CB   LEU C 178     8.745  61.794   3.455  1.00 19.12           C
ATOM  5312  CG   LEU C 178     7.369  62.313   3.918  1.00 20.74           C
ATOM  5313  CD1  LEU C 178     6.907  63.401   2.941  1.00 19.77           C
ATOM  5314  CD2  LEU C 178     6.350  61.208   3.980  1.00 17.90           C
ATOM  5315  C    LEU C 178    10.658  60.185   3.590  1.00 20.33           C
ATOM  5316  O    LEU C 178    10.880  60.030   2.389  1.00 18.61           O
ATOM  5317  N    GLY C 179    11.605  60.083   4.522  1.00 20.80           N
ATOM  5318  CA   GLY C 179    12.981  59.784   4.157  1.00 20.19           C
ATOM  5319  C    GLY C 179    13.158  58.542   3.289  1.00 21.33           C
ATOM  5320  O    GLY C 179    13.888  58.593   2.290  1.00 21.64           O
ATOM  5321  N    PRO C 180    12.511  57.405   3.623  1.00 20.85           N
ATOM  5322  CD   PRO C 180    11.812  57.063   4.869  1.00 20.80           C
ATOM  5323  CA   PRO C 180    12.683  56.209   2.788  1.00 22.14           C
ATOM  5324  CB   PRO C 180    12.034  55.102   3.623  1.00 21.88           C
ATOM  5325  CG   PRO C 180    12.181  55.603   5.029  1.00 21.93           C
ATOM  5326  C    PRO C 180    12.067  56.321   1.391  1.00 22.22           C
ATOM  5327  O    PRO C 180    12.318  55.477   0.541  1.00 22.19           O
ATOM  5328  N    ASP C 181    11.259  57.354   1.160  1.00 23.64           N
```

FIGURE 9 (cont.)

| ATOM | 5329 | CA | ASP | C | 181 | 10.637 | 57.562 | -0.155 | 1.00 | 23.93 | C |
| ATOM | 5330 | CB | ASP | C | 181 | 9.250 | 58.195 | -0.030 | 1.00 | 24.57 | C |
| ATOM | 5331 | CG | ASP | C | 181 | 8.279 | 57.314 | 0.721 | 1.00 | 26.78 | C |
| ATOM | 5332 | OD1 | ASP | C | 181 | 8.250 | 56.093 | 0.430 | 1.00 | 28.27 | O |
| ATOM | 5333 | OD2 | ASP | C | 181 | 7.548 | 57.839 | 1.597 | 1.00 | 27.16 | O |
| ATOM | 5334 | C | ASP | C | 181 | 11.537 | 58.506 | -0.920 | 1.00 | 24.76 | C |
| ATOM | 5335 | O | ASP | C | 181 | 11.236 | 58.917 | -2.047 | 1.00 | 24.62 | O |
| ATOM | 5336 | N | ASN | C | 182 | 12.642 | 58.867 | -0.283 | 1.00 | 24.35 | N |
| ATOM | 5337 | CA | ASN | C | 182 | 13.607 | 59.748 | -0.906 | 1.00 | 23.27 | C |
| ATOM | 5338 | CB | ASN | C | 182 | 14.010 | 59.193 | -2.267 | 1.00 | 23.89 | C |
| ATOM | 5339 | CG | ASN | C | 182 | 15.178 | 59.922 | -2.852 | 1.00 | 23.86 | C |
| ATOM | 5340 | OD1 | ASN | C | 182 | 16.113 | 60.270 | -2.135 | 1.00 | 24.81 | O |
| ATOM | 5341 | ND2 | ASN | C | 182 | 15.146 | 60.153 | -4.163 | 1.00 | 23.20 | N |
| ATOM | 5342 | C | ASN | C | 182 | 13.083 | 61.162 | -1.052 | 1.00 | 22.28 | C |
| ATOM | 5343 | O | ASN | C | 182 | 13.422 | 61.867 | -2.005 | 1.00 | 22.46 | O |
| ATOM | 5344 | N | ILE | C | 183 | 12.237 | 61.563 | -0.109 | 1.00 | 21.07 | N |
| ATOM | 5345 | CA | ILE | C | 183 | 11.703 | 62.916 | -0.079 | 1.00 | 21.33 | C |
| ATOM | 5346 | CB | ILE | C | 183 | 10.177 | 62.924 | 0.165 | 1.00 | 20.35 | C |
| ATOM | 5347 | CG2 | ILE | C | 183 | 9.682 | 64.351 | 0.353 | 1.00 | 17.27 | C |
| ATOM | 5348 | CG1 | ILE | C | 183 | 9.461 | 62.283 | -1.034 | 1.00 | 23.11 | C |
| ATOM | 5349 | CD1 | ILE | C | 183 | 7.950 | 62.076 | -0.846 | 1.00 | 20.39 | C |
| ATOM | 5350 | C | ILE | C | 183 | 12.420 | 63.579 | 1.100 | 1.00 | 21.61 | C |
| ATOM | 5351 | O | ILE | C | 183 | 12.348 | 63.083 | 2.226 | 1.00 | 22.32 | O |
| ATOM | 5352 | N | ARG | C | 184 | 13.151 | 64.663 | 0.848 | 1.00 | 20.00 | N |
| ATOM | 5353 | CA | ARG | C | 184 | 13.855 | 65.341 | 1.937 | 1.00 | 19.31 | C |
| ATOM | 5354 | CB | ARG | C | 184 | 15.195 | 65.895 | 1.443 | 1.00 | 18.92 | C |
| ATOM | 5355 | CG | ARG | C | 184 | 16.147 | 64.810 | 0.985 | 1.00 | 19.98 | C |
| ATOM | 5356 | CD | ARG | C | 184 | 17.502 | 65.344 | 0.527 | 1.00 | 18.66 | C |
| ATOM | 5357 | NE | ARG | C | 184 | 17.426 | 66.185 | -0.667 | 1.00 | 18.95 | N |
| ATOM | 5358 | CZ | ARG | C | 184 | 17.386 | 67.517 | -0.659 | 1.00 | 17.67 | C |
| ATOM | 5359 | NH1 | ARG | C | 184 | 17.410 | 68.190 | 0.486 | 1.00 | 16.59 | N |
| ATOM | 5360 | NH2 | ARG | C | 184 | 17.346 | 68.181 | -1.805 | 1.00 | 17.65 | N |
| ATOM | 5361 | C | ARG | C | 184 | 12.987 | 66.466 | 2.480 | 1.00 | 18.73 | C |
| ATOM | 5362 | O | ARG | C | 184 | 12.238 | 67.087 | 1.725 | 1.00 | 19.02 | O |
| ATOM | 5363 | N | VAL | C | 185 | 13.064 | 66.716 | 3.785 | 1.00 | 18.69 | N |
| ATOM | 5364 | CA | VAL | C | 185 | 12.261 | 67.780 | 4.400 | 1.00 | 17.63 | C |
| ATOM | 5365 | CB | VAL | C | 185 | 11.090 | 67.216 | 5.247 | 1.00 | 16.71 | C |
| ATOM | 5366 | CG1 | VAL | C | 185 | 10.124 | 68.341 | 5.600 | 1.00 | 17.84 | C |
| ATOM | 5367 | CG2 | VAL | C | 185 | 10.354 | 66.114 | 4.498 | 1.00 | 14.93 | C |
| ATOM | 5368 | C | VAL | C | 185 | 13.136 | 68.639 | 5.310 | 1.00 | 18.40 | C |
| ATOM | 5369 | O | VAL | C | 185 | 13.732 | 68.135 | 6.260 | 1.00 | 19.89 | O |
| ATOM | 5370 | N | ASN | C | 186 | 13.203 | 69.937 | 5.024 | 1.00 | 18.51 | N |
| ATOM | 5371 | CA | ASN | C | 186 | 14.027 | 70.853 | 5.810 | 1.00 | 18.61 | C |
| ATOM | 5372 | CB | ASN | C | 186 | 15.351 | 71.101 | 5.090 | 1.00 | 17.85 | C |
| ATOM | 5373 | CG | ASN | C | 186 | 16.149 | 69.833 | 4.886 | 1.00 | 18.12 | C |
| ATOM | 5374 | OD1 | ASN | C | 186 | 16.608 | 69.222 | 5.844 | 1.00 | 19.98 | O |
| ATOM | 5375 | ND2 | ASN | C | 186 | 16.319 | 69.429 | 3.633 | 1.00 | 17.94 | N |
| ATOM | 5376 | C | ASN | C | 186 | 13.340 | 72.189 | 6.057 | 1.00 | 19.20 | C |
| ATOM | 5377 | O | ASN | C | 186 | 12.248 | 72.437 | 5.547 | 1.00 | 20.11 | O |
| ATOM | 5378 | N | ALA | C | 187 | 13.996 | 73.055 | 6.826 | 1.00 | 19.53 | N |
| ATOM | 5379 | CA | ALA | C | 187 | 13.452 | 74.373 | 7.138 | 1.00 | 20.40 | C |
| ATOM | 5380 | CB | ALA | C | 187 | 12.873 | 74.375 | 8.546 | 1.00 | 20.34 | C |
| ATOM | 5381 | C | ALA | C | 187 | 14.502 | 75.471 | 7.019 | 1.00 | 21.00 | C |
| ATOM | 5382 | O | ALA | C | 187 | 15.703 | 75.211 | 7.122 | 1.00 | 21.18 | O |
| ATOM | 5383 | N | ILE | C | 188 | 14.046 | 76.698 | 6.785 | 1.00 | 20.87 | N |
| ATOM | 5384 | CA | ILE | C | 188 | 14.949 | 77.839 | 6.682 | 1.00 | 20.62 | C |
| ATOM | 5385 | CB | ILE | C | 188 | 14.897 | 78.504 | 5.292 | 1.00 | 21.63 | C |
| ATOM | 5386 | CG2 | ILE | C | 188 | 15.904 | 79.654 | 5.223 | 1.00 | 21.92 | C |
| ATOM | 5387 | CG1 | ILE | C | 188 | 15.221 | 77.484 | 4.207 | 1.00 | 21.54 | C |
| ATOM | 5388 | CD1 | ILE | C | 188 | 15.197 | 78.085 | 2.801 | 1.00 | 21.12 | C |
| ATOM | 5389 | C | ILE | C | 188 | 14.475 | 78.849 | 7.712 | 1.00 | 20.22 | C |
| ATOM | 5390 | O | ILE | C | 188 | 13.345 | 79.322 | 7.648 | 1.00 | 19.73 | O |
| ATOM | 5391 | N | SER | C | 189 | 15.325 | 79.156 | 8.681 | 1.00 | 19.83 | N |
| ATOM | 5392 | CA | SER | C | 189 | 14.962 | 80.110 | 9.721 | 1.00 | 18.67 | C |
| ATOM | 5393 | CB | SER | C | 189 | 15.570 | 79.677 | 11.053 | 1.00 | 17.10 | C |

FIGURE 9 (cont.)

| | | | | | | | | | | |
|---|---|---|---|---|---|---|---|---|---|---|
| ATOM | 5394 | OG | SER | C | 189 | 14.876 | 80.247 | 12.144 | 1.00 17.40 | O |
| ATOM | 5395 | C | SER | C | 189 | 15.502 | 81.468 | 9.288 | 1.00 19.24 | C |
| ATOM | 5396 | O | SER | C | 189 | 16.698 | 81.629 | 9.081 | 1.00 18.76 | O |
| ATOM | 5397 | N | ALA | C | 190 | 14.623 | 82.451 | 9.137 | 1.00 19.53 | N |
| ATOM | 5398 | CA | ALA | C | 190 | 15.079 | 83.755 | 8.691 | 1.00 20.72 | C |
| ATOM | 5399 | CB | ALA | C | 190 | 14.270 | 84.182 | 7.477 | 1.00 20.20 | C |
| ATOM | 5400 | C | ALA | C | 190 | 15.035 | 84.853 | 9.748 | 1.00 21.05 | C |
| ATOM | 5401 | O | ALA | C | 190 | 14.253 | 84.786 | 10.702 | 1.00 21.56 | O |
| ATOM | 5402 | N | SER | C | 191 | 15.897 | 85.852 | 9.570 | 1.00 20.37 | N |
| ATOM | 5403 | CA | SER | C | 191 | 15.935 | 87.007 | 10.449 | 1.00 21.04 | C |
| ATOM | 5404 | CB | SER | C | 191 | 17.300 | 87.720 | 10.359 | 1.00 20.87 | C |
| ATOM | 5405 | OG | SER | C | 191 | 17.832 | 87.692 | 9.041 | 1.00 22.05 | O |
| ATOM | 5406 | C | SER | C | 191 | 14.809 | 87.900 | 9.916 | 1.00 21.42 | C |
| ATOM | 5407 | O | SER | C | 191 | 14.350 | 87.712 | 8.787 | 1.00 21.17 | O |
| ATOM | 5408 | N | PRO | C | 192 | 14.344 | 88.870 | 10.718 | 1.00 21.44 | N |
| ATOM | 5409 | CD | PRO | C | 192 | 14.901 | 89.302 | 12.015 | 1.00 21.69 | C |
| ATOM | 5410 | CA | PRO | C | 192 | 13.261 | 89.766 | 10.297 | 1.00 21.80 | C |
| ATOM | 5411 | CB | PRO | C | 192 | 13.354 | 90.907 | 11.309 | 1.00 21.39 | C |
| ATOM | 5412 | CG | PRO | C | 192 | 13.810 | 90.209 | 12.545 | 1.00 20.43 | C |
| ATOM | 5413 | C | PRO | C | 192 | 13.331 | 90.265 | 8.852 | 1.00 21.37 | C |
| ATOM | 5414 | O | PRO | C | 192 | 14.407 | 90.572 | 8.333 | 1.00 22.93 | O |
| ATOM | 5415 | N | ILE | C | 193 | 12.175 | 90.345 | 8.206 | 1.00 20.81 | N |
| ATOM | 5416 | CA | ILE | C | 193 | 12.088 | 90.833 | 6.827 | 1.00 20.91 | C |
| ATOM | 5417 | CB | ILE | C | 193 | 12.059 | 89.658 | 5.806 | 1.00 19.04 | C |
| ATOM | 5418 | CG2 | ILE | C | 193 | 11.827 | 90.189 | 4.406 | 1.00 18.03 | C |
| ATOM | 5419 | CG1 | ILE | C | 193 | 13.385 | 88.879 | 5.861 | 1.00 18.89 | C |
| ATOM | 5420 | CD1 | ILE | C | 193 | 13.526 | 87.801 | 4.806 | 1.00 15.46 | C |
| ATOM | 5421 | C | ILE | C | 193 | 10.817 | 91.682 | 6.668 | 1.00 22.33 | C |
| ATOM | 5422 | O | ILE | C | 193 | 9.707 | 91.213 | 6.926 | 1.00 22.43 | O |
| ATOM | 5423 | N | ARG | C | 194 | 10.999 | 92.939 | 6.268 | 1.00 24.24 | N |
| ATOM | 5424 | CA | ARG | C | 194 | 9.898 | 93.887 | 6.061 | 1.00 26.31 | C |
| ATOM | 5425 | CB | ARG | C | 194 | 10.467 | 95.239 | 5.615 | 1.00 27.83 | C |
| ATOM | 5426 | CG | ARG | C | 194 | 9.430 | 96.313 | 5.335 | 1.00 30.37 | C |
| ATOM | 5427 | CD | ARG | C | 194 | 9.467 | 97.354 | 6.442 | 1.00 33.87 | C |
| ATOM | 5428 | NE | ARG | C | 194 | 10.822 | 97.899 | 6.590 | 1.00 36.16 | N |
| ATOM | 5429 | CZ | ARG | C | 194 | 11.233 | 98.626 | 7.628 | 1.00 36.37 | C |
| ATOM | 5430 | NH1 | ARG | C | 194 | 10.391 | 98.913 | 8.629 | 1.00 34.81 | N |
| ATOM | 5431 | NH2 | ARG | C | 194 | 12.498 | 99.039 | 7.675 | 1.00 35.91 | N |
| ATOM | 5432 | C | ARG | C | 194 | 8.952 | 93.374 | 4.983 | 1.00 26.26 | C |
| ATOM | 5433 | O | ARG | C | 194 | 9.157 | 93.657 | 3.799 | 1.00 27.00 | O |
| ATOM | 5434 | N | THR | C | 195 | 7.930 | 92.619 | 5.381 | 1.00 26.25 | N |
| ATOM | 5435 | CA | THR | C | 195 | 6.963 | 92.058 | 4.434 | 1.00 25.17 | C |
| ATOM | 5436 | CB | THR | C | 195 | 7.117 | 90.531 | 4.311 | 1.00 26.00 | C |
| ATOM | 5437 | OG1 | THR | C | 195 | 6.814 | 89.928 | 5.579 | 1.00 25.32 | O |
| ATOM | 5438 | CG2 | THR | C | 195 | 8.536 | 90.155 | 3.891 | 1.00 23.54 | C |
| ATOM | 5439 | C | THR | C | 195 | 5.539 | 92.315 | 4.925 | 1.00 26.43 | C |
| ATOM | 5440 | O | THR | C | 195 | 5.327 | 93.068 | 5.882 | 1.00 25.02 | O |
| ATOM | 5441 | N | LEU | C | 196 | 4.561 | 91.683 | 4.277 | 1.00 26.73 | N |
| ATOM | 5442 | CA | LEU | C | 196 | 3.178 | 91.854 | 4.688 | 1.00 27.46 | C |
| ATOM | 5443 | CB | LEU | C | 196 | 2.226 | 91.094 | 3.764 | 1.00 28.17 | C |
| ATOM | 5444 | CG | LEU | C | 196 | 1.878 | 91.726 | 2.412 | 1.00 28.10 | C |
| ATOM | 5445 | CD1 | LEU | C | 196 | 0.690 | 90.965 | 1.808 | 1.00 27.61 | C |
| ATOM | 5446 | CD2 | LEU | C | 196 | 1.520 | 93.192 | 2.597 | 1.00 26.48 | C |
| ATOM | 5447 | C | LEU | C | 196 | 2.981 | 91.370 | 6.114 | 1.00 28.07 | C |
| ATOM | 5448 | O | LEU | C | 196 | 2.161 | 91.910 | 6.849 | 1.00 28.94 | O |
| ATOM | 5449 | N | SER | C | 197 | 3.737 | 90.351 | 6.513 | 1.00 28.80 | N |
| ATOM | 5450 | CA | SER | C | 197 | 3.615 | 89.819 | 7.868 | 1.00 28.86 | C |
| ATOM | 5451 | CB | SER | C | 197 | 4.088 | 88.369 | 7.892 | 1.00 29.22 | C |
| ATOM | 5452 | OG | SER | C | 197 | 3.250 | 87.576 | 7.051 | 1.00 31.08 | O |
| ATOM | 5453 | C | SER | C | 197 | 4.363 | 90.665 | 8.903 | 1.00 28.93 | C |
| ATOM | 5454 | O | SER | C | 197 | 4.624 | 90.227 | 10.025 | 1.00 28.28 | O |
| ATOM | 5455 | N | ALA | C | 198 | 4.686 | 91.894 | 8.522 | 1.00 29.91 | N |
| ATOM | 5456 | CA | ALA | C | 198 | 5.362 | 92.821 | 9.416 | 1.00 31.12 | C |
| ATOM | 5457 | CB | ALA | C | 198 | 6.649 | 93.319 | 8.783 | 1.00 30.06 | C |
| ATOM | 5458 | C | ALA | C | 198 | 4.412 | 93.991 | 9.648 | 1.00 33.05 | C |

FIGURE 9 (cont.)

| | | | | | | | | | |
|---|---|---|---|---|---|---|---|---|---|
| ATOM | 5459 | O | ALA | C | 198 | 4.619 | 94.807 | 10.549 | 1.00 34.41 | O |
| ATOM | 5460 | N | LYS | C | 199 | 3.370 | 94.073 | 8.825 | 1.00 33.74 | N |
| ATOM | 5461 | CA | LYS | C | 199 | 2.411 | 95.159 | 8.937 | 1.00 35.03 | C |
| ATOM | 5462 | CB | LYS | C | 199 | 1.624 | 95.333 | 7.626 | 1.00 35.91 | C |
| ATOM | 5463 | CG | LYS | C | 199 | 0.733 | 96.579 | 7.564 | 1.00 35.91 | C |
| ATOM | 5464 | CD | LYS | C | 199 | 1.423 | 97.844 | 8.115 | 1.00 37.65 | C |
| ATOM | 5465 | CE | LYS | C | 199 | 2.669 | 98.258 | 7.317 | 1.00 38.13 | C |
| ATOM | 5466 | NZ | LYS | C | 199 | 2.360 | 98.689 | 5.909 | 1.00 36.91 | N |
| ATOM | 5467 | C | LYS | C | 199 | 1.482 | 94.843 | 10.078 | 1.00 35.50 | C |
| ATOM | 5468 | O | LYS | C | 199 | 0.603 | 93.983 | 9.971 | 1.00 35.96 | O |
| ATOM | 5469 | N | GLY | C | 200 | 1.699 | 95.546 | 11.181 | 1.00 36.20 | N |
| ATOM | 5470 | CA | GLY | C | 200 | 0.895 | 95.352 | 12.371 | 1.00 35.69 | C |
| ATOM | 5471 | C | GLY | C | 200 | 1.821 | 95.345 | 13.566 | 1.00 35.18 | C |
| ATOM | 5472 | O | GLY | C | 200 | 1.746 | 96.207 | 14.427 | 1.00 35.84 | O |
| ATOM | 5473 | N | VAL | C | 201 | 2.713 | 94.366 | 13.595 | 1.00 35.77 | N |
| ATOM | 5474 | CA | VAL | C | 201 | 3.681 | 94.204 | 14.674 | 1.00 34.88 | C |
| ATOM | 5475 | CB | VAL | C | 201 | 4.740 | 93.148 | 14.258 | 1.00 34.95 | C |
| ATOM | 5476 | CG1 | VAL | C | 201 | 5.015 | 93.283 | 12.781 | 1.00 34.63 | C |
| ATOM | 5477 | CG2 | VAL | C | 201 | 6.033 | 93.327 | 15.060 | 1.00 33.32 | C |
| ATOM | 5478 | C | VAL | C | 201 | 4.359 | 95.533 | 15.016 | 1.00 34.49 | C |
| ATOM | 5479 | O | VAL | C | 201 | 4.818 | 96.256 | 14.131 | 1.00 33.44 | O |
| ATOM | 5480 | N | GLY | C | 202 | 4.429 | 95.844 | 16.307 | 1.00 34.45 | N |
| ATOM | 5481 | CA | GLY | C | 202 | 5.031 | 97.100 | 16.725 | 1.00 34.98 | C |
| ATOM | 5482 | C | GLY | C | 202 | 6.545 | 97.090 | 16.771 | 1.00 35.03 | C |
| ATOM | 5483 | O | GLY | C | 202 | 7.162 | 96.022 | 16.892 | 1.00 35.59 | O |
| ATOM | 5484 | N | GLY | C | 203 | 7.143 | 98.277 | 16.672 | 1.00 34.17 | N |
| ATOM | 5485 | CA | GLY | C | 203 | 8.593 | 98.401 | 16.717 | 1.00 33.97 | C |
| ATOM | 5486 | C | GLY | C | 203 | 9.386 | 97.544 | 15.739 | 1.00 34.63 | C |
| ATOM | 5487 | O | GLY | C | 203 | 10.519 | 97.141 | 16.035 | 1.00 34.96 | O |
| ATOM | 5488 | N | PHE | C | 204 | 8.820 | 97.273 | 14.565 | 1.00 33.96 | N |
| ATOM | 5489 | CA | PHE | C | 204 | 9.525 | 96.454 | 13.581 | 1.00 33.98 | C |
| ATOM | 5490 | CB | PHE | C | 204 | 8.610 | 96.136 | 12.396 | 1.00 33.06 | C |
| ATOM | 5491 | CG | PHE | C | 204 | 9.022 | 94.910 | 11.637 | 1.00 32.38 | C |
| ATOM | 5492 | CD1 | PHE | C | 204 | 9.984 | 94.982 | 10.636 | 1.00 32.09 | C |
| ATOM | 5493 | CD2 | PHE | C | 204 | 8.479 | 93.667 | 11.960 | 1.00 33.58 | C |
| ATOM | 5494 | CE1 | PHE | C | 204 | 10.407 | 93.831 | 9.964 | 1.00 31.55 | C |
| ATOM | 5495 | CE2 | PHE | C | 204 | 8.892 | 92.498 | 11.296 | 1.00 32.90 | C |
| ATOM | 5496 | CZ | PHE | C | 204 | 9.858 | 92.585 | 10.298 | 1.00 33.16 | C |
| ATOM | 5497 | C | PHE | C | 204 | 10.812 | 97.132 | 13.089 | 1.00 33.82 | C |
| ATOM | 5498 | O | PHE | C | 204 | 11.774 | 96.469 | 12.690 | 1.00 34.25 | O |
| ATOM | 5499 | N | ASN | C | 205 | 10.835 | 98.454 | 13.119 | 1.00 33.00 | N |
| ATOM | 5500 | CA | ASN | C | 205 | 12.023 | 99.170 | 12.695 | 1.00 33.62 | C |
| ATOM | 5501 | CB | ASN | C | 205 | 11.677 | 100.644 | 12.494 | 1.00 35.59 | C |
| ATOM | 5502 | CG | ASN | C | 205 | 12.886 | 101.530 | 12.548 | 1.00 38.07 | C |
| ATOM | 5503 | OD1 | ASN | C | 205 | 13.868 | 101.312 | 11.820 | 1.00 40.77 | O |
| ATOM | 5504 | ND2 | ASN | C | 205 | 12.836 | 102.549 | 13.413 | 1.00 38.67 | N |
| ATOM | 5505 | C | ASN | C | 205 | 13.155 | 99.004 | 13.725 | 1.00 32.10 | C |
| ATOM | 5506 | O | ASN | C | 205 | 14.342 | 99.077 | 13.387 | 1.00 31.02 | O |
| ATOM | 5507 | N | THR | C | 206 | 12.782 | 98.782 | 14.984 | 1.00 31.47 | N |
| ATOM | 5508 | CA | THR | C | 206 | 13.758 | 98.587 | 16.057 | 1.00 29.28 | C |
| ATOM | 5509 | CB | THR | C | 206 | 13.100 | 98.815 | 17.441 | 1.00 29.59 | C |
| ATOM | 5510 | OG1 | THR | C | 206 | 12.826 | 100.213 | 17.603 | 1.00 31.16 | O |
| ATOM | 5511 | CG2 | THR | C | 206 | 14.018 | 98.372 | 18.568 | 1.00 28.67 | C |
| ATOM | 5512 | C | THR | C | 206 | 14.303 | 97.160 | 15.965 | 1.00 28.23 | C |
| ATOM | 5513 | O | THR | C | 206 | 15.475 | 96.896 | 16.263 | 1.00 25.64 | O |
| ATOM | 5514 | N | ILE | C | 207 | 13.434 | 96.248 | 15.534 | 1.00 27.59 | N |
| ATOM | 5515 | CA | ILE | C | 207 | 13.788 | 94.843 | 15.367 | 1.00 26.65 | C |
| ATOM | 5516 | CB | ILE | C | 207 | 12.553 | 94.031 | 14.906 | 1.00 26.82 | C |
| ATOM | 5517 | CG2 | ILE | C | 207 | 12.955 | 92.603 | 14.576 | 1.00 26.79 | C |
| ATOM | 5518 | CG1 | ILE | C | 207 | 11.480 | 94.053 | 16.003 | 1.00 26.49 | C |
| ATOM | 5519 | CD1 | ILE | C | 207 | 10.282 | 93.165 | 15.712 | 1.00 25.29 | C |
| ATOM | 5520 | C | ILE | C | 207 | 14.910 | 94.688 | 14.330 | 1.00 26.39 | C |
| ATOM | 5521 | O | ILE | C | 207 | 15.872 | 93.934 | 14.533 | 1.00 25.87 | O |
| ATOM | 5522 | N | LEU | C | 208 | 14.775 | 95.404 | 13.218 | 1.00 25.89 | N |
| ATOM | 5523 | CA | LEU | C | 208 | 15.753 | 95.354 | 12.134 | 1.00 24.46 | C |

FIGURE 9 (cont.)

| | | | | | | | | | | |
|---|---|---|---|---|---|---|---|---|---|---|
| ATOM | 5524 | CB | LEU | C | 208 | 15.192 | 96.050 | 10.887 | 1.00 22.00 | C |
| ATOM | 5525 | CG | LEU | C | 208 | 14.018 | 95.389 | 10.166 | 1.00 19.14 | C |
| ATOM | 5526 | CD1 | LEU | C | 208 | 13.400 | 96.371 | 9.203 | 1.00 17.67 | C |
| ATOM | 5527 | CD2 | LEU | C | 208 | 14.495 | 94.145 | 9.434 | 1.00 18.20 | C |
| ATOM | 5528 | C | LEU | C | 208 | 17.078 | 96.005 | 12.508 | 1.00 24.48 | C |
| ATOM | 5529 | O | LEU | C | 208 | 18.141 | 95.518 | 12.113 | 1.00 24.47 | O |
| ATOM | 5530 | N | LYS | C | 209 | 17.020 | 97.108 | 13.253 | 1.00 24.41 | N |
| ATOM | 5531 | CA | LYS | C | 209 | 18.241 | 97.816 | 13.649 | 1.00 25.49 | C |
| ATOM | 5532 | CB | LYS | C | 209 | 17.896 | 99.110 | 14.409 | 1.00 26.77 | C |
| ATOM | 5533 | CG | LYS | C | 209 | 19.009 | 100.193 | 14.408 | 1.00 29.38 | C |
| ATOM | 5534 | CD | LYS | C | 209 | 19.329 | 100.691 | 12.976 | 1.00 31.09 | C |
| ATOM | 5535 | CE | LYS | C | 209 | 20.141 | 102.003 | 12.953 | 1.00 31.76 | C |
| ATOM | 5536 | NZ | LYS | C | 209 | 21.539 | 101.899 | 13.489 | 1.00 31.70 | N |
| ATOM | 5537 | C | LYS | C | 209 | 19.086 | 96.903 | 14.531 | 1.00 25.36 | C |
| ATOM | 5538 | O | LYS | C | 209 | 20.321 | 96.905 | 14.448 | 1.00 24.89 | O |
| ATOM | 5539 | N | GLU | C | 210 | 18.410 | 96.124 | 15.373 | 1.00 25.03 | N |
| ATOM | 5540 | CA | GLU | C | 210 | 19.092 | 95.200 | 16.268 | 1.00 25.82 | C |
| ATOM | 5541 | CB | GLU | C | 210 | 18.076 | 94.460 | 17.137 | 1.00 27.57 | C |
| ATOM | 5542 | CG | GLU | C | 210 | 18.697 | 93.437 | 18.080 | 1.00 29.43 | C |
| ATOM | 5543 | CD | GLU | C | 210 | 17.666 | 92.801 | 18.978 | 1.00 29.98 | C |
| ATOM | 5544 | OE1 | GLU | C | 210 | 16.554 | 92.530 | 18.481 | 1.00 32.65 | O |
| ATOM | 5545 | OE2 | GLU | C | 210 | 17.960 | 92.566 | 20.170 | 1.00 30.56 | O |
| ATOM | 5546 | C | GLU | C | 210 | 19.926 | 94.198 | 15.472 | 1.00 25.38 | C |
| ATOM | 5547 | O | GLU | C | 210 | 21.137 | 94.111 | 15.663 | 1.00 25.01 | O |
| ATOM | 5548 | N | ILE | C | 211 | 19.285 | 93.450 | 14.572 | 1.00 25.46 | N |
| ATOM | 5549 | CA | ILE | C | 211 | 20.014 | 92.471 | 13.758 | 1.00 25.38 | C |
| ATOM | 5550 | CB | ILE | C | 211 | 19.123 | 91.872 | 12.624 | 1.00 24.90 | C |
| ATOM | 5551 | CG2 | ILE | C | 211 | 20.000 | 91.366 | 11.487 | 1.00 24.75 | C |
| ATOM | 5552 | CG1 | ILE | C | 211 | 18.296 | 90.693 | 13.151 | 1.00 24.22 | C |
| ATOM | 5553 | CD1 | ILE | C | 211 | 17.354 | 91.030 | 14.269 | 1.00 25.21 | C |
| ATOM | 5554 | C | ILE | C | 211 | 21.204 | 93.173 | 13.121 | 1.00 26.36 | C |
| ATOM | 5555 | O | ILE | C | 211 | 22.320 | 92.647 | 13.094 | 1.00 27.18 | O |
| ATOM | 5556 | N | GLU | C | 212 | 20.950 | 94.377 | 12.625 | 1.00 26.58 | N |
| ATOM | 5557 | CA | GLU | C | 212 | 21.955 | 95.191 | 11.964 | 1.00 27.42 | C |
| ATOM | 5558 | CB | GLU | C | 212 | 21.278 | 96.440 | 11.387 | 1.00 29.14 | C |
| ATOM | 5559 | CG | GLU | C | 212 | 22.215 | 97.369 | 10.638 | 1.00 32.01 | C |
| ATOM | 5560 | CD | GLU | C | 212 | 21.500 | 98.581 | 10.045 | 1.00 34.18 | C |
| ATOM | 5561 | OE1 | GLU | C | 212 | 22.157 | 99.326 | 9.284 | 1.00 36.81 | O |
| ATOM | 5562 | OE2 | GLU | C | 212 | 20.296 | 98.792 | 10.334 | 1.00 33.72 | O |
| ATOM | 5563 | C | GLU | C | 212 | 23.120 | 95.598 | 12.875 | 1.00 27.56 | C |
| ATOM | 5564 | O | GLU | C | 212 | 24.244 | 95.814 | 12.406 | 1.00 28.06 | O |
| ATOM | 5565 | N | GLU | C | 213 | 22.869 | 95.697 | 14.174 | 1.00 26.73 | N |
| ATOM | 5566 | CA | GLU | C | 213 | 23.931 | 96.092 | 15.100 | 1.00 26.77 | C |
| ATOM | 5567 | CB | GLU | C | 213 | 23.388 | 97.086 | 16.140 | 1.00 28.43 | C |
| ATOM | 5568 | CG | GLU | C | 213 | 22.751 | 98.322 | 15.521 | 1.00 34.23 | C |
| ATOM | 5569 | CD | GLU | C | 213 | 22.355 | 99.378 | 16.540 | 1.00 36.38 | C |
| ATOM | 5570 | OE1 | GLU | C | 213 | 21.663 | 99.032 | 17.534 | 1.00 38.01 | O |
| ATOM | 5571 | OE2 | GLU | C | 213 | 22.725 | 100.563 | 16.332 | 1.00 37.94 | O |
| ATOM | 5572 | C | GLU | C | 213 | 24.577 | 94.914 | 15.830 | 1.00 25.34 | C |
| ATOM | 5573 | O | GLU | C | 213 | 25.755 | 94.965 | 16.186 | 1.00 25.29 | O |
| ATOM | 5574 | N | ARG | C | 214 | 23.818 | 93.849 | 16.046 | 1.00 23.27 | N |
| ATOM | 5575 | CA | ARG | C | 214 | 24.351 | 92.711 | 16.776 | 1.00 22.65 | C |
| ATOM | 5576 | CB | ARG | C | 214 | 23.329 | 92.265 | 17.825 | 1.00 21.02 | C |
| ATOM | 5577 | CG | ARG | C | 214 | 22.918 | 93.383 | 18.798 | 1.00 21.07 | C |
| ATOM | 5578 | CD | ARG | C | 214 | 21.845 | 92.897 | 19.761 | 1.00 19.99 | C |
| ATOM | 5579 | NE | ARG | C | 214 | 22.333 | 91.724 | 20.471 | 1.00 21.51 | N |
| ATOM | 5580 | CZ | ARG | C | 214 | 21.566 | 90.806 | 21.045 | 1.00 20.52 | C |
| ATOM | 5581 | NH1 | ARG | C | 214 | 20.241 | 90.909 | 21.009 | 1.00 19.46 | N |
| ATOM | 5582 | NH2 | ARG | C | 214 | 22.140 | 89.771 | 21.641 | 1.00 20.69 | N |
| ATOM | 5583 | C | ARG | C | 214 | 24.792 | 91.516 | 15.923 | 1.00 22.47 | C |
| ATOM | 5584 | O | ARG | C | 214 | 25.788 | 90.866 | 16.244 | 1.00 23.56 | O |
| ATOM | 5585 | N | ALA | C | 215 | 24.076 | 91.229 | 14.839 | 1.00 21.28 | N |
| ATOM | 5586 | CA | ALA | C | 215 | 24.432 | 90.087 | 13.999 | 1.00 19.55 | C |
| ATOM | 5587 | CB | ALA | C | 215 | 23.458 | 89.962 | 12.835 | 1.00 18.02 | C |
| ATOM | 5588 | C | ALA | C | 215 | 25.859 | 90.230 | 13.487 | 1.00 19.43 | C |

FIGURE 9 (cont.)

| ATOM | 5589 | O | ALA C 215 | 26.305 | 91.328 | 13.164 | 1.00 | 19.38 | O |
|------|------|-----|-----------|--------|--------|--------|------|-------|---|
| ATOM | 5590 | N | PRO C 216 | 26.595 | 89.116 | 13.407 | 1.00 | 19.10 | N |
| ATOM | 5591 | CD | PRO C 216 | 26.182 | 87.761 | 13.814 | 1.00 | 20.07 | C |
| ATOM | 5592 | CA | PRO C 216 | 27.981 | 89.114 | 12.934 | 1.00 | 18.39 | C |
| ATOM | 5593 | CB | PRO C 216 | 28.312 | 87.627 | 12.853 | 1.00 | 18.89 | C |
| ATOM | 5594 | CG | PRO C 216 | 27.519 | 87.053 | 13.973 | 1.00 | 18.24 | C |
| ATOM | 5595 | C | PRO C 216 | 28.175 | 89.833 | 11.606 | 1.00 | 17.86 | C |
| ATOM | 5596 | O | PRO C 216 | 29.153 | 90.558 | 11.436 | 1.00 | 16.78 | O |
| ATOM | 5597 | N | LEU C 217 | 27.252 | 89.642 | 10.667 | 1.00 | 17.35 | N |
| ATOM | 5598 | CA | LEU C 217 | 27.370 | 90.310 | 9.374 | 1.00 | 17.96 | C |
| ATOM | 5599 | CB | LEU C 217 | 26.560 | 89.571 | 8.297 | 1.00 | 17.83 | C |
| ATOM | 5600 | CG | LEU C 217 | 27.038 | 88.187 | 7.825 | 1.00 | 18.89 | C |
| ATOM | 5601 | CD1 | LEU C 217 | 26.225 | 87.765 | 6.622 | 1.00 | 17.52 | C |
| ATOM | 5602 | CD2 | LEU C 217 | 28.509 | 88.213 | 7.450 | 1.00 | 19.21 | C |
| ATOM | 5603 | C | LEU C 217 | 26.962 | 91.800 | 9.411 | 1.00 | 18.56 | C |
| ATOM | 5604 | O | LEU C 217 | 27.177 | 92.526 | 8.440 | 1.00 | 19.97 | O |
| ATOM | 5605 | N | LYS C 218 | 26.389 | 92.249 | 10.528 | 1.00 | 17.98 | N |
| ATOM | 5606 | CA | LYS C 218 | 25.972 | 93.646 | 10.699 | 1.00 | 17.84 | C |
| ATOM | 5607 | CB | LYS C 218 | 27.195 | 94.570 | 10.793 | 1.00 | 17.96 | C |
| ATOM | 5608 | CG | LYS C 218 | 28.276 | 94.129 | 11.777 | 1.00 | 18.97 | C |
| ATOM | 5609 | CD | LYS C 218 | 27.826 | 94.206 | 13.235 | 1.00 | 22.80 | C |
| ATOM | 5610 | CE | LYS C 218 | 29.005 | 93.929 | 14.185 | 1.00 | 23.47 | C |
| ATOM | 5611 | NZ | LYS C 218 | 28.618 | 93.962 | 15.629 | 1.00 | 23.95 | N |
| ATOM | 5612 | C | LYS C 218 | 25.065 | 94.148 | 9.575 | 1.00 | 17.82 | C |
| ATOM | 5613 | O | LYS C 218 | 25.248 | 95.245 | 9.053 | 1.00 | 16.26 | O |
| ATOM | 5614 | N | ARG C 219 | 24.087 | 93.341 | 9.201 | 1.00 | 18.10 | N |
| ATOM | 5615 | CA | ARG C 219 | 23.161 | 93.726 | 8.160 | 1.00 | 20.15 | C |
| ATOM | 5616 | CB | ARG C 219 | 23.834 | 93.670 | 6.785 | 1.00 | 20.50 | C |
| ATOM | 5617 | CG | ARG C 219 | 24.105 | 92.252 | 6.263 | 1.00 | 23.24 | C |
| ATOM | 5618 | CD | ARG C 219 | 24.964 | 92.289 | 5.007 | 1.00 | 21.84 | C |
| ATOM | 5619 | NE | ARG C 219 | 25.244 | 90.965 | 4.456 | 1.00 | 22.92 | N |
| ATOM | 5620 | CZ | ARG C 219 | 24.319 | 90.135 | 3.985 | 1.00 | 22.65 | C |
| ATOM | 5621 | NH1 | ARG C 219 | 23.039 | 90.486 | 4.000 | 1.00 | 23.00 | N |
| ATOM | 5622 | NH2 | ARG C 219 | 24.674 | 88.954 | 3.485 | 1.00 | 22.65 | N |
| ATOM | 5623 | C | ARG C 219 | 21.996 | 92.763 | 8.205 | 1.00 | 21.11 | C |
| ATOM | 5624 | O | ARG C 219 | 22.102 | 91.672 | 8.770 | 1.00 | 21.20 | O |
| ATOM | 5625 | N | ASN C 220 | 20.878 | 93.177 | 7.621 | 1.00 | 22.11 | N |
| ATOM | 5626 | CA | ASN C 220 | 19.692 | 92.338 | 7.576 | 1.00 | 21.86 | C |
| ATOM | 5627 | CB | ASN C 220 | 18.443 | 93.222 | 7.575 | 1.00 | 21.68 | C |
| ATOM | 5628 | CG | ASN C 220 | 17.963 | 93.535 | 8.975 | 1.00 | 22.12 | C |
| ATOM | 5629 | OD1 | ASN C 220 | 17.428 | 92.667 | 9.657 | 1.00 | 24.47 | O |
| ATOM | 5630 | ND2 | ASN C 220 | 18.168 | 94.766 | 9.419 | 1.00 | 21.76 | N |
| ATOM | 5631 | C | ASN C 220 | 19.752 | 91.478 | 6.325 | 1.00 | 22.53 | C |
| ATOM | 5632 | O | ASN C 220 | 20.676 | 91.616 | 5.525 | 1.00 | 22.11 | O |
| ATOM | 5633 | N | VAL C 221 | 18.785 | 90.576 | 6.159 | 1.00 | 24.16 | N |
| ATOM | 5634 | CA | VAL C 221 | 18.757 | 89.721 | 4.976 | 1.00 | 24.14 | C |
| ATOM | 5635 | CB | VAL C 221 | 18.517 | 88.236 | 5.336 | 1.00 | 24.54 | C |
| ATOM | 5636 | CG1 | VAL C 221 | 19.733 | 87.684 | 6.100 | 1.00 | 24.32 | C |
| ATOM | 5637 | CG2 | VAL C 221 | 17.226 | 88.093 | 6.153 | 1.00 | 24.58 | C |
| ATOM | 5638 | C | VAL C 221 | 17.703 | 90.170 | 3.970 | 1.00 | 24.12 | C |
| ATOM | 5639 | O | VAL C 221 | 16.789 | 90.925 | 4.294 | 1.00 | 24.16 | O |
| ATOM | 5640 | N | ASP C 222 | 17.865 | 89.679 | 2.747 | 1.00 | 25.24 | N |
| ATOM | 5641 | CA | ASP C 222 | 17.021 | 89.981 | 1.584 | 1.00 | 26.69 | C |
| ATOM | 5642 | CB | ASP C 222 | 17.955 | 90.199 | 0.366 | 1.00 | 27.22 | C |
| ATOM | 5643 | CG | ASP C 222 | 17.367 | 91.101 | -0.688 | 1.00 | 32.32 | C |
| ATOM | 5644 | OD1 | ASP C 222 | 16.452 | 90.653 | -1.421 | 1.00 | 34.27 | O |
| ATOM | 5645 | OD2 | ASP C 222 | 17.823 | 92.273 | -0.797 | 1.00 | 34.36 | O |
| ATOM | 5646 | C | ASP C 222 | 16.190 | 88.718 | 1.370 | 1.00 | 25.96 | C |
| ATOM | 5647 | O | ASP C 222 | 16.676 | 87.621 | 1.668 | 1.00 | 24.77 | O |
| ATOM | 5648 | N | GLN C 223 | 14.962 | 88.839 | 0.861 | 1.00 | 24.61 | N |
| ATOM | 5649 | CA | GLN C 223 | 14.184 | 87.622 | 0.618 | 1.00 | 24.05 | C |
| ATOM | 5650 | CB | GLN C 223 | 12.686 | 87.909 | 0.358 | 1.00 | 25.43 | C |
| ATOM | 5651 | CG | GLN C 223 | 12.316 | 89.201 | -0.348 | 1.00 | 26.62 | C |
| ATOM | 5652 | CD | GLN C 223 | 12.345 | 90.427 | 0.556 | 1.00 | 25.35 | C |
| ATOM | 5653 | OE1 | GLN C 223 | 13.412 | 90.935 | 0.898 | 1.00 | 28.55 | O |

FIGURE 9 (cont.)

| | | | | | | | | | |
|---|---|---|---|---|---|---|---|---|---|
| ATOM | 5654 | NE2 | GLN C 223 | 11.172 | 90.909 | 0.942 | 1.00 | 26.10 | N |
| ATOM | 5655 | C | GLN C 223 | 14.795 | 86.811 | -0.531 | 1.00 | 23.52 | C |
| ATOM | 5656 | O | GLN C 223 | 14.464 | 85.635 | -0.730 | 1.00 | 21.28 | O |
| ATOM | 5657 | N | VAL C 224 | 15.702 | 87.434 | -1.283 | 1.00 | 23.37 | N |
| ATOM | 5658 | CA | VAL C 224 | 16.386 | 86.722 | -2.359 | 1.00 | 23.26 | C |
| ATOM | 5659 | CB | VAL C 224 | 16.961 | 87.699 | -3.428 | 1.00 | 24.36 | C |
| ATOM | 5660 | CG1 | VAL C 224 | 18.134 | 87.064 | -4.173 | 1.00 | 23.98 | C |
| ATOM | 5661 | CG2 | VAL C 224 | 15.867 | 88.049 | -4.431 | 1.00 | 23.95 | C |
| ATOM | 5662 | C | VAL C 224 | 17.510 | 85.897 | -1.710 | 1.00 | 23.30 | C |
| ATOM | 5663 | O | VAL C 224 | 17.962 | 84.897 | -2.266 | 1.00 | 22.97 | O |
| ATOM | 5664 | N | GLU C 225 | 17.961 | 86.309 | -0.526 | 1.00 | 22.82 | N |
| ATOM | 5665 | CA | GLU C 225 | 18.991 | 85.534 | 0.148 | 1.00 | 22.98 | C |
| ATOM | 5666 | CB | GLU C 225 | 19.602 | 86.313 | 1.325 | 1.00 | 24.39 | C |
| ATOM | 5667 | CG | GLU C 225 | 20.550 | 87.395 | 0.858 | 1.00 | 27.50 | C |
| ATOM | 5668 | CD | GLU C 225 | 21.409 | 87.960 | 1.967 | 1.00 | 30.74 | C |
| ATOM | 5669 | OE1 | GLU C 225 | 20.874 | 88.705 | 2.827 | 1.00 | 31.85 | O |
| ATOM | 5670 | OE2 | GLU C 225 | 22.628 | 87.658 | 1.971 | 1.00 | 30.58 | O |
| ATOM | 5671 | C | GLU C 225 | 18.360 | 84.232 | 0.627 | 1.00 | 20.81 | C |
| ATOM | 5672 | O | GLU C 225 | 18.975 | 83.168 | 0.568 | 1.00 | 21.24 | O |
| ATOM | 5673 | N | VAL C 226 | 17.122 | 84.312 | 1.091 | 1.00 | 19.26 | N |
| ATOM | 5674 | CA | VAL C 226 | 16.433 | 83.120 | 1.545 | 1.00 | 18.80 | C |
| ATOM | 5675 | CB | VAL C 226 | 15.030 | 83.457 | 2.098 | 1.00 | 18.48 | C |
| ATOM | 5676 | CG1 | VAL C 226 | 14.211 | 82.176 | 2.303 | 1.00 | 18.32 | C |
| ATOM | 5677 | CG2 | VAL C 226 | 15.160 | 84.198 | 3.402 | 1.00 | 18.57 | C |
| ATOM | 5678 | C | VAL C 226 | 16.280 | 82.206 | 0.344 | 1.00 | 19.23 | C |
| ATOM | 5679 | O | VAL C 226 | 16.469 | 80.998 | 0.453 | 1.00 | 20.73 | O |
| ATOM | 5680 | N | GLY C 227 | 15.954 | 82.811 | -0.803 | 1.00 | 20.40 | N |
| ATOM | 5681 | CA | GLY C 227 | 15.729 | 82.081 | -2.040 | 1.00 | 18.04 | C |
| ATOM | 5682 | C | GLY C 227 | 16.894 | 81.250 | -2.515 | 1.00 | 18.45 | C |
| ATOM | 5683 | O | GLY C 227 | 16.714 | 80.150 | -3.041 | 1.00 | 18.53 | O |
| ATOM | 5684 | N | LYS C 228 | 18.096 | 81.773 | -2.325 | 1.00 | 18.98 | N |
| ATOM | 5685 | CA | LYS C 228 | 19.304 | 81.077 | -2.735 | 1.00 | 20.07 | C |
| ATOM | 5686 | CB | LYS C 228 | 20.491 | 82.045 | -2.678 | 1.00 | 20.80 | C |
| ATOM | 5687 | CG | LYS C 228 | 20.402 | 83.133 | -3.756 | 1.00 | 20.29 | C |
| ATOM | 5688 | CD | LYS C 228 | 21.083 | 84.433 | -3.356 | 1.00 | 22.19 | C |
| ATOM | 5689 | CE | LYS C 228 | 22.583 | 84.313 | -3.355 | 1.00 | 22.60 | C |
| ATOM | 5690 | NZ | LYS C 228 | 23.202 | 85.590 | -2.920 | 1.00 | 23.23 | N |
| ATOM | 5691 | C | LYS C 228 | 19.550 | 79.838 | -1.879 | 1.00 | 20.19 | C |
| ATOM | 5692 | O | LYS C 228 | 20.001 | 78.810 | -2.383 | 1.00 | 20.27 | O |
| ATOM | 5693 | N | THR C 229 | 19.250 | 79.927 | -0.587 | 1.00 | 21.18 | N |
| ATOM | 5694 | CA | THR C 229 | 19.430 | 78.781 | 0.300 | 1.00 | 20.27 | C |
| ATOM | 5695 | CB | THR C 229 | 19.356 | 79.212 | 1.782 | 1.00 | 20.09 | C |
| ATOM | 5696 | OG1 | THR C 229 | 20.604 | 79.814 | 2.161 | 1.00 | 18.42 | O |
| ATOM | 5697 | CG2 | THR C 229 | 19.062 | 78.018 | 2.687 | 1.00 | 18.69 | C |
| ATOM | 5698 | C | THR C 229 | 18.346 | 77.750 | -0.018 | 1.00 | 21.60 | C |
| ATOM | 5699 | O | THR C 229 | 18.570 | 76.543 | 0.089 | 1.00 | 21.47 | O |
| ATOM | 5700 | N | ALA C 230 | 17.177 | 78.232 | -0.434 | 1.00 | 20.81 | N |
| ATOM | 5701 | CA | ALA C 230 | 16.067 | 77.356 | -0.783 | 1.00 | 20.21 | C |
| ATOM | 5702 | CB | ALA C 230 | 14.791 | 78.179 | -0.957 | 1.00 | 21.21 | C |
| ATOM | 5703 | C | ALA C 230 | 16.393 | 76.595 | -2.068 | 1.00 | 19.91 | C |
| ATOM | 5704 | O | ALA C 230 | 15.976 | 75.448 | -2.252 | 1.00 | 20.07 | O |
| ATOM | 5705 | N | ALA C 231 | 17.119 | 77.245 | -2.971 | 1.00 | 19.67 | N |
| ATOM | 5706 | CA | ALA C 231 | 17.524 | 76.609 | -4.225 | 1.00 | 18.28 | C |
| ATOM | 5707 | CB | ALA C 231 | 18.336 | 77.589 | -5.077 | 1.00 | 15.62 | C |
| ATOM | 5708 | C | ALA C 231 | 18.390 | 75.429 | -3.805 | 1.00 | 18.21 | C |
| ATOM | 5709 | O | ALA C 231 | 18.205 | 74.296 | -4.260 | 1.00 | 18.41 | O |
| ATOM | 5710 | N | TYR C 232 | 19.335 | 75.713 | -2.916 | 1.00 | 17.57 | N |
| ATOM | 5711 | CA | TYR C 232 | 20.227 | 74.696 | -2.384 | 1.00 | 17.46 | C |
| ATOM | 5712 | CB | TYR C 232 | 21.059 | 75.307 | -1.245 | 1.00 | 14.34 | C |
| ATOM | 5713 | CG | TYR C 232 | 21.756 | 74.315 | -0.350 | 1.00 | 14.14 | C |
| ATOM | 5714 | CD1 | TYR C 232 | 21.463 | 74.255 | 1.016 | 1.00 | 13.10 | C |
| ATOM | 5715 | CE1 | TYR C 232 | 22.089 | 73.317 | 1.850 | 1.00 | 12.48 | C |
| ATOM | 5716 | CD2 | TYR C 232 | 22.696 | 73.417 | -0.863 | 1.00 | 12.87 | C |
| ATOM | 5717 | CE2 | TYR C 232 | 23.326 | 72.480 | -0.042 | 1.00 | 11.80 | C |
| ATOM | 5718 | CZ | TYR C 232 | 23.016 | 72.434 | 1.313 | 1.00 | 10.68 | C |

FIGURE 9 (cont.)

| | | | | | | | | | |
|---|---|---|---|---|---|---|---|---|---|
| ATOM | 5719 | OH | TYR C 232 | 23.607 | 71.488 | 2.113 | 1.00 | 10.67 | O |
| ATOM | 5720 | C | TYR C 232 | 19.388 | 73.504 | -1.900 | 1.00 | 18.11 | C |
| ATOM | 5721 | O | TYR C 232 | 19.509 | 72.400 | -2.426 | 1.00 | 19.36 | O |
| ATOM | 5722 | N | LEU C 233 | 18.510 | 73.742 | -0.931 | 1.00 | 18.99 | N |
| ATOM | 5723 | CA | LEU C 233 | 17.656 | 72.695 | -0.360 | 1.00 | 20.66 | C |
| ATOM | 5724 | CB | LEU C 233 | 16.873 | 73.267 | 0.829 | 1.00 | 19.27 | C |
| ATOM | 5725 | CG | LEU C 233 | 17.718 | 73.641 | 2.045 | 1.00 | 18.71 | C |
| ATOM | 5726 | CD1 | LEU C 233 | 16.883 | 74.420 | 3.036 | 1.00 | 17.21 | C |
| ATOM | 5727 | CD2 | LEU C 233 | 18.277 | 72.366 | 2.685 | 1.00 | 17.78 | C |
| ATOM | 5728 | C | LEU C 233 | 16.667 | 72.023 | -1.318 | 1.00 | 21.82 | C |
| ATOM | 5729 | O | LEU C 233 | 16.423 | 70.816 | -1.231 | 1.00 | 21.58 | O |
| ATOM | 5730 | N | LEU C 234 | 16.071 | 72.795 | -2.219 | 1.00 | 22.87 | N |
| ATOM | 5731 | CA | LEU C 234 | 15.107 | 72.211 | -3.142 | 1.00 | 23.84 | C |
| ATOM | 5732 | CB | LEU C 234 | 14.225 | 73.308 | -3.740 | 1.00 | 22.76 | C |
| ATOM | 5733 | CG | LEU C 234 | 13.158 | 73.877 | -2.794 | 1.00 | 22.10 | C |
| ATOM | 5734 | CD1 | LEU C 234 | 12.476 | 75.066 | -3.437 | 1.00 | 20.67 | C |
| ATOM | 5735 | CD2 | LEU C 234 | 12.128 | 72.793 | -2.468 | 1.00 | 22.01 | C |
| ATOM | 5736 | C | LEU C 234 | 15.747 | 71.373 | -4.256 | 1.00 | 24.95 | C |
| ATOM | 5737 | O | LEU C 234 | 15.076 | 70.541 | -4.878 | 1.00 | 25.65 | O |
| ATOM | 5738 | N | SER C 235 | 17.043 | 71.567 | -4.484 | 1.00 | 24.25 | N |
| ATOM | 5739 | CA | SER C 235 | 17.756 | 70.845 | -5.536 | 1.00 | 23.83 | C |
| ATOM | 5740 | CB | SER C 235 | 18.628 | 71.820 | -6.323 | 1.00 | 24.43 | C |
| ATOM | 5741 | OG | SER C 235 | 19.642 | 72.363 | -5.491 | 1.00 | 23.88 | O |
| ATOM | 5742 | C | SER C 235 | 18.632 | 69.689 | -5.045 | 1.00 | 23.98 | C |
| ATOM | 5743 | O | SER C 235 | 18.613 | 69.323 | -3.870 | 1.00 | 23.14 | O |
| ATOM | 5744 | N | ASP C 236 | 19.421 | 69.141 | -5.970 | 1.00 | 24.97 | N |
| ATOM | 5745 | CA | ASP C 236 | 20.297 | 68.009 | -5.695 | 1.00 | 25.68 | C |
| ATOM | 5746 | CB | ASP C 236 | 20.615 | 67.280 | -7.017 | 1.00 | 28.05 | C |
| ATOM | 5747 | CG | ASP C 236 | 21.678 | 66.199 | -6.860 | 1.00 | 31.54 | C |
| ATOM | 5748 | OD1 | ASP C 236 | 22.885 | 66.552 | -6.834 | 1.00 | 33.81 | O |
| ATOM | 5749 | OD2 | ASP C 236 | 21.315 | 65.001 | -6.761 | 1.00 | 32.16 | O |
| ATOM | 5750 | C | ASP C 236 | 21.579 | 68.363 | -4.937 | 1.00 | 24.76 | C |
| ATOM | 5751 | O | ASP C 236 | 22.268 | 67.469 | -4.436 | 1.00 | 23.30 | O |
| ATOM | 5752 | N | LEU C 237 | 21.887 | 69.655 | -4.826 | 1.00 | 23.86 | N |
| ATOM | 5753 | CA | LEU C 237 | 23.081 | 70.085 | -4.089 | 1.00 | 23.15 | C |
| ATOM | 5754 | CB | LEU C 237 | 23.220 | 71.608 | -4.085 | 1.00 | 24.98 | C |
| ATOM | 5755 | CG | LEU C 237 | 24.257 | 72.307 | -4.973 | 1.00 | 26.85 | C |
| ATOM | 5756 | CD1 | LEU C 237 | 24.445 | 73.708 | -4.428 | 1.00 | 27.78 | C |
| ATOM | 5757 | CD2 | LEU C 237 | 25.600 | 71.574 | -4.975 | 1.00 | 27.25 | C |
| ATOM | 5758 | C | LEU C 237 | 23.055 | 69.643 | -2.636 | 1.00 | 21.99 | C |
| ATOM | 5759 | O | LEU C 237 | 24.104 | 69.521 | -1.998 | 1.00 | 22.43 | O |
| ATOM | 5760 | N | SER C 238 | 21.863 | 69.423 | -2.094 | 1.00 | 21.22 | N |
| ATOM | 5761 | CA | SER C 238 | 21.757 | 69.024 | -0.689 | 1.00 | 20.68 | C |
| ATOM | 5762 | CB | SER C 238 | 20.813 | 69.981 | 0.050 | 1.00 | 20.38 | C |
| ATOM | 5763 | OG | SER C 238 | 19.561 | 70.064 | -0.611 | 1.00 | 19.72 | O |
| ATOM | 5764 | C | SER C 238 | 21.270 | 67.589 | -0.528 | 1.00 | 20.09 | C |
| ATOM | 5765 | O | SER C 238 | 20.570 | 67.262 | 0.434 | 1.00 | 18.63 | O |
| ATOM | 5766 | N | SER C 239 | 21.671 | 66.734 | -1.466 | 1.00 | 20.36 | N |
| ATOM | 5767 | CA | SER C 239 | 21.261 | 65.333 | -1.467 | 1.00 | 19.87 | C |
| ATOM | 5768 | CB | SER C 239 | 22.075 | 64.543 | -2.513 | 1.00 | 18.99 | C |
| ATOM | 5769 | OG | SER C 239 | 23.473 | 64.743 | -2.365 | 1.00 | 19.61 | O |
| ATOM | 5770 | C | SER C 239 | 21.293 | 64.604 | -0.122 | 1.00 | 19.97 | C |
| ATOM | 5771 | O | SER C 239 | 20.403 | 63.804 | 0.168 | 1.00 | 22.13 | O |
| ATOM | 5772 | N | GLY C 240 | 22.293 | 64.862 | 0.709 | 1.00 | 19.56 | N |
| ATOM | 5773 | CA | GLY C 240 | 22.336 | 64.150 | 1.974 | 1.00 | 18.51 | C |
| ATOM | 5774 | C | GLY C 240 | 21.858 | 64.929 | 3.182 | 1.00 | 18.05 | C |
| ATOM | 5775 | O | GLY C 240 | 22.233 | 64.608 | 4.311 | 1.00 | 19.04 | O |
| ATOM | 5776 | N | VAL C 241 | 21.010 | 65.928 | 2.961 | 1.00 | 16.54 | N |
| ATOM | 5777 | CA | VAL C 241 | 20.530 | 66.763 | 4.055 | 1.00 | 14.70 | C |
| ATOM | 5778 | CB | VAL C 241 | 20.919 | 68.250 | 3.822 | 1.00 | 14.07 | C |
| ATOM | 5779 | CG1 | VAL C 241 | 20.383 | 69.121 | 4.934 | 1.00 | 11.77 | C |
| ATOM | 5780 | CG2 | VAL C 241 | 22.428 | 68.375 | 3.721 | 1.00 | 13.31 | C |
| ATOM | 5781 | C | VAL C 241 | 19.034 | 66.688 | 4.276 | 1.00 | 14.40 | C |
| ATOM | 5782 | O | VAL C 241 | 18.241 | 66.939 | 3.367 | 1.00 | 14.17 | O |
| ATOM | 5783 | N | THR C 242 | 18.646 | 66.346 | 5.496 | 1.00 | 13.98 | N |

FIGURE 9 (cont.)

```
ATOM   5784  CA   THR C 242      17.237  66.272   5.807  1.00 14.29           C
ATOM   5785  CB   THR C 242      16.625  64.972   5.248  1.00 14.05           C
ATOM   5786  OG1  THR C 242      15.201  65.038   5.357  1.00 12.75           O
ATOM   5787  CG2  THR C 242      17.152  63.754   5.997  1.00 15.76           C
ATOM   5788  C    THR C 242      16.975  66.412   7.305  1.00 14.01           C
ATOM   5789  O    THR C 242      17.776  65.981   8.137  1.00 16.01           O
ATOM   5790  N    GLY C 243      15.851  67.036   7.637  1.00 13.75           N
ATOM   5791  CA   GLY C 243      15.505  67.251   9.027  1.00 13.97           C
ATOM   5792  C    GLY C 243      16.358  68.367   9.593  1.00 14.84           C
ATOM   5793  O    GLY C 243      16.563  68.444  10.798  1.00 14.75           O
ATOM   5794  N    GLU C 244      16.843  69.237   8.708  1.00 16.66           N
ATOM   5795  CA   GLU C 244      17.706  70.354   9.083  1.00 18.55           C
ATOM   5796  CB   GLU C 244      18.911  70.394   8.133  1.00 19.22           C
ATOM   5797  CG   GLU C 244      19.931  71.475   8.452  1.00 20.29           C
ATOM   5798  CD   GLU C 244      20.632  71.243   9.779  1.00 21.38           C
ATOM   5799  OE1  GLU C 244      21.753  70.690   9.765  1.00 19.24           O
ATOM   5800  OE2  GLU C 244      20.053  71.605  10.837  1.00 21.99           O
ATOM   5801  C    GLU C 244      17.013  71.730   9.110  1.00 20.16           C
ATOM   5802  O    GLU C 244      15.954  71.949   8.495  1.00 20.45           O
ATOM   5803  N    ASN C 245      17.613  72.655   9.849  1.00 20.77           N
ATOM   5804  CA   ASN C 245      17.082  74.006   9.961  1.00 20.67           C
ATOM   5805  CB   ASN C 245      16.510  74.229  11.366  1.00 20.29           C
ATOM   5806  CG   ASN C 245      15.752  75.543  11.492  1.00 22.08           C
ATOM   5807  OD1  ASN C 245      15.303  75.913  12.582  1.00 23.27           O
ATOM   5808  ND2  ASN C 245      15.600  76.252  10.378  1.00 21.74           N
ATOM   5809  C    ASN C 245      18.243  74.957   9.692  1.00 21.20           C
ATOM   5810  O    ASN C 245      19.087  75.175  10.563  1.00 22.43           O
ATOM   5811  N    ILE C 246      18.290  75.502   8.477  1.00 20.91           N
ATOM   5812  CA   ILE C 246      19.348  76.427   8.069  1.00 20.31           C
ATOM   5813  CB   ILE C 246      19.639  76.269   6.566  1.00 20.53           C
ATOM   5814  CG2  ILE C 246      20.757  77.201   6.141  1.00 21.07           C
ATOM   5815  CG1  ILE C 246      20.022  74.816   6.280  1.00 20.77           C
ATOM   5816  CD1  ILE C 246      20.527  74.575   4.888  1.00 22.39           C
ATOM   5817  C    ILE C 246      18.979  77.886   8.372  1.00 20.94           C
ATOM   5818  O    ILE C 246      17.935  78.383   7.939  1.00 20.86           O
ATOM   5819  N    HIS C 247      19.840  78.573   9.119  1.00 20.45           N
ATOM   5820  CA   HIS C 247      19.576  79.963   9.483  1.00 19.41           C
ATOM   5821  CB   HIS C 247      20.120  80.284  10.886  1.00 19.34           C
ATOM   5822  CG   HIS C 247      19.540  79.440  11.983  1.00 18.69           C
ATOM   5823  CD2  HIS C 247      18.474  79.641  12.794  1.00 19.13           C
ATOM   5824  ND1  HIS C 247      20.087  78.233  12.363  1.00 17.58           N
ATOM   5825  CE1  HIS C 247      19.384  77.730  13.363  1.00 17.74           C
ATOM   5826  NE2  HIS C 247      18.400  78.564  13.644  1.00 18.10           N
ATOM   5827  C    HIS C 247      20.196  80.945   8.508  1.00 19.20           C
ATOM   5828  O    HIS C 247      21.409  80.914   8.276  1.00 19.40           O
ATOM   5829  N    VAL C 248      19.356  81.798   7.927  1.00 17.13           N
ATOM   5830  CA   VAL C 248      19.807  82.843   7.018  1.00 15.68           C
ATOM   5831  CB   VAL C 248      19.061  82.807   5.678  1.00 14.60           C
ATOM   5832  CG1  VAL C 248      19.612  83.884   4.763  1.00 13.67           C
ATOM   5833  CG2  VAL C 248      19.221  81.442   5.034  1.00 14.68           C
ATOM   5834  C    VAL C 248      19.427  84.085   7.813  1.00 16.46           C
ATOM   5835  O    VAL C 248      18.366  84.683   7.627  1.00 16.04           O
ATOM   5836  N    ASP C 249      20.319  84.451   8.721  1.00 17.85           N
ATOM   5837  CA   ASP C 249      20.095  85.558   9.633  1.00 17.97           C
ATOM   5838  CB   ASP C 249      19.612  84.996  10.954  1.00 19.25           C
ATOM   5839  CG   ASP C 249      20.583  83.963  11.521  1.00 20.96           C
ATOM   5840  OD1  ASP C 249      21.619  83.691  10.866  1.00 18.89           O
ATOM   5841  OD2  ASP C 249      20.312  83.420  12.616  1.00 23.48           O
ATOM   5842  C    ASP C 249      21.358  86.335   9.911  1.00 17.29           C
ATOM   5843  O    ASP C 249      21.487  86.913  10.988  1.00 18.42           O
ATOM   5844  N    SER C 250      22.292  86.341   8.971  1.00 16.92           N
ATOM   5845  CA   SER C 250      23.545  87.054   9.179  1.00 17.37           C
ATOM   5846  CB   SER C 250      23.289  88.559   9.231  1.00 18.75           C
ATOM   5847  OG   SER C 250      22.993  89.062   7.935  1.00 20.61           O
ATOM   5848  C    SER C 250      24.253  86.587  10.459  1.00 16.41           C
```

FIGURE 9 (cont.)

| | | | | | | | | | |
|---|---|---|---|---|---|---|---|---|---|
| ATOM | 5849 | O | SER | C | 250 | 25.056 | 87.319 | 11.048 | 1.00 14.79 | O |
| ATOM | 5850 | N | GLY | C | 251 | 23.934 | 85.361 | 10.879 | 1.00 16.52 | N |
| ATOM | 5851 | CA | GLY | C | 251 | 24.548 | 84.772 | 12.060 | 1.00 14.70 | C |
| ATOM | 5852 | C | GLY | C | 251 | 24.001 | 85.160 | 13.421 | 1.00 14.28 | C |
| ATOM | 5853 | O | GLY | C | 251 | 24.633 | 84.892 | 14.431 | 1.00 14.37 | O |
| ATOM | 5854 | N | PHE | C | 252 | 22.831 | 85.782 | 13.461 | 1.00 14.27 | N |
| ATOM | 5855 | CA | PHE | C | 252 | 22.235 | 86.189 | 14.729 | 1.00 13.72 | C |
| ATOM | 5856 | CB | PHE | C | 252 | 20.860 | 86.817 | 14.487 | 1.00 13.56 | C |
| ATOM | 5857 | CG | PHE | C | 252 | 20.318 | 87.562 | 15.672 | 1.00 12.08 | C |
| ATOM | 5858 | CD1 | PHE | C | 252 | 21.019 | 88.642 | 16.206 | 1.00 9.98 | C |
| ATOM | 5859 | CD2 | PHE | C | 252 | 19.095 | 87.209 | 16.235 | 1.00 12.38 | C |
| ATOM | 5860 | CE1 | PHE | C | 252 | 20.514 | 89.366 | 17.281 | 1.00 10.48 | C |
| ATOM | 5861 | CE2 | PHE | C | 252 | 18.574 | 87.930 | 17.320 | 1.00 13.25 | C |
| ATOM | 5862 | CZ | PHE | C | 252 | 19.286 | 89.011 | 17.841 | 1.00 11.68 | C |
| ATOM | 5863 | C | PHE | C | 252 | 22.078 | 85.010 | 15.699 | 1.00 14.22 | C |
| ATOM | 5864 | O | PHE | C | 252 | 22.288 | 85.164 | 16.905 | 1.00 15.30 | O |
| ATOM | 5865 | N | HIS | C | 253 | 21.713 | 83.845 | 15.157 | 1.00 13.96 | N |
| ATOM | 5866 | CA | HIS | C | 253 | 21.496 | 82.619 | 15.932 | 1.00 14.78 | C |
| ATOM | 5867 | CB | HIS | C | 253 | 21.067 | 81.473 | 15.008 | 1.00 16.62 | C |
| ATOM | 5868 | CG | HIS | C | 253 | 22.214 | 80.796 | 14.316 | 1.00 15.65 | C |
| ATOM | 5869 | CD2 | HIS | C | 253 | 22.807 | 79.598 | 14.538 | 1.00 16.23 | C |
| ATOM | 5870 | ND1 | HIS | C | 253 | 22.908 | 81.378 | 13.276 | 1.00 15.96 | N |
| ATOM | 5871 | CE1 | HIS | C | 253 | 23.880 | 80.569 | 12.889 | 1.00 15.78 | C |
| ATOM | 5872 | NE2 | HIS | C | 253 | 23.839 | 79.482 | 13.638 | 1.00 15.89 | N |
| ATOM | 5873 | C | HIS | C | 253 | 22.697 | 82.122 | 16.737 | 1.00 14.92 | C |
| ATOM | 5874 | O | HIS | C | 253 | 22.522 | 81.482 | 17.761 | 1.00 14.61 | O |
| ATOM | 5875 | N | ALA | C | 254 | 23.904 | 82.399 | 16.254 | 1.00 14.36 | N |
| ATOM | 5876 | CA | ALA | C | 254 | 25.127 | 81.952 | 16.906 | 1.00 15.26 | C |
| ATOM | 5877 | CB | ALA | C | 254 | 26.196 | 81.708 | 15.850 | 1.00 12.44 | C |
| ATOM | 5878 | C | ALA | C | 254 | 25.656 | 82.926 | 17.958 | 1.00 16.30 | C |
| ATOM | 5879 | O | ALA | C | 254 | 26.682 | 82.674 | 18.593 | 1.00 16.67 | O |
| ATOM | 5880 | N | ILE | C | 255 | 24.936 | 84.023 | 18.144 | 1.00 18.20 | N |
| ATOM | 5881 | CA | ILE | C | 255 | 25.312 | 85.089 | 19.076 | 1.00 18.73 | C |
| ATOM | 5882 | CB | ILE | C | 255 | 25.227 | 86.453 | 18.314 | 1.00 19.72 | C |
| ATOM | 5883 | CG2 | ILE | C | 255 | 24.379 | 87.483 | 19.070 | 1.00 19.64 | C |
| ATOM | 5884 | CG1 | ILE | C | 255 | 26.643 | 86.924 | 17.998 | 1.00 21.79 | C |
| ATOM | 5885 | CD1 | ILE | C | 255 | 27.410 | 85.950 | 17.136 | 1.00 22.77 | C |
| ATOM | 5886 | C | ILE | C | 255 | 24.474 | 85.129 | 20.359 | 1.00 18.79 | C |
| ATOM | 5887 | O | ILE | C | 255 | 23.409 | 84.523 | 20.428 | 1.00 17.42 | O |
| ATOM | 5888 | N | LYS | C | 256 | 24.965 | 85.839 | 21.374 | 1.00 19.47 | N |
| ATOM | 5889 | CA | LYS | C | 256 | 24.240 | 85.962 | 22.641 | 1.00 20.39 | C |
| ATOM | 5890 | CB | LYS | C | 256 | 24.407 | 84.694 | 23.469 | 1.00 20.98 | C |
| ATOM | 5891 | CG | LYS | C | 256 | 23.119 | 83.963 | 23.751 | 1.00 22.06 | C |
| ATOM | 5892 | CD | LYS | C | 256 | 22.185 | 84.755 | 24.620 | 1.00 22.17 | C |
| ATOM | 5893 | CE | LYS | C | 256 | 20.923 | 83.924 | 24.885 | 1.00 24.92 | C |
| ATOM | 5894 | NZ | LYS | C | 256 | 19.774 | 84.715 | 25.448 | 1.00 24.81 | N |
| ATOM | 5895 | C | LYS | C | 256 | 24.738 | 87.140 | 23.457 | 1.00 19.83 | C |
| ATOM | 5896 | O | LYS | C | 256 | 25.963 | 87.180 | 23.670 | 1.00 18.99 | O |
| ATOM | 5897 | OXT | LYS | C | 256 | 23.914 | 87.980 | 23.890 | 1.00 19.59 | O |
| TER | 5898 | | LYS | C | 256 | | | | | |
| ATOM | 5899 | CB | LEU | D | 2 | 14.724 | 73.505 | 51.054 | 1.00 40.84 | C |
| ATOM | 5900 | CG | LEU | D | 2 | 14.830 | 74.447 | 49.854 | 1.00 39.65 | C |
| ATOM | 5901 | CD1 | LEU | D | 2 | 13.431 | 74.762 | 49.305 | 1.00 38.02 | C |
| ATOM | 5902 | CD2 | LEU | D | 2 | 15.534 | 75.731 | 50.293 | 1.00 39.92 | C |
| ATOM | 5903 | C | LEU | D | 2 | 12.866 | 71.940 | 51.670 | 1.00 42.26 | C |
| ATOM | 5904 | O | LEU | D | 2 | 11.954 | 71.194 | 51.289 | 1.00 42.59 | O |
| ATOM | 5905 | N | LEU | D | 2 | 13.711 | 71.966 | 49.389 | 1.00 42.52 | N |
| ATOM | 5906 | CA | LEU | D | 2 | 14.111 | 72.122 | 50.816 | 1.00 41.87 | C |
| ATOM | 5907 | N | ASN | D | 3 | 12.812 | 72.601 | 52.819 | 1.00 42.75 | N |
| ATOM | 5908 | CA | ASN | D | 3 | 11.645 | 72.445 | 53.681 | 1.00 43.33 | C |
| ATOM | 5909 | CB | ASN | D | 3 | 11.764 | 73.303 | 54.941 | 1.00 43.19 | C |
| ATOM | 5910 | CG | ASN | D | 3 | 10.697 | 72.962 | 55.970 | 1.00 43.62 | C |
| ATOM | 5911 | OD1 | ASN | D | 3 | 9.614 | 72.469 | 55.624 | 1.00 42.69 | O |
| ATOM | 5912 | ND2 | ASN | D | 3 | 10.988 | 73.232 | 57.237 | 1.00 43.73 | N |
| ATOM | 5913 | C | ASN | D | 3 | 10.406 | 72.880 | 52.912 | 1.00 43.05 | C |

FIGURE 9 (cont.)

| ATOM | 5914 | O   | ASN | D | 3  | 10.256 | 74.067 | 52.606 | 1.00 | 42.88 | O |
|------|------|-----|-----|---|----|--------|--------|--------|------|-------|---|
| ATOM | 5915 | N   | LEU | D | 4  | 9.529  | 71.925 | 52.598 | 1.00 | 42.87 | N |
| ATOM | 5916 | CA  | LEU | D | 4  | 8.300  | 72.229 | 51.859 | 1.00 | 43.08 | C |
| ATOM | 5917 | CB  | LEU | D | 4  | 7.963  | 71.110 | 50.879 | 1.00 | 41.28 | C |
| ATOM | 5918 | CG  | LEU | D | 4  | 9.016  | 70.800 | 49.804 | 1.00 | 40.78 | C |
| ATOM | 5919 | CD1 | LEU | D | 4  | 8.356  | 69.939 | 48.725 | 1.00 | 39.61 | C |
| ATOM | 5920 | CD2 | LEU | D | 4  | 9.583  | 72.095 | 49.196 | 1.00 | 37.87 | C |
| ATOM | 5921 | C   | LEU | D | 4  | 7.129  | 72.439 | 52.807 | 1.00 | 43.70 | C |
| ATOM | 5922 | O   | LEU | D | 4  | 6.087  | 72.991 | 52.421 | 1.00 | 43.48 | O |
| ATOM | 5923 | N   | GLU | D | 5  | 7.292  | 72.000 | 54.051 | 1.00 | 44.64 | N |
| ATOM | 5924 | CA  | GLU | D | 5  | 6.230  | 72.186 | 55.020 | 1.00 | 45.48 | C |
| ATOM | 5925 | CB  | GLU | D | 5  | 6.773  | 71.942 | 56.440 | 1.00 | 46.18 | C |
| ATOM | 5926 | CG  | GLU | D | 5  | 7.659  | 70.671 | 56.516 | 1.00 | 48.20 | C |
| ATOM | 5927 | CD  | GLU | D | 5  | 7.538  | 69.894 | 57.833 | 1.00 | 49.22 | C |
| ATOM | 5928 | OE1 | GLU | D | 5  | 6.450  | 69.298 | 58.077 | 1.00 | 48.05 | O |
| ATOM | 5929 | OE2 | GLU | D | 5  | 8.536  | 69.875 | 58.615 | 1.00 | 49.46 | O |
| ATOM | 5930 | C   | GLU | D | 5  | 5.829  | 73.646 | 54.790 | 1.00 | 45.36 | C |
| ATOM | 5931 | O   | GLU | D | 5  | 6.681  | 74.476 | 54.428 | 1.00 | 45.77 | O |
| ATOM | 5932 | N   | ASN | D | 6  | 4.546  | 73.954 | 54.944 | 1.00 | 44.24 | N |
| ATOM | 5933 | CA  | ASN | D | 6  | 4.061  | 75.317 | 54.728 | 1.00 | 43.31 | C |
| ATOM | 5934 | CB  | ASN | D | 6  | 5.024  | 76.332 | 55.354 | 1.00 | 44.67 | C |
| ATOM | 5935 | CG  | ASN | D | 6  | 5.380  | 75.984 | 56.801 | 1.00 | 45.90 | C |
| ATOM | 5936 | OD1 | ASN | D | 6  | 6.083  | 75.006 | 57.058 | 1.00 | 45.81 | O |
| ATOM | 5937 | ND2 | ASN | D | 6  | 4.885  | 76.782 | 57.750 | 1.00 | 46.09 | N |
| ATOM | 5938 | C   | ASN | D | 6  | 3.883  | 75.641 | 53.244 | 1.00 | 41.98 | C |
| ATOM | 5939 | O   | ASN | D | 6  | 3.612  | 76.790 | 52.887 | 1.00 | 42.49 | O |
| ATOM | 5940 | N   | LYS | D | 7  | 4.037  | 74.631 | 52.384 | 1.00 | 40.08 | N |
| ATOM | 5941 | CA  | LYS | D | 7  | 3.882  | 74.795 | 50.933 | 1.00 | 37.71 | C |
| ATOM | 5942 | CB  | LYS | D | 7  | 5.179  | 74.392 | 50.229 | 1.00 | 37.39 | C |
| ATOM | 5943 | CG  | LYS | D | 7  | 6.344  | 75.312 | 50.537 | 1.00 | 37.95 | C |
| ATOM | 5944 | CD  | LYS | D | 7  | 6.198  | 76.636 | 49.805 | 1.00 | 38.81 | C |
| ATOM | 5945 | CE  | LYS | D | 7  | 7.005  | 77.728 | 50.484 | 1.00 | 39.26 | C |
| ATOM | 5946 | NZ  | LYS | D | 7  | 8.434  | 77.335 | 50.615 | 1.00 | 40.38 | N |
| ATOM | 5947 | C   | LYS | D | 7  | 2.724  | 73.933 | 50.411 | 1.00 | 36.21 | C |
| ATOM | 5948 | O   | LYS | D | 7  | 2.529  | 72.809 | 50.877 | 1.00 | 35.84 | O |
| ATOM | 5949 | N   | THR | D | 8  | 1.966  | 74.460 | 49.447 | 1.00 | 34.89 | N |
| ATOM | 5950 | CA  | THR | D | 8  | 0.823  | 73.743 | 48.856 | 1.00 | 33.63 | C |
| ATOM | 5951 | CB  | THR | D | 8  | -0.529 | 74.489 | 49.138 | 1.00 | 34.29 | C |
| ATOM | 5952 | OG1 | THR | D | 8  | -0.754 | 74.585 | 50.555 | 1.00 | 32.74 | O |
| ATOM | 5953 | CG2 | THR | D | 8  | -1.707 | 73.743 | 48.486 | 1.00 | 33.52 | C |
| ATOM | 5954 | C   | THR | D | 8  | 1.001  | 73.661 | 47.333 | 1.00 | 32.22 | C |
| ATOM | 5955 | O   | THR | D | 8  | 1.328  | 74.664 | 46.700 | 1.00 | 32.10 | O |
| ATOM | 5956 | N   | TYR | D | 9  | 0.783  | 72.483 | 46.750 | 1.00 | 30.39 | N |
| ATOM | 5957 | CA  | TYR | D | 9  | 0.923  | 72.317 | 45.300 | 1.00 | 29.67 | C |
| ATOM | 5958 | CB  | TYR | D | 9  | 2.235  | 71.600 | 44.958 | 1.00 | 30.09 | C |
| ATOM | 5959 | CG  | TYR | D | 9  | 3.498  | 72.292 | 45.422 | 1.00 | 29.97 | C |
| ATOM | 5960 | CD1 | TYR | D | 9  | 3.964  | 72.132 | 46.724 | 1.00 | 31.85 | C |
| ATOM | 5961 | CE1 | TYR | D | 9  | 5.149  | 72.749 | 47.156 | 1.00 | 32.03 | C |
| ATOM | 5962 | CD2 | TYR | D | 9  | 4.240  | 73.088 | 44.553 | 1.00 | 30.60 | C |
| ATOM | 5963 | CE2 | TYR | D | 9  | 5.428  | 73.707 | 44.973 | 1.00 | 31.38 | C |
| ATOM | 5964 | CZ  | TYR | D | 9  | 5.872  | 73.530 | 46.273 | 1.00 | 32.22 | C |
| ATOM | 5965 | OH  | TYR | D | 9  | 7.052  | 74.107 | 46.695 | 1.00 | 33.48 | O |
| ATOM | 5966 | C   | TYR | D | 9  | -0.227 | 71.541 | 44.649 | 1.00 | 28.42 | C |
| ATOM | 5967 | O   | TYR | D | 9  | -0.814 | 70.654 | 45.258 | 1.00 | 28.33 | O |
| ATOM | 5968 | N   | VAL | D | 10 | -0.533 | 71.874 | 43.398 | 1.00 | 27.68 | N |
| ATOM | 5969 | CA  | VAL | D | 10 | -1.598 | 71.195 | 42.656 | 1.00 | 25.85 | C |
| ATOM | 5970 | CB  | VAL | D | 10 | -2.432 | 72.205 | 41.837 | 1.00 | 25.44 | C |
| ATOM | 5971 | CG1 | VAL | D | 10 | -3.555 | 71.478 | 41.107 | 1.00 | 24.43 | C |
| ATOM | 5972 | CG2 | VAL | D | 10 | -2.998 | 73.271 | 42.761 | 1.00 | 23.76 | C |
| ATOM | 5973 | C   | VAL | D | 10 | -0.990 | 70.159 | 41.708 | 1.00 | 25.40 | C |
| ATOM | 5974 | O   | VAL | D | 10 | -0.128 | 70.487 | 40.890 | 1.00 | 24.52 | O |
| ATOM | 5975 | N   | ILE | D | 11 | -1.439 | 68.911 | 41.826 | 1.00 | 25.10 | N |
| ATOM | 5976 | CA  | ILE | D | 11 | -0.924 | 67.825 | 41.004 | 1.00 | 25.74 | C |
| ATOM | 5977 | CB  | ILE | D | 11 | -0.525 | 66.613 | 41.869 | 1.00 | 25.71 | C |
| ATOM | 5978 | CG2 | ILE | D | 11 | 0.315  | 65.652 | 41.054 | 1.00 | 24.96 | C |

FIGURE 9 (cont.)

```
ATOM   5979  CG1 ILE D  11     0.242  67.078  43.109  1.00 26.58           C
ATOM   5980  CD1 ILE D  11     1.424  68.002  42.820  1.00 26.62           C
ATOM   5981  C   ILE D  11    -1.955  67.358  39.986  1.00 26.51           C
ATOM   5982  O   ILE D  11    -2.962  66.752  40.347  1.00 26.33           O
ATOM   5983  N   MET D  12    -1.685  67.616  38.711  1.00 27.13           N
ATOM   5984  CA  MET D  12    -2.612  67.245  37.648  1.00 28.42           C
ATOM   5985  CB  MET D  12    -2.872  68.439  36.735  1.00 28.13           C
ATOM   5986  CG  MET D  12    -2.979  69.777  37.425  1.00 28.41           C
ATOM   5987  SD  MET D  12    -3.577  71.004  36.251  1.00 30.84           S
ATOM   5988  CE  MET D  12    -2.344  70.851  34.918  1.00 30.25           C
ATOM   5989  C   MET D  12    -2.099  66.104  36.775  1.00 29.46           C
ATOM   5990  O   MET D  12    -1.081  66.256  36.095  1.00 29.59           O
ATOM   5991  N   GLY D  13    -2.797  64.968  36.782  1.00 29.53           N
ATOM   5992  CA  GLY D  13    -2.367  63.875  35.932  1.00 29.98           C
ATOM   5993  C   GLY D  13    -2.122  62.535  36.588  1.00 30.63           C
ATOM   5994  O   GLY D  13    -1.314  61.737  36.092  1.00 31.17           O
ATOM   5995  N   ILE D  14    -2.796  62.279  37.704  1.00 30.19           N
ATOM   5996  CA  ILE D  14    -2.647  60.999  38.370  1.00 30.46           C
ATOM   5997  CB  ILE D  14    -2.855  61.100  39.905  1.00 30.60           C
ATOM   5998  CG2 ILE D  14    -2.961  59.684  40.510  1.00 29.47           C
ATOM   5999  CG1 ILE D  14    -1.706  61.887  40.546  1.00 28.04           C
ATOM   6000  CD1 ILE D  14    -1.740  61.891  42.065  1.00 26.43           C
ATOM   6001  C   ILE D  14    -3.715  60.078  37.807  1.00 30.70           C
ATOM   6002  O   ILE D  14    -4.897  60.428  37.799  1.00 30.98           O
ATOM   6003  N   ALA D  15    -3.297  58.915  37.315  1.00 31.12           N
ATOM   6004  CA  ALA D  15    -4.236  57.938  36.778  1.00 32.39           C
ATOM   6005  CB  ALA D  15    -3.812  57.487  35.378  1.00 32.09           C
ATOM   6006  C   ALA D  15    -4.303  56.730  37.708  1.00 32.48           C
ATOM   6007  O   ALA D  15    -5.370  56.370  38.200  1.00 32.33           O
ATOM   6008  N   ASN D  16    -3.157  56.109  37.958  1.00 33.05           N
ATOM   6009  CA  ASN D  16    -3.136  54.939  38.815  1.00 33.43           C
ATOM   6010  CB  ASN D  16    -3.352  53.685  37.963  1.00 33.00           C
ATOM   6011  CG  ASN D  16    -2.146  53.362  37.073  1.00 34.13           C
ATOM   6012  OD1 ASN D  16    -2.218  52.498  36.184  1.00 33.97           O
ATOM   6013  ND2 ASN D  16    -1.032  54.047  37.315  1.00 31.55           N
ATOM   6014  C   ASN D  16    -1.827  54.813  39.581  1.00 33.35           C
ATOM   6015  O   ASN D  16    -0.996  55.721  39.594  1.00 33.69           O
ATOM   6016  N   LYS D  17    -1.656  53.653  40.193  1.00 33.54           N
ATOM   6017  CA  LYS D  17    -0.475  53.320  40.960  1.00 34.83           C
ATOM   6018  CB  LYS D  17    -0.508  51.812  41.227  1.00 35.27           C
ATOM   6019  CG  LYS D  17     0.445  51.300  42.287  1.00 37.39           C
ATOM   6020  CD  LYS D  17     0.390  49.761  42.347  1.00 39.15           C
ATOM   6021  CE  LYS D  17     1.383  49.196  43.379  1.00 40.24           C
ATOM   6022  NZ  LYS D  17     1.368  47.687  43.437  1.00 41.19           N
ATOM   6023  C   LYS D  17     0.823  53.713  40.218  1.00 35.06           C
ATOM   6024  O   LYS D  17     1.784  54.197  40.827  1.00 35.99           O
ATOM   6025  N   ARG D  18     0.858  53.530  38.903  1.00 33.81           N
ATOM   6026  CA  ARG D  18     2.078  53.847  38.162  1.00 31.94           C
ATOM   6027  CB  ARG D  18     2.322  52.770  37.104  1.00 31.47           C
ATOM   6028  CG  ARG D  18     2.858  51.483  37.680  1.00 32.99           C
ATOM   6029  CD  ARG D  18     2.803  50.355  36.665  1.00 35.08           C
ATOM   6030  NE  ARG D  18     3.461  49.135  37.141  1.00 38.60           N
ATOM   6031  CZ  ARG D  18     3.241  48.565  38.329  1.00 41.47           C
ATOM   6032  NH1 ARG D  18     2.380  49.105  39.188  1.00 42.06           N
ATOM   6033  NH2 ARG D  18     3.866  47.433  38.658  1.00 41.97           N
ATOM   6034  C   ARG D  18     2.210  55.228  37.517  1.00 29.99           C
ATOM   6035  O   ARG D  18     3.208  55.486  36.845  1.00 29.23           O
ATOM   6036  N   SER D  19     1.249  56.124  37.732  1.00 28.26           N
ATOM   6037  CA  SER D  19     1.340  57.445  37.113  1.00 27.31           C
ATOM   6038  CB  SER D  19     0.061  58.257  37.374  1.00 25.47           C
ATOM   6039  OG  SER D  19    -1.047  57.717  36.667  1.00 21.21           O
ATOM   6040  C   SER D  19     2.565  58.229  37.600  1.00 27.83           C
ATOM   6041  O   SER D  19     2.861  58.259  38.799  1.00 27.23           O
ATOM   6042  N   ILE D  20     3.277  58.853  36.660  1.00 27.84           N
ATOM   6043  CA  ILE D  20     4.466  59.650  36.983  1.00 27.46           C
```

FIGURE 9 (cont.)

```
ATOM   6044  CB   ILE D  20      5.048  60.335  35.706  1.00 27.20           C
ATOM   6045  CG2  ILE D  20      5.979  61.488  36.087  1.00 27.11           C
ATOM   6046  CG1  ILE D  20      5.791  59.293  34.859  1.00 26.42           C
ATOM   6047  CD1  ILE D  20      6.285  59.813  33.526  1.00 24.93           C
ATOM   6048  C    ILE D  20      4.102  60.710  38.016  1.00 27.61           C
ATOM   6049  O    ILE D  20      4.877  60.987  38.944  1.00 26.09           O
ATOM   6050  N    ALA D  21      2.912  61.291  37.858  1.00 28.40           N
ATOM   6051  CA   ALA D  21      2.419  62.313  38.785  1.00 28.68           C
ATOM   6052  CB   ALA D  21      1.080  62.847  38.304  1.00 28.43           C
ATOM   6053  C    ALA D  21      2.279  61.773  40.213  1.00 28.51           C
ATOM   6054  O    ALA D  21      2.348  62.531  41.183  1.00 28.46           O
ATOM   6055  N    PHE D  22      2.067  60.467  40.346  1.00 28.82           N
ATOM   6056  CA   PHE D  22      1.932  59.874  41.671  1.00 29.03           C
ATOM   6057  CB   PHE D  22      1.344  58.460  41.581  1.00 29.14           C
ATOM   6058  CG   PHE D  22      1.184  57.781  42.927  1.00 30.16           C
ATOM   6059  CD1  PHE D  22      1.848  56.591  43.206  1.00 31.99           C
ATOM   6060  CD2  PHE D  22      0.352  58.322  43.901  1.00 30.20           C
ATOM   6061  CE1  PHE D  22      1.684  55.945  44.441  1.00 31.22           C
ATOM   6062  CE2  PHE D  22      0.180  57.689  45.133  1.00 31.08           C
ATOM   6063  CZ   PHE D  22      0.851  56.494  45.401  1.00 30.70           C
ATOM   6064  C    PHE D  22      3.309  59.811  42.322  1.00 28.37           C
ATOM   6065  O    PHE D  22      3.438  59.905  43.550  1.00 29.40           O
ATOM   6066  N    GLY D  23      4.329  59.639  41.483  1.00 26.72           N
ATOM   6067  CA   GLY D  23      5.697  59.579  41.958  1.00 25.99           C
ATOM   6068  C    GLY D  23      6.184  60.914  42.488  1.00 24.94           C
ATOM   6069  O    GLY D  23      7.074  60.961  43.340  1.00 24.75           O
ATOM   6070  N    VAL D  24      5.614  62.005  41.988  1.00 23.81           N
ATOM   6071  CA   VAL D  24      6.017  63.318  42.454  1.00 24.59           C
ATOM   6072  CB   VAL D  24      5.688  64.408  41.411  1.00 24.39           C
ATOM   6073  CG1  VAL D  24      6.201  63.980  40.046  1.00 22.84           C
ATOM   6074  CG2  VAL D  24      4.209  64.669  41.367  1.00 24.94           C
ATOM   6075  C    VAL D  24      5.305  63.612  43.772  1.00 25.43           C
ATOM   6076  O    VAL D  24      5.908  64.132  44.715  1.00 25.04           O
ATOM   6077  N    ALA D  25      4.024  63.254  43.839  1.00 25.82           N
ATOM   6078  CA   ALA D  25      3.225  63.461  45.041  1.00 26.01           C
ATOM   6079  CB   ALA D  25      1.807  62.924  44.824  1.00 27.08           C
ATOM   6080  C    ALA D  25      3.891  62.738  46.211  1.00 26.37           C
ATOM   6081  O    ALA D  25      4.085  63.313  47.288  1.00 26.51           O
ATOM   6082  N    LYS D  26      4.248  61.474  46.008  1.00 25.62           N
ATOM   6083  CA   LYS D  26      4.902  60.739  47.077  1.00 25.57           C
ATOM   6084  CB   LYS D  26      5.304  59.339  46.609  1.00 26.63           C
ATOM   6085  CG   LYS D  26      4.121  58.437  46.262  1.00 28.76           C
ATOM   6086  CD   LYS D  26      4.490  56.960  46.337  1.00 29.44           C
ATOM   6087  CE   LYS D  26      5.615  56.604  45.382  1.00 31.67           C
ATOM   6088  NZ   LYS D  26      5.849  55.121  45.298  1.00 33.22           N
ATOM   6089  C    LYS D  26      6.139  61.493  47.551  1.00 25.61           C
ATOM   6090  O    LYS D  26      6.479  61.477  48.744  1.00 26.49           O
ATOM   6091  N    VAL D  27      6.825  62.160  46.631  1.00 25.25           N
ATOM   6092  CA   VAL D  27      8.016  62.896  47.032  1.00 24.58           C
ATOM   6093  CB   VAL D  27      8.926  63.218  45.829  1.00 24.49           C
ATOM   6094  CG1  VAL D  27      9.996  64.241  46.237  1.00 25.04           C
ATOM   6095  CG2  VAL D  27      9.600  61.937  45.345  1.00 22.98           C
ATOM   6096  C    VAL D  27      7.650  64.181  47.759  1.00 24.61           C
ATOM   6097  O    VAL D  27      8.145  64.427  48.853  1.00 23.73           O
ATOM   6098  N    LEU D  28      6.777  64.993  47.166  1.00 25.00           N
ATOM   6099  CA   LEU D  28      6.365  66.245  47.806  1.00 25.64           C
ATOM   6100  CB   LEU D  28      5.405  67.008  46.898  1.00 24.07           C
ATOM   6101  CG   LEU D  28      5.953  67.334  45.510  1.00 23.41           C
ATOM   6102  CD1  LEU D  28      4.829  67.900  44.661  1.00 23.65           C
ATOM   6103  CD2  LEU D  28      7.120  68.320  45.614  1.00 22.65           C
ATOM   6104  C    LEU D  28      5.697  65.952  49.151  1.00 26.57           C
ATOM   6105  O    LEU D  28      5.821  66.720  50.101  1.00 25.66           O
ATOM   6106  N    ASP D  29      4.984  64.833  49.216  1.00 28.52           N
ATOM   6107  CA   ASP D  29      4.314  64.410  50.440  1.00 30.25           C
ATOM   6108  CB   ASP D  29      3.488  63.144  50.164  1.00 31.22           C
```

FIGURE 9 (cont.)

```
ATOM   6109  CG   ASP D  29       3.044  62.437  51.440  1.00 32.67           C
ATOM   6110  OD1  ASP D  29       2.237  63.025  52.195  1.00 30.01           O
ATOM   6111  OD2  ASP D  29       3.506  61.286  51.687  1.00 32.53           O
ATOM   6112  C    ASP D  29       5.358  64.130  51.527  1.00 31.52           C
ATOM   6113  O    ASP D  29       5.274  64.652  52.643  1.00 32.42           O
ATOM   6114  N    GLN D  30       6.353  63.320  51.188  1.00 32.32           N
ATOM   6115  CA   GLN D  30       7.420  62.940  52.121  1.00 32.26           C
ATOM   6116  CB   GLN D  30       8.361  61.960  51.405  1.00 33.35           C
ATOM   6117  CG   GLN D  30       9.724  61.682  52.047  1.00 36.31           C
ATOM   6118  CD   GLN D  30      10.672  60.942  51.076  1.00 38.76           C
ATOM   6119  OE1  GLN D  30      11.800  60.561  51.441  1.00 38.47           O
ATOM   6120  NE2  GLN D  30      10.213  60.741  49.831  1.00 38.27           N
ATOM   6121  C    GLN D  30       8.192  64.146  52.670  1.00 32.14           C
ATOM   6122  O    GLN D  30       8.856  64.037  53.708  1.00 32.28           O
ATOM   6123  N    LEU D  31       8.087  65.295  51.995  1.00 31.59           N
ATOM   6124  CA   LEU D  31       8.790  66.514  52.419  1.00 30.72           C
ATOM   6125  CB   LEU D  31       9.365  67.264  51.206  1.00 29.17           C
ATOM   6126  CG   LEU D  31      10.663  66.763  50.554  1.00 29.53           C
ATOM   6127  CD1  LEU D  31      11.737  66.565  51.628  1.00 28.23           C
ATOM   6128  CD2  LEU D  31      10.419  65.453  49.833  1.00 29.48           C
ATOM   6129  C    LEU D  31       7.956  67.487  53.254  1.00 31.38           C
ATOM   6130  O    LEU D  31       8.441  68.558  53.634  1.00 32.21           O
ATOM   6131  N    GLY D  32       6.707  67.131  53.533  1.00 31.68           N
ATOM   6132  CA   GLY D  32       5.870  67.993  54.351  1.00 31.98           C
ATOM   6133  C    GLY D  32       4.988  68.940  53.567  1.00 32.77           C
ATOM   6134  O    GLY D  32       4.412  69.884  54.121  1.00 33.13           O
ATOM   6135  N    ALA D  33       4.862  68.692  52.270  1.00 33.35           N
ATOM   6136  CA   ALA D  33       4.042  69.552  51.428  1.00 33.05           C
ATOM   6137  CB   ALA D  33       4.528  69.468  49.986  1.00 33.60           C
ATOM   6138  C    ALA D  33       2.562  69.199  51.493  1.00 32.74           C
ATOM   6139  O    ALA D  33       2.191  68.042  51.695  1.00 32.32           O
ATOM   6140  N    LYS D  34       1.711  70.203  51.318  1.00 32.23           N
ATOM   6141  CA   LYS D  34       0.277  69.974  51.317  1.00 32.34           C
ATOM   6142  CB   LYS D  34      -0.443  71.229  51.806  1.00 33.60           C
ATOM   6143  CG   LYS D  34      -1.940  71.071  51.964  1.00 37.18           C
ATOM   6144  CD   LYS D  34      -2.567  72.332  52.544  1.00 39.43           C
ATOM   6145  CE   LYS D  34      -1.946  72.671  53.904  1.00 41.06           C
ATOM   6146  NZ   LYS D  34      -2.196  71.600  54.910  1.00 41.68           N
ATOM   6147  C    LYS D  34      -0.037  69.703  49.849  1.00 32.07           C
ATOM   6148  O    LYS D  34       0.592  70.283  48.972  1.00 32.60           O
ATOM   6149  N    LEU D  35      -1.003  68.840  49.558  1.00 31.30           N
ATOM   6150  CA   LEU D  35      -1.291  68.540  48.167  1.00 29.27           C
ATOM   6151  CB   LEU D  35      -0.810  67.126  47.854  1.00 28.68           C
ATOM   6152  CG   LEU D  35       0.584  66.932  47.242  1.00 29.60           C
ATOM   6153  CD1  LEU D  35       1.644  67.633  48.059  1.00 29.53           C
ATOM   6154  CD2  LEU D  35       0.878  65.446  47.153  1.00 29.30           C
ATOM   6155  C    LEU D  35      -2.735  68.684  47.716  1.00 28.89           C
ATOM   6156  O    LEU D  35      -3.664  68.404  48.471  1.00 29.99           O
ATOM   6157  N    VAL D  36      -2.898  69.135  46.474  1.00 27.41           N
ATOM   6158  CA   VAL D  36      -4.197  69.288  45.830  1.00 28.05           C
ATOM   6159  CB   VAL D  36      -4.530  70.757  45.501  1.00 27.25           C
ATOM   6160  CG1  VAL D  36      -5.494  70.814  44.340  1.00 27.59           C
ATOM   6161  CG2  VAL D  36      -5.163  71.435  46.700  1.00 27.55           C
ATOM   6162  C    VAL D  36      -4.084  68.511  44.521  1.00 28.99           C
ATOM   6163  O    VAL D  36      -3.093  68.638  43.795  1.00 28.65           O
ATOM   6164  N    PHE D  37      -5.098  67.717  44.213  1.00 29.89           N
ATOM   6165  CA   PHE D  37      -5.066  66.911  43.012  1.00 30.23           C
ATOM   6166  CB   PHE D  37      -5.092  65.432  43.375  1.00 30.06           C
ATOM   6167  CG   PHE D  37      -4.037  65.031  44.357  1.00 31.03           C
ATOM   6168  CD1  PHE D  37      -4.163  65.350  45.704  1.00 30.74           C
ATOM   6169  CD2  PHE D  37      -2.910  64.345  43.936  1.00 30.78           C
ATOM   6170  CE1  PHE D  37      -3.176  64.991  46.620  1.00 30.28           C
ATOM   6171  CE2  PHE D  37      -1.919  63.984  44.845  1.00 31.47           C
ATOM   6172  CZ   PHE D  37      -2.056  64.309  46.188  1.00 30.69           C
ATOM   6173  C    PHE D  37      -6.233  67.189  42.090  1.00 31.51           C
```

FIGURE 9 (cont.)

```
ATOM   6174  O    PHE D  37      -7.278  67.680  42.517  1.00 31.30           O
ATOM   6175  N    THR D  38      -6.046  66.874  40.814  1.00 31.44           N
ATOM   6176  CA   THR D  38      -7.110  67.046  39.854  1.00 33.07           C
ATOM   6177  CB   THR D  38      -6.928  68.337  39.024  1.00 32.81           C
ATOM   6178  OG1  THR D  38      -5.834  68.180  38.112  1.00 33.12           O
ATOM   6179  CG2  THR D  38      -6.665  69.527  39.950  1.00 30.89           C
ATOM   6180  C    THR D  38      -7.080  65.817  38.955  1.00 34.53           C
ATOM   6181  O    THR D  38      -6.008  65.257  38.698  1.00 34.72           O
ATOM   6182  N    TYR D  39      -8.257  65.361  38.534  1.00 36.49           N
ATOM   6183  CA   TYR D  39      -8.370  64.207  37.645  1.00 37.42           C
ATOM   6184  CB   TYR D  39      -8.922  62.980  38.383  1.00 38.71           C
ATOM   6185  CG   TYR D  39     -10.122  63.275  39.257  1.00 40.83           C
ATOM   6186  CD1  TYR D  39      -9.962  63.883  40.504  1.00 41.32           C
ATOM   6187  CE1  TYR D  39     -11.069  64.247  41.280  1.00 42.17           C
ATOM   6188  CD2  TYR D  39     -11.425  63.019  38.806  1.00 41.83           C
ATOM   6189  CE2  TYR D  39     -12.549  63.382  39.579  1.00 42.06           C
ATOM   6190  CZ   TYR D  39     -12.360  64.004  40.812  1.00 42.16           C
ATOM   6191  OH   TYR D  39     -13.448  64.444  41.549  1.00 40.36           O
ATOM   6192  C    TYR D  39      -9.302  64.609  36.514  1.00 38.12           C
ATOM   6193  O    TYR D  39      -9.920  65.682  36.558  1.00 36.91           O
ATOM   6194  N    ARG D  40      -9.412  63.761  35.498  1.00 39.48           N
ATOM   6195  CA   ARG D  40     -10.258  64.098  34.366  1.00 41.04           C
ATOM   6196  CB   ARG D  40      -9.545  63.790  33.048  1.00 41.94           C
ATOM   6197  CG   ARG D  40     -10.278  64.363  31.828  1.00 43.95           C
ATOM   6198  CD   ARG D  40     -10.796  63.252  30.926  1.00 44.90           C
ATOM   6199  NE   ARG D  40      -9.722  62.659  30.136  1.00 45.00           N
ATOM   6200  CZ   ARG D  40      -9.743  61.412  29.674  1.00 46.38           C
ATOM   6201  NH1  ARG D  40     -10.791  60.623  29.938  1.00 44.50           N
ATOM   6202  NH2  ARG D  40      -8.721  60.960  28.933  1.00 46.43           N
ATOM   6203  C    ARG D  40     -11.589  63.386  34.364  1.00 41.77           C
ATOM   6204  O    ARG D  40     -12.608  63.962  33.957  1.00 41.22           O
ATOM   6205  N    LYS D  41     -11.581  62.136  34.816  1.00 42.82           N
ATOM   6206  CA   LYS D  41     -12.797  61.339  34.820  1.00 44.41           C
ATOM   6207  CB   LYS D  41     -12.516  59.976  34.177  1.00 44.19           C
ATOM   6208  CG   LYS D  41     -13.740  59.268  33.619  1.00 44.47           C
ATOM   6209  CD   LYS D  41     -14.550  58.527  34.695  1.00 43.36           C
ATOM   6210  CE   LYS D  41     -15.740  57.798  34.065  1.00 42.18           C
ATOM   6211  NZ   LYS D  41     -16.488  56.980  35.054  1.00 41.21           N
ATOM   6212  C    LYS D  41     -13.380  61.171  36.211  1.00 45.41           C
ATOM   6213  O    LYS D  41     -12.661  61.027  37.204  1.00 45.16           O
ATOM   6214  N    GLU D  42     -14.706  61.187  36.256  1.00 47.27           N
ATOM   6215  CA   GLU D  42     -15.485  61.075  37.486  1.00 48.88           C
ATOM   6216  CB   GLU D  42     -16.967  60.912  37.121  1.00 49.41           C
ATOM   6217  CG   GLU D  42     -17.325  61.364  35.685  1.00 49.86           C
ATOM   6218  CD   GLU D  42     -16.756  62.732  35.312  1.00 49.38           C
ATOM   6219  OE1  GLU D  42     -17.037  63.211  34.179  1.00 48.36           O
ATOM   6220  OE2  GLU D  42     -16.026  63.328  36.146  1.00 49.62           O
ATOM   6221  C    GLU D  42     -15.092  60.001  38.502  1.00 49.24           C
ATOM   6222  O    GLU D  42     -15.648  59.972  39.609  1.00 48.84           O
ATOM   6223  N    SER D  44     -14.137  59.134  38.149  1.00 50.30           N
ATOM   6224  CA   SER D  44     -13.710  58.068  39.064  1.00 50.94           C
ATOM   6225  CB   SER D  44     -12.941  56.968  38.306  1.00 50.79           C
ATOM   6226  OG   SER D  44     -11.872  57.495  37.526  1.00 50.90           O
ATOM   6227  C    SER D  44     -12.873  58.619  40.221  1.00 51.14           C
ATOM   6228  O    SER D  44     -11.675  58.325  40.358  1.00 50.73           O
ATOM   6229  N    ARG D  45     -13.545  59.414  41.051  1.00 51.60           N
ATOM   6230  CA   ARG D  45     -12.964  60.059  42.226  1.00 52.17           C
ATOM   6231  CB   ARG D  45     -13.895  61.205  42.655  1.00 51.11           C
ATOM   6232  CG   ARG D  45     -13.343  62.160  43.717  1.00 50.57           C
ATOM   6233  CD   ARG D  45     -14.474  62.710  44.608  1.00 48.93           C
ATOM   6234  NE   ARG D  45     -14.001  63.737  45.546  1.00 48.31           N
ATOM   6235  CZ   ARG D  45     -13.729  64.993  45.197  1.00 48.09           C
ATOM   6236  NH1  ARG D  45     -13.883  65.375  43.929  1.00 47.99           N
ATOM   6237  NH2  ARG D  45     -13.304  65.869  46.105  1.00 47.99           N
ATOM   6238  C    ARG D  45     -12.830  59.038  43.368  1.00 52.99           C
```

FIGURE 9 (cont.)

```
ATOM   6239  O    ARG D  45     -12.457  59.399  44.492  1.00 53.15           O
ATOM   6240  N    LYS D  46     -13.118  57.769  43.063  1.00 53.63           N
ATOM   6241  CA   LYS D  46     -13.097  56.666  44.047  1.00 54.02           C
ATOM   6242  CB   LYS D  46     -14.111  55.588  43.603  1.00 54.53           C
ATOM   6243  CG   LYS D  46     -14.381  54.449  44.588  1.00 54.79           C
ATOM   6244  CD   LYS D  46     -15.713  53.756  44.212  1.00 55.34           C
ATOM   6245  CE   LYS D  46     -16.000  52.529  45.090  1.00 55.49           C
ATOM   6246  NZ   LYS D  46     -15.864  52.848  46.552  1.00 55.68           N
ATOM   6247  C    LYS D  46     -11.728  56.025  44.275  1.00 54.16           C
ATOM   6248  O    LYS D  46     -11.199  56.050  45.399  1.00 53.82           O
ATOM   6249  N    GLU D  47     -11.165  55.430  43.222  1.00 54.13           N
ATOM   6250  CA   GLU D  47      -9.845  54.793  43.310  1.00 53.83           C
ATOM   6251  CB   GLU D  47      -9.602  53.891  42.095  1.00 54.62           C
ATOM   6252  CG   GLU D  47     -10.485  52.654  42.073  1.00 56.42           C
ATOM   6253  CD   GLU D  47     -10.389  51.900  40.760  1.00 57.49           C
ATOM   6254  OE1  GLU D  47     -10.673  52.523  39.703  1.00 57.38           O
ATOM   6255  OE2  GLU D  47     -10.031  50.693  40.784  1.00 57.74           O
ATOM   6256  C    GLU D  47      -8.738  55.844  43.385  1.00 53.24           C
ATOM   6257  O    GLU D  47      -7.548  55.512  43.564  1.00 53.49           O
ATOM   6258  N    LEU D  48      -9.118  57.109  43.223  1.00 51.90           N
ATOM   6259  CA   LEU D  48      -8.148  58.180  43.310  1.00 50.58           C
ATOM   6260  CB   LEU D  48      -8.681  59.464  42.666  1.00 50.74           C
ATOM   6261  CG   LEU D  48      -7.627  60.430  42.095  1.00 51.01           C
ATOM   6262  CD1  LEU D  48      -6.404  60.526  43.024  1.00 50.93           C
ATOM   6263  CD2  LEU D  48      -7.179  59.911  40.737  1.00 50.64           C
ATOM   6264  C    LEU D  48      -7.995  58.379  44.804  1.00 50.31           C
ATOM   6265  O    LEU D  48      -6.980  58.907  45.276  1.00 49.98           O
ATOM   6266  N    GLU D  49      -9.022  57.949  45.543  1.00 49.86           N
ATOM   6267  CA   GLU D  49      -9.040  58.048  47.002  1.00 49.48           C
ATOM   6268  CB   GLU D  49     -10.466  57.954  47.549  1.00 50.81           C
ATOM   6269  CG   GLU D  49     -11.351  59.179  47.357  1.00 51.93           C
ATOM   6270  CD   GLU D  49     -12.350  59.322  48.498  1.00 52.23           C
ATOM   6271  OE1  GLU D  49     -13.291  60.138  48.384  1.00 52.56           O
ATOM   6272  OE2  GLU D  49     -12.184  58.624  49.526  1.00 52.72           O
ATOM   6273  C    GLU D  49      -8.242  56.927  47.638  1.00 48.69           C
ATOM   6274  O    GLU D  49      -7.339  57.174  48.427  1.00 48.95           O
ATOM   6275  N    LYS D  50      -8.593  55.686  47.316  1.00 47.99           N
ATOM   6276  CA   LYS D  50      -7.894  54.541  47.891  1.00 47.52           C
ATOM   6277  CB   LYS D  50      -8.415  53.220  47.308  1.00 48.73           C
ATOM   6278  CG   LYS D  50      -9.903  52.959  47.555  1.00 50.16           C
ATOM   6279  CD   LYS D  50     -10.153  51.601  48.242  1.00 50.43           C
ATOM   6280  CE   LYS D  50      -9.720  51.625  49.705  1.00 50.41           C
ATOM   6281  NZ   LYS D  50     -10.385  50.511  50.458  1.00 50.18           N
ATOM   6282  C    LYS D  50      -6.402  54.622  47.664  1.00 46.26           C
ATOM   6283  O    LYS D  50      -5.629  53.935  48.344  1.00 45.33           O
ATOM   6284  N    LEU D  51      -5.999  55.464  46.713  1.00 45.50           N
ATOM   6285  CA   LEU D  51      -4.585  55.635  46.380  1.00 44.66           C
ATOM   6286  CB   LEU D  51      -4.444  56.081  44.926  1.00 43.08           C
ATOM   6287  CG   LEU D  51      -3.050  55.942  44.313  1.00 41.06           C
ATOM   6288  CD1  LEU D  51      -2.667  54.472  44.189  1.00 39.13           C
ATOM   6289  CD2  LEU D  51      -3.055  56.590  42.949  1.00 40.33           C
ATOM   6290  C    LEU D  51      -3.924  56.656  47.297  1.00 45.15           C
ATOM   6291  O    LEU D  51      -2.783  56.480  47.722  1.00 44.75           O
ATOM   6292  N    LEU D  52      -4.645  57.725  47.612  1.00 46.00           N
ATOM   6293  CA   LEU D  52      -4.105  58.756  48.491  1.00 46.91           C
ATOM   6294  CB   LEU D  52      -4.903  60.050  48.332  1.00 47.31           C
ATOM   6295  CG   LEU D  52      -5.260  60.490  46.910  1.00 47.21           C
ATOM   6296  CD1  LEU D  52      -6.133  61.734  46.984  1.00 47.76           C
ATOM   6297  CD2  LEU D  52      -4.001  60.770  46.108  1.00 47.58           C
ATOM   6298  C    LEU D  52      -4.132  58.330  49.965  1.00 47.93           C
ATOM   6299  O    LEU D  52      -3.481  58.976  50.808  1.00 48.05           O
ATOM   6300  N    GLU D  53      -4.869  57.255  50.272  1.00 48.65           N
ATOM   6301  CA   GLU D  53      -5.008  56.749  51.656  1.00 50.83           C
ATOM   6302  CB   GLU D  53      -5.858  55.467  51.699  1.00 51.19           C
ATOM   6303  CG   GLU D  53      -7.157  55.532  50.885  1.00 52.43           C
```

FIGURE 9 (cont.)

| | | | | | | | | | | |
|---|---|---|---|---|---|---|---|---|---|---|
| ATOM | 6304 | CD | GLU | D | 53 | -8.246 | 56.356 | 51.552 | 1.00 53.24 | C |
| ATOM | 6305 | OE1 | GLU | D | 53 | -7.922 | 57.429 | 52.119 | 1.00 52.87 | O |
| ATOM | 6306 | OE2 | GLU | D | 53 | -9.436 | 55.937 | 51.495 | 1.00 53.70 | O |
| ATOM | 6307 | C | GLU | D | 53 | -3.667 | 56.443 | 52.310 | 1.00 51.59 | C |
| ATOM | 6308 | O | GLU | D | 53 | -3.607 | 55.923 | 53.436 | 1.00 52.15 | O |
| ATOM | 6309 | N | GLN | D | 54 | -2.592 | 56.774 | 51.608 | 1.00 52.25 | N |
| ATOM | 6310 | CA | GLN | D | 54 | -1.246 | 56.517 | 52.099 | 1.00 52.20 | C |
| ATOM | 6311 | CB | GLN | D | 54 | -0.695 | 55.278 | 51.398 | 1.00 51.96 | C |
| ATOM | 6312 | CG | GLN | D | 54 | -0.771 | 55.387 | 49.879 | 1.00 51.66 | C |
| ATOM | 6313 | CD | GLN | D | 54 | -0.558 | 54.063 | 49.188 | 1.00 51.89 | C |
| ATOM | 6314 | OE1 | GLN | D | 54 | -1.425 | 53.181 | 49.227 | 1.00 51.93 | O |
| ATOM | 6315 | NE2 | GLN | D | 54 | 0.602 | 53.903 | 48.557 | 1.00 52.06 | N |
| ATOM | 6316 | C | GLN | D | 54 | -0.397 | 57.728 | 51.746 | 1.00 51.68 | C |
| ATOM | 6317 | O | GLN | D | 54 | 0.569 | 57.600 | 51.000 | 1.00 51.12 | O |
| ATOM | 6318 | N | LEU | D | 55 | -0.742 | 58.888 | 52.309 | 1.00 51.65 | N |
| ATOM | 6319 | CA | LEU | D | 55 | -0.031 | 60.132 | 52.005 | 1.00 51.19 | C |
| ATOM | 6320 | CB | LEU | D | 55 | -0.521 | 60.628 | 50.635 | 1.00 49.87 | C |
| ATOM | 6321 | CG | LEU | D | 55 | 0.343 | 60.714 | 49.364 | 1.00 49.88 | C |
| ATOM | 6322 | CD1 | LEU | D | 55 | 0.941 | 59.355 | 48.959 | 1.00 48.92 | C |
| ATOM | 6323 | CD2 | LEU | D | 55 | -0.537 | 61.254 | 48.243 | 1.00 48.51 | C |
| ATOM | 6324 | C | LEU | D | 55 | -0.255 | 61.241 | 53.074 | 1.00 51.99 | C |
| ATOM | 6325 | O | LEU | D | 55 | 0.214 | 61.151 | 54.220 | 1.00 50.18 | O |
| ATOM | 6326 | N | ASN | D | 56 | -0.987 | 62.279 | 52.650 | 1.00 53.82 | N |
| ATOM | 6327 | CA | ASN | D | 56 | -1.348 | 63.470 | 53.437 | 1.00 54.81 | C |
| ATOM | 6328 | CB | ASN | D | 56 | -1.762 | 64.598 | 52.478 | 1.00 53.48 | C |
| ATOM | 6329 | CG | ASN | D | 56 | -0.580 | 65.168 | 51.683 | 1.00 52.13 | C |
| ATOM | 6330 | OD1 | ASN | D | 56 | 0.320 | 64.424 | 51.260 | 1.00 51.09 | O |
| ATOM | 6331 | ND2 | ASN | D | 56 | -0.584 | 66.486 | 51.472 | 1.00 49.71 | N |
| ATOM | 6332 | C | ASN | D | 56 | -2.510 | 63.178 | 54.370 | 1.00 56.67 | C |
| ATOM | 6333 | O | ASN | D | 56 | -2.445 | 63.446 | 55.575 | 1.00 56.72 | O |
| ATOM | 6334 | N | GLN | D | 57 | -3.589 | 62.666 | 53.777 | 1.00 59.19 | N |
| ATOM | 6335 | CA | GLN | D | 57 | -4.815 | 62.278 | 54.481 | 1.00 61.37 | C |
| ATOM | 6336 | CB | GLN | D | 57 | -4.477 | 61.653 | 55.849 | 1.00 62.11 | C |
| ATOM | 6337 | CG | GLN | D | 57 | -5.386 | 60.470 | 56.237 | 1.00 62.93 | C |
| ATOM | 6338 | CD | GLN | D | 57 | -5.380 | 59.375 | 55.176 | 1.00 63.34 | C |
| ATOM | 6339 | OE1 | GLN | D | 57 | -4.394 | 59.214 | 54.442 | 1.00 63.08 | O |
| ATOM | 6340 | NE2 | GLN | D | 57 | -6.474 | 58.598 | 55.101 | 1.00 63.41 | N |
| ATOM | 6341 | C | GLN | D | 57 | -5.875 | 63.380 | 54.641 | 1.00 62.18 | C |
| ATOM | 6342 | O | GLN | D | 57 | -6.906 | 63.348 | 53.954 | 1.00 61.97 | O |
| ATOM | 6343 | N | PRO | D | 58 | -5.655 | 64.366 | 55.542 | 1.00 63.02 | N |
| ATOM | 6344 | CD | PRO | D | 58 | -4.617 | 64.586 | 56.567 | 1.00 63.26 | C |
| ATOM | 6345 | CA | PRO | D | 58 | -6.712 | 65.382 | 55.641 | 1.00 63.30 | C |
| ATOM | 6346 | CB | PRO | D | 58 | -6.146 | 66.390 | 56.655 | 1.00 63.81 | C |
| ATOM | 6347 | CG | PRO | D | 58 | -4.631 | 66.078 | 56.707 | 1.00 63.67 | C |
| ATOM | 6348 | C | PRO | D | 58 | -7.059 | 66.006 | 54.298 | 1.00 63.22 | C |
| ATOM | 6349 | O | PRO | D | 58 | -8.136 | 66.593 | 54.116 | 1.00 63.20 | O |
| ATOM | 6350 | N | GLU | D | 59 | -6.153 | 65.854 | 53.339 | 1.00 63.26 | N |
| ATOM | 6351 | CA | GLU | D | 59 | -6.386 | 66.412 | 52.014 | 1.00 62.76 | C |
| ATOM | 6352 | CB | GLU | D | 59 | -5.357 | 65.869 | 51.019 | 1.00 63.79 | C |
| ATOM | 6353 | CG | GLU | D | 59 | -4.073 | 66.670 | 51.013 | 1.00 65.73 | C |
| ATOM | 6354 | CD | GLU | D | 59 | -3.779 | 67.268 | 52.380 | 1.00 66.85 | C |
| ATOM | 6355 | OE1 | GLU | D | 59 | -4.573 | 68.125 | 52.839 | 1.00 67.87 | O |
| ATOM | 6356 | OE2 | GLU | D | 59 | -2.765 | 66.886 | 53.005 | 1.00 67.43 | O |
| ATOM | 6357 | C | GLU | D | 59 | -7.781 | 66.140 | 51.497 | 1.00 61.36 | C |
| ATOM | 6358 | O | GLU | D | 59 | -8.714 | 66.915 | 51.750 | 1.00 61.25 | O |
| ATOM | 6359 | N | ALA | D | 60 | -7.927 | 65.029 | 50.784 | 1.00 59.65 | N |
| ATOM | 6360 | CA | ALA | D | 60 | -9.204 | 64.699 | 50.182 | 1.00 57.79 | C |
| ATOM | 6361 | CB | ALA | D | 60 | -10.357 | 64.908 | 51.193 | 1.00 58.10 | C |
| ATOM | 6362 | C | ALA | D | 60 | -9.326 | 65.681 | 49.014 | 1.00 56.00 | C |
| ATOM | 6363 | O | ALA | D | 60 | -9.864 | 65.323 | 47.961 | 1.00 56.04 | O |
| ATOM | 6364 | N | HIS | D | 61 | -8.804 | 66.900 | 49.199 | 1.00 53.56 | N |
| ATOM | 6365 | CA | HIS | D | 61 | -8.841 | 67.946 | 48.161 | 1.00 51.64 | C |
| ATOM | 6366 | CB | HIS | D | 61 | -7.776 | 69.016 | 48.427 | 1.00 52.30 | C |
| ATOM | 6367 | CG | HIS | D | 61 | -8.074 | 69.883 | 49.611 | 1.00 53.67 | C |
| ATOM | 6368 | CD2 | HIS | D | 61 | -7.432 | 70.027 | 50.797 | 1.00 53.59 | C |

FIGURE 9 (cont.)

| | | | | | | | | | | |
|---|---|---|---|---|---|---|---|---|---|---|
| ATOM | 6369 | ND1 | HIS | D | 61 | -9.168 | 70.730 | 49.660 | 1.00 54.60 | N |
| ATOM | 6370 | CE1 | HIS | D | 61 | -9.184 | 71.357 | 50.826 | 1.00 54.27 | C |
| ATOM | 6371 | NE2 | HIS | D | 61 | -8.143 | 70.949 | 51.534 | 1.00 54.01 | N |
| ATOM | 6372 | C | HIS | D | 61 | -8.602 | 67.347 | 46.787 | 1.00 49.85 | C |
| ATOM | 6373 | O | HIS | D | 61 | -7.448 | 67.146 | 46.374 | 1.00 49.30 | O |
| ATOM | 6374 | N | LEU | D | 62 | -9.698 | 67.081 | 46.077 | 1.00 46.91 | N |
| ATOM | 6375 | CA | LEU | D | 62 | -9.633 | 66.468 | 44.760 | 1.00 44.45 | C |
| ATOM | 6376 | CB | LEU | D | 62 | -9.934 | 64.968 | 44.862 | 1.00 43.06 | C |
| ATOM | 6377 | CG | LEU | D | 62 | -9.059 | 64.051 | 45.712 | 1.00 41.83 | C |
| ATOM | 6378 | CD1 | LEU | D | 62 | -9.680 | 62.660 | 45.702 | 1.00 42.94 | C |
| ATOM | 6379 | CD2 | LEU | D | 62 | -7.650 | 63.994 | 45.173 | 1.00 41.48 | C |
| ATOM | 6380 | C | LEU | D | 62 | -10.666 | 67.099 | 43.852 | 1.00 43.56 | C |
| ATOM | 6381 | O | LEU | D | 62 | -11.864 | 67.010 | 44.120 | 1.00 44.22 | O |
| ATOM | 6382 | N | TYR | D | 63 | -10.208 | 67.712 | 42.766 | 1.00 42.57 | N |
| ATOM | 6383 | CA | TYR | D | 63 | -11.110 | 68.353 | 41.821 | 1.00 41.30 | C |
| ATOM | 6384 | CB | TYR | D | 63 | -10.730 | 69.817 | 41.659 | 1.00 41.35 | C |
| ATOM | 6385 | CG | TYR | D | 63 | -10.621 | 70.501 | 42.994 | 1.00 42.56 | C |
| ATOM | 6386 | CD1 | TYR | D | 63 | -9.542 | 70.240 | 43.846 | 1.00 42.32 | C |
| ATOM | 6387 | CE1 | TYR | D | 63 | -9.471 | 70.815 | 45.110 | 1.00 43.20 | C |
| ATOM | 6388 | CD2 | TYR | D | 63 | -11.626 | 71.359 | 43.441 | 1.00 42.39 | C |
| ATOM | 6389 | CE2 | TYR | D | 63 | -11.559 | 71.938 | 44.710 | 1.00 43.37 | C |
| ATOM | 6390 | CZ | TYR | D | 63 | -10.482 | 71.663 | 45.532 | 1.00 42.83 | C |
| ATOM | 6391 | OH | TYR | D | 63 | -10.412 | 72.256 | 46.774 | 1.00 44.11 | O |
| ATOM | 6392 | C | TYR | D | 63 | -11.118 | 67.674 | 40.462 | 1.00 40.70 | C |
| ATOM | 6393 | O | TYR | D | 63 | -10.069 | 67.333 | 39.903 | 1.00 39.73 | O |
| ATOM | 6394 | N | GLN | D | 64 | -12.327 | 67.488 | 39.948 | 1.00 39.88 | N |
| ATOM | 6395 | CA | GLN | D | 64 | -12.566 | 66.862 | 38.662 | 1.00 39.79 | C |
| ATOM | 6396 | CB | GLN | D | 64 | -14.024 | 66.359 | 38.653 | 1.00 41.07 | C |
| ATOM | 6397 | CG | GLN | D | 64 | -14.568 | 65.861 | 37.333 | 1.00 42.77 | C |
| ATOM | 6398 | CD | GLN | D | 64 | -15.161 | 66.991 | 36.515 | 1.00 44.49 | C |
| ATOM | 6399 | OE1 | GLN | D | 64 | -16.392 | 67.162 | 36.448 | 1.00 44.52 | O |
| ATOM | 6400 | NE2 | GLN | D | 64 | -14.288 | 67.786 | 35.896 | 1.00 44.60 | N |
| ATOM | 6401 | C | GLN | D | 64 | -12.298 | 67.952 | 37.617 | 1.00 38.95 | C |
| ATOM | 6402 | O | GLN | D | 64 | -12.954 | 69.000 | 37.621 | 1.00 39.23 | O |
| ATOM | 6403 | N | ILE | D | 65 | -11.324 | 67.731 | 36.736 | 1.00 37.19 | N |
| ATOM | 6404 | CA | ILE | D | 65 | -11.002 | 68.757 | 35.737 | 1.00 36.83 | C |
| ATOM | 6405 | CB | ILE | D | 65 | -9.889 | 69.712 | 36.227 | 1.00 36.54 | C |
| ATOM | 6406 | CG2 | ILE | D | 65 | -9.412 | 70.585 | 35.066 | 1.00 36.88 | C |
| ATOM | 6407 | CG1 | ILE | D | 65 | -10.389 | 70.574 | 37.388 | 1.00 35.99 | C |
| ATOM | 6408 | CD1 | ILE | D | 65 | -9.400 | 71.637 | 37.815 | 1.00 34.61 | C |
| ATOM | 6409 | C | ILE | D | 65 | -10.524 | 68.247 | 34.393 | 1.00 36.21 | C |
| ATOM | 6410 | O | ILE | D | 65 | -9.448 | 67.668 | 34.303 | 1.00 36.55 | O |
| ATOM | 6411 | N | ASP | D | 66 | -11.307 | 68.490 | 33.348 | 1.00 35.97 | N |
| ATOM | 6412 | CA | ASP | D | 66 | -10.914 | 68.087 | 32.007 | 1.00 36.32 | C |
| ATOM | 6413 | CB | ASP | D | 66 | -12.104 | 67.558 | 31.201 | 1.00 36.99 | C |
| ATOM | 6414 | CG | ASP | D | 66 | -11.673 | 66.944 | 29.883 | 1.00 39.04 | C |
| ATOM | 6415 | OD1 | ASP | D | 66 | -11.909 | 65.724 | 29.691 | 1.00 39.68 | O |
| ATOM | 6416 | OD2 | ASP | D | 66 | -11.081 | 67.676 | 29.042 | 1.00 38.72 | O |
| ATOM | 6417 | C | ASP | D | 66 | -10.373 | 69.341 | 31.347 | 1.00 35.47 | C |
| ATOM | 6418 | O | ASP | D | 66 | -11.130 | 70.255 | 31.030 | 1.00 36.30 | O |
| ATOM | 6419 | N | VAL | D | 67 | -9.060 | 69.380 | 31.149 | 1.00 34.68 | N |
| ATOM | 6420 | CA | VAL | D | 67 | -8.391 | 70.537 | 30.560 | 1.00 33.31 | C |
| ATOM | 6421 | CB | VAL | D | 67 | -6.873 | 70.320 | 30.502 | 1.00 32.03 | C |
| ATOM | 6422 | CG1 | VAL | D | 67 | -6.332 | 70.124 | 31.887 | 1.00 31.10 | C |
| ATOM | 6423 | CG2 | VAL | D | 67 | -6.552 | 69.104 | 29.633 | 1.00 32.04 | C |
| ATOM | 6424 | C | VAL | D | 67 | -8.867 | 70.903 | 29.163 | 1.00 34.18 | C |
| ATOM | 6425 | O | VAL | D | 67 | -8.358 | 71.862 | 28.582 | 1.00 35.41 | O |
| ATOM | 6426 | N | GLN | D | 68 | -9.824 | 70.152 | 28.613 | 1.00 34.51 | N |
| ATOM | 6427 | CA | GLN | D | 68 | -10.343 | 70.466 | 27.279 | 1.00 35.04 | C |
| ATOM | 6428 | CB | GLN | D | 68 | -10.964 | 69.229 | 26.608 | 1.00 35.08 | C |
| ATOM | 6429 | CG | GLN | D | 68 | -9.952 | 68.193 | 26.124 | 1.00 35.94 | C |
| ATOM | 6430 | CD | GLN | D | 68 | -10.597 | 67.040 | 25.347 | 1.00 36.63 | C |
| ATOM | 6431 | OE1 | GLN | D | 68 | -11.416 | 66.282 | 25.888 | 1.00 36.52 | O |
| ATOM | 6432 | NE2 | GLN | D | 68 | -10.226 | 66.902 | 24.076 | 1.00 35.23 | N |
| ATOM | 6433 | C | GLN | D | 68 | -11.389 | 71.580 | 27.371 | 1.00 35.42 | C |

FIGURE 9 (cont.)

| | | | | | | | | | | |
|---|---|---|---|---|---|---|---|---|---|---|
| ATOM | 6434 | O | GLN | D | 68 | -11.657 | 72.270 | 26.389 | 1.00 35.24 | O |
| ATOM | 6435 | N | SER | D | 69 | -11.987 | 71.757 | 28.547 | 1.00 35.96 | N |
| ATOM | 6436 | CA | SER | D | 69 | -12.978 | 72.814 | 28.704 | 1.00 36.59 | C |
| ATOM | 6437 | CB | SER | D | 69 | -14.246 | 72.284 | 29.383 | 1.00 37.26 | C |
| ATOM | 6438 | OG | SER | D | 69 | -14.057 | 72.127 | 30.779 | 1.00 39.91 | O |
| ATOM | 6439 | C | SER | D | 69 | -12.414 | 73.973 | 29.522 | 1.00 37.08 | C |
| ATOM | 6440 | O | SER | D | 69 | -11.846 | 73.776 | 30.602 | 1.00 36.08 | O |
| ATOM | 6441 | N | ASP | D | 70 | -12.577 | 75.177 | 28.981 | 1.00 37.01 | N |
| ATOM | 6442 | CA | ASP | D | 70 | -12.130 | 76.416 | 29.611 | 1.00 38.06 | C |
| ATOM | 6443 | CB | ASP | D | 70 | -12.365 | 77.603 | 28.669 | 1.00 38.66 | C |
| ATOM | 6444 | CG | ASP | D | 70 | -11.449 | 77.597 | 27.478 | 1.00 39.01 | C |
| ATOM | 6445 | OD1 | ASP | D | 70 | -11.325 | 76.545 | 26.821 | 1.00 41.00 | O |
| ATOM | 6446 | OD2 | ASP | D | 70 | -10.856 | 78.653 | 27.188 | 1.00 40.80 | O |
| ATOM | 6447 | C | ASP | D | 70 | -12.938 | 76.686 | 30.872 | 1.00 38.63 | C |
| ATOM | 6448 | O | ASP | D | 70 | -12.615 | 77.601 | 31.648 | 1.00 38.18 | O |
| ATOM | 6449 | N | GLU | D | 71 | -13.994 | 75.905 | 31.082 | 1.00 38.82 | N |
| ATOM | 6450 | CA | GLU | D | 71 | -14.830 | 76.141 | 32.238 | 1.00 39.35 | C |
| ATOM | 6451 | CB | GLU | D | 71 | -16.295 | 75.871 | 31.889 | 1.00 40.41 | C |
| ATOM | 6452 | CG | GLU | D | 71 | -16.659 | 74.417 | 31.653 | 1.00 43.86 | C |
| ATOM | 6453 | CD | GLU | D | 71 | -18.151 | 74.256 | 31.388 | 1.00 45.25 | C |
| ATOM | 6454 | OE1 | GLU | D | 71 | -18.941 | 75.070 | 31.940 | 1.00 44.90 | O |
| ATOM | 6455 | OE2 | GLU | D | 71 | -18.532 | 73.321 | 30.640 | 1.00 45.64 | O |
| ATOM | 6456 | C | GLU | D | 71 | -14.410 | 75.373 | 33.478 | 1.00 38.57 | C |
| ATOM | 6457 | O | GLU | D | 71 | -14.539 | 75.884 | 34.592 | 1.00 38.96 | O |
| ATOM | 6458 | N | GLU | D | 72 | -13.894 | 74.161 | 33.311 | 1.00 37.69 | N |
| ATOM | 6459 | CA | GLU | D | 72 | -13.456 | 73.400 | 34.479 | 1.00 37.70 | C |
| ATOM | 6460 | CB | GLU | D | 72 | -13.382 | 71.920 | 34.123 | 1.00 39.28 | C |
| ATOM | 6461 | CG | GLU | D | 72 | -14.764 | 71.302 | 33.985 | 1.00 40.64 | C |
| ATOM | 6462 | CD | GLU | D | 72 | -14.749 | 69.980 | 33.250 | 1.00 42.28 | C |
| ATOM | 6463 | OE1 | GLU | D | 72 | -13.894 | 69.120 | 33.584 | 1.00 41.17 | O |
| ATOM | 6464 | OE2 | GLU | D | 72 | -15.608 | 69.800 | 32.340 | 1.00 43.16 | O |
| ATOM | 6465 | C | GLU | D | 72 | -12.116 | 73.899 | 35.062 | 1.00 37.46 | C |
| ATOM | 6466 | O | GLU | D | 72 | -11.909 | 73.855 | 36.281 | 1.00 37.17 | O |
| ATOM | 6467 | N | VAL | D | 73 | -11.213 | 74.372 | 34.201 | 1.00 36.54 | N |
| ATOM | 6468 | CA | VAL | D | 73 | -9.918 | 74.902 | 34.644 | 1.00 35.08 | C |
| ATOM | 6469 | CB | VAL | D | 73 | -8.997 | 75.258 | 33.446 | 1.00 32.82 | C |
| ATOM | 6470 | CG1 | VAL | D | 73 | -7.610 | 75.574 | 33.944 | 1.00 31.64 | C |
| ATOM | 6471 | CG2 | VAL | D | 73 | -8.961 | 74.129 | 32.446 | 1.00 31.61 | C |
| ATOM | 6472 | C | VAL | D | 73 | -10.177 | 76.192 | 35.428 | 1.00 35.58 | C |
| ATOM | 6473 | O | VAL | D | 73 | -9.694 | 76.379 | 36.558 | 1.00 35.66 | O |
| ATOM | 6474 | N | ILE | D | 74 | -10.940 | 77.089 | 34.817 | 1.00 35.64 | N |
| ATOM | 6475 | CA | ILE | D | 74 | -11.275 | 78.361 | 35.455 | 1.00 36.42 | C |
| ATOM | 6476 | CB | ILE | D | 74 | -12.170 | 79.227 | 34.527 | 1.00 36.93 | C |
| ATOM | 6477 | CG2 | ILE | D | 74 | -12.833 | 80.349 | 35.331 | 1.00 37.06 | C |
| ATOM | 6478 | CG1 | ILE | D | 74 | -11.330 | 79.788 | 33.364 | 1.00 36.11 | C |
| ATOM | 6479 | CD1 | ILE | D | 74 | -12.097 | 80.761 | 32.444 | 1.00 35.71 | C |
| ATOM | 6480 | C | ILE | D | 74 | -12.001 | 78.139 | 36.775 | 1.00 36.09 | C |
| ATOM | 6481 | O | ILE | D | 74 | -11.634 | 78.712 | 37.801 | 1.00 37.39 | O |
| ATOM | 6482 | N | ASN | D | 75 | -13.040 | 77.312 | 36.742 | 1.00 36.95 | N |
| ATOM | 6483 | CA | ASN | D | 75 | -13.820 | 77.005 | 37.940 | 1.00 36.96 | C |
| ATOM | 6484 | CB | ASN | D | 75 | -15.126 | 76.299 | 37.571 | 1.00 36.48 | C |
| ATOM | 6485 | CG | ASN | D | 75 | -16.128 | 77.233 | 36.971 | 1.00 35.75 | C |
| ATOM | 6486 | OD1 | ASN | D | 75 | -15.983 | 78.457 | 37.070 | 1.00 35.79 | O |
| ATOM | 6487 | ND2 | ASN | D | 75 | -17.164 | 76.675 | 36.351 | 1.00 36.50 | N |
| ATOM | 6488 | C | ASN | D | 75 | -13.050 | 76.102 | 38.867 | 1.00 37.04 | C |
| ATOM | 6489 | O | ASN | D | 75 | -13.216 | 76.151 | 40.092 | 1.00 37.66 | O |
| ATOM | 6490 | N | GLY | D | 76 | -12.236 | 75.241 | 38.272 | 1.00 37.02 | N |
| ATOM | 6491 | CA | GLY | D | 76 | -11.439 | 74.323 | 39.055 | 1.00 35.65 | C |
| ATOM | 6492 | C | GLY | D | 76 | -10.484 | 75.055 | 39.976 | 1.00 35.10 | C |
| ATOM | 6493 | O | GLY | D | 76 | -10.495 | 74.822 | 41.192 | 1.00 35.36 | O |
| ATOM | 6494 | N | PHE | D | 77 | -9.663 | 75.944 | 39.417 | 1.00 33.48 | N |
| ATOM | 6495 | CA | PHE | D | 77 | -8.695 | 76.659 | 40.235 | 1.00 33.02 | C |
| ATOM | 6496 | CB | PHE | D | 77 | -7.612 | 77.304 | 39.359 | 1.00 31.77 | C |
| ATOM | 6497 | CG | PHE | D | 77 | -6.588 | 76.324 | 38.873 | 1.00 30.42 | C |
| ATOM | 6498 | CD1 | PHE | D | 77 | -6.851 | 75.511 | 37.774 | 1.00 30.36 | C |

FIGURE 9 (cont.)

| | | | | | | | | | |
|---|---|---|---|---|---|---|---|---|---|
| ATOM | 6499 | CD2 | PHE | D | 77 | -5.402 | 76.136 | 39.580 | 1.00 28.77 | C |
| ATOM | 6500 | CE1 | PHE | D | 77 | -5.950 | 74.515 | 37.387 | 1.00 30.43 | C |
| ATOM | 6501 | CE2 | PHE | D | 77 | -4.496 | 75.148 | 39.208 | 1.00 27.84 | C |
| ATOM | 6502 | CZ | PHE | D | 77 | -4.769 | 74.333 | 38.109 | 1.00 28.85 | C |
| ATOM | 6503 | C | PHE | D | 77 | -9.313 | 77.687 | 41.148 | 1.00 33.83 | C |
| ATOM | 6504 | O | PHE | D | 77 | -8.882 | 77.833 | 42.288 | 1.00 33.90 | O |
| ATOM | 6505 | N | GLU | D | 78 | -10.317 | 78.405 | 40.659 | 1.00 35.50 | N |
| ATOM | 6506 | CA | GLU | D | 78 | -10.980 | 79.408 | 41.483 | 1.00 37.16 | C |
| ATOM | 6507 | CB | GLU | D | 78 | -12.148 | 80.016 | 40.730 | 1.00 38.13 | C |
| ATOM | 6508 | CG | GLU | D | 78 | -12.892 | 81.082 | 41.519 | 1.00 41.02 | C |
| ATOM | 6509 | CD | GLU | D | 78 | -13.957 | 81.751 | 40.677 | 1.00 42.82 | C |
| ATOM | 6510 | OE1 | GLU | D | 78 | -15.046 | 81.149 | 40.496 | 1.00 43.33 | O |
| ATOM | 6511 | OE2 | GLU | D | 78 | -13.692 | 82.873 | 40.178 | 1.00 44.15 | O |
| ATOM | 6512 | C | GLU | D | 78 | -11.492 | 78.736 | 42.748 | 1.00 38.03 | C |
| ATOM | 6513 | O | GLU | D | 78 | -11.357 | 79.256 | 43.856 | 1.00 38.73 | O |
| ATOM | 6514 | N | GLN | D | 79 | -12.087 | 77.567 | 42.575 | 1.00 38.70 | N |
| ATOM | 6515 | CA | GLN | D | 79 | -12.602 | 76.807 | 43.702 | 1.00 39.94 | C |
| ATOM | 6516 | CB | GLN | D | 79 | -13.282 | 75.527 | 43.178 | 1.00 40.62 | C |
| ATOM | 6517 | CG | GLN | D | 79 | -13.907 | 74.621 | 44.236 | 1.00 41.21 | C |
| ATOM | 6518 | CD | GLN | D | 79 | -14.913 | 75.346 | 45.121 | 1.00 41.88 | C |
| ATOM | 6519 | OE1 | GLN | D | 79 | -15.599 | 76.270 | 44.673 | 1.00 40.82 | O |
| ATOM | 6520 | NE2 | GLN | D | 79 | -15.013 | 74.919 | 46.385 | 1.00 41.95 | N |
| ATOM | 6521 | C | GLN | D | 79 | -11.404 | 76.465 | 44.597 | 1.00 40.13 | C |
| ATOM | 6522 | O | GLN | D | 79 | -11.417 | 76.716 | 45.812 | 1.00 40.21 | O |
| ATOM | 6523 | N | ILE | D | 80 | -10.360 | 75.905 | 43.989 | 1.00 39.49 | N |
| ATOM | 6524 | CA | ILE | D | 80 | -9.164 | 75.534 | 44.739 | 1.00 38.96 | C |
| ATOM | 6525 | CB | ILE | D | 80 | -8.010 | 75.140 | 43.803 | 1.00 38.83 | C |
| ATOM | 6526 | CG2 | ILE | D | 80 | -6.758 | 74.827 | 44.633 | 1.00 39.46 | C |
| ATOM | 6527 | CG1 | ILE | D | 80 | -8.418 | 73.929 | 42.962 | 1.00 37.85 | C |
| ATOM | 6528 | CD1 | ILE | D | 80 | -7.262 | 73.215 | 42.290 | 1.00 37.45 | C |
| ATOM | 6529 | C | ILE | D | 80 | -8.691 | 76.674 | 45.629 | 1.00 39.31 | C |
| ATOM | 6530 | O | ILE | D | 80 | -8.383 | 76.466 | 46.800 | 1.00 38.34 | O |
| ATOM | 6531 | N | GLY | D | 81 | -8.637 | 77.880 | 45.072 | 1.00 40.08 | N |
| ATOM | 6532 | CA | GLY | D | 81 | -8.196 | 79.030 | 45.846 | 1.00 40.56 | C |
| ATOM | 6533 | C | GLY | D | 81 | -9.196 | 79.438 | 46.913 | 1.00 41.29 | C |
| ATOM | 6534 | O | GLY | D | 81 | -8.909 | 80.283 | 47.776 | 1.00 41.32 | O |
| ATOM | 6535 | N | LYS | D | 82 | -10.388 | 78.853 | 46.845 | 1.00 41.74 | N |
| ATOM | 6536 | CA | LYS | D | 82 | -11.442 | 79.145 | 47.817 | 1.00 41.81 | C |
| ATOM | 6537 | CB | LYS | D | 82 | -12.818 | 79.084 | 47.146 | 1.00 42.77 | C |
| ATOM | 6538 | CG | LYS | D | 82 | -13.992 | 79.261 | 48.111 | 1.00 44.45 | C |
| ATOM | 6539 | CD | LYS | D | 82 | -15.143 | 78.305 | 47.758 | 1.00 44.34 | C |
| ATOM | 6540 | CE | LYS | D | 82 | -16.261 | 78.347 | 48.796 | 1.00 43.54 | C |
| ATOM | 6541 | NZ | LYS | D | 82 | -17.436 | 77.503 | 48.393 | 1.00 42.42 | N |
| ATOM | 6542 | C | LYS | D | 82 | -11.354 | 78.106 | 48.928 | 1.00 41.10 | C |
| ATOM | 6543 | O | LYS | D | 82 | -11.396 | 78.446 | 50.111 | 1.00 40.75 | O |
| ATOM | 6544 | N | ASP | D | 83 | -11.233 | 76.836 | 48.548 | 1.00 40.71 | N |
| ATOM | 6545 | CA | ASP | D | 83 | -11.109 | 75.761 | 49.531 | 1.00 40.76 | C |
| ATOM | 6546 | CB | ASP | D | 83 | -11.256 | 74.397 | 48.856 | 1.00 40.99 | C |
| ATOM | 6547 | CG | ASP | D | 83 | -12.638 | 74.185 | 48.303 | 1.00 41.62 | C |
| ATOM | 6548 | OD1 | ASP | D | 83 | -13.527 | 75.008 | 48.638 | 1.00 41.52 | O |
| ATOM | 6549 | OD2 | ASP | D | 83 | -12.837 | 73.206 | 47.549 | 1.00 41.24 | O |
| ATOM | 6550 | C | ASP | D | 83 | -9.762 | 75.829 | 50.226 | 1.00 40.10 | C |
| ATOM | 6551 | O | ASP | D | 83 | -9.675 | 75.765 | 51.451 | 1.00 40.91 | O |
| ATOM | 6552 | N | VAL | D | 84 | -8.704 | 75.937 | 49.431 | 1.00 39.37 | N |
| ATOM | 6553 | CA | VAL | D | 84 | -7.344 | 76.027 | 49.959 | 1.00 38.03 | C |
| ATOM | 6554 | CB | VAL | D | 84 | -6.419 | 74.981 | 49.268 | 1.00 38.23 | C |
| ATOM | 6555 | CG1 | VAL | D | 84 | -5.168 | 74.737 | 50.104 | 1.00 37.83 | C |
| ATOM | 6556 | CG2 | VAL | D | 84 | -7.183 | 73.679 | 49.059 | 1.00 37.62 | C |
| ATOM | 6557 | C | VAL | D | 84 | -6.922 | 77.430 | 49.560 | 1.00 37.09 | C |
| ATOM | 6558 | O | VAL | D | 84 | -7.297 | 77.895 | 48.482 | 1.00 38.51 | O |
| ATOM | 6559 | N | GLY | D | 85 | -6.175 | 78.124 | 50.405 | 1.00 36.01 | N |
| ATOM | 6560 | CA | GLY | D | 85 | -5.769 | 79.475 | 50.038 | 1.00 35.75 | C |
| ATOM | 6561 | C | GLY | D | 85 | -4.846 | 79.502 | 48.828 | 1.00 35.01 | C |
| ATOM | 6562 | O | GLY | D | 85 | -4.945 | 78.654 | 47.938 | 1.00 34.79 | O |
| ATOM | 6563 | N | ASN | D | 86 | -3.940 | 80.474 | 48.797 | 1.00 34.38 | N |

FIGURE 9 (cont.)

| | | | | | | | | | | |
|---|---|---|---|---|---|---|---|---|---|---|
| ATOM | 6564 | CA | ASN | D | 86 | -2.978 | 80.614 | 47.705 | 1.00 33.84 | C |
| ATOM | 6565 | CB | ASN | D | 86 | -2.081 | 81.818 | 47.974 | 1.00 34.25 | C |
| ATOM | 6566 | CG | ASN | D | 86 | -2.822 | 83.125 | 47.855 | 1.00 34.55 | C |
| ATOM | 6567 | OD1 | ASN | D | 86 | -2.365 | 84.163 | 48.351 | 1.00 35.68 | O |
| ATOM | 6568 | ND2 | ASN | D | 86 | -3.966 | 83.093 | 47.177 | 1.00 34.41 | N |
| ATOM | 6569 | C | ASN | D | 86 | -2.111 | 79.367 | 47.536 | 1.00 33.39 | C |
| ATOM | 6570 | O | ASN | D | 86 | -1.991 | 78.553 | 48.467 | 1.00 32.46 | O |
| ATOM | 6571 | N | ILE | D | 87 | -1.508 | 79.208 | 46.352 | 1.00 32.63 | N |
| ATOM | 6572 | CA | ILE | D | 87 | -0.644 | 78.044 | 46.101 | 1.00 31.31 | C |
| ATOM | 6573 | CB | ILE | D | 87 | -1.194 | 77.170 | 44.981 | 1.00 31.33 | C |
| ATOM | 6574 | CG2 | ILE | D | 87 | -2.654 | 76.828 | 45.273 | 1.00 31.39 | C |
| ATOM | 6575 | CG1 | ILE | D | 87 | -1.056 | 77.903 | 43.648 | 1.00 30.36 | C |
| ATOM | 6576 | CD1 | ILE | D | 87 | -1.498 | 77.085 | 42.462 | 1.00 31.70 | C |
| ATOM | 6577 | C | ILE | D | 87 | 0.759 | 78.482 | 45.709 | 1.00 30.34 | C |
| ATOM | 6578 | O | ILE | D | 87 | 0.969 | 79.639 | 45.344 | 1.00 28.35 | O |
| ATOM | 6579 | N | ASP | D | 88 | 1.714 | 77.555 | 45.788 | 1.00 30.21 | N |
| ATOM | 6580 | CA | ASP | D | 88 | 3.099 | 77.872 | 45.435 | 1.00 29.68 | C |
| ATOM | 6581 | CB | ASP | D | 88 | 4.066 | 77.371 | 46.512 | 1.00 29.36 | C |
| ATOM | 6582 | CG | ASP | D | 88 | 3.634 | 77.756 | 47.899 | 1.00 29.41 | C |
| ATOM | 6583 | OD1 | ASP | D | 88 | 2.750 | 77.064 | 48.451 | 1.00 29.23 | O |
| ATOM | 6584 | OD2 | ASP | D | 88 | 4.167 | 78.753 | 48.438 | 1.00 30.76 | O |
| ATOM | 6585 | C | ASP | D | 88 | 3.503 | 77.278 | 44.090 | 1.00 28.17 | C |
| ATOM | 6586 | O | ASP | D | 88 | 4.565 | 77.601 | 43.564 | 1.00 27.57 | O |
| ATOM | 6587 | N | GLY | D | 89 | 2.669 | 76.403 | 43.537 | 1.00 26.88 | N |
| ATOM | 6588 | CA | GLY | D | 89 | 3.006 | 75.817 | 42.257 | 1.00 25.17 | C |
| ATOM | 6589 | C | GLY | D | 89 | 2.058 | 74.751 | 41.742 | 1.00 25.17 | C |
| ATOM | 6590 | O | GLY | D | 89 | 1.120 | 74.340 | 42.428 | 1.00 25.44 | O |
| ATOM | 6591 | N | VAL | D | 90 | 2.321 | 74.303 | 40.518 | 1.00 23.16 | N |
| ATOM | 6592 | CA | VAL | D | 90 | 1.518 | 73.288 | 39.868 | 1.00 22.64 | C |
| ATOM | 6593 | CB | VAL | D | 90 | 0.515 | 73.921 | 38.863 | 1.00 22.94 | C |
| ATOM | 6594 | CG1 | VAL | D | 90 | -0.341 | 72.837 | 38.235 | 1.00 20.91 | C |
| ATOM | 6595 | CG2 | VAL | D | 90 | -0.365 | 74.959 | 39.559 | 1.00 22.18 | C |
| ATOM | 6596 | C | VAL | D | 90 | 2.429 | 72.330 | 39.086 | 1.00 23.01 | C |
| ATOM | 6597 | O | VAL | D | 90 | 3.433 | 72.744 | 38.488 | 1.00 22.71 | O |
| ATOM | 6598 | N | TYR | D | 91 | 2.090 | 71.046 | 39.114 | 1.00 23.59 | N |
| ATOM | 6599 | CA | TYR | D | 91 | 2.847 | 70.049 | 38.364 | 1.00 24.61 | C |
| ATOM | 6600 | CB | TYR | D | 91 | 3.285 | 68.867 | 39.243 | 1.00 24.38 | C |
| ATOM | 6601 | CG | TYR | D | 91 | 4.210 | 67.930 | 38.488 | 1.00 25.36 | C |
| ATOM | 6602 | CD1 | TYR | D | 91 | 5.559 | 68.244 | 38.316 | 1.00 25.13 | C |
| ATOM | 6603 | CE1 | TYR | D | 91 | 6.379 | 67.479 | 37.485 | 1.00 25.80 | C |
| ATOM | 6604 | CD2 | TYR | D | 91 | 3.706 | 66.814 | 37.819 | 1.00 25.58 | C |
| ATOM | 6605 | CE2 | TYR | D | 91 | 4.513 | 66.041 | 36.982 | 1.00 25.86 | C |
| ATOM | 6606 | CZ | TYR | D | 91 | 5.848 | 66.381 | 36.814 | 1.00 26.62 | C |
| ATOM | 6607 | OH | TYR | D | 91 | 6.644 | 65.650 | 35.949 | 1.00 25.14 | O |
| ATOM | 6608 | C | TYR | D | 91 | 1.916 | 69.542 | 37.264 | 1.00 24.15 | C |
| ATOM | 6609 | O | TYR | D | 91 | 0.838 | 69.020 | 37.555 | 1.00 23.17 | O |
| ATOM | 6610 | N | HIS | D | 92 | 2.346 | 69.704 | 36.013 | 1.00 24.23 | N |
| ATOM | 6611 | CA | HIS | D | 92 | 1.588 | 69.294 | 34.828 | 1.00 22.78 | C |
| ATOM | 6612 | CB | HIS | D | 92 | 1.789 | 70.334 | 33.735 | 1.00 22.27 | C |
| ATOM | 6613 | CG | HIS | D | 92 | 1.009 | 70.068 | 32.487 | 1.00 25.03 | C |
| ATOM | 6614 | CD2 | HIS | D | 92 | 1.361 | 69.459 | 31.331 | 1.00 25.74 | C |
| ATOM | 6615 | ND1 | HIS | D | 92 | -0.305 | 70.455 | 32.333 | 1.00 24.71 | N |
| ATOM | 6616 | CE1 | HIS | D | 92 | -0.727 | 70.097 | 31.134 | 1.00 26.19 | C |
| ATOM | 6617 | NE2 | HIS | D | 92 | 0.264 | 69.490 | 30.506 | 1.00 26.88 | N |
| ATOM | 6618 | C | HIS | D | 92 | 2.071 | 67.927 | 34.338 | 1.00 22.98 | C |
| ATOM | 6619 | O | HIS | D | 92 | 3.245 | 67.744 | 34.023 | 1.00 22.56 | O |
| ATOM | 6620 | N | SER | D | 93 | 1.159 | 66.966 | 34.263 | 1.00 23.76 | N |
| ATOM | 6621 | CA | SER | D | 93 | 1.516 | 65.616 | 33.845 | 1.00 24.27 | C |
| ATOM | 6622 | CB | SER | D | 93 | 1.730 | 64.738 | 35.086 | 1.00 24.32 | C |
| ATOM | 6623 | OG | SER | D | 93 | 2.400 | 63.529 | 34.777 | 1.00 23.72 | O |
| ATOM | 6624 | C | SER | D | 93 | 0.370 | 65.083 | 33.005 | 1.00 25.37 | C |
| ATOM | 6625 | O | SER | D | 93 | -0.104 | 63.956 | 33.191 | 1.00 26.31 | O |
| ATOM | 6626 | N | ILE | D | 94 | -0.059 | 65.918 | 32.068 | 1.00 25.82 | N |
| ATOM | 6627 | CA | ILE | D | 94 | -1.165 | 65.606 | 31.186 | 1.00 25.86 | C |
| ATOM | 6628 | CB | ILE | D | 94 | -2.299 | 66.636 | 31.384 | 1.00 25.90 | C |

FIGURE 9 (cont.)

| | | | | | | | | | |
|---|---|---|---|---|---|---|---|---|---|
| ATOM | 6629 | CG2 | ILE D | 94 | -3.338 | 66.496 | 30.291 | 1.00 24.54 | C |
| ATOM | 6630 | CG1 | ILE D | 94 | -2.929 | 66.444 | 32.763 | 1.00 24.69 | C |
| ATOM | 6631 | CD1 | ILE D | 94 | -3.900 | 67.543 | 33.125 | 1.00 25.78 | C |
| ATOM | 6632 | C | ILE D | 94 | -0.749 | 65.606 | 29.719 | 1.00 26.19 | C |
| ATOM | 6633 | O | ILE D | 94 | -0.049 | 66.511 | 29.261 | 1.00 25.86 | O |
| ATOM | 6634 | N | ALA D | 95 | -1.200 | 64.579 | 29.001 | 1.00 25.93 | N |
| ATOM | 6635 | CA | ALA D | 95 | -0.931 | 64.412 | 27.584 | 1.00 25.35 | C |
| ATOM | 6636 | CB | ALA D | 95 | 0.464 | 63.847 | 27.382 | 1.00 25.13 | C |
| ATOM | 6637 | C | ALA D | 95 | -1.971 | 63.445 | 27.027 | 1.00 26.08 | C |
| ATOM | 6638 | O | ALA D | 95 | -2.520 | 62.626 | 27.757 | 1.00 25.65 | O |
| ATOM | 6639 | N | PHE D | 96 | -2.266 | 63.550 | 25.740 | 1.00 27.61 | N |
| ATOM | 6640 | CA | PHE D | 96 | -3.230 | 62.635 | 25.139 | 1.00 27.84 | C |
| ATOM | 6641 | CB | PHE D | 96 | -4.643 | 62.863 | 25.685 | 1.00 28.91 | C |
| ATOM | 6642 | CG | PHE D | 96 | -5.643 | 61.857 | 25.168 | 1.00 30.34 | C |
| ATOM | 6643 | CD1 | PHE D | 96 | -5.715 | 60.575 | 25.726 | 1.00 30.48 | C |
| ATOM | 6644 | CD2 | PHE D | 96 | -6.440 | 62.153 | 24.061 | 1.00 29.66 | C |
| ATOM | 6645 | CE1 | PHE D | 96 | -6.566 | 59.599 | 25.179 | 1.00 31.81 | C |
| ATOM | 6646 | CE2 | PHE D | 96 | -7.290 | 61.190 | 23.509 | 1.00 30.33 | C |
| ATOM | 6647 | CZ | PHE D | 96 | -7.356 | 59.911 | 24.065 | 1.00 29.68 | C |
| ATOM | 6648 | C | PHE D | 96 | -3.286 | 62.733 | 23.622 | 1.00 28.13 | C |
| ATOM | 6649 | O | PHE D | 96 | -3.260 | 63.825 | 23.049 | 1.00 27.50 | O |
| ATOM | 6650 | N | ALA D | 97 | -3.391 | 61.575 | 22.980 | 1.00 29.26 | N |
| ATOM | 6651 | CA | ALA D | 97 | -3.468 | 61.496 | 21.528 | 1.00 29.41 | C |
| ATOM | 6652 | CB | ALA D | 97 | -2.056 | 61.467 | 20.940 | 1.00 30.23 | C |
| ATOM | 6653 | C | ALA D | 97 | -4.236 | 60.251 | 21.092 | 1.00 29.81 | C |
| ATOM | 6654 | O | ALA D | 97 | -4.120 | 59.190 | 21.709 | 1.00 29.21 | O |
| ATOM | 6655 | N | ASN D | 98 | -5.023 | 60.373 | 20.029 | 1.00 31.24 | N |
| ATOM | 6656 | CA | ASN D | 98 | -5.759 | 59.213 | 19.536 | 1.00 31.79 | C |
| ATOM | 6657 | CB | ASN D | 98 | -6.540 | 59.569 | 18.272 | 1.00 30.74 | C |
| ATOM | 6658 | CG | ASN D | 98 | -7.646 | 60.570 | 18.548 | 1.00 29.20 | C |
| ATOM | 6659 | OD1 | ASN D | 98 | -8.361 | 60.441 | 19.532 | 1.00 29.44 | O |
| ATOM | 6660 | ND2 | ASN D | 98 | -7.792 | 61.567 | 17.684 | 1.00 28.53 | N |
| ATOM | 6661 | C | ASN D | 98 | -4.729 | 58.135 | 19.238 | 1.00 33.24 | C |
| ATOM | 6662 | O | ASN D | 98 | -3.748 | 58.380 | 18.530 | 1.00 33.64 | O |
| ATOM | 6663 | N | MET D | 99 | -4.949 | 56.945 | 19.790 | 1.00 34.03 | N |
| ATOM | 6664 | CA | MET D | 99 | -4.023 | 55.833 | 19.604 | 1.00 34.66 | C |
| ATOM | 6665 | CB | MET D | 99 | -4.586 | 54.569 | 20.278 | 1.00 35.65 | C |
| ATOM | 6666 | CG | MET D | 99 | -3.602 | 53.395 | 20.386 | 1.00 38.66 | C |
| ATOM | 6667 | SD | MET D | 99 | -2.486 | 53.458 | 21.835 | 1.00 42.13 | S |
| ATOM | 6668 | CE | MET D | 99 | -1.102 | 54.439 | 21.197 | 1.00 40.91 | C |
| ATOM | 6669 | C | MET D | 99 | -3.730 | 55.567 | 18.124 | 1.00 34.20 | C |
| ATOM | 6670 | O | MET D | 99 | -2.611 | 55.198 | 17.762 | 1.00 32.91 | O |
| ATOM | 6671 | N | GLU D | 100 | -4.723 | 55.775 | 17.262 | 1.00 34.34 | N |
| ATOM | 6672 | CA | GLU D | 100 | -4.532 | 55.515 | 15.838 | 1.00 33.98 | C |
| ATOM | 6673 | CB | GLU D | 100 | -5.788 | 55.920 | 15.040 | 1.00 36.44 | C |
| ATOM | 6674 | CG | GLU D | 100 | -5.969 | 57.435 | 14.872 | 1.00 38.64 | C |
| ATOM | 6675 | CD | GLU D | 100 | -7.178 | 57.805 | 14.009 | 1.00 40.62 | C |
| ATOM | 6676 | OE1 | GLU D | 100 | -7.392 | 57.148 | 12.961 | 1.00 40.92 | O |
| ATOM | 6677 | OE2 | GLU D | 100 | -7.905 | 58.770 | 14.370 | 1.00 41.25 | O |
| ATOM | 6678 | C | GLU D | 100 | -3.317 | 56.269 | 15.297 | 1.00 32.72 | C |
| ATOM | 6679 | O | GLU D | 100 | -2.612 | 55.769 | 14.416 | 1.00 32.33 | O |
| ATOM | 6680 | N | ASP D | 101 | -3.072 | 57.466 | 15.832 | 1.00 31.17 | N |
| ATOM | 6681 | CA | ASP D | 101 | -1.962 | 58.298 | 15.374 | 1.00 30.26 | C |
| ATOM | 6682 | CB | ASP D | 101 | -2.288 | 59.777 | 15.607 | 1.00 31.41 | C |
| ATOM | 6683 | CG | ASP D | 101 | -3.574 | 60.222 | 14.916 | 1.00 31.95 | C |
| ATOM | 6684 | OD1 | ASP D | 101 | -3.820 | 59.807 | 13.758 | 1.00 32.35 | O |
| ATOM | 6685 | OD2 | ASP D | 101 | -4.329 | 61.010 | 15.532 | 1.00 31.59 | O |
| ATOM | 6686 | C | ASP D | 101 | -0.594 | 57.984 | 16.002 | 1.00 29.52 | C |
| ATOM | 6687 | O | ASP D | 101 | 0.410 | 58.624 | 15.669 | 1.00 30.01 | O |
| ATOM | 6688 | N | LEU D | 102 | -0.549 | 57.021 | 16.915 | 1.00 27.18 | N |
| ATOM | 6689 | CA | LEU D | 102 | 0.707 | 56.653 | 17.557 | 1.00 26.38 | C |
| ATOM | 6690 | CB | LEU D | 102 | 0.515 | 56.518 | 19.069 | 1.00 26.23 | C |
| ATOM | 6691 | CG | LEU D | 102 | 0.258 | 57.824 | 19.850 | 1.00 26.30 | C |
| ATOM | 6692 | CD1 | LEU D | 102 | -0.900 | 58.590 | 19.231 | 1.00 26.87 | C |
| ATOM | 6693 | CD2 | LEU D | 102 | -0.043 | 57.505 | 21.292 | 1.00 23.77 | C |

FIGURE 9 (cont.)

```
ATOM   6694  C    LEU D 102       1.156  55.333  16.958  1.00 26.65           C
ATOM   6695  O    LEU D 102       1.764  54.495  17.625  1.00 24.25           O
ATOM   6696  N    ARG D 103       0.833  55.172  15.677  1.00 27.61           N
ATOM   6697  CA   ARG D 103       1.157  53.976  14.909  1.00 28.44           C
ATOM   6698  CB   ARG D 103       0.042  52.927  15.040  1.00 30.35           C
ATOM   6699  CG   ARG D 103      -0.638  52.836  16.400  1.00 34.20           C
ATOM   6700  CD   ARG D 103       0.134  51.959  17.390  1.00 37.14           C
ATOM   6701  NE   ARG D 103      -0.728  51.556  18.504  1.00 38.71           N
ATOM   6702  CZ   ARG D 103      -0.645  50.380  19.128  1.00 39.49           C
ATOM   6703  NH1  ARG D 103       0.264  49.485  18.758  1.00 39.39           N
ATOM   6704  NH2  ARG D 103      -1.491  50.083  20.106  1.00 38.57           N
ATOM   6705  C    ARG D 103       1.200  54.431  13.464  1.00 26.85           C
ATOM   6706  O    ARG D 103       0.671  55.493  13.126  1.00 27.25           O
ATOM   6707  N    GLY D 104       1.811  53.627  12.604  1.00 26.27           N
ATOM   6708  CA   GLY D 104       1.866  53.977  11.195  1.00 25.40           C
ATOM   6709  C    GLY D 104       2.677  55.208  10.844  1.00 24.71           C
ATOM   6710  O    GLY D 104       3.572  55.598  11.586  1.00 25.74           O
ATOM   6711  N    ARG D 105       2.356  55.812   9.700  1.00 24.08           N
ATOM   6712  CA   ARG D 105       3.045  56.997   9.201  1.00 22.93           C
ATOM   6713  CB   ARG D 105       2.996  57.017   7.674  1.00 23.86           C
ATOM   6714  CG   ARG D 105       3.333  55.692   7.038  1.00 25.17           C
ATOM   6715  CD   ARG D 105       3.586  55.851   5.552  1.00 27.87           C
ATOM   6716  NE   ARG D 105       4.732  56.722   5.289  1.00 29.37           N
ATOM   6717  CZ   ARG D 105       5.299  56.862   4.095  1.00 30.69           C
ATOM   6718  NH1  ARG D 105       4.828  56.189   3.052  1.00 30.27           N
ATOM   6719  NH2  ARG D 105       6.344  57.675   3.946  1.00 32.11           N
ATOM   6720  C    ARG D 105       2.475  58.314   9.727  1.00 23.20           C
ATOM   6721  O    ARG D 105       1.254  58.494   9.815  1.00 23.81           O
ATOM   6722  N    PHE D 106       3.371  59.241  10.054  1.00 21.38           N
ATOM   6723  CA   PHE D 106       2.985  60.541  10.567  1.00 20.41           C
ATOM   6724  CB   PHE D 106       4.200  61.204  11.235  1.00 20.04           C
ATOM   6725  CG   PHE D 106       4.002  62.663  11.536  1.00 17.85           C
ATOM   6726  CD1  PHE D 106       3.073  63.070  12.487  1.00 16.92           C
ATOM   6727  CD2  PHE D 106       4.688  63.635  10.805  1.00 18.25           C
ATOM   6728  CE1  PHE D 106       2.817  64.433  12.706  1.00 19.31           C
ATOM   6729  CE2  PHE D 106       4.444  65.003  11.014  1.00 18.67           C
ATOM   6730  CZ   PHE D 106       3.508  65.402  11.961  1.00 18.95           C
ATOM   6731  C    PHE D 106       2.392  61.494   9.510  1.00 21.61           C
ATOM   6732  O    PHE D 106       1.551  62.341   9.837  1.00 20.48           O
ATOM   6733  N    SER D 107       2.819  61.362   8.254  1.00 22.19           N
ATOM   6734  CA   SER D 107       2.336  62.250   7.193  1.00 23.70           C
ATOM   6735  CB   SER D 107       3.070  61.957   5.876  1.00 22.04           C
ATOM   6736  OG   SER D 107       3.101  60.573   5.580  1.00 19.91           O
ATOM   6737  C    SER D 107       0.831  62.189   6.963  1.00 25.71           C
ATOM   6738  O    SER D 107       0.228  63.112   6.417  1.00 26.91           O
ATOM   6739  N    GLU D 108       0.226  61.099   7.396  1.00 28.39           N
ATOM   6740  CA   GLU D 108      -1.200  60.897   7.228  1.00 30.39           C
ATOM   6741  CB   GLU D 108      -1.436  59.414   6.926  1.00 32.30           C
ATOM   6742  CG   GLU D 108      -2.860  58.934   7.124  1.00 37.18           C
ATOM   6743  CD   GLU D 108      -3.037  57.504   6.676  1.00 39.18           C
ATOM   6744  OE1  GLU D 108      -4.048  56.881   7.078  1.00 41.45           O
ATOM   6745  OE2  GLU D 108      -2.166  57.014   5.920  1.00 39.89           O
ATOM   6746  C    GLU D 108      -2.015  61.349   8.443  1.00 29.96           C
ATOM   6747  O    GLU D 108      -3.211  61.099   8.526  1.00 30.99           O
ATOM   6748  N    THR D 109      -1.374  62.018   9.391  1.00 29.10           N
ATOM   6749  CA   THR D 109      -2.092  62.485  10.572  1.00 28.12           C
ATOM   6750  CB   THR D 109      -1.163  63.299  11.500  1.00 27.84           C
ATOM   6751  OG1  THR D 109       0.065  62.582  11.681  1.00 28.21           O
ATOM   6752  CG2  THR D 109      -1.815  63.494  12.872  1.00 26.93           C
ATOM   6753  C    THR D 109      -3.266  63.360  10.125  1.00 27.20           C
ATOM   6754  O    THR D 109      -3.186  64.043   9.107  1.00 26.86           O
ATOM   6755  N    SER D 110      -4.355  63.337  10.884  1.00 26.66           N
ATOM   6756  CA   SER D 110      -5.530  64.114  10.532  1.00 27.40           C
ATOM   6757  CB   SER D 110      -6.805  63.365  10.936  1.00 28.05           C
ATOM   6758  OG   SER D 110      -6.865  63.154  12.348  1.00 30.41           O
```

FIGURE 9 (cont.)

| ATOM | 6759 | C | SER | D | 110 | -5.521 | 65.473 | 11.198 | 1.00 | 27.15 | C |
|------|------|------|-----|---|-----|--------|--------|--------|------|-------|---|
| ATOM | 6760 | O | SER | D | 110 | -4.989 | 65.636 | 12.297 | 1.00 | 27.64 | O |
| ATOM | 6761 | N | ARG | D | 111 | -6.121 | 66.448 | 10.528 | 1.00 | 27.11 | N |
| ATOM | 6762 | CA | ARG | D | 111 | -6.202 | 67.795 | 11.064 | 1.00 | 26.95 | C |
| ATOM | 6763 | CB | ARG | D | 111 | -7.063 | 68.675 | 10.148 | 1.00 | 25.30 | C |
| ATOM | 6764 | CG | ARG | D | 111 | -6.923 | 70.168 | 10.379 | 1.00 | 25.37 | C |
| ATOM | 6765 | CD | ARG | D | 111 | -7.898 | 70.961 | 9.525 | 1.00 | 20.97 | C |
| ATOM | 6766 | NE | ARG | D | 111 | -7.563 | 70.945 | 8.103 | 1.00 | 21.27 | N |
| ATOM | 6767 | CZ | ARG | D | 111 | -6.649 | 71.727 | 7.527 | 1.00 | 21.41 | C |
| ATOM | 6768 | NH1 | ARG | D | 111 | -5.963 | 72.601 | 8.251 | 1.00 | 21.67 | N |
| ATOM | 6769 | NH2 | ARG | D | 111 | -6.426 | 71.646 | 6.219 | 1.00 | 19.96 | N |
| ATOM | 6770 | C | ARG | D | 111 | -6.827 | 67.697 | 12.460 | 1.00 | 27.58 | C |
| ATOM | 6771 | O | ARG | D | 111 | -6.461 | 68.451 | 13.364 | 1.00 | 27.14 | O |
| ATOM | 6772 | N | GLU | D | 112 | -7.747 | 66.745 | 12.634 | 1.00 | 28.03 | N |
| ATOM | 6773 | CA | GLU | D | 112 | -8.428 | 66.548 | 13.915 | 1.00 | 28.52 | C |
| ATOM | 6774 | CB | GLU | D | 112 | -9.694 | 65.696 | 13.737 | 1.00 | 30.51 | C |
| ATOM | 6775 | CG | GLU | D | 112 | -10.378 | 65.358 | 15.065 | 1.00 | 34.57 | C |
| ATOM | 6776 | CD | GLU | D | 112 | -11.542 | 64.380 | 14.924 | 1.00 | 37.25 | C |
| ATOM | 6777 | OE1 | GLU | D | 112 | -11.346 | 63.280 | 14.337 | 1.00 | 38.72 | O |
| ATOM | 6778 | OE2 | GLU | D | 112 | -12.655 | 64.704 | 15.413 | 1.00 | 38.43 | O |
| ATOM | 6779 | C | GLU | D | 112 | -7.519 | 65.878 | 14.931 | 1.00 | 28.00 | C |
| ATOM | 6780 | O | GLU | D | 112 | -7.500 | 66.256 | 16.104 | 1.00 | 27.97 | O |
| ATOM | 6781 | N | GLY | D | 113 | -6.782 | 64.866 | 14.483 | 1.00 | 28.29 | N |
| ATOM | 6782 | CA | GLY | D | 113 | -5.870 | 64.174 | 15.375 | 1.00 | 28.58 | C |
| ATOM | 6783 | C | GLY | D | 113 | -4.823 | 65.150 | 15.868 | 1.00 | 28.98 | C |
| ATOM | 6784 | O | GLY | D | 113 | -4.629 | 65.309 | 17.069 | 1.00 | 29.31 | O |
| ATOM | 6785 | N | PHE | D | 114 | -4.162 | 65.815 | 14.923 | 1.00 | 29.47 | N |
| ATOM | 6786 | CA | PHE | D | 114 | -3.115 | 66.799 | 15.209 | 1.00 | 29.63 | C |
| ATOM | 6787 | CB | PHE | D | 114 | -2.713 | 67.504 | 13.903 | 1.00 | 29.02 | C |
| ATOM | 6788 | CG | PHE | D | 114 | -1.608 | 68.532 | 14.055 | 1.00 | 29.37 | C |
| ATOM | 6789 | CD1 | PHE | D | 114 | -1.828 | 69.734 | 14.732 | 1.00 | 28.27 | C |
| ATOM | 6790 | CD2 | PHE | D | 114 | -0.358 | 68.314 | 13.472 | 1.00 | 29.24 | C |
| ATOM | 6791 | CE1 | PHE | D | 114 | -0.825 | 70.704 | 14.823 | 1.00 | 27.75 | C |
| ATOM | 6792 | CE2 | PHE | D | 114 | 0.658 | 69.281 | 13.556 | 1.00 | 29.04 | C |
| ATOM | 6793 | CZ | PHE | D | 114 | 0.421 | 70.480 | 14.233 | 1.00 | 28.52 | C |
| ATOM | 6794 | C | PHE | D | 114 | -3.605 | 67.829 | 16.219 | 1.00 | 30.42 | C |
| ATOM | 6795 | O | PHE | D | 114 | -3.063 | 67.950 | 17.331 | 1.00 | 31.39 | O |
| ATOM | 6796 | N | LEU | D | 115 | -4.627 | 68.578 | 15.819 | 1.00 | 28.70 | N |
| ATOM | 6797 | CA | LEU | D | 115 | -5.182 | 69.617 | 16.665 | 1.00 | 28.59 | C |
| ATOM | 6798 | CB | LEU | D | 115 | -6.408 | 70.242 | 15.988 | 1.00 | 29.30 | C |
| ATOM | 6799 | CG | LEU | D | 115 | -6.071 | 71.213 | 14.852 | 1.00 | 30.62 | C |
| ATOM | 6800 | CD1 | LEU | D | 115 | -7.355 | 71.770 | 14.227 | 1.00 | 30.96 | C |
| ATOM | 6801 | CD2 | LEU | D | 115 | -5.217 | 72.348 | 15.410 | 1.00 | 30.95 | C |
| ATOM | 6802 | C | LEU | D | 115 | -5.540 | 69.124 | 18.058 | 1.00 | 27.28 | C |
| ATOM | 6803 | O | LEU | D | 115 | -5.335 | 69.837 | 19.036 | 1.00 | 28.14 | O |
| ATOM | 6804 | N | LEU | D | 116 | -6.072 | 67.913 | 18.158 | 1.00 | 25.77 | N |
| ATOM | 6805 | CA | LEU | D | 116 | -6.436 | 67.372 | 19.462 | 1.00 | 25.46 | C |
| ATOM | 6806 | CB | LEU | D | 116 | -7.144 | 66.025 | 19.308 | 1.00 | 25.12 | C |
| ATOM | 6807 | CG | LEU | D | 116 | -7.366 | 65.280 | 20.631 | 1.00 | 24.09 | C |
| ATOM | 6808 | CD1 | LEU | D | 116 | -8.381 | 66.038 | 21.469 | 1.00 | 23.59 | C |
| ATOM | 6809 | CD2 | LEU | D | 116 | -7.843 | 63.862 | 20.364 | 1.00 | 23.58 | C |
| ATOM | 6810 | C | LEU | D | 116 | -5.223 | 67.179 | 20.378 | 1.00 | 26.30 | C |
| ATOM | 6811 | O | LEU | D | 116 | -5.320 | 67.366 | 21.593 | 1.00 | 26.45 | O |
| ATOM | 6812 | N | ALA | D | 117 | -4.084 | 66.798 | 19.805 | 1.00 | 26.37 | N |
| ATOM | 6813 | CA | ALA | D | 117 | -2.886 | 66.566 | 20.612 | 1.00 | 27.12 | C |
| ATOM | 6814 | CB | ALA | D | 117 | -1.826 | 65.842 | 19.770 | 1.00 | 26.21 | C |
| ATOM | 6815 | C | ALA | D | 117 | -2.316 | 67.865 | 21.196 | 1.00 | 27.62 | C |
| ATOM | 6816 | O | ALA | D | 117 | -1.782 | 67.879 | 22.313 | 1.00 | 27.61 | O |
| ATOM | 6817 | N | GLN | D | 118 | -2.450 | 68.950 | 20.441 | 1.00 | 27.42 | N |
| ATOM | 6818 | CA | GLN | D | 118 | -1.957 | 70.267 | 20.841 | 1.00 | 28.18 | C |
| ATOM | 6819 | CB | GLN | D | 118 | -1.921 | 71.180 | 19.607 | 1.00 | 27.06 | C |
| ATOM | 6820 | CG | GLN | D | 118 | -0.817 | 70.874 | 18.596 | 1.00 | 25.60 | C |
| ATOM | 6821 | CD | GLN | D | 118 | 0.545 | 71.390 | 19.059 | 1.00 | 25.87 | C |
| ATOM | 6822 | OE1 | GLN | D | 118 | 0.623 | 72.365 | 19.807 | 1.00 | 24.55 | O |
| ATOM | 6823 | NE2 | GLN | D | 118 | 1.620 | 70.748 | 18.601 | 1.00 | 25.73 | N |

FIGURE 9 (cont.)

```
ATOM   6824  C    GLN D 118      -2.829  70.921  21.923  1.00 28.55           C
ATOM   6825  O    GLN D 118      -2.357  71.733  22.728  1.00 30.16           O
ATOM   6826  N    ASP D 119      -4.106  70.569  21.923  1.00 28.53           N
ATOM   6827  CA   ASP D 119      -5.081  71.117  22.859  1.00 27.55           C
ATOM   6828  CB   ASP D 119      -6.491  70.765  22.342  1.00 28.21           C
ATOM   6829  CG   ASP D 119      -7.607  71.373  23.173  1.00 28.18           C
ATOM   6830  OD1  ASP D 119      -7.514  72.567  23.546  1.00 28.43           O
ATOM   6831  OD2  ASP D 119      -8.598  70.659  23.435  1.00 28.83           O
ATOM   6832  C    ASP D 119      -4.870  70.580  24.272  1.00 27.62           C
ATOM   6833  O    ASP D 119      -4.792  71.344  25.235  1.00 25.46           O
ATOM   6834  N    ILE D 120      -4.764  69.258  24.381  1.00 27.88           N
ATOM   6835  CA   ILE D 120      -4.590  68.587  25.663  1.00 28.60           C
ATOM   6836  CB   ILE D 120      -5.144  67.147  25.600  1.00 29.54           C
ATOM   6837  CG2  ILE D 120      -4.820  66.398  26.894  1.00 29.84           C
ATOM   6838  CG1  ILE D 120      -6.656  67.181  25.352  1.00 30.12           C
ATOM   6839  CD1  ILE D 120      -7.281  65.813  25.181  1.00 31.57           C
ATOM   6840  C    ILE D 120      -3.146  68.504  26.150  1.00 29.08           C
ATOM   6841  O    ILE D 120      -2.879  68.615  27.358  1.00 29.57           O
ATOM   6842  N    SER D 121      -2.214  68.310  25.221  1.00 28.50           N
ATOM   6843  CA   SER D 121      -0.814  68.172  25.598  1.00 28.23           C
ATOM   6844  CB   SER D 121      -0.149  67.153  24.677  1.00 28.88           C
ATOM   6845  OG   SER D 121      -1.002  66.033  24.512  1.00 28.35           O
ATOM   6846  C    SER D 121       0.016  69.448  25.629  1.00 27.38           C
ATOM   6847  O    SER D 121       1.131  69.440  26.147  1.00 27.79           O
ATOM   6848  N    SER D 122      -0.510  70.542  25.097  1.00 25.79           N
ATOM   6849  CA   SER D 122       0.258  71.784  25.096  1.00 24.72           C
ATOM   6850  CB   SER D 122       0.837  72.026  23.706  1.00 23.70           C
ATOM   6851  OG   SER D 122       1.664  73.173  23.704  1.00 24.48           O
ATOM   6852  C    SER D 122      -0.504  73.031  25.552  1.00 25.65           C
ATOM   6853  O    SER D 122      -0.032  73.773  26.429  1.00 25.61           O
ATOM   6854  N    TYR D 123      -1.676  73.275  24.967  1.00 24.78           N
ATOM   6855  CA   TYR D 123      -2.446  74.457  25.341  1.00 23.93           C
ATOM   6856  CB   TYR D 123      -3.666  74.650  24.429  1.00 23.86           C
ATOM   6857  CG   TYR D 123      -4.502  75.820  24.873  1.00 23.80           C
ATOM   6858  CD1  TYR D 123      -4.078  77.123  24.636  1.00 24.83           C
ATOM   6859  CE1  TYR D 123      -4.765  78.210  25.162  1.00 25.28           C
ATOM   6860  CD2  TYR D 123      -5.650  75.632  25.641  1.00 23.77           C
ATOM   6861  CE2  TYR D 123      -6.344  76.708  26.171  1.00 23.44           C
ATOM   6862  CZ   TYR D 123      -5.894  77.993  25.929  1.00 24.73           C
ATOM   6863  OH   TYR D 123      -6.559  79.074  26.457  1.00 25.79           O
ATOM   6864  C    TYR D 123      -2.909  74.367  26.787  1.00 23.79           C
ATOM   6865  O    TYR D 123      -3.093  75.389  27.448  1.00 23.83           O
ATOM   6866  N    SER D 124      -3.093  73.146  27.282  1.00 24.20           N
ATOM   6867  CA   SER D 124      -3.528  72.951  28.666  1.00 24.88           C
ATOM   6868  CB   SER D 124      -3.619  71.459  28.998  1.00 24.23           C
ATOM   6869  OG   SER D 124      -2.443  70.774  28.614  1.00 22.59           O
ATOM   6870  C    SER D 124      -2.581  73.643  29.641  1.00 25.14           C
ATOM   6871  O    SER D 124      -3.021  74.244  30.627  1.00 26.54           O
ATOM   6872  N    LEU D 125      -1.282  73.575  29.370  1.00 24.64           N
ATOM   6873  CA   LEU D 125      -0.307  74.224  30.245  1.00 23.83           C
ATOM   6874  CB   LEU D 125       1.118  73.958  29.746  1.00 24.07           C
ATOM   6875  CG   LEU D 125       2.215  74.842  30.350  1.00 24.59           C
ATOM   6876  CD1  LEU D 125       2.157  74.756  31.865  1.00 23.95           C
ATOM   6877  CD2  LEU D 125       3.590  74.402  29.833  1.00 25.35           C
ATOM   6878  C    LEU D 125      -0.555  75.729  30.314  1.00 23.17           C
ATOM   6879  O    LEU D 125      -0.473  76.338  31.382  1.00 22.77           O
ATOM   6880  N    THR D 126      -0.869  76.317  29.165  1.00 23.24           N
ATOM   6881  CA   THR D 126      -1.125  77.750  29.064  1.00 24.46           C
ATOM   6882  CB   THR D 126      -1.321  78.186  27.618  1.00 24.60           C
ATOM   6883  OG1  THR D 126      -0.153  77.876  26.863  1.00 27.86           O
ATOM   6884  CG2  THR D 126      -1.574  79.684  27.556  1.00 25.40           C
ATOM   6885  C    THR D 126      -2.357  78.224  29.822  1.00 24.45           C
ATOM   6886  O    THR D 126      -2.342  79.300  30.430  1.00 24.28           O
ATOM   6887  N    ILE D 127      -3.431  77.445  29.778  1.00 23.69           N
ATOM   6888  CA   ILE D 127      -4.623  77.875  30.480  1.00 24.90           C
```

FIGURE 9 (cont.)

| | | | | | | | | | |
|---|---|---|---|---|---|---|---|---|---|
| ATOM | 6889 | CB | ILE | D | 127 | -5.907 | 77.183 | 29.928 | 1.00 25.31 | C |
| ATOM | 6890 | CG2 | ILE | D | 127 | -5.859 | 75.686 | 30.162 | 1.00 24.39 | C |
| ATOM | 6891 | CG1 | ILE | D | 127 | -7.140 | 77.821 | 30.582 | 1.00 26.03 | C |
| ATOM | 6892 | CD1 | ILE | D | 127 | -8.474 | 77.315 | 30.044 | 1.00 27.32 | C |
| ATOM | 6893 | C | ILE | D | 127 | -4.497 | 77.682 | 31.994 | 1.00 25.16 | C |
| ATOM | 6894 | O | ILE | D | 127 | -4.880 | 78.567 | 32.755 | 1.00 27.05 | O |
| ATOM | 6895 | N | VAL | D | 128 | -3.933 | 76.570 | 32.457 | 1.00 26.39 | N |
| ATOM | 6896 | CA | VAL | D | 128 | -3.818 | 76.409 | 33.903 | 1.00 26.87 | C |
| ATOM | 6897 | CB | VAL | D | 128 | -3.466 | 74.933 | 34.339 | 1.00 26.30 | C |
| ATOM | 6898 | CG1 | VAL | D | 128 | -3.835 | 73.948 | 33.236 | 1.00 25.00 | C |
| ATOM | 6899 | CG2 | VAL | D | 128 | -2.013 | 74.813 | 34.751 | 1.00 24.92 | C |
| ATOM | 6900 | C | VAL | D | 128 | -2.795 | 77.398 | 34.480 | 1.00 27.74 | C |
| ATOM | 6901 | O | VAL | D | 128 | -2.881 | 77.764 | 35.654 | 1.00 27.58 | O |
| ATOM | 6902 | N | ALA | D | 129 | -1.843 | 77.845 | 33.659 | 1.00 28.00 | N |
| ATOM | 6903 | CA | ALA | D | 129 | -0.833 | 78.806 | 34.128 | 1.00 28.81 | C |
| ATOM | 6904 | CB | ALA | D | 129 | 0.280 | 78.970 | 33.087 | 1.00 26.72 | C |
| ATOM | 6905 | C | ALA | D | 129 | -1.497 | 80.151 | 34.375 | 1.00 29.79 | C |
| ATOM | 6906 | O | ALA | D | 129 | -1.141 | 80.875 | 35.316 | 1.00 31.32 | O |
| ATOM | 6907 | N | HIS | D | 130 | -2.454 | 80.487 | 33.512 | 1.00 31.13 | N |
| ATOM | 6908 | CA | HIS | D | 130 | -3.185 | 81.751 | 33.603 | 1.00 32.06 | C |
| ATOM | 6909 | CB | HIS | D | 130 | -4.034 | 81.950 | 32.345 | 1.00 33.18 | C |
| ATOM | 6910 | CG | HIS | D | 130 | -4.741 | 83.265 | 32.296 | 1.00 34.70 | C |
| ATOM | 6911 | CD2 | HIS | D | 130 | -4.346 | 84.473 | 31.823 | 1.00 35.55 | C |
| ATOM | 6912 | ND1 | HIS | D | 130 | -5.999 | 83.456 | 32.831 | 1.00 36.41 | N |
| ATOM | 6913 | CE1 | HIS | D | 130 | -6.346 | 84.726 | 32.693 | 1.00 36.27 | C |
| ATOM | 6914 | NE2 | HIS | D | 130 | -5.360 | 85.364 | 32.085 | 1.00 36.01 | N |
| ATOM | 6915 | C | HIS | D | 130 | -4.088 | 81.746 | 34.825 | 1.00 32.61 | C |
| ATOM | 6916 | O | HIS | D | 130 | -4.257 | 82.769 | 35.504 | 1.00 31.40 | O |
| ATOM | 6917 | N | GLU | D | 131 | -4.674 | 80.582 | 35.087 | 1.00 32.67 | N |
| ATOM | 6918 | CA | GLU | D | 131 | -5.567 | 80.399 | 36.217 | 1.00 33.65 | C |
| ATOM | 6919 | CB | GLU | D | 131 | -6.468 | 79.195 | 35.961 | 1.00 34.74 | C |
| ATOM | 6920 | CG | GLU | D | 131 | -7.490 | 79.440 | 34.856 | 1.00 37.15 | C |
| ATOM | 6921 | CD | GLU | D | 131 | -8.368 | 80.643 | 35.158 | 1.00 38.67 | C |
| ATOM | 6922 | OE1 | GLU | D | 131 | -8.732 | 80.817 | 36.355 | 1.00 40.79 | O |
| ATOM | 6923 | OE2 | GLU | D | 131 | -8.696 | 81.403 | 34.210 | 1.00 37.82 | O |
| ATOM | 6924 | C | GLU | D | 131 | -4.797 | 80.191 | 37.513 | 1.00 33.69 | C |
| ATOM | 6925 | O | GLU | D | 131 | -5.298 | 80.476 | 38.600 | 1.00 35.09 | O |
| ATOM | 6926 | N | ALA | D | 132 | -3.572 | 79.696 | 37.403 | 1.00 32.99 | N |
| ATOM | 6927 | CA | ALA | D | 132 | -2.763 | 79.448 | 38.584 | 1.00 32.18 | C |
| ATOM | 6928 | CB | ALA | D | 132 | -1.724 | 78.357 | 38.290 | 1.00 31.90 | C |
| ATOM | 6929 | C | ALA | D | 132 | -2.070 | 80.710 | 39.091 | 1.00 31.71 | C |
| ATOM | 6930 | O | ALA | D | 132 | -1.678 | 80.766 | 40.249 | 1.00 31.31 | O |
| ATOM | 6931 | N | LYS | D | 133 | -1.908 | 81.713 | 38.233 | 1.00 31.87 | N |
| ATOM | 6932 | CA | LYS | D | 133 | -1.245 | 82.956 | 38.649 | 1.00 33.06 | C |
| ATOM | 6933 | CB | LYS | D | 133 | -0.930 | 83.841 | 37.436 | 1.00 33.14 | C |
| ATOM | 6934 | CG | LYS | D | 133 | -0.217 | 85.157 | 37.789 | 1.00 34.58 | C |
| ATOM | 6935 | CD | LYS | D | 133 | -0.909 | 86.382 | 37.170 | 1.00 36.11 | C |
| ATOM | 6936 | CE | LYS | D | 133 | -2.245 | 86.685 | 37.877 | 1.00 37.26 | C |
| ATOM | 6937 | NZ | LYS | D | 133 | -3.147 | 87.642 | 37.145 | 1.00 36.64 | N |
| ATOM | 6938 | C | LYS | D | 133 | -2.114 | 83.754 | 39.627 | 1.00 33.96 | C |
| ATOM | 6939 | O | LYS | D | 133 | -1.601 | 84.557 | 40.416 | 1.00 34.68 | O |
| ATOM | 6940 | N | LYS | D | 134 | -3.428 | 83.541 | 39.568 | 1.00 33.95 | N |
| ATOM | 6941 | CA | LYS | D | 134 | -4.351 | 84.254 | 40.448 | 1.00 33.61 | C |
| ATOM | 6942 | CB | LYS | D | 134 | -5.789 | 84.067 | 39.961 | 1.00 33.57 | C |
| ATOM | 6943 | CG | LYS | D | 134 | -6.052 | 84.610 | 38.566 | 1.00 31.73 | C |
| ATOM | 6944 | CD | LYS | D | 134 | -7.431 | 84.171 | 38.085 | 1.00 32.59 | C |
| ATOM | 6945 | CE | LYS | D | 134 | -7.791 | 84.840 | 36.771 | 1.00 32.33 | C |
| ATOM | 6946 | NZ | LYS | D | 134 | -9.174 | 84.507 | 36.352 | 1.00 32.80 | N |
| ATOM | 6947 | C | LYS | D | 134 | -4.215 | 83.735 | 41.874 | 1.00 33.32 | C |
| ATOM | 6948 | O | LYS | D | 134 | -4.669 | 84.363 | 42.834 | 1.00 32.91 | O |
| ATOM | 6949 | N | LEU | D | 135 | -3.576 | 82.579 | 42.003 | 1.00 33.49 | N |
| ATOM | 6950 | CA | LEU | D | 135 | -3.375 | 81.960 | 43.302 | 1.00 32.83 | C |
| ATOM | 6951 | CB | LEU | D | 135 | -3.776 | 80.486 | 43.239 | 1.00 32.67 | C |
| ATOM | 6952 | CG | LEU | D | 135 | -5.213 | 80.120 | 42.858 | 1.00 32.37 | C |
| ATOM | 6953 | CD1 | LEU | D | 135 | -5.367 | 78.603 | 42.916 | 1.00 32.65 | C |

FIGURE 9 (cont.)

| ATOM | 6954 | CD2 | LEU | D | 135 | -6.203 | 80.778 | 43.809 | 1.00 | 32.62 | C |
|------|------|-----|-----|---|-----|--------|--------|--------|------|-------|---|
| ATOM | 6955 | C | LEU | D | 135 | -1.923 | 82.074 | 43.763 | 1.00 | 33.47 | C |
| ATOM | 6956 | O | LEU | D | 135 | -1.588 | 81.612 | 44.853 | 1.00 | 33.71 | O |
| ATOM | 6957 | N | MET | D | 136 | -1.064 | 82.686 | 42.941 | 1.00 | 33.69 | N |
| ATOM | 6958 | CA | MET | D | 136 | 0.353 | 82.845 | 43.288 | 1.00 | 34.07 | C |
| ATOM | 6959 | CB | MET | D | 136 | 1.239 | 82.089 | 42.287 | 1.00 | 34.19 | C |
| ATOM | 6960 | CG | MET | D | 136 | 0.817 | 80.643 | 42.070 | 1.00 | 33.63 | C |
| ATOM | 6961 | SD | MET | D | 136 | 2.042 | 79.589 | 41.237 | 1.00 | 33.33 | S |
| ATOM | 6962 | CE | MET | D | 136 | 1.809 | 80.093 | 39.527 | 1.00 | 32.60 | C |
| ATOM | 6963 | C | MET | D | 136 | 0.756 | 84.319 | 43.313 | 1.00 | 34.34 | C |
| ATOM | 6964 | O | MET | D | 136 | 1.658 | 84.753 | 42.583 | 1.00 | 34.63 | O |
| ATOM | 6965 | N | PRO | D | 137 | 0.102 | 85.111 | 44.174 | 1.00 | 33.91 | N |
| ATOM | 6966 | CD | PRO | D | 137 | -0.876 | 84.706 | 45.198 | 1.00 | 33.49 | C |
| ATOM | 6967 | CA | PRO | D | 137 | 0.406 | 86.540 | 44.275 | 1.00 | 33.33 | C |
| ATOM | 6968 | CB | PRO | D | 137 | -0.566 | 87.022 | 45.357 | 1.00 | 32.81 | C |
| ATOM | 6969 | CG | PRO | D | 137 | -0.730 | 85.811 | 46.230 | 1.00 | 32.64 | C |
| ATOM | 6970 | C | PRO | D | 137 | 1.865 | 86.891 | 44.587 | 1.00 | 33.18 | C |
| ATOM | 6971 | O | PRO | D | 137 | 2.342 | 87.954 | 44.179 | 1.00 | 33.21 | O |
| ATOM | 6972 | N | GLU | D | 138 | 2.581 | 86.023 | 45.301 | 1.00 | 32.82 | N |
| ATOM | 6973 | CA | GLU | D | 138 | 3.980 | 86.332 | 45.631 | 1.00 | 32.03 | C |
| ATOM | 6974 | CB | GLU | D | 138 | 4.259 | 86.071 | 47.117 | 1.00 | 33.01 | C |
| ATOM | 6975 | CG | GLU | D | 138 | 3.412 | 86.879 | 48.108 | 1.00 | 36.75 | C |
| ATOM | 6976 | CD | GLU | D | 138 | 3.589 | 88.392 | 47.974 | 1.00 | 39.55 | C |
| ATOM | 6977 | OE1 | GLU | D | 138 | 4.749 | 88.867 | 47.869 | 1.00 | 41.26 | O |
| ATOM | 6978 | OE2 | GLU | D | 138 | 2.561 | 89.113 | 47.993 | 1.00 | 40.52 | O |
| ATOM | 6979 | C | GLU | D | 138 | 4.981 | 85.531 | 44.792 | 1.00 | 30.81 | C |
| ATOM | 6980 | O | GLU | D | 138 | 6.196 | 85.609 | 45.010 | 1.00 | 29.77 | O |
| ATOM | 6981 | N | GLY | D | 139 | 4.474 | 84.760 | 43.838 | 1.00 | 29.06 | N |
| ATOM | 6982 | CA | GLY | D | 139 | 5.360 | 83.968 | 43.009 | 1.00 | 27.38 | C |
| ATOM | 6983 | C | GLY | D | 139 | 5.095 | 82.492 | 43.199 | 1.00 | 26.09 | C |
| ATOM | 6984 | O | GLY | D | 139 | 4.255 | 82.109 | 44.009 | 1.00 | 27.13 | O |
| ATOM | 6985 | N | GLY | D | 140 | 5.817 | 81.656 | 42.463 | 1.00 | 24.55 | N |
| ATOM | 6986 | CA | GLY | D | 140 | 5.612 | 80.225 | 42.565 | 1.00 | 22.83 | C |
| ATOM | 6987 | C | GLY | D | 140 | 6.382 | 79.495 | 41.484 | 1.00 | 22.75 | C |
| ATOM | 6988 | O | GLY | D | 140 | 7.306 | 80.061 | 40.895 | 1.00 | 21.92 | O |
| ATOM | 6989 | N | SER | D | 141 | 5.991 | 78.250 | 41.207 | 1.00 | 22.39 | N |
| ATOM | 6990 | CA | SER | D | 141 | 6.681 | 77.429 | 40.215 | 1.00 | 21.07 | C |
| ATOM | 6991 | CB | SER | D | 141 | 7.803 | 76.648 | 40.919 | 1.00 | 20.68 | C |
| ATOM | 6992 | OG | SER | D | 141 | 8.502 | 75.793 | 40.036 | 1.00 | 22.02 | O |
| ATOM | 6993 | C | SER | D | 141 | 5.741 | 76.465 | 39.478 | 1.00 | 21.55 | C |
| ATOM | 6994 | O | SER | D | 141 | 4.881 | 75.824 | 40.083 | 1.00 | 20.36 | O |
| ATOM | 6995 | N | ILE | D | 142 | 5.917 | 76.369 | 38.163 | 1.00 | 21.87 | N |
| ATOM | 6996 | CA | ILE | D | 142 | 5.097 | 75.492 | 37.330 | 1.00 | 22.36 | C |
| ATOM | 6997 | CB | ILE | D | 142 | 4.297 | 76.301 | 36.276 | 1.00 | 21.98 | C |
| ATOM | 6998 | CG2 | ILE | D | 142 | 3.547 | 75.339 | 35.350 | 1.00 | 23.29 | C |
| ATOM | 6999 | CG1 | ILE | D | 142 | 3.326 | 77.261 | 36.966 | 1.00 | 21.66 | C |
| ATOM | 7000 | CD1 | ILE | D | 142 | 2.558 | 78.151 | 35.996 | 1.00 | 21.45 | C |
| ATOM | 7001 | C | ILE | D | 142 | 5.996 | 74.506 | 36.585 | 1.00 | 21.74 | C |
| ATOM | 7002 | O | ILE | D | 142 | 6.959 | 74.917 | 35.938 | 1.00 | 22.65 | O |
| ATOM | 7003 | N | VAL | D | 143 | 5.679 | 73.214 | 36.666 | 1.00 | 21.26 | N |
| ATOM | 7004 | CA | VAL | D | 143 | 6.490 | 72.201 | 35.994 | 1.00 | 21.19 | C |
| ATOM | 7005 | CB | VAL | D | 143 | 7.322 | 71.389 | 37.008 | 1.00 | 19.66 | C |
| ATOM | 7006 | CG1 | VAL | D | 143 | 8.105 | 70.309 | 36.285 | 1.00 | 17.76 | C |
| ATOM | 7007 | CG2 | VAL | D | 143 | 8.260 | 72.318 | 37.773 | 1.00 | 16.07 | C |
| ATOM | 7008 | C | VAL | D | 143 | 5.660 | 71.234 | 35.164 | 1.00 | 22.02 | C |
| ATOM | 7009 | O | VAL | D | 143 | 4.711 | 70.626 | 35.661 | 1.00 | 22.72 | O |
| ATOM | 7010 | N | ALA | D | 144 | 6.029 | 71.103 | 33.893 | 1.00 | 22.96 | N |
| ATOM | 7011 | CA | ALA | D | 144 | 5.342 | 70.214 | 32.956 | 1.00 | 21.81 | C |
| ATOM | 7012 | CB | ALA | D | 144 | 4.998 | 70.966 | 31.679 | 1.00 | 20.10 | C |
| ATOM | 7013 | C | ALA | D | 144 | 6.248 | 69.039 | 32.629 | 1.00 | 22.01 | C |
| ATOM | 7014 | O | ALA | D | 144 | 7.474 | 69.149 | 32.720 | 1.00 | 21.50 | O |
| ATOM | 7015 | N | THR | D | 145 | 5.642 | 67.920 | 32.235 | 1.00 | 22.12 | N |
| ATOM | 7016 | CA | THR | D | 145 | 6.396 | 66.723 | 31.896 | 1.00 | 21.51 | C |
| ATOM | 7017 | CB | THR | D | 145 | 5.736 | 65.483 | 32.458 | 1.00 | 21.33 | C |
| ATOM | 7018 | OG1 | THR | D | 145 | 5.271 | 65.770 | 33.777 | 1.00 | 23.70 | O |

FIGURE 9 (cont.)

| | | | | | | | | | |
|---|---|---|---|---|---|---|---|---|---|
| ATOM | 7019 | CG2 | THR | D | 145 | 6.744 | 64.329 | 32.530 | 1.00 22.05 | C |
| ATOM | 7020 | C | THR | D | 145 | 6.487 | 66.581 | 30.395 | 1.00 21.03 | C |
| ATOM | 7021 | O | THR | D | 145 | 5.503 | 66.776 | 29.679 | 1.00 20.25 | O |
| ATOM | 7022 | N | THR | D | 146 | 7.679 | 66.237 | 29.921 | 1.00 19.46 | N |
| ATOM | 7023 | CA | THR | D | 146 | 7.892 | 66.093 | 28.493 | 1.00 19.15 | C |
| ATOM | 7024 | CB | THR | D | 146 | 8.590 | 67.349 | 27.910 | 1.00 18.81 | C |
| ATOM | 7025 | OG1 | THR | D | 146 | 8.516 | 67.318 | 26.482 | 1.00 19.41 | O |
| ATOM | 7026 | CG2 | THR | D | 146 | 10.057 | 67.388 | 28.319 | 1.00 20.28 | C |
| ATOM | 7027 | C | THR | D | 146 | 8.720 | 64.859 | 28.166 | 1.00 18.28 | C |
| ATOM | 7028 | O | THR | D | 146 | 9.151 | 64.122 | 29.054 | 1.00 18.69 | O |
| ATOM | 7029 | N | TYR | D | 147 | 8.939 | 64.646 | 26.876 | 1.00 18.80 | N |
| ATOM | 7030 | CA | TYR | D | 147 | 9.697 | 63.502 | 26.406 | 1.00 17.61 | C |
| ATOM | 7031 | CB | TYR | D | 147 | 8.729 | 62.462 | 25.836 | 1.00 16.53 | C |
| ATOM | 7032 | CG | TYR | D | 147 | 9.367 | 61.186 | 25.340 | 1.00 16.13 | C |
| ATOM | 7033 | CD1 | TYR | D | 147 | 10.159 | 60.398 | 26.179 | 1.00 14.91 | C |
| ATOM | 7034 | CE1 | TYR | D | 147 | 10.729 | 59.211 | 25.720 | 1.00 14.01 | C |
| ATOM | 7035 | CD2 | TYR | D | 147 | 9.160 | 60.750 | 24.028 | 1.00 16.52 | C |
| ATOM | 7036 | CE2 | TYR | D | 147 | 9.723 | 59.566 | 23.562 | 1.00 16.19 | C |
| ATOM | 7037 | CZ | TYR | D | 147 | 10.507 | 58.805 | 24.406 | 1.00 15.10 | C |
| ATOM | 7038 | OH | TYR | D | 147 | 11.099 | 57.660 | 23.912 | 1.00 16.21 | O |
| ATOM | 7039 | C | TYR | D | 147 | 10.693 | 63.960 | 25.349 | 1.00 17.69 | C |
| ATOM | 7040 | O | TYR | D | 147 | 10.483 | 64.967 | 24.674 | 1.00 17.54 | O |
| ATOM | 7041 | N | LEU | D | 148 | 11.782 | 63.213 | 25.223 | 1.00 17.63 | N |
| ATOM | 7042 | CA | LEU | D | 148 | 12.836 | 63.511 | 24.265 | 1.00 18.12 | C |
| ATOM | 7043 | CB | LEU | D | 148 | 13.937 | 62.453 | 24.393 | 1.00 19.40 | C |
| ATOM | 7044 | CG | LEU | D | 148 | 15.407 | 62.846 | 24.250 | 1.00 19.80 | C |
| ATOM | 7045 | CD1 | LEU | D | 148 | 15.670 | 64.206 | 24.864 | 1.00 20.62 | C |
| ATOM | 7046 | CD2 | LEU | D | 148 | 16.253 | 61.781 | 24.932 | 1.00 19.83 | C |
| ATOM | 7047 | C | LEU | D | 148 | 12.273 | 63.530 | 22.844 | 1.00 18.01 | C |
| ATOM | 7048 | O | LEU | D | 148 | 12.816 | 64.193 | 21.959 | 1.00 16.88 | O |
| ATOM | 7049 | N | GLY | D | 149 | 11.180 | 62.796 | 22.635 | 1.00 17.67 | N |
| ATOM | 7050 | CA | GLY | D | 149 | 10.555 | 62.752 | 21.326 | 1.00 16.38 | C |
| ATOM | 7051 | C | GLY | D | 149 | 10.144 | 64.137 | 20.860 | 1.00 16.88 | C |
| ATOM | 7052 | O | GLY | D | 149 | 9.878 | 64.353 | 19.677 | 1.00 14.97 | O |
| ATOM | 7053 | N | GLY | D | 150 | 10.099 | 65.086 | 21.794 | 1.00 17.54 | N |
| ATOM | 7054 | CA | GLY | D | 150 | 9.727 | 66.445 | 21.439 | 1.00 18.25 | C |
| ATOM | 7055 | C | GLY | D | 150 | 10.899 | 67.227 | 20.867 | 1.00 19.39 | C |
| ATOM | 7056 | O | GLY | D | 150 | 10.727 | 68.340 | 20.341 | 1.00 17.72 | O |
| ATOM | 7057 | N | GLU | D | 151 | 12.097 | 66.657 | 20.979 | 1.00 18.82 | N |
| ATOM | 7058 | CA | GLU | D | 151 | 13.297 | 67.313 | 20.460 | 1.00 20.64 | C |
| ATOM | 7059 | CB | GLU | D | 151 | 14.412 | 67.344 | 21.516 | 1.00 21.31 | C |
| ATOM | 7060 | CG | GLU | D | 151 | 14.098 | 68.121 | 22.799 | 1.00 23.02 | C |
| ATOM | 7061 | CD | GLU | D | 151 | 15.268 | 68.111 | 23.786 | 1.00 24.65 | C |
| ATOM | 7062 | OE1 | GLU | D | 151 | 16.314 | 68.752 | 23.511 | 1.00 23.93 | O |
| ATOM | 7063 | OE2 | GLU | D | 151 | 15.143 | 67.449 | 24.836 | 1.00 24.25 | O |
| ATOM | 7064 | C | GLU | D | 151 | 13.814 | 66.577 | 19.231 | 1.00 20.08 | C |
| ATOM | 7065 | O | GLU | D | 151 | 14.405 | 67.181 | 18.352 | 1.00 20.89 | O |
| ATOM | 7066 | N | PHE | D | 152 | 13.597 | 65.267 | 19.185 | 1.00 20.22 | N |
| ATOM | 7067 | CA | PHE | D | 152 | 14.057 | 64.444 | 18.064 | 1.00 20.82 | C |
| ATOM | 7068 | CB | PHE | D | 152 | 15.256 | 63.589 | 18.500 | 1.00 20.69 | C |
| ATOM | 7069 | CG | PHE | D | 152 | 16.425 | 64.394 | 19.007 | 1.00 23.25 | C |
| ATOM | 7070 | CD1 | PHE | D | 152 | 17.171 | 65.189 | 18.138 | 1.00 25.17 | C |
| ATOM | 7071 | CD2 | PHE | D | 152 | 16.763 | 64.381 | 20.353 | 1.00 23.21 | C |
| ATOM | 7072 | CE1 | PHE | D | 152 | 18.244 | 65.966 | 18.604 | 1.00 25.32 | C |
| ATOM | 7073 | CE2 | PHE | D | 152 | 17.835 | 65.153 | 20.834 | 1.00 24.66 | C |
| ATOM | 7074 | CZ | PHE | D | 152 | 18.575 | 65.947 | 19.953 | 1.00 24.34 | C |
| ATOM | 7075 | C | PHE | D | 152 | 12.936 | 63.533 | 17.566 | 1.00 20.62 | C |
| ATOM | 7076 | O | PHE | D | 152 | 12.020 | 63.195 | 18.319 | 1.00 20.80 | O |
| ATOM | 7077 | N | ALA | D | 153 | 13.007 | 63.136 | 16.299 | 1.00 19.12 | N |
| ATOM | 7078 | CA | ALA | D | 153 | 11.989 | 62.257 | 15.730 | 1.00 18.90 | C |
| ATOM | 7079 | CB | ALA | D | 153 | 12.129 | 62.193 | 14.204 | 1.00 17.53 | C |
| ATOM | 7080 | C | ALA | D | 153 | 12.108 | 60.857 | 16.315 | 1.00 19.20 | C |
| ATOM | 7081 | O | ALA | D | 153 | 13.104 | 60.157 | 16.078 | 1.00 20.10 | O |
| ATOM | 7082 | N | VAL | D | 154 | 11.104 | 60.451 | 17.088 | 1.00 18.92 | N |
| ATOM | 7083 | CA | VAL | D | 154 | 11.103 | 59.114 | 17.679 | 1.00 19.55 | C |

FIGURE 9 (cont.)

| ATOM | 7084 | CB | VAL | D | 154 | 10.766 | 59.157 | 19.188 | 1.00 | 18.51 | C |
|------|------|-----|-----|---|-----|--------|--------|--------|------|-------|---|
| ATOM | 7085 | CG1 | VAL | D | 154 | 10.494 | 57.759 | 19.700 | 1.00 | 18.34 | C |
| ATOM | 7086 | CG2 | VAL | D | 154 | 11.938 | 59.751 | 19.967 | 1.00 | 19.80 | C |
| ATOM | 7087 | C | VAL | D | 154 | 10.089 | 58.224 | 16.956 | 1.00 | 19.80 | C |
| ATOM | 7088 | O | VAL | D | 154 | 9.014 | 58.681 | 16.579 | 1.00 | 19.73 | O |
| ATOM | 7089 | N | GLN | D | 155 | 10.451 | 56.961 | 16.750 | 1.00 | 20.46 | N |
| ATOM | 7090 | CA | GLN | D | 155 | 9.589 | 56.002 | 16.072 | 1.00 | 21.96 | C |
| ATOM | 7091 | CB | GLN | D | 155 | 10.224 | 54.594 | 16.114 | 1.00 | 24.82 | C |
| ATOM | 7092 | CG | GLN | D | 155 | 9.409 | 53.498 | 15.390 | 1.00 | 27.88 | C |
| ATOM | 7093 | CD | GLN | D | 155 | 9.921 | 52.069 | 15.637 | 1.00 | 30.34 | C |
| ATOM | 7094 | OE1 | GLN | D | 155 | 9.869 | 51.547 | 16.768 | 1.00 | 30.90 | O |
| ATOM | 7095 | NE2 | GLN | D | 155 | 10.405 | 51.426 | 14.574 | 1.00 | 30.25 | N |
| ATOM | 7096 | C | GLN | D | 155 | 8.210 | 55.962 | 16.724 | 1.00 | 20.85 | C |
| ATOM | 7097 | O | GLN | D | 155 | 8.100 | 55.882 | 17.939 | 1.00 | 21.51 | O |
| ATOM | 7098 | N | ASN | D | 156 | 7.166 | 56.030 | 15.905 | 1.00 | 20.93 | N |
| ATOM | 7099 | CA | ASN | D | 156 | 5.776 | 55.977 | 16.367 | 1.00 | 20.40 | C |
| ATOM | 7100 | CB | ASN | D | 156 | 5.490 | 54.649 | 17.085 | 1.00 | 18.67 | C |
| ATOM | 7101 | CG | ASN | D | 156 | 5.710 | 53.442 | 16.200 | 1.00 | 19.73 | C |
| ATOM | 7102 | OD1 | ASN | D | 156 | 5.463 | 53.486 | 15.003 | 1.00 | 20.51 | O |
| ATOM | 7103 | ND2 | ASN | D | 156 | 6.167 | 52.345 | 16.794 | 1.00 | 21.51 | N |
| ATOM | 7104 | C | ASN | D | 156 | 5.268 | 57.103 | 17.267 | 1.00 | 21.75 | C |
| ATOM | 7105 | O | ASN | D | 156 | 4.058 | 57.182 | 17.509 | 1.00 | 21.47 | O |
| ATOM | 7106 | N | TYR | D | 157 | 6.151 | 57.963 | 17.776 | 1.00 | 20.71 | N |
| ATOM | 7107 | CA | TYR | D | 157 | 5.691 | 59.033 | 18.666 | 1.00 | 21.41 | C |
| ATOM | 7108 | CB | TYR | D | 157 | 6.871 | 59.716 | 19.357 | 1.00 | 21.52 | C |
| ATOM | 7109 | CG | TYR | D | 157 | 6.484 | 60.407 | 20.648 | 1.00 | 21.99 | C |
| ATOM | 7110 | CD1 | TYR | D | 157 | 5.611 | 59.796 | 21.547 | 1.00 | 21.16 | C |
| ATOM | 7111 | CE1 | TYR | D | 157 | 5.280 | 60.401 | 22.762 | 1.00 | 22.14 | C |
| ATOM | 7112 | CD2 | TYR | D | 157 | 7.023 | 61.651 | 20.994 | 1.00 | 22.25 | C |
| ATOM | 7113 | CE2 | TYR | D | 157 | 6.704 | 62.261 | 22.213 | 1.00 | 22.78 | C |
| ATOM | 7114 | CZ | TYR | D | 157 | 5.832 | 61.625 | 23.092 | 1.00 | 22.38 | C |
| ATOM | 7115 | OH | TYR | D | 157 | 5.541 | 62.191 | 24.314 | 1.00 | 22.42 | O |
| ATOM | 7116 | C | TYR | D | 157 | 4.885 | 60.064 | 17.899 | 1.00 | 22.16 | C |
| ATOM | 7117 | O | TYR | D | 157 | 4.147 | 60.871 | 18.478 | 1.00 | 23.29 | O |
| ATOM | 7118 | N | ASN | D | 158 | 5.052 | 60.025 | 16.584 | 1.00 | 22.84 | N |
| ATOM | 7119 | CA | ASN | D | 158 | 4.369 | 60.903 | 15.649 | 1.00 | 22.10 | C |
| ATOM | 7120 | CB | ASN | D | 158 | 3.311 | 60.094 | 14.886 | 1.00 | 21.04 | C |
| ATOM | 7121 | CG | ASN | D | 158 | 3.860 | 58.772 | 14.351 | 1.00 | 20.50 | C |
| ATOM | 7122 | OD1 | ASN | D | 158 | 5.042 | 58.673 | 14.007 | 1.00 | 19.94 | O |
| ATOM | 7123 | ND2 | ASN | D | 158 | 3.001 | 57.757 | 14.262 | 1.00 | 20.12 | N |
| ATOM | 7124 | C | ASN | D | 158 | 3.751 | 62.171 | 16.240 | 1.00 | 22.41 | C |
| ATOM | 7125 | O | ASN | D | 158 | 4.461 | 63.021 | 16.786 | 1.00 | 22.32 | O |
| ATOM | 7126 | N | VAL | D | 159 | 2.429 | 62.293 | 16.138 | 1.00 | 21.70 | N |
| ATOM | 7127 | CA | VAL | D | 159 | 1.726 | 63.484 | 16.615 | 1.00 | 20.54 | C |
| ATOM | 7128 | CB | VAL | D | 159 | 0.185 | 63.305 | 16.519 | 1.00 | 20.09 | C |
| ATOM | 7129 | CG1 | VAL | D | 159 | -0.344 | 62.645 | 17.774 | 1.00 | 19.96 | C |
| ATOM | 7130 | CG2 | VAL | D | 159 | -0.487 | 64.664 | 16.300 | 1.00 | 20.16 | C |
| ATOM | 7131 | C | VAL | D | 159 | 2.056 | 63.966 | 18.035 | 1.00 | 20.21 | C |
| ATOM | 7132 | O | VAL | D | 159 | 1.866 | 65.147 | 18.343 | 1.00 | 18.63 | O |
| ATOM | 7133 | N | MET | D | 160 | 2.531 | 63.067 | 18.899 | 1.00 | 20.95 | N |
| ATOM | 7134 | CA | MET | D | 160 | 2.862 | 63.452 | 20.274 | 1.00 | 20.48 | C |
| ATOM | 7135 | CB | MET | D | 160 | 2.902 | 62.221 | 21.191 | 1.00 | 20.54 | C |
| ATOM | 7136 | CG | MET | D | 160 | 1.545 | 61.802 | 21.780 | 1.00 | 19.63 | C |
| ATOM | 7137 | SD | MET | D | 160 | 0.648 | 63.184 | 22.586 | 1.00 | 22.85 | S |
| ATOM | 7138 | CE | MET | D | 160 | 1.731 | 63.570 | 23.930 | 1.00 | 19.84 | C |
| ATOM | 7139 | C | MET | D | 160 | 4.198 | 64.193 | 20.339 | 1.00 | 21.39 | C |
| ATOM | 7140 | O | MET | D | 160 | 4.431 | 65.001 | 21.243 | 1.00 | 22.29 | O |
| ATOM | 7141 | N | GLY | D | 161 | 5.070 | 63.922 | 19.374 | 1.00 | 20.86 | N |
| ATOM | 7142 | CA | GLY | D | 161 | 6.356 | 64.589 | 19.350 | 1.00 | 21.82 | C |
| ATOM | 7143 | C | GLY | D | 161 | 6.169 | 66.057 | 19.036 | 1.00 | 22.62 | C |
| ATOM | 7144 | O | GLY | D | 161 | 6.838 | 66.921 | 19.624 | 1.00 | 23.01 | O |
| ATOM | 7145 | N | VAL | D | 162 | 5.256 | 66.343 | 18.108 | 1.00 | 21.68 | N |
| ATOM | 7146 | CA | VAL | D | 162 | 4.968 | 67.715 | 17.720 | 1.00 | 22.07 | C |
| ATOM | 7147 | CB | VAL | D | 162 | 4.080 | 67.753 | 16.461 | 1.00 | 23.87 | C |
| ATOM | 7148 | CG1 | VAL | D | 162 | 3.947 | 69.182 | 15.964 | 1.00 | 21.62 | C |

FIGURE 9 (cont.)

| | | | | | | | | | |
|---|---|---|---|---|---|---|---|---|---|
| ATOM | 7149 | CG2 | VAL | D | 162 | 4.683 | 66.850 | 15.368 | 1.00 24.37 | C |
| ATOM | 7150 | C | VAL | D | 162 | 4.268 | 68.448 | 18.869 | 1.00 22.08 | C |
| ATOM | 7151 | O | VAL | D | 162 | 4.465 | 69.648 | 19.069 | 1.00 22.67 | O |
| ATOM | 7152 | N | ALA | D | 163 | 3.457 | 67.719 | 19.631 | 1.00 20.77 | N |
| ATOM | 7153 | CA | ALA | D | 163 | 2.758 | 68.300 | 20.771 | 1.00 20.66 | C |
| ATOM | 7154 | CB | ALA | D | 163 | 1.700 | 67.324 | 21.296 | 1.00 19.93 | C |
| ATOM | 7155 | C | ALA | D | 163 | 3.762 | 68.627 | 21.876 | 1.00 19.77 | C |
| ATOM | 7156 | O | ALA | D | 163 | 3.647 | 69.645 | 22.552 | 1.00 19.50 | O |
| ATOM | 7157 | N | LYS | D | 164 | 4.741 | 67.745 | 22.060 | 1.00 20.03 | N |
| ATOM | 7158 | CA | LYS | D | 164 | 5.759 | 67.954 | 23.077 | 1.00 19.28 | C |
| ATOM | 7159 | CB | LYS | D | 164 | 6.595 | 66.685 | 23.279 | 1.00 19.18 | C |
| ATOM | 7160 | CG | LYS | D | 164 | 5.880 | 65.576 | 24.059 | 1.00 17.42 | C |
| ATOM | 7161 | CD | LYS | D | 164 | 5.358 | 66.095 | 25.399 | 1.00 17.99 | C |
| ATOM | 7162 | CE | LYS | D | 164 | 4.683 | 65.005 | 26.206 | 1.00 17.02 | C |
| ATOM | 7163 | NZ | LYS | D | 164 | 4.246 | 65.518 | 27.527 | 1.00 16.02 | N |
| ATOM | 7164 | C | LYS | D | 164 | 6.662 | 69.118 | 22.686 | 1.00 18.87 | C |
| ATOM | 7165 | O | LYS | D | 164 | 7.051 | 69.912 | 23.543 | 1.00 19.98 | O |
| ATOM | 7166 | N | ALA | D | 165 | 6.985 | 69.224 | 21.398 | 1.00 17.30 | N |
| ATOM | 7167 | CA | ALA | D | 165 | 7.829 | 70.315 | 20.918 | 1.00 17.68 | C |
| ATOM | 7168 | CB | ALA | D | 165 | 8.056 | 70.186 | 19.423 | 1.00 16.84 | C |
| ATOM | 7169 | C | ALA | D | 165 | 7.113 | 71.616 | 21.230 | 1.00 17.03 | C |
| ATOM | 7170 | O | ALA | D | 165 | 7.705 | 72.570 | 21.733 | 1.00 16.36 | O |
| ATOM | 7171 | N | SER | D | 166 | 5.817 | 71.619 | 20.941 | 1.00 17.68 | N |
| ATOM | 7172 | CA | SER | D | 166 | 4.950 | 72.760 | 21.171 | 1.00 17.31 | C |
| ATOM | 7173 | CB | SER | D | 166 | 3.555 | 72.450 | 20.619 | 1.00 18.47 | C |
| ATOM | 7174 | OG | SER | D | 166 | 2.691 | 73.565 | 20.751 | 1.00 21.76 | O |
| ATOM | 7175 | C | SER | D | 166 | 4.884 | 73.033 | 22.666 | 1.00 16.46 | C |
| ATOM | 7176 | O | SER | D | 166 | 4.884 | 74.182 | 23.102 | 1.00 15.33 | O |
| ATOM | 7177 | N | LEU | D | 167 | 4.836 | 71.972 | 23.458 | 1.00 16.21 | N |
| ATOM | 7178 | CA | LEU | D | 167 | 4.793 | 72.139 | 24.905 | 1.00 17.86 | C |
| ATOM | 7179 | CB | LEU | D | 167 | 4.582 | 70.786 | 25.606 | 1.00 16.29 | C |
| ATOM | 7180 | CG | LEU | D | 167 | 4.618 | 70.808 | 27.148 | 1.00 17.31 | C |
| ATOM | 7181 | CD1 | LEU | D | 167 | 3.509 | 71.708 | 27.686 | 1.00 14.68 | C |
| ATOM | 7182 | CD2 | LEU | D | 167 | 4.464 | 69.379 | 27.706 | 1.00 16.29 | C |
| ATOM | 7183 | C | LEU | D | 167 | 6.089 | 72.787 | 25.419 | 1.00 18.06 | C |
| ATOM | 7184 | O | LEU | D | 167 | 6.055 | 73.636 | 26.313 | 1.00 20.35 | O |
| ATOM | 7185 | N | GLU | D | 168 | 7.226 | 72.393 | 24.850 | 1.00 17.17 | N |
| ATOM | 7186 | CA | GLU | D | 168 | 8.507 | 72.942 | 25.275 | 1.00 17.48 | C |
| ATOM | 7187 | CB | GLU | D | 168 | 9.662 | 72.130 | 24.656 | 1.00 19.19 | C |
| ATOM | 7188 | CG | GLU | D | 168 | 9.987 | 70.824 | 25.412 | 1.00 22.08 | C |
| ATOM | 7189 | CD | GLU | D | 168 | 10.812 | 69.836 | 24.589 | 1.00 24.99 | C |
| ATOM | 7190 | OE1 | GLU | D | 168 | 11.800 | 70.260 | 23.942 | 1.00 25.72 | O |
| ATOM | 7191 | OE2 | GLU | D | 168 | 10.476 | 68.621 | 24.596 | 1.00 26.18 | O |
| ATOM | 7192 | C | GLU | D | 168 | 8.674 | 74.442 | 24.981 | 1.00 17.15 | C |
| ATOM | 7193 | O | GLU | D | 168 | 9.328 | 75.142 | 25.744 | 1.00 16.84 | O |
| ATOM | 7194 | N | ALA | D | 169 | 8.102 | 74.940 | 23.886 | 1.00 16.93 | N |
| ATOM | 7195 | CA | ALA | D | 169 | 8.219 | 76.368 | 23.581 | 1.00 18.51 | C |
| ATOM | 7196 | CB | ALA | D | 169 | 7.895 | 76.636 | 22.106 | 1.00 17.58 | C |
| ATOM | 7197 | C | ALA | D | 169 | 7.247 | 77.127 | 24.485 | 1.00 18.34 | C |
| ATOM | 7198 | O | ALA | D | 169 | 7.515 | 78.244 | 24.915 | 1.00 18.59 | O |
| ATOM | 7199 | N | ASN | D | 170 | 6.116 | 76.491 | 24.762 | 1.00 20.18 | N |
| ATOM | 7200 | CA | ASN | D | 170 | 5.064 | 77.035 | 25.624 | 1.00 19.97 | C |
| ATOM | 7201 | CB | ASN | D | 170 | 3.998 | 75.950 | 25.837 | 1.00 20.38 | C |
| ATOM | 7202 | CG | ASN | D | 170 | 2.619 | 76.514 | 26.128 | 1.00 21.98 | C |
| ATOM | 7203 | OD1 | ASN | D | 170 | 1.609 | 75.865 | 25.839 | 1.00 23.65 | O |
| ATOM | 7204 | ND2 | ASN | D | 170 | 2.563 | 77.709 | 26.710 | 1.00 21.64 | N |
| ATOM | 7205 | C | ASN | D | 170 | 5.707 | 77.428 | 26.956 | 1.00 18.80 | C |
| ATOM | 7206 | O | ASN | D | 170 | 5.445 | 78.506 | 27.496 | 1.00 17.90 | O |
| ATOM | 7207 | N | VAL | D | 171 | 6.550 | 76.532 | 27.472 | 1.00 18.65 | N |
| ATOM | 7208 | CA | VAL | D | 171 | 7.275 | 76.747 | 28.725 | 1.00 17.71 | C |
| ATOM | 7209 | CB | VAL | D | 171 | 8.084 | 75.478 | 29.091 | 1.00 17.93 | C |
| ATOM | 7210 | CG1 | VAL | D | 171 | 9.159 | 75.787 | 30.123 | 1.00 14.62 | C |
| ATOM | 7211 | CG2 | VAL | D | 171 | 7.129 | 74.411 | 29.622 | 1.00 19.05 | C |
| ATOM | 7212 | C | VAL | D | 171 | 8.213 | 77.963 | 28.649 | 1.00 16.75 | C |
| ATOM | 7213 | O | VAL | D | 171 | 8.311 | 78.748 | 29.601 | 1.00 16.33 | O |

FIGURE 9 (cont.)

| | | | | | | | | | | |
|---|---|---|---|---|---|---|---|---|---|---|
| ATOM | 7214 | N | LYS | D | 172 | 8.898 | 78.123 | 27.520 | 1.00 17.17 | N |
| ATOM | 7215 | CA | LYS | D | 172 | 9.812 | 79.255 | 27.346 | 1.00 17.35 | C |
| ATOM | 7216 | CB | LYS | D | 172 | 10.666 | 79.062 | 26.090 | 1.00 15.86 | C |
| ATOM | 7217 | CG | LYS | D | 172 | 11.519 | 77.822 | 26.128 | 1.00 15.72 | C |
| ATOM | 7218 | CD | LYS | D | 172 | 12.275 | 77.632 | 24.839 | 1.00 16.24 | C |
| ATOM | 7219 | CE | LYS | D | 172 | 12.857 | 76.231 | 24.761 | 1.00 17.67 | C |
| ATOM | 7220 | NZ | LYS | D | 172 | 13.392 | 75.950 | 23.394 | 1.00 20.78 | N |
| ATOM | 7221 | C | LYS | D | 172 | 9.033 | 80.560 | 27.243 | 1.00 17.83 | C |
| ATOM | 7222 | O | LYS | D | 172 | 9.454 | 81.586 | 27.772 | 1.00 17.12 | O |
| ATOM | 7223 | N | TYR | D | 173 | 7.890 | 80.521 | 26.559 | 1.00 18.37 | N |
| ATOM | 7224 | CA | TYR | D | 173 | 7.068 | 81.718 | 26.408 | 1.00 18.58 | C |
| ATOM | 7225 | CB | TYR | D | 173 | 6.095 | 81.547 | 25.235 | 1.00 18.25 | C |
| ATOM | 7226 | CG | TYR | D | 173 | 6.743 | 81.879 | 23.907 | 1.00 19.03 | C |
| ATOM | 7227 | CD1 | TYR | D | 173 | 6.840 | 83.200 | 23.475 | 1.00 17.74 | C |
| ATOM | 7228 | CE1 | TYR | D | 173 | 7.506 | 83.531 | 22.299 | 1.00 17.20 | C |
| ATOM | 7229 | CD2 | TYR | D | 173 | 7.330 | 80.885 | 23.119 | 1.00 18.53 | C |
| ATOM | 7230 | CE2 | TYR | D | 173 | 8.002 | 81.208 | 21.936 | 1.00 18.15 | C |
| ATOM | 7231 | CZ | TYR | D | 173 | 8.088 | 82.537 | 21.536 | 1.00 18.00 | C |
| ATOM | 7232 | OH | TYR | D | 173 | 8.788 | 82.884 | 20.400 | 1.00 16.64 | O |
| ATOM | 7233 | C | TYR | D | 173 | 6.332 | 82.084 | 27.696 | 1.00 18.52 | C |
| ATOM | 7234 | O | TYR | D | 173 | 6.039 | 83.258 | 27.932 | 1.00 19.97 | O |
| ATOM | 7235 | N | LEU | D | 174 | 6.039 | 81.088 | 28.530 | 1.00 17.85 | N |
| ATOM | 7236 | CA | LEU | D | 174 | 5.373 | 81.342 | 29.806 | 1.00 18.25 | C |
| ATOM | 7237 | CB | LEU | D | 174 | 4.719 | 80.067 | 30.341 | 1.00 16.65 | C |
| ATOM | 7238 | CG | LEU | D | 174 | 3.386 | 79.730 | 29.658 | 1.00 13.90 | C |
| ATOM | 7239 | CD1 | LEU | D | 174 | 2.830 | 78.431 | 30.201 | 1.00 11.16 | C |
| ATOM | 7240 | CD2 | LEU | D | 174 | 2.400 | 80.882 | 29.889 | 1.00 13.24 | C |
| ATOM | 7241 | C | LEU | D | 174 | 6.393 | 81.871 | 30.801 | 1.00 19.85 | C |
| ATOM | 7242 | O | LEU | D | 174 | 6.110 | 82.794 | 31.565 | 1.00 21.55 | O |
| ATOM | 7243 | N | ALA | D | 175 | 7.590 | 81.293 | 30.769 | 1.00 20.17 | N |
| ATOM | 7244 | CA | ALA | D | 175 | 8.674 | 81.716 | 31.641 | 1.00 20.74 | C |
| ATOM | 7245 | CB | ALA | D | 175 | 9.923 | 80.882 | 31.371 | 1.00 21.05 | C |
| ATOM | 7246 | C | ALA | D | 175 | 8.970 | 83.185 | 31.385 | 1.00 20.74 | C |
| ATOM | 7247 | O | ALA | D | 175 | 9.225 | 83.946 | 32.323 | 1.00 22.72 | O |
| ATOM | 7248 | N | LEU | D | 176 | 8.954 | 83.585 | 30.117 | 1.00 20.45 | N |
| ATOM | 7249 | CA | LEU | D | 176 | 9.216 | 84.979 | 29.780 | 1.00 20.97 | C |
| ATOM | 7250 | CB | LEU | D | 176 | 9.477 | 85.161 | 28.281 | 1.00 18.85 | C |
| ATOM | 7251 | CG | LEU | D | 176 | 9.581 | 86.645 | 27.876 | 1.00 17.00 | C |
| ATOM | 7252 | CD1 | LEU | D | 176 | 10.631 | 87.343 | 28.736 | 1.00 14.33 | C |
| ATOM | 7253 | CD2 | LEU | D | 176 | 9.934 | 86.765 | 26.395 | 1.00 16.00 | C |
| ATOM | 7254 | C | LEU | D | 176 | 8.045 | 85.866 | 30.177 | 1.00 22.12 | C |
| ATOM | 7255 | O | LEU | D | 176 | 8.246 | 86.977 | 30.664 | 1.00 23.57 | O |
| ATOM | 7256 | N | ASP | D | 177 | 6.824 | 85.372 | 29.969 | 1.00 23.12 | N |
| ATOM | 7257 | CA | ASP | D | 177 | 5.621 | 86.137 | 30.305 | 1.00 24.40 | C |
| ATOM | 7258 | CB | ASP | D | 177 | 4.366 | 85.469 | 29.710 | 1.00 24.77 | C |
| ATOM | 7259 | CG | ASP | D | 177 | 3.090 | 86.275 | 29.973 | 1.00 24.43 | C |
| ATOM | 7260 | OD1 | ASP | D | 177 | 1.978 | 85.814 | 29.617 | 1.00 21.66 | O |
| ATOM | 7261 | OD2 | ASP | D | 177 | 3.206 | 87.383 | 30.532 | 1.00 25.18 | O |
| ATOM | 7262 | C | ASP | D | 177 | 5.406 | 86.297 | 31.807 | 1.00 24.63 | C |
| ATOM | 7263 | O | ASP | D | 177 | 5.079 | 87.388 | 32.270 | 1.00 25.42 | O |
| ATOM | 7264 | N | LEU | D | 178 | 5.591 | 85.215 | 32.564 | 1.00 24.47 | N |
| ATOM | 7265 | CA | LEU | D | 178 | 5.355 | 85.250 | 34.010 | 1.00 24.43 | C |
| ATOM | 7266 | CB | LEU | D | 178 | 4.712 | 83.925 | 34.456 | 1.00 23.30 | C |
| ATOM | 7267 | CG | LEU | D | 178 | 3.519 | 83.447 | 33.616 | 1.00 21.36 | C |
| ATOM | 7268 | CD1 | LEU | D | 178 | 2.969 | 82.138 | 34.162 | 1.00 22.11 | C |
| ATOM | 7269 | CD2 | LEU | D | 178 | 2.449 | 84.497 | 33.625 | 1.00 21.60 | C |
| ATOM | 7270 | C | LEU | D | 178 | 6.582 | 85.550 | 34.878 | 1.00 24.82 | C |
| ATOM | 7271 | O | LEU | D | 178 | 6.447 | 85.800 | 36.083 | 1.00 23.41 | O |
| ATOM | 7272 | N | GLY | D | 179 | 7.768 | 85.535 | 34.270 | 1.00 25.37 | N |
| ATOM | 7273 | CA | GLY | D | 179 | 8.994 | 85.819 | 35.003 | 1.00 25.02 | C |
| ATOM | 7274 | C | GLY | D | 179 | 8.881 | 87.040 | 35.902 | 1.00 26.07 | C |
| ATOM | 7275 | O | GLY | D | 179 | 9.223 | 86.968 | 37.091 | 1.00 25.70 | O |
| ATOM | 7276 | N | PRO | D | 180 | 8.403 | 88.184 | 35.371 | 1.00 26.27 | N |
| ATOM | 7277 | CD | PRO | D | 180 | 8.162 | 88.424 | 33.936 | 1.00 26.26 | C |
| ATOM | 7278 | CA | PRO | D | 180 | 8.246 | 89.432 | 36.135 | 1.00 25.83 | C |

FIGURE 9 (cont.)

| | | | | | | | | | |
|---|---|---|---|---|---|---|---|---|---|
| ATOM | 7279 | CB | PRO | D | 180 | 7.727 | 90.416 | 35.084 | 1.00 26.85 | C |
| ATOM | 7280 | CG | PRO | D | 180 | 8.387 | 89.918 | 33.814 | 1.00 27.02 | C |
| ATOM | 7281 | C | PRO | D | 180 | 7.321 | 89.356 | 37.355 | 1.00 25.57 | C |
| ATOM | 7282 | O | PRO | D | 180 | 7.429 | 90.183 | 38.262 | 1.00 25.18 | O |
| ATOM | 7283 | N | ASP | D | 181 | 6.401 | 88.393 | 37.374 | 1.00 25.13 | N |
| ATOM | 7284 | CA | ASP | D | 181 | 5.482 | 88.243 | 38.510 | 1.00 25.43 | C |
| ATOM | 7285 | CB | ASP | D | 181 | 4.125 | 87.692 | 38.052 | 1.00 25.51 | C |
| ATOM | 7286 | CG | ASP | D | 181 | 3.480 | 88.544 | 36.967 | 1.00 27.80 | C |
| ATOM | 7287 | OD1 | ASP | D | 181 | 2.549 | 88.041 | 36.293 | 1.00 29.72 | O |
| ATOM | 7288 | OD2 | ASP | D | 181 | 3.891 | 89.714 | 36.780 | 1.00 27.81 | O |
| ATOM | 7289 | C | ASP | D | 181 | 6.131 | 87.259 | 39.472 | 1.00 25.82 | C |
| ATOM | 7290 | O | ASP | D | 181 | 5.526 | 86.814 | 40.457 | 1.00 26.30 | O |
| ATOM | 7291 | N | ASN | D | 182 | 7.373 | 86.909 | 39.154 | 1.00 25.78 | N |
| ATOM | 7292 | CA | ASN | D | 182 | 8.153 | 85.986 | 39.965 | 1.00 24.59 | C |
| ATOM | 7293 | CB | ASN | D | 182 | 8.174 | 86.467 | 41.417 | 1.00 26.08 | C |
| ATOM | 7294 | CG | ASN | D | 182 | 8.974 | 85.558 | 42.308 | 1.00 27.62 | C |
| ATOM | 7295 | OD1 | ASN | D | 182 | 10.145 | 85.295 | 42.042 | 1.00 29.17 | O |
| ATOM | 7296 | ND2 | ASN | D | 182 | 8.346 | 85.053 | 43.367 | 1.00 28.85 | N |
| ATOM | 7297 | C | ASN | D | 182 | 7.651 | 84.545 | 39.902 | 1.00 22.77 | C |
| ATOM | 7298 | O | ASN | D | 182 | 7.756 | 83.803 | 40.873 | 1.00 21.82 | O |
| ATOM | 7299 | N | ILE | D | 183 | 7.094 | 84.152 | 38.765 | 1.00 21.37 | N |
| ATOM | 7300 | CA | ILE | D | 183 | 6.621 | 82.785 | 38.604 | 1.00 21.47 | C |
| ATOM | 7301 | CB | ILE | D | 183 | 5.177 | 82.740 | 38.037 | 1.00 21.67 | C |
| ATOM | 7302 | CG2 | ILE | D | 183 | 4.741 | 81.300 | 37.832 | 1.00 22.50 | C |
| ATOM | 7303 | CG1 | ILE | D | 183 | 4.212 | 83.403 | 39.027 | 1.00 23.30 | C |
| ATOM | 7304 | CD1 | ILE | D | 183 | 2.766 | 83.494 | 38.540 | 1.00 21.31 | C |
| ATOM | 7305 | C | ILE | D | 183 | 7.599 | 82.108 | 37.646 | 1.00 21.34 | C |
| ATOM | 7306 | O | ILE | D | 183 | 7.918 | 82.659 | 36.589 | 1.00 21.32 | O |
| ATOM | 7307 | N | ARG | D | 184 | 8.105 | 80.936 | 38.035 | 1.00 20.53 | N |
| ATOM | 7308 | CA | ARG | D | 184 | 9.066 | 80.205 | 37.215 | 1.00 20.54 | C |
| ATOM | 7309 | CB | ARG | D | 184 | 10.233 | 79.710 | 38.071 | 1.00 21.66 | C |
| ATOM | 7310 | CG | ARG | D | 184 | 11.173 | 80.808 | 38.537 | 1.00 22.40 | C |
| ATOM | 7311 | CD | ARG | D | 184 | 12.344 | 80.221 | 39.310 | 1.00 23.43 | C |
| ATOM | 7312 | NE | ARG | D | 184 | 11.895 | 79.417 | 40.445 | 1.00 24.50 | N |
| ATOM | 7313 | CZ | ARG | D | 184 | 12.093 | 78.108 | 40.560 | 1.00 25.29 | C |
| ATOM | 7314 | NH1 | ARG | D | 184 | 12.742 | 77.445 | 39.609 | 1.00 26.74 | N |
| ATOM | 7315 | NH2 | ARG | D | 184 | 11.629 | 77.456 | 41.620 | 1.00 25.61 | N |
| ATOM | 7316 | C | ARG | D | 184 | 8.416 | 79.025 | 36.515 | 1.00 20.29 | C |
| ATOM | 7317 | O | ARG | D | 184 | 7.552 | 78.348 | 37.084 | 1.00 19.41 | O |
| ATOM | 7318 | N | VAL | D | 185 | 8.841 | 78.773 | 35.279 | 1.00 20.27 | N |
| ATOM | 7319 | CA | VAL | D | 185 | 8.270 | 77.684 | 34.495 | 1.00 19.38 | C |
| ATOM | 7320 | CB | VAL | D | 185 | 7.360 | 78.237 | 33.379 | 1.00 17.46 | C |
| ATOM | 7321 | CG1 | VAL | D | 185 | 6.514 | 77.125 | 32.802 | 1.00 18.24 | C |
| ATOM | 7322 | CG2 | VAL | D | 185 | 6.477 | 79.333 | 33.928 | 1.00 16.31 | C |
| ATOM | 7323 | C | VAL | D | 185 | 9.363 | 76.827 | 33.875 | 1.00 19.85 | C |
| ATOM | 7324 | O | VAL | D | 185 | 10.215 | 77.319 | 33.137 | 1.00 19.55 | O |
| ATOM | 7325 | N | ASN | D | 186 | 9.328 | 75.533 | 34.175 | 1.00 20.84 | N |
| ATOM | 7326 | CA | ASN | D | 186 | 10.329 | 74.608 | 33.660 | 1.00 20.67 | C |
| ATOM | 7327 | CB | ASN | D | 186 | 11.384 | 74.352 | 34.743 | 1.00 19.64 | C |
| ATOM | 7328 | CG | ASN | D | 186 | 12.192 | 75.596 | 35.072 | 1.00 19.27 | C |
| ATOM | 7329 | OD1 | ASN | D | 186 | 12.963 | 76.081 | 34.241 | 1.00 19.43 | O |
| ATOM | 7330 | ND2 | ASN | D | 186 | 12.016 | 76.122 | 36.279 | 1.00 16.41 | N |
| ATOM | 7331 | C | ASN | D | 186 | 9.684 | 73.294 | 33.220 | 1.00 21.40 | C |
| ATOM | 7332 | O | ASN | D | 186 | 8.485 | 73.075 | 33.427 | 1.00 22.82 | O |
| ATOM | 7333 | N | ALA | D | 187 | 10.480 | 72.423 | 32.612 | 1.00 20.41 | N |
| ATOM | 7334 | CA | ALA | D | 187 | 9.972 | 71.146 | 32.148 | 1.00 20.77 | C |
| ATOM | 7335 | CB | ALA | D | 187 | 9.790 | 71.173 | 30.625 | 1.00 21.23 | C |
| ATOM | 7336 | C | ALA | D | 187 | 10.935 | 70.052 | 32.533 | 1.00 20.50 | C |
| ATOM | 7337 | O | ALA | D | 187 | 12.115 | 70.314 | 32.761 | 1.00 21.34 | O |
| ATOM | 7338 | N | ILE | D | 188 | 10.424 | 68.830 | 32.639 | 1.00 19.80 | N |
| ATOM | 7339 | CA | ILE | D | 188 | 11.256 | 67.684 | 32.968 | 1.00 19.82 | C |
| ATOM | 7340 | CB | ILE | D | 188 | 10.843 | 67.006 | 34.286 | 1.00 19.57 | C |
| ATOM | 7341 | CG2 | ILE | D | 188 | 11.787 | 65.841 | 34.588 | 1.00 19.27 | C |
| ATOM | 7342 | CG1 | ILE | D | 188 | 10.906 | 68.002 | 35.436 | 1.00 19.69 | C |
| ATOM | 7343 | CD1 | ILE | D | 188 | 10.413 | 67.429 | 36.758 | 1.00 20.55 | C |

FIGURE 9 (cont.)

| | | | | | | | | | |
|---|---|---|---|---|---|---|---|---|---|
| ATOM | 7344 | C | ILE | D 188 | 11.073 | 66.685 | 31.842 | 1.00 20.33 | C |
| ATOM | 7345 | O | ILE | D 188 | 9.952 | 66.283 | 31.532 | 1.00 21.65 | O |
| ATOM | 7346 | N | SER | D 189 | 12.180 | 66.301 | 31.221 | 1.00 20.99 | N |
| ATOM | 7347 | CA | SER | D 189 | 12.155 | 65.351 | 30.118 | 1.00 20.46 | C |
| ATOM | 7348 | CB | SER | D 189 | 13.162 | 65.773 | 29.053 | 1.00 19.49 | C |
| ATOM | 7349 | OG | SER | D 189 | 12.959 | 65.077 | 27.849 | 1.00 17.48 | O |
| ATOM | 7350 | C | SER | D 189 | 12.528 | 63.996 | 30.687 | 1.00 21.37 | C |
| ATOM | 7351 | O | SER | D 189 | 13.687 | 63.742 | 31.018 | 1.00 23.05 | O |
| ATOM | 7352 | N | ALA | D 190 | 11.539 | 63.125 | 30.812 | 1.00 21.12 | N |
| ATOM | 7353 | CA | ALA | D 190 | 11.781 | 61.806 | 31.364 | 1.00 22.10 | C |
| ATOM | 7354 | CB | ALA | D 190 | 10.594 | 61.391 | 32.230 | 1.00 19.12 | C |
| ATOM | 7355 | C | ALA | D 190 | 11.998 | 60.791 | 30.253 | 1.00 22.35 | C |
| ATOM | 7356 | O | ALA | D 190 | 11.549 | 60.989 | 29.128 | 1.00 23.89 | O |
| ATOM | 7357 | N | SER | D 191 | 12.710 | 59.715 | 30.556 | 1.00 22.38 | N |
| ATOM | 7358 | CA | SER | D 191 | 12.901 | 58.665 | 29.571 | 1.00 21.76 | C |
| ATOM | 7359 | CB | SER | D 191 | 14.226 | 57.948 | 29.815 | 1.00 21.38 | C |
| ATOM | 7360 | OG | SER | D 191 | 14.402 | 57.691 | 31.194 | 1.00 23.79 | O |
| ATOM | 7361 | C | SER | D 191 | 11.711 | 57.707 | 29.770 | 1.00 21.72 | C |
| ATOM | 7362 | O | SER | D 191 | 10.975 | 57.825 | 30.747 | 1.00 21.08 | O |
| ATOM | 7363 | N | PRO | D 192 | 11.497 | 56.760 | 28.845 | 1.00 21.89 | N |
| ATOM | 7364 | CD | PRO | D 192 | 12.220 | 56.538 | 27.583 | 1.00 22.43 | C |
| ATOM | 7365 | CA | PRO | D 192 | 10.377 | 55.818 | 28.977 | 1.00 22.25 | C |
| ATOM | 7366 | CB | PRO | D 192 | 10.693 | 54.741 | 27.927 | 1.00 21.68 | C |
| ATOM | 7367 | CG | PRO | D 192 | 12.128 | 55.064 | 27.445 | 1.00 21.65 | C |
| ATOM | 7368 | C | PRO | D 192 | 10.121 | 55.230 | 30.372 | 1.00 22.53 | C |
| ATOM | 7369 | O | PRO | D 192 | 11.047 | 54.952 | 31.126 | 1.00 23.21 | O |
| ATOM | 7370 | N | ILE | D 193 | 8.846 | 55.064 | 30.711 | 1.00 22.51 | N |
| ATOM | 7371 | CA | ILE | D 193 | 8.441 | 54.509 | 32.000 | 1.00 23.78 | C |
| ATOM | 7372 | CB | ILE | D 193 | 8.194 | 55.612 | 33.065 | 1.00 23.97 | C |
| ATOM | 7373 | CG2 | ILE | D 193 | 7.773 | 54.972 | 34.381 | 1.00 24.25 | C |
| ATOM | 7374 | CG1 | ILE | D 193 | 9.465 | 56.431 | 33.309 | 1.00 24.70 | C |
| ATOM | 7375 | CD1 | ILE | D 193 | 9.265 | 57.596 | 34.294 | 1.00 23.36 | C |
| ATOM | 7376 | C | ILE | D 193 | 7.130 | 53.756 | 31.799 | 1.00 24.16 | C |
| ATOM | 7377 | O | ILE | D 193 | 6.245 | 54.217 | 31.079 | 1.00 23.31 | O |
| ATOM | 7378 | N | ARG | D 194 | 7.015 | 52.602 | 32.444 | 1.00 25.90 | N |
| ATOM | 7379 | CA | ARG | D 194 | 5.825 | 51.761 | 32.354 | 1.00 26.87 | C |
| ATOM | 7380 | CB | ARG | D 194 | 6.143 | 50.386 | 32.938 | 1.00 28.27 | C |
| ATOM | 7381 | CG | ARG | D 194 | 5.009 | 49.382 | 32.871 | 1.00 29.69 | C |
| ATOM | 7382 | CD | ARG | D 194 | 5.384 | 48.256 | 31.944 | 1.00 31.68 | C |
| ATOM | 7383 | NE | ARG | D 194 | 4.577 | 48.249 | 30.727 | 1.00 31.75 | N |
| ATOM | 7384 | CZ | ARG | D 194 | 4.867 | 47.512 | 29.658 | 1.00 32.21 | C |
| ATOM | 7385 | NH1 | ARG | D 194 | 5.949 | 46.735 | 29.660 | 1.00 29.64 | N |
| ATOM | 7386 | NH2 | ARG | D 194 | 4.070 | 47.542 | 28.595 | 1.00 31.92 | N |
| ATOM | 7387 | C | ARG | D 194 | 4.662 | 52.388 | 33.118 | 1.00 26.87 | C |
| ATOM | 7388 | O | ARG | D 194 | 4.687 | 52.465 | 34.345 | 1.00 27.44 | O |
| ATOM | 7389 | N | THR | D 195 | 3.645 | 52.840 | 32.392 | 1.00 27.18 | N |
| ATOM | 7390 | CA | THR | D 195 | 2.478 | 53.453 | 33.008 | 1.00 27.93 | C |
| ATOM | 7391 | CB | THR | D 195 | 2.699 | 54.966 | 33.259 | 1.00 28.57 | C |
| ATOM | 7392 | OG1 | THR | D 195 | 2.669 | 55.670 | 32.005 | 1.00 26.41 | O |
| ATOM | 7393 | CG2 | THR | D 195 | 4.047 | 55.207 | 33.933 | 1.00 27.80 | C |
| ATOM | 7394 | C | THR | D 195 | 1.308 | 53.298 | 32.045 | 1.00 28.18 | C |
| ATOM | 7395 | O | THR | D 195 | 1.450 | 52.665 | 31.010 | 1.00 27.90 | O |
| ATOM | 7396 | N | LEU | D 196 | 0.168 | 53.893 | 32.387 | 1.00 29.91 | N |
| ATOM | 7397 | CA | LEU | D 196 | -1.038 | 53.843 | 31.558 | 1.00 32.99 | C |
| ATOM | 7398 | CB | LEU | D 196 | -2.194 | 54.570 | 32.247 | 1.00 34.21 | C |
| ATOM | 7399 | CG | LEU | D 196 | -3.196 | 53.696 | 33.003 | 1.00 35.67 | C |
| ATOM | 7400 | CD1 | LEU | D 196 | -4.155 | 54.567 | 33.808 | 1.00 35.34 | C |
| ATOM | 7401 | CD2 | LEU | D 196 | -3.957 | 52.852 | 31.994 | 1.00 36.20 | C |
| ATOM | 7402 | C | LEU | D 196 | -0.844 | 54.455 | 30.180 | 1.00 34.54 | C |
| ATOM | 7403 | O | LEU | D 196 | -1.647 | 54.222 | 29.266 | 1.00 34.95 | O |
| ATOM | 7404 | N | SER | D 197 | 0.192 | 55.273 | 30.039 | 1.00 35.74 | N |
| ATOM | 7405 | CA | SER | D 197 | 0.489 | 55.893 | 28.753 | 1.00 36.75 | C |
| ATOM | 7406 | CB | SER | D 197 | 0.992 | 57.324 | 28.973 | 1.00 38.04 | C |
| ATOM | 7407 | OG | SER | D 197 | 2.033 | 57.349 | 29.944 | 1.00 40.88 | O |
| ATOM | 7408 | C | SER | D 197 | 1.524 | 55.060 | 27.976 | 1.00 36.78 | C |

FIGURE 9 (cont.)

```
ATOM   7409  O    SER D 197      2.028  55.489  26.940  1.00 37.59           O
ATOM   7410  N    ALA D 198      1.820  53.856  28.469  1.00 37.04           N
ATOM   7411  CA   ALA D 198      2.776  52.954  27.809  1.00 36.96           C
ATOM   7412  CB   ALA D 198      3.867  52.546  28.774  1.00 36.77           C
ATOM   7413  C    ALA D 198      2.043  51.709  27.311  1.00 37.75           C
ATOM   7414  O    ALA D 198      2.581  50.915  26.529  1.00 38.17           O
ATOM   7415  N    LYS D 199      0.818  51.531  27.793  1.00 37.86           N
ATOM   7416  CA   LYS D 199     -0.007  50.399  27.398  1.00 37.79           C
ATOM   7417  CB   LYS D 199     -1.159  50.211  28.377  1.00 37.66           C
ATOM   7418  CG   LYS D 199     -2.234  49.243  27.901  1.00 38.64           C
ATOM   7419  CD   LYS D 199     -3.248  49.004  29.020  1.00 39.41           C
ATOM   7420  CE   LYS D 199     -4.629  48.656  28.484  1.00 39.37           C
ATOM   7421  NZ   LYS D 199     -5.626  48.719  29.605  1.00 39.51           N
ATOM   7422  C    LYS D 199     -0.559  50.661  26.008  1.00 38.18           C
ATOM   7423  O    LYS D 199     -1.472  51.476  25.836  1.00 37.95           O
ATOM   7424  N    GLY D 200      0.012  49.967  25.022  1.00 38.16           N
ATOM   7425  CA   GLY D 200     -0.414  50.127  23.646  1.00 36.98           C
ATOM   7426  C    GLY D 200      0.740  50.466  22.720  1.00 36.66           C
ATOM   7427  O    GLY D 200      0.692  50.172  21.522  1.00 36.40           O
ATOM   7428  N    VAL D 201      1.787  51.093  23.243  1.00 36.25           N
ATOM   7429  CA   VAL D 201      2.900  51.431  22.367  1.00 36.18           C
ATOM   7430  CB   VAL D 201      3.881  52.463  23.026  1.00 35.70           C
ATOM   7431  CG1  VAL D 201      3.086  53.484  23.834  1.00 35.45           C
ATOM   7432  CG2  VAL D 201      4.907  51.766  23.882  1.00 35.76           C
ATOM   7433  C    VAL D 201      3.607  50.124  22.058  1.00 35.71           C
ATOM   7434  O    VAL D 201      4.005  49.396  22.964  1.00 35.56           O
ATOM   7435  N    GLY D 202      3.731  49.807  20.773  1.00 36.18           N
ATOM   7436  CA   GLY D 202      4.378  48.560  20.390  1.00 35.82           C
ATOM   7437  C    GLY D 202      5.827  48.491  20.831  1.00 35.92           C
ATOM   7438  O    GLY D 202      6.557  49.489  20.750  1.00 35.70           O
ATOM   7439  N    GLY D 203      6.244  47.315  21.293  1.00 35.08           N
ATOM   7440  CA   GLY D 203      7.617  47.126  21.728  1.00 34.62           C
ATOM   7441  C    GLY D 203      8.045  48.047  22.857  1.00 34.79           C
ATOM   7442  O    GLY D 203      9.029  48.791  22.728  1.00 35.42           O
ATOM   7443  N    PHE D 204      7.332  48.005  23.977  1.00 33.10           N
ATOM   7444  CA   PHE D 204      7.705  48.871  25.080  1.00 31.99           C
ATOM   7445  CB   PHE D 204      6.532  49.106  26.012  1.00 30.25           C
ATOM   7446  CG   PHE D 204      6.757  50.235  26.951  1.00 30.79           C
ATOM   7447  CD1  PHE D 204      7.261  50.012  28.217  1.00 30.44           C
ATOM   7448  CD2  PHE D 204      6.530  51.543  26.540  1.00 31.64           C
ATOM   7449  CE1  PHE D 204      7.540  51.074  29.062  1.00 30.49           C
ATOM   7450  CE2  PHE D 204      6.808  52.617  27.382  1.00 31.17           C
ATOM   7451  CZ   PHE D 204      7.315  52.373  28.644  1.00 30.99           C
ATOM   7452  C    PHE D 204      8.875  48.292  25.855  1.00 32.33           C
ATOM   7453  O    PHE D 204      9.758  49.021  26.317  1.00 32.16           O
ATOM   7454  N    ASN D 205      8.892  46.977  26.004  1.00 32.00           N
ATOM   7455  CA   ASN D 205      9.991  46.350  26.714  1.00 32.08           C
ATOM   7456  CB   ASN D 205      9.720  44.862  26.932  1.00 32.82           C
ATOM   7457  CG   ASN D 205      8.678  44.623  27.997  1.00 35.75           C
ATOM   7458  OD1  ASN D 205      8.352  43.472  28.326  1.00 36.47           O
ATOM   7459  ND2  ASN D 205      8.138  45.718  28.552  1.00 36.62           N
ATOM   7460  C    ASN D 205     11.297  46.518  25.953  1.00 30.72           C
ATOM   7461  O    ASN D 205     12.362  46.562  26.567  1.00 30.86           O
ATOM   7462  N    THR D 206     11.223  46.598  24.626  1.00 29.07           N
ATOM   7463  CA   THR D 206     12.439  46.751  23.832  1.00 28.78           C
ATOM   7464  CB   THR D 206     12.204  46.355  22.353  1.00 29.37           C
ATOM   7465  OG1  THR D 206     11.706  45.008  22.300  1.00 29.24           O
ATOM   7466  CG2  THR D 206     13.521  46.412  21.564  1.00 27.96           C
ATOM   7467  C    THR D 206     12.948  48.192  23.922  1.00 28.34           C
ATOM   7468  O    THR D 206     14.154  48.446  23.801  1.00 26.59           O
ATOM   7469  N    ILE D 207     12.011  49.120  24.138  1.00 27.81           N
ATOM   7470  CA   ILE D 207     12.308  50.538  24.297  1.00 27.23           C
ATOM   7471  CB   ILE D 207     11.012  51.378  24.295  1.00 28.09           C
ATOM   7472  CG2  ILE D 207     11.224  52.670  25.068  1.00 28.08           C
ATOM   7473  CG1  ILE D 207     10.562  51.654  22.852  1.00 28.36           C
```

FIGURE 9 (cont.)

| | | | | | | | | | |
|---|---|---|---|---|---|---|---|---|---|
| ATOM | 7474 | CD1 | ILE D 207 | 9.198 | 52.324 | 22.760 | 1.00 | 27.03 | C |
| ATOM | 7475 | C | ILE D 207 | 12.986 | 50.706 | 25.648 | 1.00 | 27.42 | C |
| ATOM | 7476 | O | ILE D 207 | 13.838 | 51.579 | 25.822 | 1.00 | 27.63 | O |
| ATOM | 7477 | N | LEU D 208 | 12.587 | 49.878 | 26.613 | 1.00 | 27.08 | N |
| ATOM | 7478 | CA | LEU D 208 | 13.176 | 49.913 | 27.947 | 1.00 | 26.27 | C |
| ATOM | 7479 | CB | LEU D 208 | 12.316 | 49.118 | 28.938 | 1.00 | 25.49 | C |
| ATOM | 7480 | CG | LEU D 208 | 11.125 | 49.898 | 29.502 | 1.00 | 25.02 | C |
| ATOM | 7481 | CD1 | LEU D 208 | 10.489 | 50.678 | 28.373 | 1.00 | 27.20 | C |
| ATOM | 7482 | CD2 | LEU D 208 | 10.113 | 48.965 | 30.152 | 1.00 | 24.02 | C |
| ATOM | 7483 | C | LEU D 208 | 14.574 | 49.318 | 27.880 | 1.00 | 27.30 | C |
| ATOM | 7484 | O | LEU D 208 | 15.518 | 49.856 | 28.469 | 1.00 | 28.63 | O |
| ATOM | 7485 | N | LYS D 209 | 14.716 | 48.220 | 27.146 | 1.00 | 26.43 | N |
| ATOM | 7486 | CA | LYS D 209 | 16.020 | 47.578 | 27.023 | 1.00 | 26.95 | C |
| ATOM | 7487 | CB | LYS D 209 | 15.951 | 46.362 | 26.087 | 1.00 | 27.60 | C |
| ATOM | 7488 | CG | LYS D 209 | 14.931 | 45.293 | 26.507 | 1.00 | 31.84 | C |
| ATOM | 7489 | CD | LYS D 209 | 15.120 | 43.963 | 25.729 | 1.00 | 33.28 | C |
| ATOM | 7490 | CE | LYS D 209 | 14.136 | 42.893 | 26.243 | 1.00 | 34.02 | C |
| ATOM | 7491 | NZ | LYS D 209 | 14.694 | 41.505 | 26.165 | 1.00 | 34.53 | N |
| ATOM | 7492 | C | LYS D 209 | 17.067 | 48.553 | 26.500 | 1.00 | 25.87 | C |
| ATOM | 7493 | O | LYS D 209 | 18.153 | 48.662 | 27.076 | 1.00 | 25.60 | O |
| ATOM | 7494 | N | GLU D 210 | 16.739 | 49.248 | 25.410 | 1.00 | 24.91 | N |
| ATOM | 7495 | CA | GLU D 210 | 17.657 | 50.207 | 24.791 | 1.00 | 25.78 | C |
| ATOM | 7496 | CB | GLU D 210 | 16.939 | 51.027 | 23.707 | 1.00 | 27.15 | C |
| ATOM | 7497 | CG | GLU D 210 | 17.838 | 52.054 | 23.027 | 1.00 | 29.22 | C |
| ATOM | 7498 | CD | GLU D 210 | 17.185 | 52.737 | 21.829 | 1.00 | 31.07 | C |
| ATOM | 7499 | OE1 | GLU D 210 | 17.865 | 53.553 | 21.170 | 1.00 | 31.71 | O |
| ATOM | 7500 | OE2 | GLU D 210 | 15.996 | 52.470 | 21.541 | 1.00 | 33.80 | O |
| ATOM | 7501 | C | GLU D 210 | 18.266 | 51.163 | 25.814 | 1.00 | 25.17 | C |
| ATOM | 7502 | O | GLU D 210 | 19.486 | 51.233 | 25.951 | 1.00 | 24.95 | O |
| ATOM | 7503 | N | ILE D 211 | 17.412 | 51.898 | 26.523 | 1.00 | 23.78 | N |
| ATOM | 7504 | CA | ILE D 211 | 17.865 | 52.838 | 27.529 | 1.00 | 23.75 | C |
| ATOM | 7505 | CB | ILE D 211 | 16.661 | 53.462 | 28.294 | 1.00 | 23.89 | C |
| ATOM | 7506 | CG2 | ILE D 211 | 17.090 | 53.871 | 29.695 | 1.00 | 22.86 | C |
| ATOM | 7507 | CG1 | ILE D 211 | 16.134 | 54.698 | 27.548 | 1.00 | 23.59 | C |
| ATOM | 7508 | CD1 | ILE D 211 | 15.745 | 54.454 | 26.136 | 1.00 | 24.74 | C |
| ATOM | 7509 | C | ILE D 211 | 18.798 | 52.138 | 28.516 | 1.00 | 24.77 | C |
| ATOM | 7510 | O | ILE D 211 | 19.842 | 52.671 | 28.878 | 1.00 | 25.14 | O |
| ATOM | 7511 | N | GLU D 212 | 18.420 | 50.940 | 28.947 | 1.00 | 24.88 | N |
| ATOM | 7512 | CA | GLU D 212 | 19.228 | 50.174 | 29.887 | 1.00 | 24.83 | C |
| ATOM | 7513 | CB | GLU D 212 | 18.413 | 48.988 | 30.416 | 1.00 | 25.84 | C |
| ATOM | 7514 | CG | GLU D 212 | 19.233 | 47.823 | 30.925 | 1.00 | 27.94 | C |
| ATOM | 7515 | CD | GLU D 212 | 18.370 | 46.742 | 31.566 | 1.00 | 29.84 | C |
| ATOM | 7516 | OE1 | GLU D 212 | 17.252 | 46.472 | 31.059 | 1.00 | 29.40 | O |
| ATOM | 7517 | OE2 | GLU D 212 | 18.816 | 46.153 | 32.579 | 1.00 | 32.19 | O |
| ATOM | 7518 | C | GLU D 212 | 20.522 | 49.685 | 29.251 | 1.00 | 24.86 | C |
| ATOM | 7519 | O | GLU D 212 | 21.524 | 49.493 | 29.946 | 1.00 | 23.81 | O |
| ATOM | 7520 | N | GLU D 213 | 20.509 | 49.502 | 27.929 | 1.00 | 24.87 | N |
| ATOM | 7521 | CA | GLU D 213 | 21.698 | 49.030 | 27.207 | 1.00 | 25.12 | C |
| ATOM | 7522 | CB | GLU D 213 | 21.296 | 48.213 | 25.964 | 1.00 | 26.44 | C |
| ATOM | 7523 | CG | GLU D 213 | 20.824 | 46.780 | 26.239 | 1.00 | 30.39 | C |
| ATOM | 7524 | CD | GLU D 213 | 20.246 | 46.076 | 24.995 | 1.00 | 33.43 | C |
| ATOM | 7525 | OE1 | GLU D 213 | 20.167 | 44.822 | 25.008 | 1.00 | 34.06 | O |
| ATOM | 7526 | OE2 | GLU D 213 | 19.858 | 46.763 | 24.012 | 1.00 | 34.36 | O |
| ATOM | 7527 | C | GLU D 213 | 22.636 | 50.144 | 26.748 | 1.00 | 24.81 | C |
| ATOM | 7528 | O | GLU D 213 | 23.856 | 49.946 | 26.684 | 1.00 | 25.97 | O |
| ATOM | 7529 | N | ARG D 214 | 22.076 | 51.309 | 26.434 | 1.00 | 22.96 | N |
| ATOM | 7530 | CA | ARG D 214 | 22.862 | 52.426 | 25.903 | 1.00 | 21.61 | C |
| ATOM | 7531 | CB | ARG D 214 | 22.279 | 52.868 | 24.555 | 1.00 | 20.29 | C |
| ATOM | 7532 | CG | ARG D 214 | 22.123 | 51.756 | 23.517 | 1.00 | 20.32 | C |
| ATOM | 7533 | CD | ARG D 214 | 21.393 | 52.306 | 22.297 | 1.00 | 17.79 | C |
| ATOM | 7534 | NE | ARG D 214 | 22.115 | 53.471 | 21.804 | 1.00 | 18.30 | N |
| ATOM | 7535 | CZ | ARG D 214 | 21.560 | 54.508 | 21.194 | 1.00 | 16.89 | C |
| ATOM | 7536 | NH1 | ARG D 214 | 20.251 | 54.538 | 20.987 | 1.00 | 14.98 | N |
| ATOM | 7537 | NH2 | ARG D 214 | 22.328 | 55.525 | 20.813 | 1.00 | 16.32 | N |
| ATOM | 7538 | C | ARG D 214 | 23.020 | 53.672 | 26.773 | 1.00 | 21.16 | C |

FIGURE 9 (cont.)

```
ATOM   7539  O    ARG D 214      23.981  54.429  26.589  1.00 21.60           O
ATOM   7540  N    ALA D 215      22.088  53.907  27.693  1.00 19.77           N
ATOM   7541  CA   ALA D 215      22.170  55.082  28.555  1.00 19.11           C
ATOM   7542  CB   ALA D 215      20.952  55.166  29.449  1.00 19.32           C
ATOM   7543  C    ALA D 215      23.439  55.024  29.399  1.00 20.41           C
ATOM   7544  O    ALA D 215      23.867  53.946  29.823  1.00 21.87           O
ATOM   7545  N    PRO D 216      24.061  56.184  29.655  1.00 19.93           N
ATOM   7546  CD   PRO D 216      23.711  57.534  29.184  1.00 19.84           C
ATOM   7547  CA   PRO D 216      25.287  56.215  30.452  1.00 19.50           C
ATOM   7548  CB   PRO D 216      25.557  57.707  30.604  1.00 19.06           C
ATOM   7549  CG   PRO D 216      25.022  58.268  29.332  1.00 19.27           C
ATOM   7550  C    PRO D 216      25.157  55.501  31.795  1.00 19.64           C
ATOM   7551  O    PRO D 216      26.085  54.823  32.223  1.00 19.55           O
ATOM   7552  N    LEU D 217      24.012  55.647  32.459  1.00 19.61           N
ATOM   7553  CA   LEU D 217      23.824  54.995  33.752  1.00 19.52           C
ATOM   7554  CB   LEU D 217      22.777  55.740  34.591  1.00 18.26           C
ATOM   7555  CG   LEU D 217      23.117  57.166  35.050  1.00 18.41           C
ATOM   7556  CD1  LEU D 217      21.960  57.743  35.842  1.00 16.44           C
ATOM   7557  CD2  LEU D 217      24.378  57.162  35.897  1.00 15.94           C
ATOM   7558  C    LEU D 217      23.440  53.520  33.613  1.00 20.29           C
ATOM   7559  O    LEU D 217      23.361  52.802  34.607  1.00 21.52           O
ATOM   7560  N    LYS D 218      23.212  53.069  32.382  1.00 20.51           N
ATOM   7561  CA   LYS D 218      22.861  51.672  32.115  1.00 20.54           C
ATOM   7562  CB   LYS D 218      24.048  50.739  32.411  1.00 19.75           C
ATOM   7563  CG   LYS D 218      25.291  50.980  31.561  1.00 19.83           C
ATOM   7564  CD   LYS D 218      25.067  50.607  30.102  1.00 23.33           C
ATOM   7565  CE   LYS D 218      26.247  51.063  29.245  1.00 25.00           C
ATOM   7566  NZ   LYS D 218      26.102  50.674  27.821  1.00 26.37           N
ATOM   7567  C    LYS D 218      21.666  51.209  32.929  1.00 19.80           C
ATOM   7568  O    LYS D 218      21.684  50.122  33.497  1.00 19.36           O
ATOM   7569  N    ARG D 219      20.630  52.032  32.987  1.00 19.16           N
ATOM   7570  CA   ARG D 219      19.434  51.669  33.726  1.00 19.96           C
ATOM   7571  CB   ARG D 219      19.681  51.731  35.229  1.00 18.12           C
ATOM   7572  CG   ARG D 219      19.709  53.155  35.774  1.00 20.99           C
ATOM   7573  CD   ARG D 219      20.124  53.162  37.227  1.00 19.92           C
ATOM   7574  NE   ARG D 219      20.326  54.500  37.768  1.00 22.01           N
ATOM   7575  CZ   ARG D 219      19.359  55.379  38.013  1.00 23.40           C
ATOM   7576  NH1  ARG D 219      18.092  55.078  37.760  1.00 24.67           N
ATOM   7577  NH2  ARG D 219      19.660  56.560  38.537  1.00 24.01           N
ATOM   7578  C    ARG D 219      18.318  52.633  33.380  1.00 21.11           C
ATOM   7579  O    ARG D 219      18.564  53.729  32.879  1.00 20.76           O
ATOM   7580  N    ASN D 220      17.091  52.210  33.655  1.00 21.73           N
ATOM   7581  CA   ASN D 220      15.918  53.029  33.405  1.00 23.07           C
ATOM   7582  CB   ASN D 220      14.723  52.131  33.054  1.00 23.47           C
ATOM   7583  CG   ASN D 220      14.671  51.788  31.583  1.00 24.47           C
ATOM   7584  OD1  ASN D 220      14.600  52.678  30.738  1.00 25.99           O
ATOM   7585  ND2  ASN D 220      14.708  50.495  31.264  1.00 23.98           N
ATOM   7586  C    ASN D 220      15.615  53.835  34.666  1.00 23.23           C
ATOM   7587  O    ASN D 220      16.121  53.512  35.750  1.00 22.78           O
ATOM   7588  N    VAL D 221      14.799  54.879  34.534  1.00 23.27           N
ATOM   7589  CA   VAL D 221      14.440  55.696  35.696  1.00 23.55           C
ATOM   7590  CB   VAL D 221      14.356  57.204  35.342  1.00 22.69           C
ATOM   7591  CG1  VAL D 221      15.728  57.716  34.881  1.00 21.77           C
ATOM   7592  CG2  VAL D 221      13.303  57.430  34.255  1.00 21.77           C
ATOM   7593  C    VAL D 221      13.077  55.251  36.206  1.00 24.02           C
ATOM   7594  O    VAL D 221      12.466  54.343  35.641  1.00 25.09           O
ATOM   7595  N    ASP D 222      12.614  55.869  37.291  1.00 25.17           N
ATOM   7596  CA   ASP D 222      11.291  55.567  37.823  1.00 25.83           C
ATOM   7597  CB   ASP D 222      11.354  54.721  39.100  1.00 28.69           C
ATOM   7598  CG   ASP D 222      12.268  55.305  40.160  1.00 30.94           C
ATOM   7599  OD1  ASP D 222      12.348  56.544  40.280  1.00 31.74           O
ATOM   7600  OD2  ASP D 222      12.896  54.511  40.892  1.00 32.94           O
ATOM   7601  C    ASP D 222      10.588  56.873  38.104  1.00 25.98           C
ATOM   7602  O    ASP D 222      11.206  57.939  38.055  1.00 26.07           O
ATOM   7603  N    GLN D 223       9.293  56.790  38.387  1.00 25.74           N
```

FIGURE 9 (cont.)

```
ATOM   7604  CA   GLN D 223       8.479  57.969  38.663  1.00 25.78           C
ATOM   7605  CB   GLN D 223       7.022  57.557  38.918  1.00 27.76           C
ATOM   7606  CG   GLN D 223       6.805  56.047  39.027  1.00 30.44           C
ATOM   7607  CD   GLN D 223       6.450  55.423  37.707  1.00 30.58           C
ATOM   7608  OE1  GLN D 223       6.179  54.218  37.619  1.00 30.70           O
ATOM   7609  NE2  GLN D 223       6.437  56.243  36.658  1.00 32.58           N
ATOM   7610  C    GLN D 223       9.010  58.741  39.859  1.00 25.15           C
ATOM   7611  O    GLN D 223       8.940  59.972  39.901  1.00 23.68           O
ATOM   7612  N    VAL D 224       9.535  58.009  40.836  1.00 25.15           N
ATOM   7613  CA   VAL D 224      10.079  58.626  42.036  1.00 24.24           C
ATOM   7614  CB   VAL D 224      10.486  57.559  43.066  1.00 25.19           C
ATOM   7615  CG1  VAL D 224      11.511  58.140  44.064  1.00 24.45           C
ATOM   7616  CG2  VAL D 224       9.247  57.077  43.809  1.00 23.37           C
ATOM   7617  C    VAL D 224      11.283  59.498  41.692  1.00 24.84           C
ATOM   7618  O    VAL D 224      11.392  60.618  42.178  1.00 24.22           O
ATOM   7619  N    GLU D 225      12.182  58.987  40.854  1.00 25.31           N
ATOM   7620  CA   GLU D 225      13.357  59.758  40.448  1.00 25.11           C
ATOM   7621  CB   GLU D 225      14.271  58.935  39.516  1.00 25.22           C
ATOM   7622  CG   GLU D 225      15.102  57.884  40.262  1.00 26.21           C
ATOM   7623  CD   GLU D 225      16.226  57.272  39.419  1.00 27.96           C
ATOM   7624  OE1  GLU D 225      15.940  56.384  38.571  1.00 26.61           O
ATOM   7625  OE2  GLU D 225      17.398  57.683  39.615  1.00 26.44           O
ATOM   7626  C    GLU D 225      12.923  61.049  39.767  1.00 23.94           C
ATOM   7627  O    GLU D 225      13.566  62.080  39.934  1.00 25.29           O
ATOM   7628  N    VAL D 226      11.838  60.997  38.994  1.00 23.05           N
ATOM   7629  CA   VAL D 226      11.332  62.195  38.335  1.00 21.94           C
ATOM   7630  CB   VAL D 226      10.138  61.891  37.402  1.00 22.52           C
ATOM   7631  CG1  VAL D 226       9.323  63.167  37.162  1.00 21.18           C
ATOM   7632  CG2  VAL D 226      10.632  61.337  36.081  1.00 22.64           C
ATOM   7633  C    VAL D 226      10.845  63.141  39.424  1.00 22.24           C
ATOM   7634  O    VAL D 226      11.125  64.342  39.383  1.00 22.34           O
ATOM   7635  N    GLY D 227      10.119  62.580  40.396  1.00 21.91           N
ATOM   7636  CA   GLY D 227       9.579  63.360  41.500  1.00 19.44           C
ATOM   7637  C    GLY D 227      10.622  64.123  42.288  1.00 19.27           C
ATOM   7638  O    GLY D 227      10.363  65.220  42.787  1.00 19.07           O
ATOM   7639  N    LYS D 228      11.813  63.552  42.410  1.00 19.49           N
ATOM   7640  CA   LYS D 228      12.875  64.222  43.149  1.00 19.39           C
ATOM   7641  CB   LYS D 228      14.046  63.257  43.384  1.00 20.00           C
ATOM   7642  CG   LYS D 228      13.672  62.094  44.324  1.00 20.91           C
ATOM   7643  CD   LYS D 228      14.868  61.264  44.782  1.00 19.63           C
ATOM   7644  CE   LYS D 228      15.521  60.504  43.633  1.00 20.67           C
ATOM   7645  NZ   LYS D 228      16.647  59.644  44.121  1.00 19.83           N
ATOM   7646  C    LYS D 228      13.331  65.477  42.400  1.00 19.87           C
ATOM   7647  O    LYS D 228      13.632  66.501  43.017  1.00 18.15           O
ATOM   7648  N    THR D 229      13.377  65.407  41.070  1.00 19.15           N
ATOM   7649  CA   THR D 229      13.774  66.575  40.296  1.00 19.56           C
ATOM   7650  CB   THR D 229      14.122  66.202  38.843  1.00 19.31           C
ATOM   7651  OG1  THR D 229      15.325  65.434  38.836  1.00 18.83           O
ATOM   7652  CG2  THR D 229      14.336  67.469  37.995  1.00 19.32           C
ATOM   7653  C    THR D 229      12.651  67.623  40.296  1.00 19.39           C
ATOM   7654  O    THR D 229      12.908  68.827  40.214  1.00 19.76           O
ATOM   7655  N    ALA D 230      11.409  67.169  40.396  1.00 18.11           N
ATOM   7656  CA   ALA D 230      10.283  68.093  40.413  1.00 18.47           C
ATOM   7657  CB   ALA D 230       8.970  67.335  40.214  1.00 18.88           C
ATOM   7658  C    ALA D 230      10.269  68.835  41.743  1.00 18.64           C
ATOM   7659  O    ALA D 230       9.828  69.986  41.825  1.00 18.89           O
ATOM   7660  N    ALA D 231      10.750  68.169  42.791  1.00 18.54           N
ATOM   7661  CA   ALA D 231      10.800  68.799  44.107  1.00 18.77           C
ATOM   7662  CB   ALA D 231      11.265  67.783  45.168  1.00 16.53           C
ATOM   7663  C    ALA D 231      11.788  69.959  43.991  1.00 17.93           C
ATOM   7664  O    ALA D 231      11.540  71.055  44.493  1.00 18.56           O
ATOM   7665  N    TYR D 232      12.903  69.705  43.307  1.00 17.47           N
ATOM   7666  CA   TYR D 232      13.933  70.723  43.086  1.00 17.85           C
ATOM   7667  CB   TYR D 232      15.093  70.113  42.289  1.00 15.86           C
ATOM   7668  CG   TYR D 232      16.009  71.099  41.596  1.00 13.50           C
```

FIGURE 9 (cont.)

| ATOM | 7669 | CD1 | TYR D 232 | 16.730 | 72.048 | 42.315 | 1.00 13.15 | C |
| ATOM | 7670 | CE1 | TYR D 232 | 17.601 | 72.924 | 41.678 | 1.00 11.49 | C |
| ATOM | 7671 | CD2 | TYR D 232 | 16.181 | 71.055 | 40.215 | 1.00 14.05 | C |
| ATOM | 7672 | CE2 | TYR D 232 | 17.053 | 71.929 | 39.563 | 1.00 12.53 | C |
| ATOM | 7673 | CZ | TYR D 232 | 17.757 | 72.857 | 40.295 | 1.00 12.22 | C |
| ATOM | 7674 | OH | TYR D 232 | 18.612 | 73.721 | 39.649 | 1.00 11.78 | O |
| ATOM | 7675 | C | TYR D 232 | 13.345 | 71.927 | 42.338 | 1.00 18.70 | C |
| ATOM | 7676 | O | TYR D 232 | 13.474 | 73.070 | 42.782 | 1.00 21.24 | O |
| ATOM | 7677 | N | LEU D 233 | 12.675 | 71.667 | 41.222 | 1.00 17.43 | N |
| ATOM | 7678 | CA | LEU D 233 | 12.089 | 72.737 | 40.419 | 1.00 19.39 | C |
| ATOM | 7679 | CB | LEU D 233 | 11.636 | 72.180 | 39.069 | 1.00 18.07 | C |
| ATOM | 7680 | CG | LEU D 233 | 12.755 | 71.728 | 38.125 | 1.00 17.71 | C |
| ATOM | 7681 | CD1 | LEU D 233 | 12.168 | 70.868 | 37.012 | 1.00 15.34 | C |
| ATOM | 7682 | CD2 | LEU D 233 | 13.484 | 72.967 | 37.570 | 1.00 14.80 | C |
| ATOM | 7683 | C | LEU D 233 | 10.919 | 73.474 | 41.078 | 1.00 19.94 | C |
| ATOM | 7684 | O | LEU D 233 | 10.733 | 74.673 | 40.868 | 1.00 19.00 | O |
| ATOM | 7685 | N | LEU D 234 | 10.128 | 72.760 | 41.867 | 1.00 20.55 | N |
| ATOM | 7686 | CA | LEU D 234 | 8.985 | 73.369 | 42.523 | 1.00 20.44 | C |
| ATOM | 7687 | CB | LEU D 234 | 7.994 | 72.276 | 42.945 | 1.00 19.31 | C |
| ATOM | 7688 | CG | LEU D 234 | 7.179 | 71.593 | 41.832 | 1.00 17.88 | C |
| ATOM | 7689 | CD1 | LEU D 234 | 6.232 | 70.569 | 42.453 | 1.00 17.94 | C |
| ATOM | 7690 | CD2 | LEU D 234 | 6.372 | 72.634 | 41.043 | 1.00 16.26 | C |
| ATOM | 7691 | C | LEU D 234 | 9.355 | 74.245 | 43.727 | 1.00 22.03 | C |
| ATOM | 7692 | O | LEU D 234 | 8.655 | 75.212 | 44.041 | 1.00 22.76 | O |
| ATOM | 7693 | N | SER D 235 | 10.455 | 73.925 | 44.395 | 1.00 22.11 | N |
| ATOM | 7694 | CA | SER D 235 | 10.850 | 74.690 | 45.568 | 1.00 23.11 | C |
| ATOM | 7695 | CB | SER D 235 | 11.437 | 73.754 | 46.619 | 1.00 24.17 | C |
| ATOM | 7696 | OG | SER D 235 | 12.546 | 73.048 | 46.085 | 1.00 25.03 | O |
| ATOM | 7697 | C | SER D 235 | 11.824 | 75.830 | 45.310 | 1.00 23.97 | C |
| ATOM | 7698 | O | SER D 235 | 12.109 | 76.185 | 44.164 | 1.00 24.14 | O |
| ATOM | 7699 | N | ASP D 236 | 12.329 | 76.394 | 46.404 | 1.00 24.78 | N |
| ATOM | 7700 | CA | ASP D 236 | 13.255 | 77.520 | 46.376 | 1.00 25.33 | C |
| ATOM | 7701 | CB | ASP D 236 | 13.257 | 78.213 | 47.749 | 1.00 28.75 | C |
| ATOM | 7702 | CG | ASP D 236 | 14.546 | 78.995 | 48.021 | 1.00 32.37 | C |
| ATOM | 7703 | OD1 | ASP D 236 | 14.779 | 80.028 | 47.343 | 1.00 33.18 | O |
| ATOM | 7704 | OD2 | ASP D 236 | 15.328 | 78.571 | 48.919 | 1.00 33.49 | O |
| ATOM | 7705 | C | ASP D 236 | 14.665 | 77.095 | 46.011 | 1.00 24.52 | C |
| ATOM | 7706 | O | ASP D 236 | 15.483 | 77.929 | 45.636 | 1.00 24.49 | O |
| ATOM | 7707 | N | LEU D 237 | 14.951 | 75.803 | 46.111 | 1.00 23.41 | N |
| ATOM | 7708 | CA | LEU D 237 | 16.289 | 75.320 | 45.786 | 1.00 23.99 | C |
| ATOM | 7709 | CB | LEU D 237 | 16.377 | 73.787 | 45.896 | 1.00 26.29 | C |
| ATOM | 7710 | CG | LEU D 237 | 17.392 | 73.163 | 46.867 | 1.00 27.93 | C |
| ATOM | 7711 | CD1 | LEU D 237 | 17.563 | 71.686 | 46.539 | 1.00 26.63 | C |
| ATOM | 7712 | CD2 | LEU D 237 | 18.732 | 73.878 | 46.769 | 1.00 28.54 | C |
| ATOM | 7713 | C | LEU D 237 | 16.669 | 75.706 | 44.372 | 1.00 23.11 | C |
| ATOM | 7714 | O | LEU D 237 | 17.855 | 75.880 | 44.074 | 1.00 23.87 | O |
| ATOM | 7715 | N | SER D 238 | 15.666 | 75.833 | 43.502 | 1.00 21.12 | N |
| ATOM | 7716 | CA | SER D 238 | 15.914 | 76.160 | 42.102 | 1.00 20.68 | C |
| ATOM | 7717 | CB | SER D 238 | 15.080 | 75.241 | 41.200 | 1.00 19.62 | C |
| ATOM | 7718 | OG | SER D 238 | 13.704 | 75.328 | 41.516 | 1.00 18.27 | O |
| ATOM | 7719 | C | SER D 238 | 15.672 | 77.610 | 41.702 | 1.00 20.42 | C |
| ATOM | 7720 | O | SER D 238 | 15.309 | 77.887 | 40.555 | 1.00 19.49 | O |
| ATOM | 7721 | N | SER D 239 | 15.861 | 78.536 | 42.637 | 1.00 20.39 | N |
| ATOM | 7722 | CA | SER D 239 | 15.671 | 79.948 | 42.323 | 1.00 20.27 | C |
| ATOM | 7723 | CB | SER D 239 | 15.846 | 80.810 | 43.588 | 1.00 18.85 | C |
| ATOM | 7724 | OG | SER D 239 | 17.147 | 80.670 | 44.141 | 1.00 18.91 | O |
| ATOM | 7725 | C | SER D 239 | 16.703 | 80.341 | 41.258 | 1.00 20.69 | C |
| ATOM | 7726 | O | SER D 239 | 17.867 | 79.935 | 41.327 | 1.00 21.99 | O |
| ATOM | 7727 | N | GLY D 240 | 16.288 | 81.128 | 40.273 | 1.00 19.78 | N |
| ATOM | 7728 | CA | GLY D 240 | 17.224 | 81.517 | 39.235 | 1.00 19.06 | C |
| ATOM | 7729 | C | GLY D 240 | 17.165 | 80.576 | 38.042 | 1.00 19.50 | C |
| ATOM | 7730 | O | GLY D 240 | 17.922 | 80.727 | 37.078 | 1.00 17.54 | O |
| ATOM | 7731 | N | VAL D 241 | 16.253 | 79.608 | 38.099 | 1.00 18.13 | N |
| ATOM | 7732 | CA | VAL D 241 | 16.111 | 78.649 | 37.015 | 1.00 17.29 | C |
| ATOM | 7733 | CB | VAL D 241 | 16.416 | 77.206 | 37.494 | 1.00 16.67 | C |

FIGURE 9 (cont.)

| | | | | | | | | | |
|---|---|---|---|---|---|---|---|---|---|
| ATOM | 7734 | CG1 | VAL | D | 241 | 16.166 | 76.216 | 36.361 | 1.00 14.58 | C |
| ATOM | 7735 | CG2 | VAL | D | 241 | 17.860 | 77.106 | 37.969 | 1.00 13.97 | C |
| ATOM | 7736 | C | VAL | D | 241 | 14.706 | 78.679 | 36.451 | 1.00 18.05 | C |
| ATOM | 7737 | O | VAL | D | 241 | 13.753 | 78.359 | 37.158 | 1.00 20.88 | O |
| ATOM | 7738 | N | THR | D | 242 | 14.575 | 79.084 | 35.189 | 1.00 18.02 | N |
| ATOM | 7739 | CA | THR | D | 242 | 13.277 | 79.119 | 34.528 | 1.00 18.11 | C |
| ATOM | 7740 | CB | THR | D | 242 | 12.520 | 80.442 | 34.802 | 1.00 18.97 | C |
| ATOM | 7741 | OG1 | THR | D | 242 | 11.150 | 80.284 | 34.407 | 1.00 18.72 | O |
| ATOM | 7742 | CG2 | THR | D | 242 | 13.124 | 81.600 | 34.002 | 1.00 18.30 | C |
| ATOM | 7743 | C | THR | D | 242 | 13.448 | 78.932 | 33.022 | 1.00 18.25 | C |
| ATOM | 7744 | O | THR | D | 242 | 14.487 | 79.283 | 32.455 | 1.00 20.06 | O |
| ATOM | 7745 | N | GLY | D | 243 | 12.427 | 78.387 | 32.371 | 1.00 18.09 | N |
| ATOM | 7746 | CA | GLY | D | 243 | 12.510 | 78.148 | 30.942 | 1.00 18.92 | C |
| ATOM | 7747 | C | GLY | D | 243 | 13.477 | 77.018 | 30.611 | 1.00 19.85 | C |
| ATOM | 7748 | O | GLY | D | 243 | 13.891 | 76.847 | 29.456 | 1.00 19.27 | O |
| ATOM | 7749 | N | GLU | D | 244 | 13.837 | 76.239 | 31.631 | 1.00 20.84 | N |
| ATOM | 7750 | CA | GLU | D | 244 | 14.766 | 75.133 | 31.463 | 1.00 20.79 | C |
| ATOM | 7751 | CB | GLU | D | 244 | 15.690 | 75.038 | 32.687 | 1.00 22.50 | C |
| ATOM | 7752 | CG | GLU | D | 244 | 16.796 | 73.985 | 32.555 | 1.00 25.04 | C |
| ATOM | 7753 | CD | GLU | D | 244 | 17.793 | 74.327 | 31.451 | 1.00 25.64 | C |
| ATOM | 7754 | OE1 | GLU | D | 244 | 18.604 | 75.252 | 31.652 | 1.00 27.45 | O |
| ATOM | 7755 | OE2 | GLU | D | 244 | 17.761 | 73.688 | 30.375 | 1.00 27.37 | O |
| ATOM | 7756 | C | GLU | D | 244 | 14.038 | 73.802 | 31.246 | 1.00 20.85 | C |
| ATOM | 7757 | O | GLU | D | 244 | 12.845 | 73.663 | 31.532 | 1.00 20.31 | O |
| ATOM | 7758 | N | ASN | D | 245 | 14.771 | 72.833 | 30.718 | 1.00 20.25 | N |
| ATOM | 7759 | CA | ASN | D | 245 | 14.242 | 71.505 | 30.454 | 1.00 20.81 | C |
| ATOM | 7760 | CB | ASN | D | 245 | 14.020 | 71.337 | 28.948 | 1.00 19.91 | C |
| ATOM | 7761 | CG | ASN | D | 245 | 13.594 | 69.933 | 28.571 | 1.00 22.17 | C |
| ATOM | 7762 | OD1 | ASN | D | 245 | 12.890 | 69.258 | 29.327 | 1.00 23.92 | O |
| ATOM | 7763 | ND2 | ASN | D | 245 | 14.003 | 69.490 | 27.388 | 1.00 23.12 | N |
| ATOM | 7764 | C | ASN | D | 245 | 15.265 | 70.492 | 30.986 | 1.00 20.48 | C |
| ATOM | 7765 | O | ASN | D | 245 | 16.302 | 70.253 | 30.372 | 1.00 21.14 | O |
| ATOM | 7766 | N | ILE | D | 246 | 14.972 | 69.919 | 32.146 | 1.00 20.50 | N |
| ATOM | 7767 | CA | ILE | D | 246 | 15.867 | 68.954 | 32.783 | 1.00 20.57 | C |
| ATOM | 7768 | CB | ILE | D | 246 | 15.746 | 69.033 | 34.319 | 1.00 20.23 | C |
| ATOM | 7769 | CG2 | ILE | D | 246 | 16.788 | 68.129 | 34.973 | 1.00 21.49 | C |
| ATOM | 7770 | CG1 | ILE | D | 246 | 15.942 | 70.482 | 34.773 | 1.00 20.82 | C |
| ATOM | 7771 | CD1 | ILE | D | 246 | 15.915 | 70.669 | 36.274 | 1.00 22.94 | C |
| ATOM | 7772 | C | ILE | D | 246 | 15.563 | 67.524 | 32.336 | 1.00 21.32 | C |
| ATOM | 7773 | O | ILE | D | 246 | 14.413 | 67.064 | 32.410 | 1.00 19.90 | O |
| ATOM | 7774 | N | HIS | D | 247 | 16.595 | 66.824 | 31.872 | 1.00 20.41 | N |
| ATOM | 7775 | CA | HIS | D | 247 | 16.428 | 65.451 | 31.410 | 1.00 19.05 | C |
| ATOM | 7776 | CB | HIS | D | 247 | 17.386 | 65.142 | 30.250 | 1.00 18.37 | C |
| ATOM | 7777 | CG | HIS | D | 247 | 17.176 | 65.992 | 29.032 | 1.00 19.09 | C |
| ATOM | 7778 | CD2 | HIS | D | 247 | 16.475 | 65.760 | 27.895 | 1.00 18.38 | C |
| ATOM | 7779 | ND1 | HIS | D | 247 | 17.766 | 67.230 | 28.871 | 1.00 20.54 | N |
| ATOM | 7780 | CE1 | HIS | D | 247 | 17.443 | 67.719 | 27.686 | 1.00 20.04 | C |
| ATOM | 7781 | NE2 | HIS | D | 247 | 16.660 | 66.847 | 27.073 | 1.00 20.84 | N |
| ATOM | 7782 | C | HIS | D | 247 | 16.709 | 64.471 | 32.531 | 1.00 19.03 | C |
| ATOM | 7783 | O | HIS | D | 247 | 17.786 | 64.495 | 33.127 | 1.00 19.47 | O |
| ATOM | 7784 | N | VAL | D | 248 | 15.731 | 63.624 | 32.830 | 1.00 18.96 | N |
| ATOM | 7785 | CA | VAL | D | 248 | 15.883 | 62.591 | 33.845 | 1.00 18.03 | C |
| ATOM | 7786 | CB | VAL | D | 248 | 14.802 | 62.699 | 34.932 | 1.00 18.17 | C |
| ATOM | 7787 | CG1 | VAL | D | 248 | 14.988 | 61.593 | 35.966 | 1.00 17.67 | C |
| ATOM | 7788 | CG2 | VAL | D | 248 | 14.903 | 64.047 | 35.605 | 1.00 18.73 | C |
| ATOM | 7789 | C | VAL | D | 248 | 15.730 | 61.294 | 33.055 | 1.00 18.09 | C |
| ATOM | 7790 | O | VAL | D | 248 | 14.690 | 60.622 | 33.079 | 1.00 17.57 | O |
| ATOM | 7791 | N | ASP | D | 249 | 16.792 | 60.963 | 32.335 | 1.00 18.13 | N |
| ATOM | 7792 | CA | ASP | D | 249 | 16.813 | 59.795 | 31.479 | 1.00 18.06 | C |
| ATOM | 7793 | CB | ASP | D | 249 | 16.690 | 60.247 | 30.034 | 1.00 19.04 | C |
| ATOM | 7794 | CG | ASP | D | 249 | 17.569 | 61.444 | 29.735 | 1.00 20.85 | C |
| ATOM | 7795 | OD1 | ASP | D | 249 | 18.613 | 61.596 | 30.415 | 1.00 21.37 | O |
| ATOM | 7796 | OD2 | ASP | D | 249 | 17.218 | 62.225 | 28.824 | 1.00 22.74 | O |
| ATOM | 7797 | C | ASP | D | 249 | 18.102 | 59.028 | 31.636 | 1.00 17.81 | C |
| ATOM | 7798 | O | ASP | D | 249 | 18.539 | 58.356 | 30.709 | 1.00 18.59 | O |

FIGURE 9 (cont.)

| | | | | | | | | | |
|---|---|---|---|---|---|---|---|---|---|
| ATOM | 7799 | N | SER | D | 250 | 18.726 | 59.152 | 32.798 | 1.00 18.47 | N |
| ATOM | 7800 | CA | SER | D | 250 | 19.977 | 58.459 | 33.059 | 1.00 19.05 | C |
| ATOM | 7801 | CB | SER | D | 250 | 19.737 | 56.948 | 33.125 | 1.00 21.97 | C |
| ATOM | 7802 | OG | SER | D | 250 | 19.814 | 56.377 | 31.827 | 1.00 26.39 | O |
| ATOM | 7803 | C | SER | D | 250 | 21.035 | 58.761 | 31.996 | 1.00 18.27 | C |
| ATOM | 7804 | O | SER | D | 250 | 21.839 | 57.891 | 31.640 | 1.00 16.69 | O |
| ATOM | 7805 | N | GLY | D | 251 | 21.015 | 59.991 | 31.480 | 1.00 17.61 | N |
| ATOM | 7806 | CA | GLY | D | 251 | 21.998 | 60.413 | 30.489 | 1.00 17.00 | C |
| ATOM | 7807 | C | GLY | D | 251 | 21.770 | 60.126 | 29.009 | 1.00 16.76 | C |
| ATOM | 7808 | O | GLY | D | 251 | 22.613 | 60.472 | 28.185 | 1.00 15.57 | O |
| ATOM | 7809 | N | PHE | D | 252 | 20.640 | 59.522 | 28.655 | 1.00 16.66 | N |
| ATOM | 7810 | CA | PHE | D | 252 | 20.366 | 59.187 | 27.259 | 1.00 17.17 | C |
| ATOM | 7811 | CB | PHE | D | 252 | 18.984 | 58.541 | 27.141 | 1.00 15.94 | C |
| ATOM | 7812 | CG | PHE | D | 252 | 18.761 | 57.809 | 25.848 | 1.00 15.46 | C |
| ATOM | 7813 | CD1 | PHE | D | 252 | 19.644 | 56.807 | 25.437 | 1.00 16.00 | C |
| ATOM | 7814 | CD2 | PHE | D | 252 | 17.650 | 58.086 | 25.058 | 1.00 14.97 | C |
| ATOM | 7815 | CE1 | PHE | D | 252 | 19.417 | 56.094 | 24.264 | 1.00 15.47 | C |
| ATOM | 7816 | CE2 | PHE | D | 252 | 17.417 | 57.377 | 23.880 | 1.00 15.40 | C |
| ATOM | 7817 | CZ | PHE | D | 252 | 18.300 | 56.379 | 23.482 | 1.00 15.80 | C |
| ATOM | 7818 | C | PHE | D | 252 | 20.463 | 60.361 | 26.272 | 1.00 19.23 | C |
| ATOM | 7819 | O | PHE | D | 252 | 20.946 | 60.189 | 25.143 | 1.00 19.77 | O |
| ATOM | 7820 | N | HIS | D | 253 | 19.999 | 61.539 | 26.692 | 1.00 19.18 | N |
| ATOM | 7821 | CA | HIS | D | 253 | 20.011 | 62.735 | 25.847 | 1.00 19.98 | C |
| ATOM | 7822 | CB | HIS | D | 253 | 19.369 | 63.918 | 26.581 | 1.00 20.82 | C |
| ATOM | 7823 | CG | HIS | D | 253 | 20.227 | 64.467 | 27.677 | 1.00 21.05 | C |
| ATOM | 7824 | CD2 | HIS | D | 253 | 21.034 | 65.554 | 27.717 | 1.00 21.40 | C |
| ATOM | 7825 | ND1 | HIS | D | 253 | 20.388 | 63.826 | 28.887 | 1.00 20.02 | N |
| ATOM | 7826 | CE1 | HIS | D | 253 | 21.259 | 64.492 | 29.624 | 1.00 21.55 | C |
| ATOM | 7827 | NE2 | HIS | D | 253 | 21.668 | 65.545 | 28.937 | 1.00 22.74 | N |
| ATOM | 7828 | C | HIS | D | 253 | 21.407 | 63.185 | 25.411 | 1.00 19.70 | C |
| ATOM | 7829 | O | HIS | D | 253 | 21.552 | 63.846 | 24.384 | 1.00 19.95 | O |
| ATOM | 7830 | N | ALA | D | 254 | 22.423 | 62.831 | 26.190 | 1.00 18.90 | N |
| ATOM | 7831 | CA | ALA | D | 254 | 23.788 | 63.254 | 25.910 | 1.00 18.54 | C |
| ATOM | 7832 | CB | ALA | D | 254 | 24.520 | 63.469 | 27.233 | 1.00 18.38 | C |
| ATOM | 7833 | C | ALA | D | 254 | 24.626 | 62.360 | 24.999 | 1.00 19.31 | C |
| ATOM | 7834 | O | ALA | D | 254 | 25.766 | 62.700 | 24.673 | 1.00 18.87 | O |
| ATOM | 7835 | N | ILE | D | 255 | 24.074 | 61.229 | 24.579 | 1.00 18.89 | N |
| ATOM | 7836 | CA | ILE | D | 255 | 24.816 | 60.310 | 23.718 | 1.00 18.39 | C |
| ATOM | 7837 | CB | ILE | D | 255 | 24.788 | 58.892 | 24.290 | 1.00 18.46 | C |
| ATOM | 7838 | CG2 | ILE | D | 255 | 25.344 | 58.903 | 25.715 | 1.00 15.55 | C |
| ATOM | 7839 | CG1 | ILE | D | 255 | 23.348 | 58.366 | 24.263 | 1.00 15.88 | C |
| ATOM | 7840 | CD1 | ILE | D | 255 | 23.243 | 56.866 | 24.357 | 1.00 18.98 | C |
| ATOM | 7841 | C | ILE | D | 255 | 24.263 | 60.245 | 22.298 | 1.00 19.27 | C |
| ATOM | 7842 | O | ILE | D | 255 | 23.189 | 60.780 | 22.008 | 1.00 17.17 | O |
| ATOM | 7843 | N | LYS | D | 256 | 25.009 | 59.585 | 21.416 | 1.00 19.87 | N |
| ATOM | 7844 | CA | LYS | D | 256 | 24.594 | 59.422 | 20.024 | 1.00 22.61 | C |
| ATOM | 7845 | CB | LYS | D | 256 | 25.071 | 60.607 | 19.175 | 1.00 22.39 | C |
| ATOM | 7846 | CG | LYS | D | 256 | 23.962 | 61.388 | 18.493 | 1.00 23.42 | C |
| ATOM | 7847 | CD | LYS | D | 256 | 23.158 | 60.538 | 17.532 | 1.00 23.49 | C |
| ATOM | 7848 | CE | LYS | D | 256 | 21.973 | 61.353 | 16.996 | 1.00 25.45 | C |
| ATOM | 7849 | NZ | LYS | D | 256 | 20.963 | 60.563 | 16.219 | 1.00 23.45 | N |
| ATOM | 7850 | C | LYS | D | 256 | 25.186 | 58.137 | 19.461 | 1.00 23.02 | C |
| ATOM | 7851 | O | LYS | D | 256 | 26.369 | 57.872 | 19.772 | 1.00 22.66 | O |
| ATOM | 7852 | OXT | LYS | D | 256 | 24.468 | 57.423 | 18.712 | 1.00 24.41 | O |
| TER | 7853 | | LYS | D | 256 | | | | | |
| ATOM | 7854 | C1 | 135 | A | 302 | 35.942 | 48.601 | 63.796 | 1.00 10.85 | C |
| ATOM | 7855 | C2 | 135 | A | 302 | 36.594 | 48.030 | 62.699 | 1.00 9.82 | C |
| ATOM | 7856 | C3 | 135 | A | 302 | 35.851 | 47.299 | 61.708 | 1.00 11.34 | C |
| ATOM | 7857 | C4 | 135 | A | 302 | 34.465 | 47.159 | 61.843 | 1.00 12.01 | C |
| ATOM | 7858 | C5 | 135 | A | 302 | 33.786 | 47.738 | 62.958 | 1.00 11.97 | C |
| ATOM | 7859 | C6 | 135 | A | 302 | 34.528 | 48.460 | 63.936 | 1.00 12.88 | C |
| ATOM | 7860 | N7 | 135 | A | 302 | 37.907 | 48.002 | 62.313 | 1.00 13.62 | N |
| ATOM | 7861 | C8 | 135 | A | 302 | 38.049 | 47.309 | 61.153 | 1.00 11.84 | C |
| ATOM | 7862 | C9 | 135 | A | 302 | 36.807 | 46.841 | 60.720 | 1.00 11.11 | C |
| ATOM | 7863 | C11 | 135 | A | 302 | 39.396 | 47.108 | 60.488 | 1.00 13.69 | C |

FIGURE 9 (cont.)

```
ATOM   7864  C15  135 A 302      36.527  46.013  59.465  1.00 12.53           C
ATOM   7865  N16  135 A 302      36.406  44.558  59.775  1.00 14.16           N
ATOM   7866  C19  135 A 302      35.226  43.829  59.722  1.00 14.72           C
ATOM   7867  C20  135 A 302      33.869  44.468  59.641  1.00 16.87           C
ATOM   7868  C21  135 A 302      32.751  43.803  59.258  1.00 16.06           C
ATOM   7869  C22  135 A 302      31.426  44.430  59.205  1.00 17.67           C
ATOM   7870  O23  135 A 302      35.192  42.607  59.787  1.00 16.66           O
ATOM   7871  C24  135 A 302      37.616  43.819  60.197  1.00 10.58           C
ATOM   7872  N28  135 A 302      29.027  44.214  59.637  1.00 17.44           N
ATOM   7873  C29  135 A 302      28.838  45.480  59.186  1.00 18.64           C
ATOM   7874  C30  135 A 302      29.913  46.301  58.716  1.00 18.53           C
ATOM   7875  C31  135 A 302      31.219  45.761  58.730  1.00 18.11           C
ATOM   7876  C32  135 A 302      30.293  43.704  59.646  1.00 18.03           C
ATOM   7877  N33  135 A 302      27.557  45.966  59.191  1.00 18.83           N
ATOM   7878  C34  135 A 302      27.124  47.057  58.484  1.00 19.56           C
ATOM   7879  C35  135 A 302      28.191  47.792  57.607  1.00 20.32           C
ATOM   7880  C36  135 A 302      29.615  47.703  58.226  1.00 18.30           C
ATOM   7881  O42  135 A 302      25.973  47.456  58.519  1.00 22.42           O
TER    7882       135 A 302
ATOM   7883  C1   135 B 302      34.579  16.741  76.134  1.00 15.80           C
ATOM   7884  C2   135 B 302      34.900  17.319  77.366  1.00 14.52           C
ATOM   7885  C3   135 B 302      33.898  18.025  78.122  1.00 13.89           C
ATOM   7886  C4   135 B 302      32.600  18.130  77.622  1.00 13.49           C
ATOM   7887  C5   135 B 302      32.258  17.544  76.370  1.00 13.90           C
ATOM   7888  C6   135 B 302      33.249  16.848  75.620  1.00 14.71           C
ATOM   7889  N7   135 B 302      36.071  17.375  78.095  1.00 15.42           N
ATOM   7890  C8   135 B 302      35.882  18.060  79.245  1.00 14.91           C
ATOM   7891  C9   135 B 302      34.544  18.499  79.332  1.00 14.52           C
ATOM   7892  C11  135 B 302      36.999  18.286  80.248  1.00 16.77           C
ATOM   7893  C15  135 B 302      33.917  19.312  80.467  1.00 14.45           C
ATOM   7894  N16  135 B 302      33.846  20.761  80.127  1.00 17.42           N
ATOM   7895  C19  135 B 302      32.693  21.459  79.840  1.00 18.29           C
ATOM   7896  C20  135 B 302      31.377  20.893  79.564  1.00 19.16           C
ATOM   7897  C21  135 B 302      30.210  21.480  79.682  1.00 19.01           C
ATOM   7898  C22  135 B 302      28.905  20.895  79.394  1.00 20.24           C
ATOM   7899  O23  135 B 302      32.668  22.685  79.729  1.00 22.78           O
ATOM   7900  C24  135 B 302      35.097  21.541  80.046  1.00 15.28           C
ATOM   7901  N28  135 B 302      26.688  21.208  78.423  1.00 20.81           N
ATOM   7902  C29  135 B 302      26.376  19.930  78.749  1.00 21.40           C
ATOM   7903  C30  135 B 302      27.286  19.061  79.412  1.00 21.43           C
ATOM   7904  C31  135 B 302      28.566  19.561  79.735  1.00 20.61           C
ATOM   7905  C32  135 B 302      27.928  21.680  78.739  1.00 21.22           C
ATOM   7906  N33  135 B 302      25.127  19.487  78.409  1.00 23.59           N
ATOM   7907  C34  135 B 302      24.516  18.366  78.902  1.00 23.50           C
ATOM   7908  C35  135 B 302      25.321  17.532  79.947  1.00 22.48           C
ATOM   7909  C36  135 B 302      26.862  17.646  79.742  1.00 22.09           C
ATOM   7910  O42  135 B 302      23.398  18.019  78.556  1.00 25.82           O
TER    7911       135 B 302
ATOM   7912  C1   135 C 302       6.873  90.085  16.510  1.00 20.50           C
ATOM   7913  C2   135 C 302       7.523  89.766  15.312  1.00 18.77           C
ATOM   7914  C3   135 C 302       6.788  89.139  14.222  1.00 19.12           C
ATOM   7915  C4   135 C 302       5.418  88.929  14.362  1.00 19.88           C
ATOM   7916  C5   135 C 302       4.749  89.250  15.578  1.00 21.50           C
ATOM   7917  C6   135 C 302       5.477  89.829  16.657  1.00 20.50           C
ATOM   7918  N7   135 C 302       8.835  89.896  14.898  1.00 18.56           N
ATOM   7919  C8   135 C 302       8.973  89.431  13.625  1.00 18.93           C
ATOM   7920  C9   135 C 302       7.731  88.969  13.142  1.00 19.13           C
ATOM   7921  C11  135 C 302      10.300  89.439  12.898  1.00 17.57           C
ATOM   7922  C15  135 C 302       7.451  88.368  11.757  1.00 21.71           C
ATOM   7923  N16  135 C 302       7.381  86.885  11.758  1.00 21.30           N
ATOM   7924  C19  135 C 302       6.218  86.143  11.602  1.00 24.34           C
ATOM   7925  C20  135 C 302       4.847  86.768  11.589  1.00 25.69           C
ATOM   7926  C21  135 C 302       3.724  86.069  11.244  1.00 28.07           C
ATOM   7927  C22  135 C 302       2.367  86.650  11.243  1.00 29.12           C
ATOM   7928  O23  135 C 302       6.205  84.906  11.502  1.00 22.95           O
```

FIGURE 9 (cont.)

| | | | | | | | | | |
|---|---|---|---|---|---|---|---|---|---|
| ATOM | 7929 | C24 | 135 | C | 302 | 8.614 | 86.128 | 11.956 | 1.00 21.21 | C |
| ATOM | 7930 | N28 | 135 | C | 302 | -0.047 | 86.289 | 11.427 | 1.00 29.91 | N |
| ATOM | 7931 | C29 | 135 | C | 302 | -0.246 | 87.626 | 11.269 | 1.00 29.30 | C |
| ATOM | 7932 | C30 | 135 | C | 302 | 0.830 | 88.548 | 11.092 | 1.00 30.08 | C |
| ATOM | 7933 | C31 | 135 | C | 302 | 2.143 | 88.043 | 11.081 | 1.00 29.13 | C |
| ATOM | 7934 | C32 | 135 | C | 302 | 1.236 | 85.811 | 11.414 | 1.00 29.29 | C |
| ATOM | 7935 | N33 | 135 | C | 302 | -1.533 | 88.078 | 11.283 | 1.00 29.95 | N |
| ATOM | 7936 | C34 | 135 | C | 302 | -1.950 | 89.310 | 10.823 | 1.00 30.06 | C |
| ATOM | 7937 | C35 | 135 | C | 302 | -0.853 | 90.248 | 10.246 | 1.00 30.93 | C |
| ATOM | 7938 | C36 | 135 | C | 302 | 0.537 | 90.022 | 10.922 | 1.00 30.17 | C |
| ATOM | 7939 | O42 | 135 | C | 302 | -3.110 | 89.676 | 10.853 | 1.00 31.09 | O |
| TER | 7940 | | 135 | C | 302 | | | | | |
| ATOM | 7941 | C1 | 135 | D | 302 | 5.937 | 55.660 | 21.263 | 1.00 23.32 | C |
| ATOM | 7942 | C2 | 135 | D | 302 | 6.236 | 55.908 | 22.606 | 1.00 21.80 | C |
| ATOM | 7943 | C3 | 135 | D | 302 | 5.246 | 56.474 | 23.469 | 1.00 21.14 | C |
| ATOM | 7944 | C4 | 135 | D | 302 | 3.977 | 56.779 | 22.966 | 1.00 21.77 | C |
| ATOM | 7945 | C5 | 135 | D | 302 | 3.657 | 56.528 | 21.604 | 1.00 21.37 | C |
| ATOM | 7946 | C6 | 135 | D | 302 | 4.641 | 55.967 | 20.747 | 1.00 23.26 | C |
| ATOM | 7947 | N7 | 135 | D | 302 | 7.375 | 55.711 | 23.365 | 1.00 21.10 | N |
| ATOM | 7948 | C8 | 135 | D | 302 | 7.168 | 56.113 | 24.635 | 1.00 20.35 | C |
| ATOM | 7949 | C9 | 135 | D | 302 | 5.855 | 56.605 | 24.773 | 1.00 20.83 | C |
| ATOM | 7950 | C11 | 135 | D | 302 | 8.246 | 56.018 | 25.698 | 1.00 19.40 | C |
| ATOM | 7951 | C15 | 135 | D | 302 | 5.208 | 57.162 | 26.042 | 1.00 21.58 | C |
| ATOM | 7952 | N16 | 135 | D | 302 | 5.198 | 58.639 | 26.054 | 1.00 22.25 | N |
| ATOM | 7953 | C19 | 135 | D | 302 | 4.070 | 59.428 | 25.866 | 1.00 24.29 | C |
| ATOM | 7954 | C20 | 135 | D | 302 | 2.745 | 58.878 | 25.442 | 1.00 24.87 | C |
| ATOM | 7955 | C21 | 135 | D | 302 | 1.570 | 59.490 | 25.737 | 1.00 25.96 | C |
| ATOM | 7956 | C22 | 135 | D | 302 | 0.261 | 58.963 | 25.319 | 1.00 28.73 | C |
| ATOM | 7957 | O23 | 135 | D | 302 | 4.072 | 60.650 | 26.002 | 1.00 24.41 | O |
| ATOM | 7958 | C24 | 135 | D | 302 | 6.468 | 59.346 | 26.261 | 1.00 20.71 | C |
| ATOM | 7959 | N28 | 135 | D | 302 | -1.927 | 59.413 | 24.329 | 1.00 29.06 | N |
| ATOM | 7960 | C29 | 135 | D | 302 | -2.262 | 58.097 | 24.472 | 1.00 28.80 | C |
| ATOM | 7961 | C30 | 135 | D | 302 | -1.379 | 57.136 | 25.037 | 1.00 28.90 | C |
| ATOM | 7962 | C31 | 135 | D | 302 | -0.100 | 57.580 | 25.465 | 1.00 28.19 | C |
| ATOM | 7963 | C32 | 135 | D | 302 | -0.693 | 59.835 | 24.744 | 1.00 28.27 | C |
| ATOM | 7964 | N33 | 135 | D | 302 | -3.509 | 57.723 | 24.042 | 1.00 30.39 | N |
| ATOM | 7965 | C34 | 135 | D | 302 | -4.146 | 56.542 | 24.344 | 1.00 30.94 | C |
| ATOM | 7966 | C35 | 135 | D | 302 | -3.370 | 55.541 | 25.260 | 1.00 30.52 | C |
| ATOM | 7967 | C36 | 135 | D | 302 | -1.822 | 55.689 | 25.163 | 1.00 29.17 | C |
| ATOM | 7968 | O42 | 135 | D | 302 | -5.264 | 56.264 | 23.929 | 1.00 31.21 | O |
| TER | 7969 | | 135 | D | 302 | | | | | |
| ATOM | 7970 | PN | NAP | A | 301 | 35.242 | 42.781 | 53.042 | 1.00 13.25 | P |
| ATOM | 7971 | O1N | NAP | A | 301 | 36.077 | 43.740 | 53.792 | 1.00 14.44 | O |
| ATOM | 7972 | O2N | NAP | A | 301 | 35.776 | 42.223 | 51.773 | 1.00 12.20 | O |
| ATOM | 7973 | O3P | NAP | A | 301 | 33.806 | 43.454 | 52.745 | 1.00 12.78 | O |
| ATOM | 7974 | O5M | NAP | A | 301 | 34.942 | 41.559 | 54.080 | 1.00 15.14 | O |
| ATOM | 7975 | C5M | NAP | A | 301 | 35.171 | 40.171 | 53.790 | 1.00 13.24 | C |
| ATOM | 7976 | C4M | NAP | A | 301 | 35.625 | 39.408 | 55.019 | 1.00 14.56 | C |
| ATOM | 7977 | O4M | NAP | A | 301 | 36.952 | 39.831 | 55.379 | 1.00 16.38 | O |
| ATOM | 7978 | C3M | NAP | A | 301 | 34.792 | 39.598 | 56.300 | 1.00 15.47 | C |
| ATOM | 7979 | O3M | NAP | A | 301 | 34.680 | 38.340 | 56.965 | 1.00 15.30 | O |
| ATOM | 7980 | C2M | NAP | A | 301 | 35.608 | 40.619 | 57.106 | 1.00 15.67 | C |
| ATOM | 7981 | O2M | NAP | A | 301 | 35.262 | 40.466 | 58.482 | 1.00 15.26 | O |
| ATOM | 7982 | C1M | NAP | A | 301 | 37.010 | 40.228 | 56.784 | 1.00 15.19 | C |
| ATOM | 7983 | N1N | NAP | A | 301 | 38.034 | 41.298 | 57.019 | 1.00 14.23 | N |
| ATOM | 7984 | C6N | NAP | A | 301 | 39.220 | 40.897 | 57.703 | 1.00 14.71 | C |
| ATOM | 7985 | C5N | NAP | A | 301 | 40.246 | 41.842 | 57.945 | 1.00 13.77 | C |
| ATOM | 7986 | C4N | NAP | A | 301 | 40.118 | 43.180 | 57.519 | 1.00 14.97 | C |
| ATOM | 7987 | C3N | NAP | A | 301 | 38.935 | 43.603 | 56.831 | 1.00 15.14 | C |
| ATOM | 7988 | C2N | NAP | A | 301 | 37.885 | 42.668 | 56.576 | 1.00 14.24 | C |
| ATOM | 7989 | C7N | NAP | A | 301 | 38.841 | 45.063 | 56.388 | 1.00 16.21 | C |
| ATOM | 7990 | O7N | NAP | A | 301 | 39.430 | 45.962 | 57.028 | 1.00 16.51 | O |
| ATOM | 7991 | N7N | NAP | A | 301 | 38.112 | 45.298 | 55.292 | 1.00 16.36 | N |
| ATOM | 7992 | PA | NAP | A | 301 | 32.558 | 43.050 | 51.829 | 1.00 12.09 | P |
| ATOM | 7993 | O1A | NAP | A | 301 | 31.341 | 43.704 | 52.382 | 1.00 14.23 | O |

FIGURE 9 (cont.)

| | | | | | | | | | |
|---|---|---|---|---|---|---|---|---|---|
| ATOM | 7994 | O2A | NAP | A | 301 | 32.915 | 43.392 | 50.430 | 1.00 14.52 | O |
| ATOM | 7995 | O5B | NAP | A | 301 | 32.406 | 41.399 | 51.889 | 1.00 17.07 | O |
| ATOM | 7996 | C5B | NAP | A | 301 | 31.752 | 40.606 | 52.915 | 1.00 15.25 | C |
| ATOM | 7997 | C4B | NAP | A | 301 | 30.480 | 39.959 | 52.387 | 1.00 17.15 | C |
| ATOM | 7998 | O4B | NAP | A | 301 | 29.658 | 39.618 | 53.508 | 1.00 16.64 | O |
| ATOM | 7999 | C3B | NAP | A | 301 | 29.567 | 40.838 | 51.597 | 1.00 19.75 | C |
| ATOM | 8000 | O3B | NAP | A | 301 | 29.765 | 41.140 | 50.237 | 1.00 25.01 | O |
| ATOM | 8001 | C2B | NAP | A | 301 | 28.177 | 40.331 | 51.887 | 1.00 19.83 | C |
| ATOM | 8002 | C1B | NAP | A | 301 | 28.523 | 39.144 | 52.783 | 1.00 16.51 | C |
| ATOM | 8003 | N9A | NAP | A | 301 | 27.379 | 38.707 | 53.687 | 1.00 14.89 | N |
| ATOM | 8004 | C4A | NAP | A | 301 | 26.655 | 37.637 | 53.397 | 1.00 13.86 | C |
| ATOM | 8005 | N3A | NAP | A | 301 | 26.632 | 36.690 | 52.394 | 1.00 14.41 | N |
| ATOM | 8006 | C2A | NAP | A | 301 | 25.703 | 35.693 | 52.445 | 1.00 16.56 | C |
| ATOM | 8007 | N1A | NAP | A | 301 | 24.798 | 35.618 | 53.466 | 1.00 14.38 | N |
| ATOM | 8008 | C6A | NAP | A | 301 | 24.773 | 36.537 | 54.492 | 1.00 13.65 | C |
| ATOM | 8009 | C5A | NAP | A | 301 | 25.740 | 37.573 | 54.441 | 1.00 13.36 | C |
| ATOM | 8010 | N7A | NAP | A | 301 | 25.885 | 38.550 | 55.328 | 1.00 13.78 | N |
| ATOM | 8011 | C8A | NAP | A | 301 | 26.915 | 39.253 | 54.842 | 1.00 11.75 | C |
| ATOM | 8012 | N6A | NAP | A | 301 | 23.899 | 36.477 | 55.486 | 1.00 11.36 | N |
| ATOM | 8013 | O2B | NAP | A | 301 | 27.232 | 40.342 | 50.727 | 1.00 23.82 | O |
| ATOM | 8014 | P2* | NAP | A | 301 | 26.166 | 41.592 | 50.559 | 1.00 27.64 | P |
| ATOM | 8015 | OP1 | NAP | A | 301 | 26.992 | 42.890 | 50.616 | 1.00 25.74 | O |
| ATOM | 8016 | OP2 | NAP | A | 301 | 25.580 | 41.297 | 49.200 | 1.00 28.92 | O |
| ATOM | 8017 | OP3 | NAP | A | 301 | 25.217 | 41.503 | 51.738 | 1.00 27.32 | O |
| TER | 8018 | | NAP | A | 301 | | | | | |
| ATOM | 8019 | PN | NAP | B | 301 | 30.944 | 22.674 | 86.316 | 1.00 15.52 | P |
| ATOM | 8020 | O1N | NAP | B | 301 | 31.998 | 21.733 | 85.854 | 1.00 15.14 | O |
| ATOM | 8021 | O2N | NAP | B | 301 | 31.114 | 23.272 | 87.681 | 1.00 12.14 | O |
| ATOM | 8022 | O3P | NAP | B | 301 | 29.503 | 21.937 | 86.227 | 1.00 15.03 | O |
| ATOM | 8023 | O5M | NAP | B | 301 | 30.898 | 23.853 | 85.203 | 1.00 14.07 | O |
| ATOM | 8024 | C5M | NAP | B | 301 | 31.021 | 25.246 | 85.489 | 1.00 13.91 | C |
| ATOM | 8025 | C4M | NAP | B | 301 | 31.803 | 25.972 | 84.403 | 1.00 15.26 | C |
| ATOM | 8026 | O4M | NAP | B | 301 | 33.187 | 25.556 | 84.413 | 1.00 15.75 | O |
| ATOM | 8027 | C3M | NAP | B | 301 | 31.340 | 25.750 | 82.954 | 1.00 15.06 | C |
| ATOM | 8028 | O3M | NAP | B | 301 | 31.375 | 27.005 | 82.275 | 1.00 17.68 | O |
| ATOM | 8029 | C2M | NAP | B | 301 | 32.352 | 24.740 | 82.407 | 1.00 14.97 | C |
| ATOM | 8030 | O2M | NAP | B | 301 | 32.385 | 24.873 | 80.994 | 1.00 11.01 | O |
| ATOM | 8031 | C1M | NAP | B | 301 | 33.619 | 25.141 | 83.083 | 1.00 14.30 | C |
| ATOM | 8032 | N1N | NAP | B | 301 | 34.658 | 24.058 | 83.147 | 1.00 15.35 | N |
| ATOM | 8033 | C6N | NAP | B | 301 | 35.994 | 24.436 | 82.831 | 1.00 17.26 | C |
| ATOM | 8034 | C5N | NAP | B | 301 | 37.030 | 23.473 | 82.884 | 1.00 16.29 | C |
| ATOM | 8035 | C4N | NAP | B | 301 | 36.754 | 22.131 | 83.254 | 1.00 17.72 | C |
| ATOM | 8036 | C3N | NAP | B | 301 | 35.415 | 21.738 | 83.574 | 1.00 17.36 | C |
| ATOM | 8037 | C2N | NAP | B | 301 | 34.364 | 22.698 | 83.522 | 1.00 15.79 | C |
| ATOM | 8038 | C7N | NAP | B | 301 | 35.158 | 20.280 | 83.967 | 1.00 16.80 | C |
| ATOM | 8039 | O7N | NAP | B | 301 | 35.937 | 19.383 | 83.605 | 1.00 20.32 | O |
| ATOM | 8040 | N7N | NAP | B | 301 | 34.080 | 20.040 | 84.706 | 1.00 16.54 | N |
| ATOM | 8041 | PA | NAP | B | 301 | 28.013 | 22.322 | 86.710 | 1.00 14.62 | P |
| ATOM | 8042 | O1A | NAP | B | 301 | 27.031 | 21.689 | 85.799 | 1.00 16.96 | O |
| ATOM | 8043 | O2A | NAP | B | 301 | 27.921 | 21.947 | 88.134 | 1.00 16.47 | O |
| ATOM | 8044 | O5B | NAP | B | 301 | 27.874 | 23.974 | 86.639 | 1.00 20.22 | O |
| ATOM | 8045 | C5B | NAP | B | 301 | 27.526 | 24.792 | 85.476 | 1.00 18.16 | C |
| ATOM | 8046 | C4B | NAP | B | 301 | 26.164 | 25.453 | 85.636 | 1.00 17.99 | C |
| ATOM | 8047 | O4B | NAP | B | 301 | 25.650 | 25.720 | 84.315 | 1.00 18.29 | O |
| ATOM | 8048 | C3B | NAP | B | 301 | 25.088 | 24.599 | 86.226 | 1.00 19.87 | C |
| ATOM | 8049 | O3B | NAP | B | 301 | 24.993 | 24.193 | 87.569 | 1.00 22.97 | O |
| ATOM | 8050 | C2B | NAP | B | 301 | 23.832 | 25.077 | 85.543 | 1.00 20.62 | C |
| ATOM | 8051 | C1B | NAP | B | 301 | 24.376 | 26.224 | 84.698 | 1.00 17.46 | C |
| ATOM | 8052 | N9A | NAP | B | 301 | 23.483 | 26.598 | 83.521 | 1.00 15.86 | N |
| ATOM | 8053 | C4A | NAP | B | 301 | 22.670 | 27.633 | 83.608 | 1.00 15.03 | C |
| ATOM | 8054 | N3A | NAP | B | 301 | 22.368 | 28.574 | 84.564 | 1.00 15.48 | N |
| ATOM | 8055 | C2A | NAP | B | 301 | 21.445 | 29.529 | 84.286 | 1.00 16.67 | C |
| ATOM | 8056 | N1A | NAP | B | 301 | 20.815 | 29.567 | 83.075 | 1.00 15.09 | N |
| ATOM | 8057 | C6A | NAP | B | 301 | 21.069 | 28.657 | 82.082 | 1.00 12.86 | C |
| ATOM | 8058 | C5A | NAP | B | 301 | 22.032 | 27.660 | 82.369 | 1.00 14.25 | C |

FIGURE 9 (cont.)

| | | | | | | | | | |
|---|---|---|---|---|---|---|---|---|---|
| ATOM | 8059 | N7A | NAP | B | 301 | 22.424 | 26.691 | 81.557 | 1.00 13.09 | N |
| ATOM | 8060 | C8A | NAP | B | 301 | 23.336 | 26.031 | 82.295 | 1.00 14.45 | C |
| ATOM | 8061 | N6A | NAP | B | 301 | 20.452 | 28.695 | 80.913 | 1.00 12.06 | N |
| ATOM | 8062 | O2B | NAP | B | 301 | 22.554 | 24.990 | 86.316 | 1.00 24.17 | O |
| ATOM | 8063 | P2* | NAP | B | 301 | 21.661 | 23.606 | 86.212 | 1.00 28.28 | P |
| ATOM | 8064 | OP1 | NAP | B | 301 | 22.492 | 22.508 | 86.871 | 1.00 29.69 | O |
| ATOM | 8065 | OP2 | NAP | B | 301 | 20.425 | 23.955 | 86.987 | 1.00 28.99 | O |
| ATOM | 8066 | OP3 | NAP | B | 301 | 21.467 | 23.309 | 84.734 | 1.00 30.38 | O |
| TER | 8067 | | NAP | B | 301 | | | | | |
| ATOM | 8068 | PN | NAP | C | 301 | 6.244 | 86.520 | 4.745 | 1.00 23.60 | P |
| ATOM | 8069 | O1N | NAP | C | 301 | 7.077 | 87.377 | 5.636 | 1.00 25.62 | O |
| ATOM | 8070 | O2N | NAP | C | 301 | 6.717 | 86.242 | 3.349 | 1.00 22.43 | O |
| ATOM | 8071 | O3P | NAP | C | 301 | 4.781 | 87.149 | 4.680 | 1.00 26.61 | O |
| ATOM | 8072 | O5M | NAP | C | 301 | 6.037 | 85.106 | 5.505 | 1.00 22.79 | O |
| ATOM | 8073 | C5M | NAP | C | 301 | 6.287 | 83.828 | 4.904 | 1.00 20.06 | C |
| ATOM | 8074 | C4M | NAP | C | 301 | 6.749 | 82.814 | 5.936 | 1.00 18.80 | C |
| ATOM | 8075 | O4M | NAP | C | 301 | 8.073 | 83.155 | 6.380 | 1.00 17.38 | O |
| ATOM | 8076 | C3M | NAP | C | 301 | 5.903 | 82.729 | 7.221 | 1.00 18.65 | C |
| ATOM | 8077 | O3M | NAP | C | 301 | 5.743 | 81.365 | 7.633 | 1.00 17.82 | O |
| ATOM | 8078 | C2M | NAP | C | 301 | 6.697 | 83.558 | 8.229 | 1.00 19.40 | C |
| ATOM | 8079 | O2M | NAP | C | 301 | 6.363 | 83.168 | 9.568 | 1.00 19.27 | O |
| ATOM | 8080 | C1M | NAP | C | 301 | 8.117 | 83.261 | 7.841 | 1.00 19.54 | C |
| ATOM | 8081 | N1N | NAP | C | 301 | 9.091 | 84.299 | 8.324 | 1.00 19.33 | N |
| ATOM | 8082 | C6N | NAP | C | 301 | 10.279 | 83.820 | 8.942 | 1.00 19.71 | C |
| ATOM | 8083 | C5N | NAP | C | 301 | 11.241 | 84.745 | 9.408 | 1.00 19.90 | C |
| ATOM | 8084 | C4N | NAP | C | 301 | 11.041 | 86.138 | 9.267 | 1.00 20.69 | C |
| ATOM | 8085 | C3N | NAP | C | 301 | 9.852 | 86.632 | 8.649 | 1.00 20.46 | C |
| ATOM | 8086 | C2N | NAP | C | 301 | 8.872 | 85.719 | 8.174 | 1.00 18.70 | C |
| ATOM | 8087 | C7N | NAP | C | 301 | 9.674 | 88.146 | 8.518 | 1.00 18.49 | C |
| ATOM | 8088 | O7N | NAP | C | 301 | 10.221 | 88.909 | 9.307 | 1.00 17.29 | O |
| ATOM | 8089 | N7N | NAP | C | 301 | 8.909 | 88.569 | 7.521 | 1.00 20.83 | N |
| ATOM | 8090 | PA | NAP | C | 301 | 3.602 | 87.071 | 3.599 | 1.00 25.83 | P |
| ATOM | 8091 | O1A | NAP | C | 301 | 2.362 | 87.538 | 4.275 | 1.00 29.53 | O |
| ATOM | 8092 | O2A | NAP | C | 301 | 4.059 | 87.853 | 2.411 | 1.00 25.00 | O |
| ATOM | 8093 | O5B | NAP | C | 301 | 3.422 | 85.500 | 3.143 | 1.00 28.17 | O |
| ATOM | 8094 | C5B | NAP | C | 301 | 2.835 | 84.429 | 3.941 | 1.00 29.70 | C |
| ATOM | 8095 | C4B | NAP | C | 301 | 1.504 | 83.955 | 3.363 | 1.00 31.68 | C |
| ATOM | 8096 | O4B | NAP | C | 301 | 0.726 | 83.325 | 4.430 | 1.00 31.70 | O |
| ATOM | 8097 | C3B | NAP | C | 301 | 0.571 | 85.039 | 2.895 | 1.00 33.08 | C |
| ATOM | 8098 | O3B | NAP | C | 301 | 0.738 | 85.854 | 1.762 | 1.00 35.82 | O |
| ATOM | 8099 | C2B | NAP | C | 301 | -0.802 | 84.453 | 3.141 | 1.00 33.10 | C |
| ATOM | 8100 | C1B | NAP | C | 301 | -0.451 | 83.061 | 3.665 | 1.00 30.53 | C |
| ATOM | 8101 | N9A | NAP | C | 301 | -1.594 | 82.424 | 4.438 | 1.00 27.87 | N |
| ATOM | 8102 | C4A | NAP | C | 301 | -2.225 | 81.355 | 3.964 | 1.00 25.73 | C |
| ATOM | 8103 | N3A | NAP | C | 301 | -2.131 | 80.553 | 2.850 | 1.00 26.27 | N |
| ATOM | 8104 | C2A | NAP | C | 301 | -2.993 | 79.506 | 2.696 | 1.00 24.56 | C |
| ATOM | 8105 | N1A | NAP | C | 301 | -3.949 | 79.241 | 3.622 | 1.00 24.22 | N |
| ATOM | 8106 | C6A | NAP | C | 301 | -4.098 | 80.009 | 4.760 | 1.00 25.67 | C |
| ATOM | 8107 | C5A | NAP | C | 301 | -3.197 | 81.096 | 4.922 | 1.00 26.10 | C |
| ATOM | 8108 | N7A | NAP | C | 301 | -3.174 | 81.950 | 5.942 | 1.00 27.15 | N |
| ATOM | 8109 | C8A | NAP | C | 301 | -2.161 | 82.778 | 5.625 | 1.00 26.84 | C |
| ATOM | 8110 | N6A | NAP | C | 301 | -5.035 | 79.765 | 5.675 | 1.00 25.48 | N |
| ATOM | 8111 | O2B | NAP | C | 301 | -1.897 | 84.859 | 2.198 | 1.00 36.31 | O |
| ATOM | 8112 | P2* | NAP | C | 301 | -2.958 | 86.079 | 2.595 | 1.00 38.67 | P |
| ATOM | 8113 | OP1 | NAP | C | 301 | -2.140 | 87.378 | 2.626 | 1.00 38.33 | O |
| ATOM | 8114 | OP2 | NAP | C | 301 | -3.912 | 85.979 | 1.444 | 1.00 39.61 | O |
| ATOM | 8115 | OP3 | NAP | C | 301 | -3.547 | 85.779 | 3.987 | 1.00 39.23 | O |
| TER | 8116 | | NAP | C | 301 | | | | | |
| ATOM | 8117 | PN | NAP | D | 301 | 2.229 | 59.081 | 32.512 | 1.00 24.76 | P |
| ATOM | 8118 | O1N | NAP | D | 301 | 3.285 | 58.234 | 31.902 | 1.00 25.32 | O |
| ATOM | 8119 | O2N | NAP | D | 301 | 2.274 | 59.360 | 33.978 | 1.00 24.20 | O |
| ATOM | 8120 | O3P | NAP | D | 301 | 0.811 | 58.450 | 32.154 | 1.00 26.16 | O |
| ATOM | 8121 | O5M | NAP | D | 301 | 2.278 | 60.493 | 31.715 | 1.00 25.41 | O |
| ATOM | 8122 | C5M | NAP | D | 301 | 2.360 | 61.787 | 32.336 | 1.00 23.25 | C |
| ATOM | 8123 | C4M | NAP | D | 301 | 3.055 | 62.796 | 31.430 | 1.00 21.67 | C |

FIGURE 9 (cont.)

| | | | | | | | | | | |
|---|---|---|---|---|---|---|---|---|---|---|
| ATOM | 8124 | O4M | NAP | D | 301 | 4.454 | 62.460 | 31.349 | 1.00 20.81 | O |
| ATOM | 8125 | C3M | NAP | D | 301 | 2.584 | 62.843 | 29.967 | 1.00 20.05 | C |
| ATOM | 8126 | O3M | NAP | D | 301 | 2.661 | 64.202 | 29.547 | 1.00 20.35 | O |
| ATOM | 8127 | C2M | NAP | D | 301 | 3.623 | 62.032 | 29.201 | 1.00 20.69 | C |
| ATOM | 8128 | O2M | NAP | D | 301 | 3.640 | 62.507 | 27.843 | 1.00 19.84 | O |
| ATOM | 8129 | C1M | NAP | D | 301 | 4.887 | 62.317 | 29.960 | 1.00 20.87 | C |
| ATOM | 8130 | N1N | NAP | D | 301 | 5.940 | 61.257 | 29.809 | 1.00 19.71 | N |
| ATOM | 8131 | C6N | NAP | D | 301 | 7.269 | 61.705 | 29.560 | 1.00 20.23 | C |
| ATOM | 8132 | C5N | NAP | D | 301 | 8.316 | 60.756 | 29.427 | 1.00 20.43 | C |
| ATOM | 8133 | C4N | NAP | D | 301 | 8.061 | 59.372 | 29.539 | 1.00 20.03 | C |
| ATOM | 8134 | C3N | NAP | D | 301 | 6.731 | 58.907 | 29.786 | 1.00 20.74 | C |
| ATOM | 8135 | C2N | NAP | D | 301 | 5.665 | 59.846 | 29.924 | 1.00 21.01 | C |
| ATOM | 8136 | C7N | NAP | D | 301 | 6.499 | 57.398 | 29.888 | 1.00 18.73 | C |
| ATOM | 8137 | O7N | NAP | D | 301 | 7.273 | 56.623 | 29.343 | 1.00 19.40 | O |
| ATOM | 8138 | N7N | NAP | D | 301 | 5.438 | 56.988 | 30.571 | 1.00 20.17 | N |
| ATOM | 8139 | PA | NAP | D | 301 | -0.634 | 58.571 | 32.824 | 1.00 27.13 | P |
| ATOM | 8140 | O1A | NAP | D | 301 | -1.644 | 58.076 | 31.831 | 1.00 28.72 | O |
| ATOM | 8141 | O2A | NAP | D | 301 | -0.556 | 57.856 | 34.125 | 1.00 27.17 | O |
| ATOM | 8142 | O5B | NAP | D | 301 | -0.898 | 60.151 | 33.137 | 1.00 28.13 | O |
| ATOM | 8143 | C5B | NAP | D | 301 | -1.298 | 61.139 | 32.162 | 1.00 29.50 | C |
| ATOM | 8144 | C4B | NAP | D | 301 | -2.686 | 61.675 | 32.470 | 1.00 30.28 | C |
| ATOM | 8145 | O4B | NAP | D | 301 | -3.186 | 62.323 | 31.284 | 1.00 29.05 | O |
| ATOM | 8146 | C3B | NAP | D | 301 | -3.763 | 60.632 | 32.736 | 1.00 31.23 | C |
| ATOM | 8147 | O3B | NAP | D | 301 | -4.069 | 59.867 | 33.877 | 1.00 34.06 | O |
| ATOM | 8148 | C2B | NAP | D | 301 | -4.996 | 61.328 | 32.256 | 1.00 31.90 | C |
| ATOM | 8149 | C1B | NAP | D | 301 | -4.475 | 62.673 | 31.799 | 1.00 29.90 | C |
| ATOM | 8150 | N9A | NAP | D | 301 | -5.385 | 63.338 | 30.771 | 1.00 28.81 | N |
| ATOM | 8151 | C4A | NAP | D | 301 | -6.136 | 64.391 | 31.080 | 1.00 27.23 | C |
| ATOM | 8152 | N3A | NAP | D | 301 | -6.363 | 65.179 | 32.201 | 1.00 28.03 | N |
| ATOM | 8153 | C2A | NAP | D | 301 | -7.255 | 66.219 | 32.127 | 1.00 27.09 | C |
| ATOM | 8154 | N1A | NAP | D | 301 | -7.923 | 66.481 | 30.962 | 1.00 28.21 | N |
| ATOM | 8155 | C6A | NAP | D | 301 | -7.734 | 65.722 | 29.807 | 1.00 27.87 | C |
| ATOM | 8156 | C5A | NAP | D | 301 | -6.809 | 64.656 | 29.889 | 1.00 27.52 | C |
| ATOM | 8157 | N7A | NAP | D | 301 | -6.491 | 63.822 | 28.899 | 1.00 26.74 | N |
| ATOM | 8158 | C8A | NAP | D | 301 | -5.601 | 63.005 | 29.465 | 1.00 26.20 | C |
| ATOM | 8159 | N6A | NAP | D | 301 | -8.378 | 65.961 | 28.663 | 1.00 27.73 | N |
| ATOM | 8160 | O2B | NAP | D | 301 | -6.243 | 61.023 | 33.016 | 1.00 34.19 | O |
| ATOM | 8161 | P2* | NAP | D | 301 | -7.258 | 59.825 | 32.521 | 1.00 37.98 | P |
| ATOM | 8162 | OP1 | NAP | D | 301 | -6.721 | 58.490 | 33.067 | 1.00 37.19 | O |
| ATOM | 8163 | OP2 | NAP | D | 301 | -8.530 | 60.293 | 33.176 | 1.00 39.77 | O |
| ATOM | 8164 | OP3 | NAP | D | 301 | -7.245 | 59.813 | 31.000 | 1.00 36.78 | O |
| TER | 8165 | | NAP | D | 301 | | | | | |
| ATOM | 8166 | S | SO4 | | 403 | 49.210 | 18.093 | 73.519 | 1.00 24.43 | S |
| ATOM | 8167 | O1 | SO4 | | 403 | 48.063 | 17.273 | 74.316 | 1.00 23.53 | O |
| ATOM | 8168 | O2 | SO4 | | 403 | 50.169 | 17.088 | 73.107 | 1.00 24.52 | O |
| ATOM | 8169 | O3 | SO4 | | 403 | 48.690 | 18.751 | 72.504 | 1.00 26.34 | O |
| ATOM | 8170 | O4 | SO4 | | 403 | 49.778 | 18.923 | 74.545 | 1.00 25.39 | O |
| ATOM | 8171 | S | SO4 | | 404 | 20.279 | 87.415 | 22.650 | 1.00 20.45 | S |
| ATOM | 8172 | O1 | SO4 | | 404 | 19.336 | 88.495 | 21.924 | 1.00 20.38 | O |
| ATOM | 8173 | O2 | SO4 | | 404 | 21.228 | 88.198 | 23.420 | 1.00 22.96 | O |
| ATOM | 8174 | O3 | SO4 | | 404 | 19.567 | 86.610 | 23.395 | 1.00 20.32 | O |
| ATOM | 8175 | O4 | SO4 | | 404 | 20.963 | 86.809 | 21.538 | 1.00 21.27 | O |
| ATOM | 8176 | S | SO4 | | 405 | 55.918 | 23.131 | 43.777 | 1.00 78.89 | S |
| ATOM | 8177 | O1 | SO4 | | 405 | 57.032 | 21.933 | 43.572 | 1.00 78.83 | O |
| ATOM | 8178 | O2 | SO4 | | 405 | 55.314 | 23.313 | 42.438 | 1.00 79.24 | O |
| ATOM | 8179 | O3 | SO4 | | 405 | 55.004 | 22.778 | 44.693 | 1.00 79.53 | O |
| ATOM | 8180 | O4 | SO4 | | 405 | 56.745 | 24.290 | 44.109 | 1.00 78.44 | O |
| ATOM | 8181 | S | SO4 | | 406 | 36.223 | 15.427 | 39.274 | 1.00 50.25 | S |
| ATOM | 8182 | O1 | SO4 | | 406 | 35.067 | 16.586 | 39.397 | 1.00 49.63 | O |
| ATOM | 8183 | O2 | SO4 | | 406 | 37.418 | 16.115 | 38.737 | 1.00 50.70 | O |
| ATOM | 8184 | O3 | SO4 | | 406 | 36.427 | 14.866 | 40.460 | 1.00 51.22 | O |
| ATOM | 8185 | O4 | SO4 | | 406 | 35.698 | 14.537 | 38.239 | 1.00 51.58 | O |
| ATOM | 8186 | S | SO4 | | 407 | 36.875 | 5.990 | 79.469 | 1.00 62.27 | S |
| ATOM | 8187 | O1 | SO4 | | 407 | 36.201 | 5.031 | 80.611 | 1.00 62.42 | O |
| ATOM | 8188 | O2 | SO4 | | 407 | 37.641 | 6.999 | 80.212 | 1.00 62.05 | O |

FIGURE 9 (cont.)

```
ATOM   8189  O3   SO4   407     37.638    5.261   78.652  1.00 62.52           O
ATOM   8190  O4   SO4   407     35.692    6.621   78.850  1.00 62.21           O
ATOM   8191  S    SO4   408      5.292   98.713   -0.732  1.00 41.96           S
ATOM   8192  O1   SO4   408      5.585   97.424    0.217  1.00 43.84           O
ATOM   8193  O2   SO4   408      4.101   98.341   -1.482  1.00 43.72           O
ATOM   8194  O3   SO4   408      5.130   99.793    0.018  1.00 42.55           O
ATOM   8195  O4   SO4   408      6.428   98.712   -1.630  1.00 42.58           O
ATOM   8196  OH2  WAT     1     13.770   69.810   48.391  1.00 23.31           O
ATOM   8197  OH2  WAT     2     53.787   15.224   74.796  1.00 15.24           O
ATOM   8198  OH2  WAT     3     24.953   90.426   24.101  1.00 23.96           O
ATOM   8199  OH2  WAT     4    -15.745   57.591   37.340  1.00 30.94           O
ATOM   8200  OH2  WAT     5     39.245   43.860   45.407  1.00 12.03           O
ATOM   8201  OH2  WAT     6     17.935   86.942   -8.272  1.00 33.78           O
ATOM   8202  OH2  WAT     7      4.870   90.113    2.067  1.00 13.05           O
ATOM   8203  OH2  WAT     8     31.243   35.690   45.668  1.00 19.40           O
ATOM   8204  OH2  WAT     9     15.860   64.038   -2.784  1.00 20.39           O
ATOM   8205  OH2  WAT    10     30.783   49.902   94.156  1.00 31.30           O
ATOM   8206  OH2  WAT    11     -2.809   59.089   56.305  1.00 39.93           O
ATOM   8207  OH2  WAT    12    -10.435   63.856   56.439  1.00 44.91           O
ATOM   8208  OH2  WAT    13     11.432   24.766   88.221  1.00 32.42           O
ATOM   8209  OH2  WAT    14     39.633   27.221  102.069  1.00 25.09           O
ATOM   8210  OH2  WAT    15    -11.346   62.835   53.467  1.00 28.65           O
ATOM   8211  OH2  WAT    16     54.242   50.754   70.667  1.00 19.49           O
ATOM   8212  OH2  WAT    17     21.306   46.373   60.409  1.00 28.32           O
ATOM   8213  OH2  WAT    18      4.531   86.784  -18.305  1.00 41.01           O
ATOM   8214  OH2  WAT    19     39.029   45.883   82.886  1.00  9.70           O
ATOM   8215  OH2  WAT    20     -5.765   97.867  -10.803  1.00 24.51           O
ATOM   8216  OH2  WAT    21     30.013   25.322   88.809  1.00 18.49           O
ATOM   8217  OH2  WAT    22     15.825   40.677   46.633  1.00 34.68           O
ATOM   8218  OH2  WAT    23      4.218   57.169    0.771  1.00 31.46           O
ATOM   8219  OH2  WAT    24     13.602   55.347   31.897  1.00 12.69           O
ATOM   8220  OH2  WAT    25    -11.530   55.082   36.557  1.00 42.71           O
ATOM   8221  OH2  WAT    26      4.406   78.309    9.343  1.00 18.71           O
ATOM   8222  OH2  WAT    27     -7.560   84.473   18.484  1.00 34.98           O
ATOM   8223  OH2  WAT    28     17.781   40.894   71.669  1.00 12.75           O
ATOM   8224  OH2  WAT    29     28.002   48.772   54.231  1.00 31.15           O
ATOM   8225  OH2  WAT    30     32.625   21.493   94.869  1.00 14.58           O
ATOM   8226  OH2  WAT    31     -9.151   84.266   33.935  1.00 34.95           O
ATOM   8227  OH2  WAT    32     27.332   33.731   49.382  1.00 18.74           O
ATOM   8228  OH2  WAT    33     24.367   21.041   85.282  1.00 13.87           O
ATOM   8229  OH2  WAT    34     39.649   32.021   68.888  1.00 15.33           O
ATOM   8230  OH2  WAT    35     34.956   21.609   96.617  1.00 20.56           O
ATOM   8231  OH2  WAT    36      0.922   45.460   37.406  1.00 37.22           O
ATOM   8232  OH2  WAT    37     30.711   14.378   44.909  1.00 17.91           O
ATOM   8233  OH2  WAT    38      9.942   82.636   34.513  1.00 18.38           O
ATOM   8234  OH2  WAT    39     29.653   14.058  100.541  1.00 15.58           O
ATOM   8235  OH2  WAT    40     25.106   72.647  -11.550  1.00 28.91           O
ATOM   8236  OH2  WAT    41     31.612   30.485   82.773  1.00 11.72           O
ATOM   8237  OH2  WAT    42     50.954   17.175   48.480  1.00 52.71           O
ATOM   8238  OH2  WAT    43     22.072   31.552   87.496  1.00 23.23           O
ATOM   8239  OH2  WAT    44     27.166   40.842   45.656  1.00 32.08           O
ATOM   8240  OH2  WAT    45     -4.512   63.620    5.043  1.00 29.69           O
ATOM   8241  OH2  WAT    46     -5.377   60.998   11.735  1.00 30.47           O
ATOM   8242  OH2  WAT    47     14.642   78.687   14.208  1.00 25.25           O
ATOM   8243  OH2  WAT    48     19.376   44.672   49.735  1.00 33.94           O
ATOM   8244  OH2  WAT    49     41.753   28.337   78.254  1.00 18.43           O
ATOM   8245  OH2  WAT    50     23.679   15.636   55.119  1.00 36.62           O
ATOM   8246  OH2  WAT    51      5.565   54.581   12.969  1.00 23.26           O
ATOM   8247  OH2  WAT    52    -12.404   56.041   41.172  1.00 49.11           O
ATOM   8248  OH2  WAT    53     26.614   43.327  101.518  1.00 38.14           O
ATOM   8249  OH2  WAT    54      0.008   94.623   -8.380  1.00 24.96           O
ATOM   8250  OH2  WAT    55     42.171   18.358   86.276  1.00 11.89           O
ATOM   8251  OH2  WAT    56    -11.709   75.589   32.515  1.00 44.44           O
ATOM   8252  OH2  WAT    57     19.028   52.080   19.243  1.00 25.49           O
ATOM   8253  OH2  WAT    58     38.459   39.844   86.974  1.00 18.25           O
```

FIGURE 9 (cont.)

```
ATOM   8254  OH2 WAT    59      -1.925  88.599  23.768  1.00 34.55      O
ATOM   8255  OH2 WAT    60      43.368  37.060  63.519  1.00 15.46      O
ATOM   8256  OH2 WAT    61      50.081  52.244  52.427  1.00 26.59      O
ATOM   8257  OH2 WAT    62      33.362  36.069  59.317  1.00 18.74      O
ATOM   8258  OH2 WAT    63      12.946  61.804  27.156  1.00 14.87      O
ATOM   8259  OH2 WAT    64      36.978  56.836  56.526  1.00 23.67      O
ATOM   8260  OH2 WAT    65      13.634  63.000   4.625  1.00 17.42      O
ATOM   8261  OH2 WAT    66      42.059  23.606  80.663  1.00 15.05      O
ATOM   8262  OH2 WAT    67       1.891  66.791  27.193  1.00 26.31      O
ATOM   8263  OH2 WAT    68      -5.329  63.140  -4.520  1.00 34.67      O
ATOM   8264  OH2 WAT    69      39.580  33.462  72.067  1.00 12.42      O
ATOM   8265  OH2 WAT    70      44.497  19.022  50.925  1.00 24.06      O
ATOM   8266  OH2 WAT    71      13.223  72.003  25.232  1.00 21.34      O
ATOM   8267  OH2 WAT    72     -19.083  76.457  33.734  1.00 31.00      O
ATOM   8268  OH2 WAT    73     -10.053  65.973  10.795  1.00 37.77      O
ATOM   8269  OH2 WAT    74     -13.895  62.234  32.426  1.00 29.08      O
ATOM   8270  OH2 WAT    75      18.978  24.082  63.377  1.00 14.09      O
ATOM   8271  OH2 WAT    76      11.883  70.887  21.501  1.00 28.91      O
ATOM   8272  OH2 WAT    77      23.243  20.101  66.312  1.00 20.32      O
ATOM   8273  OH2 WAT    78      28.961  43.380  56.144  1.00 20.01      O
ATOM   8274  OH2 WAT    79     -16.376  62.197  39.727  1.00 36.15      O
ATOM   8275  OH2 WAT    80      19.432  44.997  86.444  1.00 16.37      O
ATOM   8276  OH2 WAT    81      -7.684  88.797  -8.626  1.00 41.99      O
ATOM   8277  OH2 WAT    82     -11.036  69.466   7.632  1.00 29.82      O
ATOM   8278  OH2 WAT    83      26.928  30.125 110.773  1.00 49.58      O
ATOM   8279  OH2 WAT    84      -8.727  75.338  14.257  1.00 15.09      O
ATOM   8280  OH2 WAT    85       6.760  78.209   6.175  1.00 20.65      O
ATOM   8281  OH2 WAT    86       2.964  66.974  31.092  1.00 12.29      O
ATOM   8282  OH2 WAT    87      46.238  47.331  55.905  1.00 16.80      O
ATOM   8283  OH2 WAT    88      47.558  33.770  82.064  1.00 37.02      O
ATOM   8284  OH2 WAT    89     -10.073  81.190  43.459  1.00 36.09      O
ATOM   8285  OH2 WAT    90      13.964  85.386 -11.890  1.00 20.84      O
ATOM   8286  OH2 WAT    91      25.256  49.442  57.086  1.00 38.67      O
ATOM   8287  OH2 WAT    92      23.491  20.915  59.664  1.00 35.13      O
ATOM   8288  OH2 WAT    93      30.798  46.545  98.026  1.00 25.77      O
ATOM   8289  OH2 WAT    94       5.826  84.549   1.293  1.00 15.46      O
ATOM   8290  OH2 WAT    95      42.472  37.750  36.703  1.00 38.03      O
ATOM   8291  OH2 WAT    96      27.048  52.080  73.596  1.00 24.32      O
ATOM   8292  OH2 WAT    97      40.976  29.574  69.595  1.00 16.88      O
ATOM   8293  OH2 WAT    98      21.650  82.391   1.571  1.00 20.12      O
ATOM   8294  OH2 WAT    99      30.766  29.040  79.547  1.00 25.48      O
ATOM   8295  OH2 WAT   100      -1.911  64.325   6.913  1.00 20.50      O
ATOM   8296  OH2 WAT   101      26.932  49.258  99.352  1.00 27.87      O
ATOM   8297  OH2 WAT   102      23.653  33.671 100.932  1.00 25.94      O
ATOM   8298  OH2 WAT   103      -2.251  91.254  26.804  1.00 36.24      O
ATOM   8299  OH2 WAT   104      25.721  17.983  44.013  1.00 14.33      O
ATOM   8300  OH2 WAT   105      35.596  12.166  40.743  1.00 26.33      O
ATOM   8301  OH2 WAT   106      -1.652  79.340  -0.505  1.00 22.90      O
ATOM   8302  OH2 WAT   107      17.929  43.196  48.684  1.00 43.42      O
ATOM   8303  OH2 WAT   108      21.744  12.954  72.737  1.00 27.65      O
ATOM   8304  OH2 WAT   109      28.245  15.176  90.298  1.00 16.94      O
ATOM   8305  OH2 WAT   110      34.507  14.498  35.671  1.00 25.45      O
ATOM   8306  OH2 WAT   111      49.125  57.448  56.064  1.00 28.72      O
ATOM   8307  OH2 WAT   112      15.882  28.186  55.273  1.00 28.51      O
ATOM   8308  OH2 WAT   113      14.049  50.827  21.016  1.00 27.67      O
ATOM   8309  OH2 WAT   114      43.379  52.753  68.811  1.00 28.95      O
ATOM   8310  OH2 WAT   115      41.871  15.836  72.104  1.00 25.48      O
ATOM   8311  OH2 WAT   116      43.153  25.638  54.067  1.00 15.52      O
ATOM   8312  OH2 WAT   117      32.020  54.536  68.948  1.00 29.05      O
ATOM   8313  OH2 WAT   118      10.827  68.695  54.410  1.00 43.64      O
ATOM   8314  OH2 WAT   119      -8.703  55.833  31.327  1.00 41.41      O
ATOM   8315  OH2 WAT   120       9.783  90.825  18.927  1.00 19.06      O
ATOM   8316  OH2 WAT   121      -5.260  53.374  40.999  1.00 33.24      O
ATOM   8317  OH2 WAT   122      28.698  44.380  52.124  1.00 22.52      O
ATOM   8318  OH2 WAT   123      -7.319  55.418  17.508  1.00 28.75      O
```

FIGURE 9 (cont.)

```
ATOM   8319  OH2 WAT   124      14.286  35.938  95.114  1.00 28.34        O
ATOM   8320  OH2 WAT   125       2.512  81.269  -4.188  1.00 23.89        O
ATOM   8321  OH2 WAT   126      26.497  53.672  76.664  1.00 34.04        O
ATOM   8322  OH2 WAT   127      17.138  90.477   8.397  1.00 26.36        O
ATOM   8323  OH2 WAT   128      31.443  56.295  51.538  1.00 33.99        O
ATOM   8324  OH2 WAT   129      44.989   8.330  86.480  1.00 41.66        O
ATOM   8325  OH2 WAT   130      -4.195  65.470  -3.597  1.00 24.16        O
ATOM   8326  OH2 WAT   131      13.211  37.908  78.899  1.00 18.66        O
ATOM   8327  OH2 WAT   132      31.646  12.270  74.428  1.00 28.53        O
ATOM   8328  OH2 WAT   133      23.259  81.791   9.673  1.00 25.26        O
ATOM   8329  OH2 WAT   134      32.339  10.974  83.191  1.00 37.16        O
ATOM   8330  OH2 WAT   135      27.851  54.884  78.687  1.00 30.84        O
ATOM   8331  OH2 WAT   136      17.667  38.858  51.005  1.00 34.10        O
ATOM   8332  OH2 WAT   137      33.957  45.644  49.456  1.00 11.80        O
ATOM   8333  OH2 WAT   138      50.097  20.977  41.450  1.00 31.27        O
ATOM   8334  OH2 WAT   139      21.619  44.628  67.149  1.00 25.15        O
ATOM   8335  OH2 WAT   140      -4.560  58.870  -4.451  1.00 35.87        O
ATOM   8336  OH2 WAT   141      36.603  13.905  51.926  1.00 18.74        O
ATOM   8337  OH2 WAT   142      38.375   3.621  80.349  1.00 36.45        O
ATOM   8338  OH2 WAT   143       1.885  82.580  46.164  1.00 30.87        O
ATOM   8339  OH2 WAT   144      33.524  50.163  48.419  1.00 20.61        O
ATOM   8340  OH2 WAT   145      37.226  43.332 102.878  1.00 29.48        O
ATOM   8341  OH2 WAT   146      -0.382  81.425   0.046  1.00 23.36        O
ATOM   8342  OH2 WAT   147      24.841  17.819  96.372  1.00 19.31        O
ATOM   8343  OH2 WAT   148      41.643  49.292  69.225  1.00 25.59        O
ATOM   8344  OH2 WAT   149      -3.522  51.455  40.801  1.00 32.45        O
ATOM   8345  OH2 WAT   150      24.875  42.582  65.478  1.00 14.12        O
ATOM   8346  OH2 WAT   151      -4.321  84.994  45.668  1.00 23.83        O
ATOM   8347  OH2 WAT   152      -0.476  52.351  47.130  1.00 34.46        O
ATOM   8348  OH2 WAT   153      27.025  19.715  48.187  1.00 11.38        O
ATOM   8349  OH2 WAT   154      43.261  53.497  66.271  1.00 31.93        O
ATOM   8350  OH2 WAT   155      28.500  19.512  89.379  1.00 21.41        O
ATOM   8351  OH2 WAT   156     -12.616  70.313   3.808  1.00 26.05        O
ATOM   8352  OH2 WAT   157      -6.163  82.655 -12.062  1.00 38.80        O
ATOM   8353  OH2 WAT   158      53.111  60.609  63.336  1.00 33.31        O
ATOM   8354  OH2 WAT   159       9.221  83.632 -20.822  1.00 29.00        O
ATOM   8355  OH2 WAT   160      29.246  15.881  54.491  1.00 25.55        O
ATOM   8356  OH2 WAT   161      29.166  11.075  60.736  1.00 30.87        O
ATOM   8357  OH2 WAT   162       9.806  81.181  42.644  1.00 29.44        O
ATOM   8358  OH2 WAT   163      46.722  49.871  50.172  1.00 35.23        O
ATOM   8359  OH2 WAT   164     -10.575  72.090  24.241  1.00 31.12        O
ATOM   8360  OH2 WAT   165      -1.741  57.643  -2.101  1.00 39.31        O
ATOM   8361  OH2 WAT   166      38.301  25.429 101.259  1.00 27.02        O
ATOM   8362  OH2 WAT   167      28.259  15.030  45.952  1.00 20.32        O
ATOM   8363  OH2 WAT   168      16.572  57.122   0.617  1.00 38.42        O
ATOM   8364  OH2 WAT   169      10.171  55.431  22.406  1.00 24.86        O
ATOM   8365  OH2 WAT   170      13.840  38.236  94.370  1.00 22.70        O
ATOM   8366  OH2 WAT   171       7.158  84.822 -16.612  1.00 23.49        O
ATOM   8367  OH2 WAT   172      52.284   7.765  82.859  1.00 39.96        O
ATOM   8368  OH2 WAT   173      42.656  22.048  47.480  1.00 18.34        O
ATOM   8369  OH2 WAT   174      20.510  22.528  93.712  1.00 28.31        O
ATOM   8370  OH2 WAT   175      -2.990  85.523  -0.966  1.00 35.74        O
ATOM   8371  OH2 WAT   176      14.031  34.419  92.713  1.00 23.15        O
ATOM   8372  OH2 WAT   177      42.342  19.730  58.390  1.00  9.29        O
ATOM   8373  OH2 WAT   178      16.699  20.869  95.372  1.00 45.86        O
ATOM   8374  OH2 WAT   179     -10.113  70.047  12.641  1.00 25.62        O
ATOM   8375  OH2 WAT   180       5.896  51.586  36.723  1.00 22.86        O
ATOM   8376  OH2 WAT   181      12.930  89.666  -3.706  1.00 28.56        O
ATOM   8377  OH2 WAT   182      28.575  44.084  31.850  1.00 40.68        O
ATOM   8378  OH2 WAT   183      -0.482  53.300  27.303  1.00 47.54        O
ATOM   8379  OH2 WAT   184       8.940  93.553  -7.837  1.00 24.21        O
ATOM   8380  OH2 WAT   185      38.987   9.824  49.939  1.00 23.92        O
ATOM   8381  OH2 WAT   186      35.992  47.463  71.945  1.00 27.33        O
ATOM   8382  OH2 WAT   187      36.351  43.432  93.881  1.00 21.60        O
ATOM   8383  OH2 WAT   188      -4.057  57.501  30.986  1.00 20.40        O
```

FIGURE 9 (cont.)

```
ATOM   8384  OH2 WAT   189       2.308   98.304   -3.708  1.00 31.08           O
ATOM   8385  OH2 WAT   190      40.437   24.546   36.035  1.00 30.79           O
ATOM   8386  OH2 WAT   192      26.894   58.579   16.117  1.00 31.49           O
ATOM   8387  OH2 WAT   193      -9.163   62.366   26.746  1.00 31.34           O
ATOM   8388  OH2 WAT   194      10.096   79.860   51.606  1.00 31.43           O
ATOM   8389  OH2 WAT   195      -7.824   73.924   -4.631  1.00 28.19           O
ATOM   8390  OH2 WAT   196      -0.414   93.282   17.036  1.00 47.13           O
ATOM   8391  OH2 WAT   198      25.037   29.668   92.504  1.00 14.38           O
ATOM   8392  OH2 WAT   199      -0.250   88.265    4.562  1.00 19.92           O
ATOM   8393  OH2 WAT   200       7.717   88.539   45.148  1.00 45.25           O
ATOM   8394  OH2 WAT   201      16.429   69.915   19.894  1.00 23.66           O
ATOM   8395  OH2 WAT   202      38.116   15.663   45.518  1.00 26.01           O
ATOM   8396  OH2 WAT   203       5.818   80.529   50.117  1.00 46.00           O
ATOM   8397  OH2 WAT   204      19.610   46.537   80.559  1.00 33.75           O
ATOM   8398  OH2 WAT   205      53.971   55.851   66.655  1.00 36.91           O
ATOM   8399  OH2 WAT   206      -6.435   92.346   13.911  1.00 33.05           O
ATOM   8400  OH2 WAT   207      42.483   30.049  101.162  1.00 23.94           O
ATOM   8401  OH2 WAT   209      32.388   51.824   50.122  1.00 16.96           O
ATOM   8402  OH2 WAT   210      36.086   51.341   49.580  1.00 14.04           O
ATOM   8403  OH2 WAT   211      39.864   49.485   48.849  1.00 15.02           O
ATOM   8404  OH2 WAT   212      43.900   44.836   45.406  1.00 20.47           O
ATOM   8405  OH2 WAT   213      44.760   48.774   53.199  1.00 12.34           O
ATOM   8406  OH2 WAT   214      25.913   21.888   81.754  1.00 38.69           O
ATOM   8407  OH2 WAT   215      18.384   79.923   51.181  1.00 21.47           O
ATOM   8408  OH2 WAT   216      57.260   51.410   53.589  1.00 28.95           O
ATOM   8409  OH2 WAT   217      23.526   47.614   60.284  1.00 20.01           O
ATOM   8410  OH2 WAT   218       0.669   60.449   -0.022  1.00 32.01           O
ATOM   8411  OH2 WAT   219      40.141    8.699   85.682  1.00 25.90           O
ATOM   8412  OH2 WAT   220      51.495   22.954   41.641  1.00 25.01           O
ATOM   8413  OH2 WAT   221      53.408   24.158   40.987  1.00 30.95           O
ATOM   8414  OH2 WAT   222      48.434   23.022   42.655  1.00 27.99           O
ATOM   8415  OH2 WAT   223      50.130   24.313   43.642  1.00 16.55           O
ATOM   8416  OH2 WAT   224      28.266   36.648   49.747  1.00 19.15           O
ATOM   8417  OH2 WAT   225      35.030   40.043   50.182  1.00 14.08           O
ATOM   8418  OH2 WAT   226      27.139   38.728   48.714  1.00 27.22           O
ATOM   8419  OH2 WAT   227      29.391   27.601   70.051  1.00 22.54           O
ATOM   8420  OH2 WAT   229      25.464   54.966   19.003  1.00 13.49           O
ATOM   8421  OH2 WAT   230      31.930   11.587   53.684  1.00 17.69           O
ATOM   8422  OH2 WAT   231      30.573   14.131   53.042  1.00 20.55           O
ATOM   8423  OH2 WAT   232      37.899    7.785   50.679  1.00 22.99           O
ATOM   8424  OH2 WAT   233      37.217    7.685   53.425  1.00 16.98           O
ATOM   8425  OH2 WAT   234      31.060   10.308   50.491  1.00 18.54           O
ATOM   8426  OH2 WAT   235      38.409   16.660   77.200  1.00 21.48           O
ATOM   8427  OH2 WAT   236      42.358   18.571   78.974  1.00 32.62           O
ATOM   8428  OH2 WAT   237      36.075   13.244   75.327  1.00 22.91           O
ATOM   8429  OH2 WAT   238      15.315   92.214    6.126  1.00 27.21           O
ATOM   8430  OH2 WAT   239      10.970   94.014    1.857  1.00 15.78           O
ATOM   8431  OH2 WAT   240      10.277   89.236   -2.319  1.00 22.77           O
ATOM   8432  OH2 WAT   241      14.259   90.527   -1.944  1.00 26.71           O
ATOM   8433  OH2 WAT   242      33.149   48.759   74.023  1.00 15.24           O
ATOM   8434  OH2 WAT   243      34.965   46.870   74.532  1.00 13.38           O
ATOM   8435  OH2 WAT   244      35.374   50.091   72.209  1.00 19.46           O
ATOM   8436  OH2 WAT   245      14.006   70.037    1.719  1.00 24.70           O
ATOM   8437  OH2 WAT   246      34.669   16.507   65.474  1.00 16.91           O
ATOM   8438  OH2 WAT   247      36.422   18.446   65.611  1.00  7.35           O
ATOM   8439  OH2 WAT   248      36.836   18.104   68.150  1.00 27.13           O
ATOM   8440  OH2 WAT   249      10.806   72.235   17.746  1.00 14.29           O
ATOM   8441  OH2 WAT   250      10.408   73.429   21.088  1.00 12.27           O
ATOM   8442  OH2 WAT   251      11.604   75.543   21.401  1.00 19.99           O
ATOM   8443  OH2 WAT   252      12.151   69.970   17.700  1.00 24.80           O
ATOM   8444  OH2 WAT   253      12.230   74.456   17.672  1.00 27.67           O
ATOM   8445  OH2 WAT   254      12.743   66.713   25.914  1.00 15.79           O
ATOM   8446  OH2 WAT   255      22.625   45.362   70.269  1.00 19.51           O
ATOM   8447  OH2 WAT   256      21.507   45.474   76.999  1.00 33.32           O
ATOM   8448  OH2 WAT   257      20.472   50.104   81.459  1.00 40.71           O
```

FIGURE 9 (cont.)

| | | | | | | | | | |
|---|---|---|---|---|---|---|---|---|---|
| ATOM | 8449 | OH2 | WAT | 258 | 31.633 | 15.066 | 98.218 | 1.00 21.19 | O |
| ATOM | 8450 | OH2 | WAT | 259 | 16.380 | 38.319 | 74.572 | 1.00 38.59 | O |
| ATOM | 8451 | OH2 | WAT | 260 | 14.360 | 35.670 | 72.612 | 1.00 21.61 | O |
| ATOM | 8452 | OH2 | WAT | 261 | 17.227 | 29.542 | 72.804 | 1.00 33.47 | O |
| ATOM | 8453 | OH2 | WAT | 262 | 16.469 | 43.203 | 70.410 | 1.00 24.04 | O |
| ATOM | 8454 | OH2 | WAT | 263 | 19.471 | 41.627 | 74.437 | 1.00 25.22 | O |
| ATOM | 8455 | OH2 | WAT | 264 | 22.128 | 49.388 | 63.243 | 1.00 18.71 | O |
| ATOM | 8456 | OH2 | WAT | 265 | 19.299 | 43.199 | 60.951 | 1.00 10.23 | O |
| ATOM | 8457 | OH2 | WAT | 266 | 18.206 | 36.539 | 70.734 | 1.00 22.81 | O |
| ATOM | 8458 | OH2 | WAT | 267 | 19.851 | 36.852 | 66.013 | 1.00 23.84 | O |
| ATOM | 8459 | OH2 | WAT | 268 | 20.537 | 34.623 | 64.804 | 1.00 19.82 | O |
| ATOM | 8460 | OH2 | WAT | 269 | 19.957 | 25.180 | 80.660 | 1.00 20.40 | O |
| ATOM | 8461 | OH2 | WAT | 270 | 17.007 | 34.389 | 72.799 | 1.00 25.69 | O |
| ATOM | 8462 | OH2 | WAT | 271 | 19.341 | 30.658 | 71.347 | 1.00 34.27 | O |
| ATOM | 8463 | OH2 | WAT | 272 | 15.740 | 37.100 | 76.723 | 1.00 26.73 | O |
| ATOM | 8464 | OH2 | WAT | 273 | 21.358 | 82.380 | -7.958 | 1.00 16.50 | O |
| ATOM | 8465 | OH2 | WAT | 274 | 23.395 | 87.377 | -7.523 | 1.00 20.54 | O |
| ATOM | 8466 | OH2 | WAT | 275 | -1.051 | 83.726 | -0.648 | 1.00 26.81 | O |
| ATOM | 8467 | OH2 | WAT | 276 | 40.592 | 31.429 | 72.966 | 1.00 19.50 | O |
| ATOM | 8468 | OH2 | WAT | 277 | 41.157 | 33.707 | 68.140 | 1.00 8.48 | O |
| ATOM | 8469 | OH2 | WAT | 278 | 42.293 | 33.671 | 76.418 | 1.00 39.75 | O |
| ATOM | 8470 | OH2 | WAT | 279 | 42.614 | 33.247 | 74.077 | 1.00 40.72 | O |
| ATOM | 8471 | OH2 | WAT | 280 | 40.639 | 35.875 | 71.737 | 1.00 19.83 | O |
| ATOM | 8472 | OH2 | WAT | 281 | 43.473 | 33.943 | 69.708 | 1.00 30.01 | O |
| ATOM | 8473 | OH2 | WAT | 282 | 35.295 | 35.149 | 56.614 | 1.00 12.76 | O |
| ATOM | 8474 | OH2 | WAT | 283 | 40.267 | 48.900 | 63.599 | 1.00 27.77 | O |
| ATOM | 8475 | OH2 | WAT | 284 | 44.272 | 46.580 | 62.911 | 1.00 33.13 | O |
| ATOM | 8476 | OH2 | WAT | 285 | 39.215 | 50.457 | 66.047 | 1.00 20.90 | O |
| ATOM | 8477 | OH2 | WAT | 286 | 44.691 | 50.008 | 62.892 | 1.00 23.00 | O |
| ATOM | 8478 | OH2 | WAT | 287 | 42.666 | 49.386 | 65.120 | 1.00 37.24 | O |
| ATOM | 8479 | OH2 | WAT | 288 | 41.673 | 51.207 | 66.714 | 1.00 30.77 | O |
| ATOM | 8480 | OH2 | WAT | 289 | 46.184 | 53.262 | 69.103 | 1.00 37.72 | O |
| ATOM | 8481 | OH2 | WAT | 290 | 46.265 | 56.435 | 66.094 | 1.00 36.58 | O |
| ATOM | 8482 | OH2 | WAT | 291 | 46.657 | 56.978 | 63.272 | 1.00 18.05 | O |
| ATOM | 8483 | OH2 | WAT | 292 | 41.731 | 58.004 | 65.939 | 1.00 44.03 | O |
| ATOM | 8484 | OH2 | WAT | 293 | 39.569 | 59.435 | 60.959 | 1.00 34.06 | O |
| ATOM | 8485 | OH2 | WAT | 294 | 43.968 | 56.722 | 55.898 | 1.00 29.36 | O |
| ATOM | 8486 | OH2 | WAT | 295 | 17.741 | 33.237 | 74.766 | 1.00 17.96 | O |
| ATOM | 8487 | OH2 | WAT | 296 | 14.507 | 78.225 | 52.410 | 1.00 23.99 | O |
| ATOM | 8488 | OH2 | WAT | 297 | 19.201 | 77.515 | 42.241 | 1.00 23.39 | O |
| ATOM | 8489 | OH2 | WAT | 298 | 19.466 | 74.805 | 50.924 | 1.00 23.24 | O |
| ATOM | 8490 | OH2 | WAT | 299 | 41.400 | 31.316 | 34.538 | 1.00 28.72 | O |
| ATOM | 8491 | OH2 | WAT | 300 | 19.200 | 44.109 | 52.251 | 1.00 39.47 | O |
| ATOM | 8492 | OH2 | WAT | 301 | 17.818 | 22.046 | 64.477 | 1.00 31.59 | O |
| ATOM | 8493 | OH2 | WAT | 302 | 18.108 | 22.975 | 70.618 | 1.00 16.58 | O |
| ATOM | 8494 | OH2 | WAT | 303 | 21.881 | 22.776 | 60.431 | 1.00 30.28 | O |
| ATOM | 8495 | OH2 | WAT | 304 | 19.570 | 18.910 | 75.609 | 1.00 21.92 | O |
| ATOM | 8496 | OH2 | WAT | 305 | 21.579 | 17.690 | 76.478 | 1.00 14.72 | O |
| ATOM | 8497 | OH2 | WAT | 306 | 9.345 | 51.358 | 33.891 | 1.00 21.92 | O |
| ATOM | 8498 | OH2 | WAT | 307 | 46.320 | 39.803 | 40.181 | 1.00 21.74 | O |
| ATOM | 8499 | OH2 | WAT | 308 | 19.465 | 47.531 | 92.450 | 1.00 19.20 | O |
| ATOM | 8500 | OH2 | WAT | 309 | 29.535 | 37.532 | 68.398 | 1.00 23.16 | O |
| ATOM | 8501 | OH2 | WAT | 310 | 1.266 | 61.451 | 35.725 | 1.00 25.25 | O |
| ATOM | 8502 | OH2 | WAT | 311 | 40.048 | 16.606 | 88.507 | 1.00 14.03 | O |
| ATOM | 8503 | OH2 | WAT | 312 | 37.207 | 20.509 | 96.088 | 1.00 21.50 | O |
| ATOM | 8504 | OH2 | WAT | 313 | 34.700 | 16.236 | 91.629 | 1.00 22.77 | O |
| ATOM | 8505 | OH2 | WAT | 314 | 31.064 | 14.263 | 90.141 | 1.00 20.78 | O |
| ATOM | 8506 | OH2 | WAT | 315 | 24.954 | 17.784 | 98.794 | 1.00 13.80 | O |
| ATOM | 8507 | OH2 | WAT | 316 | 24.084 | 15.683 | 95.022 | 1.00 23.39 | O |
| ATOM | 8508 | OH2 | WAT | 317 | 26.303 | 52.796 | 19.175 | 1.00 25.27 | O |
| ATOM | 8509 | OH2 | WAT | 318 | 45.082 | 41.864 | 61.379 | 1.00 22.84 | O |
| ATOM | 8510 | OH2 | WAT | 319 | 21.247 | 45.737 | 88.873 | 1.00 20.95 | O |
| ATOM | 8511 | OH2 | WAT | 320 | 20.437 | 47.907 | 90.059 | 1.00 21.85 | O |
| ATOM | 8512 | OH2 | WAT | 321 | 43.041 | 42.932 | 102.082 | 1.00 22.83 | O |
| ATOM | 8513 | OH2 | WAT | 322 | 44.921 | 46.001 | 101.753 | 1.00 26.07 | O |

FIGURE 9 (cont.)

```
ATOM   8514  OH2 WAT   323      41.097  42.591  99.112  1.00 31.90           O
ATOM   8515  OH2 WAT   324      41.261  45.126 101.484  1.00 38.75           O
ATOM   8516  OH2 WAT   325      37.076  47.408 103.141  1.00 29.56           O
ATOM   8517  OH2 WAT   326      44.408  39.144 103.906  1.00 42.58           O
ATOM   8518  OH2 WAT   327      15.480  91.782  16.376  1.00 29.63           O
ATOM   8519  OH2 WAT   328      10.950  90.146  16.444  1.00 36.72           O
ATOM   8520  OH2 WAT   329       7.658  97.806   8.657  1.00 34.59           O
ATOM   8521  OH2 WAT   330       0.268  67.468  17.678  1.00 38.21           O
ATOM   8522  OH2 WAT   331       0.531  60.562  14.205  1.00 36.17           O
ATOM   8523  OH2 WAT   332      -4.365  62.419  17.917  1.00 28.16           O
ATOM   8524  OH2 WAT   333      -7.486  61.033  15.379  1.00 29.82           O
ATOM   8525  OH2 WAT   334      -8.055  65.643   8.338  1.00 24.89           O
ATOM   8526  OH2 WAT   335      18.040  27.951  58.354  1.00 25.83           O
ATOM   8527  OH2 WAT   336      19.644  31.918  60.280  1.00 32.67           O
ATOM   8528  OH2 WAT   345      13.332  57.188  24.823  1.00 18.82           O
ATOM   8529  OH2 WAT   346       9.042  54.606  19.958  1.00 23.92           O
ATOM   8530  OH2 WAT   347       8.017  58.792  13.990  1.00 27.05           O
ATOM   8531  OH2 WAT   348      15.309  52.512  17.849  1.00 25.60           O
ATOM   8532  OH2 WAT   349      16.108  54.735  15.053  1.00 30.32           O
ATOM   8533  OH2 WAT   350      14.223  57.301  15.791  1.00 30.89           O
ATOM   8534  OH2 WAT   351      -7.318  69.720   0.751  1.00 25.87           O
ATOM   8535  OH2 WAT   352      52.896  22.160  53.642  1.00 22.20           O
ATOM   8536  OH2 WAT   353      48.106  17.722  52.824  1.00 24.77           O
ATOM   8537  OH2 WAT   354      25.040  68.013   0.049  1.00 23.44           O
ATOM   8538  OH2 WAT   355      -9.087  86.605  33.143  1.00 29.82           O
ATOM   8539  OH2 WAT   356      -4.576  87.410  23.440  1.00 33.92           O
ATOM   8540  OH2 WAT   357      42.192  10.285  45.891  1.00 24.70           O
ATOM   8541  OH2 WAT   358      44.543   8.578  79.573  1.00 22.07           O
TER    8542      WAT   358
END
```

```
EC_FabI   1   -------------------------------MGFLSGKRILVTGVASKLSIAYGIAQAMHREGAELAF  37
HI_FabI   1   MRLVFLEILVGFVQRQIFAYTTQVFYANNIGKIMGFLTGKRILVTGIASNRSIAYGIAKSMKEQGAELAF  70
PA_FabI   1   -------------------------------MGFLTGKRALIVGVASKLSIASGIAAAMHREGAELAF  37
EF_FabI   1   -------------------------------MFLQNKNVVMGVANKKSIAYGCAKALKDQGANVIY  36
SA_FabI   1   -------------------------------MLNLENKTYVIMGIANKRSIAEGVAKVEDQLGAKLVF  37
SE_FabI   1   -------------------------------MLNLENKTYVIMGIANKRSIAEGVAKVEDRLGAKLVF  37

EC_FabI   38  TYQNDKLKGRVEEFAAQLGS--DIVLQCDVAEDASIDTMFAELGKVWPKFDGFVHSIGFAPGDQLDGDYV  105
HI_FabI   71  TYLNDKLQPRVEEFAKEFGS--DIVLPLDVATDESIQNCEAELSKRWDKFDGFIEAIAFAPGDQLDGDYV  138
PA_FabI   38  TYQNDKLRGRVEEFASGWGSRPELCFPCDVADDSQIEAVFAALGKHWDGLDIIVSVGFAPGDQLDGDET  107
EF_FabI   37  TYQNERMKKQVVKLADEND----LEVECDVASDASIQAAFETIKNEVGTIDGLVEAIAFAKKEELSGNVS  102
SA_FabI   38  TYRKERSRKELEKLLPQLNQPEAHIYQIDVQSDEEVINGFEQIGKDVGNIDGVYFSIAFANMEDLRGRES  107
SE_FabI   38  TYRKERSRKELEKLLEQLNQSEHHLYEIDVQNDEDIINGFSQIGKDVGQIDGVYFSIAFANMEDLRGRES  107

EC_FabI   106 NAVIREGFKIAHDISSYSFVAMAKACRSMLN-PGSALETLSYLGAERAIPNYNVMGLAKASLEANVRYMA  174
HI_FabI   139 NAATREGVRIAHDISAYSFVAMAQAARPYLN-PNAALLTLSYLGAERAIPNYNVLCIAKASLEAATRVMA  207
PA_FabI   108 AVTIREGFRIPHDISAYSFIALAKAGREMMKGRNGSLETLSYLGAERTMPNYNVMGMAKASLEAGVRYLA  177
EF_FabI   102 -DIIREGFLEAQDISSYSLLAUTHYAKPLLN-PGSGLVTLIYLGSEREIPNYNMMCIAKASLETAVKYLA  170
SA_FabI   107 -ETSREGFLLQDISSYSLTIVHEAKKEMP-EGGSLVATIYLCGEFAVQNYNVMGVAKASLEANVKYLA  175
SE_FabI   107 -ETSREGFLLAQDISSYSLTLVHEAKKLMP-EGGSLVATIYLGEAAVQNYNVMGVAKASLEANVKYLA  175

EC_FabI   175 NAMGPEGVRVNAISAGPIRTLAASGIKDFRKMLAHCEAVTPLRRTVTIEDVGNSAAELCSDLSAGISGEV  244
HI_FabI   208 ADLGKEGIRVNAISAGPIRTLAASGIKNEKKMLSTFEKTAALRSTVTIEDVGNSAAELCSDLSAGIEGEI  277
PA_FabI   178 GSLGAEGTRVNAISAGPIRTLAASGIKSFRKMLAANERQTFLRRNVTIEDVGNAGELCSDLSAGISGEI  247
EF_FabI   171 FELAADKIRVNCISACAIKTLAVTGVKDYDQIESISNERTFDKTGVTIEDVGNICAELVSDLSAGIVGDI  240
SA_FabI   176 LDLGFDNIRVNAISAGPIRTLSAKGVGGFNTILKEIER-APLKRNVDQVEVGKIAFYLLSDLSGGVIGEN  244
SE_FabI   176 LDLGFDNIRVNAISAGPIRTLSAKGVGGFNTILKEIFARAFLKRNVDQERVGKIAFYLLSDLSGGVIGEN  245

EC_FabI   245 VFVDGGFSIAAMNELELK  262
HI_FabI   278 VHVDAGFSITAMGELGEE  295
PA_FabI   248 LYVDGGFNTTAMGPLDDD  265
EF_FabI   241 IYVDKGVHLT--------  250
SA_FabI   245 IHVDSGFHAIK-------  255
SE_FabI   246 IHVDGGFHAIK-------  256
```

FIGURE 11

```
SE_FabI   1    MLNLENKTYVIMGIANKRSIAFGVAKVLDRLGAKLVFTYRKERSRKELEKLLEQLNQSEHHLYDIDVQNL    70
SA_FabI   1    MLNLENKTYVIMGIANKRSIAFGVAKVLDQLGAKLVFTYRKERSRKELEKLLEQLNCFEAHLYQIDVQSL    70

SE_FabI   71   EDLINGFSQIGKDVGQIDGVYHSIAFANMEDLRGRFSETSREGFLLAQEISSYSLTLVAHEAKKLMPEGG   140
SA_FabI   71   EEVINGFEQIGKDVGNIDGVYHSIAFANMEDLRGRFSETSREGFLLAQDISSYSLTIVAHEAKKLMPEGG   140

SE_FabI   141  SIVATTYIGGEAAVQNYNVMGVAKASLEANVKYLALDLGEDNIRVNAISAGPIRTLSAKGVGGFNTILKE   210
SA_FabI   141  SIVATTYLGGEFAVQNYNVMGVAKASLEANVKYLALDLGPDNIRVNAISAGPIRTLSAKGVGGFNTILKE   210

SE_FabI   211  IEARAPLKRNVDQEEVGKTAAYLLSDLSSGVTGENIHVDGGFHAIK   256
SA_FabI   211  IER-APLKRNVDCVEVGKTAAYLLSDLSSGVTGENIHVDSGFHAIK   255
```

FIGURE 12

```
EC_FabI   1  ------------------------------MGFLSGKRILVTGVASKLSIAYGIAQAMHREGAELAF  37
HI_FabI   1  MRLVFLEILVGFVQRQIFAYTTQVFYANNIGKIMGFLTGKRILVTGLASNRSIAYGIAKSMKEQGAELAF  70
PA_FabI   1  ------------------------------MGFLTGKRALIVGVASKLSIASGIAAAMHREGAELAF  37
EF_FabI   1  -------------------------------MFIQNKNVVVMGVANKKSIAWGCAKAVKDQGANVIY  36
SA_FabI   1  -------------------------------MLNLENKTYVIMGIANKRSIAFGVAKVIDQLGAKLVF  37
SE_FabI   1  -------------------------------MLNLENKTYVIMGIANKRSIAFGVAKVIDRLGAKLVF  37
PA_FabK   1  -----------------------MGVFRTRPTETFGVEHPIMQGGMQWVGRAEIAARVANAGGLATL  44
EF_FabK   1  ---------------------------MNQFECELLGINYPIFQGGMAWVADASIASRVSNAGGLGII  41
SP_FabK   1  ---------------------------MKTRITELLKIDYPIFQGGMAWVADGDIAGAVSKAGGLGII  41

EC_FabI   38 IYQNDKLKGRVEEFAADLGS--DIVLQCD---------------VAEDASIDTMPAELGKVWPKFEGF  88
HI_FabI   71 IYLNDKLQPRVEEFAKEFGS--DIVLPLD---------------VATDESIQNCFAELSKRWDKFEGF 121
PA_FabI   38 IYQNDKLRGRVEEFASGWGSRPELCFPCD---------------VADDSQIEAVFAALGKHWDGLDII  90
EF_FabI   37 IYQNERMKKQVVKLADEND----LLVECD---------------VASEASIQAAFETIKNEVGTIDGL  85
SA_FabI   38 IYRKERSRKELEKLLEQLNQPEAHLYQID---------------VQSEEEVINGFEQIGKDVGNIDGV  90
SE_FabI   38 IYRKERSRKELEKLLEQLNQSEHHLYEID---------------VQNDEDIINGFSQIGKDVGQIEGV  90
PA_FabK   45 SALTQPSPEAIAAEIARCRELTDRPFGVNLTLLPTQKPVPYAEYRAAIILAGHRVVETAGNDPGEHLAEF 114
EF_FabK   42 AGGNAP-REVVKKEIKVKELTEQPFGVNIMLLSPFA----DEIVDLVCEEQVPVVTTGAGNPAKYMARF 106
SP_FabK   42 GGGNAP-REVVKANIDKIKSLTDKPFGVNIMLLSPFV----EDIVDLVIEEGVKVVTTGAGNPSKYMERF 106

EC_FabI   89 VHS--------IGFAPGDQLDGDYVNAVTREGEKIAHDIS------SYSFVAMAKACRSMLN-----PG 138
HI_FabI  122 IHA--------IRFAPGDQLDGDYVNAATREGYRIAHDIS------AYSFVAMAQAARPYIN-----PN 171
PA_FabI   91 VHS--------VGFAPGDQLDGDFTAVTTREGERIAHDIS------AYSFIALAKAGREMMKG----RN 141
EF_FabI   86 VHA--------IRFAKKEESGNVSDIT-RECELLAQDIS------GYSLLAVTHYAKPLIN-----PG 134
SA_FabI   91 YHS--------IRFANMEDLRGRFSETS-REGELLAQDIS------GYSLTIVAHEAKKEMP-----EG 139
SE_FabI   91 YHS--------IRFANMEDLRGRFSETS-REGELLAQEIS------GYSLTLVAHEAKKEMP-----EG 139
PA_FabK  115 RRHGVKVIHKCTAVRHALKAERLGVDAVSIEGEECAGHPGEDDIPGLVLLPAAANRLVPIITASGGFADG 184
EF_FabK  107 KEHNIKVIPVVPSVELAKRMEKIGADAVIFEGMEAGGHIG--KLTTMSGLPQIVDAVSIPVAAGGIGDC 174
SP_FabK  107 HEAGIIVIPVVPSVELAKRMEKIGADAVIAEGMEAGGHIG--KLTTMTLVRQVATAISIPVAAGGIADC 174

EC_FabI  139 SALVTLSYLGAERAIPNYNVMGLAKASLEANVRYMANAMGPEVGVRVNAISAG-PIRTLAASGIKDFRKML 207
HI_FabI  172 AALVTLSYLGAERAIPNYNVMCLAKASLEAATRVMAADLGKEGIRVNAISAG-PIRTLAASGIKNEKKML 240
PA_FabI  142 GSLITLSYLGAERTMPNYNVMGMAKASLEAGVRYLAGSLGAEGTRVNAVSAG-PIRTLAASGIKSERKML 210
EF_FabI  135 SGIVTLTYLGGERAIPNYNMMGIAKASLETAVKYLAFELAADKIRVNGISAG-AIKTLAVTGVKDYDQLI 203
SA_FabI  140 GSIVATTYLGGEFAVQNYNVMGVAKASLEANVKYLALDLGPDNIRVNAISAG-PIRTLSAKGVGGENTIL 208
SE_FabI  140 GSIVATTYIGGEAAVQNYNVMGVAKASLEANVKYLALDLGEDNIRVNAISAG-PIRTLSAKGVGGENTIL 208
PA_FabK  185 RGLVAALALGALAINMGTRFLATRECPLHPVKAAIRAADERSTDLIMRSLRNTAGVARNAISQEVLAIE 254
EF_FabK  175 RGMAAAFMLGAEAVQLGTRFLIAKECNVHPDYKQKVLKARDLDAVITCQHFCHPVRTLKNKLTAQYNQLE 244
SP_FabK  175 EGAAAGFMLGAEAVQVGTRFVVAKESNAHPNYKEKILKARDIDTTISAQHFGHAVEAIKNQLTRDFELAE 244

EC_FabI  208 AHC---------EAVTPIRRTVTIEDVGNSAAFLCSDLSAGISGEVHVDGGFSIAAMNELELK---- 262
HI_FabI  241 STP---------EKTAALRRTVTIEDVGNSAAFLCSDLASGITGEIVHVDAGFSITAMGELGEE---- 295
PA_FabI  211 AAN---------EROTPLRRNVTIEEVGNAGAFLCSDLASGISGEILYVEGGFNTTAMGPLDDD---- 265
EF_FabI  204 SIS---------NERTPDKTGVTIEEVGNTCAFIVSDLAEGVGDIIYVDKGVHLT----------- 250
SA_FabI  209 KEI---------ER-APLKRNVDQVEVGKTAAYILSDLSRENIHVESGFHAIK----------- 255
SE_FabI  209 KEI---------EARAPLKRNVDQEEVGKTAAYILSDLSSCVTGENIHVDGGFHAIK----------- 256
PA_FabK  255 AR---GGAGYADIAALVSGQRGRQVYQQGDTDLGIWSAGMVQGLIDDEPACAELLRDIVEQARQLVRQRL 321
EF_FabK  245 KQELQKEVPDLEMFEKIGQGALRKAVVEGDMDYGSVMAGQIAGLIKKEETAQEIIDSLMSECKAIVHKMN 314
SP_FabK  245 KDAFKQEDPDLEIFEQMGAGALAKAVVHGDVDGGSVMAGQIAGLVSKEETABEILKDLYYGAAKKIQEEA 314

EC_FabI  262 -------------- 262
HI_FabI  295 -------------- 295
PA_FabI  265 -------------- 265
EF_FabI  250 -------------- 250
SA_FabI  255 -------------- 255
SE_FabI  256 -------------- 256
PA_FabK  322 EGMLAGV------- 328
EF_FabK  315 QRWG---------- 318
SP_FabK  315 SRWTGVVRND---  324
```

US 7,799,547 B2

PURIFIED POLYPEPTIDES FROM *STAPHYLOCOCCUS AUREUS*

RELATED APPLICATION INFORMATION

This application is a continuation-in-part of International Application No. PCT/CA04/001004, filed Jul. 9, 2004, which claims the benefit of priority to the following U.S. Provisional Patent Applications, all of which applications are hereby incorporated by reference in their entireties:

| Provisional Application Number | Attorney Docket No. | Filing Date |
|---|---|---|
| 60/486,540 | IPT-459.60 | Jul. 11, 2003 |
| 60/490,383 | IPT-459.61 | Jul. 25, 2003 |

INTRODUCTION

The discovery of novel antimicrobial agents that work by novel mechanisms is a problem researchers in all fields of drug development face today. The increasing prevalence of drug-resistant pathogens (bacteria, fungi, parasites, etc.) has led to significantly higher mortality rates from infectious diseases and currently presents a serious crisis worldwide. Despite the introduction of second and third generation antimicrobial drugs, certain pathogens have developed resistance to all currently available drugs.

One of the problems contributing to the development of multiple drug resistant pathogens is the limited number of protein targets for antimicrobial drugs. Many of the antibiotics currently in use are structurally related or act through common targets or pathways. Accordingly, adaptive mutation of a single gene may render a pathogenic species resistant to multiple classes of antimicrobial drugs. Therefore, the rapid discovery of drug targets is urgently needed in order to combat the constantly evolving threat by such infectious microorganisms.

Recent advances in bacterial and viral genomics research provides an opportunity for rapid progress in the identification of drug targets. The complete genomic sequences for a number of microorganisms are available. However, knowledge of the complete genomic sequence is only the first step in a long process toward discovery of a viable drug target. The genomic sequence must be annotated to identify open reading frames (ORFs), the essentiality of the protein encoded by the ORF must be determined and the mechanism of action of the gene product must be determined in order to develop a targeted approach to drug discovery.

There are a variety of computer programs available to annotate genomic sequences. Genome annotation involves both identification of genes as well assignment of function thereto based on sequence comparison to homologous proteins with known or predicted functions. However, genome annotation has turned out to be much more of an art than a science. Factors such as splice variants and sequencing errors coupled with the particular algorithms and databases used to annotate the genome can result in significantly different annotations for the same genome. For example, upon reanalysis of the genome of *Mycoplasma pneumoniae* using more rigorous sequence comparisons coupled with molecular biological techniques, such as gel electrophoresis and mass spectrometry, researchers were able to identify several previously unidentified coding sequences, to dismiss a previous identified coding sequence as a likely pseudogene, and to adjust the length of several previously defined ORFs (Dandkar et al. (2000) Nucl. Acids Res. 28(17): 3278-3288). Furthermore, while overall conservation between amino acid sequences generally indicates a conservation of structure and function, specific changes at key residues can lead to significant variation in the biochemical and biophysical properties of a protein. In a comparison of three different functional annotations of the *Mycoplasma genitalium* genome, it was discovered that some genes were assigned three different functions and it was estimated that the overall error rate in the annotations was at least 8% (Brenner (1999) Trends Genet 15(4): 132-3). Accordingly, molecular biological techniques are required to ensure proper genome annotation and identify valid drug targets.

However, confirmation of genome annotation using molecular biological techniques is not an easy proposition due to the unpredictability in expression and purification of polypeptide sequences. Further, in order to carry out structural studies to validate proteins as potential drug targets, it is generally necessary to modify the native proteins in order to facilitate these analyses, e.g., by labeling the protein (e.g., with a heavy atom, isotopic label, polypeptide tag, etc.) or by creating fragments of the polypeptide corresponding to functional domains of a multi-domain protein. Moreover, it is well-known that even small changes in the amino acid sequence of a protein may lead to dramatic affects on protein solubility (Eberstadt et al. (1998) Nature 392: 941-945). Accordingly, genome-wide validation of protein targets will require considerable effort even in light of the sequence of the entire genome of an organism and/or purification conditions for homologs of a particular target.

We have developed reliable, high throughput methods to address some of the shortcomings identified above. In part, using these methods, we have now identified, expressed, and purified a novel antimicrobial target from *Staphylococcus aureus*, or *S. aureus*. Various biophysical, bioinformatic and biochemical studies have been used to characterize the structure and function of the polypeptides of the invention.

TABLE OF CONTENTS

| | |
|---|---|
| RELATED APPLICATION INFORMATION | 1 |
| INTRODUCTION | 1 |
| TABLE OF CONTENTS | 3 |
| SUMMARY OF THE INVENTION | 4 |
| BRIEF DESCRIPTION OF THE FIGURES | 6 |
| DETAILED DESCRIPTION OF THE INVENTION | 11 |
|    1. Definitions | 11 |
|    2. Polypeptides of the Invention | 27 |
|    3. Nucleic Acids of the Invention | 41 |
|    4. Homology Searching of Nucleotide and Polypeptide Sequences | 50 |

-continued

| TABLE OF CONTENTS | |
|---|---|
| 5. Analysis of Protein Properties | 51 |
|    (a) Analysis of Proteins by Mass Spectrometry | 51 |
|    (b) Analysis of Proteins by Nuclear Magnetic Resonance (NMR) | 53 |
|    (c) Analysis of Proteins by X-ray Crystallography | 60 |
|       (i) X-ray Structure Determination | 60 |
|       (ii) X-ray Structure | 67 |
|       (iii) Structural Equivalents | 69 |
|       (iv) Machine Displays and Machine Readable Storage Media | 70 |
|       (v) Structurally Similar Molecules and Complexes | 72 |
|       (vi) NMR Analysis Using X-ray Structural Data | 75 |
| 6. Interacting Proteins | 76 |
| 7. Antibodies | 89 |
| 8. Diagnostic Assays | 92 |
| 9. Drug Discovery | 95 |
|    (a) Drug Design | 96 |
|    (b) In Vitro Assays | 105 |
|    (c) In Vivo Assays | 107 |
|       (i) Mouse Soft Tissue Model | 107 |
|       (ii) Diffusion Chamber Model | 107 |
|       (iii) Endocarditis Model | 108 |
|       (iv) Osteomyelitis Model | 108 |
|       (v) Murine Septic Arthritis Model | 108 |
|       (vi) Bacterial Peritonitis Model | 108 |
| 10. Vaccines | 109 |
| 11. Array Analysis | 111 |
| 12. Pharmaceutical Compositions | 114 |
| 13. Antimicrobial Agents | 115 |
| 14. Other Embodiments | 116 |
| EXEMPLIFICATION | 130 |
|    EXAMPLE 1 Isolation and Cloning of Nucleic Acid | 130 |
|    EXAMPLE 2 Test Protein Expression and Solubility | 132 |
|    EXAMPLE 3 Native Protein Expression | 133 |
|    EXAMPLE 4 Expression of Selmet Labeled Polypeptides | 134 |
|    EXAMPLE 5 Expression of $^{15}$N Labeled Polypeptides | 136 |
|    EXAMPLE 6 Method One for Purifying Polypeptides of the Invention | 136 |
|    EXAMPLE 7 Method Two for Purifying Polypeptides of the Invention | 138 |
|    EXAMPLE 8 Method Three for Purifying Polypeptides of the Invention | 139 |
|    EXAMPLE 9 Mass Spectrometry Analysis via Fingerprint Mapping | 140 |
|    EXAMPLE 10 Mass Spectrometry Analysis via High Mass | 142 |
|    EXAMPLE 11 Method One for Isolating and Identifying Interacting Proteins | 143 |
|    EXAMPLE 12 Method Two for Isolating and Identifying Interacting Proteins | 145 |
|    EXAMPLE 13 Sample for Mass Spectrometry of Interacting Proteins | 146 |
|    EXAMPLE 14 Mass Spectrometric Analysis of Interacting Proteins | 148 |
|    EXAMPLE 15 NMR Analysis | 149 |
|    EXAMPLE 16 X-ray Crystallography | 150 |
|    EXAMPLE 17 Annotations | 172 |
|    EXAMPLE 18 Essential Gene Analysis | 173 |
|    EXAMPLE 19 PDB Analysis | 173 |
|    EXAMPLE 20 Virtual Genome Analysis | 174 |
|    EXAMPLE 21 Epitopic Regions | 174 |
| CLAIMS | 178 |

SUMMARY OF THE INVENTION

As part of an effort at genome-wide structural and functional characterization of microbial targets, the present invention provides polypeptides from *S. aureus*. In various aspects, the invention provides the nucleic acid and amino acid sequences of the polypeptides of the invention. The invention also provides purified, soluble forms of the polypeptides of the invention suitable for structural and functional characterization using a variety of techniques, including, for example, affinity chromatography, mass spectrometry, NMR and x-ray crystallography. The invention further provides modified versions of the polypeptides of the invention to facilitate characterization, including polypeptides labeled with isotopic or heavy atoms and fusion proteins.

A polypeptide of the invention has been crystallized and its structure solved as described in detail below, thereby providing information about the structure of the polypeptide, and druggable regions, domains and the like contained therein, all of which may be used in rational-based drug design efforts.

In general, the biological activity of a polypeptide of the invention is expected to be characterized as having a biochemical activity substantially similar to that of enoyl-[acyl-carrier-protein] reductase (NADH), having the gene designation of FabI, as described in more detail below. This assignment has been confirmed by solving the X-ray structure of a polypeptide of the invention.

All of the information learned and described herein about the polypeptides of the invention may be used to design modulators of one or more of their biological activities. In particular, information critical to the design of therapeutic and diagnostic molecules, including, for example, the protein domain, druggable regions, structural information, and the like for the polypeptides of the invention is now available or attainable as a result of the ability to prepare, purify and characterize them, and domains, fragments, variants and derivatives thereof.

In other aspects of the invention, structural and functional information about the polypeptides of the invention has and will be obtained. Such information, for example, may be incorporated into databases containing information on the polypeptides of the invention, as well as other polypeptide targets from other microbial species. Such databases will provide investigators with a powerful tool to analyze the polypeptides of the invention and aid in the rapid discovery and design of therapeutic and diagnostic molecules.

In another aspect, modulators, inhibitors, agonists or antagonists against the polypeptides of the invention, or biological complexes containing them, or orthologues thereto, may be used to treat any disease or other treatable condition of a patient (including humans and animals), and particularly a disease caused by S. aureus, such as, for example, one of the following: a furuncle, chronic furunculosis, impetigo, acute osteomyelitis, pneumonia, endocarditis, scalded skin syndrome, toxic shock syndrome, and food poisoning.

The present invention further allows relationships between polypeptides from the same and multiple species to be compared by isolating and studying the various polypeptides of the invention and other proteins. By such comparison studies, which may involve multi-variable analysis as appropriate, it is possible to identify drugs that will affect multiple species or drugs that will affect one or a few species. In such a manner, so-called "wide spectrum" and narrow spectrum" anti-infectives may be identified. Alternatively, drugs that are selective for one or more bacterial or other non-mammalian species, and not for one or more mammalian species (especially human), may be identified (and vice-versa).

In other embodiments, the invention contemplates kits including the subject nucleic acids, polypeptides, crystallized polypeptides, antibodies, and other subject materials, and optionally instructions for their use. Uses for such kits include, for example, diagnostic and therapeutic applications.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE FIGURES

The patent or application file contains at least one drawing executed in color. Copies of the patent application publication with color drawing(s) will be provided by the Office upon request and payment of the necessary fee.

FIG. 1 shows the nucleic acid coding sequence for an exemplary polypeptide of the invention as predicted from the genomic sequence of S. aureus (SEQ ID NO: 1). This predicted nucleic acid coding sequence was cloned and sequenced to produce the polynucleotide sequence shown in FIG. 2 (SEQ ID NO: 3).

FIG. 2 shows the amino acid sequence for an exemplary polypeptide of the invention as predicted from the nucleotide sequence shown in FIG. 1 (SEQ ID NO: 2).

FIG. 3 shows the experimentally determined nucleic acid coding sequence for an exemplary polypeptide of the invention (SEQ ID NO: 3).

FIG. 4 shows the amino acid sequence for the exemplary polypeptide of the invention as predicted from the nucleotide sequence shown in FIG. 3 (SEQ ID NO: 4).

FIG. 5 shows the primer sequences used to amplify the nucleic acid of SEQ ID NO: 3. The primers are SEQ ID NO: 5 and SEQ ID NO: 6.

FIG. 6 contains Table 1, which provides among other things a variety of data and other information on the polypeptides of the invention.

FIG. 7 contains Table 2, which provides the results of several bioinformatic analyses relating to SEQ ID NO: 2.

FIG. 8 contains Tables 3 and 4, which show information related to the x-ray structure for a polypeptide of the invention as described more fully in EXAMPLE 16.

FIG. 9 lists the atomic structure coordinates for a polypeptide of the invention (SEQ ID NO: 2) derived from x-ray diffraction from a crystal of such polypeptide, as described in more detail in EXAMPLE 16. There are multiple pages to FIG. 9. The information in such Figure is presented in the following tabular format, with a generic entry provided as an example:

| Record Header | No. | Atom Type | Residue | Residue Number | X | Y | Z | OCC | B |
|---|---|---|---|---|---|---|---|---|---|
| ATOM 1 | 1 | CB | HIS | 1 | 4.497 | 15.607 | 34.172 | 1 | 70.54 |

In the table, "Record Header" describes the row type, such as "ATOM". "No." refers to the row number. The first "Atom Type" column refers to the atom whose coordinates are measured, with the first letter in the column identifying the atom by its elemental symbol and the subsequent letter defining the location of the atom in the amino acid residue or other molecule. "Residue" and "residue number" identifies the residue of the subject polypeptide. "X, Y, Z" crystallographically define the atomic position of the atom measured. "Occ" is an occupancy factor that refers to the fraction of the molecules in which each atom occupies the position specified by the coordinates. A value of "1" indicates that each atom has the same conformation, i.e., the same position, in all molecules of the crystal. "B" is a thermal factor that is related to the root mean square deviation in the position of the atom around the given atomic coordinate.

FIG. 10 depicts the alignment of the sequences for FabI from selected pathogenic organisms. The sequence identity matrix indicates that the identity between the S. aureus FabI and E. coli FabI is 42% (similarity is 69%). Abbreviations: EC—Escherichia coli (SEQ ID NO: 10), PA—Pseudomonas aeruginosa (SEQ ID NO: 12), HI—Haemophilus influenzae (SEQ ID NO: 11), EF—Enterococcus faecalis (SEQ ID NO: 13), SA—Staphylococcus aureus (SEQ ID NO: 14), and SE—Staphylococcus epidermidis (SEQ ID NO: 15).

FIG. 11 depicts the alignment of the sequences for S. aureus FabI (SEQ ID NO: 14) and S. epidermidis FabI (SEQ ID NO: 15). The identity between the S. aureus FabI and E. coli FabI is 93% (similarity is 98%).

FIG. 12 depicts the alignment of the sequences for FabI, FabL and FabK from selected pathogenic organisms (SEQ ID NOS: 10-18, respectively in order of appearance). The sequence identity matrix indicates there is very little sequence identity between FabI, FabL and FabK. Abbreviations: EC—*Escherichia coli*, PA—*Pseudomonas aeruginosa*, HI—*Haemophilus influenzae*, EF *Enterococcus faecalis*, SA—*Staphylococcus aureus*, and SE—*Staphylococcus epidermidis*.

Figure 13:
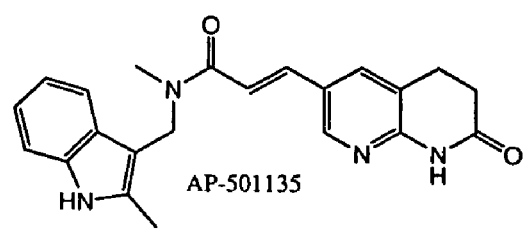

FIG. 13 depicts the chemical structure of API-1135.

Figure 14:

FIG. 14 is a ribbon diagram of the structure of the dimer of *S. aureus* FabI complexed with NADPH and the inhibitor API-1135. Monomer A is blue, and monomer B is pink. NADPH and API-1135 are shown in the binding pockets of each.

Figure 15:

FIG. 15 is a ribbon diagram of the monomer of FabI. NADPH is shown with pink carbons and API-1135 is shown with green carbons. Oxygen is red, nitrogen is blue, and phosphorus is orange.

Figure 16:
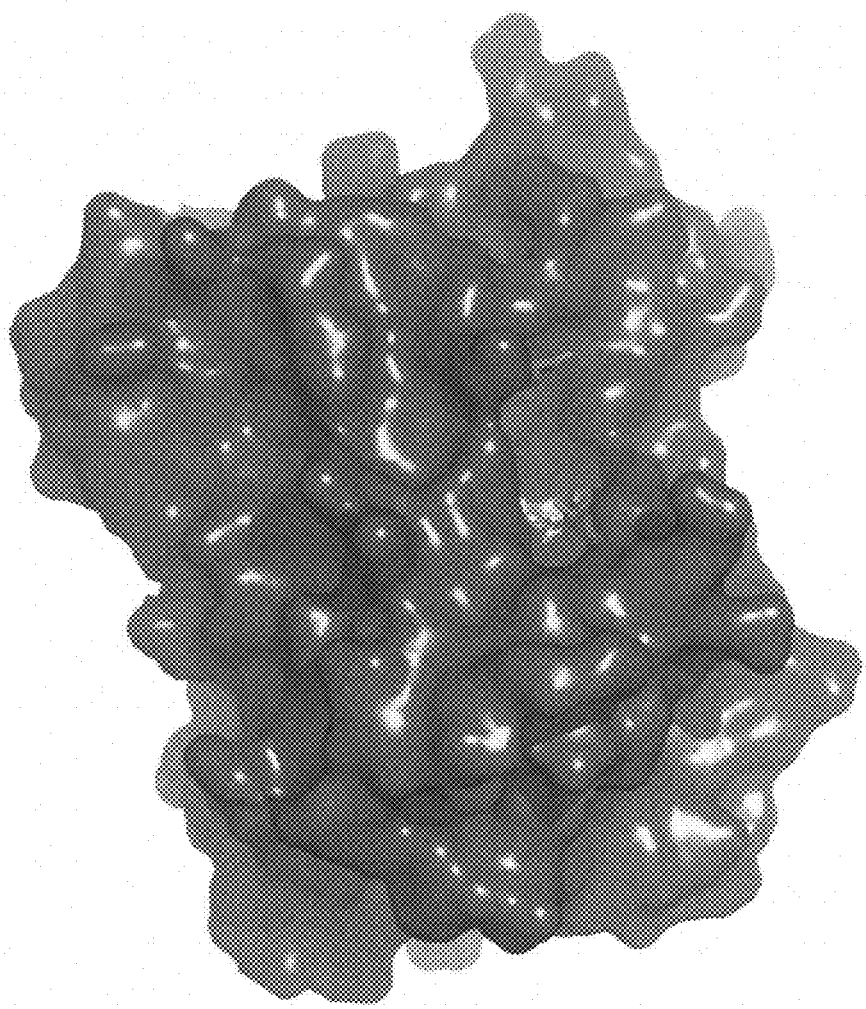

FIG. 16 shows the solvent accessible surface of the monomer. The inhibitor is hidden under the flipping loop.

Figure 17:

FIG. 17 shows the flipping loop in a ribbon trace to reveal the binding site for the inhibitor. Figures were generated with PYMOL, as were all the following figures (Delano, W. L., The PyMOL Molecular Graphics System (2002) DeLano Scientific, San Carlos, Calif., USA).

Figure 18:
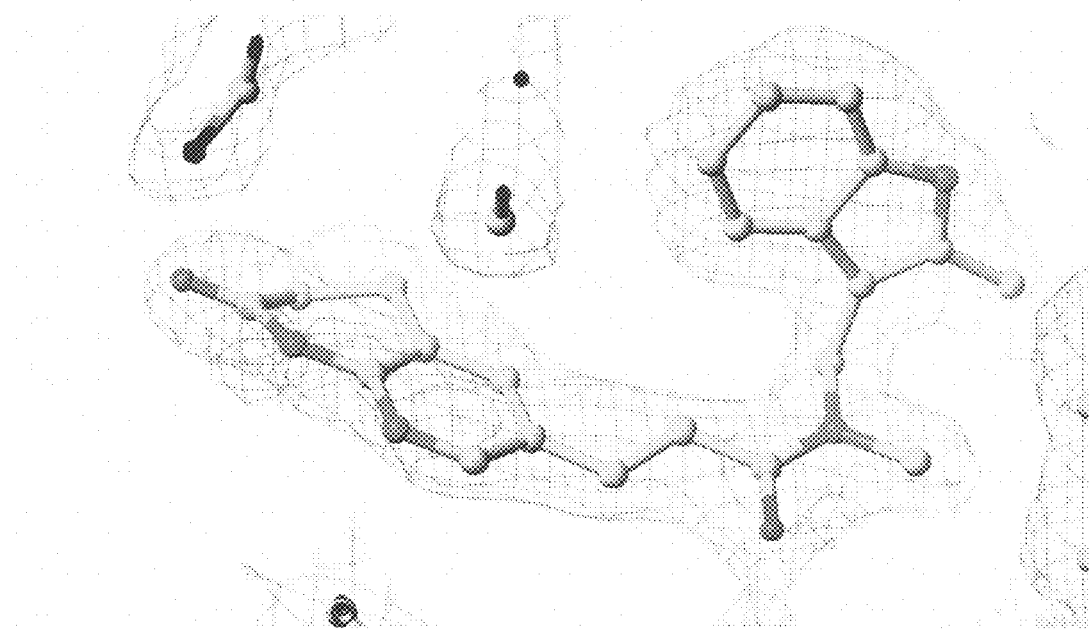

FIG. 18 depicts the sigma A weighted 2Fo-Fc electron density in the region of the catalytic site, showing the API-1135 molecule. Density is contoured at 1.0 σ. The model is shown as sticks, with carbon in yellow, nitrogen in blue, oxygen in red, and sulfur in green. The density indicates the correct orientation of the API-1135 in the binding pocket. Figure produced in Turbo-Frodo.

Figure 19:
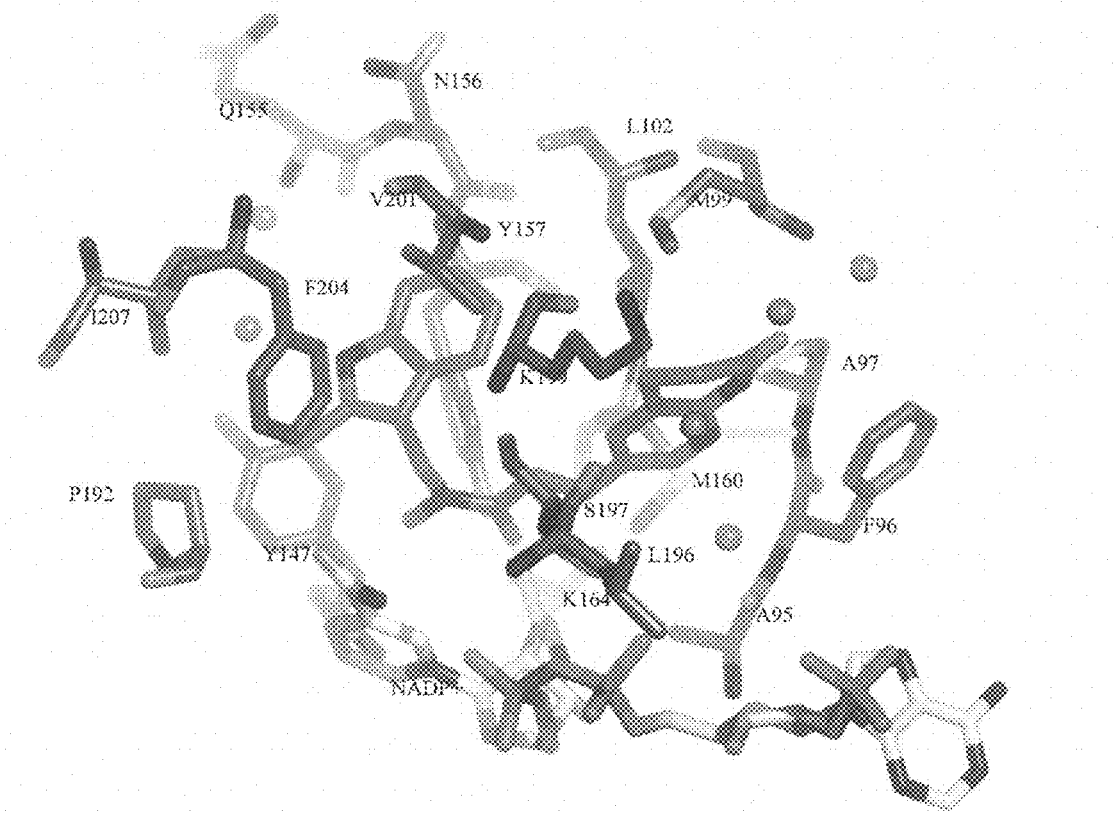

FIG. 19 depicts a view of the binding pocket of *S. aureus* FabI. Hydrogen bonds are shown in yellow dashed lines. For protein residues in the binding site, carbon is shown in blue, nitrogen in blue, oxygen in red, sulfur in yellow; for the API-1135, carbon is green, NADPH carbons are pink, and phosphate is orange. Water molecules are shown as small red spheres.

Figure 20:
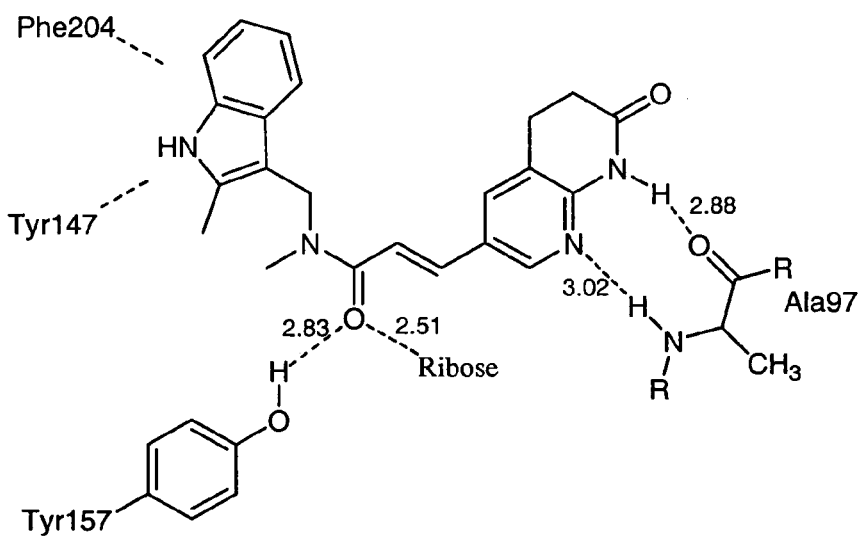

FIG. 20 depicts a schematic of the binding of API-1135 in the binding pocket. A97 and Y157 form hydrogen bonds with the inhibitor while Y147 and F204 form a hydrophobic pocket.

Figure 21:
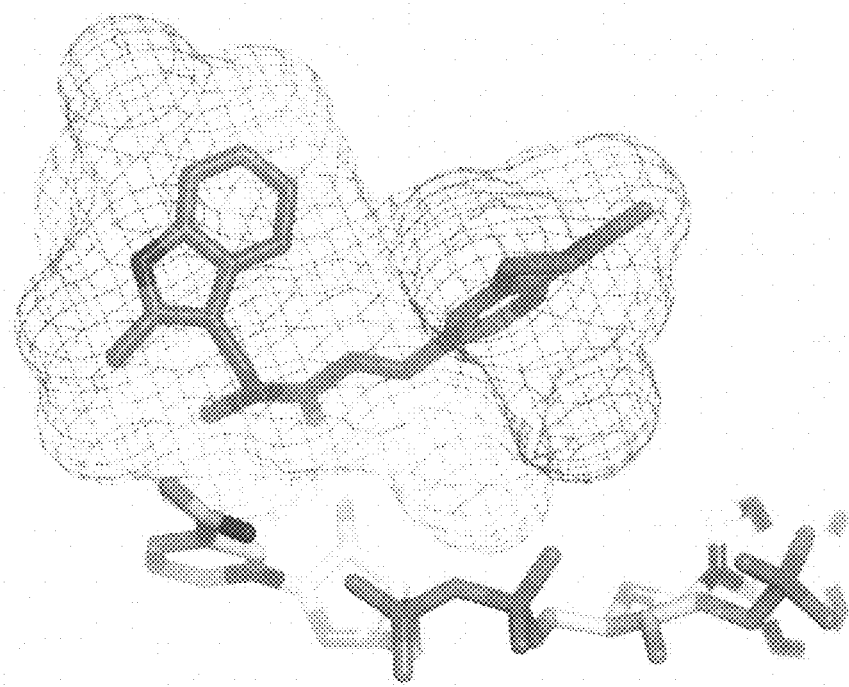

FIG. 21 depicts the accessible volume of the binding pocket of *S. aureus* FabI, which is shown as a mesh, calculated with MOE. API-1135 is shown nestled in the binding pocket, with areas available for additional changes to the compound. Red areas are hydrophilic interactions, gray indicates hydrophobic interactions.

Figure 22:

FIG. 22 depicts the accessible volume of the binding pocket of *S. aureus* FabI, shown as a mesh, when water molecules are removed from the structure, as calculated with MOE. API-1135 is shown in this giant binding pocket, which extends down the side of the protein. This may be an area where the substrate could extend. Red areas are hydrophilic interactions, gray indicates hydrophobic interactions.

Figure 23:
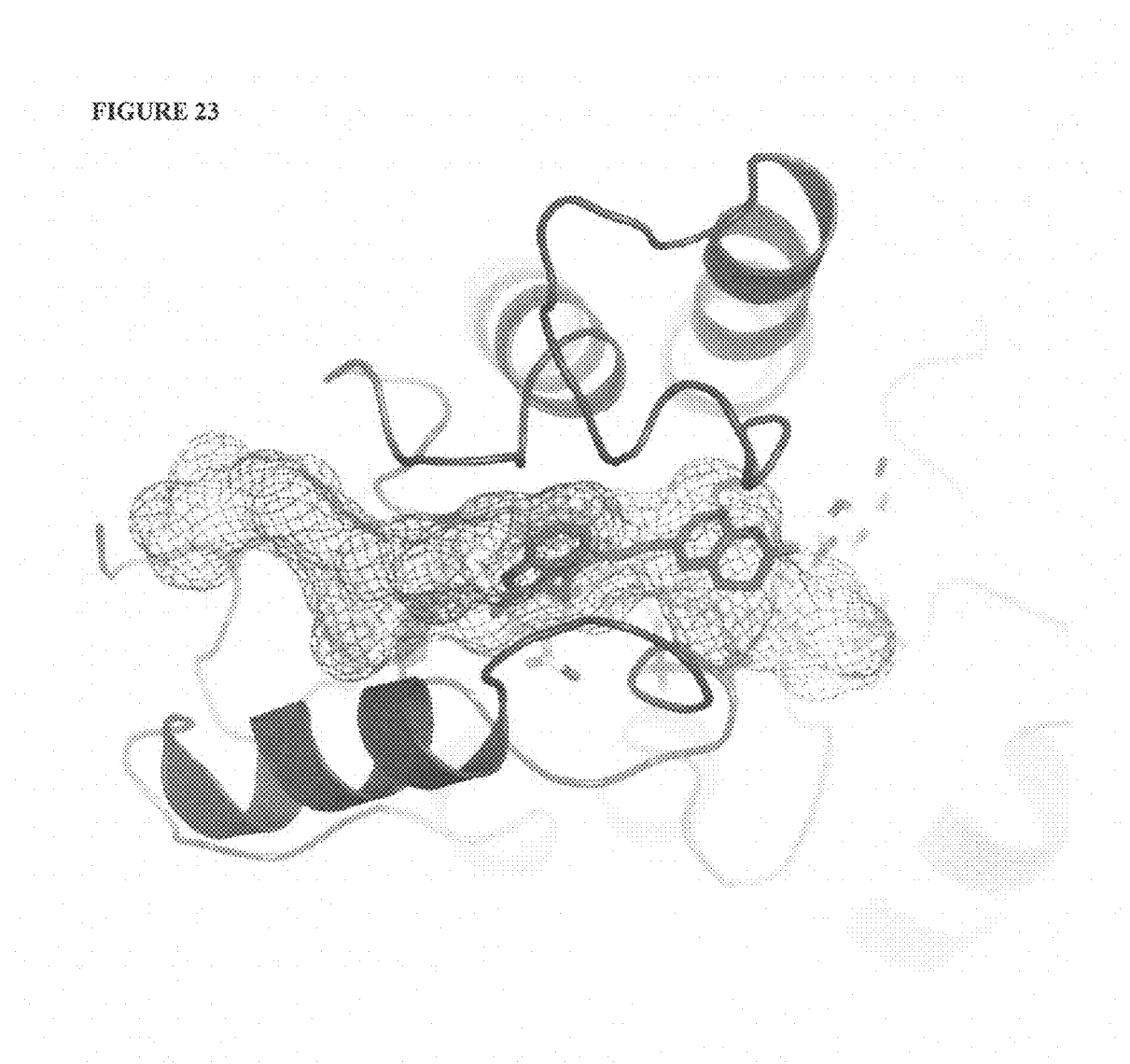

FIG. 23 depicts another view of the accessible volume of the binding pocket shown in FIG. 22.

Figure 24:
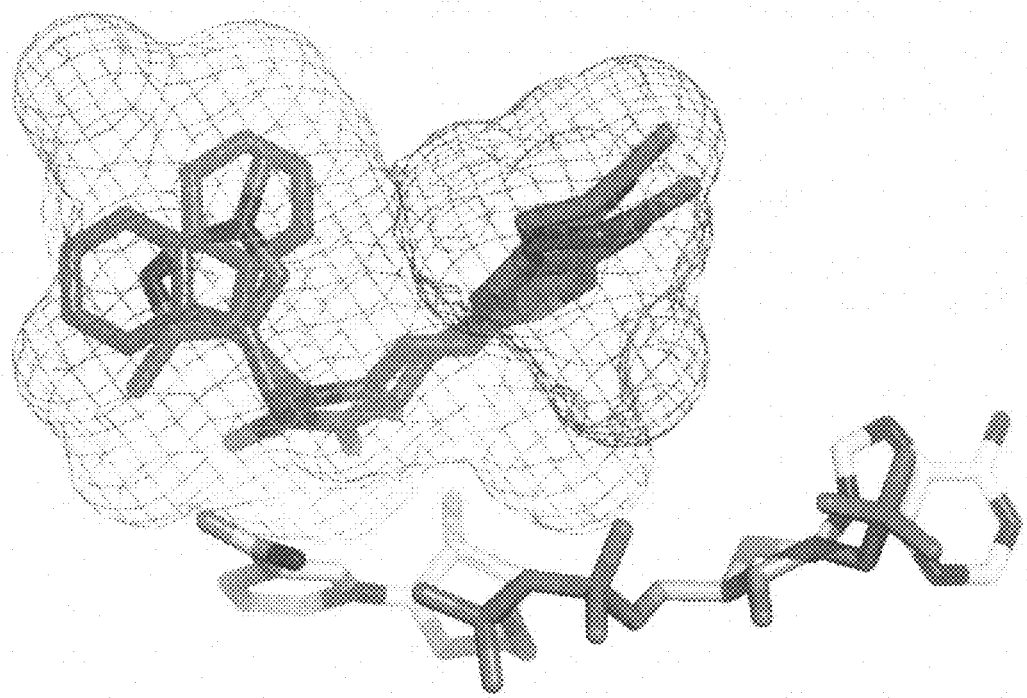

FIG. 24 depicts a comparison between the *S. aureus* FabI API-1135 structure and SB-6411113 *E. coli* structure. In green is the API-1135 from the *S. aureus* FabI complex and in blue is the SB-6411113. The mesh indicates the volume of the *S. aureus* binding site.

Figure 25:
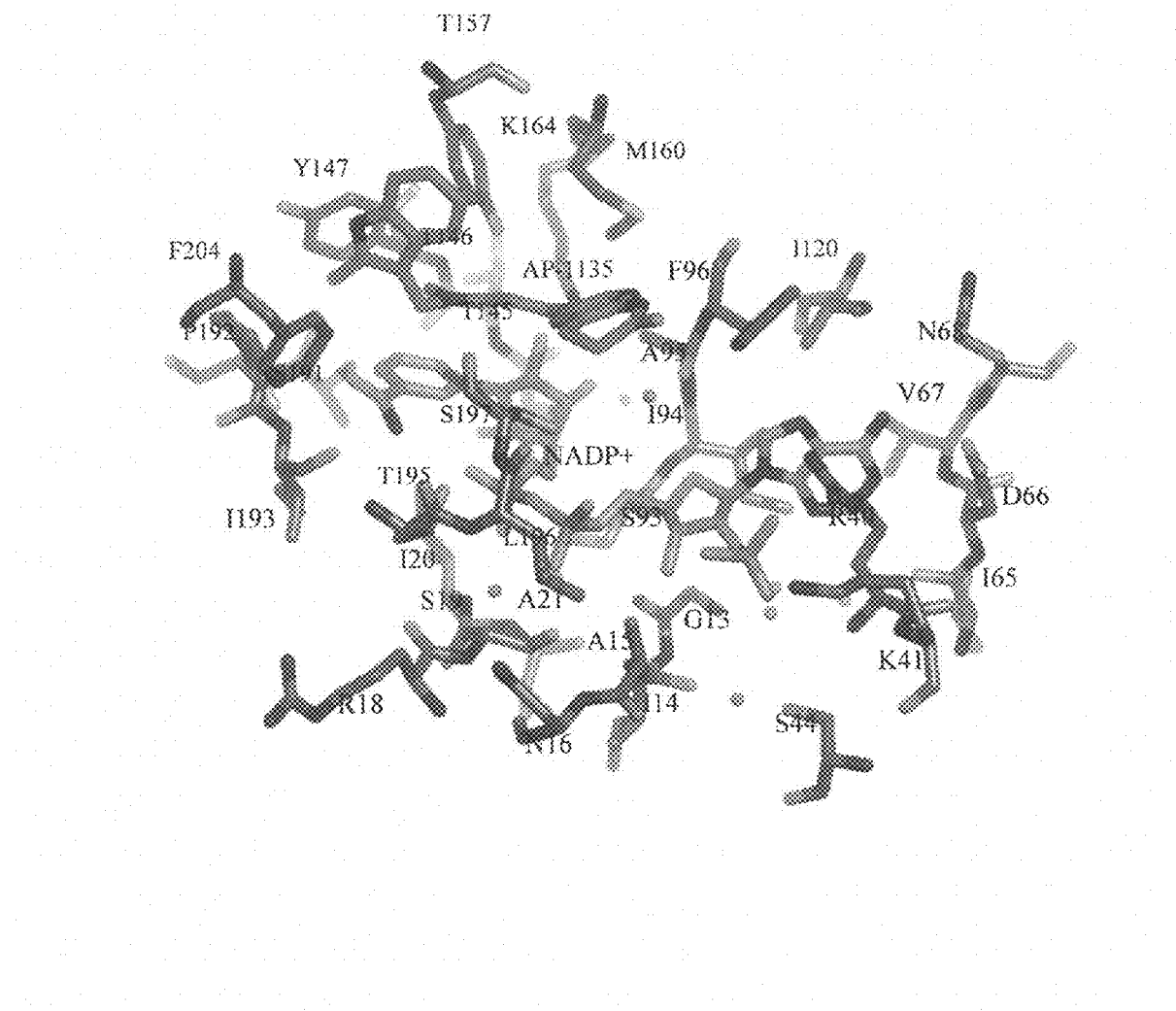

FIG. 25 depicts a view of the binding of NADPH in the *S. aureus* FabI binding pocket. For protein residues in the binding site, carbon is shown as blue, nitrogen as blue, oxygen as red, sulfur as yellow; for the API-1135, carbon is green and NADPH carbons are pink and phosphate is orange. Water molecules are shown as small red spheres.

Figure 26:
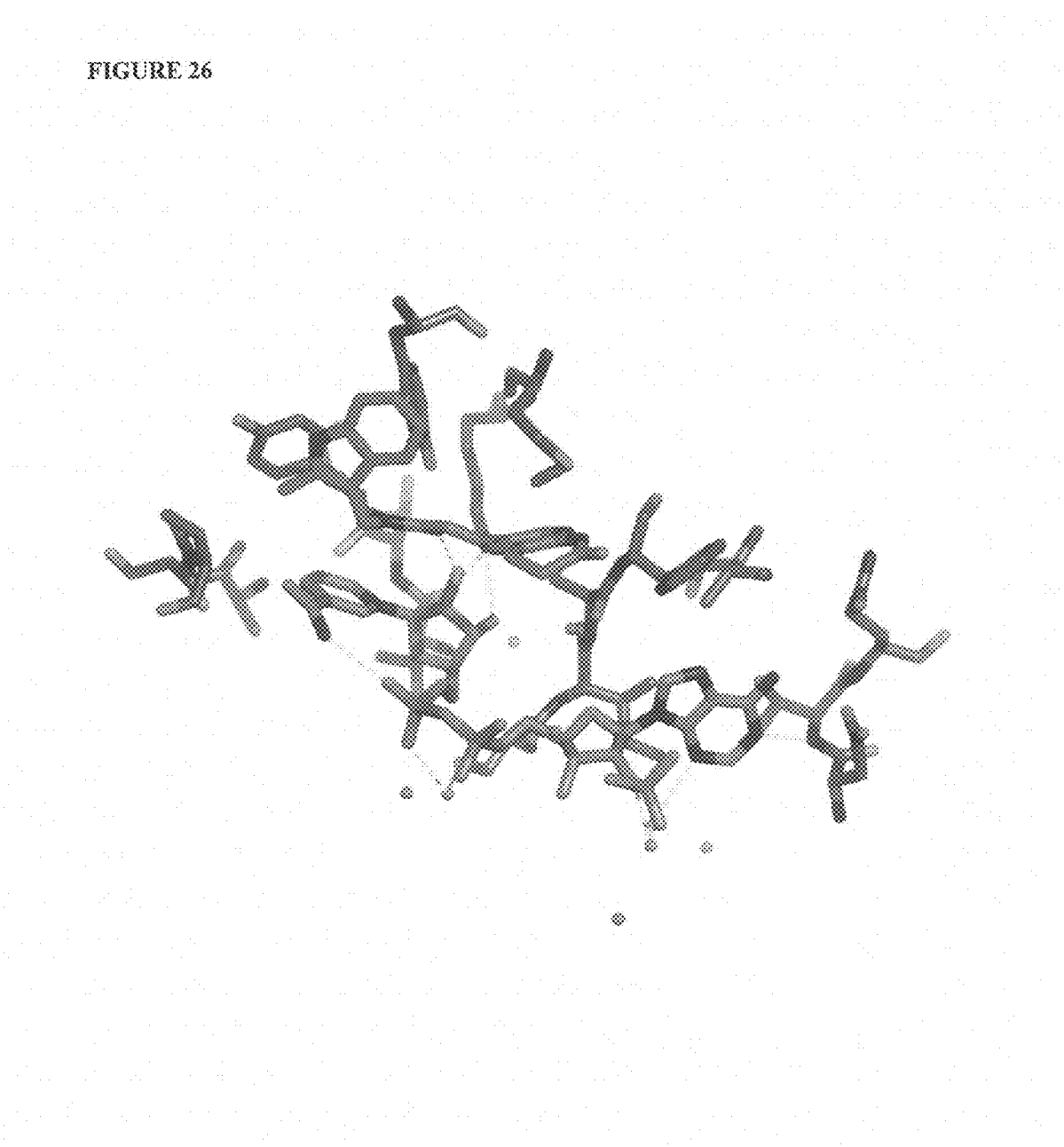

FIG. 26 depicts one half of the binding pocket depicted in FIG. 25 with hydrogen bonds shown in yellow dashed lines.

Figure 27:
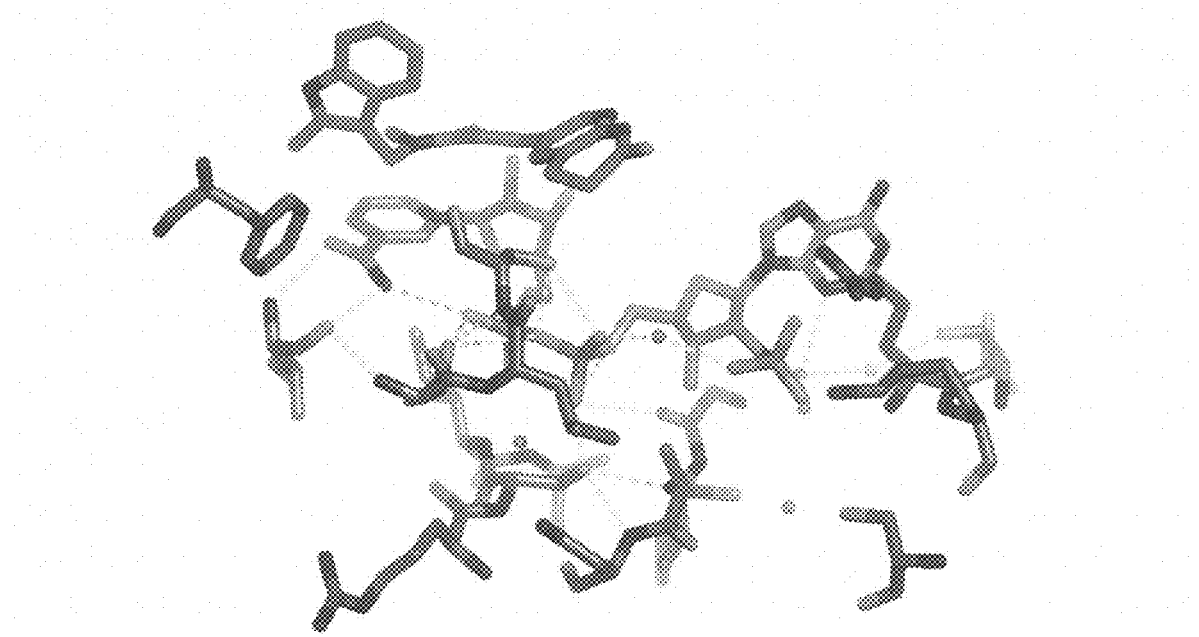

FIG. 27 depicts the second half of the binding pocket depicted in FIG. 25 with hydrogen bonds shown in yellow dashed lines.

Figure 28:
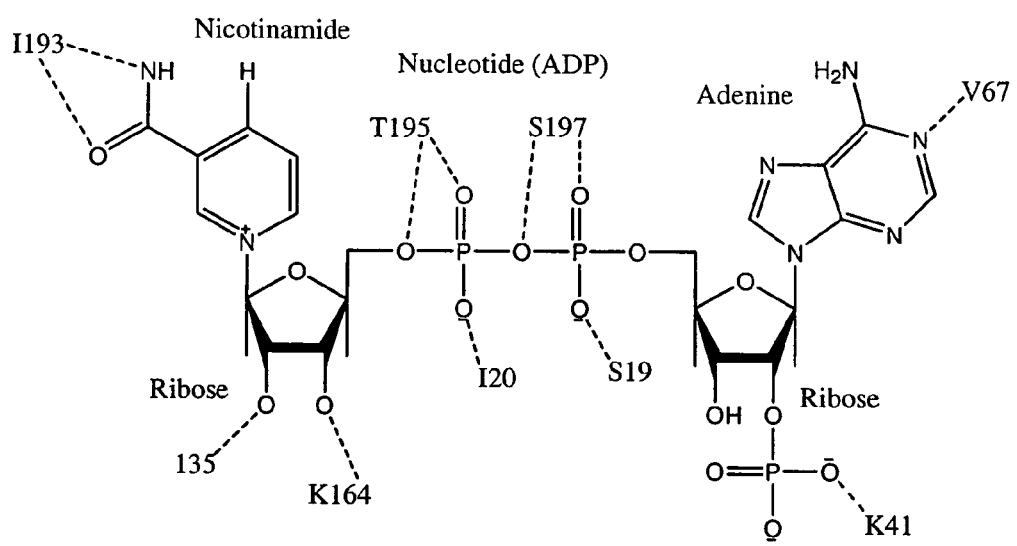

FIG. 28 depicts a schematic of the binding of NADPH in the binding pocket. Water mediated hydrogen bonds are not included for clarity. There are many contacts with the protein.

Figure 29:
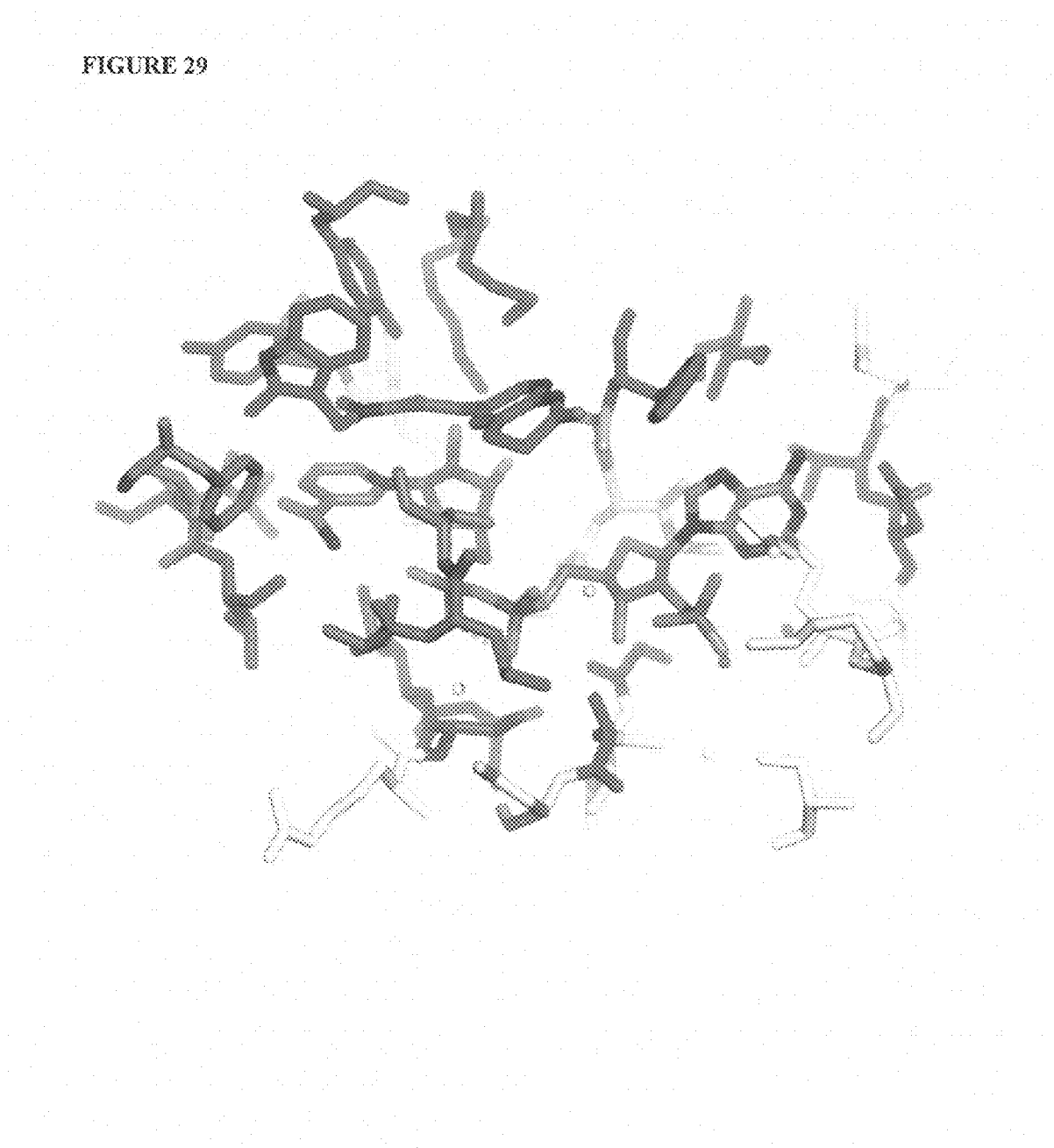

FIG. 29 shows the conservation of bacterial FabI amino acid sequences, mapped onto the *S. aureus* FabI structure. The residues surrounding most of the NADPH are highly conserved. The amino acid sequences were aligned in ClustalX and the conservation of each position was evaluated in Consurf (Armon, Graur et al. 2001; Glaser, Pupko et al. 2003). Mean conservation between sequences was 0.84, indicating an extremely high degree of sequence conservation overall. This sequence conservation metric was then projected onto the *S. aureus* FabI AP-501135 structure, with the convention that red residues are invariant, pink residues are somewhat variable but generally well conserved (with the degree of pinkness correlating with the degree of conservation), white residues show an average degree of conservation for that set, and blue residues are hyper-variable. The AP-501135 (SB-641197) molecule is shown as a green stick figure and NADPH is shown with pink carbons. There are some differences in the residues surrounding the binding pocket for the adenine ribose phosphate.

Figure 30:
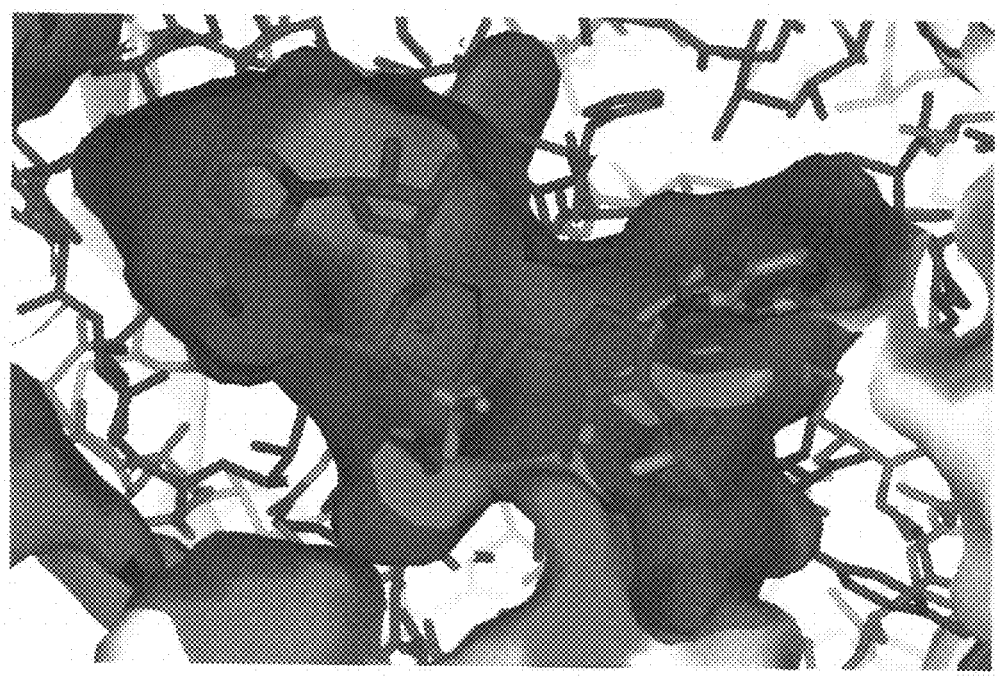

FIG. 30 depicts the surface of the NADPH binding pocket, colored by sequence conservation. The shape of the pocket complements NADPH. The variant residues surrounding the adenine ribose phosphate provides specificity for NADPH over NADH in *S. aureus* FabI.

Figure 31:

FIG. 31 depicts another view of the conservation of bacterial FabI amino acid sequences, mapped onto the *S. aureus* FabI structure. The amino acid sequences were aligned in ClustalX and the conservation of each position was evaluated in Consurf (Armon, Graur et al. 2001; Glaser, Pupko et al. 2003). Mean conservation between sequences was 0.84, indicating an extremely high degree of sequence conservation overall. This sequence conservation metric was then projected onto the *S. aureus* FabI API-1135 structure, with the convention that red residues are invariant, pink residues are somewhat variable but generally well conserved (with the degree of pinkness correlating with the degree of conservation), white residues show an average degree of conservation for that set, and blue residues are hyper-variable.

Figure 32:
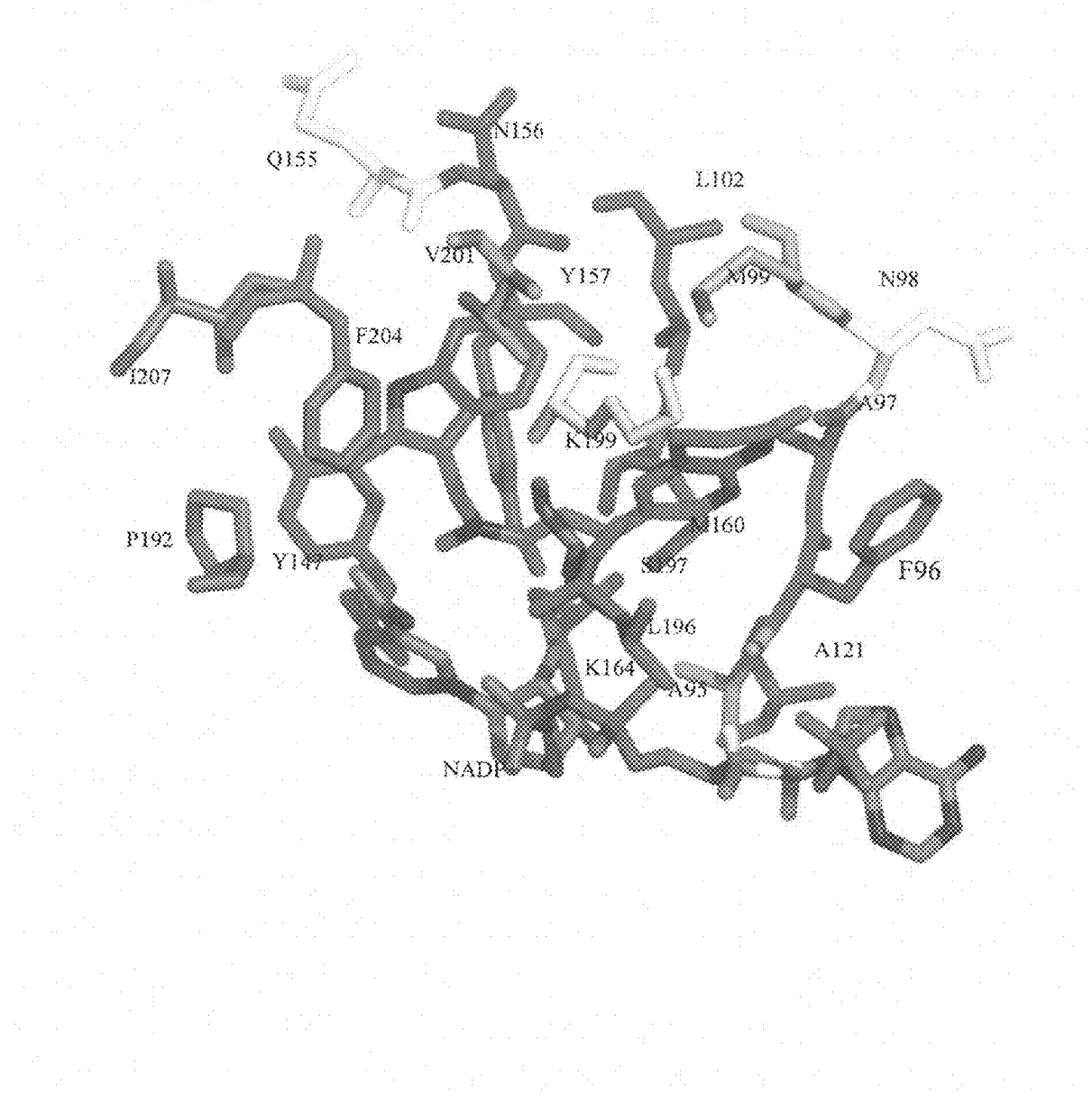

FIG. 32 also depicts the conservation of bacterial FabI amino acid sequences, mapped onto the *S. aureus* FabI structure. The API-1135 molecule is shown as a green stick figure and NADPH is shown with pink carbons. This analysis shows that the binding site is highly conserved but there are some differences in the residues surrounding the binding pocket.

Figure 33:
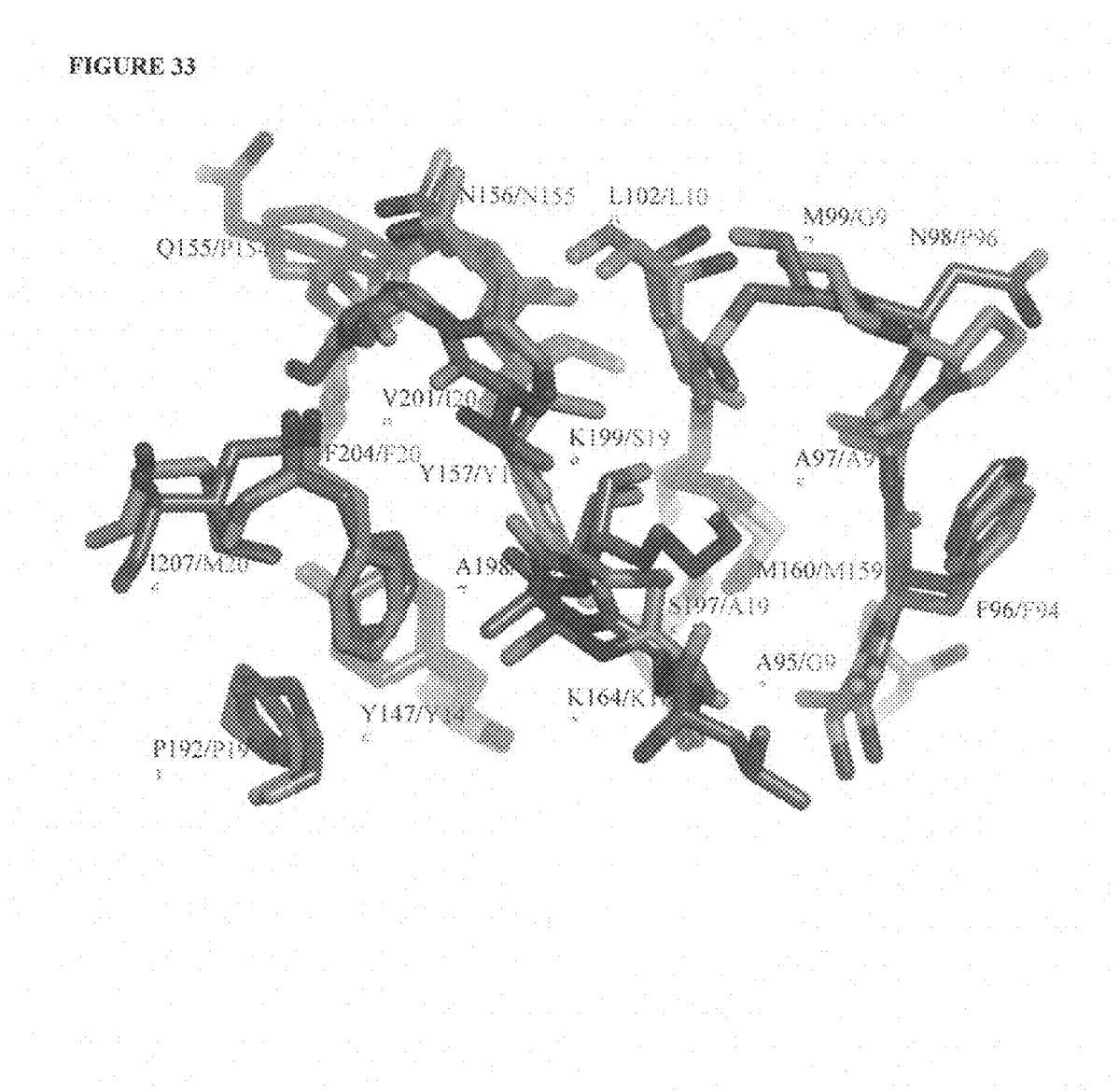

FIG. 33 depicts an overlay of the residues from the binding sites from the *S. aureus* FabI API-1135 (blue) and the *E. coli* structure with API-1135 (magenta). Swiss-PDB Viewer was used to overlay the structures (Guex, N. and Peitsch, M. C. (1997) SWISS-MODEL and the Swiss-PdbViewer: An environment for comparative protein modeling. *Electrophoresis* 18, 2714-2723.

Figure 34:
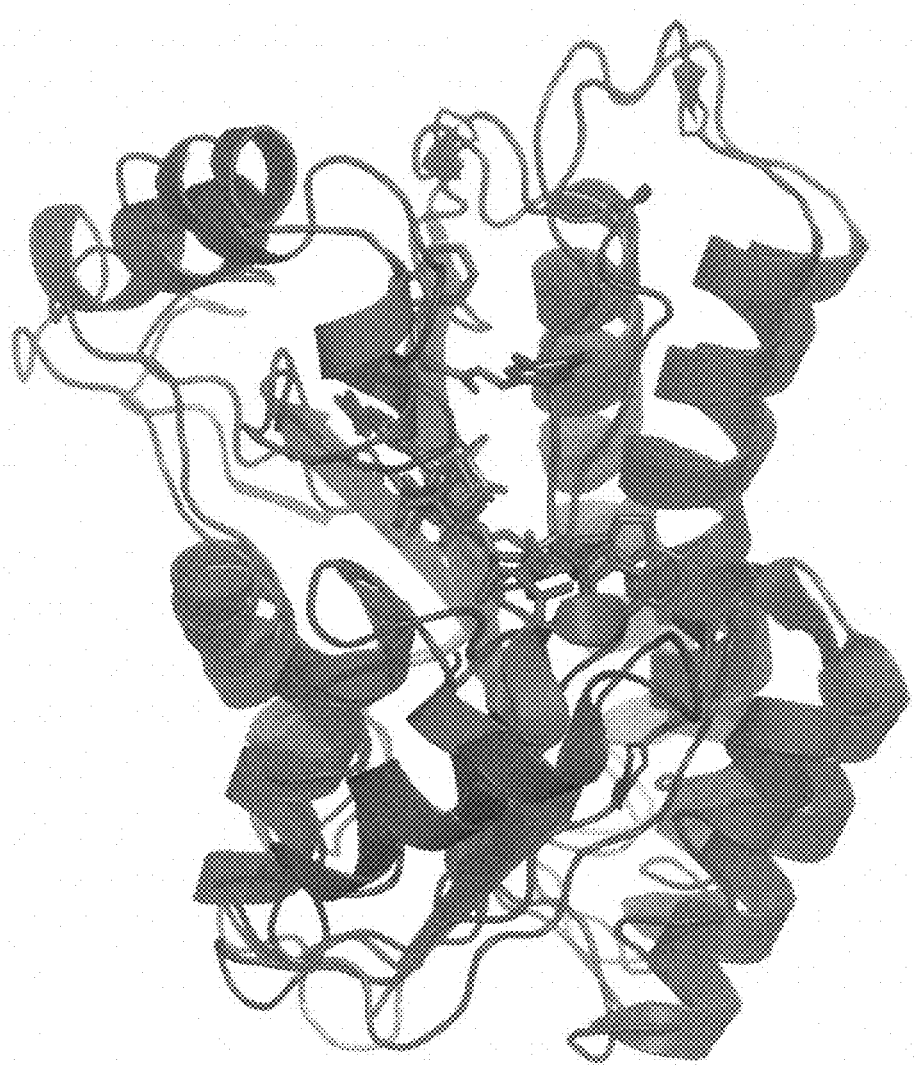

FIG. 34 depicts a comparison of the *S. aureus* FabI API-1135 complex to the *B. napus* FabG structure. In blue is the SA FabI structure with API-1135 and in purple is the *B. napus* FabG structure.

Figure 35:
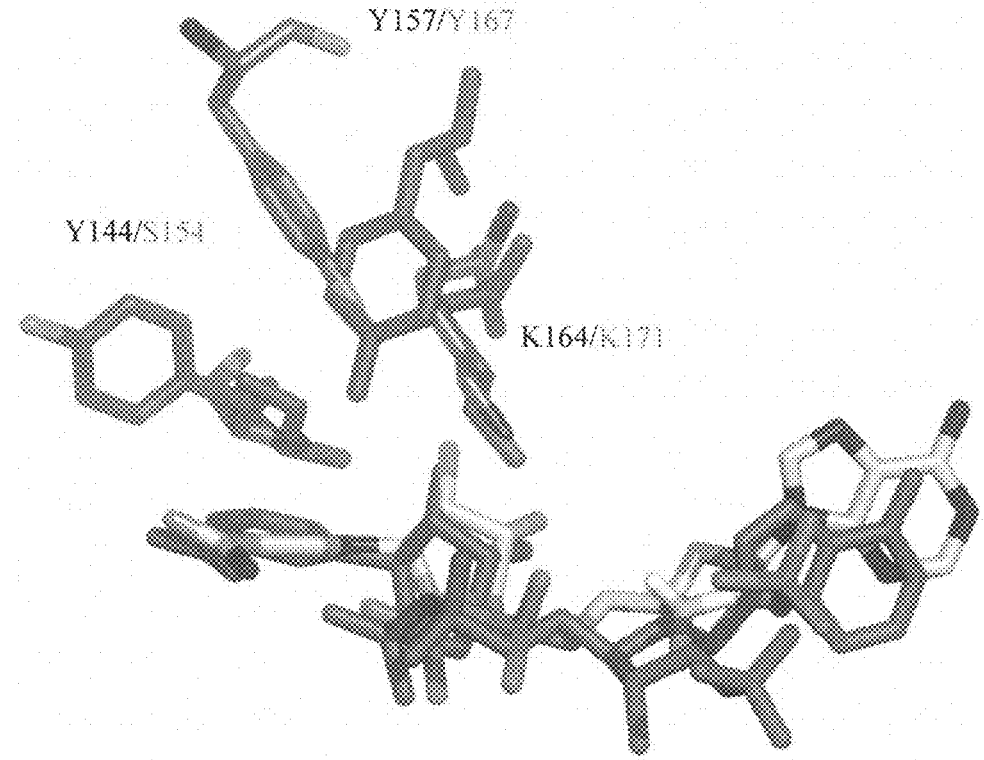

FIG. 35 depicts another view of the comparison of the *S. aureus* FabI API-1135 complex to the *B. napus* FabG structure. As in FIG. 28, in blue is the SA FabI structure with API-1135 and in purple is the *B. napus* FabG structure.

Figure 36:
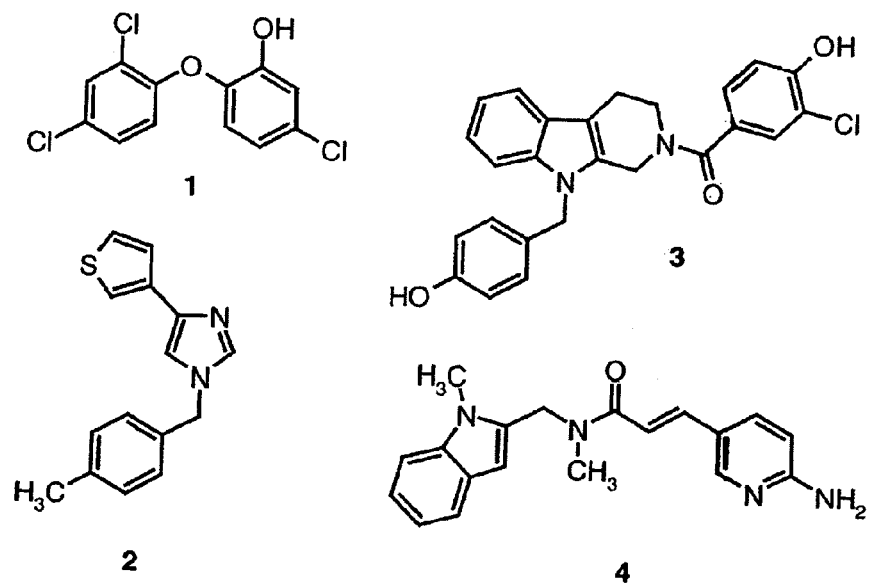

FIG. 36 shows small molecule inhibitors of FabI. Figure adapted from Seefeld et al. (Seefeld, Miller et al. 2003).

Figure 37:
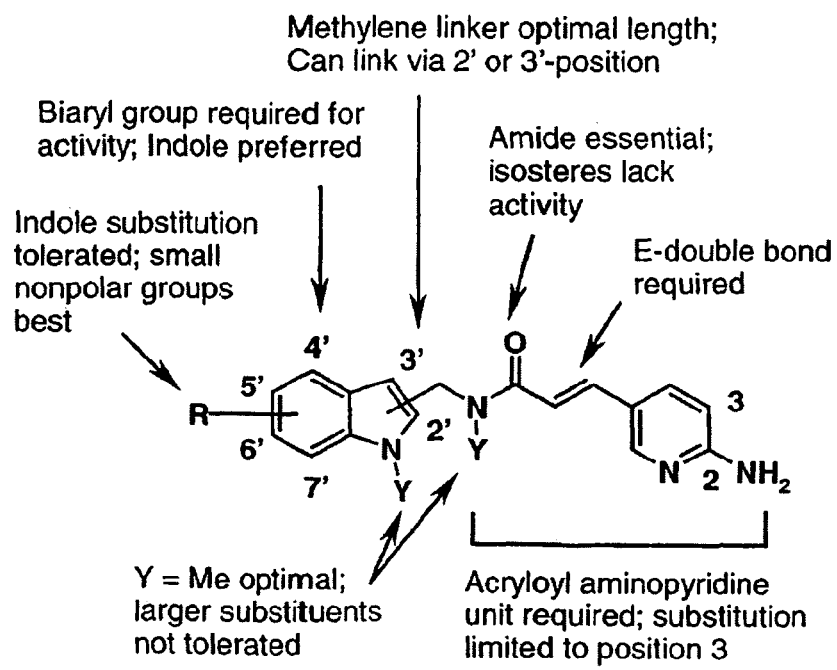

FIG. 37 depicts aminopyridine FabI SAR. Figure adapted from Seefeld et al. (Seefeld, Miller et al. 2003).

Figure 38:
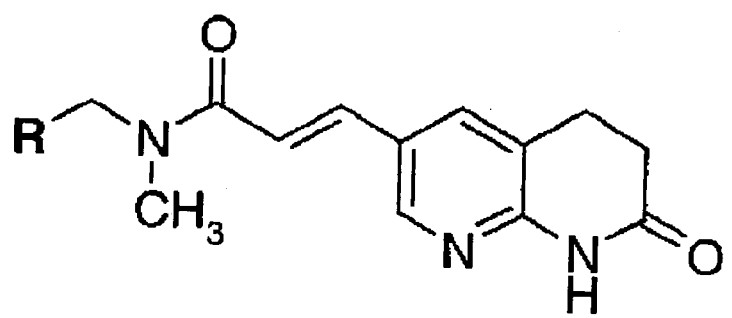

FIG. 38 depicts naphthyridinone inhibitor 29.

DETAILED DESCRIPTION OF THE INVENTION

1. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "binding" refers to an association, which may be a stable association, between two molecules, e.g., between a polypeptide of the invention and a binding partner, due to, for example, electrostatic, hydrophobic, ionic and/or hydrogen-bond interactions under physiological conditions.

A "comparison window," as used herein, refers to a conceptual segment of at least 20 contiguous amino acid positions wherein a protein sequence may be compared to a reference sequence of at least 20 contiguous amino acids and wherein the portion of the protein sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods may be identified.

The term "complex" refers to an association between at least two moieties (e.g. chemical or biochemical) that have an affinity for one another. Examples of complexes include associations between antigen/antibodies, lectin/avidin, target polynucleotide/probe oligonucleotide, antibody/anti-antibody, receptor/ligand, enzyme/ligand, polypeptide/polypeptide, polypeptide/polynucleotide, polypeptide/co-factor, polypeptide/substrate, polypeptide/inhibitor, polypeptide/small molecule, and the like. "Member of a complex" refers to one moiety of the complex, such as an antigen or ligand. "Protein complex" or "polypeptide complex" refers to a complex comprising at least one polypeptide.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

The term "domain", when used in connection with a polypeptide, refers to a specific region within such polypeptide that comprises a particular structure or mediates a particular function. In the typical case, a domain of a polypeptide of the invention is a fragment of the polypeptide. In certain instances, a domain is a structurally stable domain, as evidenced, for example, by mass spectroscopy, or by the fact that a modulator may bind to a druggable region of the domain.

The term "druggable region", when used in reference to a polypeptide, nucleic acid, complex and the like, refers to a region of the molecule which is a target or is a likely target for binding a modulator. For a polypeptide, a druggable region generally refers to a region wherein several amino acids of a polypeptide would be capable of interacting with a modulator or other molecule. For a polypeptide or complex thereof, exemplary druggable regions including binding pockets and sites, enzymatic active sites, interfaces between domains of a polypeptide or complex, surface grooves or contours or surfaces of a polypeptide or complex which are capable of participating in interactions with another molecule. In certain instances, the interacting molecule is another polypeptide, which may be naturally-occurring. In other instances, the druggable region is on the surface of the molecule.

Druggable regions may be described and characterized in a number of ways. For example, a druggable region may be characterized by some or all of the amino acids that make up the region, or the backbone atoms thereof, or the side chain atoms thereof (optionally with or without the Cα atoms). Alternatively, in certain instances, the volume of a druggable region corresponds to that of a carbon based molecule of at least about 200 amu and often up to about 800 amu. In other instances, it will be appreciated that the volume of such region may correspond to a molecule of at least about 600 amu and often up to about 1600 amu or more.

Alternatively, a druggable region may be characterized by comparison to other regions on the same or other molecules. For example, the term "affinity region" refers to a druggable region on a molecule (such as a polypeptide of the invention) that is present in several other molecules, in so much as the structures of the same affinity regions are sufficiently the same so that they are expected to bind the same or related structural analogs. An example of an affinity region is an ATP-binding site of a protein kinase that is found in several protein kinases (whether or not of the same origin). The term "selectivity region" refers to a druggable region of a molecule that may not be found on other molecules, in so much as the structures of different selectivity regions are sufficiently different so that they are not expected to bind the same or related structural analogs. An exemplary selectivity region is a catalytic domain of a protein kinase that exhibits specificity for one substrate. In certain instances, a single modulator may bind to the same affinity region across a number of proteins that have a substantially similar biological function, whereas the same modulator may bind to only one selectivity region of one of those proteins.

Continuing with examples of different druggable regions, the term "undesired region" refers to a druggable region of a molecule that upon interacting with another molecule results in an undesirable affect. For example, a binding site that oxidizes the interacting molecule (such as P-450 activity) and thereby results in increased toxicity for the oxidized molecule may be deemed a "undesired region". Other examples of potential undesired regions includes regions that upon interaction with a drug decrease the membrane permeability of the drug, increase the excretion of the drug, or increase the blood brain transport of the drug. It may be the case that, in certain circumstances, an undesired region will no longer be deemed an undesired region because the affect of the region will be favorable, e.g., a drug intended to treat a brain condition would benefit from interacting with a region that resulted in increased blood brain transport, whereas the same region could be deemed undesirable for drugs that were not intended to be delivered to the brain.

When used in reference to a druggable region, the "selectivity" or "specificity" of a molecule such as a modulator to a druggable region may be used to describe the binding between the molecule and a druggable region. For example, the selectivity of a modulator with respect to a druggable region may be expressed by comparison to another modulator, using the respective values of $K_d$ (i.e., the dissociation constants for each modulator-druggable region complex) or, in cases where a biological effect is observed below the $K_d$, the ratio of the respective $EC_{50}$'s (i.e., the concentrations that produce 50% of the maximum response for the modulator interacting with each druggable region).

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain or an immunoglobulin binding domain.

The term "gene" refers to a nucleic acid comprising an open reading frame encoding a polypeptide having exon sequences and optionally intron sequences. The term "intron" refers to a DNA sequence present in a given gene which is not translated into protein and is generally found between exons.

The term "having substantially similar biological activity", when used in reference to two polypeptides, refers to a biological activity of a first polypeptide which is substantially similar to at least one of the biological activities of a second polypeptide. A substantially similar biological activity means that the polypeptides carry out a similar function, e.g., a similar enzymatic reaction or a similar physiological process, etc. For example, two homologous proteins may have a substantially similar biological activity if they are involved in a similar enzymatic reaction, e.g., they are both kinases which catalyze phosphorylation of a substrate polypeptide, however, they may phosphorylate different regions on the same protein substrate or different substrate proteins altogether. Alternatively, two homologous proteins may also have a substantially similar biological activity if they are both involved in a similar physiological process, e.g., transcription. For example, two proteins may be transcription factors, however, they may bind to different DNA sequences or bind to different polypeptide interactors. Substantially similar biological activities may also be associated with proteins carrying out a similar structural role, for example, two membrane proteins.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, e.g. free of other S. aureus proteins, (4) is expressed by a cell from a different species, or (5) does not occur in nature.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "mammal" is known in the art, and exemplary mammals include humans, primates, bovines, porcines, canines, felines, and rodents (e.g., mice and rats).

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, antimicrobial agents, inhibitors of microbial infection or proliferation, and the like) by inclusion in assays. In such assays, many modulators may be screened at one time. The activity of a modulator may be known, unknown or partially known.

The term "motif" refers to an amino acid sequence that is commonly found in a protein of a particular structure or function. Typically, a consensus sequence is defined to represent a particular motif. The consensus sequence need not be strictly defined and may contain positions of variability, degeneracy, variability of length, etc. The consensus sequence may be used to search a database to identify other proteins that may have a similar structure or function due to the presence of the motif in its amino acid sequence. For example, on-line databases may be searched with a consensus sequence in order to identify other proteins containing a particular motif. Various search algorithms and/or programs may be used, including FASTA, BLAST or ENTREZ. FASTA and BLAST are available as a part of the GCG sequence analysis package (University of Wisconsin, Madison, Wis.). ENTREZ is available through the National Center for Biotechnology Information, National Library of Medicine, National Institutes of Health, Bethesda, Md.

The term "naturally-occurring", as applied to an object, refers to the fact that an object may be found in nature. For example, a polypeptide or polynucleotide sequence that is present in an organism (including bacteria) that may be isolated from a source in nature and which has not been intentionally modified by man in the laboratory is naturally-occurring.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" refers to a nucleic acid encoding a polypeptide of the invention, e.g., a nucleic acid comprising a sequence consisting of, or consisting essentially of, the polynucleotide sequence set forth in SEQ ID NO: 1 or SEQ ID NO: 3. A nucleic acid of the invention may comprise all, or a portion of: the nucleotide sequence of SEQ ID NO: 1 or SEQ ID NO: 3; a nucleotide sequence at least 60%, 70%, 80%, 90%, 95%, 96%, 97%, 98% or 99% identical to SEQ ID NO: 1 or SEQ ID NO: 3; a nucleotide sequence that hybridizes under stringent conditions to SEQ ID NO: 1 or SEQ ID NO: 3; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous or identical with an amino acid sequence of SEQ ID NO: 2 or SEQ ID NO: 4; nucleotide sequences encoding polypeptides having an activity of a polypeptide of the invention and having at least about 60%, 70%, 80%, 85%, 90%, 95%, 98%, 99% or more homology or identity with SEQ ID NO: 2 or SEQ ID NO: 4; nucleotide sequences that differ by 1 to about 2, 3, 5, 7, 10, 15, 20, 30, 50, 75 or more nucleotide substitutions, additions or deletions, such as allelic variants, of SEQ ID NO: 1 and SEQ ID NO: 3; nucleic acids derived from and evolutionarily related to SEQ ID NO: 1 or SEQ ID NO: 3; and complements of, and nucleotide sequences resulting from the degeneracy of the genetic code, for all of the foregoing and other nucleic acids of the invention. Nucleic acids of the invention also include homologs, e.g., orthologs and paralogs, of SEQ ID NO: 1 or SEQ ID NO: 3 and also variants of SEQ ID NO: 1 or SEQ ID NO: 3 which have been codon optimized for expression in a particular organism (e.g., host cell).

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "phenotype" refers to the entire physical, biochemical, and physiological makeup of a cell, e.g., having any one trait or any group of traits.

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a druggable region, and optionally additional amino acids on one or both sides of the druggable region, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the invention" refers to a polypeptide comprising the amino acid sequence set forth in SEQ ID NO: 2 or SEQ ID NO: 4, or an equivalent or fragment thereof, e.g., a polypeptide comprising a sequence consisting of, or consisting essentially of, the amino acid sequence set forth in SEQ ID NO: 2 or SEQ ID NO: 4. Polypeptides of the invention include polypeptides comprising all or a portion of the amino acid sequence set forth in SEQ ID NO: 2 or SEQ ID NO: 4; the amino acid sequence set forth in SEQ ID NO: 2 or SEQ ID NO: 4 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to SEQ ID NO: 2 or SEQ ID NO: 4; and functional fragments thereof. Polypeptides of the invention also include homologs, e.g., orthologs and paralogs, of SEQ ID NO: 2 or SEQ ID NO: 4.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described in the Exemplification section herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

A "reference sequence" is a defined sequence used as a basis for a sequence comparison; a reference sequence may be a subset of a larger sequence, for example, as a segment of a full-length protein given in a sequence listing such as SEQ ID NO: 2 or SEQ ID NO: 4, or may comprise a complete protein sequence. Generally, a reference sequence is at least 200, 300 or 400 nucleotides in length, frequently at least 600 nucleotides in length, and often at least 800 nucleotides in length (or the protein equivalent if it is shorter or longer in length). Because two proteins may each (1) comprise a sequence (i.e., a portion of the complete protein sequence) that is similar between the two proteins, and (2) may further comprise a sequence that is divergent between the two proteins, sequence comparisons between two (or more) proteins are typically performed by comparing sequences of the two proteins over a "comparison window" to identify and compare local regions of sequence similarity.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "reporter gene" refers to a nucleic acid comprising a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters. Generally, a reporter gene encodes a polypeptide not otherwise produced by the host cell, which is detectable by analysis of the cell(s), e.g., by the direct fluorometric, radioisotopic or spectrophotometric analysis of the cell(s) and preferably without the need to kill the cells for signal analysis. In certain instances, a reporter gene encodes an enzyme, which produces a change in fluorometric properties of the host cell, which is detectable by qualitative, quantitative or semiquantitative function or transcriptional activation. Exemplary enzymes include esterases, β-lactamase, phosphatases, peroxidases, proteases (tissue plasminogen activator or urokinase) and other enzymes whose function may be detected by appropriate chromogenic or fluorogenic substrates known to those skilled in the art or developed in the future.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "soluble" as used herein with reference to a polypeptide of the invention or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups). The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the invention will produce at least about 0.1, 0.2, 0.5, 1, 2, 5, 10, 20, 30, 40, 50 milligrams or more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of the a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available in which G-C stacking interactions, solvent effects, the desired assay temperature and the like are taken into account. For example, probes can be designed to have a dissociation temperature (Td) of approximately 60° C., using the formula: $Td=(((((3\times\#GC)+(2\times\#AT))\times 37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution comprising, or consisting of, 50% formamide, 10×Denhardt (0.2% Ficoll, 0.2% Polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N.Y.; and Tibanyenda, N. et al., Eur. J. Biochem. 139:19 (1984) and Ebel, S. et al., Biochem. 31:12083 (1992).

As applied to proteins, the term "substantial identity" means that two protein sequences, when optimally aligned, such as by the programs GAP or BESTFIT using default gap weights, typically share at least about 70 percent sequence identity, alternatively at least about 80, 85, 90, 95 percent sequence identity or more. In certain instances, residue positions that are not identical differ by conservative amino acid substitutions, which are described above.

The term "structural motif", when used in reference to a polypeptide, refers to a polypeptide that, although it may have different amino acid sequences, may result in a similar structure, wherein by structure is meant that the motif forms generally the same tertiary structure, or that certain amino acid residues within the motif, or alternatively their backbone or side chains (which may or may not include the Cα atoms of the side chains) are positioned in a like relationship with respect to one another in the motif.

The term "test compound" refers to a molecule to be tested by one or more screening method(s) as a putative modulator of a polypeptide of the invention or other biological entity or process. A test compound is usually not known to bind to a target of interest. The term "control test compound" refers to a compound known to bind to the target (e.g., a known agonist, antagonist, partial agonist or inverse agonist). The term "test compound" does not include a chemical added as a control condition that alters the function of the target to determine signal specificity in an assay. Such control chemicals or conditions include chemicals that 1) nonspecifically or substantially disrupt protein structure (e.g., denaturing agents (e.g., urea or guanidinium), chaotropic agents, sulfhydryl reagents (e.g., dithiothreitol and β-mercaptoethanol), and proteases), 2) generally inhibit cell metabolism (e.g., mitochondrial uncouplers) and 3) non-specifically disrupt electrostatic or hydrophobic interactions of a protein (e.g., high salt concentrations, or detergents at concentrations sufficient to non-specifically disrupt hydrophobic interactions). Further, the term "test compound" also does not include compounds known to be unsuitable for a therapeutic use for a particular indication due to toxicity of the subject. In certain embodiments, various predetermined concentrations of test compounds are used for screening such as 0.01 μM, 0.1 μM, 1.0 μM, and 10.0 μM. Examples of test compounds include, but are not limited to, peptides, nucleic acids, carbohydrates, and small molecules. The term "novel test compound" refers to a test compound that is not in existence as of the filing date of this application. In certain assays using novel test compounds, the novel test compounds comprise at least about 50%, 75%, 85%, 90%, 95% or more of the test compounds used in the assay or in any particular trial of the assay.

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "transfection" means the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell may express a recombinant form of a polypeptide of the invention or antisense expression may occur from the transferred gene so that the expression of a naturally-occurring form of the gene is disrupted.

The term "transgene" means a nucleic acid sequence, which is partly or entirely heterologous to a transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may include one or more regulatory sequences and any other nucleic acids, such as introns, that may be necessary for optimal expression.

The term "transgenic animal" refers to any animal, for example, a mouse, rat or other non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a protein. However, transgenic animals in which the recombinant gene is silent are also contemplated.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

2. Polypeptides of the Invention

The present invention makes available in a variety of embodiments soluble, purified and/or isolated forms of the polypeptides of the invention. Milligram quantities of an exemplary polypeptide of the invention, SEQ ID NO: 4 (optionally with a tag, and optionally labeled), have been isolated in a highly purified form. The present invention provides for expressing and purifying polypeptides of the invention in quantities that equal or exceed the quantity of polypeptide(s) of the invention expressed and purified as provided in the Exemplification section below (or smaller amount(s) thereof, such as 25%, 33%, 50% or 75% of the amount(s) so expressed and/or purified).

In one aspect, the present invention contemplates an isolated polypeptide comprising (a) the amino acid sequence set forth in SEQ ID NO: 2 or SEQ ID NO: 4, (b) the amino acid sequence set forth in SEQ ID NO: 2 or SEQ ID NO: 4 with 1 to about 20 conservative amino acid substitutions, deletions or additions, (c) an amino acid sequence that is at least 90% identical to SEQ ID NO: 2 or SEQ ID NO: 4 or (d) a functional fragment of a polypeptide having an amino acid sequence set forth in (a), (b) or (c). In another aspect, the present invention contemplates a composition comprising such an isolated polypeptide and less than about 10%, or alternatively 5%, or alternatively 1%, contaminating biological macromolecules or polypeptides.

It may be the case that the amino acid sequence of SEQ ID NO: 4 differs from that of SEQ ID NO: 2 by one or more amino acids. SEQ ID NO: 4 is determined from the experimentally determined nucleic acid sequence SEQ ID NO: 3, and SEQ ID NO: 2 is determined from SEQ ID NO: 1, which is obtained as described in EXAMPLE 1. In such a case, the present invention contemplates the specific amino acid sequences of SEQ ID NO: 2 and SEQ ID NO: 4, and variants thereof, as well as any differences (if any) in the polypeptides of the invention based on those SEQ ID NOS and nucleic acid sequences encoding the same.

In certain embodiments, a polypeptide of the invention is a fusion protein containing a domain which increases its solubility and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In another embodiment, a polypeptide of the invention may be modified so that its rate of traversing the cellular membrane is increased. For example, the polypeptide may be fused to a second peptide which promotes "transcytosis," e.g., uptake of the peptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188).

Alternatively, the internalizing peptide may be derived from the Drosophila antennapedia protein, or homologs thereof. The 60 amino acid long homeodomain of the homeo-protein antennapedia has been demonstrated to translocate through biological membranes and can facilitate the translocation of heterologous polypeptides to which it is coupled. Thus, polypeptides may be fused to a peptide consisting of about amino acids 42-58 of Drosophila antennapedia or shorter fragments for transcytosis (Derossi et al. (1996) *J Biol Chem* 271:18188-18193; Derossi et al. (1994) *J Biol Chem* 269: 10444-10450; and Perez et al. (1992) *J Cell Sci* 102:717-722). The transcytosis polypeptide may also be a non-naturally-occurring membrane-translocating sequence (MTS), such as the peptide sequences disclosed in U.S. Pat. No. 6,248,558.

In another embodiment, a polypeptide of the invention is labeled with an isotopic label to facilitate its detection and or structural characterization using nuclear magnetic resonance or another applicable technique. Exemplary isotopic labels include radioisotopic labels such as, for example, potassium-40 ($^{40}$K), carbon-14 ($^{14}$C), tritium ($^{3}$H), sulphur-35 ($^{35}$S), phosphorus-32 ($^{32}$P), technetium-99m ($^{99m}$Tc), thallium-201 ($^{201}$Tl), gallium-67 ($^{67}$Ga), indium-111 ($^{111}$In), iodine-123 ($^{123}$I), iodine-131 ($^{131}$I), yttrium-90 ($^{90}$Y), samarium-153 ($^{153}$Sm), rhenium-186 ($^{186}$Re), rhenium-188 ($^{188}$Re), dysprosium-165 ($^{165}$Dy) and holmium-166 ($^{166}$Ho). The isotopic label may also be an atom with non zero nuclear spin, including, for example, hydrogen-1 ($^{1}$H), hydrogen-2 ($^{2}$H), hydrogen-3 ($^{3}$H), phosphorous-31 ($^{31}$P), sodium-23 ($^{23}$Na), nitrogen-14 ($^{14}$N), nitrogen-15 ($^{15}$N), carbon-13 ($^{13}$C) and fluorine-19 ($^{19}$F). In certain embodiments, the polypeptide is uniformly labeled with an isotopic label, for example, wherein at least 50%, 70%, 80%, 90%, 95%, or 98% of the possible labels in the polypeptide are labeled, e.g., wherein at least 50%, 70%, 80%, 90%, 95%, or 98% of the nitrogen atoms in the polypeptide are $^{15}$N, and/or wherein at least 50%, 70%, 80%, 90%, 95%, or 98% of the carbon atoms in the polypeptide are $^{13}$C, and/or wherein at least 50%, 70%, 80%, 90%, 95%, or 98% of the hydrogen atoms in the polypeptide are $^{2}$H. In other embodiments, the isotopic label is located in one or more specific locations within the polypeptide, for example, the label may be specifically incorporated into one or more of the leucine residues of the polypeptide. The invention also encompasses the embodiment wherein a single polypeptide comprises two, three or more different isotopic labels, for example, the polypeptide comprises both $^{15}$N and $^{13}$C labeling.

In yet another embodiment, the polypeptides of the invention are labeled to facilitate structural characterization using x-ray crystallography or another applicable technique. Exemplary labels include heavy atom labels such as, for example, cobalt, selenium, krypton, bromine, strontium, molybdenum, ruthenium, rhodium, palladium, silver, cadmium, tin, iodine, xenon, barium, lanthanum, cerium, praseodymium, neodymium, samarium, europium, gadolinium, terbium, dysprosium, holmium, erbium, thulium, ytterbium, lutetium, tantalum, tungsten, rhenium, osmium, iridium, platinum, gold, mercury, thallium, lead, thorium and uranium. In an exemplary embodiment, the polypeptide is labeled with selenomethionine.

A variety of methods are available for preparing a polypeptide with a label, such as a radioisotopic label or heavy atom label. For example, in one such method, an expression vector comprising a nucleic acid encoding a polypeptide is introduced into a host cell, and the host cell is cultured in a cell culture medium in the presence of a source of the label, thereby generating a labeled polypeptide. As indicated above, the extent to which a polypeptide may be labeled may vary.

In still another embodiment, the polypeptides of the invention are labeled with a fluorescent label to facilitate their detection, purification, or structural characterization. In an exemplary embodiment, a polypeptide of the invention is fused to a heterologous polypeptide sequence which produces a detectable fluorescent signal, including, for example, green fluorescent protein (GFP), enhanced green fluorescent protein (EGFP), *Renilla Renifornis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

In other embodiments, the invention provides for polypeptides of the invention immobilized onto a solid surface, including, microtiter plates, slides, beads, films, etc. The polypeptides of the invention may be immobilized onto a "chip" as part of an array. An array, having a plurality of addresses, may comprise one or more polypeptides of the invention in one or more of those addresses. In one embodiment, the chip comprises one or more polypeptides of the invention as part of an array of *S. aureus* polypeptide sequences.

In other embodiments, the invention provides for polypeptides of the invention immobilized onto a solid surface, including, plates, microtiter plates, slides, beads, particles, spheres, films, strands, precipitates, gels, sheets, tubing, containers, capillaries, pads, slices, etc. The polypeptides of the invention may be immobilized onto a "chip" as part of an array. An array, having a plurality of addresses, may comprise one or more polypeptides of the invention in one or more of those addresses. In one embodiment, the chip comprises one or more polypeptides of the invention as part of an array that contains at least some polypeptide sequences from *S. aureus*.

In still other embodiments, the invention comprises the polypeptide sequences of the invention in computer readable format. The invention also encompasses a database comprising the polypeptide sequences of the invention.

In other embodiments, the invention relates to the polypeptides of the invention contained within a vessels useful for manipulation of the polypeptide sample. For example, the polypeptides of the invention may be contained within a microtiter plate to facilitate detection, screening or purification of the polypeptide. The polypeptides may also be contained within a syringe as a container suitable for administering the polypeptide to a subject in order to generate antibodies or as part of a vaccination regimen. The polypeptides may also be contained within an NMR tube in order to enable characterization by nuclear magnetic resonance techniques.

In still other embodiments, the invention relates to a crystallized polypeptide of the invention and crystallized polypeptides which have been mounted for examination by x-ray crystallography as described further below. In certain instances, a polypeptide of the invention in crystal form may be single crystals of various dimensions (e.g., micro-crystals) or may be an aggregate of crystalline material. In another aspect, the present invention contemplates a crystallized complex including a polypeptide of the invention and one or more of the following: a co-factor (such as a salt, metal, nucleotide, oligonucleotide or polypeptide), a modulator, or a small molecule. In another aspect, the present invention contemplates a crystallized complex including a polypeptide of the invention and any other molecule or atom (such as a metal ion) that associates with the polypeptide in vivo.

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

In certain embodiments, it may be advantageous to provide naturally-occurring or experimentally-derived homologs of a polypeptide of the invention. Such homologs may function in a limited capacity as a modulator to promote or inhibit a subset of the biological activities of the naturally-occurring form of the polypeptide. Thus, specific biological effects may be elicited by treatment with a homolog of limited function, and with fewer side effects relative to treatment with agonists or antagonists which are directed to all of the biological activities of a polypeptide of the invention. For instance, antagonistic homologs may be generated which interfere with the ability of the wild-type polypeptide of the invention to associate with certain proteins, but which do not substantially interfere with the formation of complexes between the native polypeptide and other cellular proteins.

Another aspect of the invention relates to polypeptides derived from the full-length polypeptides of the invention. Isolated peptidyl portions of those polypeptides may be obtained by screening polypeptides recombinantly produced from the corresponding fragment of the nucleic acid encoding such polypeptides. In addition, fragments may be chemically synthesized using techniques known in the art such as conventional Merrifield solid phase f-Moc or t-Boc chemistry. For example, proteins may be arbitrarily divided into fragments of desired length with no overlap of the fragments, or may be divided into overlapping fragments of a desired length. The fragments may be produced (recombinantly or by chemical synthesis) and tested to identify those peptidyl fragments having a desired property, for example, the capability of functioning as a modulator of the polypeptides of the invention. In an illustrative embodiment, peptidyl portions of a protein of the invention may be tested for binding activity, as well as inhibitory ability, by expression as, for example, thioredoxin fusion proteins, each of which contains a discrete fragment of a protein of the invention (see, for example, U.S. Pat. Nos. 5,270,181 and 5,292,646; and PCT publication WO94/02502).

In another embodiment, truncated polypeptides may be prepared. Truncated polypeptides have from 1 to 20 or more amino acid residues removed from either or both the N- and C-termini. Such truncated polypeptides may prove more amenable to expression, purification or characterization than the full-length polypeptide. For example, truncated polypeptides may prove more amenable than the full-length polypeptide to crystallization, to yielding high quality diffracting crystals or to yielding an HSQC spectrum with high intensity peaks and minimally overlapping peaks. In addition, the use of truncated polypeptides may also identify stable and active domains of the full-length polypeptide that may be more amenable to characterization.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

This invention further contemplates a method of generating sets of combinatorial mutants of polypeptides of the invention, as well as truncation mutants, and is especially useful for identifying potential variant sequences (e.g. homologs). The purpose of screening such combinatorial libraries is to generate, for example, homologs which may modulate the activity of a polypeptide of the invention, or alternatively, which possess novel activities altogether. Combinatorially-derived homologs may be generated which have a selective potency relative to a naturally-occurring protein. Such homologs may be used in the development of therapeutics.

Likewise, mutagenesis may give rise to homologs which have intracellular half-lives dramatically different than the corresponding wild-type protein. For example, the altered protein may be rendered either more stable or less stable to proteolytic degradation or other cellular process which result in destruction of, or otherwise inactivation of the protein. Such homologs, and the genes which encode them, may be utilized to alter protein expression by modulating the half-life of the protein. As above, such proteins may be used for the development of therapeutics or treatment.

In similar fashion, protein homologs may be generated by the present combinatorial approach to act as antagonists, in that they are able to interfere with the activity of the corresponding wild-type protein.

In a representative embodiment of this method, the amino acid sequences for a population of protein homologs are aligned, preferably to promote the highest homology possible. Such a population of variants may include, for example, homologs from one or more species, or homologs from the same species but which differ due to mutation. Amino acids which appear at each position of the aligned sequences are selected to create a degenerate set of combinatorial sequences. In certain embodiments, the combinatorial library is produced by way of a degenerate library of genes encoding a library of polypeptides which each include at least a portion of potential protein sequences. For instance, a mixture of synthetic oligonucleotides may be enzymatically ligated into gene sequences such that the degenerate set of potential nucleotide sequences are expressible as individual polypeptides, or alternatively, as a set of larger fusion proteins (e.g. for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. A G Walton, Amsterdam: Elsevier pp. 273-289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386-390; Roberts et al., (1992) *PNAS USA* 89:2429-2433; Devlin et al., (1990) *Science* 249: 404-406; Cwirla et al., (1990) *PNAS USA* 87: 6378-6382; as well as U.S. Pat. Nos. 5,223,409, 5,198,346, and 5,096,815).

Alternatively, other forms of mutagenesis may be utilized to generate a combinatorial library. For example, protein homologs (both agonist and antagonist forms) may be generated and isolated from a library by screening using, for example, alanine scanning mutagenesis and the like (Ruf et al., (1994) *Biochemistry* 33:1565-1572; Wang et al., (1994) *J. Biol. Chem.* 269:3095-3099; Balint et al., (1993) *Gene* 137: 109-118; Grodberg et al., (1993) *Eur. J. Biochem.* 218:597-601; Nagashima et al., (1993) *J. Biol. Chem.* 268:2888-2892; Lowman et al., (1991) *Biochemistry* 30:10832-10838; and Cunningham et al., (1989) *Science* 244:1081-1085), by linker scanning mutagenesis (Gustin et al., (1993) *Virology* 193: 653-660; Brown et al., (1992) *Mol. Cell Biol.* 12:2644-2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11-19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32-34). Linker scanning mutagenesis, particularly in a combinatorial setting, is an attractive method for identifying truncated forms of proteins that are bioactive.

A wide range of techniques are known in the art for screening gene products of combinatorial libraries made by point mutations and truncations, and for screening cDNA libraries for gene products having a certain property. Such techniques will be generally adaptable for rapid screening of the gene libraries generated by the combinatorial mutagenesis of protein homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high throughput analysis as necessary to screen large numbers of degenerate sequences created by combinatorial mutagenesis techniques.

In an illustrative embodiment of a screening assay, candidate combinatorial gene products are displayed on the surface of a cell and the ability of particular cells or viral particles to bind to the combinatorial gene product is detected in a "panning assay". For instance, the gene library may be cloned into the gene for a surface membrane protein of a bacterial cell (Ladner et al., WO 88/06630; Fuchs et al., (1991) *Bio/Technology* 9:1370-1371; and Goward et al., (1992) *TIBS* 18:136-140), and the resulting fusion protein detected by panning, e.g. using a fluorescently labeled molecule which binds the cell surface protein, e.g. FITC-substrate, to score for potentially functional homologs. Cells may be visually inspected and separated under a fluorescence microscope, or, when the morphology of the cell permits, separated by a fluorescence-activated cell sorter. This method may be used to identify substrates or other polypeptides that can interact with a polypeptide of the invention.

In similar fashion, the gene library may be expressed as a fusion protein on the surface of a viral particle. For instance, in the filamentous phage system, foreign peptide sequences may be expressed on the surface of infectious phage, thereby conferring two benefits. First, because these phage may be applied to affinity matrices at very high concentrations, a large number of phage may be screened at one time. Second, because each infectious phage displays the combinatorial gene product on its surface, if a particular phage is recovered from an affinity matrix in low yield, the phage may be amplified by another round of infection. The group of almost identical *E. coli* filamentous phages M13, fd, and fl are most often used in phage display libraries, as either of the phage gIII or gVIII coat proteins may be used to generate fusion proteins without disrupting the ultimate packaging of the viral particle (Ladner et al., PCT publication WO 90/02909; Garrard et al., PCT publication WO 92/09690; Marks et al., (1992) *J. Biol. Chem.* 267:16007-16010; Griffiths et al., (1993) *EMBO J.* 12:725-734; Clackson et al., (1991) *Nature* 352:624-628; and Barbas et al., (1992) *PNAS USA* 89:4457-4461). Other phage coat proteins may be used as appropriate.

The invention also provides for reduction of the polypeptides of the invention to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a protein which participates in a protein-protein interaction with another protein. To illustrate, the critical residues of a protein which are involved in molecular recognition of a substrate protein may be determined and used to generate peptidomimetics that may bind to the substrate protein. The peptidomimetic may then be used as an inhibitor of the wild-type protein by binding to the substrate and covering up the critical residues needed for interaction with the wild-type protein, thereby preventing interaction of the protein and the substrate. By employing, for example, scanning mutagenesis to map the amino acid residues of a protein which are involved in binding a substrate polypeptide, peptidomimetic compounds may be generated which mimic those residues in binding to the substrate. For instance, non-hydrolyzable peptide analogs of such residues may be generated using benzodiazepine (e.g., see Freidinger et al., in *Peptides: Chemistry and Biology*, G. R. Marshall ed., ESCOM Publisher: Leiden, Netherlands, 1988), azepine (e.g., see Huffman et al., in *Peptides: Chemistry and Biology*, G. R. Marshall ed., ESCOM Publisher: Leiden, Netherlands, 1988), substituted gamma lactam rings (Garvey et al., in *Peptides: Chemistry and Biology*, G. R. Marshall ed., ESCOM Publisher: Leiden, Netherlands, 1988), keto-methylene pseudopeptides (Ewenson et al., (1986) *J. Med. Chem.* 29:295; and Ewenson et al., in *Peptides: Structure and Function* (Proceedings of the 9th American Peptide Symposium) Pierce Chemical Co. Rockland, Ill., 1985), β-turn dipeptide cores (Nagai et al., (1985) *Tetrahedron Lett* 26:647; and Sato et al., (1986) *J Chem Soc Perkin Trans* 1:1231), and β-aminoalcohols (Gordon et al., (1985) *Biochem Biophys Res Commun* 126:419; and Dann et al., (1986) *Biochem Biophys Res Commun* 134:71).

The activity of a polypeptide of the invention may be identified and/or assayed using a variety of methods well known to the skilled artisan. For example, information about the activity of non-essential genes may be assayed by creating a null mutant strain of bacteria expressing a mutant form of, or lacking expression of, a protein of interest. The resulting phenotype of the null mutant strain may provide information about the activity of the mutated gene product. Essential genes may be studied by creating a bacterial strain with a conditional mutation in the gene of interest. The bacterial strain may be grown under permissive and non-permissive conditions and the change in phenotype under the non-permissive conditions may be used to identify and/or assay the activity of the gene product.

In an alternative embodiment, the activity of a protein may be assayed using an appropriate substrate or binding partner or other reagent suitable to test for the suspected activity. For catalytic activity, the assay is typically designed so that the enzymatic reaction produces a detectable signal. For example, mixture of a kinase with a substrate in the presence of $^{32}P$ will result in incorporation of the $^{32}P$ into the substrate. The labeled substrate may then be separated from the free $^{32}P$ and the presence and/or amount of radiolabeled substrate may be detected using a scintillation counter or a phosphorimager. Similar assays may be designed to identify and/or assay the activity of a wide variety of enzymatic activities. Based on the teachings herein, the skilled artisan would readily be able to develop an appropriate assay for a polypeptide of the invention.

In another embodiment, the activity of a polypeptide of the invention may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

Alternatively, it may be desirable to measure the overall rate of DNA replication, transcription and/or translation in a cell. In general this may be accomplished by growing the cell in the presence of a detectable metabolite which is incorporated into the resultant DNA, RNA, or protein product. For example, the rate of DNA synthesis may be determined by growing cells in the presence of BrdU which is incorporated into the newly synthesized DNA. The amount of BrdU may then be determined histochemically using an anti-BrdU antibody.

In general, the biological activity of a polypeptide encoded by SEQ ID NO. 2, and possibly other polypeptides of the invention, is enoyl-[acyl-carrier-protein] reductase (NADH), having the gene designation of FabI. The polypeptide encoded by SEQ ID NO. 2, and possibly other polypeptides of the invention, may be further characterized as being part of the COG category "lipid metabolism", with COG ID No. COG0623. The foregoing annotations were determined in accordance with the procedure described in EXAMPLE 17. This functionality assignment has been confirmed by completion of the X-ray structure of a polypeptide of the invention, as described in more detail below. In one aspect, the present invention contemplates a polypeptide having biological activity, or is a component of a protein complex having biological activity, substantially similar to or identical to enoyl-[acyl-carrier-protein] reductase (NADH). Alternatively, the polypeptide catalyzes, or is a component of a protein complex that catalyzes, a reaction that is substantially the same type of, or is the same as, the reaction catalyzed by enoyl-[acyl-carrier-protein] reductase (NADH). Other biological activities of polypeptides of the invention are described herein, or will be reasonably apparent to those skilled in the art in light of the present disclosure.

Antibiotic resistant pathogens are a source of universal healthcare concern. Methicillin-resistant *Staphylococcus aureus* (MRSA) and vancomycin-resistant Enterococci (VRE) have become particularly troublesome as our remaining therapeutic defenses against these pathogens become progressively less effective. With the recent emergence of vancomycin-resistant *Staphylococcus aureus*, the need for new antibiotics is of paramount importance. A potential strategy for combating antibiotic resistance is to target novel mechanisms of action.

One such approach is the inhibition of enzymes involved in bacterial fatty acid biosynthesis (FAB). Fatty acid biosynthesis may be carried out by the ubiquitous fatty-acid synthase (FAS) system. The pathway for the biosynthesis of saturated fatty acids is very similar in prokaryotes and eukaryotes. However, in yeast and vertebrates the type I FAS system may be employed, whereby fatty acid biosynthesis is carried out by a single multifunctional polypeptide complex. In contrast, most bacteria and plants employ the type II FAS system, in which each of the reactions may be catalyzed by distinct monofunctional enzymes and ACP is a discrete protein. Thus, there appears to be considerable potential for selective inhibition of the bacterial systems by broad spectrum antibacterial agents. The first step in the biosynthetic cycle is the condensation of malonyl-ACP (3C) with acetyl-CoA (2C) by FabH. Prior to this, malonyl-ACP is synthesized from ACP and malonyl-CoA by FabD, malonyl CoA:ACP transacylase. In subsequent rounds malonyl-ACP is condensed with the growing-chain acyl-ACP (4C). The second step in the elongation cycle is ketoester reduction by NADPH-dependent beta.-ketoacyl-ACP reductase (FabG). Subsequent dehydration by beta.-hydroxyacyl-ACP dehydrase (either FabA or FabZ) leads to trans-2-enoyl-ACP which is in turn converted to acyl-ACP by enoyl-ACP reductase (FabI). Further rounds of this cycle, adding two carbon atoms per cycle, eventually lead to palmitoyl-ACP whereupon the cycle is stopped largely due to feedback inhibition of FabH and I by palmitoyl-ACP. The absolute requirement of type II FAS for bacterial viability, together with its major differences with the mammalian system, suggests that enzymes in this pathway may be good targets with selective compounds as broad-spectrum antibacterial drugs.

FabI from *S. aureus* encodes one of the enzymes in this pathway. The FabI protein is an enoyl-ACP reductase (enoyl-[acyl-carrier-protein] reductase) that catalyzes the ultimate and rate-limiting step of the chain elongation process of the type II FAS system. The reaction involves the conjugate reduction of an enoyl-ACP to the corresponding acyl-ACP using the cofactor NAD(P)H as a hydride source. Reports describing the antibacterial agents isoniazid, diazaboranes, and triclosan as inhibitors of bacterial enoyl-ACP reductase support a FabI-targeted approach to antibacterial drug therapy.

FabK and FabL are other bacterial enoyl-ACP reductases expressed in several bacterial species replacing or augmenting FabI. FabK is a flavoprotein resistant to triclosan. It has been shown to be the only enoyl ACP-reductase in *Streptococcus pneumoniae* and to exist together with FabI in *Enterococcus faecalis* and *Pseudomonas aeruginosa*. The third enoyl-reductase, FabL, is present along with FabI in *Bacillus subtilus*. Therefore, an inhibitor designed to selectively target a single bacterial enoyl-ACP reductase would be expected to have a narrow spectrum of antimicrobial activity, whereas an inhibitor targeting multiple enoyl ACP-reductases should have a broader spectrum of activity.

For all of the foregoing reasons, the polypeptides of the present invention are potentially valuable targets for therapeutics and diagnostics.

3. Nucleic Acids of the Invention

One aspect of the invention pertains to isolated nucleic acids of the invention. For example, the present invention contemplates an isolated nucleic acid comprising (a) the nucleotide sequence of SEQ ID NO: 1 or SEQ ID NO: 3, (b) a nucleotide sequence at least 80% identical to SEQ ID NO: 1 or SEQ ID NO: 3, (c) a nucleotide sequence that hybridizes under stringent conditions to SEQ ID NO: 1 or SEQ ID NO: 3, or (d) the complement of the nucleotide sequence of (a), (b) or (c). In certain embodiments, nucleic acids of the invention may be labeled, with for example, a radioactive, chemiluminescent or fluorescent label.

It may be that case that the nucleic acid sequence of SEQ ID NO: 3 differs from that of SEQ ID NO: 1 by one or more nucleic acid residues. SEQ ID NO: 3 is determined experimentally, and SEQ ID NO: 1 obtained as described in EXAMPLE 1. In such a case, the present invention contemplates the specific nucleic acid sequences of SEQ ID NO: 1 and SEQ ID NO: 3, and variants thereof, as well as any differences in the applicable amino acid sequences encoded thereby.

In another aspect, the present invention contemplates an isolated nucleic acid that specifically hybridizes under stringent conditions to at least ten nucleotides of SEQ ID NO: 1 or SEQ ID NO: 3, or the complement thereof, which nucleic acid can specifically detect or amplify SEQ ID NO: 1 or SEQ ID NO: 3, or the complement thereof. In yet another aspect, the present invention contemplates such an isolated nucleic acid comprising a nucleotide sequence encoding a fragment of SEQ ID NO: 2 or SEQ ID NO: 4 at least 8 residues in length. The present invention further contemplates a method of hybridizing an oligonucleotide with a nucleic acid of the invention comprising: (a) providing a single-stranded oligonucleotide at least eight nucleotides in length, the oligonucleotide being complementary to a portion of a nucleic acid of the invention; and (b) contacting the oligonucleotide with a sample comprising a nucleic acid of the acid under conditions that permit hybridization of the oligonucleotide with the nucleic acid of the invention.

Isolated nucleic acids which differ from the nucleic acids of the invention due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the polypeptides of the invention will exist. One skilled in the art will appreciate that these variations in one or more nucleotides (from less than 1% up to about 3 or 5% or possibly more of the nucleotides) of the nucleic acids encoding a particular protein of the invention may exist among a given species due to natural allelic variation. Any and all such nucleotide variations and resulting amino acid polymorphisms are within the scope of this invention.

Bias in codon choice within genes in a single species appears related to the level of expression of the protein encoded by that gene. Accordingly, the invention encompasses nucleic acid sequences which have been optimized for improved expression in a host cell by altering the frequency of codon usage in the nucleic acid sequence to approach the frequency of preferred codon usage of the host cell. Due to codon degeneracy, it is possible to optimize the nucleotide sequence without affecting the amino acid sequence of an encoded polypeptide. Accordingly, the instant invention relates to any nucleotide sequence that encodes all or a substantial portion of the amino acid sequence set forth in SEQ ID NO: 2, SEQ ID NO: 4 or other polypeptides of the invention.

The present invention pertains to nucleic acids encoding proteins derived from S. aureus and which have amino acid sequences evolutionarily related to a polypeptide of the invention, wherein "evolutionarily related to", refers to proteins having different amino acid sequences which have arisen naturally (e.g. by allelic variance or by differential splicing), as well as mutational variants of the proteins of the invention which are derived, for example, by combinatorial mutagenesis.

Fragments of the polynucleotides of the invention encoding a biologically active portion of the subject polypeptides are also within the scope of the invention. As used herein, a fragment of a nucleic acid of the invention encoding an active portion of a polypeptide of the invention refers to a nucleotide sequence having fewer nucleotides than the nucleotide sequence encoding the full length amino acid sequence of a polypeptide of the invention, for example, SEQ ID NO: 2 or SEQ ID NO: 4, and which encodes a polypeptide which retains at least a portion of a biological activity of the full-length protein as defined herein, or alternatively, which is functional as a modulator of the biological activity of the full-length protein. For example, such fragments include a polypeptide containing a domain of the full-length protein from which the polypeptide is derived that mediates the interaction of the protein with another molecule (e.g., polypeptide, DNA, RNA, etc.). In another embodiment, the present invention contemplates an isolated nucleic acid that encodes a polypeptide having a biological activity of a protein having the amino acid sequence set forth in SEQ ID NO: 2 or SEQ ID NO: 4, or alternatively biological activity of enoyl-[acyl-carrier-protein] reductase (NADH).

Nucleic acids within the scope of the invention may also contain linker sequences, modified restriction endonuclease sites and other sequences useful for molecular cloning, expression or purification of such recombinant polypeptides.

A nucleic acid encoding a polypeptide of the invention may be obtained from mRNA or genomic DNA from any organism in accordance with protocols described herein, as well as those generally known to those skilled in the art. A cDNA encoding a polypeptide of the invention, for example, may be obtained by isolating total mRNA from an organism, e.g. a bacteria, virus, mammal, etc. Double stranded cDNAs may then be prepared from the total mRNA, and subsequently inserted into a suitable plasmid or bacteriophage vector using any one of a number of known techniques. A gene encoding a polypeptide of the invention may also be cloned using established polymerase chain reaction techniques in accordance with the nucleotide sequence information provided by the invention. In one aspect, the present invention contemplates a method for amplification of a nucleic acid of the invention, or a fragment thereof, comprising: (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample comprising a nucleic acid comprising the nucleic acid of the invention under conditions which permit amplification of the region located between the pair of oligonucleotides, thereby amplifying the nucleic acid.

Another aspect of the invention relates to the use of nucleic acids of the invention in "antisense therapy". As used herein, antisense therapy refers to administration or in situ generation of oligonucleotide probes or their derivatives which specifically hybridize or otherwise bind under cellular conditions with the cellular mRNA and/or genomic DNA encoding one of the polypeptides of the invention so as to inhibit expression of that polypeptide, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention may be delivered, for example, as an expression plasmid which, when transcribed in the cell, produces RNA which is complementary to at least a unique portion of the mRNA which encodes a polypeptide of the invention. Alternatively, the antisense construct may be an oligonucleotide probe which is generated ex vivo and which, when introduced into the cell causes inhibition of expression by hybridizing with the mRNA and/or genomic sequences encoding a polypeptide of the invention. Such oligonucleotide probes may be modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al., (1988) *Biotechniques* 6:958-976; and Stein et al., (1988) *Cancer Res* 48:2659-2668.

In a further aspect, the invention provides double stranded small interfering RNAs (siRNAs), and methods for administering the same. siRNAs decrease or block gene expression. While not wishing to be bound by theory, it is generally thought that siRNAs inhibit gene expression by mediating sequence specific mRNA degradation. RNA interference (RNAi) is the process of sequence-specific, post-transcriptional gene silencing, particularly in animals and plants, initiated by double-stranded RNA (dsRNA) that is homologous in sequence to the silenced gene (Elbashir et al. Nature 2001;

411(6836): 494-8). Accordingly, it is understood that siRNAs and long dsRNAs having substantial sequence identity to all or a portion of SEQ ID NO: 1 or SEQ ID NO: 3 may be used to inhibit the expression of a nucleic acid of the invention, and particularly when the polynucleotide is expressed in a mammalian or plant cell.

The nucleic acids of the invention may be used as diagnostic reagents to detect the presence or absence of the target DNA or RNA sequences to which they specifically bind, such as for determining the level of expression of a nucleic acid of the invention. In one aspect, the present invention contemplates a method for detecting the presence of a nucleic acid of the invention or a portion thereof in a sample, the method comprising: (a) providing an oligonucleotide at least eight nucleotides in length, the oligonucleotide being complementary to a portion of a nucleic acid of the invention; (b) contacting the oligonucleotide with a sample comprising at least one nucleic acid under conditions that permit hybridization of the oligonucleotide with a nucleic acid comprising a nucleotide sequence complementary thereto; and (c) detecting hybridization of the oligonucleotide to a nucleic acid in the sample, thereby detecting the presence of a nucleic acid of the invention or a portion thereof in the sample. In another aspect, the present invention contemplates a method for detecting the presence of a nucleic acid of the invention or a portion thereof in a sample, the method comprising: (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample comprising at least one nucleic acid under hybridization conditions; (c) amplifying the nucleotide sequence between the two oligonucleotide primers; and (d) detecting the presence of the amplified sequence, thereby detecting the presence of a nucleic acid comprising the nucleic acid of the invention or a portion thereof in the sample.

In another aspect of the invention, the subject nucleic acid is provided in an expression vector comprising a nucleotide sequence encoding a polypeptide of the invention and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

The subject nucleic acids may be used to cause expression and over-expression of a polypeptide of the invention in cells propagated in culture, e.g. to produce proteins or polypeptides, including fusion proteins or polypeptides.

This invention pertains to a host cell transfected with a recombinant gene in order to express a polypeptide of the invention. The host cell may be any prokaryotic or eukaryotic cell. For example, a polypeptide of the invention may be expressed in bacterial cells, such as *E. coli*, insect cells (baculovirus), yeast, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the polypeptide will be known to those in the art.

The present invention further pertains to methods of producing the polypeptides of the invention. For example, a host cell transfected with an expression vector encoding a polypeptide of the invention may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the invention.

Thus, a nucleotide sequence encoding all or a selected portion of polypeptide of the invention, may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Expression vehicles for production of a recombinant protein include plasmids and other vectors. For instance, suitable vectors for the expression of a polypeptide of the invention include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989)

Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment containing the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Coding sequences for a polypeptide of interest may be incorporated as a part of a fusion gene including a nucleotide sequence encoding a different polypeptide. The present invention contemplates an isolated nucleic acid comprising a nucleic acid of the invention and at least one heterologous sequence encoding a heterologous peptide linked in frame to the nucleotide sequence of the nucleic acid of the invention so as to encode a fusion protein comprising the heterologous polypeptide. The heterologous polypeptide may be fused to (a) the C-terminus of the polypeptide encoded by the nucleic acid of the invention, (b) the N-terminus of the polypeptide, or (c) the C-terminus and the N-terminus of the polypeptide. In certain instances, the heterologous sequence encodes a polypeptide permitting the detection, isolation, solubilization and/or stabilization of the polypeptide to which it is fused. In still other embodiments, the heterologous sequence encodes a polypeptide selected from the group consisting of a polyhis tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

The present invention further contemplates a transgenic non-human animal having cells which harbor a transgene comprising a nucleic acid of the invention.

In other embodiments, the invention provides for nucleic acids of the invention immobilized onto a solid surface, including, plates, microtiter plates, slides, beads, particles, spheres, films, strands, precipitates, gels, sheets, tubing, containers, capillaries, pads, slices, etc. The nucleic acids of the invention may be immobilized onto a chip as part of an array.

The array may comprise one or more polynucleotides of the invention as described herein. In one embodiment, the chip comprises one or more polynucleotides of the invention as part of an array of *S. aureus* polynucleotide sequences.

In still other embodiments, the invention comprises the sequence of a nucleic acid of the invention in computer readable format. The invention also encompasses a database comprising the sequence of a nucleic acid of the invention.

4. Homology Searching of Nucleotide and Polypeptide Sequences

The nucleotide or amino acid sequences of the invention, including those set forth in the appended Figures, may be used as query sequences against databases such as GenBank, SwissProt, PDB, BLOCKS, and Pima II. These databases contain previously identified and annotated sequences that may be searched for regions of homology (similarity) using BLAST, which stands for Basic Local Alignment Search Tool (Altschul S F (1993) J Mol Evol 36:290-300; Altschul, S F et al (1990) J Mol Biol 215:403-10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992; Protein Engineering 5:35-51) may be used when dealing with primary sequence patterns and secondary structure gap penalties. In the usual course using BLAST, sequences have lengths of at least 49 nucleotides and no more than 12% uncalled bases (where N is recorded rather than A, C, G, or T).

The BLAST approach, as detailed in Karlin and Altschul (1993; Proc Nat Acad Sci 90:5873-7) searches matches between a query sequence and a database sequence, to evaluate the statistical significance of any matches found, and to report only those matches which satisfy the user-selected threshold of significance. The threshold is typically set at about 10-25 for nucleotides and about 3-15 for peptides.

5. Analysis of Protein Properties (a) Analysis of Proteins by Mass Spectrometry Typically, protein characterization by mass spectroscopy first requires protein isolation followed by either chemical or enzymatic digestion of the protein into smaller peptide fragments, whereupon the peptide fragments may be analyzed by mass spectrometry to obtain a peptide map. Mass spectrometry may also be used to identify post-translational modifications (e.g., phosphorylation, etc.) of a polypeptide.

Various mass spectrometers may be used within the present invention. Representative examples include: triple quadrupole mass spectrometers, magnetic sector instruments (magnetic tandem mass spectrometer, JEOL, Peabody, Mass.), ionspray mass spectrometers (Bruins et al., Anal Chem. 59:2642-2647, 1987), electrospray mass spectrometers (including tandem, nano- and nano-electrospray tandem) (Fenn et al., Science 246:64-71, 1989), laser desorption time-of-flight mass spectrometers (Karas and Hillenkamp, Anal. Chem. 60:2299-2301, 1988), and a Fourier Transform Ion Cyclotron Resonance Mass Spectrometer (Extrel Corp., Pittsburgh, Mass.).

MALDI ionization is a technique in which samples of interest, in this case peptides and proteins, are co-crystallized with an acidified matrix. The matrix is typically a small molecule that absorbs at a specific wavelength, generally in the ultraviolet (UV) range, and dissipates the absorbed energy thermally. Typically a pulsed laser beam is used to transfer energy rapidly (i.e., a few ns) to the matrix. This transfer of energy causes the matrix to rapidly dissociate from the MALDI plate surface and results in a plume of matrix and the co-crystallized analytes being transferred into the gas phase. MALDI is considered a "soft-ionization" method that typically results in singly-charged species in the gas phase, most often resulting from a protonation reaction with the matrix. MALDI may be coupled in-line with time of flight (TOF) mass spectrometers. TOF detectors are based on the principle that an analyte moves with a velocity proportional to its mass. Analytes of higher mass move slower than analytes of lower mass and thus reach the detector later than lighter analytes. The present invention contemplates a composition comprising a polypeptide of the invention and a matrix suitable for mass spectrometry. In certain instances, the matrix is a nicotinic acid derivative or a cinnamic acid derivative.

MALDI-TOF MS is easily performed with modern mass spectrometers. Typically the samples of interest, in this case peptides or proteins, are mixed with a matrix and spotted onto a polished stainless steel plate (MALDI plate). Commercially available MALDI plates can presently hold up to 1536 samples per plate. Once spotted with sample, the MALDI sample plate is then introduced into the vacuum chamber of a MALDI mass spectrometer. The pulsed laser is then activated and the mass to charge ratios of the analytes are measured utilizing a time of flight detector. A mass spectrum representing the mass to charge ratios of the peptides/proteins is generated.

As mentioned above, MALDI can be utilized to measure the mass to charge ratios of both proteins and peptides. In the case of proteins, a mixture of intact protein and matrix are co-crystallized on a MALDI target (Karas, M. and Hillenkamp, F. Anal. Chem. 1988, 60 (20) 2299-2301). The spectrum resulting from this analysis is employed to determine the molecular weight of a whole protein. This molecular weight can then be compared to the theoretical weight of the protein and utilized in characterizing the analyte of interest, such as whether or not the protein has undergone post-translational modifications (e.g., example phosphorylation).

In certain embodiments, MALDI mass spectrometry is used for determination of peptide maps of digested proteins. The peptide masses are measured accurately using a MALDI-TOF or a MALDI-Q-Star mass spectrometer, with detection precision down to the low ppm (parts per million) level. The ensemble of the peptide masses observed in a protein digest, such as a tryptic digest, may be used to search protein/DNA databases in a method called peptide mass fingerprinting. In this approach, protein entries in a database are ranked according to the number of experimental peptide masses that match the predicted trypsin digestion pattern. Commercially available software utilizes a search algorithm that provides a scoring scheme based on the size of the databases, the number of matching peptides, and the different peptides. Depending on the number of peptides observed, the accuracy of the measurement, and the size of the genome of the particular species, unambiguous protein identification may be obtained.

Statistical analysis may be performed upon each protein match to determine the validity of the match. Typical constraints include error tolerances within 0.1 Da for monoisotopic peptide masses, cysteines may be alkylated and searched as carboxyamidomethyl modifications, 0 or 1 missed enzyme cleavages, and no methionine oxidations allowed. Identified proteins may be stored automatically in a relational database with software links to SDS-PAGE images and ligand sequences. Often even a partial peptide map is specific enough for identification of the protein. If no protein match is found, a more error-tolerant search can be used, for example using fewer peptides or allowing a larger margin error with respect to mass accuracy.

Other mass spectroscopy methods such as tandem mass spectrometry or post source decay may be used to obtain sequence information about proteins that cannot be identified by peptide mass mapping, or to confirm the identity of proteins that are tentatively identified by an error-tolerant peptide mass search described above. (Griffin et al, Rapid Commun. Mass. Spectrom. 1995, 9, 1546-51).

(b) Analysis of Proteins by Nuclear Magnetic Resonance (NMR)

NMR may be used to characterize the structure of a polypeptide in accordance with the methods of the invention. In particular, NMR can be used, for example, to determine the three dimensional structure, the conformational state, the aggregation level, the state of protein folding/unfolding or the dynamic properties of a polypeptide. For example, the present invention contemplates a method for determining three dimensional structure information of a polypeptide of the invention, the method comprising: (a) generating a purified isotopically labeled polypeptide of the invention; and (b) subjecting the polypeptide to NMR spectroscopic analysis, thereby determining information about its three dimensional structure.

Interaction between a polypeptide and another molecule can also be monitored using NMR. Thus, the invention encompasses methods for detecting, designing and characterizing interactions between a polypeptide and another molecule, including polypeptides, nucleic acids and small molecules, utilizing NMR techniques. For example, the present invention contemplates a method for determining three dimensional structure information of a polypeptide of the invention, or a fragment thereof, while the polypeptide is complexed with another molecule, the method comprising: (a) generating a purified isotopically labeled polypeptide of the invention, or a fragment thereof; (b) forming a complex between the polypeptide and the other molecule; and (c) subjecting the complex to NMR spectroscopic analysis, thereby determining information about the three dimensional structure of the polypeptide. In another aspect, the present invention contemplates a method for identifying compounds that bind to a polypeptide of the invention, or a fragment thereof, the method comprising: (a) generating a first NMR spectrum of an isotopically labeled polypeptide of the invention, or a fragment thereof; (b) exposing the polypeptide to one or more chemical compounds; (c) generating a second NMR spectrum of the polypeptide which has been exposed to one or more chemical compounds; and (d) comparing the first and second spectra to determine differences between the first and the second spectra, wherein the differences are indicative of one or more compounds that have bound to the polypeptide.

Briefly, the NMR technique involves placing the material to be examined (usually in a suitable solvent) in a powerful magnetic field and irradiating it with radio frequency (rf) electromagnetic radiation. The nuclei of the various atoms will align themselves with the magnetic field until energized by the rf radiation. They then absorb this resonant energy and re-radiate it at a frequency dependent on i) the type of nucleus and ii) its atomic environment. Moreover, resonant energy may be passed from one nucleus to another, either through bonds or through three-dimensional space, thus giving information about the environment of a particular nucleus and nuclei in its vicinity.

However, it is important to recognize that not all nuclei are NMR active. Indeed, not all isotopes of the same element are active. For example, whereas "ordinary" hydrogen, $^1$H, is NMR active, heavy hydrogen (deuterium), $^2$H, is not active in the same way. Thus, any material that normally contains $^1$H hydrogen may be rendered "invisible" in the hydrogen NMR spectrum by replacing all or almost all the $^1$H hydrogens with $^2$H. It is for this reason that NMR spectroscopic analyses of water-soluble materials frequently are performed in $^2$H$_2$O (or deuterium) to eliminate the water signal.

Conversely, "ordinary" carbon, $^{12}$C, is NMR inactive whereas the stable isotope, $^{13}$C, present to about 1% of total carbon in nature, is active. Similarly, while "ordinary" nitrogen, $^{14}$N, is NMR active, it has undesirable properties for NMR and resonates at a different frequency from the stable isotope $^{15}$N, present to about 0.4% of total nitrogen in nature.

By labeling proteins with $^{15}$N and $^{15}$N/$^{13}$C, it is possible to conduct analytical NMR of macromolecules with weights of 15 kD and 40 kD, respectively. More recently, partial deuteration of the protein in addition to $^{13}$C- and $^{15}$N-labeling has increased the possible weight of proteins and protein complexes for NMR analysis still further, to approximately 60-70 kD. See Shan et al., J. Am. Chem. Soc., 118:6570-6579 (1996); L. E. Kay, Methods Enzymol., 339:174-203 (2001); and K. H. Gardner & L. E. Kay, Annu Rev Biophys Biomol Struct., 27:357-406 (1998); and references cited therein.

Isotopic substitution may be accomplished by growing a bacterium or yeast or other type of cultured cells, transformed by genetic engineering to produce the protein of choice, in a growth medium containing $^{13}$C-, $^{15}$N- and/or $^2$H-labeled substrates. In certain instances, bacterial growth media consists of $^{13}$C-labeled glucose and/or $^{15}$N-labeled ammonium salts dissolved in D$_2$O where necessary. Kay, L. et al., Science, 249:411 (1990) and references therein and Bax, A., J. Am. Chem. Soc., 115, 4369 (1993). More recently, isotopically labeled media especially adapted for the labeling of bacterially produced macromolecules have been described. See U.S. Pat. No. 5,324,658.

The goal of these methods has been to achieve universal and/or random isotopic enrichment of all of the amino acids of the protein. By contrast, other methods allow only certain residues to be relatively enriched in $^1$H, $^2$H, $^{13}$C and $^{15}$N. For example, Kay et al., J. Mol. Biol., 263, 627-636 (1996) and Kay et al., J. Am. Chem. Soc., 119, 7599-7600 (1997) have described methods whereby isoleucine, alanine, valine and leucine residues in a protein may be labeled with $^2$H, $^{13}$C and $^{15}$N, and may be specifically labeled with $^1$H at the terminal methyl position. In this way, study of the proton-proton interactions between some amino acids may be facilitated. Similarly, a cell-free system has been described by Yokoyama et al., J. Biomol. NMR, 6(2), 129-134 (1995), wherein a transcription-translation system derived from *E. coli* was used to express human Ha-Ras protein incorporating $^{15}$N into serine and/or aspartic acid.

Techniques for producing isotopically labeled proteins and macromolecules, such as glycoproteins, in mammalian or insect cells have been described. See U.S. Pat. Nos. 5,393,669 and 5,627,044; Weller, C. T., Biochem., 35, 8815-23 (1996) and Lustbader, J. W., J. Biomol. NMR, 7, 295-304 (1996). Other methods for producing polypeptides and other molecules with labels appropriate for NMR are known in the art.

The present invention contemplates using a variety of solvents which are appropriate for NMR. For $^1$H NMR, a deuterium lock solvent may be used. Exemplary deuterium lock solvents include acetone (CD$_3$COCD$_3$), chloroform (CDCl$_3$), dichloro methane (CD$_2$Cl$_2$), methylnitrile (CD$_3$CN), benzene (C$_6$D$_6$), water (D$_2$O), diethylether ((CD$_3$CD$_2$)$_2$O), dimethylether ((CD$_3$)$_2$O), N,N-dimethylformamide ((CD$_3$)$_2$NCDO), dimethyl sulfoxide (CD$_3$SOCD$_3$), ethanol (CD$_3$CD$_2$OD), methanol (CD$_3$OD), tetrahydrofuran (C$_4$D$_8$O), toluene (C$_6$D$_5$CD$_3$), pyridine (C$_5$D$_5$N) and cyclohexane (C$_6$H$_{12}$). For example, the present invention contemplates a composition comprising a polypeptide of the invention and a deuterium lock solvent.

The 2-dimensional $^1$H-$^{15}$N HSQC (Heteronuclear Single Quantum Correlation) spectrum provides a diagnostic fingerprint of conformational state, aggregation level, state of protein folding, and dynamic properties of a polypeptide (Yee et al, PNAS 99, 1825-30 (2002)). Polypeptides in aqueous solution usually populate an ensemble of 3-dimensional structures which can be determined by NMR. When the polypeptide is a stable globular protein or domain of a protein, then the ensemble of solution structures is one of very closely related conformations. In this case, one peak is expected for each non-proline residue with a dispersion of resonance frequencies with roughly equal intensity. Additional pairs of peaks from side-chain NH$_2$ groups are also often observed, and correspond to the approximate number of Gln and Asn residues in the protein. This type of HSQC spectra usually indicates that the protein is amenable to structure determination by NMR methods.

If the HSQC spectrum shows well-dispersed peaks but there are either too few or too many in number, and/or the peak intensities differ throughout the spectrum, then the protein likely does not exist in a single globular conformation. Such spectral features are indicative of conformational heterogeneity with slow or nonexistent inter-conversion between states (too many peaks) or the presence of dynamic processes on an intermediate timescale that can broaden and obscure the NMR signals. Proteins with this type of spectrum can sometimes be stabilized into a single conformation by changing either the protein construct, the solution conditions, temperature or by binding of another molecule.

The $^1$H-$^{15}$N HSQC can also indicate whether a protein has formed large nonspecific aggregates or has dynamic properties. Alternatively, proteins that are largely unfolded, e.g., having very little regular secondary structure, result in $^1$H-$^{15}$N HSQC spectra in which the peaks are all very narrow and intense, but have very little spectral dispersion in the $^{15}$N-dimension. This reflects the fact that many or most of the amide groups of amino acids in unfolded polypeptides are solvent exposed and experience similar chemical environments resulting in similar $^1$H chemical shifts.

The use of the $^1$H-$^{15}$N HSQC, can thus allow the rapid characterization of the conformational state, aggregation level, state of protein folding, and dynamic properties of a polypeptide. Additionally, other 2D spectra such as $^1$H-$^{13}$C HSQC, or HNCO spectra can also be used in a similar manner. Further use of the $^1$H-$^{15}$N HSQC combined with relaxation measurements can reveal the molecular rotational correlation time and dynamic properties of polypeptides. The rotational correlation time is proportional to size of the protein and therefore can reveal if it forms specific homo-oligomers such as homodimers, homotetramers, etc.

The structure of stable globular proteins can be determined through a series of well-described procedures. For a general review of structure determination of globular proteins in solution by NMR spectroscopy, see Wüthrich, Science 243: 45-50 (1989). See also, Billeter et al., J. Mol. Biol. 155: 321-346 (1982). Current methods for structure determination usually require the complete or nearly complete sequence-specific assignment of $^1$H-resonance frequencies of the protein and subsequent identification of approximate inter-hydrogen distances (from nuclear Overhauser effect (NOE) spectra) for use in restrained molecular dynamics calculations of the protein conformation. One approach for the analysis of NMR resonance assignments was first outlined by Wüthrich, Wagner and co-workers (Wüthrich, "NMR or proteins and nucleic acids" Wiley, New York, N.Y. (1986); Wüthrich, Science 243: 45-50 (1989); Billeter et al., J. Mol. Biol. 155: 321-346 (1982)). Newer methods for determining the structures of globular proteins include the use of residual dipolar coupling restraints (Tian et al., J Am Chem Soc. 2001 Nov. 28; 123 (47):11791-6; Bax et al, Methods Enzymol. 2001; 339:127-74) and empirically derived conformational restraints (Zweckstetter & Bax, J Am Chem Soc. 2001 Sep. 26; 123 (38):9490-1). It has also been shown that it may be possible to determine structures of globular proteins using only un-assigned NOE measurements. NMR may also be used to determine ensembles of many inter-converting, unfolded conformations (Choy and Forman-Kay, J Mol Biol. 2001 May 18; 308(5):1011-32).

NMR analysis of a polypeptide in the presence and absence of a test compound (e.g., a polypeptide, nucleic acid or small molecule) may be used to characterize interactions between a polypeptide and another molecule. Because the $^1$H-$^{15}$N HSQC spectrum and other simple 2D NMR experiments can be obtained very quickly (on the order of minutes depending on protein concentration and NMR instrumentation), they are very useful for rapidly testing whether a polypeptide is able to bind to another molecule. Changes in the resonance frequency (in one or both dimensions) of one or more peaks in the HSQC spectrum indicate an interaction with another molecule. Often only a subset of the peaks will have changes in resonance frequency upon binding to anther molecule, allowing one to map onto the structure those residues directly involved in the interaction or involved in conformational changes as a result of the interaction. If the interacting molecule is relatively large (protein or nucleic acid) the peak widths will also broaden due to the increased rotational correlation time of the complex. In some cases the peaks involved in the interaction may actually disappear from the NMR spectrum if the interacting molecule is in intermediate exchange on the NMR timescale (i.e., exchanging on and off the polypeptide at a frequency that is similar to the resonance frequency of the monitored nuclei).

To facilitate the acquisition of NMR data on a large number of compounds (e.g., a library of synthetic or naturally-occurring small organic compounds), a sample changer may be employed. Using the sample changer, a larger number of samples, numbering 60 or more, may be run unattended. To facilitate processing of the NMR data, computer programs are used to transfer and automatically process the multiple one-dimensional NMR data.

In one embodiment, the invention provides a screening method for identifying small molecules capable of interacting with a polypeptide of the invention. In one example, the screening process begins with the generation or acquisition of either a T$_2$-filtered or a diffusion-filtered one-dimensional proton spectrum of the compound or mixture of compounds. Means for generating T$_2$-filtered or diffusion-filtered one-dimensional proton spectra are well known in the art (see, e.g., S. Meiboom and D. Gill, Rev. Sci. Instrum. 29:688 (1958), S. J. Gibbs and C. S. Johnson, Jr. J. Main. Reson. 93:395-402 (1991) and A. S. Altieri, et al. J. Am. Chem. Soc. 117: 7566-7567 (1995)).

Following acquisition of the first spectrum for the molecules, the $^{15}$N- or $^{13}$C-labeled polypeptide is exposed to one or more molecules. Where more than one test compound is to be tested simultaneously, it is preferred to use a library of compounds such as a plurality of small molecules. Such molecules are typically dissolved in perdeuterated dimethylsulfoxide. The compounds in the library may be purchased from vendors or created according to desired needs.

Individual compounds may be selected inter alia on the basis of size and molecular diversity for maximizing the possibility of discovering compounds that interact with widely diverse binding sites of a polypeptide of the invention.

The NMR screening process of the present invention utilizes a range of test compound concentrations, e.g., from about 0.05 to about 1.0 mM. At those exemplary concentrations, compounds which are acidic or basic may significantly change the pH of buffered protein solutions. Chemical shifts are sensitive to pH changes as well as direct binding interactions, and false-positive chemical shift changes, which are not the result of test compound binding but of changes in pH, may therefore be observed. It may therefore be necessary to ensure that the pH of the buffered solution does not change upon addition of the test compound.

Following exposure of the test compounds to a polypeptide (e.g., the target molecule for the experiment) a second one-dimensional $T_2$- or diffusion-filtered spectrum is generated. For the $T_2$-filtered approach, that second spectrum is generated in the same manner as set forth above. The first and second spectra are then compared to determine whether there are any differences between the two spectra. Differences in the one-dimensional $T_2$-filtered spectra indicate that the compound is binding to, or otherwise interacting with, the target molecule. Those differences are determined using standard procedures well known in the art. For the diffusion-filtered method, the second spectrum is generated by looking at the spectral differences between low and high gradient strengths—thus selecting for those compounds whose diffusion rates are comparable to that observed in the absence of target molecule.

To discover additional molecules that bind to the protein, molecules are selected for testing based on the structure/activity relationships from the initial screen and/or structural information on the initial leads when bound to the protein. By way of example, the initial screening may result in the identification of compounds, all of which contain an aromatic ring. The second round of screening would then use other aromatic molecules as the test compounds.

In another embodiment, the methods of the invention utilize a process for detecting the binding of one ligand to a polypeptide in the presence of a second ligand. In accordance with this embodiment, a polypeptide is bound to the second ligand before exposing the polypeptide to the test compounds.

For more information on NMR methods encompassed by the present invention, see also: U.S. Pat. Nos. 5,668,734; 6,194,179; 6,162,627; 6,043,024; 5,817,474; 5,891,642; 5,989,827; 5,891,643; 6,077,682; WO 00/05414; WO 99/22019; Cavanagh, et al., Protein NMR Spectroscopy, Principles and Practice, 1996, Academic Press; Clore, et al., NMR of Proteins. In Topics in Molecular and Structural Biology, 1993, S. Neidle, Fuller, W., and Cohen, J. S., eds., Macmillan Press, Ltd., London; and Christendat et al., Nature Structural Biology 7: 903-909 (2000).

(c) Analysis of Proteins by X-Ray Crystallography (i) X-Ray Structure Determination Exemplary methods for obtaining the three dimensional structure of the crystalline form of a molecule or complex are described herein and, in view of this specification, variations on these methods will be apparent to those skilled in the art (see Ducruix and Geige 1992, IRL Press, Oxford, England).

A variety of methods involving x-ray crystallography are contemplated by the present invention. For example, the present invention contemplates producing a crystallized polypeptide of the invention, or a fragment thereof, by: (a) introducing into a host cell an expression vector comprising a nucleic acid encoding for a polypeptide of the invention, or a fragment thereof; (b) culturing the host cell in a cell culture medium to express the polypeptide or fragment; (c) isolating the polypeptide or fragment from the cell culture; and (d) crystallizing the polypeptide or fragment thereof. Alternatively, the present invention contemplates determining the three dimensional structure of a crystallized polypeptide of the invention, or a fragment thereof, by: (a) crystallizing a polypeptide of the invention, or a fragment thereof, such that the crystals will diffract x-rays to a resolution of 3.5 Å or better; and (b) analyzing the polypeptide or fragment by x-ray diffraction to determine the three-dimensional structure of the crystallized polypeptide.

X-ray crystallography techniques generally require that the protein molecules be available in the form of a crystal. Crystals may be grown from a solution containing a purified polypeptide of the invention, or a fragment thereof (e.g., a stable domain), by a variety of conventional processes. These processes include, for example, batch, liquid, bridge, dialysis, vapour diffusion (e.g., hanging drop or sitting drop methods). (See for example, McPherson, 1982 John Wiley, New York; McPherson, 1990, Eur. J. Biochem. 189: 1-23; Webber. 1991, Adv. Protein Chem. 41:1-36).

In certain embodiments, native crystals of the invention may be grown by adding precipitants to the concentrated solution of the polypeptide. The precipitants are added at a concentration just below that necessary to precipitate the protein. Water may be removed by controlled evaporation to produce precipitating conditions, which are maintained until crystal growth ceases.

The formation of crystals is dependent on a number of different parameters, including pH, temperature, protein concentration, the nature of the solvent and precipitant, as well as the presence of added ions or ligands to the protein. In addition, the sequence of the polypeptide being crystallized will have a significant affect on the success of obtaining crystals. Many routine crystallization experiments may be needed to screen all these parameters for the few combinations that might give crystal suitable for x-ray diffraction analysis (See, for example, Jancarik, J & Kim, S. H., J. Appl. Cryst. 1991 24: 409-411).

Crystallization robots may automate and speed up the work of reproducibly setting up large number of crystallization experiments. Once some suitable set of conditions for growing the crystal are found, variations of the condition may be systematically screened in order to find the set of conditions which allows the growth of sufficiently large, single, well ordered crystals. In certain instances, a polypeptide of the invention is co-crystallized with a compound that stabilizes the polypeptide.

A number of methods are available to produce suitable radiation for x-ray diffraction. For example, x-ray beams may be produced by synchrotron rings where electrons (or positrons) are accelerated through an electromagnetic field while traveling at close to the speed of light. Because the admitted wavelength may also be controlled, synchrotrons may be used as a tunable x-ray source (Hendrickson W A., Trends Biochem Sci 2000 December; 25(12):637-43). For less conventional Laue diffraction studies, polychromatic x-rays covering a broad wavelength window are used to observe many diffraction intensities simultaneously (Stoddard, B. L., Curr. Opin. Struct Biol 1998 Oct.; 8(5):612-8).

Neutrons may also be used for solving protein crystal structures (Gutberlet T, Heinemann U & Steiner M., Acta Crystallogr D 2001; 57: 349-54).

Before data collection commences, a protein crystal may be frozen to protect it from radiation damage. A number of different cryo-protectants may be used to assist in freezing the crystal, such as methyl pentanediol (MPD), isopropanol, ethylene glycol, glycerol, formate, citrate, mineral oil, or a low-molecular-weight polyethylene glycol (PEG). The present invention contemplates a composition comprising a polypeptide of the invention and a cryo-protectant. As an alternative to freezing the crystal, the crystal may also be used for diffraction experiments performed at temperatures above the freezing point of the solution. In these instances, the crystal may be protected from drying out by placing it in a narrow capillary of a suitable material (generally glass or quartz) with some of the crystal growth solution included in order to maintain vapour pressure.

X-ray diffraction results may be recorded by a number of ways know to one of skill in the art. Examples of area electronic detectors include charge coupled device detectors, multi-wire area detectors and phosphorimager detectors (Amemiya, Y, 1997. Methods in Enzymology, Vol. 276. Academic Press, San Diego, pp. 233-243; Westbrook, E. M., Naday, I. 1997. Methods in Enzymology, Vol. 276. Academic Press, San Diego, pp. 244-268; 1997. Kahn, R. & Fourme, R. Methods in Enzymology, Vol. 276. Academic Press, San Diego, pp. 268-286).

A suitable system for laboratory data collection might include a Bruker AXS Proteum R system, equipped with a copper rotating anode source, Confocal Max-Flux™ optics and a SMART 6000 charge coupled device detector. Collection of x-ray diffraction patterns are well documented by those skilled in the art (See, for example, Ducruix and Geige, 1992, IRL Press, Oxford, England).

The theory behind diffraction by a crystal upon exposure to x-rays is well known. Because phase information is not directly measured in the diffraction experiment, and is needed to reconstruct the electron density map, methods that can recover this missing information are required. One method of solving structures ab initio are the real/reciprocal space cycling techniques. Suitable real/reciprocal space cycling search programs include shake-and-bake (Weeks C M, DeTitta G T, Hauptman H A, Thuman P, Miller R Acta Crystallogr A 1994; V50: 210-20).

Other methods for deriving phases may also be needed. These techniques generally rely on the idea that if two or more measurements of the same reflection are made where strong, measurable, differences are attributable to the characteristics of a small subset of the atoms alone, then the contributions of other atoms can be, to a first approximation, ignored, and positions of these atoms may be determined from the difference in scattering by one of the above techniques. Knowing the position and scattering characteristics of those atoms, one may calculate what phase the overall scattering must have had to produce the observed differences.

One version of this technique is isomorphous replacement technique, which requires the introduction of new, well ordered, x-ray scatterers into the crystal. These additions are usually heavy metal atoms, (so that they make a significant difference in the diffraction pattern); and if the additions do not change the structure of the molecule or of the crystal cell, the resulting crystals should be isomorphous. Isomorphous replacement experiments are usually performed by diffusing different heavy-metal metals into the channels of a pre-existing protein crystal. Growing the crystal from protein that has been soaked in the heavy atom is also possible (Petsko, G. A., 1985. Methods in Enzymology, Vol. 114. Academic Press, Orlando, pp. 147-156). Alternatively, the heavy atom may also be reactive and attached covalently to exposed amino acid side chains (such as the sulfur atom of cysteine) or it may be associated through non-covalent interactions. It is sometimes possible to replace endogenous light metals in metallo-proteins with heavier ones, e.g., zinc by mercury, or calcium by samarium (Petsko, G. A., 1985. Methods in Enzymology, Vol. 114. Academic Press, Orlando, pp. 147-156). Exemplary sources for such heavy compounds include, without limitation, sodium bromide, sodium selenate, trimethyl lead acetate, mercuric chloride, methyl mercury acetate, platinum tetracyanide, platinum tetrachloride, nickel chloride, and europium chloride.

A second technique for generating differences in scattering involves the phenomenon of anomalous scattering. X-rays that cause the displacement of an electron in an inner shell to a higher shell are subsequently rescattered, but there is a time lag that shows up as a phase delay. This phase delay is observed as a (generally quite small) difference in intensity between reflections known as Friedel mates that would be identical if no anomalous scattering were present. A second effect related to this phenomenon is that differences in the intensity of scattering of a given atom will vary in a wavelength dependent manner, given rise to what are known as dispersive differences. In principle anomalous scattering occurs with all atoms, but the effect is strongest in heavy atoms, and may be maximized by using x-rays at a wavelength where the energy is equal to the difference in energy between shells. The technique therefore requires the incorporation of some heavy atom much as is needed for isomorphous replacement, although for anomalous scattering a wider variety of atoms are suitable, including lighter metal atoms (copper, zinc, iron) in metallo-proteins. One method for preparing a protein for anomalous scattering involves replacing the methionine residues in whole or in part with selenium containing seleno-methionine. Soaks with halide salts such as bromides and other non-reactive ions may also be effective (Dauter Z, Li M, Wlodawer A., Acta Crystallogr D 2001; 57: 239-49).

In another process, known as multiple anomalous scattering or MAD, two to four suitable wavelengths of data are collected. (Hendrickson, W. A. and Ogata, C. M. 1997 Methods in Enzymology 276, 494-523). Phasing by various combinations of single and multiple isomorphous and anomalous scattering are possible too. For example, SIRAS (single isomorphous replacement with anomalous scattering) utilizes both the isomorphous and anomalous differences for one derivative to derive phases. More traditionally, several different heavy atoms are soaked into different crystals to get sufficient phase information from isomorphous differences while ignoring anomalous scattering, in the technique known as multiple isomorphous replacement (MIR) (Petsko, G. A., 1985. Methods in Enzymology, Vol. 114. Academic Press, Orlando, pp. 147-156).

Additional restraints on the phases may be derived from density modification techniques. These techniques use either generally known features of electron density distribution or known facts about that particular crystal to improve the phases. For example, because protein regions of the crystal scatter more strongly than solvent regions, solvent flattening/flipping may be used to adjust phases to make solvent density a uniform flat value (Zhang, K. Y. J., Cowtan, K. and Main, P. Methods in Enzymology 277, 1997 Academic Press, Orlando pp 53-64). If more than one molecule of the protein is present in the asymmetric unit, the fact that the different molecules should be virtually identical may be exploited to further reduce phase error using non-crystallographic symmetry averaging (Villieux, F. M. D. and Read, R. J. Methods in Enzymology 277, 1997 Academic Press, Orlando pp 18-52). Suitable programs for performing these processes include DM and other programs of the CCP4 suite (Collaborative Computational Project, Number 4. 1994. Acta Cryst. D50, 760-763) and CNX.

The unit cell dimensions, symmetry, vector amplitude and derived phase information can be used in a Fourier transform function to calculate the electron density in the unit cell, i.e., to generate an experimental electron density map. This may be accomplished using programs of the CNX or CCP4 packages. The resolution is measured in Ångstrom (Å) units, and is closely related to how far apart two objects need to be before they can be reliably distinguished. The smaller this number is, the higher the resolution and therefore the greater the amount of detail that can be seen. Preferably, crystals of the invention diffract x-rays to a resolution of better than about 4.0, 3.5, 3.0, 2.5, 2.0, 1.5, 1.0, 0.5 Å or better.

As used herein, the term "modeling" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry and other structure-based constraint models.

Model building may be accomplished by either the crystallographer using a computer graphics program such as TURBO or O (Jones, T A. et al., Acta Crystallogr. A47, 100-119, 1991) or, under suitable circumstances, by using a fully automated model building program, such as wARP (Anastassis Perrakis, Richard Morris & Victor S. Lamzin; Nature Structural Biology, May 1999 Volume 6 Number 5 pp 458-463) or MAID (Levitt, D. G., Acta Crystallogr. D 2001 V57: 1013-9). This structure may be used to calculate model-derived diffraction amplitudes and phases. The model-derived and experimental diffraction amplitudes may be compared and the agreement between them can be described by a parameter referred to as R-factor. A high degree of correlation in the amplitudes corresponds to a low R-factor value, with 0.0 representing exact agreement and 0.59 representing a completely random structure. Because the R-factor may be lowered by introducing more free parameters into the model, an unbiased, cross-correlated version of the R-factor known as the R-free gives a more objective measure of model quality. For the calculation of this parameter a subset of reflections (generally around 10%) are set aside at the beginning of the refinement and not used as part of the refinement target. These reflections are then compared to those predicted by the model (Kleywegt G J, Brunger A T, Structure 1996 Aug. 15; 4(8): 897-904).

The model may be improved using computer programs that maximize the probability that the observed data was produced from the predicted model, while simultaneously optimizing the model geometry. For example, the CNX program may be used for model refinement, as can the XPLOR program (1992, Nature 355:472-475, G. N. Murshudov, A. A. Vagin and E. J. Dodson, (1997) Acta Cryst. D 53, 240-255). In order to maximize the convergence radius of refinement, simulated annealing refinement using torsion angle dynamics may be employed in order to reduce the degrees of freedom of motion of the model (Adams P D, Pannu N S, Read R J, Brunger A T., Proc Natl Acad Sci USA 1997 May 13; 94(10):5018-23). Where experimental phase information is available (e.g. where MAD data was collected) Hendrickson-Lattman phase probability targets may be employed. Isotropic or anisotropic domain, group or individual temperature factor refinement, may be used to model variance of the atomic position from its mean. Well defined peaks of electron density not attributable to protein atoms are generally modeled as water molecules. Water molecules may be found by manual inspection of electron density maps, or with automatic water picking routines. Additional small molecules, including ions, cofactors, buffer molecules or substrates may be included in the model if sufficiently unambiguous electron density is observed in a map.

In general, the R-free is rarely as low as 0.15 and may be as high as 0.35 or greater for a reasonably well-determined protein structure. The residual difference is a consequence of approximations in the model (inadequate modeling of residual structure in the solvent, modeling atoms as isotropic Gaussian spheres, assuming all molecules are identical rather than having a set of discrete conformers, etc.) and errors in the data (Lattman E E., Proteins 1996; 25: i-ii). In refined structures at high resolution, there are usually no major errors in the orientation of individual residues, and the estimated errors in atomic positions are usually around 0.1-0.2 up to 0.3 Å.

The three dimensional structure of a new crystal may be modeled using molecular replacement. The term "molecular replacement" refers to a method that involves generating a preliminary model of a molecule or complex whose structure coordinates are unknown, by orienting and positioning a molecule whose structure coordinates are known within the unit cell of the unknown crystal, so as best to account for the observed diffraction pattern of the unknown crystal. Phases may then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. Lattman, E., "Use of the Rotation and Translation Functions", in Methods in Enzymology, 115, pp. 55-77 (1985); M. G. Rossmann, ed., "The Molecular Replacement Method", Int. Sci. Rev. Ser., No. 13, Gordon & Breach, New York, (1972).

Commonly used computer software packages for molecular replacement are CNX, X-PLOR (Brunger 1992, Nature 355: 472-475), AMoRE (Navaza, 1994, Acta Crystallogr. A50:157-163), the CCP4 package, the MERLOT package (P. M. D. Fitzgerald, J. Appl. Cryst., Vol. 21, pp. 273-278, 1988) and XTALVIEW (McCree et al (1992) J. Mol. Graphics 10: 44-46). The quality of the model may be analyzed using a program such as PROCHECK or 3D-Profiler (Laskowski et al 1993 J. Appl. Cryst. 26:283-291; Luthy R. et al, Nature 356: 83-85, 1992; and Bowie, J. U. et al, Science 253: 164-170, 1991).

Homology modeling (also known as comparative modeling or knowledge-based modeling) methods may also be used to develop a three dimensional model from a polypeptide sequence based on the structures of known proteins. The method utilizes a computer model of a known protein, a computer representation of the amino acid sequence of the polypeptide with an unknown structure, and standard computer representations of the structures of amino acids. This method is well known to those skilled in the art (Greer, 1985, Science 228, 1055; Bundell et al 1988, Eur. J. Biochem. 172, 513; Knighton et al., 1992, Science 258:130-135, http://biochem.vt.edu/courses/-modeling/homology.htn). Computer programs that can be used in homology modeling are QUANTA and the Homology module in the Insight II modeling package distributed by Molecular Simulations Inc, or MODELLER (Rockefeller University, www.iucr.ac.uk/sinris-top/logical/prg-modeller.html).

Once a homology model has been generated it is analyzed to determine its correctness. A computer program available to assist in this analysis is the Protein Health module in QUANTA which provides a variety of tests. Other programs that provide structure analysis along with output include PROCHECK and 3D-Profiler (Luthy R. et al, Nature 356: 83-85, 1992; and Bowie, J. U. et al, Science 253: 164-170, 1991). Once any irregularities have been resolved, the entire structure may be further refined.

Other molecular modeling techniques may also be employed in accordance with this invention. See, e.g., Cohen, N. C. et al, J. Med. Chem., 33, pp. 883-894 (1990). See also, Navix, M. A. and M. A. Marko, Current Opinions in Structural Biology, 2, pp. 202-210 (1992).

Under suitable circumstances, the entire process of solving a crystal structure may be accomplished in an automated fashion by a system such as ELVES (http://ucxray.berkeley.edu/~jamesh/elves/index.html) with little or no user intervention.

(ii) X-Ray Structure

The present invention provides methods for determining some or all of the structural coordinates for amino acids of a polypeptide of the invention, or a complex thereof.

In another aspect, the present invention provides methods for identifying a druggable region of a polypeptide of the invention. For example, one such method includes: (a) obtaining crystals of a polypeptide of the invention or a fragment thereof such that the three dimensional structure of the crystallized protein can be determined to a resolution of 3.5 Å or better; (b) determining the three dimensional structure of the crystallized polypeptide or fragment using x-ray diffraction; and (c) identifying a druggable region of a polypeptide of the invention based on the three-dimensional structure of the polypeptide or fragment.

A three dimensional structure of a molecule or complex may be described by the set of atoms that best predict the observed diffraction data (that is, which possesses a minimal R value). Files may be created for the structure that defines each atom by its chemical identity, spatial coordinates in three dimensions, root mean squared deviation from the mean observed position and fractional occupancy of the observed position.

Those of skill in the art understand that a set of structure coordinates for an protein, complex or a portion thereof, is a relative set of points that define a shape in three dimensions. Thus, it is possible that an entirely different set of coordinates could define a similar or identical shape. Moreover, slight variations in the individual coordinates may have little affect on overall shape. Such variations in coordinates may be generated because of mathematical manipulations of the structure coordinates. For example, structure coordinates could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little affect on overall shape. If such variations are within an acceptable standard error as compared to the original coordinates, the resulting three-dimensional shape is considered to be structurally equivalent. It should be noted that slight variations in individual structure coordinates of a polypeptide of the invention or a complex thereof would not be expected to significantly alter the nature of modulators that could associate with a druggable region thereof. Thus, for example, a modulator that bound to the active site of a polypeptide of the invention would also be expected to bind to or interfere with another active site whose structure coordinates define a shape that falls within the acceptable error.

A crystal structure of the present invention may be used to make a structural or computer model of the polypeptide, complex or portion thereof. A model may represent the secondary, tertiary and/or quaternary structure of the polypeptide, complex or portion. The configurations of points in space derived from structure coordinates according to the invention can be visualized as, for example, a holographic image, a stereodiagram, a model or a computer-displayed image, and the invention thus includes such images, diagrams or models.

(iii) Structural Equivalents

Various computational analyses can be used to determine whether a molecule or the active site portion thereof is structurally equivalent with respect to its three-dimensional structure, to all or part of a structure of a polypeptide of the invention or a portion thereof.

For the purpose of this invention, any molecule or complex or portion thereof, that has a root mean square deviation of conserved residue backbone atoms (N, Cα, C, O) of less than about 1.75 Å, when superimposed on the relevant backbone atoms described by the reference structure coordinates of a polypeptide of the invention, is considered "structurally equivalent" to the reference molecule. That is to say, the crystal structures of those portions of the two molecules are substantially identical, within acceptable error. Alternatively, the root mean square deviation may be is less than about 1.50, 1.40, 1.25, 1.0, 0.75, 0.5 or 0.35 Å.

The term "root mean square deviation" is understood in the art and means the square root of the arithmetic mean of the squares of the deviations. It is a way to express the deviation or variation from a trend or object.

In another aspect, the present invention provides a scalable three-dimensional configuration of points, at least a portion of said points, and preferably all of said points, derived from structural coordinates of at least a portion of a polypeptide of the invention and having a root mean square deviation from the structure coordinates of the polypeptide of the invention of less than 1.50, 1.40, 1.25, 1.0, 0.75, 0.5 or 0.35 Å. In certain embodiments, the portion of a polypeptide of the invention is 25%, 33%, 50%, 66%, 75%, 85%, 90% or 95% or more of the amino acid residues contained in the polypeptide.

In another aspect, the present invention provides a molecule or complex including a druggable region of a polypeptide of the invention, the druggable region being defined by a set of points having a root mean square deviation of less than about 1.75 Å from the structural coordinates for points representing (a) the backbone atoms of the amino acids contained in a druggable region of a polypeptide of the invention, (b) the side chain atoms (and optionally the Cα atoms) of the amino acids contained in such druggable region, or (c) all the atoms of the amino acids contained in such druggable region. In certain embodiments, only a portion of the amino acids of a druggable region may be included in the set of points, such as 25%, 33%, 50%, 66%, 75%, 85%, 90% or 95% or more of the amino acid residues contained in the druggable region. In certain embodiments, the root mean square deviation may be less than 1.50, 1.40, 1.25, 1.0, 0.75, 0.5, or 0.35 Å. In still other embodiments, instead of a druggable region, a stable domain, fragment or structural motif is used in place of a druggable region.

(iv) Machine Displays and Machine Readable Storage Media

The invention provides a machine-readable storage medium including a data storage material encoded with machine readable data which, when using a machine programmed with instructions for using said data, displays a graphical three-dimensional representation of any of the molecules or complexes, or portions thereof, of this invention. In another embodiment, the graphical three-dimensional representation of such molecule, complex or portion thereof includes the root mean square deviation of certain atoms of such molecule by a specified amount, such as the backbone atoms by less than 0.8 Å. In another embodiment, a structural equivalent of such molecule, complex, or portion thereof, may be displayed. In another embodiment, the portion may include a druggable region of the polypeptide of the invention.

According to one embodiment, the invention provides a computer for determining at least a portion of the structure coordinates corresponding to x-ray diffraction data obtained from a molecule or complex, wherein said computer includes: (a) a machine-readable data storage medium comprising a data storage material encoded with machine-readable data, wherein said data comprises at least a portion of the structural coordinates of a polypeptide of the invention; (b) a machine-readable data storage medium comprising a data storage material encoded with machine-readable data, wherein said data comprises x-ray diffraction data from said molecule or complex; (c) a working memory for storing instructions for processing said machine-readable data of (a) and (b); (d) a central-processing unit coupled to said working memory and to said machine-readable data storage medium of (a) and (b) for performing a Fourier transform of the machine readable data of (a) and for processing said machine readable data of (b) into structure coordinates; and (e) a display coupled to said central-processing unit for displaying said structure coordinates of said molecule or complex. In certain embodiments, the structural coordinates displayed are structurally equivalent to the structural coordinates of a polypeptide of the invention.

In an alternative embodiment, the machine-readable data storage medium includes a data storage material encoded with a first set of machine readable data which includes the Fourier transform of the structure coordinates of a polypeptide of the invention or a portion thereof, and which, when using a machine programmed with instructions for using said data, can be combined with a second set of machine readable data including the x-ray diffraction pattern of a molecule or complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

In one embodiment, the present invention contemplates a computer readable storage medium comprising structural data, wherein the data include the identity and three-dimensional coordinates of a polypeptide of the invention or portion thereof. In another aspect, the present invention contemplates a database comprising the identity and three-dimensional coordinates of a polypeptide of the invention or a portion thereof. Alternatively, the present invention contemplates a database comprising a portion or all of the atomic coordinates of a polypeptide of the invention or portion thereof.

(v) Structurally Similar Molecules and Complexes

Structural coordinates for a polypeptide of the invention can be used to aid in obtaining structural information about another molecule or complex. This method of the invention allows determination of at least a portion of the three-dimensional structure of molecules or molecular complexes which contain one or more structural features that are similar to structural features of a polypeptide of the invention. Similar structural features can include, for example, regions of amino acid identity, conserved active site or binding site motifs, and similarly arranged secondary structural elements (e.g., (α helices and β sheets). Many of the methods described above for determining the structure of a polypeptide of the invention may be used for this purpose as well.

For the present invention, a "structural homolog" is a polypeptide that contains one or more amino acid substitutions, deletions, additions, or rearrangements with respect to the amino acid sequence of SEQ ID NO: 4 or other polypeptide of the invention, but that, when folded into its native conformation, exhibits or is reasonably expected to exhibit at least a portion of the tertiary (three-dimensional) structure of the polypeptide encoded by SEQ ID NO: 4 or such other polypeptide of the invention. For example, structurally homologous molecules can contain deletions or additions of one or more contiguous or noncontiguous amino acids, such as a loop or a domain. Structurally homologous molecules also include modified polypeptide molecules that have been chemically or enzymatically derivatized at one or more constituent amino acids, including side chain modifications, backbone modifications, and N- and C-terminal modifications including acetylation, hydroxylation, methylation, amidation, and the attachment of carbohydrate or lipid moieties, cofactors, and the like.

By using molecular replacement, all or part of the structure coordinates of a polypeptide of the invention can be used to determine the structure of a crystallized molecule or complex whose structure is unknown more quickly and efficiently than attempting to determine such information ab initio. For example, in one embodiment this invention provides a method of utilizing molecular replacement to obtain structural information about a molecule or complex whose structure is unknown including: (a) crystallizing the molecule or complex of unknown structure; (b) generating an x-ray diffraction pattern from said crystallized molecule or complex; and (c) applying at least a portion of the structure coordinates for a polypeptide of the invention to the x-ray diffraction pattern to generate a three-dimensional electron density map of the molecule or complex whose structure is unknown.

In another aspect, the present invention provides a method for generating a preliminary model of a molecule or complex whose structure coordinates are unknown, by orienting and positioning the relevant portion of a polypeptide of the invention within the unit cell of the crystal of the unknown molecule or complex so as best to account for the observed x-ray diffraction pattern of the crystal of the molecule or complex whose structure is unknown.

Structural information about a portion of any crystallized molecule or complex that is sufficiently structurally similar to a portion of a polypeptide of the invention may be resolved by this method. In addition to a molecule that shares one or more structural features with a polypeptide of the invention, a molecule that has similar bioactivity, such as the same catalytic activity, substrate specificity or ligand binding activity as a polypeptide of the invention, may also be sufficiently structurally similar to a polypeptide of the invention to permit use of the structure coordinates for a polypeptide of the invention to solve its crystal structure.

In another aspect, the method of molecular replacement is utilized to obtain structural information about a complex containing a polypeptide of the invention, such as a complex between a modulator and a polypeptide of the invention (or a domain, fragment, ortholog, homolog etc. thereof). In certain instances, the complex includes a polypeptide of the invention (or a domain, fragment, ortholog, homolog etc. thereof) co-complexed with a modulator. For example, in one embodiment, the present invention contemplates a method for making a crystallized complex comprising a polypeptide of the invention, or a fragment thereof, and a compound having a molecular weight of less than 5 kDa, the method comprising: (a) crystallizing a polypeptide of the invention such that the crystals will diffract x-rays to a resolution of 3.5 Å or better; and (b) soaking the crystal in a solution comprising the compound having a molecular weight of less than 5 kDa, thereby producing a crystallized complex comprising the polypeptide and the compound.

Using homology modeling, a computer model of a structural homolog or other polypeptide can be built or refined without crystallizing the molecule. For example, in another aspect, the present invention provides a computer-assisted method for homology modeling a structural homolog of a polypeptide of the invention including: aligning the amino acid sequence of a known or suspected structural homolog with the amino acid sequence of a polypeptide of the invention and incorporating the sequence of the homolog into a model of a polypeptide of the invention derived from atomic structure coordinates to yield a preliminary model of the homolog; subjecting the preliminary model to energy minimization to yield an energy minimized model; remodeling regions of the energy minimized model where stereochemistry restraints are violated to yield a final model of the homolog.

In another embodiment, the present invention contemplates a method for determining the crystal structure of a homolog of a polypeptide having SEQ ID NO: 2 or SEQ ID NO: 4, or equivalent thereof, the method comprising: (a) providing the three dimensional structure of a crystallized polypeptide having SEQ ID NO: 2 or SEQ ID NO: 4, or a fragment thereof; (b) obtaining crystals of a homologous polypeptide comprising an amino acid sequence that is at least 80% identical to the amino acid sequence set forth in SEQ ID NO: 2 or SEQ ID NO: 4 such that the three dimensional structure of the crystallized homologous polypeptide may be determined to a resolution of 3.5 Å or better; and (c) determining the three dimensional structure of the crystallized homologous polypeptide by x-ray crystallography based on the atomic coordinates of the three dimensional structure provided in step (a). In certain instances of the foregoing method, the atomic coordinates for the homologous polypeptide have a root mean square deviation from the backbone atoms of the polypeptide having SEQ ID NO: 2 or SEQ ID NO: 4, or a fragment thereof, of not more than 1.5 Å for all backbone atoms shared in common with the homologous polypeptide and the polypeptide having SEQ ID NO: 2 or SEQ ID NO: 4, or a fragment thereof.

(vi) NMR Analysis Using X-Ray Structural Data

In another aspect, the structural coordinates of a known crystal structure may be applied to nuclear magnetic resonance data to determine the three dimensional structures of polypeptides with uncharacterized or incompletely characterized structure. (See for example, Wuthrich, 1986, John Wiley and Sons, New York: 176-199; Pflugrath et al., 1986, J. Molecular Biology 189: 383-386; Kline et al., 1986 J. Molecular Biology 189:377-382). While the secondary structure of a polypeptide may often be determined by NMR data, the spatial connections between individual pieces of secondary structure are not as readily determined. The structural coordinates of a polypeptide defined by x-ray crystallography can guide the NMR spectroscopist to an understanding of the spatial interactions between secondary structural elements in a polypeptide of related structure. Information on spatial interactions between secondary structural elements can greatly simplify NOE data from two-dimensional NMR experiments. In addition, applying the structural coordinates after the determination of secondary structure by NMR techniques simplifies the assignment of NOE's relating to particular amino acids in the polypeptide sequence.

In an embodiment, the invention relates to a method of determining three dimensional structures of polypeptides with unknown structures, by applying the structural coordinates of a crystal of the present invention to nuclear magnetic resonance data of the unknown structure. This method comprises the steps of: (a) determining the secondary structure of an unknown structure using NMR data; and (b) simplifying the assignment of through-space interactions of amino acids. The term "through-space interactions" defines the orientation of the secondary structural elements in the three dimensional structure and the distances between amino acids from different portions of the amino acid sequence. The term "assignment" defines a method of analyzing NMR data and identifying which amino acids give rise to signals in the NMR spectrum.

For all of this section on x-ray crystallography, see also Brooks et al. (1983) *J Comput Chem* 4:187-217; Weiner et al (1981) *J. Comput. Chem.* 106: 765; Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488; Ryckaert et al. (1977) *J Comput Phys* 23:327; Van Gunsteren et al. (1977) *Mol Phys* 34:1311; Anderson (1983) *J Comput Phys* 52:24; *J. Mol. Biol.* 48: 442-453, 1970; Dayhoff et al., Meth. Enzymol. 91: 524-545, 1983; Henikoff and Henikoff, Proc. Nat. Acad. Sci. USA 89: 10915-10919, 1992; J. Mol. Biol. 233: 716-738, 1993; Methods in Enzymology, Volume 276, Macromolecular crystallography, Part A, ISBN 0-12-182177-3 and Volume 277, Macromolecular crystallography, Part B, ISBN 0-12-182178-1, Eds. Charles W. Carter, Jr. and Robert M. Sweet (1997), Academic Press, San Diego; Pfuetzner, et al., J. Biol. Chem. 272: 430-434 (1997).

6. Interacting Proteins

The present invention also provides methods for isolating specific protein interactors of a polypeptide of the invention, and complexes comprising a polypeptide of the invention and one or more interacting proteins. In one aspect, the present invention contemplates an isolated protein complex comprising a polypeptide of the invention and at least one protein that interacts with the polypeptide of the invention. The protein may be naturally-occurring. The interacting protein may be of *S. aureus* origin. Alternatively, the interacting protein may be of mammalian origin or human origin. Either the polypeptide of the invention or the interacting protein or both may be a fusion protein.

The present invention contemplates a method for identifying a protein capable of interacting with a polypeptide of the invention or a fragment thereof, the method comprising: (a) exposing a sample to a solid substrate coupled to a polypeptide of the invention or a fragment thereof under conditions which promote protein-protein interactions; (b) washing the solid substrate so as to remove any polypeptides interacting non-specifically with the polypeptide or fragment; (c) eluting the polypeptides which specifically interact with the polypeptide or fragment; and (d) identifying the interacting protein. The sample may be an extract of *S. aureus*, a mammalian cell extract, a human cell extract, a purified protein (or a fragment thereof), or a mixture of purified proteins (or fragments thereof). The interacting protein may be identified by a number of methods, including mass spectrometry or protein sequencing.

In another aspect, the present invention contemplates a method for identifying a protein capable of interacting with a polypeptide of present invention or a fragment thereof, the method comprising: (a) subjecting a sample to protein-affinity chromatography on multiple columns, the columns having a polypeptide of the invention or a fragment thereof coupled to the column matrix in varying concentrations, and eluting bound components of the extract from the columns; (b) separating the components to isolate a polypeptide capable of interacting with the polypeptide or fragment; and (c) analyzing the interacting protein by mass spectrometry to identify the interacting protein. In certain instances, the foregoing method will use polyacrylamide gel electrophoresis without SDS.

In another aspect, the present invention contemplates a method for identifying a protein capable of interacting with a polypeptide of the invention, the method comprising: (a) subjecting a cellular extract or extracellular fluid to protein-affinity chromatography on multiple columns, the columns having a polypeptide of the invention or a fragment thereof coupled to the column matrix in varying concentrations, and eluting bound components of the extract from the columns; (b) gel-separating the components to isolate an interacting protein; wherein the interacting protein is observed to vary in amount in direct relation to the concentration of coupled polypeptide or fragment; (c) digesting the interacting protein to give corresponding peptides; (d) analyzing the peptides by MALDI-TOF mass spectrometry or post source decay to determine the peptide masses; and (d) performing correlative database searches with the peptide, or peptide fragment, masses, whereby the interacting protein is identified based on the masses of the peptides or peptide fragments. The foregoing method may include the further step of including the identifies of any interacting proteins into a relational database.

In another aspect, the invention further contemplates a method for identifying modulators of a protein complex, the method comprising: (a) contacting a protein complex comprising a polypeptide of the invention and an interacting protein with one or more test compounds; and (b) determining the effect of the test compound on (i) the activity of the protein complex, (ii) the amount of the protein complex, (iii) the stability of the protein complex, (iv) the conformation of the protein complex, (v) the activity of at least one polypeptide included in the protein complex, (vi) the conformation of at least one polypeptide included in the protein complex, (vii) the intracellular localization of the protein complex or a component thereof, (viii) the transcription level of a gene dependent on the complex, and/or (ix) the level of second messenger levels in a cell; thereby identifying modulators of the protein complex. The foregoing method may be carried out in vitro or in vivo as appropriate.

Typically, it will be desirable to immobilize a polypeptide of the invention to facilitate separation of complexes comprising a polypeptide of the invention from uncomplexed forms of the interacting proteins, as well as to accommodate automation of the assay. The polypeptide of the invention, or ligand, may be immobilized onto a solid support (e.g., column matrix, microtiter plate, slide, etc.). In certain embodiments, the ligand may be purified. In certain instances, a fusion protein may be provided which adds a domain that permits the ligand to be bound to a support.

In various in vitro embodiments, the set of proteins engaged in a protein-protein interaction comprises a cell extract, a clarified cell extract, or a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-protein interaction are present in the mixture to at least about 50% purity relative to all other proteins in the mixture, and more preferably are present in greater, even 90-95%, purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-protein interaction.

Complex formation involving a polypeptide of the invention and another component polypeptide or a substrate polypeptide, may be detected by a variety of techniques. For instance, modulation in the formation of complexes can be quantitated using, for example, detectably labeled proteins (e.g. radiolabeled, fluorescently labeled, or enzymatically labeled), by immunoassay, or by chromatographic detection.

The present invention also provides assays for identifying molecules which are modulators of a protein-protein interaction involving a polypeptide of the invention, or are a modulator of the role of the complex comprising a polypeptide of the invention in the infectivity or pathogenicity of S. aureus. In one embodiment, the assay detects agents which inhibit formation or stabilization of a protein complex comprising a polypeptide of the invention and one or more additional proteins. In another embodiment, the assay detects agents which modulate the intrinsic biological activity of a protein complex comprising a polypeptide of the invention, such as an enzymatic activity, binding to other cellular components, cellular compartmentalization, signal transduction, and the like. Such modulators may be used, for example, in the treatment of S. aureus related diseases or disorders. In certain embodiments, the compound is a mechanism based inhibitor which chemically alters one member of a protein-protein interaction involving a polypeptide of the invention and which is a specific inhibitor of that member, e.g. has an inhibition constant about 10-fold, 100-fold, or 1000-fold different compared to homologous proteins.

In one embodiment, proteins that interact with a polypeptide of the invention may be isolated using immunoprecipitation. A polypeptide of the invention may be expressed in S. aureus, or in a heterologous system. The cells expressing a polypeptide of the invention are then lysed under conditions which maintain protein-protein interactions, and complexes comprising a polypeptide of the invention are isolated. For example, a polypeptide of the invention may be expressed in mammalian cells, including human cells, in order to identify mammalian proteins that interact with a polypeptide of the invention and therefore may play a role in S. aureus infectivity or proliferation. In one embodiment, a polypeptide of the invention is expressed in the cell type for which it is desirable to find interacting proteins. For example, a polypeptide of the invention may be expressed in S. aureus in order to find S. aureus derived interacting proteins.

In an alternative embodiment, a polypeptide of the invention is expressed and purified and then mixed with a potential interacting protein or mixture of proteins to identify complex formation. The potential interacting protein may be a single purified or semi-purified protein, or a mixture of proteins, including a mixture of purified or semi-purified proteins, a cell lysate, a clarified cell lysate, a semi-purified cell lysate, etc.

In certain embodiments, it may be desirable to use a tagged version of a polypeptide of the invention in order to facilitate isolation of complexes from the reaction mixture. Suitable tags for immunoprecipitation experiments include HA, myc, FLAG, HIS, GST, protein A, protein G, etc. Immunoprecipitation from a cell lysate or other protein mixture may be carried out using an antibody specific for a polypeptide of the invention or using an antibody which recognizes a tag to which a polypeptide of the invention is fused (e.g., anti-HA, anti-myc, anti-FLAG, etc.). Antibodies specific for a variety of tags are known to the skilled artisan and are commercially available from a number of sources. In the case where a polypeptide of the invention is fused to a His, GST, or protein A/G tag, immunoprecipitation may be carried out using the appropriate affinity resin (e.g., beads functionalized with Ni, glutathione, Fc region of IgG, etc.). Test compounds which modulate a protein-protein interaction involving a polypeptide of the invention may be identified by carrying out the immunoprecipitation reaction in the presence and absence of the test agent and comparing the level and/or activity of the protein complex between the two reactions.

In another embodiment, proteins that interact with a polypeptide of the invention may be identified using affinity chromatography. Some examples of such chromatography are described in U.S. Ser. No. 09/727,812, filed Nov. 30, 2000, and the PCT Application filed Nov. 30, 2001 and entitled "Methods for Systematic Identification of Protein-Protein Interactions and other Properties", which claims priority to such U.S. application.

In one aspect, for affinity chromatography using a solid support, a polypeptide of the invention or a fragment thereof may be attached by a variety of means known to those of skill in the art. For example, the polypeptide may be coupled directly (through a covalent linkage) to commercially available pre-activated resins as described in Formosa et al., Methods in Enzymology 1991, 208, 24-45; Sopta et al, J. Biol. Chem. 1985, 260, 10353-60; Archambault et al., Proc. Natl. Acad. Sci. USA 1997, 94, 14300-5. Alternatively, the polypeptide may be tethered to the solid support through high affinity binding interactions. If the polypeptide is expressed fused to a tag, such as GST, the fusion tag can be used to anchor the polypeptide to the matrix support, for example Sepharose beads containing immobilized glutathione. Solid supports that take advantage of these tags are commercially available.

In another aspect, the support to which a polypeptide may be immobilized is a soluble support, which may facilitate certain steps performed in the methods of the present invention. For example, the soluble support may be soluble in the conditions employed to create a binding interaction between a target and the polypeptide, and then used under conditions in which it is a solid for elution of the proteins or other biological materials that bind to a polypeptide.

The concentration of the coupled polypeptide may have an affect on the sensitivity of the method. In certain embodiments, to detect interactions most efficiently, the concentration of the polypeptide bound to the matrix should be at least 10-fold higher than the $K_d$ of the interaction. Thus, the concentration of the polypeptide bound to the matrix should be highest for the detection of the weakest protein-protein interactions. However, if the concentration of the immobilized polypeptide is not as high as may be ideal, it may still be possible to observe protein-protein interactions of interest by, for example, increasing the concentration of the polypeptide or other moiety that interacts with the coupled polypeptide. The level of detection will of course vary with each different polypeptide, interactor, conditions of the assay, etc. In certain instances, the interacting protein binds to the polypeptide with a $K_d$ of about $10^{-5}$ M to about $10^{-8}$ M or $10^{-10}$ M.

In another aspect, the coupling may be done at various ratios of the polypeptide to the resin. An upper limit of the protein:resin ratio may be determined by the isoelectric point and the ionic nature of the protein, although it may be possible to achieve higher polypeptide concentrations by use of various methods.

In certain embodiments, several concentrations of the polypeptide immobilized on a solid or soluble support may be used. One advantage of using multiple concentrations, although not a requirement, is that one may be able to obtain an estimate for the strength of the protein-protein interaction that is observed in the affinity chromatography experiment. Another advantage of using multiple concentrations is that a binding curve which has the proper shape may indicate that the interaction that is observed is biologically important rather than a spurious interaction with denatured protein.

In one example of such an embodiment, a series of columns may be prepared with varying concentrations of polypeptide (mg polypeptide/ml resin volume). The number of columns employed may be between 2 to 8, 10, 12, 15, 25 or more, each with a different concentration of attached polypeptide. Larger numbers of columns may be used if appropriate for the polypeptide being examined, and multiple columns may be used with the same concentration as any methods may require. In certain embodiments, 4 to 6 columns are prepared with varying concentrations of polypeptide. In another aspect of this embodiment, two control columns may be prepared: one that contains no polypeptide and a second that contains the highest concentration of polypeptide but is not treated with extract. After elution of the columns and separation of the eluent components (by one of the methods described below), it may be possible to distinguish the interacting proteins (if any) from the non-specific bound proteins as follows. The concentration of the interacting proteins, as determined by the intensity of the band on the gel, will increase proportionally to the increase in polypeptide concentration but will be missing from the second control column. This allows for the identification of unknown interacting proteins.

The method of the invention may be used for small-scale analysis. A variety of column sizes, types, and geometries may be used. In addition, other vessel shapes and sizes having a smaller scale than is usually found in laboratory experiments may be used as well, including a plurality of wells in a plate. For high throughput analysis, it is advantageous to use small volumes, from about 20, 30, 50, 80 or 100 µl. Larger or small volumes may be used, as necessary, and it may be possible to achieve high throughput analysis using them. The entire affinity chromatography procedure may be automated by assembling the micro-columns into an array (e.g. with 96 micro-column arrays).

A variety of materials may be used as the source of potential interacting proteins. In one embodiment, a cellular extract or extracellular fluid may be used. The choice of starting material for the extract may be based upon the cell or tissue type or type of fluid that would be expected to contain proteins that interact with the target protein. Micro-organisms or other organisms are grown in a medium that is appropriate for that organism and can be grown in specific conditions to promote the expression of proteins that may interact with the target protein. Exemplary starting material that may be used to make a suitable extract are: 1) one or more types of tissue derived from an animal, plant, or other multi-cellular organism, 2) cells grown in tissue culture that were derived from an animal or human, plant or other source, 3) micro-organisms grown in suspension or non-suspension cultures, 4) virus-infected cells, 5) purified organelles (including, but not restricted to nuclei, mitochondria, membranes, Golgi, endoplasmic reticulum, lysosomes, or peroxisomes) prepared by differential centrifugation or another procedure from animal, plant or other kinds of eukaryotic cells, 6) serum or other bodily fluids including, but not limited to, blood, urine, semen, synovial fluid, cerebrospinal fluid, amniotic fluid, lymphatic fluid or interstitial fluid. In other embodiments, a total cell extract may not be the optimal source of interacting proteins. For example, if the ligand is known to act in the nucleus, a nuclear extract can provide a 10-fold enrichment of proteins that are likely to interact with the ligand. In addition, proteins that are present in the extract in low concentrations may be enriched using another chromatographic method to fractionate the extract before screening various pools for an interacting protein.

Extracts are prepared by methods known to those of skill in the art. The extracts may be prepared at a low temperature (e.g., 4° C.) in order to retard denaturation or degradation of proteins in the extract. The pH of the extract may be adjusted to be appropriate for the body fluid or tissue, cellular, or organellar source that is used for the procedure (e.g. pH 7-8 for cytosolic extracts from mammals, but low pH for lysosomal extracts). The concentration of chaotropic or non-chaotropic salts in the extracting solution may be adjusted so as to extract the appropriate sets of proteins for the procedure. Glycerol may be added to the extract, as it aids in maintaining the stability of many proteins and also reduces background non-specific binding. Both the lysis buffer and column buffer may contain protease inhibitors to minimize proteolytic degradation of proteins in the extract and to protect the polypeptide. Appropriate co-factors that could potentially interact with the interacting proteins may be added to the extracting solution. One or more nucleases or another reagent may be added to the extract, if appropriate, to prevent protein-protein interactions that are mediated by nucleic acids. Appropriate detergents or other agents may be added to the solution, if desired, to extract membrane proteins from the cells or tissue. A reducing agent (e.g. dithiothreitol or 2-mercaptoethanol or glutathione or other agent) may be added. Trace metals or a chelating agent may be added, if desired, to the extracting solution.

Usually, the extract is centrifuged in a centrifuge or ultracentrifuge or filtered to provide a clarified supernatant solution. This supernatant solution may be dialyzed using dialysis tubing, or another kind of device that is standard in the art, against a solution that is similar to, but may not be identical with, the solution that was used to make the extract. The extract is clarified by centrifugation or filtration again immediately prior to its use in affinity chromatography.

In some cases, the crude lysate will contain small molecules that can interfere with the affinity chromatography. This can be remedied by precipitating proteins with ammonium sulfate, centrifugation of the precipitate, and re-suspending the proteins in the affinity column buffer followed by dialysis. An additional centrifugation of the sample may be needed to remove any particulate matter prior to application to the affinity columns.

The amount of cell extract applied to the column may be important for any embodiment. If too little extract is applied to the column and the interacting protein is present at low concentration, the level of interacting protein retained by the column may be difficult to detect. Conversely, if too much extract is applied to the column, protein may precipitate on the column or competition by abundant interacting proteins for the limited amount of protein ligand may result in a difficulty in detecting minor species.

The columns functionalized with a polypeptide of the invention are loaded with protein extract from an appropriate source that has been dialyzed against a buffer that is consistent with the nature of the expected interaction. The pH, salt concentrations and the presence or absence of reducing and chelating agents, trace metals, detergents, and co-factors may be adjusted according to the nature of the expected interaction. Most commonly, the pH and the ionic strength are chosen so as to be close to physiological for the source of the extract. The extract is most commonly loaded under gravity onto the columns at a flow rate of about 4-6 column volumes per hour, but this flow rate can be adjusted for particular circumstances in an automated procedure.

The volume of the extract that is loaded on the columns can be varied but is most commonly equivalent to about 5 to 10 column volumes. When large volumes of extract are loaded on the columns, there is often an improvement in the signal-to-noise ratio because more protein from the extract is available to bind to the protein ligand, whereas the background binding of proteins from the extract to the solid support saturates with low amounts of extract.

A control column may be included that contains the highest concentration of protein ligand, but buffer rather than extract is loaded onto this column. The elutions (eluates) from this column will contain polypeptide that failed to be attached to the column in a covalent manner, but no proteins that are derived from the extract.

The columns may be washed with a buffer appropriate to the nature of the interaction being analyzed, usually, but not necessarily, the same as the loading buffer. An elution buffer with an appropriate pH, glycerol, and the presence or absence of reducing agent, chelating agent, cofactors, and detergents are all important considerations. The columns may be washed with anywhere from about 5 to 20 column volumes of each wash buffer to eliminate unbound proteins from the natural extract. The flow rate of the wash is usually adjusted to about 4 to 6 column volumes per hour by using gravity or an automated procedure, but other flow rates are possible in specific circumstances.

In order to elute the proteins that have been retained by the column, the interactions between the extract proteins and the column ligand should be disrupted. This is performed by eluting the column with a solution of salt or detergent. Retention of activity by the eluted proteins may require the presence of glycerol and a buffer of appropriate pH, as well as proper choices of ionic strength and the presence or absence of appropriate reducing agent, chelating agent, trace metals, cofactors, detergents, chaotropic agents, and other reagents. If physical identification of the bound proteins is the objective, the elution may be performed sequentially, first with buffer of high ionic strength and then with buffer containing a protein denaturant, most commonly, but not restricted to sodium dodecyl sulfate (SDS), urea, or guanidine hydrochloride. In certain instances, the column is eluted with a protein denaturant, particularly SDS, for example as a 1% SDS solution. Using only the SDS wash, and omitting the salt wash, may result in SDS-gels that have higher resolution (sharper bands with less smearing). Also, using only the SDS wash results in half as many samples to analyze. The volume of the eluting solution may be varied but is normally about 2 to 4 column volumes. For 20 ml columns, the flow rate of the eluting procedures are most commonly about 4 to 6 column volumes per hour, under gravity, but can be varied in an automated procedure.

The proteins from the extract that were bound to and are eluted from the affinity columns may be most easily resolved for identification by an electrophoresis procedure, but this procedure may be modified, replaced by another suitable method, or omitted. Any of the denaturing or non-denaturing electrophoresis procedures that are standard in the art may be used for this purpose, including SDS-PAGE, gradient gels, capillary electrophoresis, and two-dimensional gels with iso-electric focusing in the first dimension and SDS-PAGE in the second. Typically, the individual components in the column eluent are separated by polyacrylamide gel electrophoresis.

After electrophoresis, protein bands or spots may be visualized using any number of methods know to those of skill in the art, including staining techniques such as Coomassie blue or silver staining, or some other agent that is standard in the art. Alternatively, autoradiography can be used for visualizing proteins isolated from organisms cultured on media containing a radioactive label, for example $^{35}SO_4^{2-}$ or $^{35}[S]$methionine, that is incorporated into the proteins. The use of radioactively labeled extract allows a distinction to be made between extract proteins that were retained by the column and proteolytic fragments of the ligand that may be released from the column.

Protein bands that are derived from the extract (i.e. it did not elute from the control column that was not loaded with protein from the extract) and bound to an experimental column that contained polypeptide covalently attached to the solid support, and did not bind to a control column that did not contain any polypeptide, may be excised from the stained electrophoretic gel and further characterized.

To identify the protein interactor by mass spectrometry, it may be desirable to reduce the disulfide bonds of the protein followed by alkylation of the free thiols prior to digestion of the protein with protease. The reduction may be performed by treatment of the gel slice with a reducing agent, for example with dithiothreitol, whereupon, the protein is alkylated by treating the gel slice with a suitable alkylating agent, for example iodoacetamide.

Prior to analysis by mass spectrometry, the protein may be chemically or enzymatically digested. The protein sample in the gel slice may be subjected to in-gel digestion. Shevchenko A. et al., Mass Spectrometric Sequencing of Proteins from Silver Stained Polyacrylamide Gels. Analytical Chemistry 1996, 58, 850-858. One method of digestion is by treatment with the enzyme trypsin. The resulting peptides are extracted from the gel slice into a buffer.

The peptide fragments may be purified, for example by use of chromatography. A solid support that differentially binds the peptides and not the other compounds derived from the gel slice, the protease reaction or the peptide extract may be used. The peptides may be eluted from the solid support into a small volume of a solution that is compatible with mass spectrometry (e.g. 50% acetonitrile/0.1% trifluoroacetic acid).

The preparation of a protein sample from a gel slice that is suitable for mass spectrometry may also be done by an automated procedure.

Peptide samples derived from gel slices may be analyzed by any one of a variety of techniques in mass spectrometry as further described above. This technique may be used to assign function to an unknown protein based upon the known function of the interacting protein in the same or a homologous/orthologous organism.

Eluates from the affinity chromatography columns may also be analyzed directly without resolution by electrophoretic methods, by proteolytic digestion with a protease in solution, followed by applying the proteolytic digestion products to a reverse phase column and eluting the peptides from the column.

In yet another embodiment, proteins that interact with a polypeptide of the invention may be identified using an interaction trap assay (see also, U.S. Pat. No. 5,283,317; Zervos et al. (1993) *Cell* 72:223-232; Madura et al. (1993) *J Biol Chem* 268:12046-12054; Bartel et al. (1993) *Biotechniques* 14:920-924; and Iwabuchi et al. (1993) *Oncogene* 8:1693-1696).

In another embodiment, a method of the present invention makes use of chimeric genes which express hybrid proteins. To illustrate, a first hybrid gene comprises the coding sequence for a DNA-binding domain of a transcriptional activator fused in frame to the coding sequence for a "bait" protein, e.g., a polypeptide of the invention of sufficient length to bind to a potential interacting protein. The second hybrid protein encodes a transcriptional activation domain fused in frame to a gene encoding a "fish" protein, e.g., a potential interacting protein of sufficient length to interact with a polypeptide of the invention portion of the bait fusion protein. If the bait and fish proteins are able to interact, e.g., form a protein-protein interaction, they bring into close proximity the two domains of the transcriptional activator. This proximity causes transcription of a reporter gene which is operably linked to a transcriptional regulatory site responsive to the transcriptional activator, and expression of the reporter gene can be detected and used to score for the interaction of the bait and fish proteins.

In accordance with the present invention, the method includes providing a host cell, typically a yeast cell, e.g., *Kluyverei lactis, Schizosaccharomyces pombe, Ustilago maydis, Saccharomyces cerevisiae, Neurospora crassa, Aspergillus niger, Aspergillus nidulans, Pichia pastoris, Candida tropicalis*, and *Hansenula polymorpha*, though most preferably *S cerevisiae* or *S. pombe*. The host cell contains a reporter gene having a binding site for the DNA-binding domain of a transcriptional activator used in the bait protein, such that the reporter gene expresses a detectable gene product when the gene is transcriptionally activated. The first chimeric gene may be present in a chromosome of the host cell, or as part of an expression vector.

The host cell also contains a first chimeric gene which is capable of being expressed in the host cell. The gene encodes a chimeric protein, which comprises (a) a DNA-binding domain that recognizes the responsive element on the reporter gene in the host cell, and (b) a bait protein (e.g., a polypeptide of the invention).

A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DNA-binding domain of the first hybrid protein and the transcriptional activation domain of the second hybrid protein may be derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, a polypeptide of the invention-mediated interaction, if any, between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a protein complex containing a polypeptide of the invention results in a detectable signal produced by the expression of the reporter gene.

In still further embodiments, the protein-protein interaction of interest is generated in whole cells, taking advantage of cell culture techniques to support the subject assay. For example, the protein-protein interaction of interest can be constituted in a prokaryotic or eukaryotic cell culture system. Advantages to generating the protein complex in an intact cell includes the ability to screen for inhibitors of the level or activity of the complex which are functional in an environment more closely approximating that which therapeutic use of the inhibitor would require, including the ability of the agent to gain entry into the cell. Furthermore, certain of the in vivo embodiments of the assay are amenable to high throughput analysis of candidate agents.

The components of the protein complex comprising a polypeptide of the invention can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

The interaction trap assay of the invention may also be used to identify test agents capable of modulating formation of a complex comprising a polypeptide of the invention. In general, the amount of expression from the reporter gene in the presence of the test compound is compared to the amount of expression in the same cell in the absence of the test compound. Alternatively, the amount of expression from the reporter gene in the presence of the test compound may be compared with the amount of transcription in a substantially identical cell that lacks a component of the protein-protein interaction involving a polypeptide of the invention.

7. Antibodies

Another aspect of the invention pertains to antibodies specifically reactive with a polypeptide of the invention. For example, by using peptides based on a polypeptide of the invention, e.g., having an amino acid sequence of SEQ ID NO: 2 or SEQ ID NO: 4 or an immunogenic fragment thereof, antisera or monoclonal antibodies may be made using standard methods. An exemplary immunogenic fragment may contain eight, ten or more consecutive amino acid residues of SEQ ID NO: 2 or SEQ ID NO: 4. Certain fragments that are predicted to be immunogenic for the subject amino acid sequences (predicted) are set forth in Table 2 contained in FIG. 7

The term "antibody" as used herein is intended to include fragments thereof which are also specifically reactive with a polypeptide of the invention. Antibodies can be fragmented using conventional techniques and the fragments screened for utility in the same manner as is suitable for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules, as well as single chain (scFv) antibodies. Also within the scope of the invention are trimeric antibodies, humanized antibodies, human antibodies, and single chain antibodies. All of these modified forms of antibodies as well as fragments of antibodies are intended to be included in the term "antibody".

In one aspect, the present invention contemplates a purified antibody that binds specifically to a polypeptide of the invention and which does not substantially cross-react with a protein which is less than about 80%, or less than about 90%, identical to SEQ ID NO: 2 or SEQ ID NO: 4. In another aspect, the present invention contemplates an array comprising a substrate having a plurality of address, wherein at least one of the addresses has disposed thereon a purified antibody that binds specifically to a polypeptide of the invention.

Antibodies may be elicited by methods known in the art. For example, a mammal such as a mouse, a hamster or rabbit may be immunized with an immunogenic form of a polypeptide of the invention (e.g., an antigenic fragment which is capable of eliciting an antibody response). Alternatively, immunization may occur by using a nucleic acid of the acid, which presumably in vivo expresses the polypeptide of the invention giving rise to the immunogenic response observed. Techniques for conferring immunogenicity on a protein or peptide include conjugation to carriers or other techniques well known in the art. For instance, a peptidyl portion of a polypeptide of the invention may be administered in the presence of adjuvant. The progress of immunization may be monitored by detection of antibody titers in plasma or serum. Standard ELISA or other immunoassays may be used with the immunogen as antigen to assess the levels of antibodies.

Following immunization, antisera reactive with a polypeptide of the invention may be obtained and, if desired, polyclonal antibodies isolated from the serum. To produce monoclonal antibodies, antibody producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256: 495-497), as the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with the polypeptides of the invention and the monoclonal antibodies isolated.

Antibodies directed against the polypeptides of the invention can be used to selectively block the action of the polypeptides of the invention. Antibodies against a polypeptide of the invention may be employed to treat infections, particularly bacterial infections and diseases. For example, the present invention contemplates a method for treating a subject suffering from a *S. aureus* related disease or disorder, comprising administering to an animal having the condition a therapeutically effective amount of a purified antibody that binds specifically to a polypeptide of the invention. In another example, the present invention contemplates a method for inhibiting SEQ ID NO: 2 or SEQ ID NO: 4 dependent growth or infectivity of *S. aureus*, comprising contacting *S. aureus* with a purified antibody that binds specifically to a polypeptide of the invention.

In one embodiment, antibodies reactive with a polypeptide of the invention are used in the immunological screening of cDNA libraries constructed in expression vectors, such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a polypeptide of the invention can then be detected with antibodies, as, for example, reacting nitrocellulose filters lifted from phage infected bacterial plates with an antibody specific for a polypeptide of the invention. Phage scored by this assay can then be isolated from the infected plate. Thus, homologs of a polypeptide of the invention can be detected and cloned from other sources.

Antibodies may be employed to isolate or to identify clones expressing the polypeptides to purify the polypeptides by affinity chromatography.

In other embodiments, the polypeptides of the invention may be modified so as to increase their immunogenicity. For example, a polypeptide, such as an antigenically or immunologically equivalent derivative, may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

In other embodiments, the antibodies of the invention, or variants thereof, are modified to make them less immunogenic when administered to a subject. For example, if the subject is human, the antibody may be "humanized"; where the complimentarity determining region(s) of the hybridoma-derived antibody has been transplanted into a human monoclonal antibody, for example as described in Jones, P. et al. (1986), Nature 321, 522-525 or Tempest et al. (1991) Biotechnology 9, 266-273. Also, transgenic mice, or other mammals, may be used to express humanized antibodies. Such humanization may be partial or complete.

The use of a nucleic acid of the invention in genetic immunization may employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989:264, 16985), coprecipitation of DNA with calcium phosphate (Benvenisty & Reshef, PNAS USA, 1986:83, 9551), encapsulation of DNA in various forms of liposomes (Kaneda et al., Science 1989:243, 375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81, 5849).

8. Diagnostic Assays

The invention further provides a method for detecting the presence of S. aureus in a biological sample. Detection of S. aureus in a subject, particularly a mammal, and especially a human, will provide a diagnostic method for diagnosis of a S. aureus related disease or disorder. In general, the method involves contacting the biological sample with a compound or an agent capable of detecting a polypeptide of the invention or a nucleic acid of the invention. The term "biological sample" when used in reference to a diagnostic assay is intended to include tissues, cells and biological fluids isolated from a subject, as well as tissues, cells and fluids present within a subject.

The detection method of the invention may be used to detect the presence of S. aureus in a biological sample in vitro as well as in vivo. For example, in vitro techniques for detection of a nucleic acid of the invention include Northern hybridizations and in situ hybridizations. In vitro techniques for detection of polypeptides of the invention include enzyme linked immunosorbent assays (ELISAs), Western blots, immunoprecipitations, immunofluorescence, radioimmunoassays and competitive binding assays. Alternatively, polypeptides of the invention can be detected in vivo in a subject by introducing into the subject a labeled antibody specific for a polypeptide of the invention. For example, the antibody can be labeled with a radioactive marker whose presence and location in a subject can be detected by standard imaging techniques. It may be possible to use all of the diagnostic methods disclosed herein for pathogens in addition to S. aureus.

Nucleic acids for diagnosis may be obtained from an infected individual's cells and tissues, such as bone, blood, muscle, cartilage, and skin. Nucleic acids, e.g., DNA and RNA, may be used directly for detection or may be amplified, e.g., enzymatically by using PCR or other amplification technique, prior to analysis. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing a nucleic acid, e.g., amplified DNA, to a nucleic acid of the invention, which nucleic acid may be labeled. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g. Myers et al., Science, 230: 1242 (1985). Sequence changes at specific locations also may be revealed by nuclease protection assays, such as RNase and S1 protection or a chemical cleavage method. See, e.g., Cotton et al., Proc. Natl. Acad. Sci., USA, 85: 4397-4401 (1985).

Agents for detecting a nucleic acid of the invention, e.g., comprising the sequence set forth in SEQ ID NO: 1 or SEQ ID NO: 3, include labeled or labelable nucleic acid probes capable of hybridizing to a nucleic acid of the invention. The nucleic acid probe can comprise, for example, the full length sequence of a nucleic acid of the invention, or an equivalent thereof, or a portion thereof, such as an oligonucleotide of at least 15, 30, 50, 100, 250 or 500 nucleotides in length and sufficient to specifically hybridize under stringent conditions to SEQ ID NO: 1 or SEQ ID NO: 3, or the complement thereof. Agents for detecting a polypeptide of the invention, e.g., comprising an amino acid sequence of SEQ ID NO: 2 or SEQ ID NO: 4, include labeled or labelable antibodies capable of binding to a polypeptide of the invention. Antibodies may be polyclonal, or alternatively, monoclonal. An intact antibody, or a fragment thereof (e.g., Fab or $F(ab')_2$) can be used. Labeling the probe or antibody also encompasses direct labeling of the probe or antibody by coupling (e.g., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In certain embodiments, detection of a nucleic acid of the invention in a biological sample involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for distinguishing between orthologs of polynucleotides of the invention (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a nucleic acid of the invention under conditions such that hybridization and amplification of the polynucleotide (if present) occurs, and detecting the presence or absence of an amplification product, or detecting the size of the amplification product and comparing the length to a control sample.

In one aspect, the present invention contemplates a method for detecting the presence of S. aureus in a sample, the method comprising: (a) providing a sample to be tested for the presence of S. aureus; (b) contacting the sample with an antibody reactive against eight consecutive amino acid residues of SEQ ID NO: 2 or SEQ ID NO: 4 under conditions which permit association between the antibody and its ligand; and (c) detecting interaction of the antibody with its ligand, thereby detecting the presence of S. aureus in the sample.

In another aspect, the present invention contemplates a method for detecting the presence of S. aureus in a sample, the method comprising: (a) providing a sample to be tested for the presence of S. aureus; (b) contacting the sample with an antibody that binds specifically to a polypeptide of the invention under conditions which permit association between the antibody and its ligand; and (c) detecting interaction of the antibody with its ligand, thereby detecting the presence of S. aureus in the sample.

In yet another example, the present invention contemplates a method for diagnosing a patient suffering from a S. aureus related disease or disorder, comprising: (a) obtaining a biological sample from a patient; (b) detecting the presence or absence of a polypeptide of the invention, or a nucleic acid encoding a polypeptide of the invention, in the sample; and (c) diagnosing a patient suffering from a *S. aureus* related disease or disorder based on the presence of a polypeptide of the invention, or a nucleic acid encoding a polypeptide of the invention, in the patient sample.

The diagnostic assays of the invention may also be used to monitor the effectiveness of an anti-*S. aureus* treatment in an individual suffering from an *S. aureus* related disease or disorder. For example, the presence and/or amount of a nucleic acid of the invention or a polypeptide of the invention can be detected in an individual suffering from an *S. aureus* related disease or disorder before and after treatment with anti-*S. aureus* therapeutic agent. Any change in the level of a polynucleotide or polypeptide of the invention after treatment of the individual with the therapeutic agent can provide information about the effectiveness of the treatment course. In particular, no change, or a decrease, in the level of a polynucleotide or polypeptide of the invention present in the biological sample will indicate that the therapeutic is successfully combating the *S. aureus* related disease or disorder.

The invention also encompasses kits for detecting the presence of *S. aureus* in a biological sample. For example, the kit can comprise a labeled or labelable compound or agent capable of detecting a polynucleotide or polypeptide of the invention in a biological sample; means for determining the amount of *S. aureus* in the sample; and means for comparing the amount of *S. aureus* in the sample with a standard. The compound or agent can be packaged in a suitable container. The kit can further comprise instructions for using the kit to detect a polynucleotide or polypeptide of the invention.

9. Drug Discovery

Modulators to polypeptides of the invention and other structurally related molecules, and complexes containing the same, may be identified and developed as set forth below and otherwise using techniques and methods known to those of skill in the art. The modulators of the invention may be employed, for instance, to inhibit and treat *S. aureus* associated diseases or conditions, such as a furuncle, chronic furunculosis, impetigo, acute osteomyelitis, pneumonia, endocarditis, scalded skin syndrome, toxic shock syndrome, and food poisoning.

A variety of methods for inhibiting the growth or infectivity of *S. aureus* are contemplated by the present invention. For example, exemplary methods involve contacting *S. aureus* with a polypeptide of the invention that modulates the same or another polypeptide from such pathogen, a nucleic acid encoding such polypeptide of the invention, or a compound thought or shown to be effective against such pathogen.

For example, in one aspect, the present invention contemplates a method for treating a patient suffering from an infection of *S. aureus*, comprising administering to the patient an amount of a SEQ ID NO: 2 or SEQ ID NO: 4 inhibitor effective to inhibit the expression and/or activity of a polypeptide of the invention. In certain instances, the animal is a human or a livestock animal such as a cow, pig, goat or sheep. The present invention further contemplates a method for treating a subject suffering from a *S. aureus* related disease or disorder, comprising administering to an animal having the condition a therapeutically effective amount of a molecule identified using one of the methods of the present invention.

The present invention contemplates making any molecule that is shown to modulate the activity of a polypeptide of the invention.

In another embodiment, inhibitors, modulators of the subject polypeptides, or biological complexes containing them, may be used in the manufacture of a medicament for any number of uses, including, for example, treating any disease or other treatable condition of a patient (including humans and animals), and particularly a disease caused by *S. aureus*, such as, for example, one of the following: a furuncle, chronic furunculosis, impetigo, acute osteomyelitis, pneumonia, endocarditis, scalded skin syndrome, toxic shock syndrome, and food poisoning.

(a) Drug Design

A number of techniques can be used to screen, identify, select and design chemical entities capable of associating with polypeptides of the invention, structurally homologous molecules, and other molecules. Knowledge of the structure for a polypeptide of the invention, determined in accordance with the methods described herein, permits the design and/or identification of molecules and/or other modulators which have a shape complementary to the conformation of a polypeptide of the invention, or more particularly, a druggable region thereof. It is understood that such techniques and methods may use, in addition to the exact structural coordinates and other information for a polypeptide of the invention, structural equivalents thereof described above (including, for example, those structural coordinates that are derived from the structural coordinates of amino acids contained in a druggable region as described above).

The term "chemical entity," as used herein, refers to chemical compounds, complexes of two or more chemical compounds, and fragments of such compounds or complexes. In certain instances, it is desirable to use chemical entities exhibiting a wide range of structural and functional diversity, such as compounds exhibiting different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings).

In one aspect, the method of drug design generally includes computationally evaluating the potential of a selected chemical entity to associate with any of the molecules or complexes of the present invention (or portions thereof). For example, this method may include the steps of (a) employing computational means to perform a fitting operation between the selected chemical entity and a druggable region of the molecule or complex; and (b) analyzing the results of said fitting operation to quantify the association between the chemical entity and the druggable region.

A chemical entity may be examined either through visual inspection or through the use of computer modeling using a docking program such as GRAM, DOCK, or AUTODOCK (Dunbrack et al., Folding & Design, 2:27-42 (1997)). This procedure can include computer fitting of chemical entities to a target to ascertain how well the shape and the chemical structure of each chemical entity will complement or interfere with the structure of the subject polypeptide (Bugg et al., Scientific American, December: 92-98 (1993); West et al., TIPS, 16:67-74 (1995)). Computer programs may also be employed to estimate the attraction, repulsion, and steric hindrance of the chemical entity to a druggable region, for example. Generally, the tighter the fit (e.g., the lower the steric hindrance, and/or the greater the attractive force) the more potent the chemical entity will be because these properties are consistent with a tighter binding constant. Furthermore, the more specificity in the design of a chemical entity the more likely that the chemical entity will not interfere with related proteins, which may minimize potential side-effects due to unwanted interactions.

A variety of computational methods for molecular design, in which the steric and electronic properties of druggable regions are used to guide the design of chemical entities, are known: Cohen et al. (1990) *J. Med. Cam.* 33: 883-894; Kuntz et al. (1982) *J. Mol. Biol* 161: 269-288; DesJarlais (1988) *J. Med. Cam.* 31: 722-729; Bartlett et al. (1989) *Spec. Publ., Roy. Soc. Chem.* 78: 182-196; Goodford et al. (1985) *J. Med. Cam.* 28: 849-857; and DesJarlais et al. *J. Med. Cam.* 29: 2149-2153. Directed methods generally fall into two categories: (1) design by analogy in which 3-D structures of known chemical entities (such as from a crystallographic database) are docked to the druggable region and scored for goodness-of-fit; and (2) de novo design, in which the chemical entity is constructed piece-wise in the druggable region. The chemical entity may be screened as part of a library or a database of molecules. Databases which may be used include ACD (Molecular Designs Limited), NCI (National Cancer Institute), CCDC (Cambridge Crystallographic Data Center), CAST (Chemical Abstract Service), Derwent (Derwent Information Limited), Maybridge (Maybridge Chemical Company Ltd), Aldrich (Aldrich Chemical Company), DOCK (University of California in San Francisco), and the Directory of Natural Products (Chapman & Hall). Computer programs such as CONCORD (Tripos Associates) or DB-Converter (Molecular Simulations Limited) can be used to convert a data set represented in two dimensions to one represented in three dimensions.

Chemical entities may be tested for their capacity to fit spatially with a druggable region or other portion of a target protein. As used herein, the term "fits spatially" means that the three-dimensional structure of the chemical entity is accommodated geometrically by a druggable region. A favorable geometric fit occurs when the surface area of the chemical entity is in close proximity with the surface area of the druggable region without forming unfavorable interactions. A favorable complementary interaction occurs where the chemical entity interacts by hydrophobic, aromatic, ionic, dipolar, or hydrogen donating and accepting forces. Unfavorable interactions may be steric hindrance between atoms in the chemical entity and atoms in the druggable region.

If a model of the present invention is a computer model, the chemical entities may be positioned in a druggable region through computational docking. If, on the other hand, the model of the present invention is a structural model, the chemical entities may be positioned in the druggable region by, for example, manual docking. As used herein the term "docking" refers to a process of placing a chemical entity in close proximity with a druggable region, or a process of finding low energy conformations of a chemical entity/druggable region complex.

In an illustrative embodiment, the design of potential modulator begins from the general perspective of shape complimentary for the druggable region of a polypeptide of the invention, and a search algorithm is employed which is capable of scanning a database of small molecules of known three-dimensional structure for chemical entities which fit geometrically with the target druggable region. Most algorithms of this type provide a method for finding a wide assortment of chemical entities that are complementary to the shape of a druggable region of the subject polypeptide. Each of a set of chemical entities from a particular data-base, such as the Cambridge Crystallographic Data Bank (CCDB) (Allen et al. (1973) *J. Chem. Doc.* 13: 119), is individually docked to the druggable region of a polypeptide of the invention in a number of geometrically permissible orientations with use of a docking algorithm. In certain embodiments, a set of computer algorithms called DOCK, can be used to characterize the shape of invaginations and grooves that form the active sites and recognition surfaces of the druggable region (Kuntz et al. (1982) *J. Mol. Biol* 161: 269-288). The program can also search a database of small molecules for templates whose shapes are complementary to particular binding sites of a polypeptide of the invention (DesJarlais et al. (1988) *J Med Chem* 31: 722-729).

The orientations are evaluated for goodness-of-fit and the best are kept for further examination using molecular mechanics programs, such as AMBER or CHARMM. Such algorithms have previously proven successful in finding a variety of chemical entities that are complementary in shape to a druggable region.

Goodford (1985, *J Med Chem* 28:849-857) and Boobbyer et al. (1989, *J Med Chem* 32:1083-1094) have produced a computer program (GRID) which seeks to determine regions of high affinity for different chemical groups (termed probes) of the druggable region. GRID hence provides a tool for suggesting modifications to known chemical entities that might enhance binding. It may be anticipated that some of the sites discerned by GRID as regions of high affinity correspond to "pharmacophoric patterns" determined inferentially from a series of known ligands. As used herein, a "pharmacophoric pattern" is a geometric arrangement of features of chemical entities that is believed to be important for binding. Attempts have been made to use pharmacophoric patterns as a search screen for novel ligands (Jakes et al. (1987) *J Mol Graph* 5:4148; Brint et al. (1987) *J Mol Graph* 5:49-56; Jakes et al. (1986) *J Mol Graph* 4:12-20).

Yet a further embodiment of the present invention utilizes a computer algorithm such as CLIX which searches such databases as CCDB for chemical entities which can be oriented with the druggable region in a way that is both sterically acceptable and has a high likelihood of achieving favorable chemical interactions between the chemical entity and the surrounding amino acid residues. The method is based on characterizing the region in terms of an ensemble of favorable binding positions for different chemical groups and then searching for orientations of the chemical entities that cause maximum spatial coincidence of individual candidate chemical groups with members of the ensemble. The algorithmic details of CLIX is described in Lawrence et al. (1992) *Proteins* 12:3141.

In this way, the efficiency with which a chemical entity may bind to or interfere with a druggable region may be tested and optimized by computational evaluation. For example, for a favorable association with a druggable region, a chemical entity must preferably demonstrate a relatively small difference in energy between its bound and fine states (i.e., a small deformation energy of binding). Thus, certain, more desirable chemical entities will be designed with a deformation energy of binding of not greater than about 10 kcal/mole, and more preferably, not greater than 7 kcal/mole. Chemical entities may interact with a druggable region in more than one conformation that is similar in overall binding energy. In those cases, the deformation energy of binding is taken to be the difference between the energy of the free entity and the average energy of the conformations observed when the chemical entity binds to the target.

In this way, the present invention provides computer-assisted methods for identifying or designing a potential modulator of the activity of a polypeptide of the invention including: supplying a computer modeling application with a set of structure coordinates of a molecule or complex, the molecule or complex including at least a portion of a druggable region from a polypeptide of the invention; supplying the computer modeling application with a set of structure coordinates of a chemical entity; and determining whether the chemical entity is expected to bind to the molecule or complex, wherein binding to the molecule or complex is indicative of potential modulation of the activity of a polypeptide of the invention.

In another aspect, the present invention provides a computer-assisted method for identifying or designing a potential modulator to a polypeptide of the invention, supplying a computer modeling application with a set of structure coordinates of a molecule or complex, the molecule or complex including at least a portion of a druggable region of a polypeptide of the invention; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity, and determining whether the modified chemical entity is expected to bind to the molecule or complex, wherein binding to the molecule or complex is indicative of potential modulation of the polypeptide of the invention.

In one embodiment, a potential modulator can be obtained by screening a peptide library (Scott and Smith, Science, 249:386-390 (1990); Cwirla et al., Proc. Natl. Acad. Sci., 87:6378-6382 (1990); Devlin et al., Science, 249:404-406 (1990)). A potential modulator selected in this manner could then be systematically modified by computer modeling programs until one or more promising potential drugs are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). Alternatively a potential modulator may be selected from a library of chemicals such as those that can be licensed from third parties, such as chemical and pharmaceutical companies. A third alternative is to synthesize the potential modulator de novo.

For example, in certain embodiments, the present invention provides a method for making a potential modulator for a polypeptide of the invention, the method including synthesizing a chemical entity or a molecule containing the chemical entity to yield a potential modulator of a polypeptide of the invention, the chemical entity having been identified during a computer-assisted process including supplying a computer modeling application with a set of structure coordinates of a molecule or complex, the molecule or complex including at least one druggable region from a polypeptide of the invention; supplying the computer modeling application with a set of structure coordinates of a chemical entity; and determining whether the chemical entity is expected to bind to the molecule or complex at the active site, wherein binding to the molecule or complex is indicative of potential modulation. This method may further include the steps of evaluating the potential binding interactions between the chemical entity and the active site of the molecule or molecular complex and structurally modifying the chemical entity to yield a set of structure coordinates for a modified chemical entity, which steps may be repeated one or more times.

Once a potential modulator is identified, it can then be tested in any standard assay for the macromolecule depending of course on the macromolecule, including in high throughput assays. Further refinements to the structure of the modulator will generally be necessary and can be made by the successive iterations of any and/or all of the steps provided by the particular screening assay, in particular further structural analysis by e.g., $^{15}N$ NMR relaxation rate determinations or x-ray crystallography with the modulator bound to the subject polypeptide. These studies may be performed in conjunction with biochemical assays.

Once identified, a potential modulator may be used as a model structure, and analogs to the compound can be obtained. The analogs are then screened for their ability to bind the subject polypeptide. An analog of the potential modulator might be chosen as a modulator when it binds to the subject polypeptide with a higher binding affinity than the predecessor modulator.

In a related approach, iterative drug design is used to identify modulators of a target protein. Iterative drug design is a method for optimizing associations between a protein and a modulator by determining and evaluating the three dimensional structures of successive sets of protein/modulator complexes. In iterative drug design, crystals of a series of protein/modulator complexes are obtained and then the three-dimensional structures of each complex is solved. Such an approach provides insight into the association between the proteins and modulators of each complex. For example, this approach may be accomplished by selecting modulators with inhibitory activity, obtaining crystals of this new protein/modulator complex, solving the three dimensional structure of the complex, and comparing the associations between the new protein/modulator complex and previously solved protein/modulator complexes. By observing how changes in the modulator affected the protein/modulator associations, these associations may be optimized.

In addition to designing and/or identifying a chemical entity to associate with a druggable region, as described above, the same techniques and methods may be used to design and/or identify chemical entities that either associate, or do not associate, with affinity regions, selectivity regions or undesired regions of protein targets. By such methods, selectivity for one or a few targets, or alternatively for multiple targets, from the same species or from multiple species, can be achieved.

For example, a chemical entity may be designed and/or identified for which the binding energy for one druggable region, e.g., an affinity region or selectivity region, is more favorable than that for another region, e.g., an undesired region, by about 20%, 30%, 50% to about 60% or more. It may be the case that the difference is observed between (a) more than two regions, (b) between different regions (selectivity, affinity or undesirable) from the same target, (c) between regions of different targets, (d) between regions of homologs from different species, or (e) between other combinations. Alternatively, the comparison may be made by reference to the $K_d$, usually the apparent $K_d$, of said chemical entity with the two or more regions in question.

In another aspect, prospective modulators are screened for binding to two nearby druggable regions on a target protein. For example, a modulator that binds a first region of a target polypeptide does not bind a second nearby region. Binding to the second region can be determined by monitoring changes in a different set of amide chemical shifts in either the original screen or a second screen conducted in the presence of a modulator (or potential modulator) for the first region. From an analysis of the chemical shift changes, the approximate location of a potential modulator for the second region is identified. Optimization of the second modulator for binding to the region is then carried out by screening structurally related compounds (e.g., analogs as described above). When modulators for the first region and the second region are identified, their location and orientation in the ternary complex can be determined experimentally. On the basis of this structural information, a linked compound, e.g., a consolidated modulator, is synthesized in which the modulator for the first region and the modulator for the second region are linked. In certain embodiments, the two modulators are covalently linked to form a consolidated modulator. This consolidated modulator may be tested to determine if it has a higher binding affinity for the target than either of the two individual modulators. A consolidated modulator is selected as a modulator when it has a higher binding affinity for the target than either of the two modulators. Larger consolidated modulators can be constructed in an analogous manner, e.g., linking three modulators which bind to three nearby regions on the target to form a multilinked consolidated modulator that has an even higher affinity for the target than the linked modulator. In this example, it is assumed that is desirable to have the modulator bind to all the druggable regions. However, it may be the case that binding to certain of the druggable regions is not desirable, so that the same techniques may be used to identify modulators and consolidated modulators that show increased specificity based on binding to at least one but not all druggable regions of a target.

The present invention provides a number of methods that use drug design as described above. For example, in one aspect, the present invention contemplates a method for designing a candidate compound for screening for inhibitors of a polypeptide of the invention, the method comprising: (a) determining the three dimensional structure of a crystallized polypeptide of the invention or a fragment thereof; and (b) designing a candidate inhibitor based on the three dimensional structure of the crystallized polypeptide or fragment.

In another aspect, the present invention contemplates a method for identifying a potential inhibitor of a polypeptide of the invention, the method comprising: (a) providing the three-dimensional coordinates of a polypeptide of the invention or a fragment thereof; (b) identifying a druggable region of the polypeptide or fragment; and (c) selecting from a database at least one compound that comprises three dimensional coordinates which indicate that the compound may bind the druggable region; (d) wherein the selected compound is a potential inhibitor of a polypeptide of the invention.

In another aspect, the present invention contemplates a method for identifying a potential modulator of a molecule comprising a druggable region similar to that of SEQ ID NO: 2 or SEQ ID NO: 4, the method comprising: (a) using the atomic coordinates of amino acid residues from SEQ ID NO: 2 or SEQ ID NO: 4, or a fragment thereof, ±a root mean square deviation from the backbone atoms of the amino acids of not more than 1.5 Å, to generate a three-dimensional structure of a molecule comprising a druggable region that is a portion of SEQ ID NO: 2 or SEQ ID NO: 4; (b) employing the three dimensional structure to design or select the potential modulator; (c) synthesizing the modulator; and (d) contacting the modulator with the molecule to determine the ability of the modulator to interact with the molecule.

In another aspect, the present invention contemplates an apparatus for determining whether a compound is a potential inhibitor of a polypeptide having SEQ ID NO: 2 or SEQ ID NO: 4, the apparatus comprising: (a) a memory that comprises: (i) the three dimensional coordinates and identities of the atoms of a polypeptide of the invention or a fragment thereof that form a druggable site; and (ii) executable instructions; and (b) a processor that is capable of executing instructions to: (i) receive three-dimensional structural information for a candidate compound; (ii) determine if the three-dimensional structure of the candidate compound is complementary to the structure of the interior of the druggable site; and (iii) output the results of the determination.

In another aspect, the present invention contemplates a method for designing a potential compound for the prevention or treatment of S. aureus related disease or disorder, the method comprising: (a) providing the three dimensional structure of a crystallized polypeptide of the invention, or a fragment thereof; (b) synthesizing a potential compound for the prevention or treatment of S. aureus related disease or disorder based on the three dimensional structure of the crystallized polypeptide or fragment; (c) contacting a polypeptide of the present invention or an S. aureus with the potential compound; and (d) assaying the activity of a polypeptide of the present invention, wherein a change in the activity of the polypeptide indicates that the compound may be useful for prevention or treatment of a S. aureus related disease or disorder.

In another aspect, the present invention contemplates a method for designing a potential compound for the prevention or treatment of S. aureus related disease or disorder, the method comprising: (a) providing structural information of a druggable region derived from NMR spectroscopy of a polypeptide of the invention, or a fragment thereof; (b) synthesizing a potential compound for the prevention or treatment of S. aureus related disease or disorder based on the structural information; (c) contacting a polypeptide of the present invention or an S. aureus with the potential compound; and (d) assaying the activity of a polypeptide of the present invention, wherein a change in the activity of the polypeptide indicates that the compound may be useful for prevention or treatment of a S. aureus related disease or disorder.

(b) In Vitro Assays

Polypeptides of the invention may be used to assess the activity of small molecules and other modulators in in vitro assays. In one embodiment of such an assay, agents are identified which modulate the biological activity of a protein, protein-protein interaction of interest or protein complex, such as an enzymatic activity, binding to other cellular components, cellular compartmentalization, signal transduction, and the like. In certain embodiments, the test agent is a small organic molecule.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

The invention also provides a method of screening compounds to identify those which modulate the action of polypeptides of the invention, or polynucleotides encoding the same. The method of screening may involve high-throughput techniques. For example, to screen for modulators, a synthetic reaction mix, a cellular compartment, such as a membrane, cell envelope or cell wall, or a preparation of any thereof, comprising a polypeptide of the invention and a labeled substrate or ligand of such polypeptide is incubated in the absence or the presence of a candidate molecule that may be a modulator of a polypeptide of the invention. The ability of the candidate molecule to modulate a polypeptide of the invention is reflected in decreased binding of the labeled ligand or decreased production of product from such substrate. Detection of the rate or level of production of product from substrate may be enhanced by using a reporter system. Reporter systems that may be useful in this regard include but are not limited to colorimetric labeled substrate converted into product, a reporter gene that is responsive to changes in a nucleic acid of the invention or polypeptide activity, and binding assays known in the art.

Another example of an assay for a modulator of a polypeptide of the invention is a competitive assay that combines a polypeptide of the invention and a potential modulator with molecules that bind to a polypeptide of the invention, recombinant molecules that bind to a polypeptide of the invention, natural substrates or ligands, or substrate or ligand mimetics, under appropriate conditions for a competitive inhibition assay. Polypeptides of the invention can be labeled, such as by radioactivity or a colorimetric compound, such that the number of molecules of a polypeptide of the invention bound to a binding molecule or converted to product can be determined accurately to assess the effectiveness of the potential modulator.

A number of methods for identifying a molecule which modulates the activity of a polypeptide are known in the art. For example, in one such method, a subject polypeptide is contacted with a test compound, and the activity of the subject polypeptide in the presence of the test compound is determined, wherein a change in the activity of the subject polypeptide is indicative that the test compound modulates the activity of the subject polypeptide. In certain instances, the test compound agonizes the activity of the subject polypeptide, and in other instances, the test compound antagonizes the activity of the subject polypeptide.

In another example, a compound which modulates SEQ ID NO: 2 or SEQ ID NO: 4 dependent growth or infectivity of *S. aureus* may be identified by (a) contacting a polypeptide of the invention with a test compound; and (b) determining the activity of the polypeptide in the presence of the test compound, wherein a change in the activity of the polypeptide is indicative that the test compound may modulate the growth or infectivity of *S. aureus*.

(c) In Vivo Assays

Animal models of bacterial infection and/or disease may be used as an in vivo assay for evaluating the effectiveness of a potential drug target in treating or preventing diseases or disorders. A number of suitable animal models are described briefly below, however, these models are only examples and modifications, or completely different animal models, may be used in accord with the methods of the invention.

(i) Mouse Soft Tissue Model

The mouse soft tissue infection model is a sensitive and effective method for measurement of bacterial proliferation. In these models (Vogelman et al., 1988, J. Infect. Dis. 157: 287-298) anesthetized mice are infected with the bacteria in the muscle of the hind thigh. The mice can be either chemically immune compromised (e.g., cytoxin treated at 125 mg/kg on days −4, −2, and 0) or immunocompetent. The dose of microbe necessary to cause an infection is variable and depends on the individual microbe, but commonly is on the order of $10^5$-$10^6$ colony forming units per injection for bacteria. A variety of mouse strains are useful in this model although Swiss Webster and DBA2 lines are most commonly used. Once infected the animals are conscious and show no overt ill effects of the infections for approximately 12 hours. After that time virulent strains cause swelling of the thigh muscle, and the animals can become bacteremic within approximately 24 hours. This model most effectively measures proliferation of the microbe, and this proliferation is measured by sacrifice of the infected animal and counting colonies from homogenized thighs.

(ii) Diffusion Chamber Model

A second model useful for assessing the virulence of microbes is the diffusion chamber model (Malouin et al., 1990, Infect. Immun. 58: 1247-1253; Doy et al., 1980, J. Infect. Dis. 2: 39-51; Kelly et al., 1989, Infect. Immun. 57: 344-350. In this model rodents have a diffusion chamber surgically placed in the peritoneal cavity. The chamber consists of a polypropylene cylinder with semipermeable membranes covering the chamber ends. Diffusion of peritoneal fluid into and out of the chamber provides nutrients for the microbes. The progression of the "infection" may be followed by examining growth, the exoproduct production or RNA messages. The time experiments are done by sampling multiple chambers.

(iii) Endocarditis Model

For bacteria, an important animal model effective in assessing pathogenicity and virulence is the endocarditis model (J. Santoro and M. E. Levinson, 1978, Infect. Immun. 19: 915-918). A rat endocarditis model can be used to assess colonization, virulence and proliferation.

(iv) Osteomyelitis Model

A fourth model useful in the evaluation of pathogenesis is the osteomyelitis model (Spagnolo et al., 1993, Infect. Immun. 61: 5225-5230). Rabbits are used for these experiments. Anesthetized animals have a small segment of the tibia removed and microorganisms are microinjected into the wound. The excised bone segment is replaced and the progression of the disease is monitored. Clinical signs, particularly inflammation and swelling are monitored. Termination of the experiment allows histolic and pathologic examination of the infection site to complement the assessment procedure.

(v) Murine Septic Arthritis Model

A fifth model relevant to the study of microbial pathogenesis is a murine septic arthritis model (Abdelnour et al., 1993, Infect. Immun. 61: 3879-3885). In this model mice are infected intravenously and pathogenic organisms are found to cause inflammation in distal limb joints. Monitoring of the inflammation and comparison of inflammation vs. inocula allows assessment of the virulence of related strains.

(vi) Bacterial Peritonitis Model

Finally, bacterial peritonitis offers rapid and predictive data on the virulence of strains (M. G. Bergeron, 1978, Scand. J. Infect. Dis. Suppl. 14: 189-206; S. D. Davis, 1975, Antimicrob. Agents Chemother. 8: 50-53). Peritonitis in rodents, such as mice, can provide essential data on the importance of targets. The end point may be lethality or clinical signs can be monitored. Variation in infection dose in comparison to outcome allows evaluation of the virulence of individual strains.

A variety of other in vivo models are available and may be used when appropriate for specific pathogens or specific test agents. For example, target organ recovery assays (Gordee et al., 1984, J. Antibiotics 37:1054-1065; Bannatyne et al., 1992, Infect. 20:168-170) may be useful for fungi and for bacterial pathogens which are not acutely virulent to animals.

It is also relevant to note that the species of animal used for an infection model, and the specific genetic make-up of that animal, may contribute to the effective evaluation of the effects of a particular test agent. For example, immuno-incompetent animals may, in some instances, be preferable to immuno-competent animals. For example, the action of a competent immune system may, to some degree, mask the effects of the test agent as compared to a similar infection in an immuno-incompetent animal. In addition, many opportunistic infections, in fact, occur in immuno-compromised patients, so modeling an infection in a similar immunological environment is appropriate.

10. Vaccines

There are provided by the invention, products, compositions and methods for raising immunological response against a pathogen, especially *S. aureus*. In one aspect, a polypeptide of the invention or a nucleic acid of the invention, or an antigenic fragment thereof, may be administered to a subject, optionally with a booster, adjuvant, or other composition that stimulates immune responses.

Another aspect of the invention relates to a method for inducing an immunological response in an individual, particularly a mammal which comprises inoculating the individual with a polypeptide of the invention and/or a nucleic acid of the invention, adequate to produce antibody and/or T cell immune response to protect said individual from infection, particularly bacterial infection and most particularly *S. aureus* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of a polypeptide of the invention and/or a nucleic acid of the invention in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a nucleic acid of the invention and/or a polypeptide encoded therefrom, wherein the composition comprises a recombinant nucleic acid of the invention and/or polypeptide encoded therefrom and/or comprises DNA and/or RNA which encodes and expresses an antigen of said nucleic acid of the invention, polypeptide encoded therefrom, or other polypeptide of the invention. The immunological response may be used therapeutically or prophylactically and may take the form of antibody immunity and/or cellular immunity, such as cellular immunity arising from CTL or CD4+T cells.

In another embodiment, the invention relates to compositions comprising a polypeptide of the invention and an adjuvant. The adjuvant can be any vehicle which would typically enhance the antigenicity of a polypeptide, e.g., minerals (for instance, alum, aluminum hydroxide or aluminum phosphate), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, liposomes, or any of the other adjuvants known in the art. A polypeptide of the invention can be emulsified with, absorbed onto, or coupled with the adjuvant.

A polypeptide of the invention may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, may further comprise an antigenic co-protein, such as lipoprotein D from Hemophilus influenzae, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of a polypeptide of the invention.

Provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *S. aureus*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *S. aureus* infection, in mammals, particularly humans.

A polypeptide of the invention may be used as an antigen for vaccination of a host to produce specific antibodies which protect against invasion of bacteria, for example by blocking adherence of bacteria to damaged tissue.

11. Array Analysis

In part, the present invention is directed to the use of subject nucleic acids in arrays to assess gene expression. In another part, the present invention is directed to the use of subject nucleic acids in arrays for *S. aureus*. In yet another part, the present invention contemplates using the subject nucleic acids to interact with probes contained on arrays.

In one aspect, the present invention contemplates an array comprising a substrate having a plurality of addresses, wherein at least one of the addresses has disposed thereon a capture probe that can specifically bind to a nucleic acid of the invention. In another aspect, the present invention contemplates a method for detecting expression of a nucleotide sequence which encodes a polypeptide of the invention, or a fragment thereof, using the foregoing array by: (a) providing a sample comprising at least one mRNA molecule; (b) exposing the sample to the array under conditions which promote hybridization between the capture probe disposed on the array and a nucleic acid complementary thereto; and (c) detecting hybridization between an mRNA molecule of the sample and the capture probe disposed on the array, thereby detecting expression of a sequence which encodes for a polypeptide of the invention, or a fragment thereof.

Arrays are often divided into microarrays and macroarrays, where microarrays have a much higher density of individual probe species per area. Microarrays may have as many as 1000 or more different probes in a 1 $cm^2$ area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome. In certain embodiments, the binding site or site is a nucleic acid or nucleic acid analogue to which a particular cognate cDNA can specifically hybridize. The nucleic acid or analogue of the binding site may be, e.g., a synthetic oligomer, a full-length cDNA, a less-than full length cDNA, or a gene fragment.

Although in certain embodiments the microarray contains binding sites for products of all or almost all genes in the target organism's genome, such comprehensiveness is not necessarily required. Usually the microarray will have binding sites corresponding to at least 100, 500, 1000, 4000 genes or more. In certain embodiments, arrays will have anywhere from about 50, 60, 70, 80, 90, or even more than 95% of the genes of a particular organism represented. The microarray typically has binding sites for genes relevant to testing and confirming a biological network model of interest. Several exemplary human microarrays are publicly available.

The probes to be affixed to the arrays are typically polynucleotides. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (e.g., fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In an alternative embodiment, the binding (hybridization) sites are made from plasmid or phage clones of genes, cDNAs (e.g., expressed sequence tags), or inserts therefrom (Nguyen et al., 1995, Genomics 29:207-209).

A number of methods are known in the art for affixing the nucleic acids or analogues to a solid support that makes up the array (Schena et al., 1995, Science 270:467-470; DeRisi et al., 1996, Nature Genetics 14:457-460; Shalon et al., 1996, Genome Res. 6:639-645; and Schena et al., 1995, Proc. Natl. Acad. Sci. USA 93:10539-11286).

Another method for making microarrays is by making high-density oligonucleotide arrays (Fodor et al., 1991, Science 251:767-773; Pease et al., 1994, Proc. Natl. Acad. Sci. USA 91:5022-5026; Lockhart et al., 1996, Nature Biotech 14:1675; U.S. Pat. Nos. 5,578,832; 5,556,752; and 5,510,270; Blanchard et al., 1996, 11: 687-90).

Other methods for making microarrays, e.g., by masking (Maskos and Southern, 1992, Nuc. Acids Res. 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989), could be used, although, as will be recognized by those of skill in the art.

The nucleic acids to be contacted with the microarray may be prepared in a variety of ways, and may include nucleotides of the subject invention. Such nucleic acids are often labeled fluorescently. Nucleic acid hybridization and wash conditions are chosen so that the population of labeled nucleic acids will specifically hybridize to appropriate, complementary nucleic acids affixed to the matrix. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array may be detected by scanning confocal laser microscopy. When two fluorophores are used, a separate scan, using the appropriate excitation line, is carried out for each of the two fluorophores used. Fluorescent microarray scanners are commercially available from Affymetrix, Packard BioChip Technologies, BioRobotics and many other suppliers. Signals are recorded, quantitated and analyzed using a variety of computer software.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

In addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In certain embodiments, the data obtained from such experiments reflects the relative expression of each gene represented in the microarray. Expression levels in different samples and conditions may now be compared using a variety of statistical methods.

12. Pharmaceutical Compositions

Pharmaceutical compositions of this invention include any modulator identified according to the present invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. The term parenteral as used herein includes subcutaneous, intracutaneous, intravenous, intramuscular, intra articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the modulators described herein are useful for the prevention and treatment of disease and conditions, including *S. aureus* mediated diseases and conditions. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

13. Antimicrobial Agents

The polypeptides of the invention may be used to develop antimicrobial agents for use in a wide variety of applications. The uses are as varied as surface disinfectants, topical pharmaceuticals, personal hygiene applications (e.g., antimicrobial soap, deodorant or the like), additives to cell culture medium, and systemic pharmaceutical products. Antimicrobial agents of the invention may be incorporated into a wide variety of products and used to treat an already existing microbial infection/contamination or may be used prophylactically to suppress future infection/contamination.

The antimicrobial agents of the invention may be administered to a site, or potential site, of infection/contamination in either a liquid or solid form. Alternatively, the agent may be applied as a coating to a surface of an object where microbial growth is undesirable using nonspecific absorption or covalent attachment. For example, implants or devices (such as linens, cloth, plastics, heart pacemakers, surgical stents, catheters, gastric tubes, endotracheal tubes, prosthetic devices) can be coated with the antimicrobials to minimize adherence or persistence of bacteria during storage and use. The antimicrobials may also be incorporated into such devices to provide slow release of the agent locally for several weeks during healing. The antimicrobial agents may also be used in association with devices such as ventilators, water reservoirs, air-conditioning units, filters, paints, or other substances. Antimicrobials of the invention may also be given orally or systemically after transplantation, bone replacement, during dental procedures, or during implantation to prevent colonization with bacteria.

In another embodiment, antimicrobial agents of the invention may be used as a food preservative or in treating food products to eliminate potential pathogens. The latter use might be targeted to the fish and poultry industries that have serious problems with enteric pathogens which cause severe human disease. In a further embodiment, the agents of the invention may be used as antimicrobials for food crops, either as agents to reduce post harvest spoilage or to enhance host resistance. The antimicrobials may also be used as preservatives in processed foods either alone or in combination with antibacterial food additives such as lysozymes.

In another embodiment, the antimicrobials of the invention may be used as an additive to culture medium to prevent or eliminate infection of cultured cells with a pathogen.

14. Other Embodiments

In addition to other embodiments, aspects and objects of the present invention disclosed herein, including the claims appended hereto, the following paragraphs set forth additional, non-limiting embodiments and other aspects of the present invention (with all references to paragraphs contained in this section referring to other paragraphs set for this section):

1. A composition comprising an isolated, recombinant polypeptide, wherein the polypeptide comprises: (a) an amino acid sequence set forth in SEQ ID NO: 2 or SEQ ID NO: 4; (b) an amino acid sequence having at least about 95% identity with the amino acid sequence set forth in SEQ ID NO: 2 or SEQ ID NO: 4; or (c) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; and wherein the polypeptide of (a), (b) or (c) is at least about 90% pure in a sample of the composition.

2. The composition of paragraph 1, wherein the polypeptide is at least about 95% pure as determined by gel electrophoresis.

3. The composition of paragraph 1, wherein the polypeptide is purified to essential homogeneity.

4. The composition of paragraph 1, wherein at least about two-thirds of the polypeptide in the sample is soluble.

5. The composition of paragraph 1, wherein the polypeptide is fused to at least one heterologous polypeptide that increases the solubility or stability of the polypeptide.

6. The composition of paragraph 1, which further comprises a matrix suitable for mass spectrometry.

7. The composition of paragraph 6, wherein the matrix is a nicotinic acid derivative or a cinnamic acid derivative.

8. A sample comprising an isolated, recombinant polypeptide, wherein the polypeptide comprises: (a) an amino acid sequence set forth in SEQ ID NO: 2 or SEQ ID NO: 4; (b) an amino acid sequence having at least about 95% identity with the amino acid sequence set forth in SEQ ID NO: 2 or SEQ ID NO: 4; or (c) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; and wherein the polypeptide of (a), (b) or (c) is labeled with a heavy atom.

9. The sample of paragraph 8, wherein the heavy atom is one of the following: cobalt, selenium, krypton, bromine, strontium, molybdenum, ruthenium, rhodium, palladium, silver, cadmium, tin, iodine, xenon, barium, lanthanum, cerium, praseodymium, neodymium, samarium, europium, gadolinium, terbium, dysprosium, holmium, erbium, thulium, ytterbium, lutetium, tantalum, tungsten, rhenium, osmium, iridium, platinum, gold, mercury, thallium, lead, thorium and uranium.

10. The sample of paragraph 8, wherein the polypeptide is labeled with seleno-methionine.

11. The sample of paragraph 8, further comprising a cryo-protectant.

12. The sample of paragraph 11, wherein the cryo-protectant is one of the following: methyl pentanediol, isopropanol, ethylene glycol, glycerol, formate, citrate, mineral oil and a low-molecular-weight polyethylene glycol.

13. A crystallized, recombinant polypeptide comprising: (a) an amino acid sequence set forth in SEQ ID NO: 2 or SEQ ID NO: 4; (b) an amino acid sequence having at least about 95% identity with the amino acid sequence set forth in SEQ ID NO: 2 or SEQ ID NO: 4; or (c) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; wherein the polypeptide of (a), (b) or (c) is in crystal form.

14. A crystallized complex comprising the crystallized, recombinant polypeptide of paragraph 13 and a co-factor, wherein the complex is in crystal form.

15. A crystallized complex comprising the crystallized, recombinant polypeptide of paragraph 13 and a small organic molecule, wherein the complex is in crystal form.

16. The crystallized, recombinant polypeptide of paragraph 13, which diffracts x-rays to a resolution of about 3.5 Å or better.

17. The crystallized, recombinant polypeptide of paragraph 13, wherein the polypeptide comprises at least one heavy atom label.

18. The crystallized, recombinant polypeptide of paragraph 17, wherein the polypeptide is labeled with selenomethionine.

19. A method for designing a modulator for the prevention or treatment of S. aureus related disease or disorder, comprising:
 (a) providing a three-dimensional structure for a crystallized, recombinant polypeptide of paragraph 13;
 (b) identifying a potential modulator for the prevention or treatment of S. aureus related disease or disorder by reference to the three-dimensional structure;
 (c) contacting a polypeptide of the composition of paragraph 1 or S. aureus with the potential modulator; and
 (d) assaying the activity of the polypeptide or determining the viability of S. aureus after contact with the modulator, wherein a change in the activity of the polypeptide or the viability of S. aureus indicates that the modulator may be useful for prevention or treatment of a S. aureus related disease or disorder.

20. A sample comprising an isolated, recombinant polypeptide, wherein the polypeptide comprises: (a) an amino acid sequence set forth in SEQ ID NO: 2 or SEQ ID NO: 4; (b) an amino acid sequence having at least about 95% identity with the amino acid sequence set forth in SEQ ID NO: 2 or SEQ ID NO: 4; or (c) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; and wherein the polypeptide of (a), (b) or (c) is enriched in at least one NMR isotope.

21. The sample of paragraph 20, wherein the NMR isotope is one of the following: hydrogen-1 ($^1$H), hydrogen-2 ($^2$H), hydrogen-3 ($^3$H), phosphorous-31 ($^{31}$P), sodium-23 ($^{23}$Na), nitrogen-14 ($^{14}$N), nitrogen-15 ($^{15}$N), carbon-13 ($^{13}$C) and fluorine-19 ($^{19}$F).

22. The sample of paragraph 20, further comprising a deuterium lock solvent.

23. The sample of paragraph 22, wherein the deuterium lock solvent is one of the following: acetone ($CD_3COCD_3$), chloroform ($CDCl_3$), dichloro methane ($CD_2Cl_2$), methylnitrile ($CD_3CN$), benzene ($C_6D_6$), water ($D_2O$), diethylether (($CD_3CD_2)_2O$), dimethylether (($CD_3)_2O$), N,N-dimethylformamide (($CD_3)_2NCDO$), dimethyl sulfoxide ($CD_3SOCD_3$), ethanol ($CD_3CD_2OD$), methanol ($CD_3OD$), tetrahydrofuran ($C_4D_8O$), toluene ($C_6D_5CD_3$), pyridine ($C_5D_5N$) and cyclohexane ($C6H_{12}$).

24. The sample of paragraph 20, which is contained within an NMR tube.

25. A method for identifying small molecules that bind to a polypeptide of the composition of paragraph 1, comprising:
 (a) generating a first NMR spectrum of an isotopically labeled polypeptide of the composition of paragraph 1;
 (b) exposing the polypeptide to one or more small molecules;
 (c) generating a second NMR spectrum of the polypeptide which has been exposed to one or more small molecules; and
 (d) comparing the first and second spectra to determine differences between the first and the second spectra, wherein the differences are indicative of one or more small molecules that have bound to the polypeptide.

26. A host cell comprising a nucleic acid encoding a polypeptide comprising: (a) an amino acid sequence set forth in SEQ ID NO: 2 or SEQ ID NO: 4; (b) an amino acid sequence having at least about 95% identity with the amino acid sequence set forth in SEQ ID NO: 2 or SEQ ID NO: 4; or (c) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; wherein a culture of the host cell produces at least about 1 mg of the polypeptide per liter of culture and the polypeptide is at least about one-third soluble as measured by gel electrophoresis.

27. An isolated, recombinant polypeptide, comprising: (a) an amino acid sequence having at least about 90% identity with the amino acid sequence set forth in SEQ ID NO: 4; or (b) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; and wherein the polypeptide comprises one or more of the following amino acid residues at the specified position of the polypeptide: A95, M99, Q155, N156, P192, K199, L196, A97, F204, Y147, Y157, V201, G202, I207, S197, V154, M160, L102, F96, and K164.

28. A method for obtaining structural information of a crystallized polypeptide, the method comprising:
 (a) crystallizing a recombinant polypeptide, wherein the polypeptide comprises: (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus; and wherein the crystallized polypeptide is capable of diffracting X-rays to a resolution of 3.5 Å or better; and
 (b) analyzing the crystallized polypeptide by X-ray diffraction to determine the three-dimensional structure of at least a portion of the crystallized polypeptide.

29. The method of paragraph 28, wherein the three-dimensional structure of the portion of the crystallized polypeptide is determined to a resolution of 3.5 Å or better.

30. A method for identifying a druggable region of a polypeptide, the method comprising:
 (a) obtaining crystals of a polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from S. aureus, such that the three dimensional structure of the crystallized polypeptide may be determined to a resolution of 3.5 Å or better;
 (b) determining the three dimensional structure of the crystallized polypeptide using X-ray diffraction; and
 (c) identifying a druggable region of the crystallized polypeptide based on the three-dimensional structure of the crystallized polypeptide.

31. The method of paragraph 30, wherein the druggable region is an active site.

32. The method of paragraph 31, wherein the druggable region is on the surface of the polypeptide.

33. Crystalline enoyl-[acyl-carrier-protein] reductase (NADH) from *S. aureus* comprising a crystal having unit cell dimensions a=82.2 Å, b=79.1 Å, c=93.6 Å, α=γ=90°, β=97.6°, with space group $P2_1$.

34. A crystallized polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*; wherein the crystal has a $P2_1$ space group.

35. A crystallized polypeptide comprising a structure of a polypeptide that is defined by a substantial portion of the atomic coordinates set forth in FIG. 9.

36. A method for determining the crystal structure of a homolog of a polypeptide, the method comprising:
(a) providing the three dimensional structure of a first crystallized polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*;
(b) obtaining crystals of a second polypeptide comprising an amino acid sequence that is at least 70% identical to the amino acid sequence set forth in SEQ ID NO: 2 or SEQ ID NO: 4, such that the three dimensional structure of the second crystallized polypeptide may be determined to a resolution of 3.5 Å or better; and
(c) determining the three dimensional structure of the second crystallized polypeptide by x-ray crystallography based on the atomic coordinates of the three dimensional structure provided in step (a).

37. The method of paragraph 36, wherein the atomic coordinates for the second crystallized polypeptide have a root mean square deviation from the backbone atoms of the first polypeptide of not more than 1.5 Å for all backbone atoms shared in common with the first polypeptide and the second polypeptide.

38. A method for homology modeling a homolog of enoyl-[acyl-carrier-protein] reductase (NADH) from *S. aureus*, comprising:
(a) aligning the amino acid sequence of a homolog of enoyl-[acyl-carrier-protein] reductase (NADH) from *S. aureus* with an amino acid sequence of SEQ ID NO: 2 or SEQ ID NO: 4 and incorporating the sequence of the homolog of enoyl-[acyl-carrier-protein] reductase (NADH) from *S. aureus* into a model of enoyl-[acyl-carrier-protein] reductase (NADH) from *S. aureus* derived from structure coordinates as listed in FIG. 9 to yield a preliminary model of the homolog of enoyl-[acyl-carrier-protein] reductase (NADH) from *S. aureus*;
(b) subjecting the preliminary model to energy minimization to yield an energy minimized model;
(c) remodeling regions of the energy minimized model where stereochemistry restraints are violated to yield a final model of the homolog of enoyl-[acyl-carrier-protein] reductase (NADH) from *S. aureus*.

39. A method for obtaining structural information about a molecule or a molecular complex of unknown structure comprising:
(a) crystallizing the molecule or molecular complex;
(b) generating an x-ray diffraction pattern from the crystallized molecule or molecular complex;
(c) applying at least a portion of the structure coordinates set forth in FIG. 9 to the x-ray diffraction pattern to generate a three-dimensional electron density map of at least a portion of the molecule or molecular complex whose structure is unknown.

40. A method for attempting to make a crystallized complex comprising a polypeptide and a modulator having a molecular weight of less than 5 kDa, the method comprising:
(a) crystallizing a polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*; such that crystals of the crystallized polypeptide will diffract x-rays to a resolution of 5 Å or better; and
(b) soaking the crystals in a solution comprising a potential modulator having a molecular weight of less than 5 kDa.

41. A method for incorporating a potential modulator in a crystal of a polypeptide, comprising placing a crystal of enoyl-[acyl-carrier-protein] reductase (NADH) from *S. aureus* having unit cell dimensions a=82.2 Å, b=79.1 Å, c=93.6 Å, α=γ=90°, β=97.6°, with space group $P2_1$ in a solution comprising the potential modulator.

42. A computer readable storage medium comprising digitally encoded structural data, wherein the data comprises structural coordinates as listed in FIG. 9 for the backbone atoms of at least about six amino acid residues from a druggable region of enoyl-[acyl-carrier-protein] reductase (NADH) from *S. aureus*.

43. A scalable three-dimensional configuration of points, at least a portion of the points derived from some or all of the structure coordinates as listed in FIG. 9 for a plurality of amino acid residues from a druggable region of enoyl-[acyl-carrier-protein] reductase (NADH) from *S. aureus*.

44. The scalable three-dimensional configuration of points of paragraph 43, wherein the structure coordinates as listed in FIG. 9 for the backbone atoms of at least about five amino acid residues from a druggable region of enoyl-[acyl-carrier-protein] reductase (NADH) from *S. aureus* are used to derive part or all of the portion of points.

45. The scalable three-dimensional configuration of points of paragraph 43, wherein the structure coordinates as listed in FIG. 9 for the backbone and optionally the side chain atoms of at least about ten amino acid residues from a druggable region of enoyl-[acyl-carrier-protein] reductase (NADH) from *S. aureus* are used to derive part or all of the portion of points.

46. The scalable three-dimensional configuration of points of paragraph 43, wherein the structure coordinates as listed in FIG. 9 for the backbone atoms of at least about fifteen amino acid residues from a druggable region of enoyl-[acyl-carrier-protein] reductase (NADH) from *S. aureus* are used to derive part or all of the portion of points.

47. The scalable three-dimensional configuration of points of paragraph 43, wherein substantially all of the points are derived from structure coordinates as listed in FIG. 9.

48. The scalable three-dimensional configuration of points of paragraph 43, wherein the structure coordinates as listed in FIG. 9 for the atoms of the amino acid residues from any of the above-described druggable regions of enoyl-[acyl-carrier-protein] reductase (NADH) from *S. aureus* are used to derive part or all of the portion of points:

49. A scalable three-dimensional configuration of points, comprising points having a root mean square deviation of less than about 1.5 Å from the three dimensional coordinates as listed in FIG. 9 for the backbone atoms of at least five amino acid residues, wherein the five amino acid residues are from a druggable region of enoyl-[acyl-carrier-protein] reductase (NADH) from *S. aureus*.

50. The scalable three-dimensional configuration of points of paragraph 49, wherein any point-to-point distance, calculated from the three dimensional coordinates as listed in FIG. 9, between one of the backbone atoms for one of the five amino acid residues and another backbone atom of a different one of the five amino acid residues is not more than about 10 Å.

51. A scalable three-dimensional configuration of points comprising points having a root mean square deviation of less than about 1.5 Å from the three dimensional coordinates as listed in FIG. 9 for the atoms of the amino acid residues from any of the above-described druggable regions of enoyl-[acyl-carrier-protein] reductase (NADH) from *S. aureus*:

52. A computer readable storage medium comprising digitally encoded structural data, wherein the data comprise the identity and three-dimensional coordinates as listed in FIG. 9 for the atoms of the amino acid residues from any of the above-described druggable regions of enoyl-[acyl-carrier-protein] reductase (NADH) from *S. aureus*:

53. A scalable three-dimensional configuration of points, wherein the points have a root mean square deviation of less than about 1.5 Å from the three dimensional coordinates as listed in FIG. 9 for the atoms of the amino acid residues from any of the above-described druggable regions of enoyl-[acyl-carrier-protein] reductase (NADH) from *S. aureus*, wherein up to one amino acid residue in each of the regions may have a conservative substitution thereof.

54. A scalable three-dimensional configuration of points derived from a druggable region of a polypeptide, wherein the points have a root mean square deviation of less than about 1.5 Å from the three dimensional coordinates as listed in FIG. 9 for the backbone atoms of at least ten amino acid residues that participate in the intersubunit contacts of enoyl-[acyl-carrier-protein] reductase (NADH) from *S. aureus*.

55. A computer-assisted method for identifying an inhibitor of the activity of enoyl-[acyl-carrier-protein] reductase (NADH) from *S. aureus*, comprising:
(a) supplying a computer modeling application with a set of structure coordinates as listed in FIG. 9 for the atoms of the amino acid residues from any of the above-described druggable regions of enoyl-[acyl-carrier-protein] reductase (NADH) from *S. aureus* so as to define part or all of a molecule or complex;
(b) supplying the computer modeling application with a set of structure coordinates of a chemical entity; and
(c) determining whether the chemical entity is expected to bind to or interfere with the molecule or complex.

56. The method of paragraph 55, wherein determining whether the chemical entity is expected to bind to or interfere with the molecule or complex comprises performing a fitting operation between the chemical entity and a druggable region of the molecule or complex, followed by computationally analyzing the results of the fitting operation to quantify the association between the chemical entity and the druggable region.

57. The method of paragraph 55, further comprising screening a library of chemical entities.

58. A computer-assisted method for designing an inhibitor of enoyl-[acyl-carrier-protein] reductase (NADH) activity comprising:
(a) supplying a computer modeling application with a set of structure coordinates having a root mean square deviation of less than about 1.5 Å from the structure coordinates as listed in FIG. 9 for the atoms of the amino acid residues from any of the above-described druggable regions of enoyl-[acyl-carrier-protein] reductase (NADH) from *S. aureus* so as to define part or all of a molecule or complex;
(b) supplying the computer modeling application with a set of structure coordinates for a chemical entity;
(c) evaluating the potential binding interactions between the chemical entity and the molecule or complex;
(d) structurally modifying the chemical entity to yield a set of structure coordinates for a modified chemical entity; and
(e) determining whether the modified chemical entity is an inhibitor expected to bind to or interfere with the molecule or complex, wherein binding to or interfering with the molecule or molecular complex is indicative of potential inhibition of enoyl-[acyl-carrier-protein] reductase (NADH) activity.

59. The method of paragraph 58, wherein determining whether the modified chemical entity is an inhibitor expected to bind to or interfere with the molecule or complex comprises performing a fitting operation between the chemical entity and the molecule or complex, followed by computationally analyzing the results of the fitting operation to evaluate the association between the chemical entity and the molecule or complex.

60. The method of paragraph 58, wherein the set of structure coordinates for the chemical entity is obtained from a chemical library.

61. A computer-assisted method for designing an inhibitor of enoyl-[acyl-carrier-protein] reductase (NADH) activity de novo comprising:
(a) supplying a computer modeling application with a set of three-dimensional coordinates derived from the structure coordinates as listed in FIG. 9 for the atoms of the amino acid residues from any of the above-described druggable regions of enoyl-[acyl-carrier-protein] reductase (NADH) from *S. aureus* so as to define part or all of a molecule or complex;
(b) computationally building a chemical entity represented by a set of structure coordinates; and
(c) determining whether the chemical entity is an inhibitor expected to bind to or interfere with the molecule or complex, wherein binding to or interfering with the molecule or complex is indicative of potential inhibition of enoyl-[acyl-carrier-protein] reductase (NADH) activity.

62. The method of paragraph 61, wherein determining whether the chemical entity is an inhibitor expected to bind to or interfere with the molecule or complex comprises performing a fitting operation between the chemical entity and a druggable region of the molecule or complex, followed by computationally analyzing the results of the fitting operation to quantify the association between the chemical entity and the druggable region.

63. The method of any of paragraphs 55, 58 or 61, further comprising supplying or synthesizing the potential inhibitor, then assaying the potential inhibitor to determine whether it inhibits enoyl-[acyl-carrier-protein] reductase (NADH) activity.

64. A method for identifying a potential modulator for the prevention or treatment of a *S. aureus* related disease or disorder, the method comprising:

(a) providing the three dimensional structure of a crystallized polypeptide comprising: (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*;

(b) obtaining a potential modulator for the prevention or treatment of *S. aureus* related disease or disorder based on the three dimensional structure of the crystallized polypeptide;

(c) contacting the potential modulator with a second polypeptide comprising: (i) an amino acid sequence set forth in SEQ ID NO: 2 or SEQ ID NO: 4; (ii) an amino acid sequence having at least about 95% identity with the amino acid sequence set forth in SEQ ID NO: 2 or SEQ ID NO: 4; or (iii) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*; which second polypeptide may optionally be the same as the crystallized polypeptide; and (d) assaying the activity of the second polypeptide, wherein a change in the activity of the second polypeptide indicates that the compound may be useful for prevention or treatment of a *S. aureus* related disease or disorder.

65. A method for designing a candidate modulator for screening for inhibitors of a polypeptide, the method comprising:

(a) providing the three dimensional structure of a druggable region of a polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*; and (b) designing a candidate modulator based on the three dimensional structure of the druggable region of the polypeptide.

66. A method for identifying a potential modulator of a polypeptide from a database, the method comprising:

(a) providing the three-dimensional coordinates for a plurality of the amino acids of a polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*;

(b) identifying a druggable region of the polypeptide; and (c) selecting from a database at least one potential modulator comprising three dimensional coordinates which indicate that the modulator may bind or interfere with the druggable region.

67. The method of paragraph 66, wherein the modulator is a small molecule.

68. A method for preparing a potential modulator of a druggable region contained in a polypeptide, the method comprising:

(a) using the atomic coordinates for the backbone atoms of at least about six amino acid residues from a polypeptide of SEQ ID NO: 4, with a ±a root mean square deviation from the backbone atoms of the amino acid residues of not more than 1.5 Å, to generate one or more three-dimensional structures of a molecule comprising a druggable region from the polypeptide;

(b) employing one or more of the three dimensional structures of the molecule to design or select a potential modulator of the druggable region; and (c) synthesizing or obtaining the modulator.

69. An apparatus for determining whether a compound is a potential modulator of a polypeptide, the apparatus comprising:

(a) a memory that comprises:

(i) the three dimensional coordinates and identities of at least about fifteen atoms from a druggable region of a polypeptide comprising (1) an amino acid sequence set forth in SEQ ID NO: 2 or SEQ ID NO: 4; (2) an amino acid sequence having at least about 95% identity with the amino acid sequence set forth in SEQ ID NO: 2 or SEQ ID NO: 4; or (3) an amino acid sequence encoded by a polynucleotide that hybridizes under stringent conditions to the complementary strand of a polynucleotide having SEQ ID NO: 1 or SEQ ID NO: 3 and has at least one biological activity of enoyl-[acyl-carrier-protein] reductase (NADH) from *S. aureus*;

(ii) executable instructions; and (b) a processor that is capable of executing instructions to:

(i) receive three-dimensional structural information for a candidate modulator;

(ii) determine if the three-dimensional structure of the candidate modulator is complementary to the three dimensional coordinates of the atoms from the druggable region; and (iii) output the results of the determination.

70. A method for making an inhibitor of enoyl-[acyl-carrier-protein] reductase (NADH) activity, the method comprising chemically or enzymatically synthesizing a chemical entity to yield an inhibitor of enoyl-[acyl-carrier-protein] reductase (NADH) activity, the chemical entity having been identified during a computer-assisted process comprising supplying a computer modeling application with a set of structure coordinates of a molecule or complex, the molecule or complex comprising at least a portion of at least one druggable region from enoyl-[acyl-carrier-protein] reductase (NADH) from *S. aureus*; supplying the computer modeling application with a set of structure coordinates of a chemical entity; and determining whether the chemical entity is expected to bind or to interfere with the molecule or complex at a druggable region, wherein binding to or interfering with the molecule or complex is indicative of potential inhibition of enoyl-[acyl-carrier-protein] reductase (NADH) activity.

71. A computer readable storage medium comprising digitally encoded data, wherein the data comprises structural coordinates for a druggable region that is structurally homologous to the structure coordinates as listed in FIG. 9 for a druggable region of enoyl-[acyl-carrier-protein] reductase (NADH) from *S. aureus*.

72. A computer readable storage medium comprising digitally encoded structural data, wherein the data comprise a majority of the three-dimensional structure coordinates as listed in FIG. 9.

73. The computer readable storage medium of paragraph 72, further comprising the identity of the atoms for the majority of the three-dimensional structure coordinates as listed in FIG. 9.

74. The computer readable storage medium of paragraph 72, wherein the data comprise substantially all of the three-dimensional structure coordinates as listed in FIG. 9.

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Isolation and Cloning of Nucleic Acid

*Staphylococcus aureus* is a Gram-positive cocci that is implicated in a wide number of skin infections, and is of particular concern in hospitals and other health institutions. The high virulence of the organism and the ability of many strains to resist numerous anti-microbial agents, presents difficult therapeutic issues. *S. aureus* polynucleotide sequences were obtained from The Institute of Genomic Research (TIGR) (Rockville, Md.; www.tigr.org). *S. aureus* genomic DNA is extracted from a crushed cell pellet (strain ColA) and subjected to 10% sucrose and 2% SDS in a 60° C. water bath, followed by the addition of 1 M NaCl for a 40 minute incubation on ice. Impurities, including RNA and proteins, are removed by enzymatic degradation via RNAse and phenol-chloroform extractions, respectively. The DNA is then precipitated, washed with ethanol, and quantified by UV absorption.

The coding sequences of the subject nucleic acid sequences (predicted) are obtained by reference to either publicly available databases or from the use of a bioinformatics program that is used to select the coding sequence of interest from the applicable genome. For example, bioinformatics programs that may be used to select the coding sequence of interest from the genome of *S. aureus* include that described in Nucleic Acids Research, 1999, 27:4636-4641 and the ContigExpress and Translate functionalities of Vector NTI Suite (InforMax).

The coding DNA is amplified from purified genomic DNA using PCR with primers that are identified with a computer program. The PCR primers are selected so as to introduce restriction enzyme cleavage sites at the flanking regions of the DNA (e.g., Nde1 and BglII). The forward and reverse primers have SEQ ID NO: 5 and SEQ ID NO: 6. The sequences of the primers are shown in FIG. 5, and their respective restriction sites and melting temperatures are shown in Table 1 of FIG. 6.

The PCR reaction is performed using 50-100 ng of chromosomal DNA and 2 Units of a high fidelity DNA Polymerase (for example Pfu Turbo (Stratagene) or Platinum Pfx (Invitrogen)). The thermocycling conditions for the PCR process include a DNA melting step at 94° C. for 45 sec, a primer annealing step at 48° C.-58° C. (depending on Primer [Tm]) for 45 sec, and an extension step at 68° C.-72° C. (depending on enzyme) for 1 min 45 sec-2 min 30 sec (depending on size of DNA). After 25-30 cycles, a final blocking step at 72° C. for 9 min is carried out.

The amplified nucleic acid product is isolated from the PCR cocktail using silica-gel membrane based column chromatography (Qiagen). The quality of the PCR product is assessed by resolving an aliquot of amplified product on a 1% agarose gel. The DNA is quantified spectrophotometrically at $A_{260}$ or by visualizing the resolved genes with a 302 nm UV-B light source.

The PCR product is directionally cloned into the polylinker region of any of three expression vectors: pET28 (Novagen), pET15 (Novagen) or pGEX (Pharmacia/LKB Biotechnology). Additional restriction enzyme sites may be engineered into the expressions vectors to allow for simultaneous clones to be prepared having different purification tags. After the ligation reaction, the DNA is transformed into competent *E. coli* cells (Strains XL1-Blue (Stratagene) or DH5α (Invitrogen)) via heat shock or electroporation as described in Sambrook, et al., Molecular Cloning: A Laboratory Manual, $2^{nd}$ Ed., Cold Spring Harbor Laboratory Press, Cold Spring Harbor, N.Y. (1989). The expression vectors contain the bacteriophage T7 promoter for RNA polymerase, and the *E. coli* strain used produces T7 RNA polymerase upon induction with isopropyl-β-D-thiogalactoside (IPTG). The sequence of the cloning site adds a Glutathione S-transferase (GST) tag, or a polyhistidine (6×His) tag (SEQ ID NO: 25), at the N- or C-terminus of the recombinant protein. The cloning site also inserts a cleavage site for the thrombin or Tev (Invitrogen) enzymes between the recombinant protein and the N- or C-terminal GST or polyhistidine tag.

Transformants are selected using the appropriate antibiotic (Ampicillin or Kanamycin) and identified using PCR, or another method, to analyze their DNA. The polynucleotide sequence cloned into the expression construct is then isolated using a modified alkaline lysis method (Birnboim, H. C., and Doly, J. (1979) *Nucl. Acids Res.* 7, 1513-1522.) The sequence of the clone is verified by standard polynucleotide sequencing methods. The published nucleic acid and amino acid sequences are presented in FIG. 1 and FIG. 2. The experimentally determined nucleic acid sequence is presented in FIG. 3, and the amino acid sequence predicted from the sequence of FIG. 3 is presented in FIG. 4.

The expression construct is transformed into a bacterial host strain BL21-Gold (DE3) supplemented with a plasmid called pUBS520, which directs expression of tRNA for arginine (agg and aga) and serves to augment the expression of the recombinant protein in the host cell (Gene, vol. 85 (1989) 109-114). The expression construct may also be transformed into BL21-Gold (DE3) without pUBS520, BL21-Gold (DE3) Codon-Plus (RIL) or (RP) (Stratagene) or Roseatta (DE3) (Novagen), the latter two of which contain genes encoding tRNAs. Alternatively, the expression construct may be transformed into BL21 STAR *E. coli* (Invitrogen) cells which has an Rnase deficiency that reduces degradation of recombinant mRNA transcript and therefore increases the protein yield. The recombinant protein is then assayed for positive overexpression in the host and the presence of the protein in the cytoplasmic (water soluble) region of the cell.

Example 2

Test Protein Expression and Solubility (a) Test Expression

Transformed cells are grown in LB medium supplemented with the appropriate antibiotics up to a final concentration of 100 μg/ml. The cultures are shaken at 37° C. until they reach an optical density ($OD_{600}$) between 0.6 and 0.7. The cultures are then induced with isopropyl-beta-D-thiogalactopyranoside (IPTG) to a final concentration of 0.5 mM at 15° C. for 10 hours, 25° C. for 4 hours, or 30° C. for 4 hours.

(b) Method One for Determining Protein Solubility Levels

The cells are harvested by centrifugation and subjected to a freeze/thaw cycle. The cells are lysed using detergent, sonication, or incubation with lysozyme. Total and soluble proteins are assayed using a 26-well BioRad Criterion gel running system. The proteins are stained with an appropriate dye (Coomassie, Silver stain, or Sypro-Red) and visualized with the appropriate visualization system. Typically, recombinant protein is seen as a prominent band in the lanes of the gel representing the soluble fraction.

(c) Method Two for Determining Protein Solubility Levels

The soluble and insoluble fractions (in the presence of 6M urea) of the cell pellet are bound to the appropriate affinity column. The purified proteins from both fractions are analysed by SDS-PAGE and the levels of protein in the soluble fraction are determined.

The approximate percent solubility of the polypeptide having the sequence of SEQ ID NO: 4 is determined using one of the foregoing methods, and the resulting percent solubility is presented in Table 1 of FIG. 6.

Example 3

Native Protein Expression

The expression construct clone encoding the soluble polypeptide having the amino acid sequence of SEQ ID NO: 4 is introduced into an expression host. The resultant cell line is then grown in culture. The method of growth is dependant on whether the protein to be purified is a native protein or a labeled protein. For native and $^{15}$N labeled protein production, a Gold-pUBS520 (as described above), BL21-Gold (DE3) Codon-Plus (RIL) or (RP), or BL21 STAR E. Coli cell line is used. For generating proteins metabolically labeled with selenium, the clone is introduced into a strain called B834 (Novagen). The methods for expressing labeled polypeptides of the invention are described in the Examples that follow.

In one method for expressing an unlabeled polypeptide of the invention, 2 L LB cultures or 1 L TB cultures are inoculated with a 1% (v/v) starter culture ($OD_{600}$ of 0.8). The cultures are shaken at 37° C. and 200 rpm and grown to an $OD_{600}$ of 0.6-0.8 followed by induction with 0.5 mM IPTG at 15° C. and 200 rpm for at least 10 hours or at 25° C. for 4 hours.

The cells are harvested by centrifugation and the pellets are resuspended in 25 ml HEPES buffer (50 mM, pH 7.5), supplemented with 100 µl of protease inhibitors (PMSF and benzamidine (Sigma)) and flash-frozen in liquid nitrogen.

Alternatively, for an unlabeled polypeptide of the invention, a starter culture is prepared in a 300 mL Tunair flask (Shelton Scientific) by adding 20 mL of medium having 47.6 g/L of Terrific Broth and 1.5% glycerol in $dH_2O$ followed by autoclaving for 30 minutes at 121° C. and 15 psi. When the broth cools to room temperature, the medium is supplemented with 6.3 µM $CoCl_2\text{-}6H_2O$, 33.2 µM $MnSO_4\text{-}5H_2O$, 5.9 µM $CuCl_2\text{-}2H_2O$, 8.1 µM $H_3BO_3$, 8.3 µM $Na_2MoO_4\text{-}2H_2O$, 7 µM $ZnSO_4\text{-}7H_2O$, 108 µM $FeSO_4\text{-}7H_2O$, 68 µM $CaCl_2\text{-}2H_2O$, 4.1 µM $AlCl_3\text{-}6H_2O$, 8.4 µM $NiCl_2\text{-}6H_2O$, 1 mM $MgSO_4$, 0.5% v/v of Kao and Michayluk vitamins mix (Sigma; Cat. No. K3129), 25 µg/mL Carbenicillin, and 50 µg/mL Kanamycin. The medium is then inoculated with several colonies of the freshly transformed expression construct of interest. The culture is incubated at 37° C. and 260 rpm for about 3 hours and then transferred to a 2.5 L Tunair Flask containing 1 L of the above media. The 1 L culture is then incubated at 37° C. with shaking at 230-250 rpm on an orbital shaker having a 1 inch orbital diameter. When the culture reaches an $OD_{600}$ of 3-6 it is induced with 0.5 mM IPTG. The induced culture is then incubated at 15° C. with shaking at 230-250 rpm or faster for about 6-15 hours. The cells are harvested by centrifugation at 3500 rpm at 4° C. for 20 minutes and the cell pellet is resuspended in 15 mL ice cold binding buffer (Hepes 50 mM, pH 7.5) and 100 µl of protease inhibitors (50 mM PMSF and 100 mM Benzamidine, stock concentration) and flash frozen.

Example 4

Expression of Selmet Labeled Polypeptides

The freshly transformed cell, harboring a plasmid with a nucleic acid encoding a polypeptide of the invention, is inoculated into 20 ml of NMM (New Minimal Medium) and shaken at 37° C. for 8-9 hours. This culture is then transferred into a 6 L Erlenmeyer flask containing 2 L of minimum medium (M9). The media is supplemented with all amino acids except methionine. All amino acids are added as a solution except for Tyrosine, Tryptophan and Phenylalanine which are added to the media in powder format. As well the media is supplemented with $MgSO_4$ (2 mM final concentration), $FeSO_4.7H_2O$ (25 mg/L final concentration), Glucose (0.4% final concentration), $CaCl_2$ (0.1 mM final concentration) and Seleno-L-Methionine (40 mg/L final concentration). When the $OD_{600}$ of the cell culture reaches 0.8-0.9, IPTG (0.4 mM final concentration) is added to the medium for protein induction, and the cell culture is kept shaking at 15° C. for 10 hours. The cells are harvested by centrifugation at 3500 rpm at 4° C. for 20 minutes and the cell pellet is resuspended in 15 mL cold binding buffer (Hepes 50 mM, pH 7.5) and 100 µl of protease inhibitors (PMSF and Benzamidine) and flash frozen.

Alternatively, a starter culture is prepared in a 300 mL Tunair flask (Shelton Scientific) by adding 50 mL of sterile medium having 10% 10×M9 (37.4 mM $NH_4Cl$ (Sigma; Cat. No. A4514), 44 mM $KH_2PO_4$ (Bioshop, Ontario, Canada; Cat. No. PPM 302), 96 mM $Na_2HPO_4$ (Sigma; Cat. No. S2429256), and 96 mM $Na_2HPO_4 7H_2O$ (Sigma; Cat. No. S9390) final concentration), 450 µM alanine, 190 µM arginine, 302 µM asparagine, 300 µM aspartic acid, 330 µM cysteine, 272 µM glutamic acid, 274 µM glutamine, 533 µM glycine, 191 µM histidine, 305 µM isoleucine, 305 µM leucine, 220 µM lysine, 242 µM phenylalanine, 348 µM proline, 380 µM serine, 336 µM threonine, 196 µM tryptophan, 220 µM tyrosine, and 342 µM valine, 204 µM Seleno-L-Methionine (Sigma; Cat. No. S3132), 0.5% v/v of Kao and Michayluk vitamins mix (Sigma; Cat. No. K3129), 2 mM $MgSO_4$ (Sigma; Cat. No. M7774), 90 µM $FeSO_47H_2O$ (Sigma; Cat. No. F8633), 0.4% glucose (Sigma; Cat. No. G-5400), 100 µM $CaCl_2$ (Bioshop, Ontario, Canada; Cat. No. CCL 302), 50 µg/mL Ampicillin, and 50 µg/mL Kanamycin in $dH_2O$. The medium is then inoculated with several colonies of E. coli B834 cells (Novagen) freshly transformed with an expression construct clone encoding the polypeptide of interest. The culture is then incubated at 37° C. and 200 rpm until it reaches an $OD_{600}$ of ~1 and is then transferred to a 2.5 L Tunair Flask containing 1 L of the above media. The 1 L culture is incubated at 37° C. with shaking at 200 rpm until the culture reaches an $OD_{600}$ of 0.6-0.8 and is then induced with 0.5 mM IPTG. The induced culture is incubated overnight at 15° C. with shaking at 200 rpm. The cells are harvested by centrifugation at 4200 rpm at 4° C. for 20 minutes and the cell pellet is resuspended in 15 mL ice cold binding buffer (Hepes 50 mM, pH 7.5) and 100 µl of protease inhibitors (50 mM PMSF and 100 mM Benzamidine, stock concentration) and flash frozen.

Alternatively, the cell harboring a plasmid with a nucleic acid encoding a polypeptide of the invention is inoculated into 10 ml of M9 minimum medium and kept shaking at 37° C. for 8-9 hours. This culture is then transferred into a 2 L Baffled Flask (Corning) containing 1 L minimum medium. The media is supplemented with all amino acids except methionine. All are added as a solution, except for Phenylalanine, Alanine, Valine, Leucine, Isoleucine, Proline, and Tryptophan which are added to the media in powder format. As well the media is supplemented with $MgSO_4$ (2 mM final concentration), $FeSO_4 7H_2O$ (25 mg/L final concentration), Glucose (0.5% final concentration), $CaCl_2$ (0.1 mM final concentration) and Seleno-Methionine (50 mg/L final concentration). When the $OD_{600}$ of the cell culture reaches 0.8-0.9, IPTG (0.8 mM final concentration) is added to the medium for protein induction, and the cell culture is kept shaking at 25° C. for 4 hours. The cells are harvested by centrifuged at 3500 rpm at 4° C. for 20 minutes and the cell pellet is resuspended in 10 mL cold binding buffer (Hepes 50 mM, pH 7.5) and 100 µl of protease inhibitors (PMSF and Benzamidine) and flash frozen.

Example 5

Expression of $^{15}N$ Labeled Polypeptides

The cell, harboring a plasmid with a nucleic acid encoding a polypeptide of the invention, is inoculated into 2 L of minimal media (containing $^{15}N$ isotope, Cambridge Isotope Lab) in a 6 L Erlenmeyer flask. The minimal media is supplemented with 0.01 mM $ZnSO_4$, 0.1 mM $CaCl_2$, 1 mM $MgSO_4$, 5 mg/L Thiamine.HCl, and 0.4% glucose. The 2 L culture is grown at 37° C. and 200 rpm to an $OD_{600}$ of between 0.7-0.8. The culture is then induced with 0.5 mM IPTG and allowed to shake at 15° C. for 14 hours. The cells are harvested by centrifugation and the cell pellet is resuspended in 15 mL cold binding buffer and 100 µl of protease inhibitor and flash frozen. The protein is then purified as described below.

Alternatively, the freshly transformed cell, harboring a plasmid with the gene of interest, is inoculated into 10 mL of M9 media (with $^{15}N$ isotope) and supplemented with with 0.01 mM $ZnSO_4$, 0.1 mM $CaCl_2$, 1 mM $MgSO_4$, 5 mg/L Thiamine.HCl, and 0.4% glucose. After 8-10 hours of growth at 37° C., the culture is transferred to a 2 L Baffled flask (Corning) containing 990 mL of the same media. When $OD_{600}$ of the culture is between 0.7-0.8, protein production is initiated by adding IPTG to a final concentration of 0.8 mM and lowering the temperature to 25° C. After 4 hours of incubation at this temperature, the cells are harvested, and the cell pellet is resuspended in 10 mL cold binding buffer (Hepes 50 mM, pH 7.5) and 100 µl of protease inhibitor and flash frozen.

Example 6

Method One for Purifying Polypeptides of the Invention

The frozen pellets are thawed and sonicated to lyse the cells (5×30 seconds, output 4 to 5, 80% duty cycle, in a Branson Sonifier, VWR). The lysates are clarified by centrifugation at 14,000 rpm for 60 min at 4° C. to remove insoluble cellular debris. The supernatants are removed and supplemented with 1 µl of Benzonase Nuclease (25 U/µl, Novagen).

The recombinant protein is purified using DE52 (anion exchanger, Whatman) and Ni-NTA columns (Qiagen). The DE52 columns (30 mm wide, Biorad) are prepared by mixing 10 grams of DE52 resin in 25 ml of 2.5 M NaCl per protein sample, applying the resin to the column and equilibrating with 30 ml of binding buffer (50 mM in HEPES, pH 7.5, 5% glycerol (v/v), 0.5 M NaCl, 5 mM imidazole). Ni-NTA columns are prepared by adding 3.5-8 ml of resin to the column (20 mm wide, Biorad) based on the level of expression of the recombinant protein and equilibrating the column with 30 ml of binding buffer. The columns are arranged in tandem so that the protein sample is first passed over the DE52 column and then loaded directly onto the Ni-NTA column.

The Ni-NTA columns are washed with at least 150 ml of wash buffer (50 M HEPES, pH 7.5, 5% glycerol (v/v), 0.5 M NaCl, 30 mM imidazole) per column. A pump may be used to load and/or wash the columns. The protein is eluted off of the Ni-NTA column using elution buffer (50 mM in HEPES, pH 7.5, 5% glycerol (v/v), 0.5 M NaCl, 250 mM imidazole) until no more protein is observed in the aliquots of eluate as measured using Bradford reagent (Biorad). The eluate is supplemented with 1 mM of EDTA and 0.2 mM DTT.

The samples are assayed by SDS-PAGE and stained with Coomassie Blue, with protein purity determined by visual staining.

Two methods may be used to remove the His tag located at either the C or N-terminus. In certain instances, the His tag may not be removed. In either case, the expressed polypeptide will have additional residues attributable to the His tag, as shown in the following table:

| SEQ ID NO for Additional Residues | Additional Residues | Type of Tag and Whether or Not Removed |
|---|---|---|
| N/A | GSH | His tag removed from N-terminus |
| SEQ ID NO:7 | MGSSHHHHHHSSGLVPRGSH | His tag not removed from N-terminus |
| SEQ ID NO:8 | GSENLYFQGHHHHHH | His tag not removed from C-terminus |
| SEQ ID NO:9 | GSENLYFQ | His tag removed from C-terminus |

In method one, a sample of purified polypeptide is supplemented with 2.5 mM $CaCl_2$ and an appropriate amount of thrombin (the amount added will vary depending on the activity of the enzyme preparation) and incubated for ~20-30 minutes on ice in order to remove the His tag. In method two, a sample of purified polypeptide is combined with thirty units of recombinant TEV protease in 50 mmol TRIS HCl pH=8.0, 0.5 mmol EDTA and 1 mmol DTT, followed by incubation at 4° C. overnight, to remove the His tag.

The protein sample is then dialyzed in dialysis buffer (10 mM HEPES, pH 7.5, 5% glycerol (v/v) and 0.5 M NaCl) for at least 8 hours using a Slide-A-Lyzer (Pierce) appropriate for the molecular weight of the recombinant protein. An aliquot of the cleaved and dialyzed samples is then assayed by SDS-PAGE and stained with Coomassie Blue to determine the purity of the protein and the success of cleavage.

The remainder of the sample is centrifuged at 2700 rpm at 4° C. for 10-15 minutes to remove any precipitant and supplemented with 100 µl of protease inhibitor cocktail (0.1 M benzamidine and 0.05 M PMSF) (NO Bioshop). The protein is then applied to a second Ni-NTA column (~8 ml of resin) to remove the His-tags and eluted with binding buffer or wash buffer until no more protein is eluting off the column as assayed using the Bradford reagent. The eluted sample is supplemented with 1 mM EDTA and 0.6 mM of DTT and concentrated to a final volume of ~15 mls using a Millipore Concentrator with an appropriately sized filter at 2700 rpm at 4° C. The samples are then dialyzed overnight against crystallization buffer and concentrated to final volume of 0.3-0.7 ml.

Example 7

Method Two for Purifying Polypeptides of the Invention

The frozen pellets are thawed and supplemented with 100 µl of protease inhibitor (0.1 M benzamidine and 0.05 M PMSF), 0.5% CHAPS, and 4 U/ml Benzonase Nuclease. The sample is then gently rocked on a Nutator (VWR, setting 3) at room temperature for 30 minutes. The cells are then lysed by sonication (1×30 seconds, output 4 to 5, 80% duty cycle, in a Branson Sonifier, VWR) and an aliquot is saved for a gel sample.

The recombinant protein is purified using a three column system. The columns are set up in tandem so that the lysate flows from a Biorad Econo (5.0×30 cm×589 ml) "lysate" column onto a Biorad Econo (2.5×20 cm×98 ml) DE52 column and finally onto a Biorad Econo (1.5×15 cm×27 ml) Ni-NTA column. The lysate is mixed with 10 g of equilibrated DE52 resin and diluted to a total volume of 300 ml with binding buffer. This mixture is poured into the first column which is empty. The remainder of the purification procedure is described in EXAMPLE 6 above.

Example 8

Method Three for Purifying Polypeptides of the Invention

The frozen pellets are thawed and sonicated to lyse the cells (5×30 seconds, output 4 to 5, 80% duty cycle, in a Branson Sonifier, VWR). The lysates are clarified by centrifugation at 14000 rpm for 60 min at 4° C. to remove insoluble cellular debris. The supernatants are removed and supplemented with 1 µl of Benzonase Nuclease (25 U/µl, Novagen).

The recombinant protein is purified using DE52 (anion exchanger, Whatman) and Glutathione sepharose columns (Glutathione-Superflow resin, Clontech). The DE52 columns (30 mm wide, Biorad) are prepared by mixing 10 grams of DE52 resin in 20 ml of 2.5 M NaCl per protein sample, applying the resin to the column and equilibrating with 30 ml of loading buffer (50 mM in HEPES, pH 7.5, 10% glycerol (v/v), 0.5 M NaCl, 1 mM EDTA, 1 mM DTT). Glutathione sepharose columns are prepared by adding 3 ml of resin to the column (20 mm wide, Biorad) and equilibrating the column with 30 ml of loading buffer. The columns are arranged in tandem so that the protein sample is first passed over the DE52 column and then loads directly onto the Glutathione sepharose column.

The columns are washed with at least 150 ml of loading buffer supplemented with protease inhibitor cocktail (0.1 M benzamidine and 0.05 M PMSF) per column. A pump may be used to load and/or wash the columns. The protein is eluted off of the Glutathione sepharose column using elution buffer (20 mM HEPES, pH 7.5, 0.5 M NaCl, 1 mM EDTA, 1 mM DTT; 25 mM glutathione (reduced form)) until no more protein is observed in the aliquots of eluate as measured using Biorad Bradford reagent.

The GST tag may be removed using thrombin or other procedures known in the art. The protein samples are then dialyzed into crystallization buffer (10 mM Hepes, pH 7.5, 500 mM NaCl) to remove free glutathione and assayed by SDS-PAGE followed by staining with Coomassie blue. Prior to use or storage, the samples are concentrated to final volume of 0.3-0.5 ml.

Using one or more of the methods described above, purified polypeptide having SEQ ID NO: 4 is obtained in a yield of approximately 72 mg per liter of culture. The purified polypeptide is essentially the only protein visualized in the SDS-PAGE assay using Coomassie Blue described above, which is at least about 95% or greater purity. The polypeptide so expressed and purified is His tagged (having sequence MGSSHHHHHHSSGLVPRGSH) (SEQ ID NO: 7) at the N-terminus.

The protein samples so prepared and purified may be used in the biophysical studies that follow, with or without the His tag or the residual amino acids resulting from removal of the His tag. In certain instances, such as EXAMPLE 12, the polypeptide used may be a fusion protein with a specific tag.

A stable solution of purified polypeptide having SEQ ID NO: 4, prepared and purified as described above, may be prepared with 22.5 mg (or a lesser amount) of protein in one ml of either the dialysis or crystallization buffers (or possibly both) described above in EXAMPLE 7 or EXAMPLE 9, respectively.

Certain of the foregoing information is also set forth in Table 1 of FIG. 6.

For certain polypeptides of the invention, truncated polypeptides are prepared. Truncated polypeptides are generated via a "shot gun" approach whereby 1 to about 15 or more residues may be deleted from the N and/or C termini of the polypeptide of interest in a sequential pattern, in a variety of combinations of deletions. Alternatively, truncated polypeptides may be prepared by rational design, using multiple sequence alignments of the protein and other orthologues, secondary structure prediction and tertiary structure of a related protein (if available) as guiding tools. In such cases, from 1 to about 20 amino acids or more may be deleted from the N and/or C termini. Truncated constructs are PCR amplified from genomic DNA and cloned into expression vectors as described above for the various pathogens. Truncation constructs are then tested for expression and solubility as described above. The most highly expressed and soluble truncated polypeptides may be subject to further purification and characterization as provided herein.

Example 9

Mass Spectrometry Analysis via Fingerprint Mapping

A gel slice from a purification protocol described above containing a polypeptide of the invention is cut into 1 mm cubes and 10 to 20 µl of 1% acetic acid is added. After washing with 100-150 µl HPLC grade water and removal of the liquid, acetonitrile (~200 µl, approximately 3 to 4 times the volume of the gel particles) is added followed by incubation at room temperature for 10 to 15 minutes with vortexing. A second acetonitrile wash may be required to completely dehydrate the gel particles. The protein in the gel particles is reduced at 50 degrees Celsius using 10 mM dithiothreitol (in 100 mM ammonium bicarbonate) and then alkylated at room temperature in the dark using 55 mM iodoacetamide (in 100 mM ammonium bicarbonate). The gel particles are rinsed with a minimal volume of 100 mM ammonium bicarbonate before a trypsin (50 mM ammonium bicarbonate, 5 mM $CaCl_2$, and 12.5 ng/µl trypsin) solution is added. The gel particles are left on ice for 30 to 45 minutes (after 20 minutes incubation more trypsin solution is added). The excess trypsin solution is removed and 10 to 15 µl digestion buffer without trypsin is added to ensure the gel particles remain hydrated during digestion. After digestion at 37° C., the supernatant is removed from the gel particles. The peptides are extracted from the gel particles with 2 changes of 100 µl of 100 mM ammonium bicarbonate with shaking for 45 minutes and pooled with the initial gel supernatant. The extracts are acidified to 1% (v/v) with 100% acetic acid.

The tryptic peptides are purified with a C18 reverse phase resin. 250 µL of dry resin is washed twice with methanol and twice with 75% acetonitrile/1% acetic acid. A 5:1 slurry of solvent:resin is prepared with 75% acetonitrile/1% acetic acid. To the extracted peptides, 2 µL of the resin slurry is added and the solution is shaken for 30 minutes at room temperature. The supernatant is removed and replaced with 200 µL of 2% acetonitrile/1% acetic acid and shaken for 5-15 minutes. The supernatant is removed and the peptides are eluted from the resin with 15 µL of 75% acetonitrile/1% acetic acid with shaking for about 5 minutes. The peptide and slurry mixture is applied to a filter plate and centrifuged, and the filtrate is collected and stored at −70° C. until use.

Alternatively, the tryptic peptides are purified using Zip-Tip$_{C18}$ (Millipore, Cat #ZTC18S960). The ZipTips are first pre-wetted by aspirating and dispensing 100% methanol. The tips are then washed with 2% acetonitrile/1% acetic acid (5 times), followed by 65% acetonitrile/1% acetic (5 times) and returned to 2% acetonitrile/1% acetic (10 times). The digested peptides are bound to the ZipTips by aspirating and dispensing the samples 5 times. Salts are removed by washing ZipTips with 2% acetonitrile/1% acetic acid (5 times). 10 µL of 65% acetonitrile/1% acetic acid is collected by the ZipTips and dispensed into a 96-well microtitre plate.

Analytical samples containing tryptic peptides are subjected to MALDI-TOF mass spectrometry. Samples are mixed 1:1 with a matrix of α-cyano-4-hydroxy-trans-cinnamic acid. The sample/matrix mixture is spotted on to the MALDI sample plate with a robot, either a Gilson 215 liquid handler or BioMek FX laboratory automation workstation (Beckman). The sample/matrix mixture is allowed to dry on the plate and is then introduced into the mass spectrometer. Analysis of the peptides in the mass spectrometer is conducted using both delayed extraction mode (400 ns delay) and an ion reflector to ensure high resolution of the peptides.

Internally-calibrated tryptic peptide masses are searched against databases using a correlative mass matching algorithm. The Proteometrics software package (ProteoMetrics) is utilized for batch database searching of tryptic peptide mass spectra. Statistical analysis is performed on each protein match to determine its validity. Typical search constraints include error tolerances within 0.1 Da for monoisotopic peptide masses, carboxyamidomethylation of cysteines, no oxidation of methionines allowed, and 0 or 1 missed enzyme cleavages. The software calculates the probability that a candidate in the database search is the protein being analyzed, which is expressed as the Z-score. The Z-score is the distance to the population mean in unit of standard deviation and corresponds to the percentile of the search in the random match population. If a search is in the 95th percentile, for example, about 5% of random matches could yield a higher Z-score than the search. A Z-score of 1.282 for a search indicates that the search is in the 90th percentile, a Z-score of 1.645 indicates that the search is in the 95th percentile, a Z-score of 2.326 indicates that the search is in the 99th percentile, and a Z-score of 3.090 indicates that the search is in the 99.9th percentile.

Example 10

Mass Spectrometry Analysis Via High Mass

A matrix solution of 25 mg/mL of 3,5-dimethoxy-4-hydroxycinnamic acid (sinapinic acid) in 66% (v/v) acetonitrile/1% (v/v) acetic acid is prepared along with an internal calibrant of carbonic anhydrase. On to a stainless steel polished MALDI target, 1.5 µL of a protein solution (concentration of 2 µg/µL) is spotted, followed immediately by 1.5 µL of matrix. 3 µL of 40% (v/v) acetonitrile/1% (v/v) acetic acid is then added to each spot has dried. The sample is either spotted manually or utilizing a Gilson 215 liquid handler or BioMek FX laboratory automation workstation (Beckman). The MALDI-TOF instrument utilizes positive ion and linear detection modes. Spectra are acquired automatically over a mass to charge range from 0-150,000 Da, pulsed ion extraction delay is set at 200 ns, and 600 summed shots of 50-shot steps are completed.

The theoretical molecular weight of the protein for MALDI-TOF is determined from its amino acid sequence, taking into account any purification tag or residue thereof still present and any labels (e.g., selenomethionine or $^{15}N$). To account for $^{15}N$ incorporation, an amount equal to the theoretical molecular weight of the protein divided by 70 is added. The mass of water is subtracted from the overall molecular weight. The MALDI-TOF spectrum is calibrated with the internal calibrant of carbonic anhydrase (observed as either $[MH^+_{avg}]$ 29025 or $[MH_2^{2+}]$ 14513).

Example 11

Method One for Isolating and Identifying Interacting Proteins (a) Method One for Preparation of Affinity Column Micro-columns are prepared using forceps to bend the ends of P200 pipette tips and adding 10 µl of glass beads to act as a column frit. Six micro-columns are required for every polypeptide to be studied. The micro-columns are placed in a 96-well plate that has 1 mL wells. Next, a series of solutions of the polypeptide having SEQ ID NO: 4 or other polypeptide of the invention, prepared and purified as described above and with a GST tag on either terminus, is prepared so as to give final amounts of 0, 0.1, 0.5, 1.0, and 2.0 mg of ligand per ml of resin volume.

A slurry of Glutathione-Sepharose 4B (Amersham) is prepared and 0.5 ml slurry/ligand is removed (enough for six 40-µg aliquots of resin). Using a glass frit Buchner funnel, the resin is washed sequentially with three 10 ml portions each of distilled $H_2O$ and 1 M ACB (20 mM HEPES pH 7.9, 1 M NaCl, 10% glycerol, 1 mM DTT, and 1 mM EDTA). The Glutathione-Sepharose 4B is completely drained of buffer, but not dried. The Glutathione-Sepharose 4B is resuspended as a 50% slurry in 1 M ACB and 80 µl is added to each micro-column to obtain 40 µg/column. The buffer containing the ligand concentration series is added to the columns and allowed to flow by gravity. The resin and ligand are allowed to cross-link overnight at 4° C. In the morning, micro-columns are washed with 100 µl of 1 M ACB and allowed to flow by gravity. This is repeated twice more and the elutions are tested for cross-linking efficiency by measuring the amount of unbound ligand. After washing, the micro-columns are equilibrated using 200 µl of 0.1 M ACB (20 mM HEPES pH 7.5, 0.1 M NaCl, 10% glycerol, 1 mM DTT, 1 mM EDTA).

In another method, the recombinant GST fusion protein can be replaced by a hexa-histidine fusion peptide for use with NTA-Agarose (Qiagen) as the solid support. No adaptation to the above protocol is required for the substitution of NTA agarose for GST Sepharose except that the recombinant protein requires a six histidine fusion peptide in place of the GST fusion.

(b) Method Two for Preparation of Affinity Column

In an alternative method, GST-Sepharose 4B may be replaced by Affi-gel 10 Gel (Bio-Rad). The column resin for affinity chromatography could also be Affigel 10 resin which allows for covalent attachment of the protein ligand to the micro affinity column. An adaptation to the above protocol for the use of this resin is a pre-wash of the resin with 100% isopropanol. No fusion peptides or proteins are required for the use of Affigel 10 resin.

(c) Method One for Bacterial Extract Preparation

A S. aureus extract is prepared from cell pellets using nuclease and lysostaphin digestion followed by sonication. A S. aureus cell pellet (12 g) is suspended in 12 ml of 20 mM HEPES pH 7.5, 150 mM NaCl, 10% glycerol, 10 mM $MgSO_4$, 10 mM $CaCl_2$, 1 mM DTT, 1 mM PMSF, 1 mM benzamidine, 1000 units of lysostaphin, 0.5 mg RNAse A, 750 units micrococcal nuclease, and 375 units DNAse I. The cell suspension is incubated at 37° C. for 30 minutes, cooled to 4° C., and brought to a final concentration of 1 mM EDTA and 500 mM NaCl. The lysate is sonicated on ice using three bursts of 20 seconds each. The lysate is centrifuged at 20,000 rpm for 1 hr in a Ti70 fixed angle Beckman rotor. The supernatant is removed and dialyzed overnight in a 10,000 Mr dialysis membrane against dialysis buffer (20 mM HEPES pH 7.5, 10% glycerol, 1 mM DTT, 1 mM EDTA, 100 mM NaCl, 10 mM $MgSO_4$, 10 mM $CaCl_2$, 1 mM benzamidine, and 1 mM PMSF). The dialyzed protein extract is removed from the dialysis tubing and frozen in one ml aliquots at −70° C.

(d) Method Two for Bacterial Extract Preparation

Bacterial cell extracts from S. aureus are prepared from cell pellets using a Bead-Beater apparatus (Bio-spec Products Inc.) and zirconia beads (0.1 mm diameter). The bacterial cell pellet is suspended (~6 g) is suspended in 3 pellet volumes (~20 ml final volume) of 20 mM HEPES pH 7.5, 150 mM NaCl, 10% glycerol, 10 mM $MgSO_4$, 10 mM $CaCl_2$, 1 mM DTT, 1 mM PMSF, 1 mM benzamidine, 40 µg/ml RNAse A, 75 units/ml S1 nuclease, and 40 units/ml DNAse 1. The cells are lysed with 10 pulses of 30 sec between 90 sec pauses at a temperature of −5° C. The lysate is separated from the zirconia beads using a standard column apparatus. The lysate is centrifuged at 20000 rpm (48000×g) in a Beckman JA25.50 rotor. The supernatant is removed and dialyzed overnight at 4° C. against dialysis buffer (20 mM HEPES pH 7.5, 10% glycerol, 1 mM DTT, 1 mM EDTA, 100 mM NaCl, 10 mM $MgSO_4$, 10 mM $CaCl_2$, 1 mM benzamidine, and 1 mM PMSF). The dialyzed protein extract is removed from the dialysis tubing and frozen in one ml aliquots at −70° C.

(e) HeLa Cell Extract Preparation

A HeLa cell extract is prepared in the presence of protease inhibitors. Approximately 30 g of Hela cells are submitted to a freeze/thaw cycle and then divided into two tubes. To each tube 20 ml of Buffer A (10 mM HEPES pH 7.9, 1.5 mM MgCl, 10 mM KCl, 0.5 mM DTT, 0.5 mM PMSF) and a protease inhibitor cocktail are added. The cell suspension is homogenized with 10 strokes (2×5 strokes) to lyse the cells. Buffer B (15 ml per tube) is added (50 mM HEPES pH 7.9, 1.5 mM MgCl, 1.26 M NaCl, 0.5 mM DTT, 0.5 mM PMSF, 0.5 mM EDTA, 75% glycerol) to each tube followed by a second round of homogenization (2×5 strokes). The lysates are stirred on ice for 30 minutes followed by centrifugation 37,000 rpm for 3 hr at 4° C. in a Ti70 fixed angle Beckman rotor. The supernatant is removed and dialyzed overnight in a 10,000 Mr dialysis membrane against dialysis buffer (20 mM HEPES pH 7.9, 10% glycerol, 1 mM DTT, 1 mM EDTA, and 1 M NaCl. The dialyzed protein extract is removed from the dialysis tubing and frozen in one ml aliquots at −70° C.

(f) Affinity Chromatography

Cell extract is thawed and diluted to 5 mg/ml prior to loading 5 column volumes onto each micro-column. Each column is washed with 5 column volumes of 0.1 M ACB. This washing is repeated once. Each column is then washed with 5 column volumes of 0.1 M ACB containing 0.1% Triton X-100. The columns are eluted with 4 column volumes of 1% sodium dodecyl sulfate into a 96 well PCR plate. To each eluted fraction is added one-tenth volume of 10-fold concentrated loading buffer for SDS-PAGE.

(g) Resolution of the Eluted Proteins and Detection of Bound Proteins

The components of the eluted samples are resolved on SDS-polyacrylamide gels containing 13.8% polyacrylamide using the Laemmli buffer system and stained with silver nitrate. The bands containing the interacting protein are excised with a clean scalpel. The gel volume is kept to a minimum by cutting as close to the band as possible. The gel slice is placed into one well of a low protein binding, 96-well round-bottom plate. To the gel slices is added 20 µl of 1% acetic acid.

Example 12

Method Two for Isolating and Identifying Interacting Proteins

Interacting proteins may be isolated using immunoprecipitation. Naturally-occurring bacterial or eukaryotic cells are grown in defined growth conditions or the cells can be genetically manipulated with a protein expression vector. The protein expression vector is used to transiently transfect the cDNA of interest into eukaryotic or prokaryotic cells and the protein is expressed for up to 24 or 48 hours. The cells are harvested and washed three times in sterile 20 mM HEPES (pH7.4)/Hanks balanced salts solution (H/H). The cells are finally resuspended in culture media and incubated at 37° C. for 4-8 hr.

The harvested cells may be subjected to one or more culture conditions that may alter the protein profile of the cells for a given period of time. The cells are collected and washed with ice-cold H/H that includes 10 mM sodium pyrophosphate, 10 mM sodium fluoride, 10 mM EDTA, and 1 mM sodium orthovanadate. The cells are then lysed in lysis buffer (50 mM Tris-HCl (pH 8.0), 150 mM NaCl, 1% Triton X-100, 10 mM sodium pyrophosphate, 10 mM sodium fluoride, 10 mM EDTA, 1 mM sodium orthovanadate, 1 µg/mL PMSF, 1 µg/mL aprotinin, 1 µg/mL leupeptin, and 1 µg/mL pepstatin A) by gentle mixing, and placed on ice for 5 minutes. After lysis, the lysate is transferred to centrifuge tubes and centrifuged in an ultracentrifuge at 75000 rpm for 15 min at 4° C. The supernatant is transferred to eppendorf tubes and pre-cleared with 10 µl of rabbit pre-immune antibody on a rotator at 4° C. for 1 hr. Forty µl of protein A-Sepharose (Amersham) is then added and incubated at 4° C. overnight on a rotator.

The protein A-Sepharose beads are harvested and the supernatant removed to a fresh eppendorf tube. Immune antibody is added to supernatant and rotated for 1 hr at 4° C. Thirty µl of protein A-Sepharose is then added and the mixture is further rotated at 4° C. for 1 hr. The beads are harvested and the supernatant is aspirated. The beads are washed three times with 50 mM Tris (pH 8.0), 150 mM NaCl, 0.1% Triton X-100, 10 mM sodium fluoride, 10 mM sodium pyrophosphate, 10 mM sodium orthovanadate, and 10 mM EDTA. Dry the beads with a 50 µl Hamilton syringe. Laemmli loading buffer containing 100 mM DTT is added to the beads and samples are boiled for 5 min. The beads are spun down and the supernatant is loaded onto SDS-PAGE gels. Comparison of the control and experimental samples allows for the selection of polypeptides that interact with the protein of interest.

Example 13

Sample for Mass Spectrometry of Interacting Proteins

The gel slices are cut into 1 mm cubes and 10 to 20 µl of 1% acetic acid is added. The gel particles are washed with 100-150 µl of HPLC grade water (5 minutes with occasional mixing), briefly centrifuged, and the liquid is removed. Acetonitrile (~200 µl, approximately 3 to 4 times the volume of the gel particles) is added followed by incubation at room temperature for 10 to 15 minutes with vortexing. A second acetonitrile wash may be required to completely dehydrate the gel particles. The sample is briefly centrifuged and all the liquid is removed.

The protein in the gel particles is reduced at 50 degrees Celsius using 10 mM dithiothreitol (in 100 mM ammonium bicarbonate) for 30 minutes and then alkylated at room temperature in the dark using 55 mM iodoacetamide (in 100 mM ammonium bicarbonate). The gel particles are rinsed with a minimal volume of 100 mM ammonium bicarbonate before a trypsin (50 mM ammonium bicarbonate, 5 mM $CaCl_2$, and 12.5 ng/µl trypsin) solution is added. The gel particles are left on ice for 30 to 45 minutes (after 20 minutes incubation more trypsin solution is added). The excess trypsin solution is removed and 10 to 15 µl digestion buffer without trypsin is added to ensure the gel particles remain hydrated during digestion. The samples are digested overnight at 37° C.

The following day, the supernatant is removed from the gel particles. The peptides are extracted from the gel particles with 2 changes of 100 µL of 100 mM ammonium bicarbonate with shaking for 45 minutes and pooled with the initial gel supernatant. The extracts are acidified to 1% (v/v) with 100% acetic acid.

(a) Method One for Purification of Tryptic Peptides

The tryptic peptides are purified with a C18 reverse phase resin. 250 µL of dry resin is washed twice with methanol and twice with 75% acetonitrile/1% acetic acid. A 5:1 slurry of solvent:resin is prepared with 75% acetonitrile/1% acetic acid. To the extracted peptides, 2 µL of the resin slurry is added and the solution is shaken at moderate speed for 30 minutes at room temperature. The supernatant is removed and replaced with 200 µL of 2% acetonitrile/1% acetic acid and shaken for 5-15 minutes with moderate speed. The supernatant is removed and the peptides are eluted from the resin with 15 µL of 75% acetonitrile/1% acetic acid with shaking for about 5 minutes. The peptide and slurry mixture is applied to a filter plate and centrifuged for 1-2 minutes at 1000 rpm, the filtrate is collected and stored at −70° C. until use.

(b) Method Two for Purification of Tryptic Peptides

Alternatively, the tryptic peptides may be purified using ZipTip$_{C18}$ (Millipore, Cat # ZTC18S960). The ZipTips are first pre-wetted by aspirating and dispensing 100% methanol 5 times. The tips are then washed with 2% acetonitrile/1% acetic acid (5 times), followed by 65% acetonitrile/1% acetic (5 times) and returned to 2% acetonitrile/1% acetic acid (5 times). The ZipTips are replaced in their rack and the residual solvent is eliminated. The ZipTips are washed again with 2% acetonitrile/1% acetic acid (5 times). The digested peptides are bound to the ZipTips by aspirating and dispensing the samples 5 times. Salts are removed by washing ZipTips with 2% acetonitrile/1% acetic acid (5 times). 10 µL of 65% acetonitrile/1% acetic acid is collected by the ZipTips and dispensed into a 96-well microtitre plate. 1 µL of sample and 1 µL of matrix are spotted on a MALDI-TOF sample plate for analysis.

Example 14

Mass Spectrometric Analysis of Interacting Proteins (a) Method One for Analysis of Tryptic Peptides Analytical samples containing tryptic peptides are subjected to Matrix Assisted Laser Desorption/Ionization Time Of Flight (MALDI-TOF) mass spectrometry. Samples are mixed 1:1 with a matrix of α-cyano-4-hydroxy-trans-cinnamic acid. The sample/matrix mixture is spotted on to the MALDI sample plate with a robot. The sample/matrix mixture is allowed to dry on the plate and is then introduced into the mass spectrometer. Analysis of the peptides in the mass spectrometer is conducted using both delayed extraction mode and an ion reflector to ensure high resolution of the peptides.

Internally-calibrated tryptic peptide masses are searched against both in-house proprietary and public databases using a correlative mass matching algorithm. Statistical analysis is performed on each protein match to determine its validity. Typical search constraints include error tolerances within 0.1 Da for monoisotopic peptide masses and carboxyamidomethylation of cysteines. Identified proteins are stored automatically in a relational database with software links to SDS-PAGE images and ligand sequences.

(b) Method Two for Analysis of Tryptic Peptides

Alternatively, samples containing tryptic peptides are analyzed with an ion trap instrument. The peptide extracts are first dried down to approximately 1 µL of liquid. To this, 0.1% trifluoroacetic acid (TFA) is added to make a total volume of approximately 5 µL. Approximately 1-2 µL of sample are injected onto a capillary column (C8, 150 µm ID, 15 cm long) and run at a flow rate of 800 µL/min. using the following gradient program:

| Time (minutes) | % Solvent A | % Solvent B |
| --- | --- | --- |
| 0 | 95 | 5 |
| 30 | 65 | 35 |
| 40 | 20 | 80 |
| 41 | 95 | 5 |

Where Solvent A is composed of water/0.5% acetic acid and Solvent B is acetonitrile/0.5% acetic acid. The majority of the peptides will elute between the 20-40% acetonitrile gradient. Two types of data from the eluting HPLC peaks are acquired with the ion trap mass spectrometer. In the MS[1] dimension, the mass to charge range for scanning is set at 400-1400—this will determine the parent ion spectrum. Secondly, the instrument has MS² capabilities whereby it will acquire fragmentation spectra of any parent ions whose intensities are detected to be greater than a predetermined threshold (Mann and Wilm, *Anal Chem* 66(24): 4390-4399 (1994)). A significant amount of information is collected for each protein sample as both a parent ion spectrum and many daughter ion spectra are generated with this instrumentation.

All resulting mass spectra are submitted to a database search algorithm for protein identification. A correlative mass algorithm is utilized along with a statistical verification of each match to identify a protein's identification (Ducret A, et al., *Protein Sci* 7(3): 706-719 (1998)). This method proves much more robust than MALDI-TOF mass spectrometry for identifying the components of complex mixtures of proteins.

No interacting proteins were observed using at least one of the methods described above.

Example 15

NMR Analysis

The purified protein sample is centrifuged at 13,000 rpm for 10 minutes with a bench-top microcentrifuge to eliminate any precipitated protein. The supernatant is then transferred into a clean tube and the sample volume is measured. If the sample volume is less than 450 µl, an appropriate amount of crystal buffer is added to the sample to reach that volume. Then 50 µl of $D_2O$ (99.9%) is added to the sample to make an NMR sample of 500 µl. The usual concentration of the protein sample is usually approximately 1 mmol or greater.

NMR screening experiments are performed on a Bruker AV600 spectrometer equipped with a cryoprobe, or other equivalent instrumentation. All spectra are recorded at 25° C. Standard ID proton pulse sequence with presaturation is used for ID screening. Normally, a sweepwidth of 6400 Hz, and eight or sixteen scans are used, although different pulse sequences are known to those of skill in the art and may be readily determined. For $^1H$, $^{15}N$ HSQC experiments, a pulse sequence with "flip-back" water suppression may be used. Typically, sweepwidths of 8000 Hz and 2000 Hz are used for F2 and F1 dimension, respectively. Four to sixteen scans are normally adequate. The data is then processed on a Sun Ultra 5 computer with NMRpipe software.

Example 16

X-Ray Crystallography (a) Crystallization

Suitable crystals for x-ray experimentation were obtained by sitting drop vapor diffusion against a 100 µl reservoir solution containing 24% PEG 4000, Na HEPES pH 7.5, 0.2M ammonium sulfate in a 96 well sitting plate format. 1.5 µl of 15 mg/ml protein was mixed with 1.5 mM NADPH, ½₀₀ DTT and 1.5 mM API-1135, and 1.5 µl reservoir solutions were set in each drop. These reservoir conditions are different from previously published conditions for the *E. coli* FabI complexes (Qiu et al., 1999 and GSK communication). The crystals were soaked for 1 minute in a solution consisting of three parts mother liquor (from the well of the drop) to one part glycerol, and were then frozen at 100K in a cold gas stream. The crystal diffracted to 3.0 Å. Data was collected from these crystals on our in house Bruker diffractometer equipped with Osmic confocal lenses and a SMART 6000 CCD. Data was processed using the Proteum software suite, integrated using Saint and scaled using Proscale. Crystals proved to be of the space group $P2_1$ with cell dimensions a=82.2 Å, b=79.1 Å, c=93.6 Å, $\alpha=\gamma=90°$, $\beta=97.6°$. Synchrotron data was obtained from Advanced Photon Source at Argonne National Labs, COM-CAT beamline equipped with a MAR CCD detector. All data were collected on crystals frozen in reservoir solution containing 20% glycerol at 100 K in a cold gas stream generated by an Oxford Cryostream crystal cooling device. Data were indexed, integrated and scaled using Mosflm (Powell 1999) and Scala (Potterton, McNicholas et al. 2002).

(b) Co-Crystallization

A variety of methods known in the art may be used for preparation of co-crystals comprising the subject polypeptides and one or more compounds that interact with the subject polypeptides, such as, for example, an inhibitor, co-factor, substrate, polynucleotide, polypeptide, and/or other molecule. In one exemplary method, crystals of the subject polypeptide may be soaked, for an appropriate period of time, in a solution containing a compound that interacts with a subject polypeptide. In another method, solutions of the subject polypeptide and/or compound that interacts with the subject polypeptide may be prepared for crystallization as described above and mixed into the above-described sitting drops. In certain embodiments, the molecule to be co-crystallized with the subject polypeptide may be present in the buffer in the sitting drop prior to addition of the solution comprising the subject polypeptide. In other embodiments, the subject polypeptide may be mixed with another molecule before adding the mixture to the sitting drop. Based on the teachings herein, one of skill in the art may determine the co-crystallization method yielding a co-crystal comprising the subject polypeptide.

(c) Heavy Atom Substitution

For preparation of crystals containing heavy atoms, crystals of the subject polypeptide may be soaked in a solution of a compound containing the appropriate heavy atom for such period as time as may be experimentally determined is necessary to obtain a useful heavy atom derivative for x-ray purposes. Likewise, for other compounds that may be of interest, including, for example, inhibitors or other molecules that interact with the subject polypeptide, crystals of the subject polypeptide may be soaked in a solution of such compound for an appropriate period of time.

(d) Data Collection and Processing

The *S. aureus* FabI complex structure was solved by molecular replacement using the coordinates of the protein dimer of the *E. coli* FabI API-1135 complex (sequence identity 42%) as the search model for molecular replacement using EPMR (Kissinger, Gehlhaar et al. 1999). The correlation coefficient using EPMR was 0.324 after placing two dimers in the asymmetric unit. Ten percent of the reflections being randomly excluded from the refinement, and used to monitor $R_{free}$ in CNX. The structure was rebuilt using TURBO-FRODO (Roussel A. and Cambillau C. (1989) TURBO-FRODO. Silicon Graphics Geometry Partner Directory, Silicon Graphics, Mountain View, Calif.). A maximum likelihood target (with a flat bulk solvent correction and no low resolution or sigma cutoff applied to the data) was used in the refinement protocol. NCS averaging was used during the refinement. Refinement of the model using simulated annealing torsion angle refinement and group temperature factor refinement protocol was alternated with manual inspection and rebuilding of the model using TURBO-FRODO. After several cycles of refinement and manual rebuilding, almost all of the protein has been modeled for all chains, with the exception of residue 1 for all chains and the N terminal histidine tag. In addition to the protein chain, it was found that a NADPH molecule and the inhibitor API-1135 are visible in each of the active sites. Six sulfate molecules were added to the model. 346 solvent molecules were picked manually using a combination of sigma A weighted 2Fo-Fc and Fo-Fc maps. A Ramachandran plot of the model shows no non-glycine residues within the disallowed regions, with N156 and N158, which lie in the generously allowed regions (due to hydrogen bonding contacts).

Structure solution and refined statistics for are reported in Tables 3 and 4, contained in FIG. 8. FIG. 9 contains a list of the atomic coordinates of the subject polypeptide and other molecules contained in the crystal. FIGS. 10 to 38 depict various features of the crystal structure and other properties of a subject polypeptide, as well as various inhibitors of FabI.

(e) Analysis of the X-ray Structure of the Subject Polypeptide

General Description of Structure and Druggable Regions

The functional *S. aureus* FabI protein forms a homotetramer in solution. There are 2 dimers in the asymmetric unit, with symmetry related molecules forming the tetramer. A large portion of each subunit of the tetramer is involved in intramolecular contacts. Two long helices from each of the monomers are involved in the formation of the tetramer. The contacts along the subunit interfaces may comprise druggable regions.

Each FabI subunit forms a single domain, with a core region which supports the cofactor. The overall fold of *S. aureus* FabI is composed of a seven-stranded parallel β-sheet flanked on each side by three α-helices with a further helix lying at the C terminus of the β-sheet. The cofactor is bound in an extended conformation at the COOH-terminal end of the β-sheet, with the nicotinamide ring lying deep in a pocket on the enzyme surface. A loop of the protein, termed here as the flipping loop (residues 193-203), covers the binding pocket. This configuration forms a deep crevice, hiding the inhibitor in the substrate binding site. The flipping loop may comprise a druggable region.

Structurally, FabI appears to be a typical example of the short-chain dehydrogenase/reductase (SDR) family. This family contains a wide variety of enzymes in organisms ranging from bacteria to mammals. These molecules share the common function of adding or removing hydrogen in a NAD(H)- or NADP(H)-dependent manner from specific substrates. These proteins, containing approximately 250 amino acids, exist as a tetramer and have an α/β structure with the signature Rossmann fold motif. This Rossmann fold creates a "topological switch point" at the carboxy termini of two central, strands, and the cleft formed at this point creates a nucleotide-binding site which binds the cofactor. Although this family is involved in a wide variety of biological processes and share a common fold, each is specific for a certain substrate. Substrate specificity is dictated by differences in amino acid sequence, particularly at the active site for substrate recognition.

Flexibility of the Flipping Loop

The electron density for the flipping loop is visible in the *S. aureus* FabI complex structure, forming a slightly opened helix-turn-helix conformation, and encompasses part of the inhibitor binding site (FIGS. 16 and 17). The flipping loop may be mobile and in this case, the ternary complex helps to order this part of the molecule. The structure of the ternary *E. coli* FabI A138G-NAD1-thienodiazaborine complex revealed that the part of the chain comprising the flipping loop is significantly shifted from the position observed in the binary complexes with NAD+ or NADH (Roujeinikova, Sedelnikova et al. 1999). In the new crystal form, this loop adopts a regular helical conformation, which forms an additional edge of the diazaborine-binding site and makes it less accessible to the solvent. This conformation also draws the residues A240 and A241 closer to the diazaborine so that now both their side-chain and main-chain atoms make extensive van der Waals contacts with the edge of the fused rings of the inhibitor.

Active Site and Other Druggable Regions

*S. aureus* FabI has a "U-shaped" binding site available for inhibitor or substrate binding above NADPH. One side of the cavity is open and exposed to solvent (termed here as the left hand side, above the adenine ribose of the NADPH) and the other side contains a small opening (termed here as the right hand side, above the nicotinamide ring of NADPH). Overall, the pocket is hydrophobic in nature, with many aromatic residues clustered on the left hand side of the binding pocket. The residues of the binding site may comprise a druggable region.

The specificity of API-1135 is evident in the binding mode between the inhibitor and protein molecule. The linking amide carbonyl of the inhibitor is well-positioned for a hydrogen bond interaction with the 2'-hydroxyl of NADPH and the hydroxyl of Y157. The central cis-amide fragment appears to participate in a π-stacking interaction with the nicotinamide portion of NADPH. The right hand side of the molecule makes specific, directional interactions with the protein while the left hand side of the molecule is nestled in a hydrophobic pocket. The peptide backbone of A97 is involved in hydrogen bond interactions that bind both the pyridylamine and the N-acyl hydrogen of the naphthyridinone functionality. The indole portion of the left hand side of API-1135 is flanked by lipophilic residues (I207, F204, Y157 and Y147) creating tight hydrophobic packing. Ordered solvent molecules are found on either side of the inhibitor, with solvent molecules on the left hand side forming a hydrogen bonding network with the protein. FIGS. 13 through 15, and FIGS. 18-24 depict various views of the mode of API-1135 binding and its binding pocket. The residues responsible for the binding of API-1135 may comprise a druggable region.

Specificity for NADPH

Studies have proposed that enoyl-[acyl-carrier-protein] reductase (ENR) from *E. coli* can utilize either NADH or NADPH as cofactors in the enzyme's catalytic cycle (Bergler et al., 1996) whilst *B. napus* and *M. tuberculosis* ENR can only utilize NADH (Slabas et al., 1986; Quemard et al., 1995) and *S. aureus* can only utilize NADPH. To investigate this, crystals of *E. coli* ENR were cocrystallized with NADP+, but had no interpretable density for the NADP+ cofactor (Baldock, Rafferty et al. 1998). In the absence of direct structural data for the mode of NADP+ binding to the *E. coli* enzyme, a superposition of the structures of *E. coli* ENR, *B. napus* ENR and *S. aureus* ENR can explain the apparent difference in cofactor specificity as resulting from variability in the residues near the adenine ribose. The residues near the nicotinamide ribose are highly conserved across species while the residues near the adenine ribose are not as well conserved. A positive charge from R40 may provide a stabilizing effect for the NADPH. The equivalent residue in *B. napus* ENR is a tryptophan, while in *E. coli* ENR the residue at this position is a glutamine. FIGS. 25 through 30 depicts various aspects of the NADPH binding pocket and mode of NADPH binding. Residues involved in binding NADPH and/or residues in the NADPH binding pocket may comprise a druggable region.

Substrate Binding Site

Most proteins of the SDR family contain the highly conserved catalytic $YX_3K$ sequence motif, which is usually present near the carboxy terminus of an α-helix. FabI however does not contain this sequence motif. Instead, the orientation of Y157 and K164 in the structure mimic those of the tyrosine and lysine involved in the YX₃K motif of the other proteins in the SDR family. Although the precise catalytic mechanism mediated by these residues is a matter of debate, it appears that the tyrosine and lysine residues are involved in actual catalysis (Chen, Jiang et al. 1993). According to this scheme, K164 and Y157 cooperate to catalyze a syn addition of hydrogen via a 2-Re, 3-Si attack on the double bond of crotonyl-ACP (Saito, Kawaguchi et al. 1981). This involves the hydride transfer from the C4 position of the NAD(P)H to the C-3 position at the double bond in the enoyl substrate. This leads to the formation of an enolate anion intermediate which can then be protonated on the oxygen atom to form an enol. Subsequent tautomerization of the enol would then lead to the production of the reduced acyl product. K164 (K163 in *E. coli*) is thought to be to stabilize the negative charge of the transition state and Y157 (Y156 in *E. coli*) is thought to be the proton donor to the enolate anion. Both of these residues are conserved in the sequences of a number of bacterial ENRs.

There is a patch of predominantly hydrophobic residues adjacent to the position of the nicotinamide ring and presumed to be important in binding the hydrophobic component of the growing fatty acid chain (Baldock, Rafferty et al. 1998). However, of the residues in this cluster (Y147, P192 and 1207), only P192 is completely conserved. In order to initiate modeling studies, coordinates for a butyryl-CoA moiety were taken from the X-ray crystallographic structure of acyl ACP (PDB entry 1L0H) and modeled into the active site of the *S. aureus* ENR-NADPH complex. The position of the butyryl CoA was selected such that the growing fatty acid chain is pointed out of the substrate binding pocket. This places the fatty acid chain near the conserved residues Q155 and P192 from one subunit and Y147, V154, N156 and I207 from a different subunit of the tetramer. The binding of the fatty acid substrate is not exclusively dependent on the attachment of the acyl group to ACP as acyl-CoAs also serve as substrate for enoyl reductase.

Insight into the key binding interactions and modes of ENR inhibitors extracted from the various inhibitor/ENR co-structures allow the modeling of bound natural enoyl substrate. The arrangement of the key residues around the nicotinamide moiety of the cofactor in the ENR active site and the mode of diazaborine binding to ENR allowed Roujeinikova et al. (Roujeinikova, Sedelnikova et al. 1999) to propose a model for the binding of the natural enoyl substrate. In this model, the acyl chain of enoyl ACP is placed above the nicotinamide ring of the cofactor in such a way that the double bond reduced by ENR during catalysis (between the C2 and C3 positions in the enoyl moiety of the substrate) lies over and parallel to the C4-C5 double bond in the nicotinamide ring, with the carbonyl group and the C2, C3, and C4 atoms of the enoyl moiety lying in the plane of the aromatic bicyclic ring of the various inhibitors. The angle formed between the C3 atom of the enoyl moiety of the substrate and the C4 and N1 atoms of the nicotinamide ring is close to 100°. With this arrangement of the modeled enoyl moiety of the substrate and the nicotinamide ring of the cofactor, the geometry requirements for hydride attack on the natural enoyl substrate are fulfilled. The proposed position of the carbonyl oxygen atom of the enoyl moiety is close to that of the oxygen atom in API-1135 and implies formation of the hydrogen bonds with both the 29-hydroxyl of the nicotinamide ribose and the phenolic oxygen of the catalytic Y157. In this mode of binding of the substrate, the panteheine moiety, covalently attached to the C1 atom of the enoyl moiety of the substrate, would fit into the tunnel formed by the protein residues 96-97, 160, and 197-201 and the atoms of the nicotinamide ribose. In the enzyme-substrate complex, the flipping loop might adopt a helical conformation, stabilizing the substrate bound to ENR through van der Waals contacts.

The residues involved in substrate binding, as discussed above, may comprise a druggable region.

Summary of Some Key Residues and Interactions

Table 5 summarizes the location and identity of important residues comprising the various catalytic domains of FabI from various bacterial species. Such residues may comprise a druggable region.

TABLE 5

| Location | SA Average conservation | E. coli | H. influenzae | P. aeruginosa | E. faecalis | S. aureus | S. epidermidis |
|---|---|---|---|---|---|---|---|
| Binding site[1] | 0.941 | G93 | A126 | A95 | A90 | A95 | A95 |
| Binding site | 0.609 | G97 | G130 | G99 | K94 | M99 | M99 |
| Binding site | 0.876 | P154 | P187 | P157 | P150 | Q155 | Q155 |
| Binding site | 1.000 | N155 | N188 | N158 | N151 | N156 | N156 |
| Binding site | 0.996 | P191 | P224 | P194 | A187 | P192 | P192 |
| Binding site | 0.807 | S198 | S231 | S201 | T194 | K199 | K199 |
| Binding site | 1.000 | L195 | L228 | L198 | L191 | L196 | L196 |
| Binding site | 1.000 | A95 | A128 | A97 | A92 | A97 | A97 |
| Binding site | 0.969 | F203 | F236 | F206 | Y199 | F204 | F204 |
| Binding site | 1.000 | Y146 | Y179 | Y149 | Y142 | Y147 | Y147 |
| Binding site | 1.000 | Y156 | Y189 | Y159 | Y152 | Y157 | T157 |
| Binding site | 0.945 | I200 | I233 | I203 | V196 | V201 | V201 |
| Binding site | 0.772 | K201 | K234 | K204 | K197 | G202 | G202 |

TABLE 5-continued

| Location | SA Average conservation | E. coli | H. influenzae | P. aeruginosa | E. faecalis | S. aureus | S. epidermidis |
|---|---|---|---|---|---|---|---|
| Binding site | 0.968 | M206 | M239 | M209 | L202 | I207 | I207 |
| Binding site | 0.967 | A196 | A229 | A199 | A192 | S197 | S197 |
| Binding site | 0.926 | I153 | I186 | M156 | I149 | V154 | V154 |
| Binding site | 1.000 | M159 | M192 | M162 | M155 | M160 | M160 |
| Binding site | 1.000 | L100 | L133 | L102 | L97 | L102 | L102 |
| Binding site | 1.000 | F94 | F127 | F96 | F91 | F96 | F96 |
| Binding site | 1.000 | K163 | K196 | K166 | K159 | K164 | K164 |
| Flipping loop | 0.912 | 192 IRTLAASGIKD 202 (SEQ ID NO: 19) | 225 IRTLAASGIKN 235 (SEQ ID NO: 20) | 195 IRTLAASGIKS 205 (SEQ ID NO: 21) | 188 IKTLAVTGVKD 198 (SEQ ID NO: 22) | 193 IRTLSAKGVGG 203 (SEQ ID NO: 23) | 193 IRTLSAKGVGG 203 (SEQ ID NO: 24) |

[1]Binding site of the inhibitor and not residues involved in binding NAD(P)

Table 6 summarizes the potential interaction sites in the binding pocket of S. aureus FabI. The residues in such sites may comprise a druggable region.

TABLE 6

| Binding Site No. | Amino Acid residue | Atom(s) involved | Atom no. in FIG. 9 | Binding Interaction[2] |
|---|---|---|---|---|
| 1 | A95 | O | 751 | HB |
| 2 | F96 | CG | 755 | HI |
|  |  | CD1 | 756 |  |
|  |  | CD2 | 757 |  |
|  |  | CE1 | 758 |  |
|  |  | CE2 | 759 |  |
|  |  | CZ | 760 |  |
| 3 | A97 | N | 763 | HB |
|  |  | O | 767 | HB |
| 4 | M99 | CG | 779 | HI |
|  |  | SD | 780 |  |
|  |  | CE | 781 |  |
| 5 | L102 | CB | 803 | HI |
|  |  | CG | 804 |  |
|  |  | CD1 | 805 |  |
|  |  | CD2 | 806 |  |
|  |  | O | 808 | HB |
| 6 | Y147 | CG | 1145 | HI |
|  |  | CD1 | 1146 |  |
|  |  | CE2 | 1147 |  |
|  |  | CD2 | 1148 |  |
|  |  | CE2 | 1149 |  |
|  |  | CZ | 1150 |  |
|  |  | OH | 1151 | HB |
| 7 | V154 | CB | 1197 | HI |
|  |  | CG1 | 1198 |  |
|  |  | CG2 | 1199 |  |
| 8 | Q155 | O | 1210 | HB |
| 9 | Y157 | CG | 1222 | HI |
|  |  | CD1 | 1223 |  |
|  |  | CE1 | 1224 |  |
|  |  | CD2 | 1225 |  |
|  |  | CE2 | 1226 |  |
|  |  | CZ | 1227 |  |
|  |  | OH | 1228 | HB |
| 10 | M160 | CG | 1249 | HI |
|  |  | SD | 1250 |  |
|  |  | CE | 1251 |  |

TABLE 6-continued

| Binding Site No. | Amino Acid residue | Atom(s) involved | Atom no. in FIG. 9 | Binding Interaction[2] |
|---|---|---|---|---|
| 11 | P192 | CD | 1477 | HI |
|  |  | CA | 1478 |  |
|  |  | CB | 1479 |  |
|  |  | CG | 1480 |  |
| 12 | L196 | O | 1516 | HB |
| 13 | S197 | OG | 1520 | HB |
|  |  | O | 1522 | HB |
| 14 | K199 | O | 1536 | HB |
| 15 | V201 | CB | 1543 | HI |
|  |  | CG1 | 1544 |  |
|  |  | CG2 | 1545 |  |
| 16 | G202 | N | 1552 | HB |
|  |  | O | 1555 | HB |
| 17 | F204 | CB | 1558 | HI |
|  |  | CG | 1559 |  |
|  |  | CD1 | 1560 |  |
|  |  | CD2 | 1561 |  |
|  |  | CE1 | 1562 |  |
|  |  | CE2 | 1563 |  |
|  |  | CZ | 1564 |  |
| 18 | I207 | CB | 1584 | HI |
|  |  | CG2 | 1585 |  |
|  |  | CG1 | 1586 |  |
|  |  | CD1 | 1587 |  |
| 19 | NAP301 | O2M | 7981 | HB |
|  |  | O3P | 7973 | HB |
|  |  | O1A | 7993 | HB |

[1]Atom number in FIG. 9 refers to chain A; this implies that corresponding residues in other chains are also interaction sites
[2]HB = Hydrogen bond; HI = Hydrophobic interaction Table 7 summarizes the location and identity of important residues comprising the various NADPH binding site in FabI from various bacterial species. Such residues may comprise a druggable region.

TABLE 7

| Location | SA Average[2] conservation | E. coli | H. influenzae | P. aeruginosa | E. faecalis | S. aureus | S. epidermidis |
|---|---|---|---|---|---|---|---|
| Binding site[1] | 1.000 | G13 | G46 | G13 | G12 | G13 | G13 |
| Binding site | 0.886 | V14 | L47 | V14 | V13 | I14 | I14 |
| Binding site | 1.000 | A15 | A48 | A15 | A14 | A15 | A15 |
| Binding site | 0.915 | S16 | S49 | S16 | N15 | N16 | N16 |
| Binding site | 0.805 | L18 | R51 | L18 | K17 | R18 | R18 |
| Binding site | 1.000 | S19 | S52 | S19 | S18 | S19 | S19 |
| Binding site | 1.000 | I20 | I53 | I20 | I19 | I20 | I20 |
| Binding site | 1.000 | A21 | A54 | A21 | A20 | A21 | A21 |
| Binding site | 0.753 | Q40 | L73 | Q40 | Q39 | R40 | R40 |
| Binding site | 0.881 | N41 | N74 | N41 | N40 | K41 | K41 |
| Binding site | 0.778 | L44 | L77 | L44 | M43 | S44 | S44 |
| Binding site | 0.732 | C63 | L96 | C65 | C60 | I65 | I65 |
| Binding site | 1.000 | D64 | D97 | D66 | D61 | D66 | D66 |
| Binding site | 1.000 | V65 | V98 | V67 | V62 | V67 | V67 |
| Binding site | 0.876 | A66 | A99 | A68 | A63 | Q68 | Q68 |
| Binding site | 0.918 | S91 | A124 | S93 | A88 | S93 | S93 |
| Binding site | 0.945 | I92 | I125 | V94 | I89 | I94 | I94 |
| Binding site | 0.941 | G93 | A126 | G95 | A90 | A95 | A95 |
| Binding site | 1.000 | F94 | F127 | F96 | F91 | F96 | F96 |
| Binding site | 1.000 | I119 | I152 | I121 | I115 | I120 | I120 |
| Binding site | 0.855 | L144 | L177 | L147 | L140 | T145 | T145 |
| Binding site | 0.942 | S145 | S178 | S148 | T141 | T146 | T146 |
| Binding site | 1.000 | Y146 | Y179 | Y149 | Y142 | Y147 | Y147 |
| Binding site | 1.000 | Y156 | Y189 | Y159 | Y152 | Y157 | Y157 |
| Binding site | 1.000 | M159 | M192 | M162 | M155 | M160 | M160 |
| Binding site | 1.000 | K163 | K196 | K166 | K159 | K164 | K164 |
| Binding site | 1.000 | A189 | A222 | A192 | A185 | A190 | A190 |
| Binding site | 1.000 | G190 | G223 | G193 | G186 | G191 | G191 |
| Binding site | 0.996 | P191 | P224 | P194 | A187 | P192 | P192 |
| Binding site | 1.000 | I192 | I225 | I195 | I188 | I193 | I193 |
| Binding site | 1.000 | T194 | T227 | T197 | T190 | T195 | T195 |
| Binding site | 1.000 | L195 | L228 | L198 | L191 | L196 | L196 |
| Binding site | 0.967 | A196 | A229 | A199 | A192 | S197 | S197 |
| Binding site | 0.969 | F203 | F236 | F206 | Y199 | F204 | F204 |

[1] Binding site of NADPH and not residues involved in binding the inhibitor
[2] Overall average conservation = 0.836; Std Deviation = 0.210

Table 8 summarizes the potential interaction sites for binding NADPH in S. aureus FabI. The residues in such sites may comprise a druggable region.

TABLE 8

| Binding Site No. | Amino Acid residue | Atom(s) involved | Atom no. in FIG. 9 | Binding Interaction[2] |
|---|---|---|---|---|
| 1 | G13 | O | 96 | HB |
| 2 | I14 | O | 104 | HB |
| 3 | N16 | OD1 | 114 | HB |
|   |   | ND2 | 115 | HB |
| 4 | R18 | O | 137 | HB |
| 5 | S19 | O | 143 | HB |
| 6 | I20 | N | 144 | HB |
|   |   | CB | 146 | HI |
|   |   | CG2 | 147 |   |
|   |   | CG1 | 148 |   |
|   |   | CD1 | 149 |   |
| 7 | R40 | N | 296 | HB |
|   |   | NH1 | 303 | HB |
|   |   | NH2 | 304 | HB |
| 8 | K41 | NZ | 313 | HB |
| 9 | S44 | OG | 339 | HB |
| 10 | I65 | O | 523 | HB |
| 11 | D66 | OD1 | 528 | HB |
|   |   | OD2 | 529 | HB |
| 12 | V67 | CB | 534 | HI |
|   |   | CG1 | 535 |   |
|   |   | CG2 | 536 |   |
| 13 | Q68 | N | 539 | HB |
|   |   | OE1 | 544 | HB |
| 14 | S93 | OG | 736 | HB |
|   |   | O | 738 | HB |
| 15 | I94 | CB | 741 | HI |
|   |   | CG2 | 742 |   |
|   |   | CG1 | 743 |   |
|   |   | CD1 | 744 |   |
| 16 | A95 | N | 747 | HB |
|   |   | O | 751 | HB |
| 17 | F96 | CB | 754 | HI |
|   |   | CG | 755 |   |
|   |   | CD1 | 756 |   |
|   |   | CD2 | 757 |   |
|   |   | CE1 | 758 |   |
|   |   | CE2 | 759 |   |
|   |   | CZ | 760 |   |
| 18 | I120 | CB | 949 | HI |
|   |   | CG2 | 950 |   |
|   |   | CG1 | 951 |   |
|   |   | CD1 | 952 |   |
| 19 | T145 | O | 1134 | HB |
| 20 | Y147 | CB | 1144 | HI |
|   |   | CG | 1445 |   |
|   |   | CD1 | 1146 |   |
|   |   | CE1 | 1147 |   |
|   |   | CD2 | 1148 |   |
|   |   | CE2 | 1149 |   |
|   |   | CZ | 1150 |   |
|   |   | OH | 1151 | HB |
| 21 | Y157 | OH | 1228 | HB |
| 22 | M160 | CB | 1248 | HI |
|   |   | CG | 1249 |   |
|   |   | SD | 1250 |   |
|   |   | CE | 1251 |   |
| 23 | K164 | CB | 1272 | HI |
|   |   | CG | 1273 |   |
|   |   | CD | 1274 |   |
|   |   | CE | 1275 |   |
|   |   | NZ | 1276 | HB |
| 24 | A190 | N | 1465 | HB |
|   |   | O | 1469 | HB |
| 25 | S191 | O | 1475 | HB |
| 26 | I193 | N | 1483 | HB |
|   |   | CB | 1485 | HI |
|   |   | CG2 | 1486 |   |
|   |   | CG1 | 1487 |   |
|   |   | CD1 | 1488 |   |
|   |   | O | 1490 | HB |
| 27 | T195 | OG1 | 1505 | HB |
| 28 | L196 | N | 1509 | HB |
| 29 | S197 | N | 1517 | HB |
|   |   | OG | 1520 | HB |
|   |   | O | 1522 | HB |
| 30 | F204 | CB | 1558 | HI |
|   |   | CG | 1559 |   |
|   |   | CD1 | 1560 |   |
|   |   | CD2 | 1561 |   |
|   |   | CE1 | 1562 |   |
|   |   | CE2 | 1563 |   |
|   |   | CZ | 1564 |   |
| 31 | 135 | O23 | 7928 | HB |
|   |   | N28 | 7930 | HB |
|   |   | N33 | 7935 | HB |

[1] Atom number in FIG. 9 refers to chain A; this implies that corresponding residues in other chains are also interaction sites
[2] HB = Hydrogen bond; HI = Hydrophobic interaction Conservation of Binding Site Residues Many structures of the E. coli FabI complexed with various inhibitors and structures of various other FabI (and related proteins) have been solved. The sequence similarity between the S. aureus FabI and the E. coli FabI is moderate (42% identity) and examination of the structure conservation is important to design specific inhibitors for S. aureus. E. coli FabI and S. aureus FabI have similar specific activities, and S. aureus FabI expression complements a E. coli FabI(Ts) mutant, illustrating that the Gram-positive FabI is interchangeable with the Gram-negative FabI enzyme (Heath, Li et al. 2000). However, E. coli FabI is specific for NADH, whereas S. aureus FabI exhibits specific and positive cooperative binding of NADPH. Triclosan and hexachlorophene inhibited both E. coli FabI and S. aureus FabI (Heath, Li et al. 2000).

A comparison of the S. aureus FabI binding site with the E. coli pocket shows several important differences in the side chains (FIGS. 29-32). Although the residues for hydrogen bonding to the inhibitor are conserved, differences surrounding the pocket can change the complementary fit of the inhibitor/protein interaction. A good example of such a change is V201 in S. aureus to 1200 in E. coli. Although these two amino acids are considered to be a relatively conservative substitution, the molecular surface presented to the inhibitor is very different. The change from M99 in S. aureus to G97 in E. coli is very dramatic. M99 forms a nice curved hydrophobic surface for the inhibitor as well, steric differences in the side chains at this position could change the ability of the flipping loop to close over the substrate. Differences in the orientation of the side chains, even when they are the same amino acid, also indicates variability between the structures and shows the conformational flexibility allowed in the area.

If the conservation of bacterial FabI amino acid sequences are mapped onto the S. aureus FabI structure (FIGS. 10-12, FIGS. 29-35), variability is tolerated in many areas of the structure. Most residues near the binding pocket are fairly well conserved, but some areas allow variability between bacterial species. Although the residues involved in hydrogen bonding with the inhibitor are conserved, changes in the residues encompassing the binding pocket will considerably alter the size and shape of the pocket. Any differences in side chains also change the distribution of potential interaction sites for inhibitors.

For example, in the S. aureus structure, there are specific residues which are different in the other bacterial species which create a specific constellation of residues for the binding pocket. In particular, certain residues on the flipping loop are different in each bacterial species. G202, K199 and A198 have a high degree of variability, where a variety of residues can be present (i.e. glycine to aspartic acid). V201 and S197 have a moderate degree of variability, so the changes here are restricted to more conservative substitutions (i.e. valine to isoleucine). A change in side chain creates differences in the binding pocket as the flipping loop closes around the inhibitor. On the other hand, similarity in residues in the binding pocket can allow the design of broad spectrum inhibitors. Common elements found in each species, even if the particular structure is unknown can be utilized to design inhibitors which interact specifically in this family of proteins. If alternate residues are modeled using the S. aureus FabI structure as a base, inhibitors could be designed so they are complementary to a variety of bacterial species.

Comparison with FabG

The fatty acid elongation cycle contains two reductive steps. β-Keto acyl carrier protein reductase (BKR) catalyzes the pyridine-nucleotide-dependent reversible reduction of a 3-oxoacyl form of ACP to its hydroxyl product as the first reductive step in de novo fatty acid biosynthesis. The FabG enzyme requires NADPH for its activity, has a monomeric molecular weight of about 25.5K, and exists as a tetramer in solution. FabG is highly conserved across species and is the only known isozyme to catalyze reduction of the β-keto group. Therefore, it is an essential enzyme in bacteria and an ideal target for the development of new antibiotics. FabG is not targeted by any known inhibitors. Sequence comparisons have shown that BKR belongs to a short-chain alcohol dehydrogenase (SDR) family, which possesses a characteristic Ser-Tyr-Lys triad motif involved in catalysis and substrate binding. BKR also shows a notable sequence similarity to the other oxidoreductase of the fatty acid elongation cycle, enoyl acyl carrier protein reductase (ENR). The aligned sequences of the two enzymes in B. napus that catalyze these steps, BKR and ENR, share 16% overall sequence identity over the 260 residues of BKR (Fisher, Kroon et al. 2000). A structure similarity search with the B. napus FabG produced good matches with the deposited structures of the enoyl reductase enzymes from B. napus, E. coli and Mycobacterium tuberculosis.

The B. napus FabG structure is solved as a binary complex containing bound NADP+ (Fisher, Kroon et al. 2000), whereas this cofactor is absent from the E. coli structure (Price, Zhang et al. 2001). A comparison between the two structures shows that the binding of NADP+ is associated with significant conformational changes in FabG enzymes. The flipping loop moves to close the binding pocket. An important consequence of the conformational change is the reorientation of the three active-site residues.

An analysis of conserved residues between BKR and ENR from B. napus were plotted onto the structure of BKR (Fisher, Kroon et al. 2000). This showed some limited clustering of residues within the hydrophobic core of the enzyme, but otherwise the conserved residues appear distributed throughout the secondary structure elements. There is apparently little conservation of sequence near the active site, with the notable exception of the putative catalytic residue Lys171 in BKR, which corresponds to Lys206 (K164 in S. aureus) in ENR. The phenolic hydroxyl groups of Tyr167 in BKR and the proposed catalytic residue Tyr198 in ENR (Y157 in S. aureus), although not picked out by the sequence alignment, are also located in similar, but not identical, positions in the three-dimensional structures. The catalytic Ser154 of BKR corresponds to Tyr188 (Y147 in S. aureus) of ENR in both the sequence alignment and the structural superimposition, but this residue has not been shown to have a role in the catalytic mechanism of ENR. The small difference in the positions of the phenolic oxygens, which are believed to be the proton donors in the reaction mechanisms of BKR and ENR, might reflect the difference in the substrates of the two enzymes. There are an additional two bonds separating the site of hydride transfer and that of proton donation in the double-bond-containing substrate of ENR compared with the keto substrate of BKR.

It is clear that a common underlying structure, comprising a single domain formed from the classical dinucleotide binding fold, has been utilized to carry out the two reductive steps in FAS. In addition, the regions forming the substrate-binding sites in BKR and ENR would seem to have notable similarities in terms of the use of an α-helix to act as a flexible lid on the pocket that might occlude solvent during catalysis. Furthermore, lysine side chains and tyrosine phenolic hydroxyl groups that are structurally conserved between BKR and ENR are used to carry out the catalytic mechanisms. These structural features, taken together with the sequence similarity distributed throughout the polypeptide chains of the enzymes, suggest that the two enzymes have diverged from a common reductase ancestor in the evolution of the FAS elongation cycle.

In spite of the structural similarities in the active sites of ENR and BKR described above, there have been no reports of the inhibition of BKR by the triclosan, diazaborine or isoniazid compounds known to inhibit ENR (Baldock, Rafferty et al. 1996; Rozwarski, Grant et al. 1998; Levy, Roujeinikova et al. 1999). A superimposition of the active site of BKR with that of ENR in complex with triclosan, diazaborine or isoniazid suggests a number of steric clashes between BKR and these drugs plus the probable absence of certain favorable interactions (Fisher, Kroon et al. 2000). The triclosan and diazaborine compounds bind to ENR in an analogous manner (Baldock, Rafferty et al. 1996; Levy, Roujeinikova et al. 1999) and the substitution of Ala95, Met159 and Ala196 in E. coli ENR by the equivalent residues Thr106, Tyr167 and Met204 in B. napus BKR is likely to cause severe steric clashes and prevent drug binding (Fisher, Kroon et al. 2000). Examination of the superimposition of BKR with the complex of M. tuberculosis ENR (also known as InhA) and a derivative of isoniazid (Rozwarski, Grant et al. 1998) reveals favorable interactions formed with the drug by residues Phe149 and Tyr158 of InhA; these interactions would not be replicated in B. napus BKR.

Known Inhibitors of FabI and Related Enzymes

The study of FabI as a drug target has gained much attention in connection with the discovery that three distinctly different synthetic anti-bacterial drugs, isoniazid (Quemard, Sacchettini et al. 1995), diazaborine (Bergler, Wallner et al. 1994), and triclosan (1, FIG. 36) (McMurry, Oethinger et al. 1998; Levy, Roujeinikova et al. 1999) block lipid biosynthesis in bacteria by inhibiting ENR. Generating three novel lead compounds from the GlaxoSmithKline proprietary compound collection (1,4-disubstituted imidazole, 2,9-disubstituted 1,2,3,4-tetrahydropyrido[3,4-b]indole and benzodiazepine) involved a combination of iterative medicinal chemistry and structure based design (Heerding, Chan et al. 2001; Seefeld, Miller et al. 2001; Miller, Seefeld et al. 2002; Seefeld, Miller et al. 2003).

Aminopyridine and Naphthyridinone-Based Inhibitor

The group from GlaxoSmithKline Pharmaceuticals have described two series of small molecule-FabI inhibitors, exemplified by compounds 2 (Heerding, Chan et al. 2001) and 3 (Seefeld, Miller et al. 2001) in FIG. 36, which were optimized from screening leads obtained from the Glaxo- SmithKline proprietary compound collection. Additional research from these labs led to the discovery of an aminopyridine-based FabI inhibitor 4 (AP500467, SB-422805) (Miller, Seefeld et al. 2002) that exhibits in vivo efficacy against *S. aureus* (FIG. 37). The discovery of a naphthyridinone-based series of FabI inhibitors by the same group demonstrates improvements in potency, spectrum, and in vivo efficacy over previously reported selective FASII inhibitors (Seefeld, Miller et al. 2003). Significantly, selected compounds from this novel class of inhibitors display dual FabI/FabK inhibition.

The SAR (structure-activity relationship) depicted in FIG. 37 shows the key pharmacophoric elements required for selective FabI inhibition in the series of aminopyridine-based FabI inhibitors (Seefeld, Miller et al. 2003). A bicyclic aromatic structure, preferably indole, is linked at the 2' or 3' position to a methylamide via a methylene linker. The amide functionality is connected to the 5-position of a 2-aminopyridine through an (E)-olefin. Substitution on the indole moiety is limited to small lipophilic functionality, and substitution on the olefin results in a loss of enzyme inhibitory activity. The most accessible site for further chemical manipulation on the aminopyridine moiety is at the 3-position, and this is where optimization to the naphthyridinone-based series occurred.

An X-ray cocrystallization study with naphthyridinone 29 (FIG. 38) (FabI *E. coli* $IC_{50}$) 0.07 µM) and *E. coli* FabINAD+ (PDB ID: 1MFP) reveals the key binding interactions. As expected, the binding characteristics of 29 are quite similar to those previously described for compound 4 (AP-501135, SB-422805) (Miller, Seefeld et al. 2002) (PDB ID: 1LXC) and for triclosan (Qiu, Janson et al. 1999; Heerding, Chan et al. 2001) (PDB ID: 1C14; 1I2Z). The linking amide carbonyl of 29 is well-positioned for an H-bond interaction with the 2'-hydroxyl of NAD+ and the hydroxyl of Y156 (*E. coli* numbering). The central cis-amide fragment of 29 appears to participate in a π-stacking interaction with the nicotinamide portion of NAD+ as seen in 4 (Miller, Seefeld et al. 2002). A95 is involved in H-bond interactions that bind both the pyridylamine and the N-acyl hydrogen of the naphthyridinone functionality. The contribution of the naphthyridinone carbonyl of 29 is not apparent in the crystal structure. The indole portion of inhibitor 29 is flanked by lipophilic residues (M206, F203, Y156, Y146; *E. coli* numbering) creating tight hydrophobic packing. Substitution at indole sites other than 1', 2', and 7' of 29 would appear to create unfavorable steric interactions with neighboring backbone residues. Similar observations for other FabI inhibitors in this region of the active site have been described (Levy, Baldock et al. 2001; Miller, Seefeld et al. 2002).

An extensive characterization of the biological activities of these series of compounds, and in particular compound API-1135, has been discussed (Payne, Miller et al. 2002). All naphthyridinones were tested against bacterial strains of overexpressing *S. aureus* and H. influenzae FabI and showed elevated MICs (>4-fold) versus WT strains. Additionally, all compounds were shown to selectively inhibit acetate incorporation in 14C-labeled precursor pathway macromolecular synthesis studies using *S. aureus*. The naphthyridinone inhibitors had no detectable activity against the human fatty acid biosynthetic enzyme (IC50>100 µM) and showed no significant cytotoxicity (TC50s>64 µg/mL). Together, these studies support a mode of action (MOA) for these compounds as fatty acid synthesis (FASII) inhibitors.

A tertiary profile was run with selected naphthyridinones against a panel of clinical isolates of *S. aureus* that were resistant to different classes of currently available antibiotics. Several naphthyridinones displayed levels of inhibition better than marketed antibiotics, with compound API-1135 achieving MIC90s>500-fold lower than those exhibited by the commercial antibiotics tested. In in vivo studies, following oral administration at 50 mg/kg, API-1135 was found to be effective in a rat groin abscess model (infected with the MRSA strain WCUH29), providing a 3.5-log reduction in bacterial counts relative to untreated controls (Payne, Miller et al. 2002).

Inhibition by Isoniazid

*M. tuberculosis* ENR is the target for a metabolite of isoniazid, which is used in the front-line treatment of tuberculosis. However, strains of *M. tuberculosis* are emerging that are resistant to one or more of the main antituberculosis drugs including isoniazid with consequent severe problems in treatment.

Inhibition by Diazaborines

*E. coli* ENR is inhibited by a range of diazaborines, a family of antibacterial agents whose action is thought to lead to the inhibition of cell growth by preventing lipopolysaccharide synthesis (Hogenauer & Woisetschlager, 1981).

Inhibition by Triclosan

The crystal structure of the *E. coli* enoyl reductase-NAD+ triclosan complex (Heath, Rubin et al. 1999) shows that unlike diazaborines and isoniazid that bind to the cofactor NAD covalently, triclosan interacts with both the enzyme and the cofactor in a noncovalent fashion. The potent noncovalent interactions ~IC50 of 120 nm as reported by Levy et al. (Levy, Roujeinikova et al. 1999), have been mainly attributed to the face-to-face stacking of its phenol ring to the nicotinamide ring, and the hydrogen bonds between the phenolic hydroxyl and the hydroxyls of Tyr156 and 29 nicotinamide ribose (*E. coli* numbering). Additional interactions with the flipping active site loop is crucial for defining the molecular basis for triclosan's potent inhibitory activity (Qiu, Janson et al. 1999).

Mutagenesis Studies

The clinically relevant (F204C) mutation in the active site of *S. aureus* FabI (F203C in *E. coli*) negatively affects triclosan potency, but has no significant effect on the MIC of the naphthyridinone series of compounds (Fan, Yan et al. 2002). Seefeld et al. (Seefeld, Miller et al. 2003) speculate that the binding orientation of naphthyridinone compounds in *S. aureus* positions the molecule away from the mutation site. In general, the antibacterial potency of the indole naphthyridinones remains relatively unaffected by the active-site mutations that confer susceptibility to triclosan.

Resistance to the diazaborines arises from a missense mutation in the FabI gene that leads to the expression of a FabIG93S mutant protein. Similarly, the FabI analog in *Mycobacterium tuberculosis*, the inhA gene, encodes a cellular target for isoniazid and ethionamide. A point mutation in the inhA gene confers resistance to the drugs. Structural studies on diazaborine-bound *E. coli* ENR (Baldock, Rafferty et al. 1996) elucidated the mechanism by which diazaborine inhibits bacterial ENR and also threw light onto the molecular nature of the *E. coli* ENR G93S mutant's resistance to diazaborines (Turnowsky, Fuchs et al. 1989). These studies indicate that a G93S substitution puts the larger amino acid side chain at the position where it would clash with the sulfonyl oxygens of the diazaborine molecule.

Subtle differences between the binding characteristics of triclosan and the indole naphthyridinone inhibitors suggest that these compounds will be active against triclosan resistant strains. Mode of action and cytotoxicity studies have shown that the naphthyridinone compounds are selective FabI inhibitors with no detectable FASI inhibition.

The foregoing information on other inhibitors and mutagenesis studies may aid in the design or optimization of S. aureus-specific FabI inhibitors which may target the subject druggable regions.

Based in part on the structural information described above, in one aspect, the present invention is directed towards druggable regions of a subject polypeptide or other enoyl-[acyl-carrier-protein] reductase comprising the majority of the amino acid residues contained in any of the above-described druggable regions. In another aspect, the present invention is directed toward a modulator or that interacts with an active or binding site of an enoyl-[acyl-carrier-protein] reductase. In certain embodiments, the active or binding site may be comprised of at least one of the residues listed in Table 5 or Table 6. In another embodiment, this site is the NADPH binding region. In certain embodiments, the NADPH binding region may be comprised of at least one of the residues listed in Table 7 or Table 8. In another aspect, the present invention is directed towards a an modulator that interacts with the flipping loop enoyl-[acyl-carrier-protein] reductase so as to modulate its movement, thereby modulating the activity of such enzyme. In certain embodiments, the loop is comprised of at least one residue selected from the region 193 IRTL-SAKGVGG 203 (SEQ ID NO: 23). In yet another aspect, the present invention is directed toward a modulator that interacts with an active or binding site of a FabI or FabG. In certain embodiments, the modulator prevents a conformational change, such as for example, the movement of the flipping loop. In other embodiments, the modulator may prevent a substrate from binding to an active or binding site.

Example 17

Annotations

The functional annotation is arrived at by comparing the amino acid sequence of the ORF against all available ORFs in the NCBI database using BLAST. The closest match is selected to provide the probable function of the polypeptide having the sequence of SEQ ID NO: 2. Results of this comparison are described above and set forth in Table 2 of FIG. 7.

The COGs database (Tatusov R L, Koonin E V, Lipman D J. Science 1997; 278 (5338) 631-37) classifies proteins encoded in twenty-one completed genomes on the basis of sequence similarity. Members of the same Cluster of Orthologous Group, ("COG"), are expected to have the same or similar domain architecture and the same or substantially similar biological activity. The database may be used to predict the function of uncharacterised proteins through their homology to characterized proteins. The COGs database may be searched from NCBI's website (http://www.ncbi.nlm.nih.gov/COG/) to determine functional annotation descriptions, such as "information storage and processing" (translation, ribosomal structure and biogenesis, transcription, DNA replication, recombination and repair); "cellular processes" (cell division and chromosome partitioning, post-translational modification, protein turnover, chaperones, cell envelope biogenesis, outer membrane, cell motility and secretion, inorganic ion transport and metabolism, signal transduction mechanisms); or "metabolism" (energy production and conversion, carbohydrate transport and metabolism, amino acid transport and metabolism, nucleotide transport and metabolism, coenzyme metabolism, lipid metabolism). For certain polypeptides, there is no entry available. Results of this analysis are described above and set forth in Table 2 of FIG. 7.

Example 18

Essential Gene Analysis

SEQ ID NO: 2 is compared to a number of publicly available "essential genes" lists to determine whether that protein is encoded by an essential gene. An example of such a list is descended from a free release at the www.shigen.nig.ac.jp PEC (profiling of E. coli chromosome) site, http://www:shigen.nig.ac.jp/ecoli/pec/. The list is prepared as follows: a wildcard search for all genes in class "essential" yields the list of essential E. coli proteins encoded by essential genes, which number 230. These 230 hits are pruned by comparing against an NCBI E. coli genome. Only 216 of the 230 genes on the list are found in the NCBI genome. These 216 are termed the essential-216-ecoli list. The essential-216-ecoli list is used to garner "essential" genes lists for other microbial genomes by blasting. For instance, formatting the 216-ecoli as a BLAST database, then BLASTing a genome (e.g. S. aureus) against it, elucidates all S. aureus genes with significant homology to a gene in the 216-essential list. SEQ ID NO: 2 is compared against the appropriate list and a match with a score of $e^{-25}$ or better is considered an essential gene according to that list. In addition to the list described above, other lists of essential genes are publicly available or may be determined by methods disclosed publicly, and such lists and methods are considered in deciding whether a gene is essential. See, for example, Thanassi et al., Nucleic Acids Res 2002 Jul. 15; 30(14):3152-62; Forsyth et al., Mol Microbiol 2002 March; 43(6):1387-400; Ji et al., Science 2001 Sep. 21; 293(5538): 2266-9; Sassetti et al., Proc Natl Acad Sci USA 2001 Oct. 23; 98(22):12712-7; Reich et al., J Bacteriol 1999 August; 181 (16):4961-8; Akerley et al., Proc Natl Acad Sci USA 2002 Jan. 22; 99(2):966-71). Also, other methods are known in the art for determining whether a gene is essential, such as that disclosed in U.S. patent application Ser. No. 10/202,442 (filed Jul. 24, 2002). The conclusion as to whether the gene encoding the amino acid sequence set forth in SEQ ID NO: 2 is essential is set forth in Table 2 of FIG. 7.

Example 19

PDB Analysis

SEQ ID NO: 2 is compared against the amino acid sequences in a database of proteins whose structures have been solved and released to the PDB (protein data bank). The identity/information about the top PDB homolog (most similar "hit", if any; a PDB entry is only considered a hit if the score is $e^{-4}$ or better) is annotated, and the percent similarity and identity between SEQ ID NO: 2 and the closest hit is calculated, with both being indicated in Table 2 of FIG. 7.

Example 20

Virtual Genome Analysis

VGDB or VG is a queryable collection of microbial genome databases annotated with biophysical and protein information. The organisms present in VG include:

| File | GRAM | Species | Source | Genome file date |
|---|---|---|---|---|
| ecoli.faa | G− | Escherichia coli | NCBI | Nov. 18, 1998 |
| hpyl.faa | G− | Helicobacter pylori | NCBI | Apr. 19, 1999 |
| paer.faa | G− | Pseudomonas aeruginosa | NCBI | Sep. 22, 2000 |
| ctra.faa | G− | Chlamydia trachomatis | NCBI | Dec. 22, 1999 |
| hinf.faa | G− | Haemophilus influenzae | NCBI | Nov. 26, 1999 |
| nmen.faa | G− | Neisseria meningitidis | NCBI | Dec. 28, 2000 |
| rpxx.faa | G− | Rickettsia prowazekii | NCBI | Dec. 22, 1999 |
| bbur.faa | G− | Borrelia burgdorferi | NCBI | Nov. 11, 1998 |
| bsub.faa | G+ | Bacillus subtilis | NCBI | Dec. 1, 1999 |
| staph.faa | G+ | Staphylococcus aureus | TIGR | Mar. 8, 2001 |
| spne.faa | G+ | Streptococcus pneumoniae | TIGR | Feb. 22, 2001 |
| mgen.faa | G+ | Mycoplasma genitalium | NCBI | Nov. 23, 1999 |
| efae.faa | G+ | Enterococcus faecalis | TIGR | Mar. 8, 2001 |

The VGDB comprises 13 microbial genomes, annotated with biophysical information (pI, MW, etc), and a wealth of other information. These 13 organism genomes are stored in a single flatfile (the VGDB) against which PSI-blast queries can be done.

SEQ ID NO: 2 is queried against the VGDB to determine whether this sequence is found, conserved, in many microbial genomes. There are certain criteria that must be met for a positive hit to be returned (beyond the criteria inherent in a basic PSI-blast).

When an ORF is queried it may have a maximum of 13 VG-organism hits. A hit is classified as such as long as it matches the following criteria: Minimum Length (as percentage of query length): 75 (Ensure hit protein is at least 75% as long as query); Maximum Length (as percentage of query length): 125 (Ensure hit protein is no more than 125% as long as query); eVal: −10 (Ensure hit has an e-Value of e-10 or better); Id%:>:25 (Ensure hit protein has at least 25% identity to query). The e-Value is a standard parameter of BLAST sequence comparisons, and represents a measure of the similarity between two sequences based on the likelihood that any similarities between the two sequences could have occurred by random chance alone. The lower the e-Value, the less likely that the similarities could have occurred randomly and, generally, the more similar the two sequences are.

The organisms having an orthologue of the polypeptide having SEQ ID NO: 2 are listed in Table 2, shown in FIG. 7.

Example 21

Epitopic Regions

The three most likely epitopic regions of a polypeptide having SEQ ID NO: 2 are predicted using the semi-empirical method of Kolaskar and Tongaonkar (FEBS Letters 1990 v276 172-174), the software package called Protean (DNAS-TAR), or MacVectors's Protein analysis tools (Accerlyrs). The antigenic propensity of each amino acid is calculated by the ratio between frequency of occurrence of amino acids in 169 antigenic determinants experimentally determined and the calculated frequency of occurrence of amino acids at the surface of protein. The results of these bioinformatics analyses are presented in Table 2, shown in FIG. 7.

EQUIVALENTS

The present invention provides among other things, novel proteins, protein structures and protein-protein interactions.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

All publications and patents mentioned herein, including those items listed below, are hereby incorporated by reference in their entirety as if each individual publication or patent was specifically and individually indicated to be incorporated by reference. In case of conflict, the present application, including any definitions herein, will control. To the extent that any U.S. Provisional Patent Applications to which this patent application claims priority incorporate by reference another U.S. Provisional Patent Application, such other U.S. Provisional Patent Application is not incorporated by reference herein unless this patent application expressly incorporates by reference, or claims priority to, such other U.S. Provisional Patent Application.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

Also incorporated by reference are the following: WO 00/45168, WO 00/79238, WO 00/77712, EP 1047108, EP 1047107, WO 00/72004, WO 00/73787, WO 00/67017, WO 00/48004, WO 01/48209, WO 00/45168, WO 00/45164, U.S. Ser. No. 09/720,272; PCT/CA99/00640; U.S. patent application Ser. Nos. 10/097,125 (filed Mar. 12, 2002); 10/097,193 (filed Mar. 12, 2002); 10/202,442 (filed Jul. 24, 2002); 10/097,194 (filed Mar. 12, 2002); 09/671,817 (filed Sep. 17, 2000); 09/965,654 (filed Sep. 27, 2001); 09/727,812 (filed Nov. 30, 2000); 60/370,667 (filed Apr. 8, 2002); a utility patent application entitled "Methods and Apparatuses for Purification" (filed Sep. 18, 2002); U.S. Pat. Nos. 6,451,591; 6,254,833; 6,232,114; 6,229,603; 6,221,612; 6,214,563; 6,200,762; 6,171,780; 6,143,492; 6,124,128; 6,107,477; D428,157; 6,063,338; 6,004,808; 5,985,214; 5,981,200; 5,928,888; 5,910,287; 6,248,550; 6,232,114; 6,229,603; 6,221,612; 6,214,563; 6,200,762; 6,197,928; 6,180,411; 6,171,780; 6,150,176; 6,140,132; 6,124,128; 6,107,066; 6,270,988; 6,077,707; 6,066,476; 6,063,338; 6,054,321; 6,054,271; 6,046,925; 6,031,094; 6,008,378; 5,998,204; 5,981,200; 5,955,604; 5,955,453; 5,948,906; 5,932,474; 5,925,558; 5,912,137; 5,910,287; 5,866,548; 6,214,602; 5,834,436; 5,777,079; 5,741,657; 5,693,521; 5,661,035; 5,625,048; 5,602,258; 5,552,555; 5,439,797; 5,374,710; 5,296,703; 5,283,433; 5,141,627; 5,134,232; 5,049,673; 4,806,604; 4,689,432; 4,603,209; 6,217,873; 6,174,530; 6,168,784; 6,271,037; 6,228,654; 6,184,344; 6,040,133; 5,910,437; 5,891,993; 5,854,389; 5,792,664; 6,248,558; 6,341,256; 5,854,922; and 5,866,343.

Baldock, C., et al. (1996) *Science* 274(5295): 2107-10; Baldock, C., J. B. Rafferty, et al. (1998) *J Mol Biol* 284(5): 1529-46; Bergler, H., et al. (1994) *J Biol Chem* 269(8): 5493-6; Chen, Z., et al. (1993) *Biochemistry* 32(13): 3342-6; Fan, F., et al. (2002) *Antimicrob Agents Chemother* 46(11): 3343-7; Fisher, M., et al. (2000) *Structure Fold Des* 8(4): 339-47; Heath, R. J., et al. (2000) *J Biol Chem* 275(7): 4654-9; Heath, R. J., et al. (1999) *J Biol Chem* 274(16): 11110-4; Heerding, D. A., et al. (2001) *Bioorg Med Chem Lett* 11(16): 2061-5; Kissinger, C. R., et al. (1999) *Acta Crystallogr D Biol Crystallogr* 55 (Pt 2): 484-91; Levy, C. W., et al. (2001) *J Mol Biol*

309(1): 171-80; Levy, C. W., et al. (1999) *Nature* 398(6726): 383-4; McMurry, L. M., et al. (1998) *Nature* 394(6693): 531-2; Miller, W. H., et al. (2002) *J Med Chem* 45(15): 3246-56; Payne, D. J., et al. (2002) *Antimicrob Agents Chemother* 46(10): 3118-24; Perozzo, R., et al. (2002) *J Biol Chem* 277(15): 13106-14; Potterton, E., et al. (2002) *Acta Crystallogr D Biol Crystallogr* 58(Pt 11): 1955-7; Powell, H. R. (1999) *Acta Crystallogr D Biol Crystallogr* 55 (Pt 10): 1690-5; Price, A. C., et al. (2001) *Biochemistry* 40(43): 12772-81; Qiu, X., et al. (1999) *Protein Sci* 8(11): 2529-32; Quemard, A., et al. (1995) *Biochemistry* 34(26): 8235-41; Rafferty, J. B., et al. (1995) *Structure* 3(9): 927-38; Roujeinikova, A., et al. (1999) *J Mol Biol* 294(2): 527-35; Roujeinikova, A., et al. (1999) *J Biol Chem* 274(43): 30811-7; Rozwarski, D. A., et al. (1998) *Science* 279(5347): 98-102; Rozwarski, D. A., et al. (1999) *J Biol Chem* 274(22): 15582-9; Saito, K., et al. (1981) *Eur J Biochem* 116(3): 581-6. Seefeld, M. A., (2003) *J Med Chem* 46(9): 1627-35; Seefeld, M. A., et al. (2001) *Bioorg Med Chem Lett* 11(17): 2241-4; Turnowsky, F., et al. (1989) *J Bacteriol* 171(12): 6555-65; Ward, W. H., et al. (1999) *Biochemistry* 38(38): 12514-25.

The following U.S. patent applications are hereby incorporated by reference in their entireties: U.S. Ser. No. 08/790,043, filed Jan. 28, 1997, entitled "Polynucleotide Encoding the Enoyl-Acyl Carrier Protein Reductase of *Staphylococcus Aureus*, Fab I"; and U.S. Ser. No. 10/009,219, filed May 4, 2000, entitled "Methods of Using FabI and Compounds Modulating FabI Activity".

---

We claim:

1. A crystallized, recombinant polypeptide as set forth in SEQ ID NO: 2 or SEQ ID NO: 4; wherein the polypeptide is in crystal form and has unit cell dimensions a=82.2 Å, b=79.1 Å, c=93.6 Å, α=γ=90°, β=97.6°, with space group P2$_1$, which is capable of diffracting x-rays to a resolution of about 3.5 Å, and wherein the polypeptide is complexed to NADPH and API-1135.

* * * * *

SEQUENCE LISTING

<160> NUMBER OF SEQ ID NOS: 25

<210> SEQ ID NO 1
<211> LENGTH: 771
<212> TYPE: DNA
<213> ORGANISM: Staphylococcus aureus

<400> SEQUENCE: 1

```
atgttaaatc ttgaaaacaa aacatatgtc atcatgggaa tcgctaataa gcgtagtatt      60
gcttttggtg tcgctaaagt tttagatcaa ttaggtgcta aattagtatt tacttaccgt     120
aaagaacgta gccgtaaaga gcttgaaaaa ttattagaac aattaaatca accagaagcg     180
cacttatatc aaattgatgt tcaaagcgat gaagaggtta ttaatggttt tgagcaaatt     240
ggtaaagatg ttggcaatat tgatggtgta tatcattcaa tcgcatttgc taatatggaa     300
gacttacgcg gacgcttttc tgaaacttca cgtgaaggct tcttgttagc tcaagacatt     360
agttcttact cattaacaat tgtggctcat gaagctaaaa aattaatgcc agaaggtggt     420
agcattgttg caacaacata tttaggtggc gaattcgcag ttcaaaacta taatgtgatg     480
ggtgttgcta aagcgagctt agaagcaaat gttaaatatt tagcattaga cttaggtcca     540
gataatattc gcgttaatgc aatttcagct ggtccaatcc gtacattaag tgcaaaaggt     600
gtgggtggtt tcaatacaat tcttaaagaa atcgaagagc gtgcaccttt aaaacgtaat     660
gttgatcaag tagaagtagg taaaactgcg gcttacttat taagtgattt atcaagtggc     720
gttacaggtg aaaatattca tgtagatagc ggattccacg caattaaata a              771
```

<210> SEQ ID NO 2
<211> LENGTH: 256
<212> TYPE: PRT
<213> ORGANISM: Staphylococcus aureus

<400> SEQUENCE: 2

```
Met Leu Asn Leu Glu Asn Lys Thr Tyr Val Ile Met Gly Ile Ala Asn
  1               5                  10                  15

Lys Arg Ser Ile Ala Phe Gly Val Ala Lys Val Leu Asp Gln Leu Gly
             20                  25                  30

Ala Lys Leu Val Phe Thr Tyr Arg Lys Glu Arg Ser Arg Lys Glu Leu
         35                  40                  45

Glu Lys Leu Leu Glu Gln Leu Asn Gln Pro Glu Ala His Leu Tyr Gln
     50                  55                  60

Ile Asp Val Gln Ser Asp Glu Glu Val Ile Asn Gly Phe Glu Gln Ile
 65                  70                  75                  80
```

Gly Lys Asp Val Gly Asn Ile Asp Gly Val Tyr His Ser Ile Ala Phe
                85                  90                  95

Ala Asn Met Glu Asp Leu Arg Gly Arg Phe Ser Glu Thr Ser Arg Glu
            100                 105                 110

Gly Phe Leu Leu Ala Gln Asp Ile Ser Ser Tyr Ser Leu Thr Ile Val
        115                 120                 125

Ala His Glu Ala Lys Lys Leu Met Pro Glu Gly Ser Ile Val Ala
    130                 135                 140

Thr Thr Tyr Leu Gly Gly Glu Phe Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175

Asp Leu Gly Pro Asp Asn Ile Arg Val Asn Ala Ile Ser Ala Gly Pro
            180                 185                 190

Ile Arg Thr Leu Ser Ala Lys Gly Val Gly Gly Phe Asn Thr Ile Leu
        195                 200                 205

Lys Glu Ile Glu Glu Arg Ala Pro Leu Lys Arg Asn Val Asp Gln Val
    210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Ser Gly Phe His Ala Ile Lys
                245                 250                 255

<210> SEQ ID NO 3
<211> LENGTH: 771
<212> TYPE: DNA
<213> ORGANISM: Staphylococcus aureus

<400> SEQUENCE: 3
atgttaaatc ttgaaaacaa aacatatgtc atcatgggaa tcgctaataa gcgtagtatt      60
gcttttggtg tcgctaaagt tttagatcaa ttaggtgcta aattagtatt tacttaccgt     120
aaagaacgta gccgtaaaga gcttgaaaaa ttattagaac aattaaatca accagaagcg     180
cacttatatc aaattgatgt tcaaagcgat gaagaggtta ttaatggttt tgagcaaatt     240
ggtaaagatg ttggcaatat tgatggtgta tatcattcaa tcgcatttgc taatatggaa     300
gacttacgcg gacgcttttc tgaaacttca cgtgaaggct tcttgttagc tcaagacatt     360
agttcttact cattaacaat tgtggctcat gaagctaaaa aattaatgcc agaaggtggt     420
agcattgttg caacaacata tttaggtggc gaattcgcag ttcaaaacta taatgtgatg     480
ggtgttgcta agcgagctt agaagcaaat gttaaatatt tagcattaga cttaggtcca     540
gataatattc gcgttaatgc aatttcagct ggtccaatcc gtacattaag tgcaaaaggt     600
gtgggtggtt tcaatacaat tcttaaagaa atcgaagagc gtgcaccttt aaaacgtaat     660
gttgatcaag tagaagtagg taaaactgcg gcttacttat taagtgattt atcaagtggc     720
gttacaggtg aaaatattca tgtagatagc ggattccacg caattaaata a              771

<210> SEQ ID NO 4
<211> LENGTH: 256
<212> TYPE: PRT
<213> ORGANISM: Staphylococcus aureus

<400> SEQUENCE: 4

Met Leu Asn Leu Glu Asn Lys Thr Tyr Val Ile Met Gly Ile Ala Asn
  1               5                  10                  15

-continued

```
Lys Arg Ser Ile Ala Phe Gly Val Ala Lys Val Leu Asp Gln Leu Gly
            20                  25                  30

Ala Lys Leu Val Phe Thr Tyr Arg Lys Glu Arg Ser Arg Lys Glu Leu
        35                  40                  45

Glu Lys Leu Leu Glu Gln Leu Asn Gln Pro Glu Ala His Leu Tyr Gln
    50                  55                  60

Ile Asp Val Gln Ser Asp Glu Glu Val Ile Asn Gly Phe Glu Gln Ile
65                  70                  75                  80

Gly Lys Asp Val Gly Asn Ile Asp Gly Val Tyr His Ser Ile Ala Phe
                85                  90                  95

Ala Asn Met Glu Asp Leu Arg Gly Arg Phe Ser Glu Thr Ser Arg Glu
            100                 105                 110

Gly Phe Leu Leu Ala Gln Asp Ile Ser Ser Tyr Ser Leu Thr Ile Val
        115                 120                 125

Ala His Glu Ala Lys Lys Leu Met Pro Glu Gly Gly Ser Ile Val Ala
    130                 135                 140

Thr Thr Tyr Leu Gly Gly Glu Phe Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175

Asp Leu Gly Pro Asp Asn Ile Arg Val Asn Ala Ile Ser Ala Gly Pro
            180                 185                 190

Ile Arg Thr Leu Ser Ala Lys Gly Val Gly Gly Phe Asn Thr Ile Leu
        195                 200                 205

Lys Glu Ile Glu Glu Arg Ala Pro Leu Lys Arg Asn Val Asp Gln Val
    210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Ser Gly Phe His Ala Ile Lys
                245                 250                 255

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcggggtac catgttaaat cttgaaaaca aaacatatg                              39

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgcggatcc tttaattgcg tggaatccgc                                        30

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 7

Met Gly Ser Ser His His His His His His Ser Ser Gly Leu Val Pro
1               5                   10                  15

Arg Gly Ser His
            20

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Glu Asn Leu Tyr Phe Gln Gly His His His His His
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ser Glu Asn Leu Tyr Phe Gln
1               5

<210> SEQ ID NO 10
<211> LENGTH: 262
<212> TYPE: PRT
<213> ORGANISM: Escherichia coli

<400> SEQUENCE: 10

Met Gly Phe Leu Ser Gly Lys Arg Ile Leu Val Thr Gly Val Ala Ser
1               5                   10                  15

Lys Leu Ser Ile Ala Tyr Gly Ile Ala Gln Ala Met His Arg Glu Gly
            20                  25                  30

Ala Glu Leu Ala Phe Thr Tyr Gln Asn Asp Lys Leu Lys Gly Arg Val
        35                  40                  45

Glu Glu Phe Ala Ala Gln Leu Gly Ser Asp Ile Val Leu Gln Cys Asp
    50                  55                  60

Val Ala Glu Asp Ala Ser Ile Asp Thr Met Phe Ala Glu Leu Gly Lys
65                  70                  75                  80

Val Trp Pro Lys Phe Asp Gly Phe Val His Ser Ile Gly Phe Ala Pro
                85                  90                  95

Gly Asp Gln Leu Asp Gly Asp Tyr Val Asn Ala Val Thr Arg Glu Gly
            100                 105                 110

Phe Lys Ile Ala His Asp Ile Ser Ser Tyr Ser Phe Val Ala Met Ala
        115                 120                 125

Lys Ala Cys Arg Ser Met Leu Asn Pro Gly Ser Ala Leu Leu Thr Leu
    130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Val Arg Val Asn Ala Ile Ser Ala Gly Pro Ile

```
                        180                 185                 190
Arg Thr Leu Ala Ala Ser Gly Ile Lys Asp Phe Arg Lys Met Leu Ala
            195                 200                 205

His Cys Glu Ala Val Thr Pro Ile Arg Arg Thr Val Thr Ile Glu Asp
        210                 215                 220

Val Gly Asn Ser Ala Ala Phe Leu Cys Ser Asp Leu Ser Ala Gly Ile
225                 230                 235                 240

Ser Gly Glu Val Val His Val Asp Gly Gly Phe Ser Ile Ala Ala Met
                245                 250                 255

Asn Glu Leu Glu Leu Lys
            260

<210> SEQ ID NO 11
<211> LENGTH: 295
<212> TYPE: PRT
<213> ORGANISM: Haemophilus influenzae

<400> SEQUENCE: 11

Met Arg Leu Val Phe Leu Glu Ile Leu Val Gly Phe Val Gln Arg Gln
 1               5                  10                  15

Ile Phe Ala Tyr Thr Thr Gln Val Phe Tyr Ala Asn Asn Ile Gly Lys
            20                  25                  30

Ile Met Gly Phe Leu Thr Gly Lys Arg Ile Leu Val Thr Gly Leu Ala
        35                  40                  45

Ser Asn Arg Ser Ile Ala Tyr Gly Ile Ala Lys Ser Met Lys Glu Gln
    50                  55                  60

Gly Ala Glu Leu Ala Phe Thr Tyr Leu Asn Asp Lys Leu Gln Pro Arg
65                  70                  75                  80

Val Glu Glu Phe Ala Lys Glu Phe Gly Ser Asp Ile Val Leu Pro Leu
                85                  90                  95

Asp Val Ala Thr Asp Glu Ser Ile Gln Asn Cys Phe Ala Glu Leu Ser
            100                 105                 110

Lys Arg Trp Asp Lys Phe Asp Gly Phe Ile His Ala Ile Ala Phe Ala
        115                 120                 125

Pro Gly Asp Gln Leu Asp Gly Asp Tyr Val Asn Ala Ala Thr Arg Glu
    130                 135                 140

Gly Tyr Arg Ile Ala His Asp Ile Ser Ala Tyr Ser Phe Val Ala Met
145                 150                 155                 160

Ala Gln Ala Ala Arg Pro Tyr Leu Asn Pro Asn Ala Ala Leu Leu Thr
                165                 170                 175

Leu Ser Tyr Leu Gly Ala Glu Arg Ala Ile Pro Asn Tyr Asn Val Met
            180                 185                 190

Cys Leu Ala Lys Ala Ser Leu Glu Ala Ala Thr Arg Val Met Ala Ala
        195                 200                 205

Asp Leu Gly Lys Glu Gly Ile Arg Val Asn Ala Ile Ser Ala Gly Pro
    210                 215                 220

Ile Arg Thr Leu Ala Ala Ser Gly Ile Lys Asn Phe Lys Lys Met Leu
225                 230                 235                 240

Ser Thr Phe Glu Lys Thr Ala Ala Leu Arg Arg Thr Val Thr Ile Glu
                245                 250                 255

Asp Val Gly Asn Ser Ala Ala Phe Leu Cys Ser Asp Leu Ala Ser Gly
            260                 265                 270

Ile Thr Gly Glu Ile Val His Val Asp Ala Gly Phe Ser Ile Thr Ala
        275                 280                 285
```

```
Met Gly Glu Leu Gly Glu Glu
    290             295
```

<210> SEQ ID NO 12
<211> LENGTH: 265
<212> TYPE: PRT
<213> ORGANISM: Pseudomonas aeruginosa

<400> SEQUENCE: 12

```
Met Gly Phe Leu Thr Gly Lys Arg Ala Leu Ile Val Gly Val Ala Ser
  1               5                  10                  15
Lys Leu Ser Ile Ala Ser Gly Ile Ala Ala Met His Arg Glu Gly
             20                  25                  30
Ala Glu Leu Ala Phe Thr Tyr Gln Asn Asp Lys Leu Arg Gly Arg Val
         35                  40                  45
Glu Glu Phe Ala Ser Gly Trp Gly Ser Arg Pro Glu Leu Cys Phe Pro
     50                  55                  60
Cys Asp Val Ala Asp Ser Gln Ile Glu Ala Val Phe Ala Ala Leu
 65                  70                  75                  80
Gly Lys His Trp Asp Gly Leu Asp Ile Ile Val His Ser Val Gly Phe
                 85                  90                  95
Ala Pro Gly Asp Gln Leu Asp Gly Asp Phe Thr Ala Val Thr Thr Arg
            100                 105                 110
Glu Gly Phe Arg Ile Ala His Asp Ile Ser Ala Tyr Ser Phe Ile Ala
        115                 120                 125
Leu Ala Lys Ala Gly Arg Glu Met Met Lys Gly Arg Asn Gly Ser Leu
    130                 135                 140
Leu Thr Leu Ser Tyr Leu Gly Ala Glu Arg Thr Met Pro Asn Tyr Asn
145                 150                 155                 160
Val Met Gly Met Ala Lys Ala Ser Leu Glu Ala Gly Val Arg Tyr Leu
                165                 170                 175
Ala Gly Ser Leu Gly Ala Glu Gly Thr Arg Val Asn Ala Val Ser Ala
            180                 185                 190
Gly Pro Ile Arg Thr Leu Ala Ala Ser Gly Ile Lys Ser Phe Arg Lys
        195                 200                 205
Met Leu Ala Ala Asn Glu Arg Gln Thr Pro Leu Arg Arg Asn Val Thr
    210                 215                 220
Ile Glu Glu Val Gly Asn Ala Gly Ala Phe Leu Cys Ser Asp Leu Ala
225                 230                 235                 240
Ser Gly Ile Ser Gly Glu Ile Leu Tyr Val Asp Gly Gly Phe Asn Thr
                245                 250                 255
Thr Ala Met Gly Pro Leu Asp Asp Asp
            260                 265
```

<210> SEQ ID NO 13
<211> LENGTH: 250
<212> TYPE: PRT
<213> ORGANISM: Enterococcus faecalis

<400> SEQUENCE: 13

```
Met Phe Leu Gln Asn Lys Asn Val Val Val Met Gly Val Ala Asn Lys
  1               5                  10                  15
Lys Ser Ile Ala Trp Gly Cys Ala Lys Ala Leu Lys Asp Gln Gly Ala
             20                  25                  30
Asn Val Ile Tyr Thr Tyr Gln Asn Glu Arg Met Lys Lys Gln Val Val
         35                  40                  45
```

```
Lys Leu Ala Asp Glu Asn Asp Leu Leu Val Glu Cys Asp Val Ala Ser
    50                  55                  60
Asp Ala Ser Ile Gln Ala Ala Phe Glu Thr Ile Lys Asn Glu Val Gly
 65                  70                  75                  80
Thr Ile Asp Gly Leu Val His Ala Ile Ala Phe Ala Lys Lys Glu Glu
                 85                  90                  95
Leu Ser Gly Asn Val Ser Asp Ile Thr Arg Asp Gly Phe Leu Leu Ala
                100                 105                 110
Gln Asp Ile Ser Ser Tyr Ser Leu Leu Ala Val Thr His Tyr Ala Lys
            115                 120                 125
Pro Leu Leu Asn Pro Gly Ser Gly Ile Val Thr Leu Thr Tyr Leu Gly
    130                 135                 140
Ser Glu Arg Ala Ile Pro Asn Tyr Asn Met Met Gly Ile Ala Lys Ala
145                 150                 155                 160
Ser Leu Glu Thr Ala Val Lys Tyr Leu Ala Phe Glu Leu Ala Ala Asp
                165                 170                 175
Lys Ile Arg Val Asn Gly Ile Ser Ala Gly Ala Ile Lys Thr Leu Ala
                180                 185                 190
Val Thr Gly Val Lys Asp Tyr Asp Gln Leu Ile Ser Ile Ser Asn Glu
            195                 200                 205
Arg Thr Pro Asp Lys Thr Gly Val Thr Ile Glu Glu Val Gly Asn Thr
    210                 215                 220
Cys Ala Phe Leu Val Ser Asp Leu Ala Ser Gly Val Val Gly Asp Ile
225                 230                 235                 240
Ile Tyr Val Asp Lys Gly Val His Leu Thr
                245                 250

<210> SEQ ID NO 14
<211> LENGTH: 255
<212> TYPE: PRT
<213> ORGANISM: Staphylococcus aureus

<400> SEQUENCE: 14

Met Leu Asn Leu Glu Asn Lys Thr Tyr Val Ile Met Gly Ile Ala Asn
  1               5                  10                  15
Lys Arg Ser Ile Ala Phe Gly Val Ala Lys Val Leu Asp Gln Leu Gly
                 20                  25                  30
Ala Lys Leu Val Phe Thr Tyr Arg Lys Glu Arg Ser Arg Lys Glu Leu
             35                  40                  45
Glu Lys Leu Leu Glu Gln Leu Asn Gln Pro Glu Ala His Leu Tyr Gln
     50                  55                  60
Ile Asp Val Gln Ser Asp Glu Glu Val Ile Asn Gly Phe Glu Gln Ile
 65                  70                  75                  80
Gly Lys Asp Val Gly Asn Ile Asp Gly Val Tyr His Ser Ile Ala Phe
                 85                  90                  95
Ala Asn Met Glu Asp Leu Arg Gly Arg Phe Ser Glu Thr Ser Arg Glu
            100                 105                 110
Gly Phe Leu Leu Ala Gln Asp Ile Ser Ser Tyr Ser Leu Thr Ile Val
        115                 120                 125
Ala His Glu Ala Lys Lys Leu Met Pro Glu Gly Gly Ser Ile Val Ala
    130                 135                 140
Thr Thr Tyr Leu Gly Gly Glu Phe Ala Val Gln Asn Tyr Asn Val Met
145                 150                 155                 160
Gly Val Ala Lys Ala Ser Leu Glu Ala Asn Val Lys Tyr Leu Ala Leu
                165                 170                 175
```

Asp Leu Gly Pro Asp Asn Ile Arg Val Asn Ala Ile Ser Ala Gly Pro
            180                 185                 190

Ile Arg Thr Leu Ser Ala Lys Gly Val Gly Gly Phe Asn Thr Ile Leu
        195                 200                 205

Lys Glu Ile Glu Arg Ala Pro Leu Lys Arg Asn Val Asp Gln Val Glu
    210                 215                 220

Val Gly Lys Thr Ala Ala Tyr Leu Leu Ser Asp Leu Ser Ser Gly Val
225                 230                 235                 240

Thr Gly Glu Asn Ile His Val Asp Ser Gly Phe His Ala Ile Lys
                245                 250                 255

<210> SEQ ID NO 15
<211> LENGTH: 256
<212> TYPE: PRT
<213> ORGANISM: Staphylococcus epidermidis

<400> SEQUENCE: 15

Met Leu Asn Leu Glu Asn Lys Thr Tyr Val Ile Met Gly Ile Ala Asn
1               5                   10                  15

Lys Arg Ser Ile Ala Phe Gly Val Ala Lys Val Leu Asp Arg Leu Gly
            20                  25                  30

Ala Lys Leu Val Phe Thr Tyr Arg Lys Glu Arg Ser Arg Lys Glu Leu
        35                  40                  45

Glu Lys Leu Leu Glu Gln Leu Asn Gln Ser Glu His His Leu Tyr Glu
    50                  55                  60

Ile Asp Val Gln Asn Asp Glu Asp Ile Ile Asn Gly Phe Ser Gln Ile
65                  70                  75                  80

Gly Lys Asp Val Gly Gln Ile Asp Gly Val Tyr His Ser Ile Ala Phe
                85                  90                  95

Ala Asn Met Glu Asp Leu Arg Gly Arg Phe Ser Glu Thr Ser Arg Glu
            100                 105                 110

Gly Phe Leu Leu Ala Gln Glu Ile Ser Ser Tyr Ser Leu Thr Leu Val
        115                 120                 125

Ala His Glu Ala Lys Lys Leu Met Pro Glu Gly Gly Ser Ile Val Ala
    130                 135                 140

Thr Thr Tyr Ile Gly Gly Glu Ala Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175

Asp Leu Gly Glu Asp Asn Ile Arg Val Asn Ala Ile Ser Ala Gly Pro
            180                 185                 190

Ile Arg Thr Leu Ser Ala Lys Gly Val Gly Gly Phe Asn Thr Ile Leu
        195                 200                 205

Lys Glu Ile Glu Ala Arg Ala Pro Leu Lys Arg Asn Val Asp Gln Glu
    210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Gly Gly Phe His Ala Ile Lys
                245                 250                 255

<210> SEQ ID NO 16
<211> LENGTH: 328
<212> TYPE: PRT
<213> ORGANISM: Pseudomonas aeruginosa

<400> SEQUENCE: 16

Met Gly Val Phe Arg Thr Arg Phe Thr Glu Thr Phe Gly Val Glu His
1               5                   10                  15

Pro Ile Met Gln Gly Gly Met Gln Trp Val Gly Arg Ala Glu Met Ala
            20                  25                  30

Ala Ala Val Ala Asn Ala Gly Gly Leu Ala Thr Leu Ser Ala Leu Thr
            35                  40                  45

Gln Pro Ser Pro Glu Ala Leu Ala Ala Glu Ile Ala Arg Cys Arg Glu
50                      55                  60

Leu Thr Asp Arg Pro Phe Gly Val Asn Leu Thr Leu Pro Thr Gln
65                  70                  75                  80

Lys Pro Val Pro Tyr Ala Glu Tyr Arg Ala Ile Ile Glu Ala Gly
                85                  90                  95

Ile Arg Val Val Glu Thr Ala Gly Asn Asp Pro Gly Glu His Ile Ala
            100                 105                 110

Glu Phe Arg Arg His Gly Val Lys Val Ile His Lys Cys Thr Ala Val
            115                 120                 125

Arg His Ala Leu Lys Ala Glu Arg Leu Gly Val Asp Ala Val Ser Ile
130                 135                 140

Asp Gly Phe Glu Cys Ala Gly His Pro Gly Glu Asp Ile Pro Gly
145                 150                 155                 160

Leu Val Leu Leu Pro Ala Ala Ala Asn Arg Leu Arg Val Pro Ile Ile
                165                 170                 175

Ala Ser Gly Gly Phe Ala Asp Gly Arg Gly Leu Val Ala Ala Leu Ala
            180                 185                 190

Leu Gly Ala Asp Ala Ile Asn Met Gly Thr Arg Phe Leu Ala Thr Arg
            195                 200                 205

Glu Cys Pro Ile His Pro Ala Val Lys Ala Ala Ile Arg Ala Ala Asp
210                 215                 220

Glu Arg Ser Thr Asp Leu Ile Met Arg Ser Leu Arg Asn Thr Ala Arg
225                 230                 235                 240

Val Ala Arg Asn Ala Ile Ser Gln Glu Val Leu Ala Ile Glu Ala Arg
            245                 250                 255

Gly Gly Ala Gly Tyr Ala Asp Ile Ala Ala Leu Val Ser Gly Gln Arg
            260                 265                 270

Gly Arg Gln Val Tyr Gln Gly Asp Thr Asp Leu Gly Ile Trp Ser
            275                 280                 285

Ala Gly Met Val Gln Gly Leu Ile Asp Asp Glu Pro Ala Cys Ala Glu
            290                 295                 300

Leu Leu Arg Asp Ile Val Glu Gln Ala Arg Gln Leu Val Arg Gln Arg
305                 310                 315                 320

Leu Glu Gly Met Leu Ala Gly Val
                325

<210> SEQ ID NO 17
<211> LENGTH: 318
<212> TYPE: PRT
<213> ORGANISM: Enterococcus faecalis

<400> SEQUENCE: 17

Met Asn Gln Glu Leu Cys Glu Leu Leu Gly Ile Asn Tyr Pro Ile Phe
1               5                   10                  15

Gln Gly Gly Met Ala Trp Val Ala Asp Ala Ser Leu Ala Ser Ala Val
            20                  25                  30

Ser Asn Ala Gly Gly Leu Gly Ile Ile Ala Gly Gly Asn Ala Pro Lys

-continued

```
                35                  40                  45
Glu Val Val Lys Lys Glu Ile Lys Lys Val Lys Glu Leu Thr Glu Gln
 50                  55                  60

Pro Phe Gly Val Asn Ile Met Leu Leu Ser Pro Phe Ala Asp Glu Ile
 65                  70                  75                  80

Val Asp Leu Val Cys Glu Glu Gln Val Pro Val Val Thr Thr Gly Ala
                 85                  90                  95

Gly Asn Pro Ala Lys Tyr Met Ala Arg Phe Lys Glu His Asn Ile Lys
                100                 105                 110

Val Ile Pro Val Pro Ser Val Ala Leu Ala Lys Arg Met Glu Lys
             115                 120                 125

Ile Gly Ala Asp Ala Val Ile Phe Glu Gly Met Glu Ala Gly Gly His
130                 135                 140

Ile Gly Lys Leu Thr Thr Met Ser Gly Leu Pro Gln Ile Val Asp Ala
145                 150                 155                 160

Val Ser Ile Pro Val Ile Ala Ala Gly Gly Ile Gly Asp Gly Arg Gly
                165                 170                 175

Met Ala Ala Ala Phe Met Leu Gly Ala Glu Ala Val Gln Leu Gly Thr
            180                 185                 190

Arg Phe Leu Ile Ala Lys Glu Cys Asn Val His Pro Asp Tyr Lys Gln
            195                 200                 205

Lys Val Leu Lys Ala Arg Asp Leu Asp Ala Val Ile Thr Cys Gln His
            210                 215                 220

Phe Gly His Pro Val Arg Thr Leu Lys Asn Lys Leu Thr Ala Gln Tyr
225                 230                 235                 240

Asn Gln Leu Glu Lys Gln Glu Leu Gln Lys Glu Val Pro Asp Leu Glu
                245                 250                 255

Met Phe Glu Lys Ile Gly Gln Gly Ala Leu Arg Lys Ala Val Val Asp
            260                 265                 270

Gly Asp Met Asp Tyr Gly Ser Val Met Ala Gly Gln Ile Ala Gly Leu
            275                 280                 285

Ile Lys Lys Glu Glu Thr Ala Gln Glu Ile Ile Asp Ser Leu Met Ser
            290                 295                 300

Glu Cys Lys Ala Ile Val His Lys Met Asn Gln Arg Trp Gly
305                 310                 315
```

<210> SEQ ID NO 18
<211> LENGTH: 324
<212> TYPE: PRT
<213> ORGANISM: Streptococcus pneumoniae

<400> SEQUENCE: 18

```
Met Lys Thr Arg Ile Thr Glu Leu Leu Lys Ile Asp Tyr Pro Ile Phe
  1               5                  10                  15

Gln Gly Gly Met Ala Trp Val Ala Asp Gly Asp Leu Ala Gly Ala Val
                 20                  25                  30

Ser Lys Ala Gly Gly Leu Gly Ile Ile Gly Gly Asn Ala Pro Lys
             35                  40                  45

Glu Val Val Lys Ala Asn Ile Asp Lys Ile Lys Ser Leu Thr Asp Lys
 50                  55                  60

Pro Phe Gly Val Asn Ile Met Leu Leu Ser Pro Phe Val Glu Asp Ile
 65                  70                  75                  80

Val Asp Leu Val Ile Glu Glu Gly Val Lys Val Thr Thr Gly Ala
                 85                  90                  95
```

```
Gly Asn Pro Ser Lys Tyr Met Glu Arg Phe His Glu Ala Gly Ile Ile
                100                 105                 110

Val Ile Pro Val Val Pro Ser Val Ala Leu Ala Lys Arg Met Glu Lys
            115                 120                 125

Ile Gly Ala Asp Ala Val Ile Ala Glu Gly Met Glu Ala Gly Gly His
        130                 135                 140

Ile Gly Lys Leu Thr Thr Met Thr Leu Val Arg Gln Val Ala Thr Ala
145                 150                 155                 160

Ile Ser Ile Pro Val Ile Ala Ala Gly Gly Ile Ala Asp Gly Glu Gly
                165                 170                 175

Ala Ala Ala Gly Phe Met Leu Gly Ala Glu Ala Val Gln Val Gly Thr
            180                 185                 190

Arg Phe Val Val Ala Lys Glu Ser Asn Ala His Pro Asn Tyr Lys Glu
        195                 200                 205

Lys Ile Leu Lys Ala Arg Asp Ile Asp Thr Thr Ile Ser Ala Gln His
210                 215                 220

Phe Gly His Ala Val Arg Ala Ile Lys Asn Gln Leu Thr Arg Asp Phe
225                 230                 235                 240

Glu Leu Ala Glu Lys Asp Ala Phe Lys Gln Asp Pro Asp Leu Glu
            245                 250                 255

Ile Phe Glu Gln Met Gly Ala Gly Ala Leu Ala Lys Ala Val Val His
        260                 265                 270

Gly Asp Val Asp Gly Gly Ser Val Met Ala Gly Gln Ile Ala Gly Leu
                275                 280                 285

Val Ser Lys Glu Glu Thr Ala Glu Glu Ile Leu Lys Asp Leu Tyr Tyr
            290                 295                 300

Gly Ala Ala Lys Lys Ile Gln Glu Glu Ala Ser Arg Trp Thr Gly Val
305                 310                 315                 320

Val Arg Asn Asp

<210> SEQ ID NO 19
<211> LENGTH: 11
<212> TYPE: PRT
<213> ORGANISM: Escherichia coli

<400> SEQUENCE: 19

Ile Arg Thr Leu Ala Ala Ser Gly Ile Lys Asp
  1               5                  10

<210> SEQ ID NO 20
<211> LENGTH: 11
<212> TYPE: PRT
<213> ORGANISM: Haemophilus influenzae

<400> SEQUENCE: 20

Ile Arg Thr Leu Ala Ala Ser Gly Ile Lys Asn
  1               5                  10

<210> SEQ ID NO 21
<211> LENGTH: 11
<212> TYPE: PRT
<213> ORGANISM: Pseudomonas aeruginosa

<400> SEQUENCE: 21

Ile Arg Thr Leu Ala Ala Ser Gly Ile Lys Ser
  1               5                  10

<210> SEQ ID NO 22
```

-continued

```
<211> LENGTH: 11
<212> TYPE: PRT
<213> ORGANISM: Enterococcus faecalis

<400> SEQUENCE: 22

Ile Lys Thr Leu Ala Val Thr Gly Val Lys Asp
 1               5                  10

<210> SEQ ID NO 23
<211> LENGTH: 11
<212> TYPE: PRT
<213> ORGANISM: Staphylococcus aureus

<400> SEQUENCE: 23

Ile Arg Thr Leu Ser Ala Lys Gly Val Gly Gly
 1               5                  10

<210> SEQ ID NO 24
<211> LENGTH: 11
<212> TYPE: PRT
<213> ORGANISM: Staphylococcus epidermidis

<400> SEQUENCE: 24

Ile Arg Thr Leu Ser Ala Lys Gly Val Gly Gly
 1               5                  10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
 1               5
```